(12) United States Patent
Estrada et al.

(10) Patent No.: US 10,131,676 B2
(45) Date of Patent: Nov. 20, 2018

(54) COMPOUNDS, COMPOSITIONS AND METHODS

(71) Applicant: Denali Therapeutics Inc., South San Francisco, CA (US)

(72) Inventors: Anthony A. Estrada, San Mateo, CA (US); Jianwen A. Feng, San Mateo, CA (US); Brian Fox, Brisbane, CA (US); Colin Philip Leslie, Pozzolengo (IT); Joseph P. Lyssikatos, South San Francisco, CA (US); Alfonso Pozzan, Monticello Conte Otto (IT); Zachary K. Sweeney, Redwood City, CA (US); Javier de Vicente Fidalgo, Foster City, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

(21) Appl. No.: 15/721,470

(22) Filed: Sep. 29, 2017

(65) Prior Publication Data
US 2018/0099981 A1   Apr. 12, 2018

Related U.S. Application Data

(62) Division of application No. 15/424,216, filed on Feb. 3, 2017, now Pat. No. 9,815,850.

(60) Provisional application No. 62/417,219, filed on Nov. 3, 2016, provisional application No. 62/385,217, filed on Sep. 8, 2016, provisional application No. 62/363,775, filed on Jul. 18, 2016, provisional application No. 62/341,019, filed on May 24, 2016, provisional application No. 62/292,202, filed on Feb. 5, 2016.

(51) Int. Cl.

| | |
|---|---|
| C07D 471/04 | (2006.01) |
| C07D 513/04 | (2006.01) |
| C07D 261/18 | (2006.01) |
| C07D 267/14 | (2006.01) |
| C07D 403/12 | (2006.01) |
| C07D 413/12 | (2006.01) |
| C07D 413/14 | (2006.01) |
| C07D 417/12 | (2006.01) |
| C07D 487/04 | (2006.01) |
| C07D 495/04 | (2006.01) |
| C07D 498/04 | (2006.01) |
| C07D 498/14 | (2006.01) |
| C07D 491/048 | (2006.01) |

(52) U.S. Cl.
CPC ......... *C07D 513/04* (2013.01); *C07D 261/18* (2013.01); *C07D 267/14* (2013.01); *C07D 403/12* (2013.01); *C07D 413/12* (2013.01); *C07D 413/14* (2013.01); *C07D 417/12* (2013.01); *C07D 471/04* (2013.01); *C07D 487/04* (2013.01); *C07D 491/048* (2013.01); *C07D 495/04* (2013.01); *C07D 498/04* (2013.01); *C07D 498/14* (2013.01)

(58) Field of Classification Search
CPC ..................................................... C07D 471/04
See application file for complete search history.

(56) References Cited

U.S. PATENT DOCUMENTS

| | | | |
|---|---|---|---|
| 4,477,464 | A | 10/1984 | Slade et al. |
| 4,871,842 | A | 10/1989 | Sugihara et al. |
| 5,055,464 | A | 10/1991 | Murakami et al. |
| 5,206,234 | A | 4/1993 | Bock et al. |
| 5,206,235 | A | 4/1993 | Fisher et al. |
| 5,283,241 | A | 2/1994 | Bochis et al. |
| 5,284,841 | A | 2/1994 | Chu et al. |
| 5,310,737 | A | 5/1994 | Fisher et al. |
| 5,330,987 | A | 7/1994 | Allen et al. |
| 5,420,271 | A | 5/1995 | Warshawsky et al. |
| 5,428,158 | A | 6/1995 | Warshawsky et al. |
| 5,457,196 | A | 10/1995 | Warshawsky et al. |
| 5,484,917 | A | 1/1996 | Lowe, III |
| 5,596,000 | A | 1/1997 | Esser et al. |
| 5,606,054 | A | 2/1997 | Fisher et al. |
| 5,672,596 | A | 9/1997 | Wyvratt et al. |
| 5,710,153 | A | 1/1998 | Ohmoto et al. |
| 5,712,273 | A | 1/1998 | Schnorrenberg et al. |
| 5,726,307 | A | 3/1998 | Schoen et al. |
| 5,747,235 | A | 5/1998 | Farid et al. |
| 5,783,573 | A | 7/1998 | Rozsa et al. |
| 5,789,587 | A | 8/1998 | Fisher et al. |
| 5,958,924 | A | 9/1999 | McCort et al. |
| 6,028,195 | A | 2/2000 | Cho et al. |
| 6,211,174 | B1 | 4/2001 | Devita et al. |
| 6,335,363 | B1 | 1/2002 | Gerlach et al. |
| 6,350,741 | B1 | 2/2002 | Golec et al. |
| 6,376,484 | B1 | 4/2002 | Ohmoto et al. |
| 7,098,235 | B2 | 8/2006 | Sher et al. |
| 7,109,357 | B2 | 9/2006 | Wannamaker et al. |
| 7,208,600 | B2 | 4/2007 | Cottrell et al. |
| 7,491,743 | B2 | 2/2009 | Cuny et al. |
| 7,842,686 | B2 | 11/2010 | Anderson et al. |

(Continued)

FOREIGN PATENT DOCUMENTS

| | | |
|---|---|---|
| CN | 103664904 | 3/2014 |
| EP | 0322779 | 7/1989 |

(Continued)

OTHER PUBLICATIONS

Bacqué et al., "Tin-free radical cyclizations for the synthesis of 7-azaoxindoles, 7-azaindolines, tetrahydro[1,8]naphthyridines, and tetrahydro-5H-pyrido[2,3-b]azepin-8-ones", Org Lett. 2004, 6(21), 3671-3674.

(Continued)

*Primary Examiner* — Bruck Kifle
(74) *Attorney, Agent, or Firm* — Sheppard Mullin Richter & Hampton LLP

(57) ABSTRACT

The present disclosure relates generally to compounds and compositions, and their use as kinase inhibitors.

33 Claims, No Drawings

(56) References Cited

U.S. PATENT DOCUMENTS

| | | |
|---|---|---|
| 7,884,074 B2 | 2/2011 | Petzelbauer et al. |
| 8,088,890 B2 | 1/2012 | Petzelbauer et al. |
| 8,242,150 B2 | 8/2012 | Fischer et al. |
| 8,569,286 B2 | 10/2013 | Hipskind et al. |
| 8,586,732 B2 | 11/2013 | Corkey et al. |
| 9,062,002 B2 | 6/2015 | Takhi et al. |
| 9,062,075 B2 | 6/2015 | Takhi et al. |
| 2003/0191049 A1 | 10/2003 | Amblard et al. |
| 2004/0002495 A1 | 1/2004 | Sher et al. |
| 2004/0142938 A1 | 7/2004 | Sher et al. |
| 2007/0010428 A1 | 1/2007 | McMurray et al. |
| 2011/0046195 A1 | 2/2011 | Blackwell et al. |
| 2011/0135600 A1 | 6/2011 | Stieber et al. |
| 2011/0152253 A1 | 6/2011 | Motoki et al. |
| 2011/0230414 A1 | 9/2011 | Hendricks et al. |
| 2011/0306626 A1 | 12/2011 | Selnick et al. |
| 2012/0315247 A1 | 12/2012 | Xi |
| 2013/0165446 A1 | 6/2013 | Fujita et al. |
| 2015/0315210 A1 | 11/2015 | Hu et al. |
| 2015/0353533 A1 | 12/2015 | Bandyopadhyay et al. |
| 2015/0374662 A1 | 12/2015 | Bode et al. |
| 2017/0008878 A1 | 1/2017 | Bandyopadhyay et al. |

FOREIGN PATENT DOCUMENTS

| | | |
|---|---|---|
| EP | 0462800 | 12/1991 |
| EP | 0703222 | 3/1996 |
| EP | 0728746 | 8/1996 |
| EP | 1939187 | 7/2008 |
| EP | 2493888 | 4/2016 |
| EP | 3017825 | 5/2016 |
| ES | 2081747 | 3/1996 |
| GB | 2272439 | 5/1994 |
| JP | 334977 | 2/1991 |
| JP | 5-239065 | 9/1993 |
| JP | 9-295996 | 11/1997 |
| JP | 10-251295 | 9/1998 |
| JP | 2000-256318 | 9/2000 |
| JP | 2005-035933 | 2/2005 |
| WO | WO-1992/016524 | 10/1992 |
| WO | WO-1994/001421 | 1/1994 |
| WO | WO-1994/004531 | 3/1994 |
| WO | WO-1994/007483 | 4/1994 |
| WO | WO-1994/007486 | 4/1994 |
| WO | WO-1994/08683 | 4/1994 |
| WO | WO-1994/024149 | 10/1994 |
| WO | WO-1995/003290 | 2/1995 |
| WO | WO-1995/016692 | 6/1995 |
| WO | WO-1995/028419 | 10/1995 |
| WO | WO-1995/030687 | 11/1995 |
| WO | WO-1996/005195 | 2/1996 |
| WO | WO-1996/011691 | 4/1996 |
| WO | WO-1996/011701 | 4/1996 |
| WO | WO-1996/011940 | 4/1996 |
| WO | WO-1996/016008 | 5/1996 |
| WO | WO-1996/040653 | 12/1996 |
| WO | WO-1996/040654 | 12/1996 |
| WO | WO-1996/040655 | 12/1996 |
| WO | WO-1996/040656 | 12/1996 |
| WO | WO-1997/022619 | 6/1997 |
| WO | WO-1998/000402 | 1/1998 |
| WO | WO-1999/007731 | 2/1999 |
| WO | WO-2000/005246 | 2/2000 |
| WO | WO-2001/074783 | 10/2001 |
| WO | WO-2001/074784 | 10/2001 |
| WO | WO-2001/079261 | 10/2001 |
| WO | WO-2001/090084 | 11/2001 |
| WO | WO-2001/092235 | 12/2001 |
| WO | WO-2002/018382 | 3/2002 |
| WO | WO-2002/020500 | 3/2002 |
| WO | WO-2003/007945 | 1/2003 |
| WO | WO-2003/010141 | 2/2003 |
| WO | WO-2003/014377 | 2/2003 |
| WO | WO-2003/031376 | 4/2003 |
| WO | WO-2004/002960 | 1/2004 |
| WO | WO-2004/055008 | 7/2004 |
| WO | WO-2004/082602 | 9/2004 |
| WO | WO-2004/098589 | 11/2004 |
| WO | WO-2005/056577 | 6/2005 |
| WO | WO-2006/031606 | 3/2006 |
| WO | WO-2006/044449 | 4/2006 |
| WO | WO-2006/044504 | 4/2006 |
| WO | WO-2006/059164 | 6/2006 |
| WO | WO-2006/063178 | 6/2006 |
| WO | WO-2006/071775 | 7/2006 |
| WO | WO-2006/079077 | 7/2006 |
| WO | WO-2006/103559 | 10/2006 |
| WO | WO-2006/105222 | 10/2006 |
| WO | WO-2006/113432 | 10/2006 |
| WO | WO-2006/116713 | 11/2006 |
| WO | WO-2007/035935 | 3/2007 |
| WO | WO-2007/067416 | 6/2007 |
| WO | WO-2007/109251 | 9/2007 |
| WO | WO-2007/126871 | 11/2007 |
| WO | WO-2007/145922 | 12/2007 |
| WO | WO-2008/009122 | 1/2008 |
| WO | WO-2008/040778 | 4/2008 |
| WO | WO-2008/045484 | 4/2008 |
| WO | WO-2008/080056 | 7/2008 |
| WO | WO-2008/106077 | 9/2008 |
| WO | WO-2008/135525 | 11/2008 |
| WO | WO-2008/156580 | 12/2008 |
| WO | WO-2009/019115 | 2/2009 |
| WO | WO-2009/085256 | 7/2009 |
| WO | WO-2009/095759 | 8/2009 |
| WO | WO-2009/095788 | 8/2009 |
| WO | WO-2009/095789 | 8/2009 |
| WO | WO-2009/103432 | 8/2009 |
| WO | WO-2009/105348 | 8/2009 |
| WO | WO-2009/140549 | 11/2009 |
| WO | WO-2010/019899 | 2/2010 |
| WO | WO-2010/083725 | 7/2010 |
| WO | WO-2011/035019 | 3/2011 |
| WO | WO-2011/133964 | 10/2011 |
| WO | WO-2011/149963 | 12/2011 |
| WO | WO-2012/061408 | 5/2012 |
| WO | WO-2013/000994 | 1/2013 |
| WO | WO-2013/012918 | 1/2013 |
| WO | WO-2013/013826 | 1/2013 |
| WO | WO-2013/059791 | 4/2013 |
| WO | WO-2013/151739 | 10/2013 |
| WO | WO-2013/189241 | 12/2013 |
| WO | WO-2014/009495 | 1/2014 |
| WO | WO-2014/023708 | 2/2014 |
| WO | WO-2014/072930 | 5/2014 |
| WO | WO-2014/125444 | 8/2014 |
| WO | WO-2014/144547 | 9/2014 |
| WO | WO-2014/155016 | 10/2014 |
| WO | WO-2014/170892 | 10/2014 |
| WO | WO-2015/027137 | 2/2015 |
| WO | WO-2015/103583 | 7/2015 |
| WO | WO-2015/104677 | 7/2015 |
| WO | WO-2015/184257 | 12/2015 |
| WO | WO-2016/023918 | 2/2016 |
| WO | WO-2016/027253 | 2/2016 |
| WO | WO-2016/055028 | 4/2016 |
| WO | WO-2016/101885 | 6/2016 |
| WO | WO-2016/101887 | 6/2016 |
| WO | WO-2016/113668 | 7/2016 |
| WO | WO-2016/128936 | 8/2016 |
| WO | WO-2016/168014 | 10/2016 |
| WO | WO-2017/004500 | 1/2017 |
| WO | WO-2017/022962 | 2/2017 |
| WO | WO-2017/069279 | 4/2017 |
| WO | WO-2017/109724 | 6/2017 |

OTHER PUBLICATIONS

Berger et al., "Characterization of GSK'963: a structurally distinct, potent and selective inhibitor of RIP1 kinase", Cell Death Discovery, 2015, 1, 15009. (7 pages).

Berger et al., "Drilling into RIP1 biology: what compounds are in your toolkit?", Cell Death and Disease, 2015, 6:E1889, 2 pages.

(56) References Cited

OTHER PUBLICATIONS

Bolin et al., "Peptide and Peptide Mimetic Inhibitors of Antigen Presentation by HLA-DR Class II MHC Molecules, Design, Structure-Activity Relationships, and X-ray Crystal Structures", J. Med. Chem., 2000, 43, 2135-2148.
CAS RN 1222532-89-9 Registry, 1-Piperidinecarboxamide, 4-(1,4-dihydro-2-oxo-3(2H)-quinazolinyl)-N-[2,3,4,5-tetrahydro-1-(1-methylethyl)-2-oxo-1H-1-benzazepin-3-yl]-(CA Index Name), Entered STN: May 12, 2010, Database: ChEBI (European Bioinformatics Institute). (1 page).
Cristau et al. "Reaction of lithium diphenylphosphonium di(methylide) with carbonic acid derivatives. A novel access to polyfunctional unsaturated esters and amides", Heteroatom Chemistry, 1992, 3(4), 415-422.
Degterev et al., "Identification of RIP1 kinase as a specific cellular target of necrostatins." Nature Chemical Biology, 2008, 4, 313-321.
Dhanik et al., "Binding Modes of Peptidomimetics Designed to Inhibit STAT3", PLoS ONE 7(12): e51603 (2012). (18 pages).
Fischer et al., "Discovery of novel triazolobenzazepinones as ?-secretase modulators with central Aß42 lowering in rodents and rhesus monkeys." Bioorganic & Medicinal Chemistry Letters, 2015, 25(17), 3488-3494.
GlaxoSmithKline, "A Safety and Tolerability Study of GSK2982772, in Single (in Both Fed and Fasted States) and Repeat Oral Doses in Healthy Male Subjects." ClinicalTrials.gov, record processed Aug. 2, 2016. (7 pages).
GlaxoSmithKline, "Safety, Tolerability, Pharmacokinetics, Pharmacodynamics, and Efficacy of Repeat Doses of GSK2982772." ClinicalTrials.gov, record processed Aug. 2, 2016. (5 pages).
Harris et al., "Discovery of a First-in-Class Receptor Interacting Protein 1 (RIP1) Kinase Specific Clinical Candidate (GSK2982772) for the Treatment of Inflammatory Diseases." J Med Chem., 2017, 60(4), 1247-1261.
Harris et al., "DNA-Encoded Library Screening Identifies Benzo[b][1,4]oxazepin-4-ones as Highly Potent and Monoselective Receptor Interacting Protein 1 Kinase Inhibitors." J. Med. Chem., 2016, 59(5), 2163-2178.
Herpin et al., "Directed sorting approach for the synthesis of large combinatorial libraries of discrete compounds." Methods Enzymol., 2003, 369, 75-99.
Hoyt et al., "Benzazepinone Nav1.7 blockers: potential treatments for neuropathic pain." Bioorganic & Medicinal Chemistry Letters, 2007, 17(22), 6172-6177.

International Search Report and Written Opinion for International Application No. PCT/US2017/016509, dated Aug. 7, 2017. (26 pages).
Klapars et al., "Synthesis of medium ring nitrogen heterocycles via a tandem copper-catalyzed C—N bond formation-ring-expansion process." J Am Chem Soc., 2004, 126(11), 3529-33.
Mandal et al., "Conformationally Constrained Peptidomimetic Inhibitors of Signal Transducer and Activator of Transcription 3: Evaluation and Molecular Modeling." J. Med. Chem., 2009, 52(8), 2429-2442.
Ofengeim et al., "Activation of necroptosis in multiple sclerosis." Cell Rep., 2015, 10(11), 1836-1849.
Paone et al., "Orally bioavailable imidazoazepanes as calcitonin gene-related peptide (CGRP) receptor antagonists: Discovery of MK-2918," Bioorganic & Medicinal Chemistry Letters, 2011, 21, 2683-2686.
Rosauer et al., "Novel 3,4-Dihydroquinolin-2(1H)-one inhibitors of human glycogen phosphorylase a." Bioorganic & Medicinal Chemistry Letters, 2003, 13(24), 4385-4388.
Rosloniec et al., "Second-generation peptidomimetic inhibitors of antigen presentation effectively treat autoimmune diseases in HLA-DR-transgenic mouse models." J Autoimmun., 2006, 27(3), 182-195.
Sarabu et al., "Oxazole- and Imidazole-Based Ser-Leu Dipeptide Mimetics in Potent Inhibitors of Antigen Presentation by MHC Class II DR Molecules." Drug Design and Discovery, 2002, 18(1), 3-7.
Teng et al., "Structure activity relationship and liver microsome stability studies of pyrrole necroptosis inhibitors." Bioorg Med Chem Lett., 2008, 18(11), 3219-3223.
Teng et al., "Structure-activity relationship study of [1,2,3]thiadiazole necroptosis inhibitors." Bioorganic & Medicinal Chemistry Letters, 2007, 17(24), 6836-6840.
Teng et al., "Structure-activity relationship study of novel necroptosis inhibitors." Bioorganic & Medicinal Chemistry Letters 2005, 15, 5039-5044.
Wei et al., "Modeling Ligand-Receptor Interaction for Some MHC Class II HLA-DR4 Peptide Mimetic Inhibitors Using Several Molecular Docking and 3D QSAR Techniques." J. Chem. Inf. Model., 2005, 45(5), 1343-1351.
Williams et al., "Characterization of a New Class of Potent Inhibitors of the Voltage-Gated Sodium Channel Nav1.7." Biochemistry, 2007, 46(50), 14693-14703.
Xie et al., "Structural basis of RIP1 inhibition by necrostatins." Structure, 2013, 21(3), 493-499.

COMPOUNDS, COMPOSITIONS AND METHODS

CROSS REFERENCE TO RELATED APPLICATIONS

This application is a divisional of U.S. application Ser. No. 15/424,216, filed Feb. 3, 2017, now U.S. Pat. No. 9,815,850, which application claims priority under 35 U.S.C. 119(e) of U.S. Provisional Application Nos. 62/292,202, filed Feb. 5, 2016, 62/341,019, filed May 24, 2016, 62/363,775, filed Jul. 18, 2016, 62/385,217, filed Sep. 8, 2016, and 62/417,219, filed Nov. 3, 2016. The entire contents of these applications are incorporated by reference into this application.

FIELD

The present disclosure relates generally to inhibitors of kinase, therapeutic methods of use, and manufacture thereof.

BACKGROUND

Although inflammation can be a protective mechanism in response to harmful stimuli such as invasion of pathogens and tissue damages, chronic inflammation is an important underlying factor in many human diseases such as neurodegeneration, rheumatoid arthritis, autoimmune and inflammatory diseases, and cancer. Similarly, the activation of cell death pathways, such as necrosis and apoptosis which are useful in eliminating infected or damaged cells, is also an important underlying mechanism for human diseases, including acute and chronic neurodegenerative diseases.

Receptor-interacting protein kinase 1 is a key regulator of inflammation, apoptosis and necroptosis. Receptor-interacting protein kinase 1 has an important role in modulating inflammatory responses mediated by nuclear-factor kappa-light chain enhancer of activated B cells (NF-κB). More recent research has shown that its kinase activity controls necroptosis, a form of necrotic cell death, which was traditionally thought to be passive and unregulated, and is characterized by a unique morphology. Further, receptor-interacting protein kinase 1 is part of a pro-apoptotic complex indicating its activity in regulating apoptosis.

The receptor-interacting protein kinase 1 is subject to complex and intricate regulatory mechanisms, including ubiquitylation, deubiquitylation and phosphorylation. These regulatory events collectively determine whether a cell will survive and activate an inflammatory response or die through apoptosis or necroptosis. Dysregulation of receptor-interacting protein kinase 1 signaling can lead to excessive inflammation or cell death, and conversely, research has shown that inhibition of receptor-interacting protein kinase 1 can be effective therapies for diseases involving inflammation or cell death.

DESCRIPTION

Provided herein are compounds that are useful as inhibitors of receptor-interacting protein kinase 1. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated by receptor-interacting protein kinase 1. Moreover, the disclosure provides uses of the compounds or compositions thereof in the manufacture of a medicament for the treatment of a disease, disorder or condition that is mediated by (or mediated, at least in part, by) receptor-interacting protein kinase 1.

In certain embodiments, provided is a compound of Formula I. In certain embodiments, provided is a compound of Formula IIc. In certain embodiments, provided is a compound of Formula IIe. In certain embodiments, provided is a compound of Formula IIf. In certain embodiments, provided is a compound of Formula V. In certain embodiments, provided is a compound of Formula Va. In certain embodiments, provided is a compound of Formula VI. In certain embodiments, provided is a compound as in Table 1, or a pharmaceutically acceptable salt, prodrug, tautomer, stereoisomer or mixture of stereoisomers thereof. In certain embodiments, provided is a compound as in Table 2, or a pharmaceutically acceptable salt, prodrug, tautomer, stereoisomer or mixture of stereoisomers thereof. In certain embodiments, provided is a compound as in Table 3, or a pharmaceutically acceptable salt, prodrug, tautomer, stereoisomer or mixture of stereoisomers thereof. In certain embodiments, provided is a compound as in Table 4, or a pharmaceutically acceptable salt, prodrug, tautomer, stereoisomer or mixture of stereoisomers thereof.

Provided herein is a pharmaceutical composition comprising a compound, including those of any Formula described herein, and an excipient.

Provided herein are compounds and compositions for use in medicine. In certain embodiments, the compounds and compositions are for use in the treatment of a receptor-interacting protein kinase 1-mediated disease or disorder.

Provided herein is a method of treating a receptor-interacting protein kinase 1-mediated disease or disorder comprising administering a therapeutically effective amount of a compound or pharmaceutical composition disclosed herein to a subject in need thereof.

In certain embodiments, the disease or disorder is inflammatory bowel disease, Crohn's disease, ulcerative colitis, psoriasis, retinal detachment, retinitis pigmentosa, macular degeneration, pancreatitis, atopic dermatitis, rheumatoid arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis, autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, or peridontitis. In certain embodiments, the disease or disorder is trauma, ischemia, stroke, cardiac infarction, infection, lysomal storage disease, Gaucher's disease, Krabbe disease, Niemann-Pick disease, sepsis, Parkinson's disease, Alzheimer's disease, amyotrophic lateral sclerosis (ALS/Lou Gehrig's Disease), Huntington's disease, HIV-associated dementia, retinal degenerative disease, glaucoma, age-related macular degeneration, rheumatoid arthritis, psoriasis, psoriatic arthritis or inflammatory bowel disease. In certain embodiments, the disease or disorder is Alzheimer's disease, ALS, Friedreich's ataxia, Huntington's disease, Lewy body disease, Parkinson's disease, or spinal muscular atrophy. In certain embodiments, the disease or disorder is brain injury, spinal cord injury, dementia, stroke, Alzheimer's disease, ALS, Parkinson's disease, Huntington's disease, multiple sclerosis, diabetic neuropathy, poly glutamine (polyQ) diseases, stroke, Fahr disease, Menke's disease, Wilson's disease, cerebral ischemia, or a prion disorder.

1. Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In certain embodiments, the term "about" includes the indicated amount±5%. In certain embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). In certain embodiments, alkyl has 1 to 12 carbon atoms (i.e., $C_{1-12}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Alkylthio" refers to the group "alkyl-S—".

"Acyl" refers to a group —C(O)R, wherein R is hydrogen, alkyl, alkenyl, alkynyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, cycloalkyl, haloalkyl, aryl, or heteroaryl; each of which may be optionally substituted.

"Amidino" refers to —C(NH)(NH$_2$). In certain embodiments, "Amidino" refers to —C(NR)(NR$_2$), wherein each R is independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). In certain embodiments, aryl has 6 to 18 carbon ring atoms (i.e., $C_{6-18}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to —N$_3$.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Carboxyl ester" or "ester" refer to both —OC(O)R and —C(O)OR, wherein R is hydrogen, alkyl, alkenyl, alkynyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). In certain embodiments, cycloalkyl has from 3 to 15 ring carbon atoms (i.e., $C_{3-15}$ cycloalkyl). Examples of cycloalkyl groups include cyclopropyl, cyclobutyl, cyclopentyl, and cyclohexyl. Further, the term cycloalkyl is intended to encompass any non-aromatic ring which may be fused to an aryl ring, regardless of the attachment to the remainder of the molecule.

In certain embodiments, cycloalkyl also includes "spiro cycloalkyl" when there are two positions for substitution on the same carbon atom. Monocyclic radicals include, for example, cyclopropyl, cyclobutyl, cyclopentyl, cyclohexyl, cycloheptyl and cyclooctyl. Polycyclic radicals include, for example, adamantyl, norbornyl, decalinyl, 7,7-dimethyl-bicyclo[2.2.1]heptanyl and the like.

"Guanidino" refers to $-NHC(NH)(NH_2)$. In certain embodiments, "guanidino" refers to $-NRC(NR)(NR_2)$, wherein each R is hydrogen, alkyl, alkenyl, alkynyl, cycloalkyl, heterocyclyl, aryl, heteroalkyl or heteroaryl; each of which may be optionally substituted, as defined herein.

"Cycloalkylalkyl" refers to the group "cycloalkyl-alkyl-".

"Hydrazino" refers to $-NHNH_2$.

"Imino" refers to a group $-C(NR)R$, wherein each R is independently hydrogen alkyl, alkenyl, alkynyl, cycloalkyl, heterocyclyl, aryl, heteroalkyl, or heteroaryl; each of which may be optionally substituted, as defined herein.

"Imido" refers to a group $-C(O)NRC(O)R$, wherein each R is independently hydrogen alkyl, alkenyl, alkynyl, cycloalkyl, heterocyclyl, aryl, heteroalkyl, or heteroaryl; each of which may be optionally substituted, as defined herein.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl ($-CHF_2$) and trifluoromethyl ($-CF_3$). In certain embodiments, examples of haloalkyl include difluoromethyl, trifluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more hydrogen atoms are replaced by a halogen.

"Hydroxyalkyl" refers to an alkyl group as defined above, wherein one or more hydrogen atoms are replaced by a hydroxy group.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, $-NR-$, $-O-$, $-S-$, $-S(O)-$, $-S(O)_2-$, and the like, where R is H, alkyl, alkenyl, alkynyl, aryl, cycloalkyl, heteroalkyl, heteroaryl or heterocyclyl, each of which may be optionally substituted. Examples of heteroalkyl groups include $-OCH_3$, $-CH_2OCH_3$, $-SCH_3$, $-CH_2SCH_3$, $-NRCH_3$, and $-CH_2NRCH_3$, where R is hydrogen, alkyl, aryl, arylalkyl, heteroalkyl, or heteroaryl, each of which may be optionally substituted. In certain embodiments, examples of heteroalkyl groups include $-CH_2OCH_3$, $-CH_2SCH_3$, and $-CH_2NRCH_3$, where R is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom. In certain embodiments, the term "heteroalkyl" requires that the point of attachment to the remainder of the molecule is through a carbon atom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. In certain embodiments, the term "heteroaryl" refers to a 5-14 membered ring system. In certain embodiments, heteroaryl includes 1 to 13 ring carbon atoms (i.e., $C_{3-12}$ heteroaryl). In certain embodiments, heteroaryl includes 1 to 6 heteroatoms. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. In certain embodiments, examples of heteroaryl groups include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl). Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. In certain embodiments, heterocyclyl may comprise one or more oxo (C=O) or N-oxide (N—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. In certain embodiments, examples of heterocyclyl groups include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro [3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Hydroxy" or "hydroxyl" refers to the group —OH.

"Oxo" refers to the group (=O) or (O).

"Nitro" refers to the group —NO$_2$.

"Heterocyclylalkyl" refers to the group "heterocyclyl-alkyl-".

"Oxime" refers to the group —CR(=NOH) wherein R is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"Sulfinyl" refers to the group —S(O)R, where R is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NRR and —NRSO$_2$R, where each R is independently hydrogen, alkyl, alkenyl, alkynyl, cycloalkyl, heterocyclyl, aryl, heteroalkyl or heteroaryl; each of which may be optionally substituted, as defined herein.

"Alkylsulfonyl" refers to the group —S(O)$_2$R, where R is alkyl.

"Alkylsulfinyl" refers to the group —S(O)R, where R is alkyl.

"Thiocyanate" refers to the group —SCN.

"Thiol" refers to the group —SH.

"Thioxo" or "thione" refer to the group (=S) or (S).

In certain embodiments of any of the terms defined above, $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

In certain embodiments of any of the terms defined above, R is hydrogen, alkyl, alkenyl, alkynyl, cycloalkyl, heterocyclyl, aryl, heteroalkyl or heteroaryl; each of which may be optionally substituted, as defined herein. Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof.

In certain embodiments, the term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^{100}$)$_3$ wherein each $R^{100}$ is independently hydrogen, alkyl, alkenyl, alkynyl, heteroalkyl, cycloalkyl, aryl, heteroaryl or heterocyclyl.

In certain embodiments, the term "substituted" used herein means any of the above groups (i.e., alkyl, alkylene, alkoxy, haloalkoxy, aryl, cycloalkyl, haloalkyl, heterocyclyl, heteroaryl, hydroxyalkyl and/or alkoxyalkyl) wherein at least one hydrogen atom is replaced by a bond to a non-hydrogen atom such as, but not limited to: an alkyl group, a haloalkyl group, a halogen atom such as F, Cl, Br, and I; an alkenyl, a haloalkenyl group, an alkynyl group, a haloalkynyl group, a cyclic group such as an aryl, heteroaryl, cycloalkyl, or heterocyclyl group, an oxygen atom in groups such as hydroxy groups, alkoxy groups, and ester groups; a sulfur atom in groups such as thiol groups, thioalkyl groups, thiohaloalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, formyl, carboxyl, carbonate, and ester groups; and nitrogen in groups such as imines, oximes, hydrazones, and nitriles.

In certain embodiments, "substituted" includes any of the above alkyl, alkenyl, alkynyl, cycloalkyl, heterocyclyl, aryl or heteroaryl groups in which one or more hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —NR$^g$R$^h$, —NR$^g$C(=O)R$^h$, —NR$^g$C(=O)NR$^g$R$^h$, —NR$^g$C(=O)OR$^h$, —NR$^g$S(=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, —SCF$_3$ or —OCF$_3$. In certain embodiments, "substituted" also means any of the above groups in which one or more hydrogen atoms are replaced with —C(=O)R$^g$, —C(=O)OR$^g$, —C(=O)NR$^g$R$^h$, —CH$_2$SO$_2$R$^g$, —CH$_2$SO$_2$NR$^g$R$^h$. In certain embodiments, "substituted" further means any of the above groups in which one or more hydrogen atoms are replaced by —NR$^g$S(O)$_{1-2}$NR$^g$R$^h$, —CH$_2$S(O)R$^g$, —CH$_2$S(O)NR$^g$R$^h$, —OC(=O)OR$^g$, —SF$_5$, —SCF$_3$ or —OCF$_3$. In certain embodiments, "substituted" further means any of the above groups in which one or more hydrogen atoms are replaced by a bond to an amino, cyano, hydroxy, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl group. In the foregoing, R$^g$ and R$^h$ and R$^i$ are the same or different and independently hydrogen, halo, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl, or two of R$^g$ and R$^h$ and R$^i$ are taken together with the atoms to which they are attached to form a heterocyclyl ring optionally substituted with oxo, halo or alkyl optionally substituted with oxo, halo, amino, hydroxy or alkoxy. In an embodiment, each of said alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl are independently optionally substituted with one or more oxo, alkyl, halo, amino, hydroxy or alkoxy. In addition, each of the foregoing substituents may also be optionally substituted with one or more of the above substituents.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in certain embodiments, the term "substituted alkyl" refers to an alkyl group having one or more substituents including hydroxy, halo, alkoxy, acyl, oxo, amino, cycloalkyl, heterocyclyl, aryl, and heteroaryl. In other embodiments, the one or more substituents may be further substituted with halo, alkyl, haloalkyl, hydroxy, alkoxy, cycloalkyl, heterocyclyl, aryl, or heteroaryl, each of which is substituted. In other embodiments, the substituents may be further substituted with halo, alkyl, haloalkyl, alkoxy, hydroxy, cycloalkyl, heterocyclyl, aryl, or heteroaryl, each of which is unsubstituted.

Any compound or formula given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^{3}$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), di(substituted alkyl) amines (i.e., N(substituted alkyl)$_3$), alkenyl amines (i.e., $NH_2$(alkenyl)), dialkenyl amines (i.e., HN(alkenyl)$_2$), dialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), di(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "hydrate" refers to the complex formed by the combining of a compound of Formula I and water.

A "solvate" refers to an association or complex of one or more solvent molecules and a compound of the invention. Examples of solvents that form solvates include, but are not limited to, water, isopropanol, ethanol, methanol, dimethylsulfoxide, ethylacetate, acetic acid, and ethanolamine.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds disclosed herein, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

"Stereoisomers" are isomers that differ only in the way the atoms are arranged in space and include enantiomers and diastereomers. In certain embodiments, a "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another.

"Enantiomers" are a pair of stereoisomers that are non-superimposable mirror images of each other. A 1:1 mixture of a pair of enantiomers is a "racemic" mixture.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

"Prodrugs" means any compound which releases an active parent drug according to Formula I or any other formula described herein in vivo when such prodrug is administered to a mammalian subject. Prodrugs of a compound of Formula I or any other formula described herein are prepared by modifying functional groups present in the compound of Formula I or any other formula described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I or any other formula described herein wherein a hydroxy, amino, carboxyl or sulfhydryl group in a compound of Formula I or any other formula described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds of Formula I or any other formula described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

2. List of Abbreviations and Acronyms

| Abbreviation | Meaning |
|---|---|
| aq. | Aqueous |
| BOC | tert-butyloxycarbonyl |
| br | Broad |
| d | Doublet |
| DAD | Diode array detector |
| DAST | Diethylaminosulfur trifluoride |
| dd | doublet of doublets |
| ddd | doublet of doublet of doublets |
| dddd | doublet of doublet of doublet of doublets |
| dt | Doublet of triplets |
| DIPEA/DIEA | Diisopropylethylamine |
| DMF | Dimethylformamide |
| DMSO | Dimethylsulfoxide |
| ee/e.e. | Enantiomer excess |
| ES | Electrospray |
| ESI | Electrospray ion source |
| Et | Ethyl |
| EtOH | Ethanol |
| EtOAC | Ethyl acetate |
| HATU | 1-[Bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl)uronium hexafluorophosphate |
| HOBt | 1-hydroxybenzotriazole |
| HPLC | High pressure liquid chromatography |
| hrs/h | Hours |
| Hz | Hertz |
| J | Coupling constant (MHz) |
| LCMS/LC-MS | Liquid chromatography-mass spectrometry |
| M | Molar |
| MeCN | Acetonitrile |
| MeOH | Methanol |
| m | Multiplet (when used with a J) |
| m/z | Mass-to-charge ratio |
| $[M + H]^+$ | Mass peak plus hydrogen |
| min | Minute(s) |
| MS | Mass spectrometry |
| N | Normal |
| NCS | N-Chlorosuccinimide |
| NMR | Nuclear magnetic resonance |
| o/n | Overnight |
| PDA | Photodiode array detector |
| quin | Quintuplet |
| rt | Room temperature |
| s | Singlet (when used with J) |
| s | Second(s) |
| sat. | Saturated |
| t | Triplet |
| THF | Tetrahydrofuran |
| TFA | Trifluoroacetic acid |
| TIC | Total ion current |
| TLC | Thin layer chromatography |
| TMEDA | N,N,N',N',-Tetramethylethylenediamine |
| TMIS | Iodotrimethylsilane |
| v/v | Volume/volume |
| δ | Chemical shift (ppm) |

3. Compounds

Provided herein are compounds that are useful as inhibitors of receptor-interacting protein kinase 1. In certain embodiments, provided is a compound of Formula I:

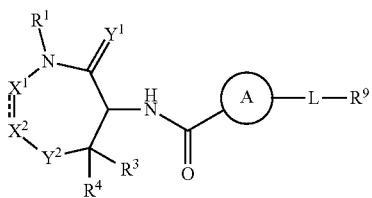

or a pharmaceutically acceptable salt, prodrug, tautomer, stereoisomer or mixture of stereoisomers thereof;

wherein $Y^1$ is O or $NR_2$;

$X^1$ and $X^2$ are each independently nitrogen or carbon and either $X^1$ and $X^2$ together form an optionally substituted cycloalkyl, optionally substituted heterocyclyl, optionally substituted aryl, or optionally substituted heteroaryl and $R^1$ is H or $C_1$-$C_6$ alkyl optionally substituted with halo, hydroxy or cyano or when $Y^1$ is $NR_2$, then $R^2$ and $R^1$ together with the nitrogen atoms to which they are attached, form an optionally substituted heterocyclyl or optionally substituted heteroaryl ring, or $X^1$ and $R^1$ together with the atoms to which they are attached, form an optionally substituted heterocyclyl or optionally substituted heteroaryl ring, and $X^2$ is —$CH_2$—;

$Y^2$ is —O—, —S—, —S(O)—, —S(O)$_2$—, —S(O)(NH)—, —$NR_5$— or —$C(R_6)_2$—;

$R^5$ is H or optionally substituted $C_1$-$C_6$ alkyl;

$Y^2$ is —O—, —S—, —S(O)—, —S(O)$_2$—, —S(O)(NH)—, —$NR_5$— or —$C(R_6)_2$—;

$R^5$ is H or optionally substituted $C_1$-$C_6$ alkyl;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —$NR^7$— or —$C(R^8)_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring; and $R^9$ is optionally substituted cycloalkyl, optionally substituted heterocyclyl, optionally substituted aryl or optionally substituted heteroaryl;

provided that when the moiety

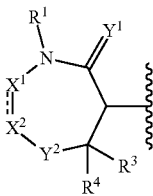 is 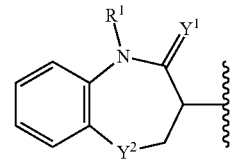

and the aromatic ring is optionally substituted then at least one of the following occurs:

(1) L is absent or —$C(R^8)_2$—, and each $R^8$ is optionally substituted $C_1$-$C_6$ alkyl or halo, or two $R^8$ together with the carbon atom to which they are attached, form an optionally substituted cycloalkyl or optionally substituted heterocyclyl ring;

(2) $Y^2$ is —$C(R_6)_2$— and at least one $R^6$ is other than hydrogen;

(3) $Y^2$ is —O— and A is substituted with halo or cyano or A is thiazolyl or a 3- or 4-membered ring;

(4) $Y^2$ is —S—, —S(O)—, or —S(O)$_2$—; and A is other than isoxazole and phenyl or $Y^2$ is —S(O)(NH)—;

(5) $Y^2$ is —$NR_5$— and A is other than isoxazole, pyrazole and triazole;

(6) the carbonyl moiety and L are substituted other than 1,3- on ring A; or (7) $R^9$ is substituted cycloalkyl, substituted heterocyclyl, substituted aryl or substituted heteroaryl, wherein at least one substituent is cyano;

(8) $R^1$ is $C_2$-$C_6$ alkyl optionally substituted with halo, hydroxy or cyano; or (9) when $X^1$ and $X^2$ form an optionally substituted phenyl ring as in the moiety

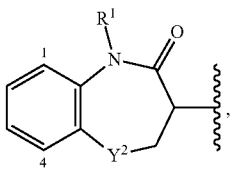

at least one substituent is at the 1 or 4 position and is (a) other than fluoro, chloro or methyl at the 1 position, and/or (b) other than fluoro or methyl for the 4 position; and further provided the moiety

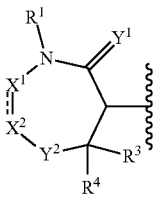

is not

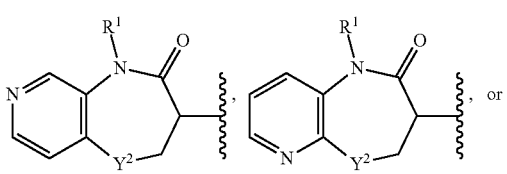

-continued

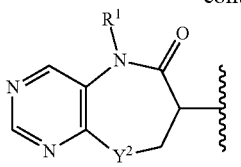

wherein the nitrogen containing aromatic ring is optionally substituted;

and with the further proviso that the compound is not: 5-(difluoro(phenyl)methyl)-N-(4-oxo-2,3,4,5-tetrahydrobenzo[b][1,4]oxazepin-3-yl)isoxazole-3-carboxamide; 5-(difluoro(phenyl)methyl)-N-(5-methyl-4-oxo-2,3,4,5-tetrahydrobenzo[b][1,4]oxazepin-3-yl)isoxazole-3-carboxamide; 2-(4-bromobenzyl)-N-(5-methyl-4-oxo-2,3,4,5-tetrahydrobenzo[b][1,4]oxazepin-3-yl)thiazole-4-carboxamide; 2-benzyl-N-(5-methyl-4-oxo-2,3,4,5-tetrahydrobenzo[b][1,4]oxazepin-3-yl)thiazole-4-carboxamide; 4-(1,4-dihydro-2-oxo-3(2H)-quinazolinyl)-N-[2,3,4,5-tetrahydro-1-(1-methylethyl)-2-oxo-1H-1-benzazepin-3-yl]-1-piperidinecarboxamide; 4-(2-amino-7-chloro-4-quinolinyl)-[(3S)-2,3,4,5-tetrahydro-2-oxo-1H-1-benzazepin-3-yl]-1-piperazinecarboxamide; or 4-(2-amino-7-chloro-4-quinolinyl)-N-[(3S)-2,3,4,5-tetrahydro-1-methyl-2-oxo-1H-1-benzazepin-3-yl]-1-piperazinecarboxamide.

In certain embodiments, provided is a compound of Formula I or a pharmaceutically acceptable salt, prodrug, tautomer, stereoisomer or mixture of stereoisomers thereof wherein $Y^1$ is O or $NR_2$;

$X^1$ and $X^2$ are each independently nitrogen or carbon and either $X^1$ and $X^2$ together form an optionally substituted cycloalkyl, optionally substituted heterocyclyl, optionally substituted aryl, or optionally substituted heteroaryl and $R^1$ is H or $C_1$-$C_6$ alkyl optionally substituted with halo, hydroxy or cyano or when $Y^1$ is $NR_2$, then $R^2$ and $R^1$ together with the nitrogen atoms to which they are attached, form an optionally substituted heterocyclyl or optionally substituted heteroaryl ring, or $X^1$ and $R^1$ together with the atoms to which they are attached, form an optionally substituted heterocyclyl or optionally substituted heteroaryl ring, and $X^2$ is —$CH_2$—;

$Y^2$ is —O—, —S—, —S(O)—, —S(O)$_2$—, —S(O)(NH)—, —$NR_5$— or —$C(R_6)_2$—;

$R^5$ is H or optionally substituted $C_1$-$C_6$ alkyl;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —$NR^7$— or —$C(R^8)_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring; and $R^9$ is optionally substituted cycloalkyl, optionally substituted heterocyclyl, optionally substituted aryl or optionally substituted heteroaryl;

provided that when the moiety

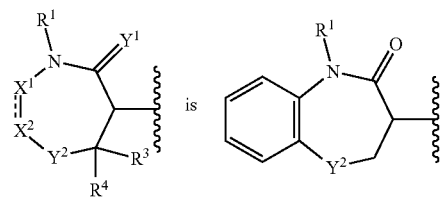

and the aromatic ring is optionally substituted then at least one of the following occurs:

(1) L is absent or —$C(R^8)_2$—, and each $R^8$ is optionally substituted $C_1$-$C_6$ alkyl or halo, or two $R^8$ together with the carbon atom to which they are attached, form an optionally substituted cycloalkyl or optionally substituted heterocyclyl ring;

(2) $Y^2$ is —$C(R_6)_2$— and at least one $R^6$ is other than hydrogen;

(3) $Y^2$ is —O— and A is substituted with halo or cyano or A is thiazolyl or a 3- or 4-membered ring;

(4) $Y^2$ is —S—, —S(O)—, or —S(O)$_2$—; and A is other than isoxazole and phenyl or $Y^2$ is —S(O)(NH)—;

(5) $Y^2$ is —$NR_5$— and A is other than isoxazole, pyrazole and triazole; or (6) the carbonyl moiety and L are substituted other than 1,3- on ring A;

(7) $R^1$ is $C_2$-$C_6$ alkyl optionally substituted with halo, hydroxy or cyano; or (8) when $X^1$ and $X^2$ form an optionally substituted phenyl ring as in the moiety

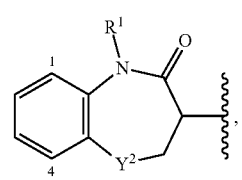

at least one substituent is at the 1 or 4 position and is (a) other than fluoro, chloro or methyl at the 1 position, and/or (b) other than fluoro or methyl for the 4 position; and further provided the moiety

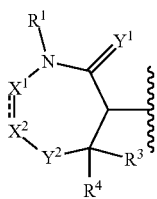

is not

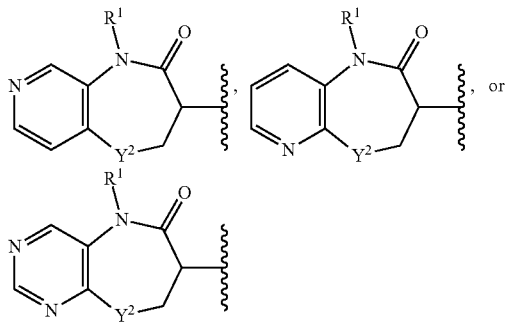

wherein the nitrogen containing aromatic ring is optionally substituted;

and with the further proviso that the compound is not: 5-(difluoro(phenyl)methyl)-N-(4-oxo-2,3,4,5-tetrahydrobenzo[b][1,4]oxazepin-3-yl)isoxazole-3-carboxamide; 5-(difluoro(phenyl)methyl)-N-(5-methyl-4-oxo-2,3,4,5-tetrahydrobenzo[b][1,4]oxazepin-3-yl)isoxazole-3-carboxamide; 2-(4-bromobenzyl)-N-(5-methyl-4-oxo-2,3,4,5-tetrahydrobenzo[b][1,4]oxazepin-3-yl) thiazole-4-carboxamide; 2-benzyl-N-(5-methyl-4-oxo-2,3,4,5-tetrahydrobenzo[b][1,4]oxazepin-3-yl) thiazole-4-carboxamide; 4-(1,4-dihydro-2-oxo-3(2H)-quinazolinyl)-N-[2,3,4,5-tetrahydro-1-(1-methylethyl)-2-oxo-1H-1-benzazepin-3-yl]-1-piperidinecarboxamide; 4-(2-amino-7-chloro-4-quinolinyl)-N-[(3S)-2,3,4,5-tetrahydro-2-oxo-1H-1-benzazepin-3-yl]-1-piperazinecarboxamide; or 4-(2-amino-7-chloro-4-quinolinyl)-N-[(3S)-2,3,4,5-tetrahydro-1-methyl-2-oxo-1H-1-benzazepin-3-yl]-1-piperazinecarboxamide.

In certain embodiments, at least one of $R^3$ and $R^4$ are halo or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring.

In certain embodiments, L is absent or —C($R^8$)$_2$—, and each $R^8$ is optionally substituted $C_1$-$C_6$ alkyl or halo, or two $R^8$ together with the carbon atom to which they are attached, form an optionally substituted cycloalkyl or optionally substituted heterocyclyl ring.

In certain embodiments, $Y^1$ is $NR_2$.

In certain embodiments, $X^1$ and $X^2$ are each independently nitrogen or carbon, and together form a 5 membered optionally substituted cycloalkyl, optionally substituted heterocyclyl, optionally substituted aryl, or optionally substituted heteroaryl.

In certain embodiments, $X^1$ and $R^1$ together with the atoms to which they are attached, form a 5 or 6 membered optionally substituted heterocyclyl or optionally substituted heteroaryl ring; and $X^2$ is —CH$_2$—.

In certain embodiments, $Y^2$ is —C($R_6$)$_2$—; and one $R^6$ is hydrogen, halo, or optionally substituted $C_1$-$C_6$ alkyl, and the other $R^6$ is halo or optionally substituted $C_1$-$C_6$ alkyl; or two $R^6$ together with the carbon atom to which they are attached, form a $C_1$-$C_6$ alken-1-yl, optionally substituted cycloalkyl or optionally substituted heterocyclyl ring.

In certain embodiments, $Y^2$ is —O— and A is substituted with halo or cyano; or A is thiazolyl or a 3- or 4-membered ring.

In certain embodiments, $Y^2$ is —S—, —S(O)—, or —S(O)$_2$—; and A is other than isoxazole and phenyl or $Y^2$ is —S(O)(NH)—.

In certain embodiments, $Y^2$ is —NR$_5$—; $X^1$ and $X^2$ together form an optionally substituted phenyl, and A is other than isoxazole, pyrazole and triazole; $X^1$ and $X^2$ together form an optionally substituted pyridyl, and A is other than triazole; or $X^1$ and $X^2$ are optionally substituted pyrimidyl, and A is other than pyrazole and triazole.

In certain embodiments, the carbonyl moiety and L are substituted other than 1,3- on ring A.

In certain embodiments, provided is a compound of Formula I or a pharmaceutically acceptable salt, prodrug, tautomer, stereoisomer or mixture of stereoisomers thereof; wherein $Y^1$ is O or NR$_2$;

$X^1$ and $X^2$ are each independently nitrogen or carbon and either $X^1$ and $X^2$ together form an optionally substituted cycloalkyl, optionally substituted heterocyclyl, optionally substituted aryl, or optionally substituted heteroaryl and $R^1$ is H or $C_1$-$C_6$ alkyl optionally substituted with halo, hydroxy or cyano or when $Y^1$ is NR$_2$, then $R^2$ and $R^1$ together with the nitrogen atoms to which they are attached, form an optionally substituted heterocyclyl or optionally substituted heteroaryl ring, or $X^1$ and $R^1$ together with the atoms to which they are attached, form an optionally substituted heterocyclyl or optionally substituted heteroaryl ring, and $X^2$ is —CH$_2$—;

$Y^2$ is —O—, —S—, —S(O)—, —S(O)$_2$—, —S(O)(NH)—, —NR$_5$— or —C($R_6$)$_2$—;

$R^5$ is H or optionally substituted $C_1$-$C_6$ alkyl;

each $R^6$ is independently H, halo, or optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C($R^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring; and $R^9$ is optionally substituted cycloalkyl, optionally substituted heterocyclyl, optionally substituted aryl or optionally substituted heteroaryl;

provided that at least one of the following occurs:

(1) at least one of $R^3$ and $R^4$ are halo or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;

(2) L is absent or —C($R^8$)$_2$—, and each $R^8$ is optionally substituted $C_1$-$C_6$ alkyl or halo, or two $R^8$ together with the carbon atom to which they are attached, form an optionally substituted cycloalkyl or optionally substituted heterocyclyl ring;

(3) $Y^1$ is $NR_2$;

(4) $X^1$ and $X^2$ are each independently nitrogen or carbon, and together form a 5 membered optionally substituted cycloalkyl, optionally substituted heterocyclyl, optionally substituted aryl, or optionally substituted heteroaryl;

(5) $X^1$ and $R^1$ together with the atoms to which they are attached, form a 5 or 6 membered optionally substituted heterocyclyl or optionally substituted heteroaryl ring; and $X^2$ is —$CH_2$—;

(6) $Y^2$ is —C($R_6$)$_2$—; and one $R^6$ is hydrogen, halo, or optionally substituted $C_1$-$C_6$ alkyl, and the other $R^6$ is halo or optionally substituted $C_1$-$C_6$ alkyl; or two $R^6$ together with the carbon atom to which they are attached, form a $C_1$-$C_6$ alken-1-yl, optionally substituted cycloalkyl or optionally substituted heterocyclyl ring;

(7) $Y^2$ is —O—; and A is substituted with halo or cyano; or A is thiazolyl or a 3- or 4-membered ring;

(8) $Y^2$ is —S—, —S(O)—, or —S(O)$_2$—; and A is other than isoxazole and phenyl or $Y^2$ is —S(O)(NH)—;

(9) $Y^2$ is —$NR^5$—; $X^1$ and $X^2$ together form an optionally substituted phenyl, and A is other than isoxazole, pyrazole and triazole; $X^1$ and $X^2$ together form an optionally substituted pyridyl, and A is other than triazole; or $X^1$ and $X^2$ are optionally substituted pyrimidyl, and A is other than pyrazole and triazole;

(10) the carbonyl moiety and L are substituted other than 1,3- on ring A;

(11) $Y^2$ is —O—; $X^1$ and $X^2$ together form an optionally substituted pyridyl, and A is other than isoxazole;

(12) $R^1$ is $C_2$-$C_6$ alkyl optionally substituted with halo, hydroxy or cyano; or

(13) when $X^1$ and $X^2$ form an optionally substituted phenyl ring as in the moiety

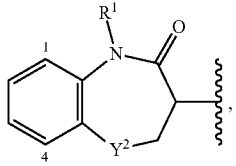

at least one substituent is at the 1 or 4 position and is (a) other than fluoro, chloro or methyl at the 1 position, and/or (b) other than fluoro or methyl for the 4 position;

and with the further proviso that the compound is not: 5-(difluoro(phenyl)methyl)-N-(4-oxo-2,3,4,5-tetrahydrobenzo[b][1,4]oxazepin-3-yl)isoxazole-3-carboxamide; 5-(difluoro(phenyl)methyl)-N-(5-methyl-4-oxo-2,3,4,5-tetrahydrobenzo[b][1,4]oxazepin-3-yl)isoxazole-3-carboxamide; 2-(4-bromobenzyl)-N-(5-methyl-4-oxo-2,3,4,5-tetrahydrobenzo[b][1,4]oxazepin-3-yl) thiazole-4-carboxamide; 2-benzyl-N-(5-methyl-4-oxo-2,3,4,5-tetrahydrobenzo[b][1,4]oxazepin-3-yl) thiazole-4-carboxamide; 4-(1,4-dihydro-2-oxo-3(2H)-quinazolinyl)-N-[2,3,4,5-tetrahydro-1-(1-methylethyl)-2-oxo-1H-1-benzazepin-3-yl]-1-piperidinecarboxamide; 4-(2-amino-7-chloro-4-quinolinyl)-N-[(3S)-2,3,4,5-tetrahydro-2-oxo-1H-1-benzazepin-3-yl]-1-piperazinecarboxamide; or 4-(2-amino-7-chloro-4-quinolinyl)-N-[(3S)-2,3,4,5-tetrahydro-1-methyl-2-oxo-1H-1-benzazepin-3-yl]-1-piperazinecarboxamide.

In certain embodiments, the compound is not 5-(difluorophenylmethyl)-N-[(3S)-2,3,4,5-tetrahydro-5-methyl-4-oxo-1,5-benzoxazepin-3-yl]-3-isoxazolecarboxamide or 5-(difluorophenylmethyl)-N-[(3S)-2,3,4,5-tetrahydro-4-oxo-1,5-benzoxazepin-3-yl]-3-isoxazolecarboxamide.

Also provided herein are compounds that are useful as inhibitors of receptor-interacting protein kinase 1. In certain embodiments, provided is a compound of Formula I wherein $R^1$ is H or optionally substituted $C_1$-$C_6$ alkyl;

(a) $X^1$ and $X^2$ are each independently nitrogen or carbon, and together form an optionally substituted cycloalkyl, optionally substituted heterocyclyl, optionally substituted aryl, or optionally substituted heteroaryl; or (b) $X^1$ and $R^1$ together with the atoms to which they are attached, form an optionally substituted heterocyclyl or optionally substituted heteroaryl ring; and $X^2$ is —$CH_2$—;

$Y^1$ is O or $NR_2$, where $R^2$ and $R^1$ together with the nitrogen atoms to which they are attached, form an optionally substituted heterocyclyl or optionally substituted heteroaryl ring;

$Y^2$ is —O—, —S—, —S(O)—, —S(O)$_2$—, —S(O)(NH)—, —$NR_5$— or —C($R_6$)$_2$—;

$R^5$ is H or optionally substituted $C_1$-$C_6$ alkyl;

each $R^6$ is independently H, halo, optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;

$R^3$ and $R^4$ are independently H, halo, optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl ring or optionally substituted heteroaryl ring;

L is absent, —O—, —S—, —S(O)—, —S(O)$_2$—, —$NR^7$— or —C($R^8$)$_2$—;

$R^7$ is H or optionally substituted $C_1$-$C_6$ alkyl;

each $R^8$ is independently H, halo, optionally substituted $C_1$-$C_6$ alkyl, or two $R^8$ together with the carbon atom to which they are attached, form a optionally substituted cycloalkyl or optionally substituted heterocyclyl ring; and R⁹ is optionally substituted cycloalkyl, optionally substituted heterocyclyl, optionally substituted aryl or optionally substituted heteroaryl;

provided that at least one of the following occurs:

(1) at least one of R³ and R⁴ are halo or optionally substituted C₁-C₆ alkyl, R³ and R⁴ together with the carbon atoms to which they are attached, form an optionally substituted cycloalkyl or optionally substituted heterocyclyl ring, or R³ and R⁶ together with the carbon atoms to which they are attached, form a optionally substituted cycloalkyl or optionally substituted heterocyclyl ring;

(2) L is absent or —C(R⁸)₂—, and each R⁸ is optionally substituted C₁-C₆ alkyl or halo provided that the compound is not 5-(difluoro(phenyl)methyl)-N-(4-oxo-2,3,4,5-tetrahydrobenzo[b][1,4]oxazepin-3-yl)isoxazole-3-carboxamide or not 5-(difluoro(phenyl)methyl)-N-(5-methyl-4-oxo-2,3,4,5-tetrahydrobenzo[b][1,4]oxazepin-3-yl)isoxazole-3-carboxamide or two R⁸ together with the carbon atom to which they are attached, form an optionally substituted cycloalkyl or optionally substituted heterocyclyl ring;

(3) Y¹ is NR₂;

(4) X¹ and X² are each independently nitrogen or carbon, and together form a 5 membered optionally substituted cycloalkyl, optionally substituted heterocyclyl, optionally substituted aryl, or optionally substituted heteroaryl;

(5) X¹ and R¹ together with the atoms to which they are attached, form a 5 or 6 membered optionally substituted heterocyclyl or optionally substituted heteroaryl ring; and X² is —CH₂—;

(6) Y² is —C(R₆)₂—; and one R⁶ is hydrogen, halo, or optionally substituted C₁-C₆ alkyl, and the other R⁶ is halo or optionally substituted C₁-C₆ alkyl; or two R⁶ together with the carbon atom to which they are attached, form a C₁-C₆ alken-1-yl, optionally substituted cycloalkyl or optionally substituted heterocyclyl ring;

(7) Y² is —O—; and A is substituted with halo or cyano; or A is thiazolyl or a 3- or 4-membered ring; provided that the compound is not 2-(4-bromobenzyl)-N-(5-methyl-4-oxo-2,3,4,5-tetrahydrobenzo[b][1,4]oxazepin-3-yl)thiazole-4-carboxamide or 2-benzyl-N-(5-methyl-4-oxo-2,3,4,5-tetrahydrobenzo[b][1,4]oxazepin-3-yl)thiazole-4-carboxamide;

(8) Y² is —S—, —S(O)—, or —S(O)₂—; and A is other than 1,3-isoxazole or Y² is —S(O)N(H)—;

(9) Y² is —NR⁵—; X¹ and X² together form an optionally substituted phenyl, and A is other than isoxazole, pyrazole and triazole; X¹ and X² together form an optionally substituted pyridyl, and A is other than triazole; or X¹ and X² are optionally substituted pyrimidyl, and A is other than pyrazole and triazole; or

(10) the carbonyl moiety and L are substituted other than 1,3- on ring A;

or a pharmaceutically acceptable salt, prodrug, tautomer, stereoisomer or mixture of stereoisomers thereof.

In certain embodiments, R¹ is C₁-C₆ alkyl. In certain embodiments, R¹ is methyl.

In certain embodiments, the moiety:

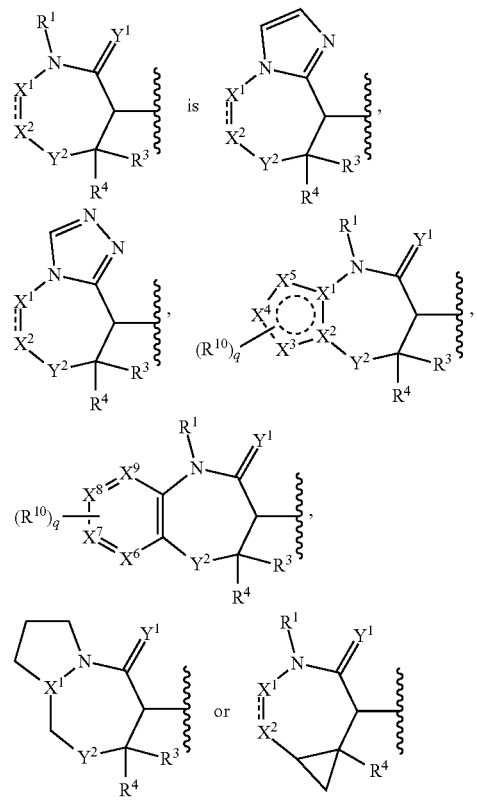

wherein
X³, X⁴ and X⁵ are each S, O, N, NH, or CH;
X⁶, X⁷, X⁸ and X⁹ are each N or CH;
q is 0, 1 or 2;
each R¹⁰ is independently cyano, halo, optionally substituted C₁-C₆ alkyl or —S(O)₂—C₁-C₆ alkyl.

In certain embodiments, the moiety:

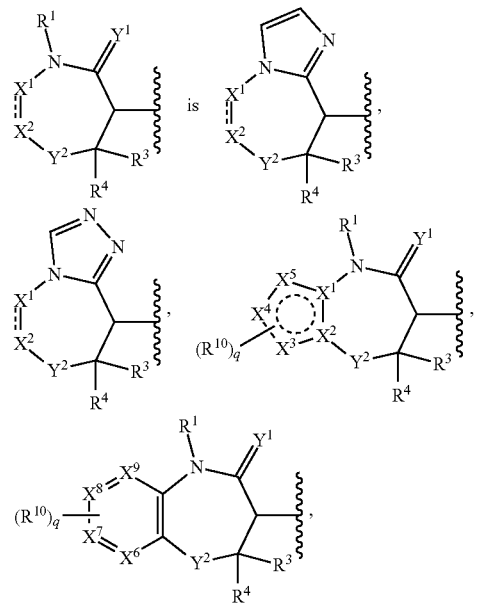

-continued

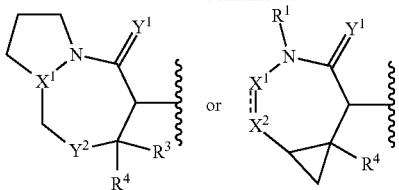  or wherein
X³, X⁴ and X⁵ are each S, O, N, NH, or CH;
X⁶, X⁷, X⁸ and X⁹ are each N or CH;
q is 0, 1 or 2;
each $R^{10}$ is independently cyano, halo or optionally substituted alkyl.

In certain embodiments, the moiety:

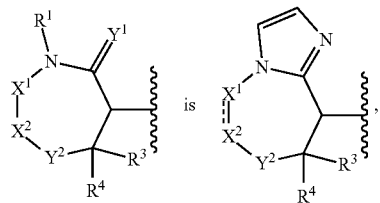

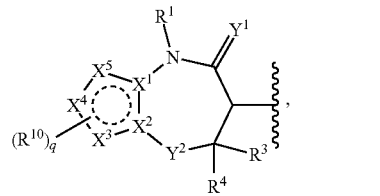

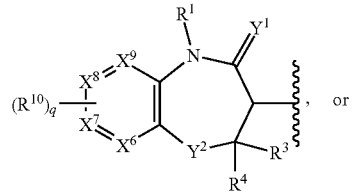 or

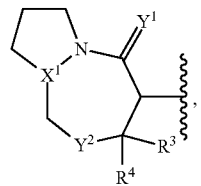, wherein
X³, X⁴ and X⁵ are each S, O, N, NH, or CH;
X⁶, X⁷, X⁸ and X⁹ are each N or CH;
q is 0, 1 or 2;
each $R^{10}$ is independently halo or optionally substituted alkyl.

In certain embodiments, the moiety:

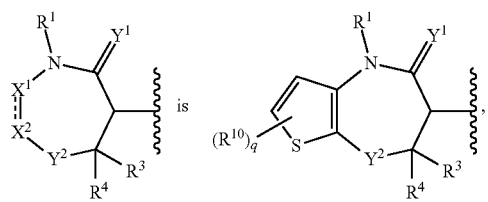

-continued

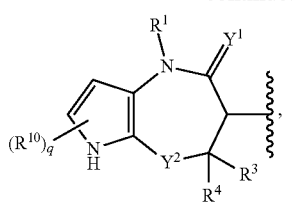

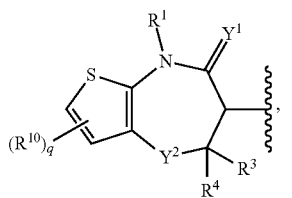

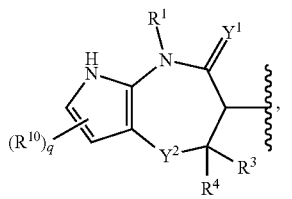

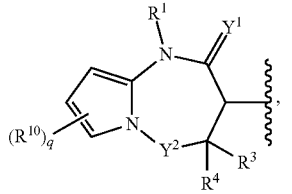

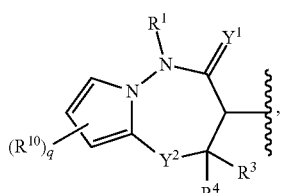

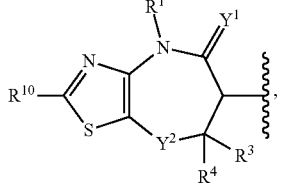

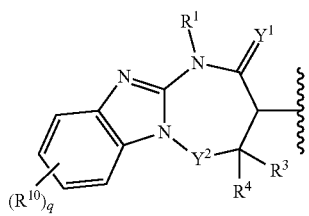

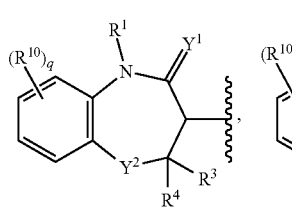

-continued

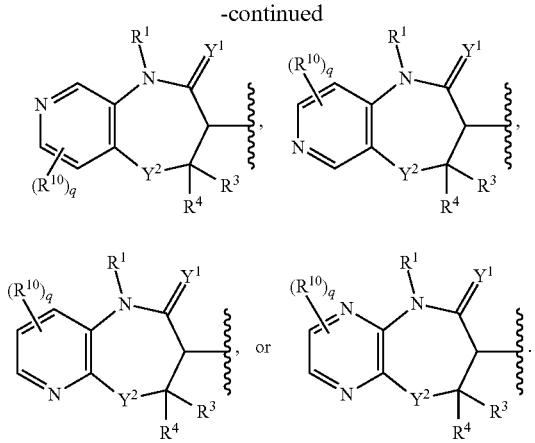

In certain embodiments, the moiety

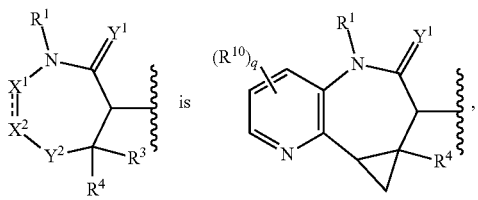

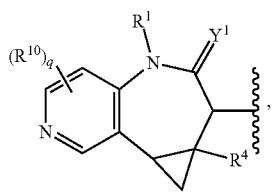

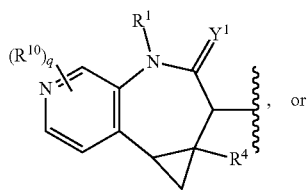

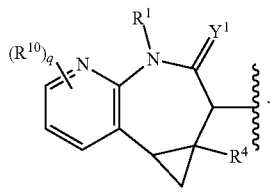

In certain embodiments, the moiety

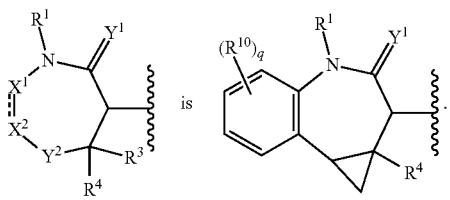

In certain embodiments, the moiety

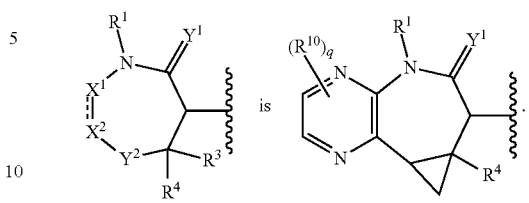

In certain embodiments, $Y^1$ is O.

In certain embodiments, $R^1$ is methyl. In certain embodiments, $R^1$ is ethyl.

In certain embodiments, $Y^2$ is

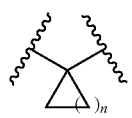

where n is 1, 2, 3 or 4,

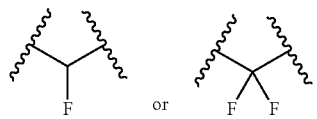

In certain embodiments, $Y^2$ is —O—; and A is substituted with halo or cyano; or A is thiazolyl or a 3- or 4-membered cycloalkyl or 3- or 4-membered heterocycloalkyl ring.

In certain embodiments, both $R^3$ and $R^4$ are fluoro, or either $R^3$ or $R^4$ are fluoro and the other is hydrogen, or $R^3$ and $R^4$ form a cyclopropyl or $R^3$ joins with $R^6$ to form a cyclopropyl. In certain embodiments, $R^3$ or $R^4$ is methyl.

In certain embodiments, A is phenyl, phenylbenzo[d]thiazolyl, isoxazolyl, oxazolyl, pyrazolyl, triazolyl, 5,6-dihydro-4H-pyrrolo[1,2-b]pyrazolyl, pyrrolyl, thiazolyl, imidazolyl, thiadiazolyl, cyclobutyl, cyclopropyl, or azetidinyl.

In certain embodiments, A is isoxazolyl, oxazolyl, pyrazolyl, triazolyl, 5,6-dihydro-4H-pyrrolo[1,2-b]pyrazolyl, pyrrolyl, thiazolyl, imidazolyl, thiadiazolyl, cyclobutyl, cyclopropyl, or azetidinyl.

In certain embodiments, A is phenyl.

In certain embodiments, L is absent, —S(O)$_2$— or —C(R$^8$)$_2$—.

In certain embodiments, two $R^8$ together with the carbon atom to which they are attached, form an optionally substituted cycloalkyl or optionally substituted heterocyclyl ring.

In certain embodiments, $R^9$ is phenyl or 2,3-dihydro-1H-indenyl. In certain embodiments, $R^9$ is phenyl. In certain embodiments, $R^9$ is 2-F-phenyl. In certain embodiments, $R^9$ is pyridyl. In certain embodiments, $R^9$ is optionally substituted pyridyl, phenyl or 2,3-dihydro-1H-indenyl.

In certain embodiments, q is 0. In certain embodiments, q is 1. In certain embodiments, $R^{10}$ is methyl.

In one aspect, provided is a compound of Formula Ia:

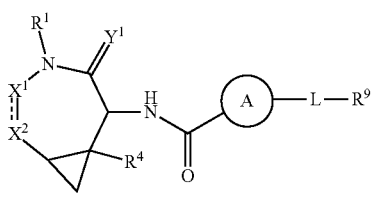

or a pharmaceutically acceptable salt, prodrug, tautomer, stereoisomer or mixture of stereoisomers thereof;
wherein
$Y^1$ is O or $NR_2$;
$X^1$ and $X^2$ are each independently nitrogen or carbon and either
  $X^1$ and $X^2$ together form an optionally substituted cycloalkyl, optionally substituted heterocyclyl, optionally substituted aryl, or optionally substituted heteroaryl and $R^1$ is H or $C_1$-$C_6$ alkyl optionally substituted with halo, hydroxy or cyano or when $Y^1$ is $NR_2$, then $R^2$ and $R^1$ together with the nitrogen atoms to which they are attached, form an optionally substituted heterocyclyl or optionally substituted heteroaryl ring, or
  $X^1$ and $R^1$ together with the atoms to which they are attached, form an optionally substituted heterocyclyl or optionally substituted heteroaryl ring, and $X^2$ is —$CH_2$—;
$Y^2$ is —O—, —S—, —S(O)—, —S(O)$_2$—, —S(O)(NH)—, —$NR_5$— or —C($R_6$)$_2$—;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —$NR^7$— or —C($R^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring; and
$R^9$ is optionally substituted cycloalkyl, optionally substituted heterocyclyl, optionally substituted aryl or optionally substituted heteroaryl.

In certain embodiments, the moiety

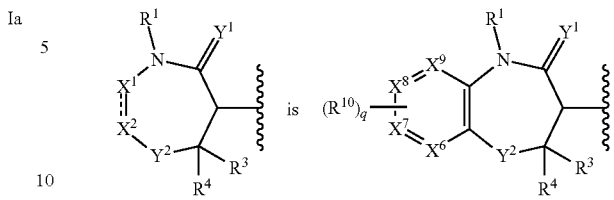

In certain embodiments, when the moiety

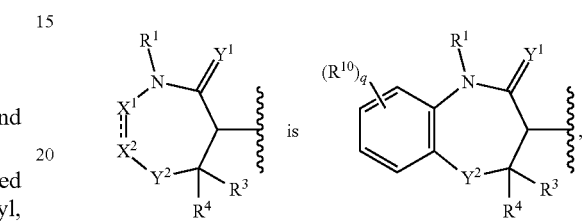

q is 0 or $R^{10}$ is halo or alkyl, and L is absent, then ring A is a 3-, 4- or 5-membered monocyclic ring. In certain embodiments, the moiety

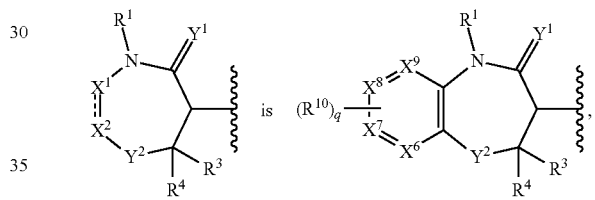

and when the moiety

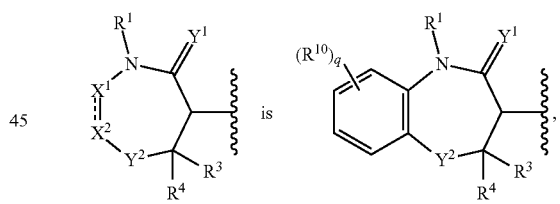

q is 0 or $R^{10}$ is halo or alkyl, and L is absent, then ring A is a 3-, 4- or 5-membered monocyclic ring.

In certain embodiments, in any Formula disclosed herein, $R^9$ is substituted with at least one cyano.

In certain embodiments, the compound is of Formula II:

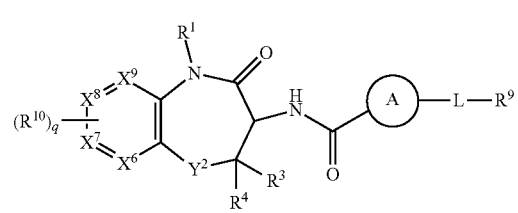

or a pharmaceutically acceptable salt, prodrug, tautomer, stereoisomer or mixture of stereoisomers thereof;

wherein
q is 0, 1, or 2;
$X^6$, $X^7$, $X^8$ and $X^9$ are each N or CH;
$R^1$ is H or $C_1$-$C_6$ alkyl optionally substituted with halo, hydroxy or cyano;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo or optionally substituted alkyl;
provided that at least one of the following occurs:
(1) at least one of $R^3$ and $R^4$ are halo or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;
(2) L is absent or —C(R$^8$)$_2$—, and each $R^8$ is optionally substituted $C_1$-$C_6$ alkyl or halo, or two $R^8$ together with the carbon atom to which they are attached, form an optionally substituted cycloalkyl or optionally substituted heterocyclyl ring;
(3) $Y^2$ is —C(R$_6$)$_2$—; and one $R^6$ is hydrogen, halo, or optionally substituted $C_1$-$C_6$ alkyl, and the other $R^6$ is halo or optionally substituted $C_1$-$C_6$ alkyl; or two $R^6$ together with the carbon atom to which they are attached, form a $C_1$-$C_6$ alken-1-yl, optionally substituted cycloalkyl or optionally substituted heterocyclyl ring;
(4) $Y^2$ is —O—; and A is substituted with halo or cyano; or A is thiazolyl or a 3- or 4-membered ring;
(5) $Y^2$ is —S—, —S(O)—, or —S(O)$_2$—; and A is other than isoxazole or $Y^2$ is —S(O)(NH)—;
(6) $Y^2$ is —NR$^5$—; $X^6$, $X^7$, $X^8$ and $X^9$ together form an optionally substituted phenyl, and A is other than isoxazole, pyrazole and triazole; $X^6$, $X^7$, $X^8$ and $X^9$ together form an optionally substituted pyridyl, and A is other than triazole; or $X^6$, $X^7$, $X^8$ and $X^9$ are optionally substituted pyrimidyl, and A is other than pyrazole and triazole; or
(7) $Y^2$ is —O—; $X^1$ and $X^2$ together form an optionally substituted pyridyl, and A is other than isoxazole;
(8) $R^1$ is $C_2$-$C_6$ alkyl optionally substituted with halo, hydroxy or cyano; or
(9) when $X^1$ and $X^2$ form an optionally substituted phenyl ring as in the moiety

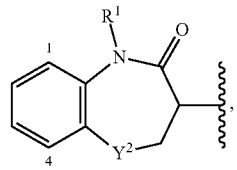

at least one substituent is at the 1 or 4 position and is (a) other than fluoro, chloro or methyl at the 1 position, and/or (b) other than fluoro or methyl for the 4 position;
and with the further proviso that the compound is not:
5-(difluoro(phenyl)methyl)-N-(4-oxo-2,3,4,5-tetrahydrobenzo[b][1,4]oxazepin-3-yl)isoxazole-3-carboxamide; 5-(difluoro(phenyl)methyl)-N-(5-methyl-4-oxo-2,3,4,5-tetrahydrobenzo[b][1,4]oxazepin-3-yl)isoxazole-3-carboxamide; 2-(4-bromobenzyl)-N-(5-methyl-4-oxo-2,3,4,5-tetrahydrobenzo[b][1,4]oxazepin-3-yl)thiazole-4-carboxamide; 2-benzyl-N-(5-methyl-4-oxo-2,3,4,5-tetrahydrobenzo[b][1,4]oxazepin-3-yl)thiazole-4-carboxamide; 4-(1,4-dihydro-2-oxo-3(2H)-quinazolinyl)-N-[2,3,4,5-tetrahydro-1-(1-methylethyl)-2-oxo-1H-1-benzazepin-3-yl]-1-piperidinecarboxamide; 4-(2-amino-7-chloro-4-quinolinyl)-N-[(3S)-2,3,4,5-tetrahydro-2-oxo-1H-1-benzazepin-3-yl]-1-piperazinecarboxamide; or 4-(2-amino-7-chloro-4-quinolinyl)-N-[(3S)-2,3,4,5-tetrahydro-1-methyl-2-oxo-1H-1-benzazepin-3-yl]-1-piperazinecarboxamide.

In certain embodiments, the compound is of Formula II wherein
q is 0, 1, or 2;
$X^6$, $X^7$, $X^8$ and $X^9$ are each N or CH;
$R^1$ is H or optionally substituted $C_1$-$C_6$ alkyl;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl ring or optionally substituted heteroaryl ring;
L is absent, —O—, —S—, —S(O)—, —S(O)$_2$—, —NR$^7$— or —C(R$^8$)$_2$—;

$R^1$ is H or optionally substituted $C_1$-$C_6$ alkyl;

each $R^8$ is independently H, halo, optionally substituted $C_1$-$C_6$ alkyl, or two $R^8$ together with the carbon atom to which they are attached, form a optionally substituted cycloalkyl or optionally substituted heterocyclyl ring;

$R^9$ is optionally substituted cycloalkyl, optionally substituted heterocyclyl, optionally substituted aryl or optionally substituted heteroaryl; and each $R^{10}$ is independently halo or optionally substituted alkyl;

provided that at least one of the following occurs:

(1) at least one of $R^3$ and $R^4$ are halo or optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;

(2) L is absent or —C($R^8$)$_2$—, and each $R^8$ is optionally substituted $C_1$-$C_6$ alkyl or halo provided that the compound is not 5-(difluoro(phenyl)methyl)-N-(4-oxo-2,3,4,5-tetrahydrobenzo[b][1,4]oxazepin-3-yl)isoxazole-3-carboxamide or not 5-(difluoro(phenyl)methyl)-N-(5-methyl-4-oxo-2,3,4,5-tetrahydrobenzo[b][1,4]oxazepin-3-yl)isoxazole-3-carboxamide or two $R^8$ together with the carbon atom to which they are attached, form an optionally substituted cycloalkyl or optionally substituted heterocyclyl ring;

(3) $Y^2$ is —C($R_6$)$_2$—; and one $R^6$ is hydrogen, halo, or optionally substituted $C_1$-$C_6$ alkyl, and the other $R^6$ is halo or optionally substituted $C_1$-$C_6$ alkyl; or two $R^6$ together with the carbon atom to which they are attached, form a $C_1$-$C_6$ alken-1-yl, optionally substituted cycloalkyl or optionally substituted heterocyclyl ring;

(4) $Y^2$ is —O—; and A is substituted with halo or cyano; or A is thiazolyl or a 3- or 4-membered ring; provided that the compound is not 2-(4-bromobenzyl)-N-(5-methyl-4-oxo-2,3,4,5-tetrahydrobenzo[b][1,4]oxazepin-3-yl)thiazole-4-carboxamide or 2-benzyl-N-(5-methyl-4-oxo-2,3,4,5-tetrahydrobenzo[b][1,4]oxazepin-3-yl)thiazole-4-carboxamide;

(5) $Y^2$ is —S—, —S(O)—, or —S(O)$_2$—; and A is other than 1,3-isoxazole or $Y^2$ is —S(O)N(H)—;

(6) $Y^2$ is —NR$^5$—; $X^6$, $X^7$, $X^8$ and $X^9$ together form an optionally substituted phenyl, and A is other than isoxazole, pyrazole and triazole; $X^6$, $X^7$, $X^8$ and $X^9$ together form an optionally substituted pyridyl, and A is other than triazole; or $X^6$, $X^7$, $X^8$ and $X^9$ are optionally substituted pyrimidyl, and A is other than pyrazole and triazole; or or a pharmaceutically acceptable salt, prodrug, tautomer, stereoisomer or mixture of stereoisomers thereof.

In certain embodiments, the compound is of Formula II and L is absent or —C($R^8$)$_2$—, and two $R^8$ together with the carbon atom to which they are attached, form an optionally substituted cycloalkyl or optionally substituted heterocyclyl ring.

In any of the embodiments of Formula II (or subformula thereof), $R^1$ is H or optionally substituted $C_1$-$C_6$ alkyl. In any of the embodiments of Formula II (or subformula thereof), $R^1$ is H or $C_1$-$C_6$ alkyl.

In any of the embodiments of Formula II (or subformula thereof), q is 0, 1 or 2 and when present, each $R^{10}$ is independently cyano, halo, optionally substituted $C_1$-$C_6$ alkyl or —S(O)$_2$—$C_1$-$C_6$ alkyl. In any of the embodiments of Formula II (or subformula thereof), q is 0, 1 or 2 and when present, each $R^{10}$ is independently cyano, halo or optionally substituted alkyl. In any of the embodiments of Formula II (or subformula thereof), each $R^{10}$ is independently halo. In certain embodiments, each $R^{10}$ is independently fluoro. In any of the embodiments of Formula II (or subformula thereof), q is 0. In any of the embodiments of Formula II (or subformula thereof), q is 1. In any of the embodiments of Formula II (or subformula thereof), q is 2.

In certain embodiments, the compound is of Formula IIa:

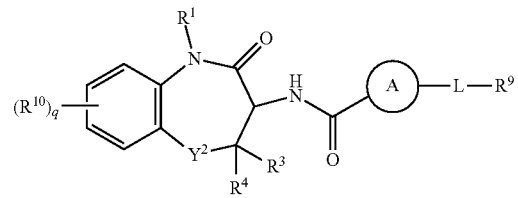

IIa or a pharmaceutically acceptable salt, prodrug, tautomer, stereoisomer or mixture of stereoisomers thereof;

wherein q is 0, 1 or 2;

$R^1$ is H or $C_1$-$C_6$ alkyl optionally substituted with halo, hydroxy or cyano;

$Y^2$ is —O—, —S—, —S(O)—, —S(O)$_2$—, —S(O)(NH)—, —NR$_5$— or —C($R_6$)$_2$—;

$R^5$ is H or optionally substituted $C_1$-$C_6$ alkyl;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C($R^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or heterocyclyl ring;

$R^9$ is optionally substituted cycloalkyl, optionally substituted heterocyclyl, optionally substituted aryl or optionally substituted heteroaryl; and each $R^{10}$ is independently cyano, halo or optionally substituted alkyl;

provided that at least one of the following occurs:

(1) at least one of $R^3$ and $R^4$ are halo or optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;

(2) L is absent or —C(R⁸)₂—, and two R⁸ together with the carbon atom to which they are attached, form an optionally substituted cycloalkyl or optionally substituted heterocyclyl ring;
(3) Y² is —C(R₆)₂—; and two R⁶ together with the carbon atom to which they are attached, form a C₁-C₆ alken-1-yl, optionally substituted cycloalkyl or optionally substituted heterocyclyl ring;
(4) R¹ is C₂-C₆ alkyl optionally substituted with halo, hydroxy or cyano; or
(5) when X¹ and X² form an optionally substituted phenyl ring as in the moiety

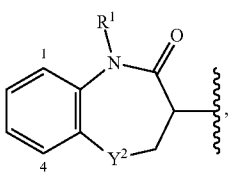

at least one substituent is at the 1 or 4 position and is (a) other than fluoro, chloro or methyl at the 1 position, and/or (b) other than fluoro or methyl for the 4 position;
and with the further proviso that the compound is not: 5-(difluoro(phenyl)methyl)-N-(4-oxo-2,3,4,5-tetrahydrobenzo[b][1,4]oxazepin-3-yl)isoxazole-3-carboxamide; 5-(difluoro(phenyl)methyl)-N-(5-methyl-4-oxo-2,3,4,5-tetrahydrobenzo[b][1,4]oxazepin-3-yl)isoxazole-3-carboxamide; 2-(4-bromobenzyl)-N-(5-methyl-4-oxo-2,3,4,5-tetrahydrobenzo[b][1,4]oxazepin-3-yl) thiazole-4-carboxamide; 2-benzyl-N-(5-methyl-4-oxo-2,3,4,5-tetrahydrobenzo[b][1,4]oxazepin-3-yl) thiazole-4-carboxamide; 4-(1,4-dihydro-2-oxo-3(2H)-quinazolinyl)-N-[2,3,4,5-tetrahydro-1-(1-methylethyl)-2-oxo-1H-1-benzazepin-3-yl]-1-piperidinecarboxamide; 4-(2-amino-7-chloro-4-quinolinyl)-N-[(3S)-2,3,4,5-tetrahydro-2-oxo-1H-1-benzazepin-3-yl]-1-piperazinecarboxamide; or 4-(2-amino-7-chloro-4-quinolinyl)-N-[(3S)-2,3,4,5-tetrahydro-1-methyl-2-oxo-1H-1-benzazepin-3-yl]-1-piperazinecarboxamide.

In certain embodiments, the compound is of Formula IIa wherein
R¹ is H or optionally substituted C₁-C₆ alkyl;
Y² is —O—, —S—, —S(O)—, —S(O)₂—, —S(O)(NH)—, —NR₅— or —C(R₆)₂—;
R⁵ is H or optionally substituted C₁-C₆ alkyl;
each R⁶ is independently H, halo, optionally substituted C₁-C₆ alkyl, or two R⁶ together with the carbon atom to which they are attached, form a C₁-C₆ alken-1-yl, optionally substituted cycloalkyl or optionally substituted heterocyclyl ring;
R³ and R⁴ are independently H, halo, optionally substituted C₁-C₆ alkyl, R³ and R⁴ together with the carbon atoms to which they are attached, form an optionally substituted cycloalkyl or heterocyclyl ring, or R³ and R⁶ together with the carbon atoms to which they are attached, form an optionally substituted cycloalkyl or optionally substituted heterocyclyl ring;
A is an optionally substituted cycloalkyl, optionally substituted heterocyclyl ring or optionally substituted heteroaryl ring;
L is absent, —O—, —S—, —S(O)—, —S(O)₂—, —NR⁷— or —C(R⁸)₂—;

R¹ is H or optionally substituted C₁-C₆ alkyl;
each R⁸ is independently H, halo, optionally substituted C₁-C₆ alkyl, or two R⁸ together with the carbon atom to which they are attached, form a optionally substituted cycloalkyl or heterocyclyl ring; and
R⁹ is optionally substituted cycloalkyl, optionally substituted heterocyclyl, optionally substituted aryl or optionally substituted heteroaryl;
provided that at least one of the following occurs:
(1) at least one of R³ and R⁴ are halo or optionally substituted C₁-C₆ alkyl, R³ and R⁴ together with the carbon atoms to which they are attached, form an optionally substituted cycloalkyl or optionally substituted heterocyclyl ring, or R³ and R⁶ together with the carbon atoms to which they are attached, form a optionally substituted cycloalkyl or optionally substituted heterocyclyl ring;
(2) L is absent or —C(R⁸)₂—, and two R⁸ together with the carbon atom to which they are attached, form an optionally substituted cycloalkyl or optionally substituted heterocyclyl ring; or
(3) Y² is —C(R₆)₂—; and two R⁶ together with the carbon atom to which they are attached, form a C₁-C₆ alken-1-yl, optionally substituted cycloalkyl or optionally substituted heterocyclyl ring;
or a pharmaceutically acceptable salt, prodrug, tautomer, stereoisomer or mixture of stereoisomers thereof.

In certain embodiments, the compound is of Formula IIa-1:

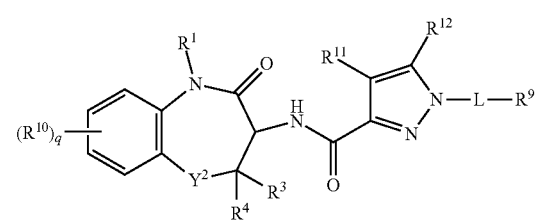

wherein one of R¹¹ or R¹² is halo and the other is C₁₋₆ alkyl or C₁₋₆ cycloalkyl and the remaining variables are as defined throughout.

In certain embodiments, the compound is of Formula IIa-2:

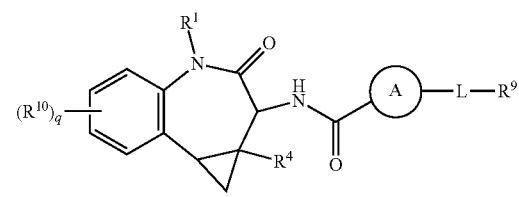

or a pharmaceutically acceptable salt, prodrug, tautomer, stereoisomer or mixture of stereoisomers thereof;
wherein
q is 0, 1 or 2;
R¹ is H or C₁-C₆ alkyl optionally substituted with halo, hydroxy or cyano;
R⁴ is H, halo, or optionally substituted C₁-C₆ alkyl;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C(R$^8$)$_2$—;

R$^7$ is H or optionally substituted C$_1$-C$_6$ alkyl;

each R$^8$ is independently H, halo, or optionally substituted C$_1$-C$_6$ alkyl, or two R$^8$ together with the carbon atom to which they are attached, form a optionally substituted cycloalkyl or heterocyclyl ring;

R$^9$ is optionally substituted cycloalkyl, optionally substituted heterocyclyl, optionally substituted aryl or optionally substituted heteroaryl; and each R$^{10}$ is independently cyano, halo or optionally substituted alkyl.

In certain embodiments, the compound is of Formula IIa-2a. In certain embodiments, the compound is of Formula IIa-2b. In certain embodiments, the compound is of Formula IIa-3. In certain embodiments, the compound is of Formula IIa-4. In certain embodiments, the compound is of Formula IIa-5.

IIa-2a
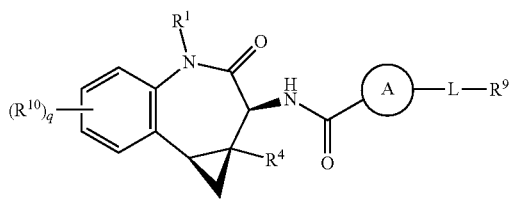

IIa-2b
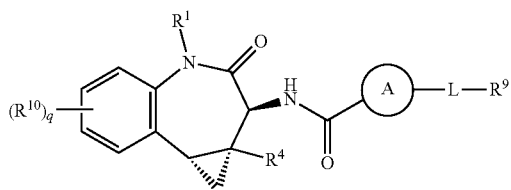

IIa-3
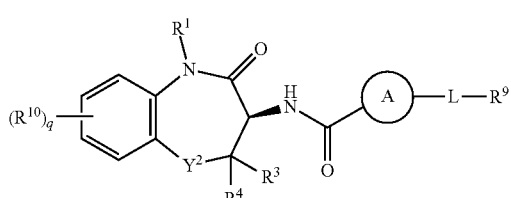

IIa-4
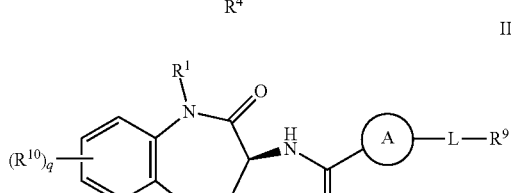

IIa-5
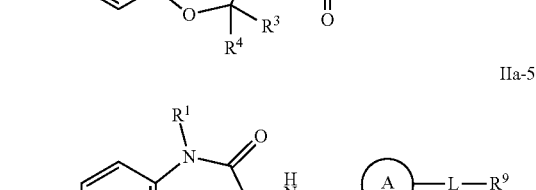

In certain embodiments, the compound is of Formula IIb:

IIb
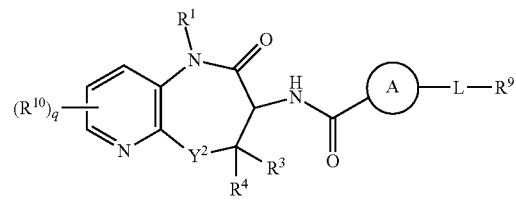

or a pharmaceutically acceptable salt, prodrug, tautomer, stereoisomer or mixture of stereoisomers thereof;

wherein q is 0, 1 or 2;

R$^1$ is H or C$_1$-C$_6$ alkyl optionally substituted with halo, hydroxy or cyano;

Y$^2$ is —O—, —S—, —S(O)—, —S(O)$_2$—, —S(O)(NH)—, —NR$_5$— or —C(R$_6$)$_2$—;

R$^5$ is H or optionally substituted C$_1$-C$_6$ alkyl;

each R$^6$ is independently H, halo, or optionally substituted C$_1$-C$_6$ alkyl, or two R$^6$ together with the carbon atom to which they are attached, form a C$_1$-C$_6$alken-1-yl, optionally substituted cycloalkyl or optionally substituted heterocyclyl ring;

R$^3$ and R$^4$ are independently H, halo, or optionally substituted C$_1$-C$_6$ alkyl, or R$^3$ and R$^4$ together with the carbon atoms to which they are attached, form an optionally substituted cycloalkyl or optionally substituted heterocyclyl ring, or R$^3$ and R$^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C(R$^8$)$_2$—;

R$^1$ is H or optionally substituted C$_1$-C$_6$ alkyl;

each R$^8$ is independently H, halo, or optionally substituted C$_1$-C$_6$ alkyl, or two R$^8$ together with the carbon atom to which they are attached, form a optionally substituted cycloalkyl or optionally substituted heterocyclyl ring;

R$^9$ is optionally substituted cycloalkyl, optionally substituted heterocyclyl, optionally substituted aryl or optionally substituted heteroaryl; and each R$^{10}$ is independently cyano, halo or optionally substituted alkyl;

provided that at least one of the following occurs:

(1) at least one of R$^3$ and R$^4$ are halo or optionally substituted C$_1$-C$_6$ alkyl, or R$^3$ and R$^4$ together with the carbon atoms to which they are attached, form an optionally substituted cycloalkyl or optionally substituted heterocyclyl ring, or R$^3$ and R$^6$ together with the carbon atoms to which they are attached, form a optionally substituted cycloalkyl or optionally substituted heterocyclyl ring;

(2) L is absent or —C(R$^8$)$_2$—, and two R$^8$ together with the carbon atom to which they are attached, form an optionally substituted cycloalkyl or optionally substituted heterocyclyl ring;

(3) Y$^2$ is —C(R$_6$)$_2$—; and two R$^6$ together with the carbon atom to which they are attached, form a C$_1$-C$_6$ alken- 1-yl, optionally substituted cycloalkyl or optionally substituted heterocyclyl ring; or (4) the compound is not 5-(phenylmethyl)-N-[(3S)-1,2,3, 4-tetrahydro-7-methyl-2-oxopyrido[2,3-b][1,4]oxazepin-3-yl]-3-isoxazolecarboxamide; N-[(3S)-8-fluoro-2, 3,4,5-tetrahydro-1-methyl-2-oxo-1H-pyrido[2,3-b][1, 4]diazepin-3-yl]-3-(phenylmethyl)-1H-1,2,4-triazole-5-carboxamide; 5-(phenylmethyl)-N-[(3S)-1,2,3,4-tetrahydro-7-methyl-2-oxopyrido[2,3-b][1,4]oxazepin-3-yl]-3-isoxazolecarboxamide; or N-[(3S)-8-fluoro-2, 3,4,5-tetrahydro-1-methyl-2-oxo-1H-pyrido[2,3-b][1, 4]diazepin-3-yl]-3-(phenylmethyl)-1H-1,2,4-triazole-5-carboxamide.

In certain embodiments, the compound is of Formula IIb wherein $R^1$ is H or optionally substituted $C_1$-$C_6$ alkyl;

$Y^2$ is —O—, —S—, —S(O)—, —S(O)$_2$—, —S(O)(NH)—, —NR$_5$— or —C(R$_6$)$_2$—;

$R^5$ is H or optionally substituted $C_1$-$C_6$ alkyl;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl ring or optionally substituted heteroaryl ring;

L is absent, —O—, —S—, —S(O)—, —S(O)$_2$—, —NR$^7$— or —C(R$^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring; and $R^9$ is optionally substituted cycloalkyl, optionally substituted heterocyclyl, optionally substituted aryl or optionally substituted heteroaryl;

provided that at least one of the following occurs:

(1) at least one of $R^3$ and $R^4$ are halo or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;

(2) L is absent or —C(R$^8$)$_2$—, and two $R^8$ together with the carbon atom to which they are attached, form an optionally substituted cycloalkyl or optionally substituted heterocyclyl ring; or (3) $Y^2$ is —C(R$_6$)$_2$—; and two $R^6$ together with the carbon atom to which they are attached, form a $C_1$-$C_6$ alken-1-yl, optionally substituted cycloalkyl or optionally substituted heterocyclyl ring;

or a pharmaceutically acceptable salt, prodrug, tautomer, stereoisomer or mixture of stereoisomers thereof.

In certain embodiments, the compound is of Formula IIb-1:

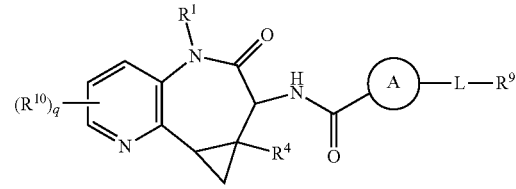

or a pharmaceutically acceptable salt, prodrug, tautomer, stereoisomer or mixture of stereoisomers thereof;

wherein q is 0, 1 or 2;

$R^1$ is H or $C_1$-$C_6$ alkyl optionally substituted with halo, hydroxy or cyano;

$R^4$ is H, halo, or optionally substituted $C_1$-$C_6$ alkyl;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C(R$^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or heterocyclyl ring;

$R^9$ is optionally substituted cycloalkyl, optionally substituted heterocyclyl, optionally substituted aryl or optionally substituted heteroaryl; and each $R^{10}$ is independently cyano, halo or optionally substituted alkyl.

In certain embodiments, the compound is of Formula IIb-2. In certain embodiments, the compound is of Formula IIb-3. In certain embodiments, the compound is of Formula IIb-4. In certain embodiments, the compound is of Formula IIb-5. In certain embodiments, the compound is of Formula

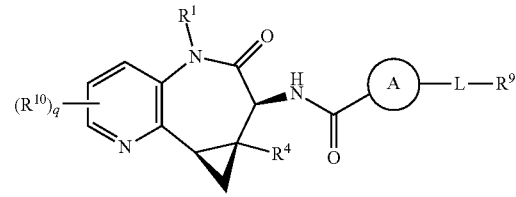

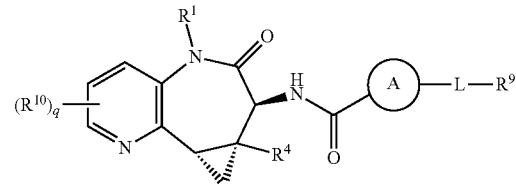

-continued

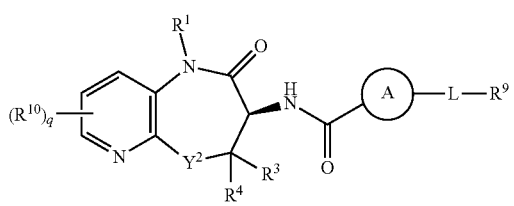

IIb-4

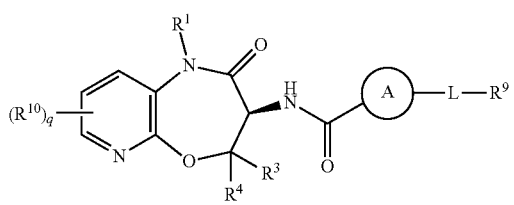

IIb-5

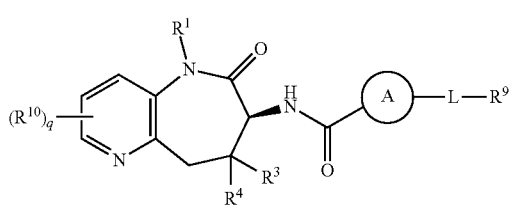

IIb-6

In certain embodiments, the compound is of Formula IIc:

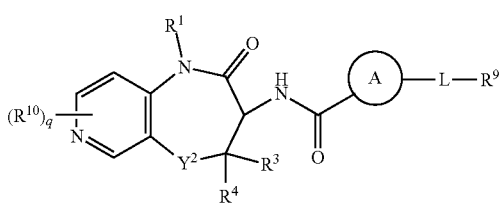

IIc or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl ring, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo or optionally substituted alkyl.

In certain embodiments, the compound is of Formula IIc wherein
$R^1$ is H or optionally substituted $C_1$-$C_6$ alkyl;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl ring or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, optionally substituted $C_1$-$C_6$ alkyl, or two $R^8$ together with the carbon atom to which they are attached, form a optionally substituted cycloalkyl or optionally substituted heterocyclyl ring; and
$R^9$ is optionally substituted cycloalkyl, optionally substituted heterocyclyl, optionally substituted aryl or optionally substituted heteroaryl;
provided that at least one of the following occurs:
(1) at least one of $R^3$ and $R^4$ are halo or optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;
(2) L is absent or —C(R$^8$)$_2$—, and two $R^8$ together with the carbon atom to which they are attached, form an optionally substituted cycloalkyl or optionally substituted heterocyclyl ring; or
(3) $Y^2$ is —C(R$_6$)$_2$—; and two $R^6$ together with the carbon atom to which they are attached, form a $C_1$-$C_6$ alken-1-yl, optionally substituted cycloalkyl or optionally substituted heterocyclyl ring;
or a pharmaceutically acceptable salt, prodrug, tautomer, stereoisomer or mixture of stereoisomers thereof.

In certain embodiments, provided is a compound of Formula IIc or a pharmaceutically acceptable salt, prodrug, tautomer, stereoisomer or mixture of stereoisomers thereof;

wherein
q is 0, 1 or 2;
$R^1$ is H or $C_1$-$C_6$ alkyl;
$Y^2$ is —O— or —C($R_6$)$_2$—;
each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O— or —C($R^8$)$_2$—;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo, optionally substituted $C_1$-$C_6$ alkyl or —S(O)$_2$—$C_1$-$C_6$ alkyl.

In certain embodiments, the compound is of Formula IIc-1:

IIc-1

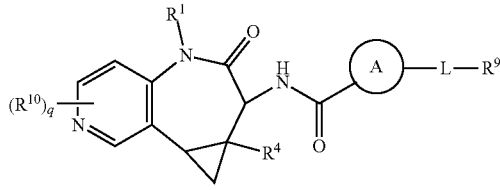

or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$R^4$ is H, halo, or optionally substituted $C_1$-$C_6$ alkyl;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C($R^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or heterocyclyl ring;
$R^9$ is optionally substituted cycloalkyl, optionally substituted heterocyclyl, optionally substituted aryl or optionally substituted heteroaryl; and
each $R^{10}$ is independently cyano, halo, or optionally substituted alkyl.

In certain embodiments, the compound is of Formula IIc-2. In certain embodiments, the compound is of Formula IIc-3. In certain embodiments, the compound is of Formula IIc-4. In certain embodiments, the compound is of Formula IIc-5. In certain embodiments, the compound is of Formula IIc-6.

IIc-2

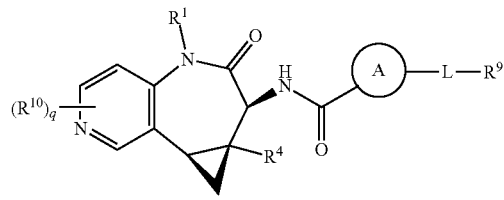

IIc-3

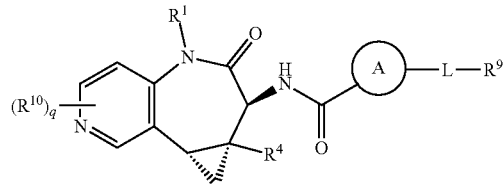

IIc-4

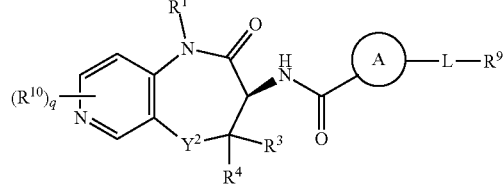

IIc-5

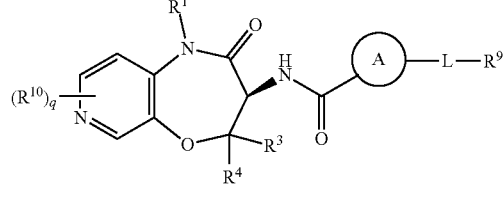

IIc-6

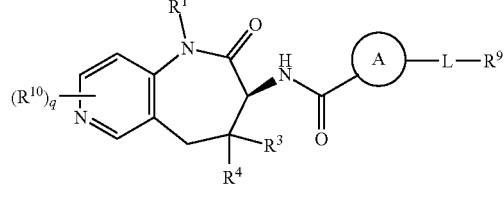

In certain embodiments, provided is a compound of Formula IIc-4:

IIc-4

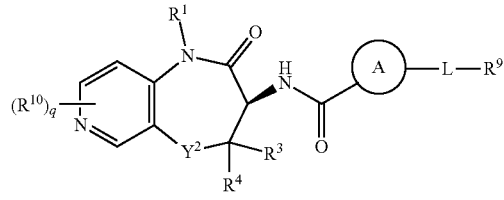

or a pharmaceutically acceptable salt, prodrug, tautomer, stereoisomer or mixture of stereoisomers thereof;

wherein q is 0, 1 or 2;

$R^1$ is H or $C_1$-$C_6$ alkyl;

$Y^2$ is —O— or —C($R_6$)$_2$—;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O— or —C($R^8$)$_2$—;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;

$R^9$ is optionally substituted cycloalkyl, optionally substituted heterocyclyl, optionally substituted aryl or optionally substituted heteroaryl; and each $R^{10}$ is independently cyano, halo, optionally substituted $C_1$-$C_6$ alkyl or —S(O)$_2$—$C_1$-$C_6$ alkyl.

In certain embodiments, the compound is of Formula IId:

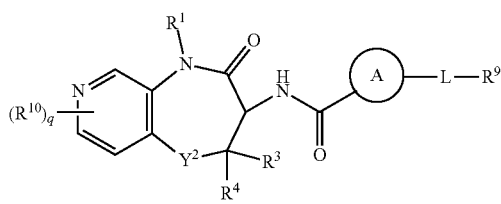

IId or a pharmaceutically acceptable salt, prodrug, tautomer, stereoisomer or mixture of stereoisomers thereof;

wherein q is 0, 1 or 2;

$R^1$ is H or $C_1$-$C_6$ alkyl optionally substituted with halo, hydroxy or cyano;

$Y^2$ is —O—, —S—, —S(O)—, —S(O)$_2$—, —S(O)(NH)—, —NR$_5$— or —C($R_6$)$_2$—;

$R^5$ is H or optionally substituted $C_1$-$C_6$ alkyl;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C($R^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;

$R^9$ is optionally substituted cycloalkyl, optionally substituted heterocyclyl, optionally substituted aryl or optionally substituted heteroaryl; and each $R^{10}$ is independently cyano, halo or optionally substituted alkyl;

provided that at least one of the following occurs:

(1) at least one of $R^3$ and $R^4$ are halo or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;

(2) L is absent or —C($R^8$)$_2$—, and two $R^8$ together with the carbon atom to which they are attached, form an optionally substituted cycloalkyl or optionally substituted heterocyclyl ring;

(3) $Y^2$ is —C($R_6$)$_2$—; and two $R^6$ together with the carbon atom to which they are attached, form a $C_1$-$C_6$ alken-1-yl, optionally substituted cycloalkyl or optionally substituted heterocyclyl ring; or (4) the compound is not 5-(phenylmethyl)-N-[(3S)-2,3,4,5-tetrahydro-4-oxopyrido[4,3-b][1,4]oxazepin-3-yl]-3-isoxazolecarboxamide; or 5-(phenylmethyl)-N-[(3S)-2,3,4,5-tetrahydro-4-oxopyrido[4,3-b][1,4]oxazepin-3-yl]-3-isoxazolecarboxamide.

In certain embodiments, the compound is of Formula IId wherein $R^1$ is H or optionally substituted $C_1$-$C_6$ alkyl;

$Y^2$ is —O—, —S—, —S(O)—, —S(O)$_2$—, —S(O)(NH)—, —NR$_5$— or —C($R_6$)$_2$—;

$R^5$ is H or optionally substituted $C_1$-$C_6$ alkyl;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl ring or optionally substituted heteroaryl ring;

L is absent, —O—, —S—, —S(O)—, —S(O)$_2$—, —NR$^7$— or —C($R^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring; and R⁹ is optionally substituted cycloalkyl, optionally substituted heterocyclyl, optionally substituted aryl or optionally substituted heteroaryl;

provided that at least one of the following occurs:
(1) at least one of R³ and R⁴ are halo or optionally substituted $C_1$-$C_6$ alkyl, or R³ and R⁴ together with the carbon atoms to which they are attached, form an optionally substituted cycloalkyl or optionally substituted heterocyclyl ring, or R³ and R⁶ together with the carbon atoms to which they are attached, form a optionally substituted cycloalkyl or optionally substituted heterocyclyl ring;
(2) L is absent or —C(R⁸)₂—, and two R⁸ together with the carbon atom to which they are attached, form an optionally substituted cycloalkyl or optionally substituted heterocyclyl ring; or
(3) Y² is —C(R₆)₂—; and two R⁶ together with the carbon atom to which they are attached, form a $C_1$-$C_6$ alken-1-yl, optionally substituted cycloalkyl or optionally substituted heterocyclyl ring;

or a pharmaceutically acceptable salt, prodrug, tautomer, stereoisomer or mixture of stereoisomers thereof.

In certain embodiments, the compound is of Formula IId-1:

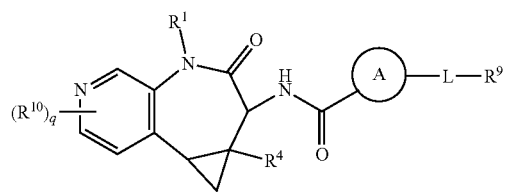

IId-1 or a pharmaceutically acceptable salt, prodrug, tautomer, stereoisomer or mixture of stereoisomers thereof;
wherein
q is 0, 1 or 2;
R¹ is H or $C_1$-$C_6$ alkyl optionally substituted with halo, hydroxy or cyano;
R⁴ is H, halo, or optionally substituted $C_1$-$C_6$ alkyl;
A is an optionally substituted cycloalkyl, optionally substituted heterocyclyl, optionally substituted aryl or optionally substituted heteroaryl ring;
L is absent, —O—, —S—, —S(O)—, —S(O)₂—, —NR⁷— or —C(R⁸)₂—;
R⁷ is H or optionally substituted $C_1$-$C_6$ alkyl;
each R⁸ is independently H, halo, or optionally substituted $C_1$-$C_6$ alkyl, or two R⁸ together with the carbon atom to which they are attached, form a optionally substituted cycloalkyl or heterocyclyl ring;
R⁹ is optionally substituted cycloalkyl, optionally substituted heterocyclyl, optionally substituted aryl or optionally substituted heteroaryl; and
each R¹⁰ is independently cyano, halo or optionally substituted alkyl.

In certain embodiments, the compound is of Formula IId-2. In certain embodiments, the compound is of Formula IId-3. In certain embodiments, the compound is of Formula IId-4. In certain embodiments, the compound is of Formula IId-5. In certain embodiments, the compound is of Formula IId-6.

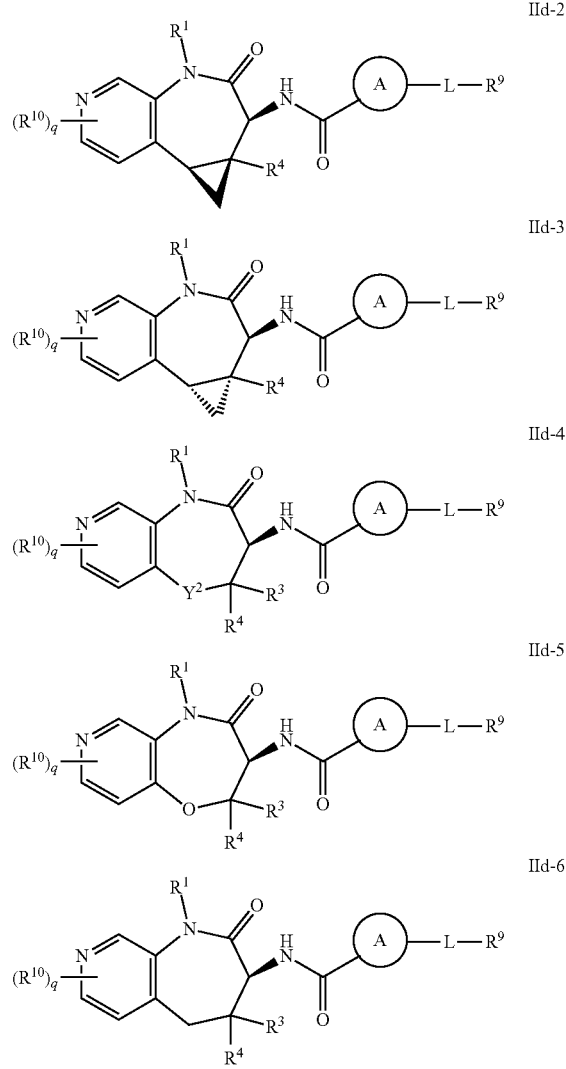

In certain embodiments, provided is a compound of Formula IIe:

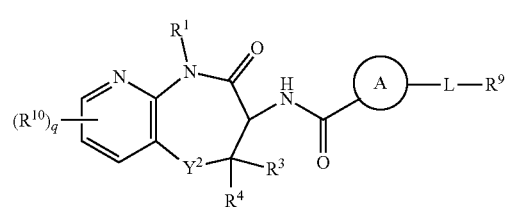

IIe or a pharmaceutically acceptable salt, prodrug, tautomer, stereoisomer or mixture of stereoisomers thereof;
wherein
q is 0, 1 or 2;
R¹ is H or $C_1$-$C_6$ alkyl optionally substituted with halo, hydroxy or cyano;
Y² is —O—, —S—, —S(O)—, —S(O)₂—, —S(O)(NH)—, —NR₅— or —C(R₆)₂—;
R⁵ is H or optionally substituted $C_1$-$C_6$ alkyl;
each R⁶ is independently H, halo, or optionally substituted $C_1$-$C_6$ alkyl, or two R⁶ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C(R$^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;

$R^9$ is optionally substituted cycloalkyl, optionally substituted heterocyclyl, optionally substituted aryl or optionally substituted heteroaryl; and each $R^{10}$ is independently cyano, halo, optionally substituted $C_1$-$C_6$ alkyl or —S(O)$_2$—$C_1$-$C_6$ alkyl.

In certain embodiments, the compound is of Formula IIe or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo or optionally substituted alkyl.

In certain embodiments, the compound is of Formula IIe wherein
$R^1$ is H or optionally substituted $C_1$-$C_6$ alkyl;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl ring or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, optionally substituted $C_1$-$C_6$ alkyl, or two $R^8$ together with the carbon atom to which they are attached, form a optionally substituted cycloalkyl or optionally substituted heterocyclyl ring; and
$R^9$ is optionally substituted cycloalkyl, optionally substituted heterocyclyl, optionally substituted aryl or optionally substituted heteroaryl; provided that at least one of the following occurs:
(1) at least one of $R^3$ and $R^4$ are halo or optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;
(2) L is absent or —C(R$^8$)$_2$—, and two $R^8$ together with the carbon atom to which they are attached, form an optionally substituted cycloalkyl or optionally substituted heterocyclyl ring; or
(3) $Y^2$ is —C(R$_6$)$_2$—; and two $R^6$ together with the carbon atom to which they are attached, form a $C_1$-$C_6$ alken-1-yl, optionally substituted cycloalkyl or optionally substituted heterocyclyl ring;
or a pharmaceutically acceptable salt, prodrug, tautomer, stereoisomer or mixture of stereoisomers thereof.

In certain embodiments, provided is a compound of Formula IIe or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl;
$Y^2$ is —O— or —C(R$_6$)$_2$—;
each $R^6$ is independently H, halo or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O— or —C(R$^8$)$_2$—;

each R$^8$ is independently H, halo, or optionally substituted C$_1$-C$_6$ alkyl, or two R$^8$ together with the carbon atom to which they are attached, form a optionally substituted cycloalkyl or optionally substituted heterocyclyl ring;

R$^9$ is optionally substituted cycloalkyl, optionally substituted heterocyclyl, optionally substituted aryl or optionally substituted heteroaryl; and each R$^{10}$ is independently cyano, halo, optionally substituted C$_1$-C$_6$ alkyl or —S(O)$_2$—C$_1$-C$_6$ alkyl.

In certain embodiments, the compound is of Formula IIe-1:

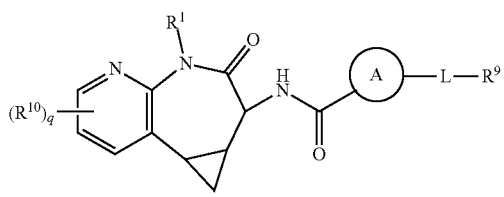

IIe-1 wherein or a pharmaceutically acceptable salt, prodrug, tautomer, stereoisomer or mixture of stereoisomers thereof;

q is 0, 1 or 2;

R$^1$ is H or C$_1$-C$_6$ alkyl optionally substituted with halo, hydroxy or cyano;

R$^4$ is H, halo, or optionally substituted C$_1$-C$_6$ alkyl;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C(R$^8$)$_2$—;

R$^7$ is H or optionally substituted C$_1$-C$_6$ alkyl;

each R$^8$ is independently H, halo, or optionally substituted C$_1$-C$_6$ alkyl, or two R$^8$ together with the carbon atom to which they are attached, form a optionally substituted cycloalkyl or heterocyclyl ring;

R$^9$ is optionally substituted cycloalkyl, optionally substituted heterocyclyl, optionally substituted aryl or optionally substituted heteroaryl; and each R$^{10}$ is independently cyano, halo or optionally substituted alkyl.

In certain embodiments, the compound is of Formula IIe-2. In certain embodiments, the compound is of Formula IIe-3. In certain embodiments, the compound is of Formula IIe-4. In certain embodiments, the compound is of Formula IIe-5. In certain embodiments, the compound is of Formula IIe-6.

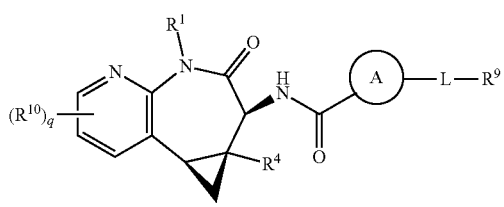

IIe-2

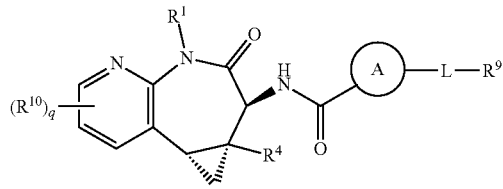

IIe-3

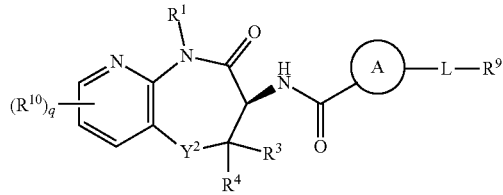

IIe-4

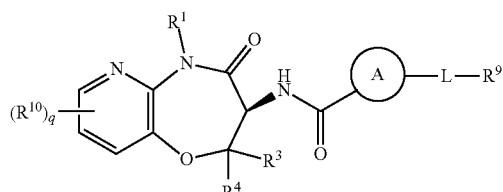

IIe-5

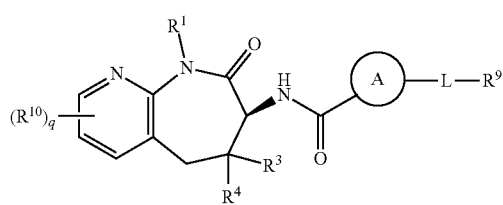

IIe-6

In certain embodiments, provided is a compound of Formula IIe-4 or a pharmaceutically acceptable salt, prodrug, tautomer, stereoisomer or mixture of stereoisomers thereof;

wherein q is 0, 1 or 2;

R$^1$ is H or C$_1$-C$_6$ alkyl;

Y$^2$ is —O— or —C(R$_6$)$_2$—;

each R$^6$ is independently H, halo, or optionally substituted C$_1$-C$_6$ alkyl, or two R$^6$ together with the carbon atom to which they are attached, form a C$_1$-C$_6$alken-1-yl, optionally substituted cycloalkyl or optionally substituted heterocyclyl ring;

R$^3$ and R$^4$ are independently H, halo, or optionally substituted C$_1$-C$_6$ alkyl, or R$^3$ and R$^4$ together with the carbon atoms to which they are attached, form an optionally substituted cycloalkyl or optionally substituted heterocyclyl ring, or R$^3$ and R$^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O— or —C(R$^8$)$_2$—;

each R$^8$ is independently H, halo, or optionally substituted C$_1$-C$_6$ alkyl, or two R$^8$ together with the carbon atom to which they are attached, form a optionally substituted cycloalkyl or optionally substituted heterocyclyl ring;

R$^9$ is optionally substituted cycloalkyl, optionally substituted heterocyclyl, optionally substituted aryl or optionally substituted heteroaryl; and each $R^{10}$ is independently cyano, halo, optionally substituted $C_1$-$C_6$ alkyl or —S(O)$_2$—$C_1$-$C_6$ alkyl.

In certain embodiments, provided is a compound of Formula IIf:

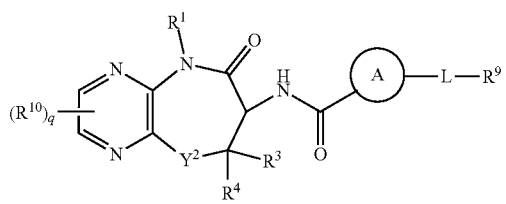

IIf or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo, optionally substituted $C_1$-$C_6$ alkyl or —S(O)$_2$—$C_1$-$C_6$ alkyl.

In certain embodiments, the compound is of Formula IIf or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo or optionally substituted alkyl.

In certain embodiments, the compound is of Formula IIf wherein
$R^1$ is H or optionally substituted $C_1$-$C_6$ alkyl;
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl ring or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, optionally substituted $C_1$-$C_6$ alkyl, or two $R^8$ together with the carbon atom to which they are attached, form a optionally substituted cycloalkyl or optionally substituted heterocyclyl ring; and
$R^9$ is optionally substituted cycloalkyl, optionally substituted heterocyclyl, optionally substituted aryl or optionally substituted heteroaryl; provided that at least one of the following occurs:
(1) at least one of $R^3$ and $R^4$ are halo or optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;

(2) L is absent or —C(R$^8$)$_2$—, and two R$^8$ together with the carbon atom to which they are attached, form an optionally substituted cycloalkyl or optionally substituted heterocyclyl ring; or (3) Y$^2$ is —C(R$_6$)$_2$—; and two R$^6$ together with the carbon atom to which they are attached, form a C$_1$-C$_6$ alken-1-yl, optionally substituted cycloalkyl or optionally substituted heterocyclyl ring;

or a pharmaceutically acceptable salt, prodrug, tautomer, stereoisomer or mixture of stereoisomers thereof.

In certain embodiments, provided is a compound of Formula IIf or a pharmaceutically acceptable salt, prodrug, tautomer, stereoisomer or mixture of stereoisomers thereof; wherein q is 0, 1 or 2;

R$^1$ is H or C$_1$-C$_6$ alkyl;

Y$^2$ is —O— or —C(R$_6$)$_2$—;

each R$^6$ is independently H, halo, or optionally substituted C$_1$-C$_6$ alkyl, or two R$^6$ together with the carbon atom to which they are attached, form a C$_1$-C$_6$ alken-1-yl, optionally substituted cycloalkyl or optionally substituted heterocyclyl ring;

R$^3$ and R$^4$ are independently H, halo, or optionally substituted C$_1$-C$_6$ alkyl, or R$^3$ and R$^4$ together with the carbon atoms to which they are attached, form an optionally substituted cycloalkyl or optionally substituted heterocyclyl ring, or R$^3$ and R$^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally heteroaryl ring;

L is absent, —O— or —C(R$^8$)$_2$—;

each R$^8$ is independently H, halo, or optionally substituted C$_1$-C$_6$ alkyl, or two R$^8$ together with the carbon atom to which they are attached, form a optionally substituted cycloalkyl or optionally substituted heterocyclyl ring;

R$^9$ is optionally substituted cycloalkyl, optionally substituted heterocyclyl, optionally substituted aryl or optionally substituted heteroaryl; and each R$^{10}$ is independently cyano, halo, optionally substituted C$_1$-C$_6$ alkyl or —S(O)$_2$—C$_1$-C$_6$ alkyl.

In certain embodiments, the compound is of Formula IIf-1:

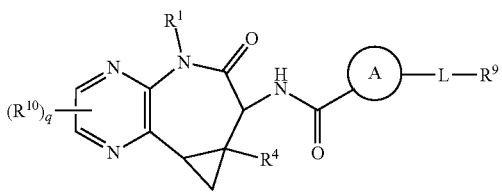

IIf-1 wherein or a pharmaceutically acceptable salt, prodrug, tautomer, stereoisomer or mixture of stereoisomers thereof;

q is 0, 1 or 2;

R$^1$ is H or C$_1$-C$_6$ alkyl optionally substituted with halo, hydroxy or cyano;

R$^4$ is H, halo, or optionally substituted C$_1$-C$_6$ alkyl;

A is an optionally substituted cycloalkyl, optionally substituted heterocyclyl, optionally substituted aryl or optionally substituted heteroaryl ring;

L is absent, —O—, —S—, —S(O)—, —S(O)$_2$—, —NR$^7$— or —C(R$^8$)$_2$—;

R$^7$ is H or optionally substituted C$_1$-C$_6$ alkyl;

each R$^8$ is independently H, halo, or optionally substituted C$_1$-C$_6$ alkyl, or two R$^8$ together with the carbon atom to which they are attached, form a optionally substituted cycloalkyl or heterocyclyl ring;

R$^9$ is optionally substituted cycloalkyl, optionally substituted heterocyclyl, optionally substituted aryl or optionally substituted heteroaryl; and each R$^{10}$ is independently cyano, halo or optionally substituted alkyl.

In certain embodiments, the compound is of Formula IIf-2. In certain embodiments, the compound is of Formula IIf-3. In certain embodiments, the compound is of Formula IIf-4. In certain embodiments, the compound is of Formula IIf-5. In certain embodiments, the compound is of Formula IIf-6.

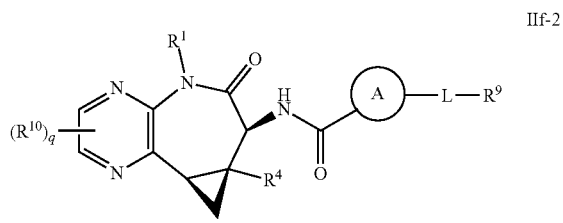

IIf-2

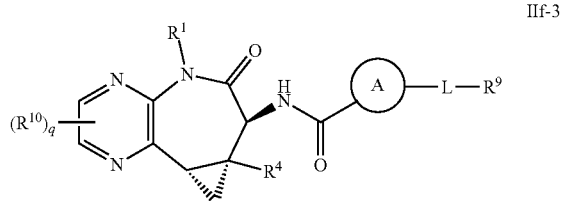

IIf-3

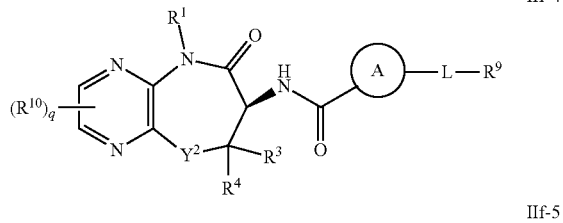

IIf-4

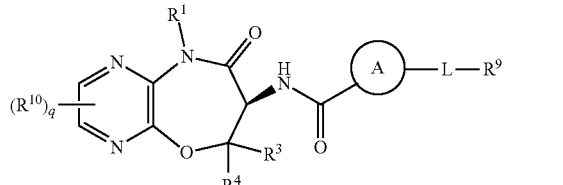

IIf-5

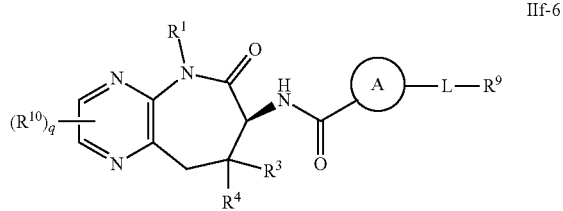

IIf-6

In certain embodiments, provided is a compound of Formula IIf-4 or a pharmaceutically acceptable salt, prodrug, tautomer, stereoisomer or mixture of stereoisomers thereof;

wherein q is 0, 1 or 2;

$R^1$ is H or $C_1$-$C_6$ alkyl;

$Y^2$ is —O— or —C($R_6$)$_2$—;

each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;

$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl, optionally substituted aryl or optionally substituted heteroaryl ring;

L is absent, —O— or —C($R^8$)$_2$—;

each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;

$R^9$ is optionally substituted cycloalkyl, optionally substituted heterocyclyl, optionally substituted aryl or optionally substituted heteroaryl; and each $R^{10}$ is independently cyano, halo, optionally substituted $C_1$-$C_6$ alkyl or —S(O)$_2$—$C_1$-$C_6$ alkyl.

In certain embodiments of compounds of Formula I (or subformula thereof), $R^3$ is H. In certain embodiments of compounds of Formula I (or subformula thereof), $R^4$ is optionally substituted $C_1$-$C_6$ alkyl. In certain embodiments of compounds of Formula I (or subformula thereof), $R^3$ is H and $R^4$ is optionally substituted $C_1$-$C_6$ alkyl. In certain embodiments of compounds of Formula I (or subformula thereof), $R^3$ is H and $R^4$ is methyl.

In certain embodiments of compounds of Formula I (or subformula thereof), $R^3$ is H and $R^4$ is H.

In certain embodiments of compounds of Formula II (or subformula thereof), $R^3$ is H. In certain embodiments of compounds of Formula II (or subformula thereof), $R^4$ is optionally substituted $C_1$-$C_6$ alkyl. In certain embodiments of compounds of Formula II (or subformula thereof), $R^3$ is H and $R^4$ is optionally substituted $C_1$-$C_6$ alkyl. In certain embodiments of compounds of Formula II (or subformula thereof), $R^3$ is H and $R^4$ is $C_1$-$C_6$ alkyl. In certain embodiments of compounds of Formula II (or subformula thereof), $R^3$ is H and $R^4$ is methyl.

In certain embodiments of compounds of Formula IIa, IIb, IIc, IId, IIe and IIf (or subformula thereof), $R^3$ is H and $R^4$ is H. In certain embodiments of compounds of Formula IIe-4 and IIe-5, $R^3$ is H and $R^4$ is H.

In certain embodiments of compounds of Formula I (or subformula thereof), the A ring is an optionally substituted heteroaryl ring. In certain embodiments of compounds of Formula I (or subformula thereof), the A ring is an unsubstituted heteroaryl ring. In certain embodiments of compounds of Formula I (or subformula thereof), the A ring is a pyrazolyl, isoxazolyl, oxadiazolyl or triazolyl. In certain embodiments of compounds of Formula I (or subformula thereof), the A ring is a oxadiazolyl. In certain embodiments of compounds of Formula I (or subformula thereof), the A ring is a triazolyl.

In certain embodiments of compounds of Formula II (or subformula thereof), the A ring is an optionally substituted heteroaryl ring. In certain embodiments of compounds of Formula II (or subformula thereof), the A ring is an unsubstituted heteroaryl ring. In certain embodiments of compounds of Formula II (or subformula thereof), the A ring is an optionally substituted 5-membered heteroaryl ring. In certain embodiments of compounds of Formula II (or subformula thereof), the A ring is an unsubstituted 5-membered heteroaryl ring. In certain embodiments of compounds of Formula II (or subformula thereof), the A ring is an optionally substituted 6-membered heteroaryl ring. In certain embodiments of compounds of Formula II (or subformula thereof), the A ring is a heteroaryl ring substituted with at least one halo. In certain embodiments of compounds of Formula II (or subformula thereof), the A ring is a 5-membered heteroaryl ring substituted with at least one halo. In certain embodiments of compounds of Formula II (or subformula thereof), the A ring is a pyrazolyl, isoxazolyl, oxadiazolyl or triazolyl. In certain embodiments of compounds of Formula II (or subformula thereof), the A ring is oxadiazolyl. In certain embodiments of compounds of Formula II (or subformula thereof), the A ring is a triazolyl.

In certain embodiments of compounds of Formula II (or subformula thereof), the A ring is of the formula:

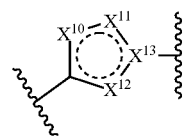

wherein $X^{10}$, $X^{11}$ and $X^{12}$ are each S, O, N, $CR^{13}$ or $NR^{13}$, and $X^{13}$ is C or N; and each $R^{13}$ is independently H, halo, cyano or optionally substituted $C_1$-$C_6$ alkyl.

In certain embodiments, at least one of $X^{10}$, $X^{11}$ and $X^{12}$ is $CR^{13}$ or $NR^{13}$ and at least one $R^{13}$ is halo, cyano or optionally substituted $C_1$-$C_6$ alkyl. In certain embodiments, at least one of $X^{10}$, $X^{11}$ and $X^{12}$ is $CR^{13}$ or $NR^{13}$ and at least one $R^{13}$ is halo. In certain embodiments, each $R^{13}$ is independently H, fluoro, chloro, cyano or methyl.

In certain embodiments of compounds of Formula II (or subformula thereof), the A ring is one of the following:

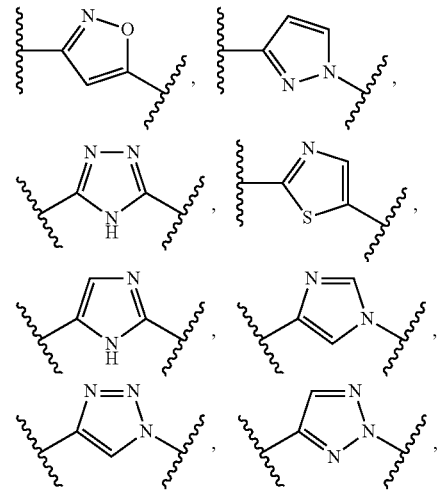

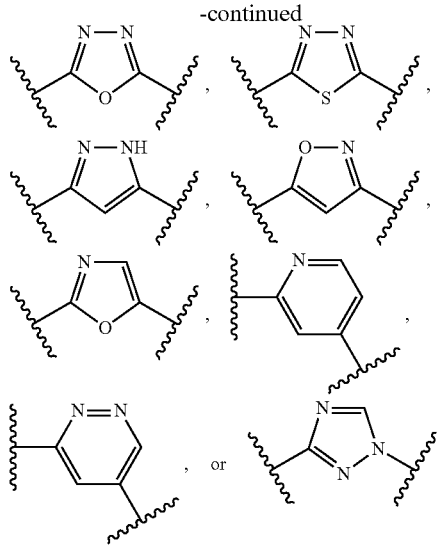

wherein each ring may optionally substituted with one or more halo, cyano or $C_1$-$C_6$ alkyl.

In certain embodiments of compounds of Formula II (or subformula thereof), the A ring is one of the following:

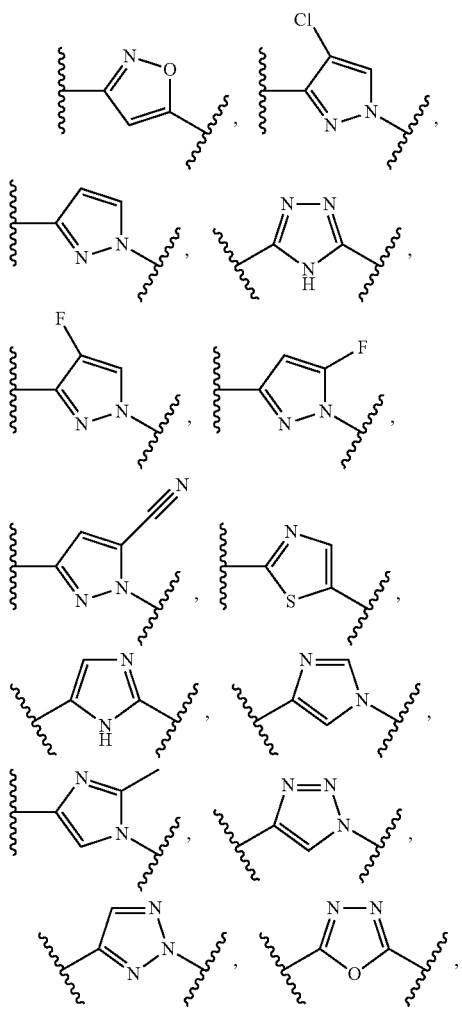

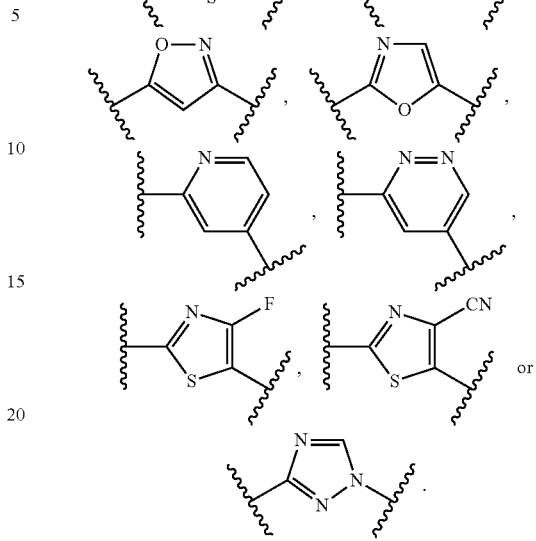

In certain embodiments of compounds of Formula I (or subformula thereof), L is absent, —O— or —C($R^8$)$_2$—; and each $R^8$ is independently H or $C_1$-$C_6$ alkyl, or two $R^8$ together with the carbon atom to which they are attached, form a optionally substituted cycloalkyl. In certain embodiments of compounds of Formula I (or subformula thereof), L is —C($R^8$)$_2$— and each $R^8$ is taken together with the carbon atom to which they are attached to form cyclopropyl.

In certain embodiments of compounds of Formula II (or subformula thereof), L is absent, —O— or —C($R^8$)$_2$—; and each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring. In certain embodiments of compounds of Formula II (or subformula thereof), L is absent, —O— or —C($R^8$)$_2$—; and each $R^8$ is independently H or two $R^8$ together with the carbon atom to which they are attached, form a optionally substituted cycloalkyl.

In certain embodiments of compounds of Formula II (or subformula thereof), L is absent. In certain embodiments of compounds of Formula II (or subformula thereof), L is —O—. In certain embodiments of compounds of Formula II (or subformula thereof), L is —C($R^8$)$_2$— and each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring. In certain embodiments of compounds of Formula II (or subformula thereof), L is —C($R^8$)$_2$— and each $R^8$ is independently H, or two $R^8$ together with the carbon atom to which they are attached, form a optionally substituted cycloalkyl. In certain embodiments of compounds of Formula II (or subformula thereof), L is —C($R^8$)$_2$— and each $R^8$ is taken together with the carbon atom to which they are attached to form cyclopropyl.

In certain embodiments of compounds of Formula I (or subformula thereof), $R^9$ is optionally substituted aryl. In certain embodiments of compounds of Formula I (or subformula thereof), $R^9$ is phenyl optionally substituted with one or more halo, cyano or $C_1$-$C_6$ alkyl optionally substituted with halo. In certain embodiments of compounds of Formula I (or subformula thereof), $R^9$ is phenyl.

In certain embodiments of compounds of Formula II (or subformula thereof), $R^9$ is optionally substituted cycloalkyl, optionally substituted aryl or optionally substituted heteroaryl. In certain embodiments of compounds of Formula II (or subformula thereof), $R^9$ is phenyl, dihydroindenyl, pyridyl, 2-fluorophenyl, 3-fluorophenyl, 4-fluorophenyl, 2-cyanophenyl, 3-cyanophenyl, 4-cyanophenyl, 2,4-difluorophenyl, 3-cyano-4-fluorophenyl, or 5-fluoropyridin-3-yl.

In certain embodiments of compounds of Formula II (or subformula thereof), q is 0. In certain embodiments of compounds of Formula II (or subformula thereof), q is 1 or 2; and each $R^{10}$ is independently cyano, halo, optionally substituted $C_1$-$C_6$ alkyl, or —S(O)$_2$—$C_1$-$C_6$ alkyl. In certain embodiments of compounds of Formula II (or subformula thereof), q is 1 or 2; and each $R^{10}$ is independently cyano, halo, methyl, or —S(O)$_2$-methyl.

In certain embodiments, the compound is of Formula III:

III or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$X^1$ and $X^2$ are each N or CH;
$X^3$, $X^4$ and $X^5$ are each S, O, N, NH, or CH
$Y^2$ is —O—, —S—, —S(O)—, —S(O)$_2$—, —S(O)(NH)—, —NR$_5$— or —C(R$_6$)$_2$—;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;

$R^9$ is optionally substituted cycloalkyl, optionally substituted heterocyclyl, optionally substituted aryl or optionally substituted heteroaryl; and
each $R^{10}$ is independently cyano, halo or optionally substituted alkyl.

In certain embodiments, at least one of the following occurs:
(1) at least one of $R^3$ and $R^4$ are halo or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form a optionally substituted cycloalkyl or optionally substituted heterocyclyl ring;
(2) L is absent or —C(R$^8$)$_2$—, and each $R^8$ is optionally substituted $C_1$-$C_6$ alkyl or halo or two $R^8$ together with the carbon atom to which they are attached, form an optionally substituted cycloalkyl or optionally substituted heterocyclyl ring; or
(3) $Y^2$ is —C(R$_6$)$_2$—; and one $R^6$ is hydrogen, halo, or optionally substituted $C_1$-$C_6$ alkyl, and the other $R^6$ is halo or optionally substituted $C_1$-$C_6$ alkyl; or two $R^6$ together with the carbon atom to which they are attached, form a $C_1$-$C_6$ alken-1-yl, optionally substituted cycloalkyl or optionally substituted heterocyclyl ring.

In certain embodiments, the compound is of Formula III wherein
$X^1$ and $X^2$ are each N or CH;
$X^3$, $X^4$ and $X^5$ are each S, O, N, NH, or CH
$Y^2$ is —O—, —S—, —S(O)—, —S(O)$_2$—, —S(O)(NH)—, —NR$_5$— or —C(R$^6$)$_2$—;
$R^5$ is H or optionally substituted $C_1$-$C_6$ alkyl;
each $R^6$ is independently H, halo, optionally substituted $C_1$-$C_6$ alkyl, or two $R^6$ together with the carbon atom to which they are attached, form a $C_1$-$C_6$ alken-1-yl, optionally substituted cycloalkyl or optionally substituted heterocyclyl ring;
$R^3$ and $R^4$ are independently H, halo, optionally substituted $C_1$-$C_6$ alkyl, $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl ring or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, optionally substituted $C_1$-$C_6$ alkyl, or two $R^8$ together with the carbon atom to which they are attached, form a optionally substituted cycloalkyl or optionally substituted heterocyclyl ring; and
$R^9$ is optionally substituted cycloalkyl, optionally substituted heterocyclyl, optionally substituted aryl or optionally substituted heteroaryl;
or a pharmaceutically acceptable salt, prodrug, tautomer, stereoisomer or mixture of stereoisomers thereof.

In certain embodiments, the compound is of Formula IIIa, IIIb, or IIIc:

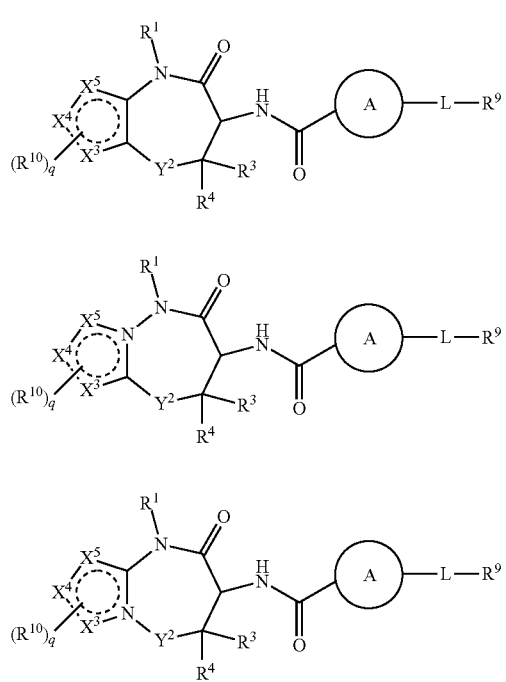

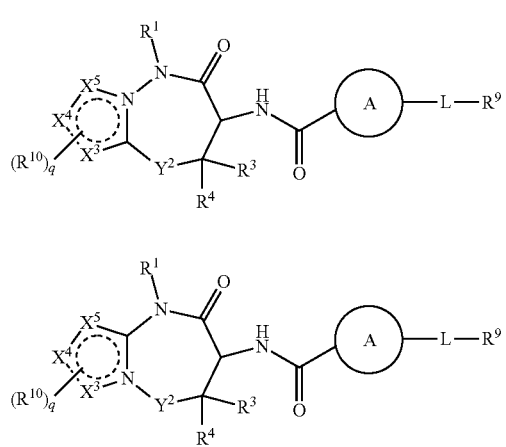

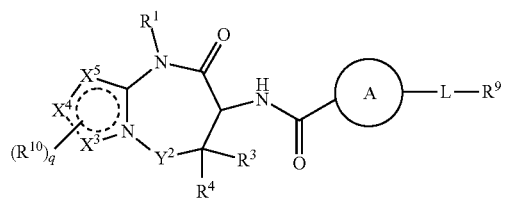

or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$X^3$, $X^4$ and $X^5$ are each S, O, N, NH, or CH
$Y^2$ is —O—, —S—, —S(O)—, —S(O)$_2$—, —S(O)(NH)—, —NR$_5$— or —C(R$_6$)$_2$—;
$R^1$ is H or $C_1$-$C_6$ alkyl;
$R^5$ is H or optionally substituted $C_1$-$C_6$ alkyl;
each $R^6$ is independently H, halo, or optionally substituted $C_1$-$C_6$ alkyl, or two $R^6$ together with the carbon atom to which they are attached, form a $C_1$-$C_6$alken-1-yl, optionally substituted cycloalkyl or optionally substituted heterocyclyl ring;
$R^3$ and $R^4$ are independently H, halo, or optionally substituted $C_1$-$C_6$ alkyl, or $R^3$ and $R^4$ together with the carbon atoms to which they are attached, form an optionally substituted cycloalkyl or optionally substituted heterocyclyl ring, or $R^3$ and $R^6$ together with the carbon atoms to which they are attached, form an optionally substituted cycloalkyl or optionally substituted heterocyclyl ring;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;

$R^9$ is optionally substituted cycloalkyl, optionally substituted heterocyclyl, optionally substituted aryl or optionally substituted heteroaryl; and
each $R^{10}$ is independently cyano, halo or optionally substituted alkyl.

In certain embodiments, the compound is of Formula IIIa-1, IIIb-1, or IIIc-1:

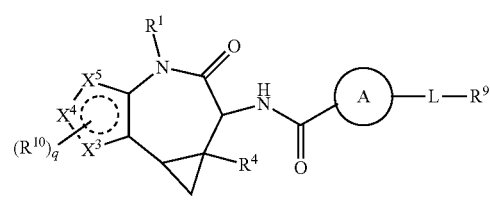

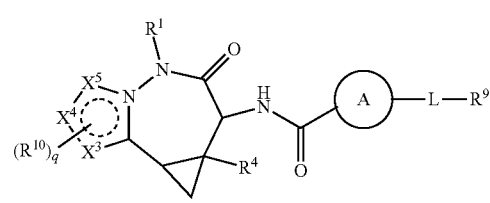

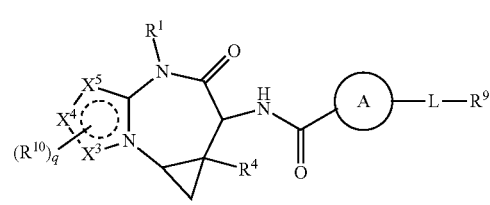

or a pharmaceutically acceptable salt, prodrug, tautomer, stereoisomer or mixture of stereoisomers thereof;
wherein
q is 0, 1 or 2;
$R^1$ is H or $C_1$-$C_6$ alkyl optionally substituted with halo, hydroxy or cyano;
$X^3$, $X^4$ and $X^1$ are each S, O, N, NH, or CH;
$R^1$ is H or $C_1$-$C_6$ alkyl;
$R^4$ is H, halo, or optionally substituted $C_1$-$C_6$ alkyl;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo or optionally substituted alkyl.

In certain embodiments, the compound is of Formula IIIa, IIIb, or IIIc:

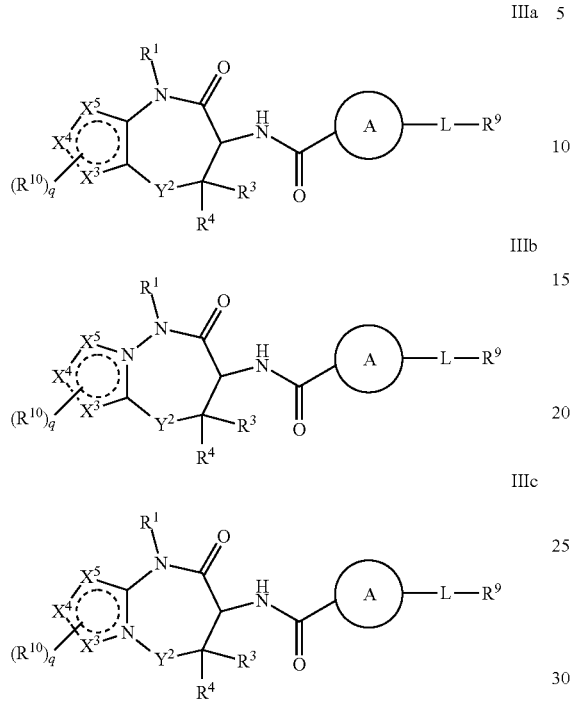

IIIa

IIIb

IIIc wherein
X³, X⁴ and X⁵ are each S, O, N, NH, or CH
Y² is —O—, —S—, —S(O)—, —S(O)₂—, —S(O)(NH)—, —NR₅— or —C(R₆)₂—;
R⁵ is H or optionally substituted $C_1$-$C_6$ alkyl;
each R⁶ is independently H, halo, optionally substituted $C_1$-$C_6$ alkyl, or two R⁶ together with the carbon atom to which they are attached, form a $C_1$-$C_6$ alken-1-yl, optionally substituted cycloalkyl or optionally substituted heterocyclyl ring;
R³ and R⁴ are independently H, halo, optionally substituted $C_1$-$C_6$ alkyl, R³ and R⁴ together with the carbon atoms to which they are attached, form an optionally substituted cycloalkyl or optionally substituted heterocyclyl ring, or R³ and R⁶ together with the carbon atoms to which they are attached, form an optionally substituted cycloalkyl or optionally substituted heterocyclyl ring;
A is an optionally substituted cycloalkyl, optionally substituted heterocyclyl ring or optionally substituted heteroaryl ring;
L is absent, —O—, —S—, —S(O)—, —S(O)₂—, —NR⁷— or —C(R⁸)₂—;
R⁷ is H or optionally substituted $C_1$-$C_6$ alkyl;
each R⁸ is independently H, halo, optionally substituted $C_1$-$C_6$ alkyl, or two R⁸ together with the carbon atom to which they are attached, form a optionally substituted cycloalkyl or optionally substituted heterocyclyl ring; and
R⁹ is optionally substituted cycloalkyl, optionally substituted heterocyclyl, optionally substituted aryl or optionally substituted heteroaryl;
or a pharmaceutically acceptable salt, prodrug, tautomer, stereoisomer or mixture of stereoisomers thereof.

In certain embodiments, the compound is of Formula IIIa-1, IIIa-2, IIIa-3, IIIa-4, IIIa-5, IIIa-6, IIIa-7, IIIa-8 or IIIa-9:

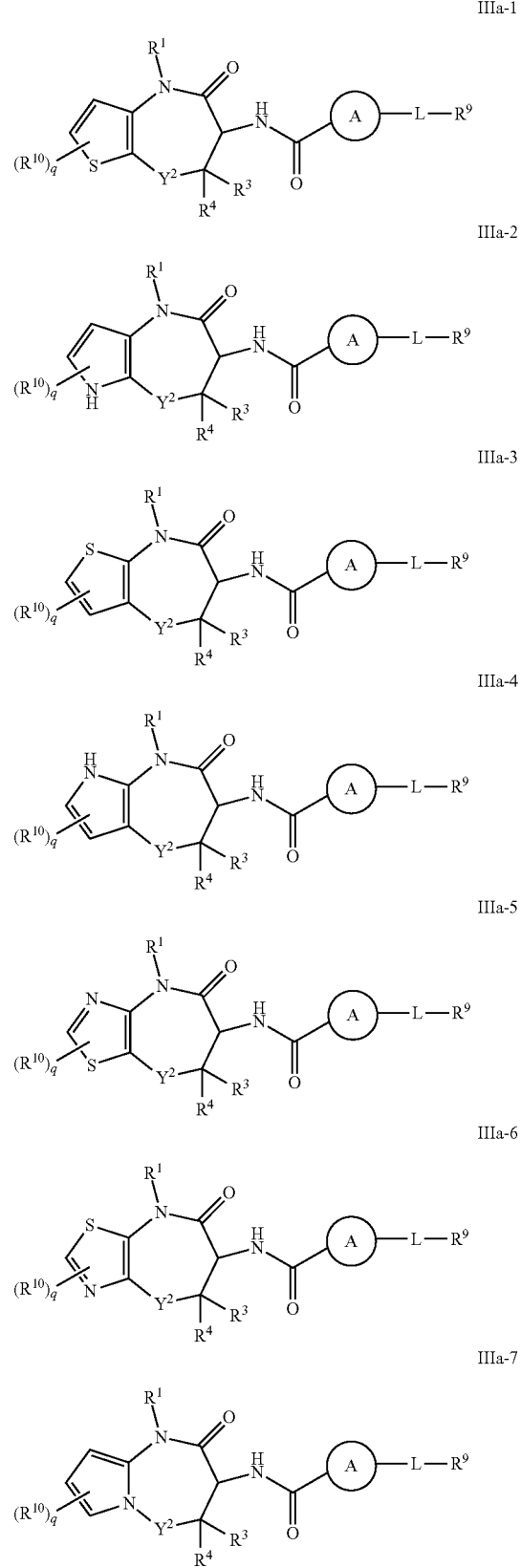

IIIa-1

IIIa-2

IIIa-3

IIIa-4

IIIa-5

IIIa-6

IIIa-7

67

-continued

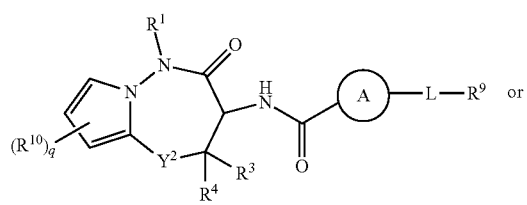
IIIa-8

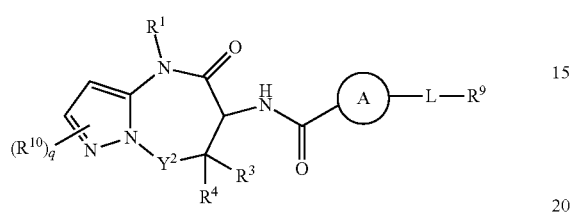
IIIa-9 wherein the variables of Formula IIIa-1 to IIIa-9 are defined throughout.

In certain embodiments, the compound is of Formula IVa, IVb, IVc, IVd, IVe, IVf or IVg:

IVa

[structure]

IVb

[structure]

IVc

[structure]

IVd

[structure]

68

-continued

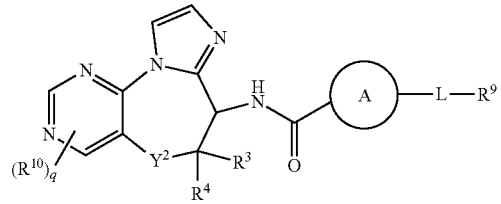
IVe

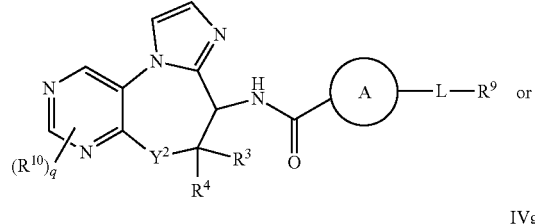
IVf

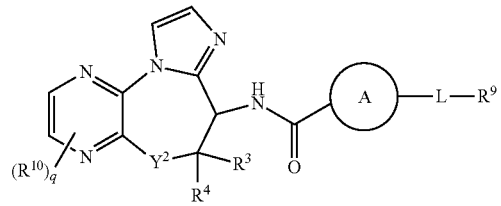
IVg or a pharmaceutically acceptable salt, prodrug, tautomer, stereoisomer or mixture of stereoisomers thereof;
wherein
q is 0, 1 or 2;
$R^4$ is H, halo, or optionally substituted $C_1$-$C_6$ alkyl;
A is an optionally substituted cycloalkyl, optionally substituted heterocyclyl, optionally substituted aryl or optionally substituted heteroaryl ring;
L is absent, —O—, —S—, —S(O)—, —S(O)$_2$—, —NR$^7$— or —C(R$^8$)$_2$—;
$R^7$ is H or optionally substituted $C_1$-$C_6$ alkyl;
each $R^8$ is independently H, halo, or optionally substituted $C_1$-$C_6$ alkyl, or two $R^8$ together with the carbon atom to which they are attached, form a optionally substituted cycloalkyl or optionally substituted heterocyclyl ring;
$R^9$ is optionally substituted cycloalkyl, optionally substituted heterocyclyl, optionally substituted aryl or optionally substituted heteroaryl; and
each $R^{10}$ is independently cyano, halo, optionally substituted $C_1$-$C_6$ alkyl, or —S(O)$_2$—$C_1$-$C_6$ alkyl.

In certain embodiments, provided is a compound of Formula V:

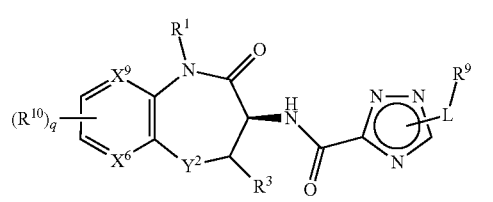
V or a pharmaceutically acceptable salt, prodrug, tautomer, stereoisomer or mixture of stereoisomers thereof, wherein q is 0, 1, or 2;
$X^6$ and $X^9$ are independently N or $CR^{14}$;
$R^1$ is H or optionally substituted $C_1$-$C_6$ alkyl;
$Y^2$ is —O— or —C(R$_6$)$_2$—;
each $R^6$ is independently H, halo, optionally substituted $C_1$-$C_6$ alkyl;
$R^3$ is H, halo, optionally substituted $C_1$-$C_6$ alkyl, or $R^3$ and $R^6$ together with the carbon atoms to which they are attached, form an optionally substituted cycloalkyl or optionally substituted heterocyclyl ring;
L is —C(R$^8$)$_2$—;
each $R^8$ is independently H, halo, optionally substituted $C_1$-$C_6$ alkyl, or two $R^8$ together with the carbon atom to which they are attached form an optionally substituted cycloalkyl or optionally substituted heterocyclyl ring;
$R^9$ is optionally substituted aryl or optionally substituted heteroaryl;
each $R^{10}$ is independently cyano, halo, optionally substituted $C_1$-$C_6$ alkyl, optionally substituted heteroaryl, optionally substituted aryl, optionally substituted heterocyclyl, optionally substituted cycloalkyl, optionally substituted $C_1$-$C_6$ alkoxy, or —S(O)$_2$—$C_1$-$C_6$alkyl; and
each $R^{14}$ is independently hydrogen, cyano, halo, $C_1$-$C_3$ alkyl optionally substituted with halo, or $C_1$-$C_3$ alkoxy optionally substituted with halo;
provided that when both of $X^6$ and $X^9$ are $CR^{14}$, one or more of (i), (ii), (iii), (iv) and (v) is true: (i) $R^3$ and $R^6$ together with the carbon atoms to which they are attached form an optionally substituted cycloalkyl or optionally substituted heterocyclyl ring, (ii) L is —C(R$^8$)$_2$— and each $R^8$ is taken together with the carbon atom to which they are attached to form cyclopropyl, (iii) $R^9$ is substituted with at least one cyano, (iv) $X^9$ is other than C—H, C—F, C—Cl or C—CH$_3$ and/or (v) $X^6$ is other than C—H, C—F or C—CH$_3$.

In certain embodiments of compounds of Formula V (or subformula thereof), $X^9$ is N. In certain embodiments $X^9$ is N and $X^6$ is $CR^{14}$. In certain embodiments $X^9$ and $X^6$ are N.

In certain embodiments of compounds of Formula V (or subformula thereof), $Y^2$ is O. In certain embodiments $R^3$ is H. In certain embodiments $R^3$ is methyl. In certain embodiments $R^3$ and $R^6$ together with the carbon atoms to which they are attached form an optionally substituted cycloalkyl. In certain embodiments $R^3$ and $R^6$ together with the carbon atoms to which they are attached form an optionally substituted cyclopropyl ring.

In certain embodiments of compounds of Formula V (or subformula thereof), $X^6$ and $X^9$ are $CR^{14}$ and $R^3$ and $R^6$ together with the carbon atoms to which they are attached form an optionally substituted cycloalkyl. In certain embodiments $R^3$ and $R^6$ together with the carbon atoms to which they are attached form an optionally substituted cyclopropyl ring. In certain embodiments $X^9$ is CH. In certain embodiments $X^9$ is CF.

In certain embodiments of compounds of Formula V (or subformula thereof), $X^6$ and $X^9$ are $CR^{14}$ and L is —C(R$^8$)$_2$— and each $R^8$ is taken together with the carbon atom to which they are attached to form cyclopropyl.

In certain embodiments of compounds of Formula V (or subformula thereof), $X^6$ and $X^9$ are $CR^{14}$, L is —C(R$^8$)$_2$— and each $R^8$ is taken together with the carbon atom to which they are attached to form cyclopropyl and $R^3$ and $R^6$ together with the carbon atoms to which they are attached form an optionally substituted cyclopropyl ring.

In certain embodiments of compounds of Formula V (or subformula thereof), each $R^{10}$ is independently cyano, halo, or —S(O)$_2$—$C_1$-$C_6$alkyl. In certain embodiments, q is 1 or 2 and each $R^{10}$ is independently cyano, halo, or —S(O)$_2$—$C_1$-$C_6$alkyl. In certain embodiments, q is two and both $R^{10}$ are halo. In certain embodiments, q is two and both $R^{10}$ are fluoro. In certain embodiments, q is two and at least one $R^{10}$ is fluoro.

In certain embodiments of compounds of Formula V (or subformula thereof), $R^1$ is H or methyl. In certain embodiments of compounds of Formula V (or subformula thereof), $R^1$ is H.

In certain embodiments of compounds of Formula V (or subformula thereof), $R^1$ is methyl.

In certain embodiments of compounds of Formula V (or subformula thereof), L is CH$_2$ or two $R^8$ together with the carbon atom to which they are attached form a cycloalkyl ring. In certain embodiments L is CH$_2$. In certain embodiments $R^9$ is optionally substituted phenyl. In certain embodiments $R^9$ is phenyl. In certain embodiments $R^9$ is phenyl substituted by one to two substituents independently selected from the group consisting of cyano and halo. In certain embodiments $R^9$ is phenyl substituted by cyano.

In certain embodiments of compounds of Formula V (or subformula thereof), $R^{14}$ is hydrogen, halo or methyl optionally substituted with 1-3 fluoro. In certain embodiments, $R^{14}$ is hydrogen or halo. In certain embodiments, $R^{14}$ is hydrogen. In certain embodiments, $R^{14}$ is halo. In certain embodiments, $R^{14}$ is fluoro.

In certain embodiments, provided is a compound of Formula Va:

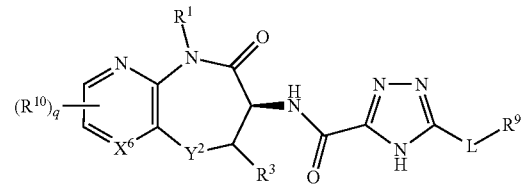

Va or a pharmaceutically acceptable salt, prodrug, tautomer, stereoisomer or mixture of stereoisomers thereof, wherein
q is 0, 1, or 2;
$X^6$ is N or $CR^{14}$;
$R^1$ is H or optionally substituted $C_1$-$C_6$ alkyl;
$Y^2$ is —O— or —C(R$_6$)$_2$—;
each $R^6$ is independently H, halo, optionally substituted $C_1$-$C_6$ alkyl;
$R^3$ is H, halo, optionally substituted $C_1$-$C_6$ alkyl, or $R^3$ and $R^6$ together with the carbon atoms to which they are attached form an optionally substituted cycloalkyl or optionally substituted heterocyclyl ring;
L is —C(R$^8$)$_2$—;
each $R^8$ is independently H, halo, optionally substituted $C_1$-$C_6$ alkyl, or two $R^8$ together with the carbon atom to which they are attached form a optionally substituted cycloalkyl or optionally substituted heterocyclyl ring;
$R^9$ is optionally substituted aryl or optionally substituted heteroaryl;
each $R^{10}$ is independently cyano, halo, optionally substituted $C_1$-$C_6$ alkyl, optionally substituted heteroaryl, optionally substituted aryl, optionally substituted heterocyclyl, optionally substituted cycloalkyl, optionally substituted $C_1$-$C_6$ alkoxy, or —S(O)$_2$—$C_1$-$C_6$alkyl; and $R^{14}$ is hydrogen, cyano, halo, $C_1$-$C_3$ alkyl optionally substituted with halo or oxo, or $C_1$-$C_3$ alkoxy optionally substituted with halo or oxo.

In certain embodiments of compounds of Formula Va, $X^6$ is $CR^{14}$. In certain embodiments $X^6$ is N.

In certain embodiments of compounds of Formula Va, each $R^{10}$ is independently cyano, halo, or —S(O)$_2$—$C_1$-$C_6$ alkyl. In certain embodiments, q is at least one and at least one $R^{10}$ is halo. In certain embodiments, q is at least one and at least one $R^{10}$ is fluoro. In certain embodiments, q is at least one and at least one $R^{10}$ is cyano.

In certain embodiments of compounds of Formula Va, q is 0.

In certain embodiments of compounds of Formula Va, $Y^2$ is O. In certain embodiments $R^3$ is H. In certain embodiments $R^3$ is methyl. In certain embodiments $R^3$ and $R^6$ together with the carbon atoms to which they are attached form an optionally substituted cycloalkyl. In certain embodiments $R^3$ and $R^6$ together with the carbon atoms to which they are attached form an optionally substituted cyclopropyl ring.

In certain embodiments of compounds of Formula Va, $R^1$ is H or methyl.

In certain embodiments of compounds of Formula Va, $R^1$ is methyl.

In certain embodiments of compounds of Formula Va, L is CH$_2$ or two $R^8$ together with the carbon atom to which they are attached form a cycloalkyl ring. In certain embodiments L is CH$_2$.

In certain embodiments of compounds of Formula Va, $R^9$ is optionally substituted phenyl. In certain embodiments $R^9$ is phenyl. In certain embodiments $R^9$ is phenyl substituted by one to two substituents independently selected from the group consisting of cyano and halo. In certain embodiments $R^9$ is phenyl substituted by cyano.

In certain embodiments of compounds of Formula Va (or subformula thereof), $R^{14}$ is hydrogen, cyano, halo or methyl optionally substituted with 1-3 fluoro or oxo. In certain embodiments, $R^{14}$ is hydrogen or halo. In certain embodiments, $R^{14}$ is hydrogen. In certain embodiments, $R^{14}$ is cyano.

In certain embodiments the compounds of Formula V and Va do not readily cross the blood brain barrier. In certain embodiments the compounds of Formula V and Va have a MDCKII-MDR1 efflux ratio of greater than 2.5. In certain embodiments the compounds of Formula II, Va and V wherein at least one of $X^6$ and $X^9$ are N, have a hepatic clearance of less than 5, 4, 3, 2, or 1 mL/min/kg when tested according to the human hepatic stability assay described below.

In certain embodiments, the compound is of Formula VI:

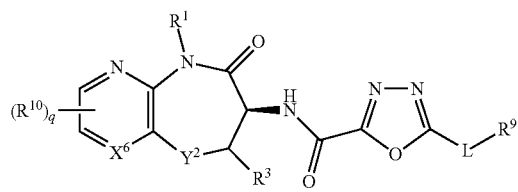

VI or a pharmaceutically acceptable salt, prodrug, tautomer, stereoisomer or mixture of stereoisomers thereof, wherein q is 0, 1, or 2;
$X^6$ is N or $CR^{14}$;
$R^1$ is H or optionally substituted $C_1$-$C_6$ alkyl;
$Y^2$ is —O— or —C(R$_6$)$_2$—;
each $R^6$ is independently H, halo, optionally substituted $C_1$-$C_6$ alkyl;
$R^3$ is H, halo, optionally substituted $C_1$-$C_6$ alkyl, or $R^3$ and $R^6$ together with the carbon atoms to which they are attached, form an optionally substituted cycloalkyl or optionally substituted heterocyclyl ring;
L is —C(R$^8$)$_2$—;
each $R^8$ is independently H, halo, optionally substituted $C_1$-$C_6$ alkyl, or two $R^8$ together with the carbon atom to which they are attached form a optionally substituted cycloalkyl or optionally substituted heterocyclyl ring;
$R^9$ is optionally substituted aryl;
each $R^{10}$ is independently halo, optionally substituted $C_1$-$C_6$ alkyl, optionally substituted heteroaryl, optionally substituted aryl, optionally substituted heterocyclyl, optionally substituted cycloalkyl, or optionally substituted $C_1$-$C_6$ alkoxy; and
$R^{14}$ is hydrogen, cyano, halo, $C_1$-$C_3$ alkyl optionally substituted with halo or oxo, or $C_1$-$C_3$ alkoxy optionally substituted with halo or oxo.

In certain embodiments of compounds of Formula VI, $X^6$ is $CR^{14}$. In certain embodiments $X^6$ is N.

In certain embodiments of compounds of Formula VI, each $R^{10}$ is independently halo. In certain embodiments, q is one and $R^{10}$ is fluoro.

In certain embodiments of compounds of Formula VI, $Y^2$ is O. In certain embodiments $R^3$ is H. In certain embodiments $R^3$ is methyl. In certain embodiments $R^3$ and $R^6$ together with the carbon atoms to which they are attached form an optionally substituted cycloalkyl. In certain embodiments $R^3$ and $R^6$ together with the carbon atoms to which they are attached form an optionally substituted cyclopropyl ring.

In certain embodiments of compounds of Formula VI, $R^1$ is H or methyl. In certain embodiments of compounds of Formula VI, $R^1$ is methyl.

In certain embodiments of compounds of Formula VI, L is CH$_2$ or two $R^8$ together with the carbon atom to which they are attached form a cycloalkyl ring. In certain embodiments L is CH$_2$.

In certain embodiments of compounds of Formula VI, $R^9$ is phenyl. In certain embodiments $R^9$ is optionally substituted phenyl. In certain embodiments $R^9$ is phenyl substituted by one to two halo.

In certain embodiments of compounds of Formula VI, $R^{14}$ is hydrogen, halo or methyl optionally substituted with 1-3 fluoro or oxo. In certain embodiments, $R^{14}$ is hydrogen or halo. In certain embodiments, $R^{14}$ is hydrogen.

In certain embodiments the compounds of Formula VI readily cross the blood brain barrier. In certain embodiments the compounds of Formula VI have a MDCKII-MDR1 efflux ratio of 2.5 or less. In certain embodiments the compounds of Formula VI have a hepatic clearance of less than 10, 9, 8, 7, 6, 5, 4, 3, 2, or 1 µL/min/kg when tested according to the human hepatic stability assay described below.

In any of the embodiments described throughout, q is 0, 1 or 2; and each $R^{10}$ is independently cyano, halo or optionally substituted alkyl. In any of the embodiments described throughout, q is 0, 1 or 2; and each $R^{10}$ is independently cyano, halo, or alkyl optionally substituted with 1-3 halo or oxo.

In any of the embodiments described throughout, q is 0, 1 or 2; and each $R^{10}$ is independently cyano, halo, optionally substituted $C_1$-$C_6$ alkyl, or —S(O)$_2$—$C_1$-$C_6$ alkyl. In any of the embodiments described throughout, q is 1 or 2; and each $R^{10}$ is independently cyano, halo, optionally substituted $C_1$-$C_6$ alkyl, or —S(O)$_2$—$C_1$-$C_6$ alkyl. In any of the embodiments described throughout, q is 0, 1 or 2; and each $R^{10}$ is independently cyano, fluoro, chloro, bromo, methyl, trifluoromethyl, or —S(O)$_2$-methyl. In any of the embodiments described throughout, q is 1 or 2; and each $R^{10}$ is independently cyano, fluoro, chloro, bromo, methyl, trifluoromethyl, or —S(O)$_2$-methyl.

In any of the embodiments described throughout, the A ring is an optionally substituted heteroaryl ring. In any of the embodiments described throughout, the A ring is an unsubstituted heteroaryl ring. In any of the embodiments described throughout, the A ring is an optionally substituted 5-membered heteroaryl ring. In any of the embodiments described throughout, the A ring is an unsubstituted 5-membered heteroaryl ring. In any of the embodiments described throughout, the A ring is an optionally substituted 6-membered heteroaryl ring. In any of the embodiments described throughout, the A ring is a heteroaryl ring substituted with at least one halo. In any of the embodiments described throughout, the A ring is a 5-membered heteroaryl ring substituted with at least one halo.

In any of the embodiments described throughout, the A ring is optionally substituted isoxazolyl, pyrazolyl, oxadiazolyl or triazolyl; and L is —C($R^8$)$_2$— and each $R^8$ is taken together with the carbon atom to which they are attached to form cyclopropyl.

In any of the embodiments described throughout, the A ring is optionally substituted isoxazolyl, pyrazolyl, oxadiazolyl or triazolyl; and $R^3$ and $R^6$ together with the carbon atoms to which they are attached form an optionally substituted cyclopropyl ring.

In any of the embodiments described throughout, the A ring is of the formula:

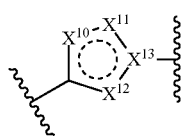

wherein
$X^{10}$, $X^{11}$ and $X^{12}$ are each S, O, N, $CR^{13}$ or $NR^{13}$, and $X^{13}$ is C or N; and
each $R^{13}$ is independently H, halo, cyano or optionally substituted $C_1$-$C_6$ alkyl.

In certain embodiments, at least one of $X^{10}$, $X^{11}$ and $X^{12}$ is $CR^{13}$ or $NR^{13}$ and at least one $R^{13}$ is halo, cyano or optionally substituted $C_1$-$C_6$ alkyl. In certain embodiments, at least one of $X^{10}$, $X^{11}$ and $X^{12}$ is $CR^{13}$ or $NR^{14}$ and at least one $R^{13}$ is halo.

In any of the embodiments described throughout, the A ring is one of the following:

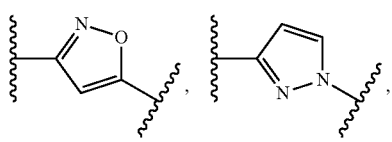

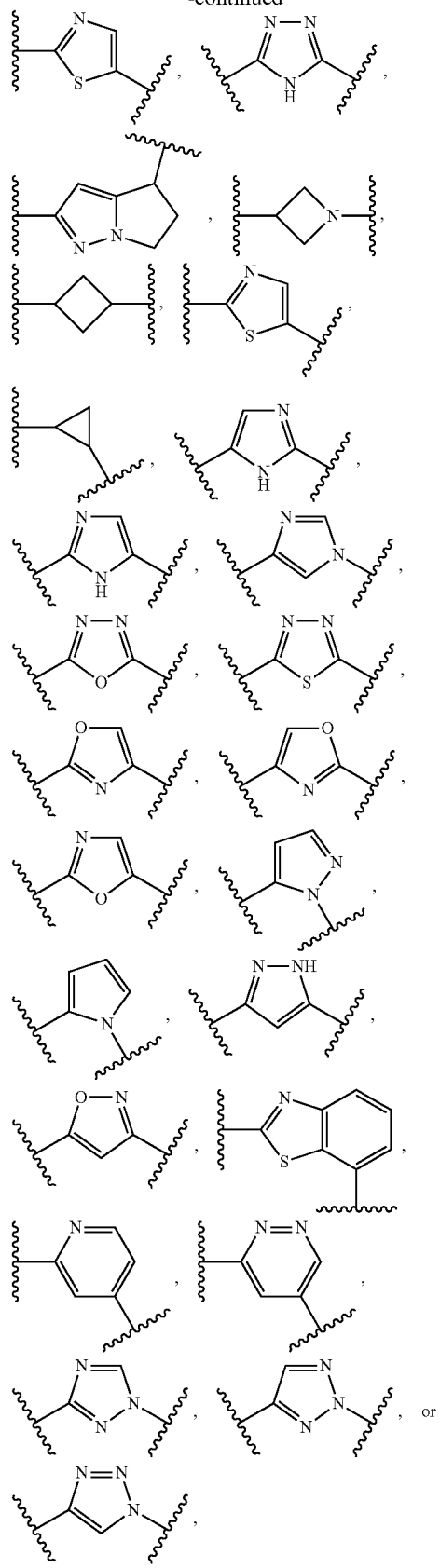

wherein each ring may be optionally substituted.

In any of the embodiments described throughout, the A ring is one of the following:
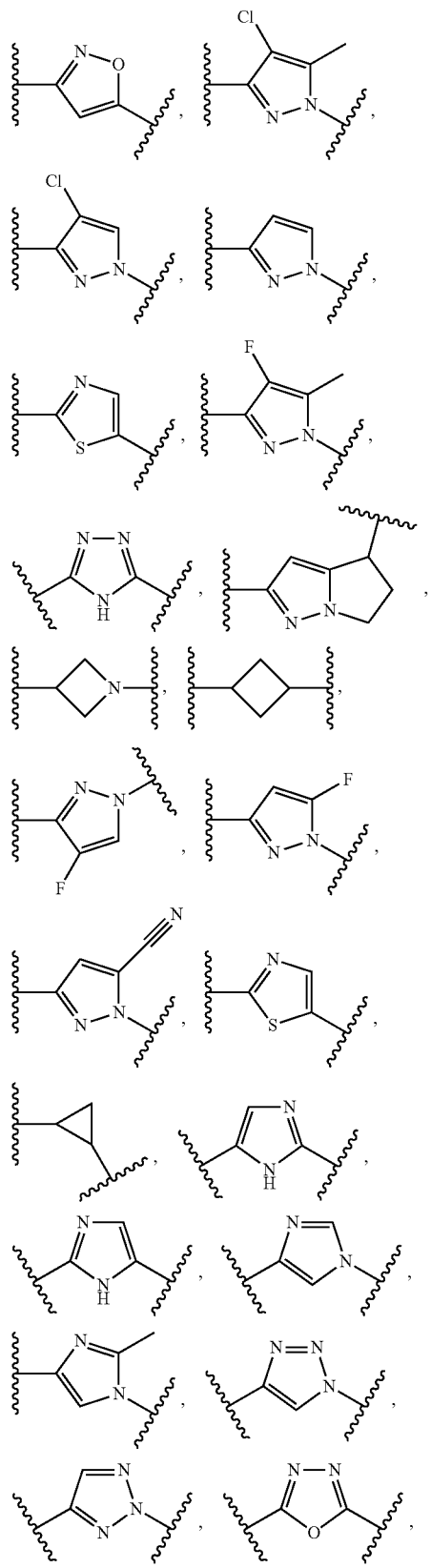
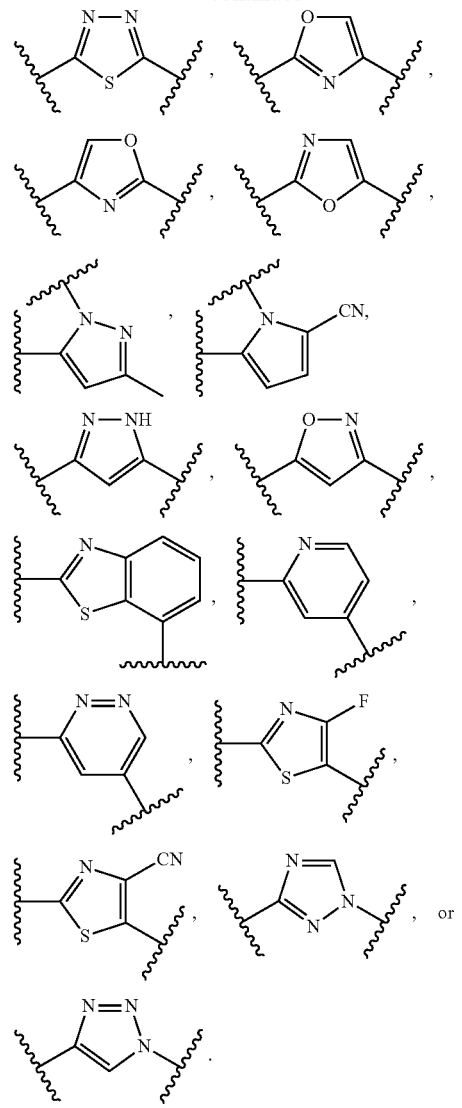
In any of the embodiments described throughout, the A ring is one of the following:
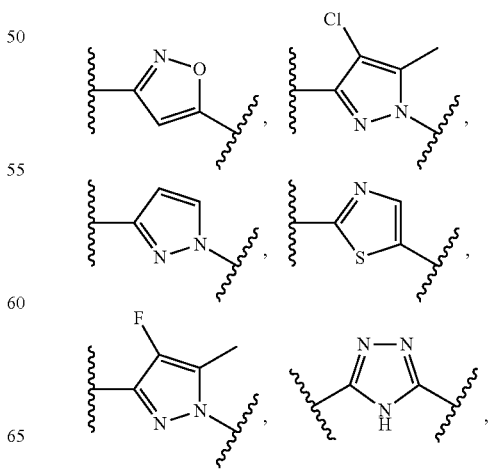

In any of the embodiments described throughout, the A ring is one of the following:

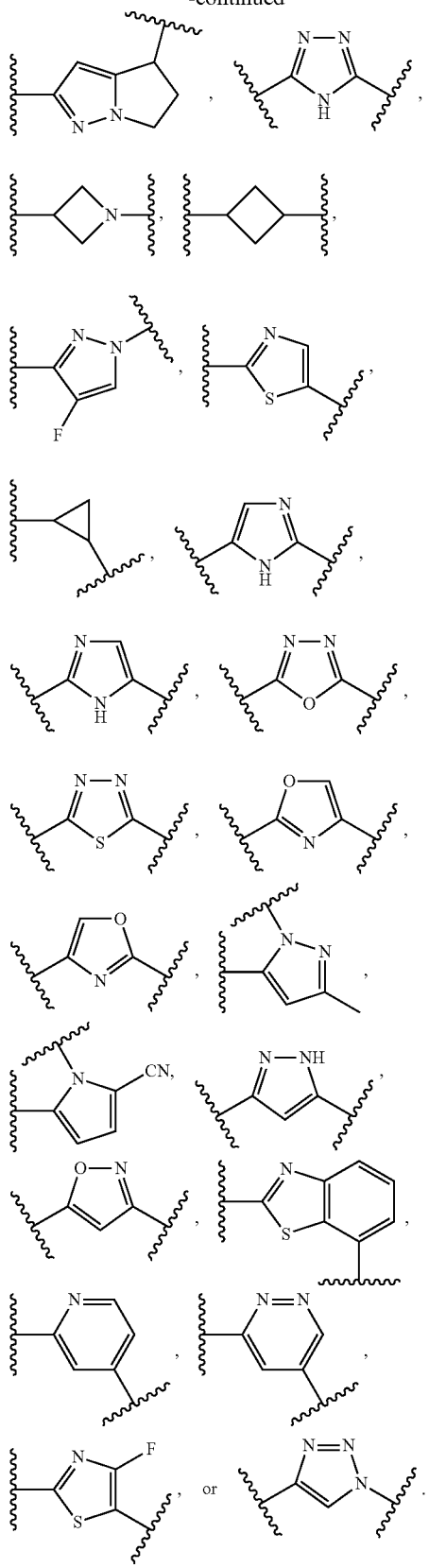
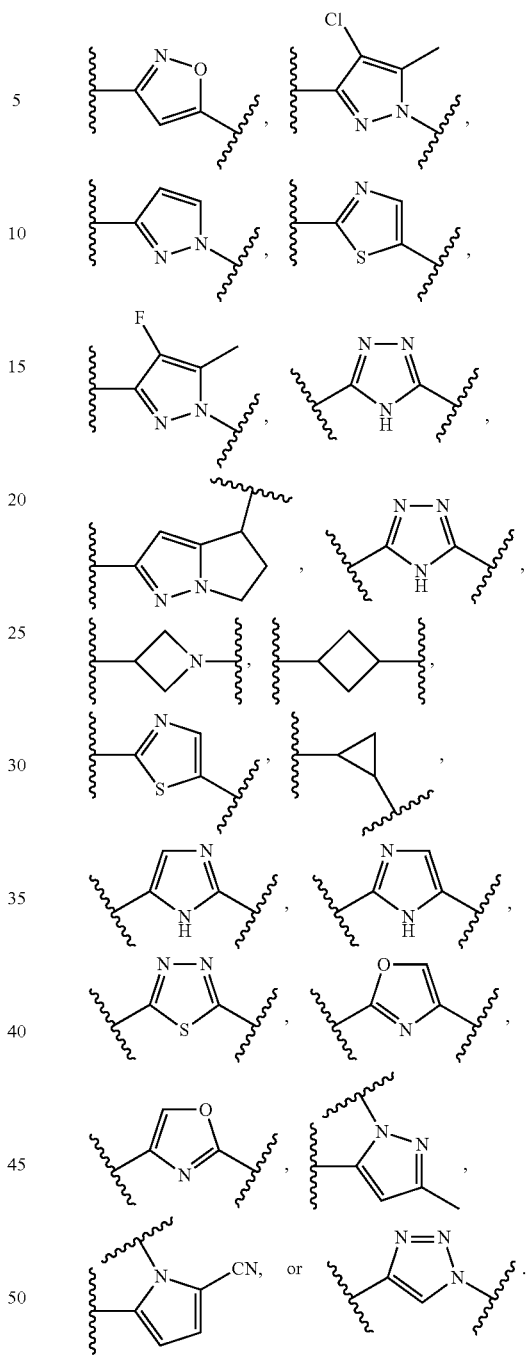

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I (and all other Formulas described herein), are specifically embraced by herein just as if each and every combination was individually and explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, such as those conditions or disorders mediated by receptor-interacting protein kinase 1, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

In certain embodiments, a compound may be selected from those compounds in Table 1, 2, 3 or 4. Also included within the disclosure are stereoisomers and mixtures of stereoisomers thereof. Also included within the disclosure is a compound selected from Table 1, 2, 3 or 4, or pharmaceutically acceptable salt thereof.

TABLE 1

| No. | Structure |
|---|---|
| 1 | 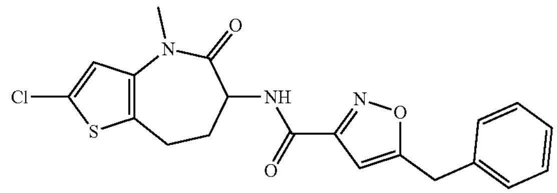 |
| 1A | 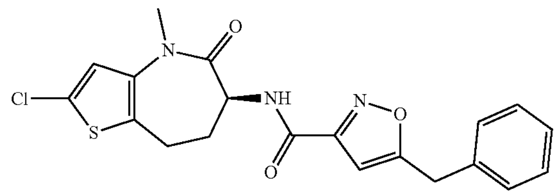 [SMILES: CN1C(=O)C(NC(=O)c2cc(Cc3ccccc3)on2)CCc2sc(Cl)cc21] |
| 1B | 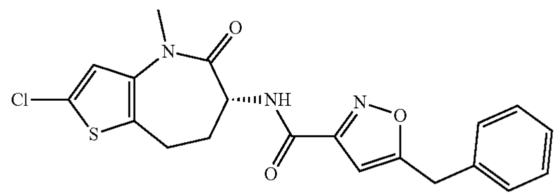 [SMILES: CN1C(=O)[C@H](NC(=O)c2cc(Cc3ccccc3)on2)CCc2sc(Cl)cc21] |
| 2 | 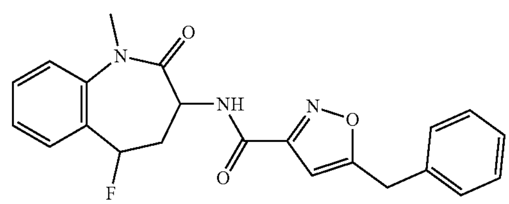 [SMILES: CN1C(=O)C(NC(=O)c2cc(Cc3ccccc3)on2)CC(F)c2ccccc21] |
| 3 | 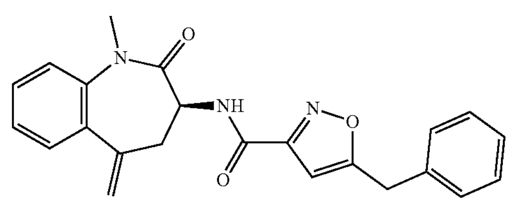 [SMILES: C=C1C[C@H](NC(=O)c2cc(Cc3ccccc3)on2)C(=O)N(C)c2ccccc21] |
| 4 | 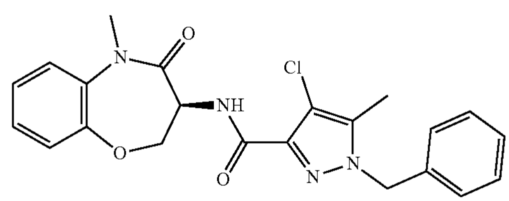 [SMILES: Cc1c(Cl)c(C(=O)N[C@H]2COc3ccccc3N(C)C2=O)nn1Cc1ccccc1] |

TABLE 1-continued

| No. | Structure |
|-----|-----------|
| 5 | 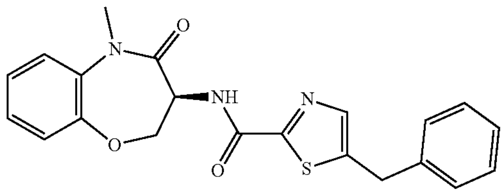 [SMILES: CN1C(=O)[C@@H](NC(=O)c2ncc(Cc3ccccc3)s2)COc2ccccc21] |
| 6 | 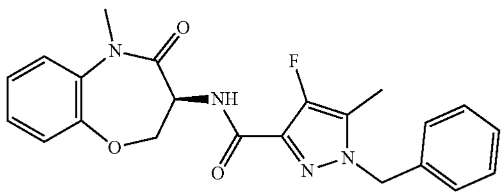 |
| 7 | 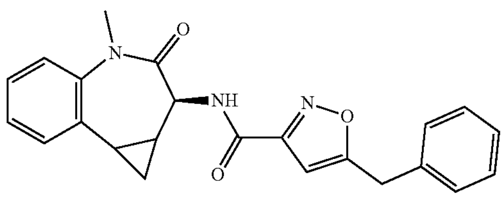 [SMILES: CN1C(=O)[C@@H](NC(=O)c2cc(Cc3ccccc3)on2)C2CC2c2ccccc21] |
| 7A | 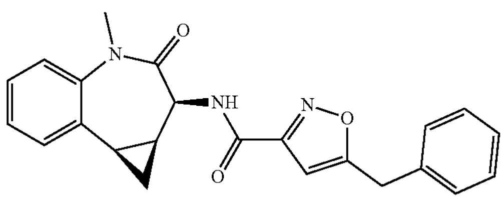 |
| 7B | 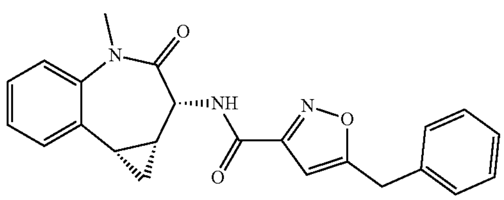 |
| 8 | 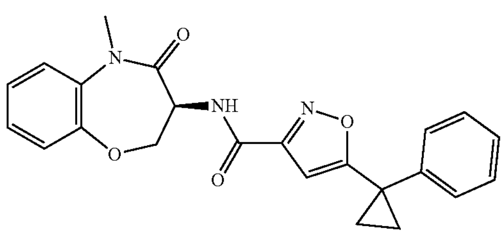 [SMILES: CN1C(=O)[C@@H](NC(=O)c2cc(C3(c4ccccc4)CC3)on2)COc2ccccc21] |
| 9 | 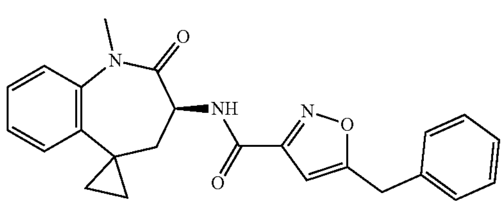 [SMILES: CN1C(=O)[C@@H](NC(=O)c2cc(Cc3ccccc3)on2)CC2(CC2)c2ccccc21] |

TABLE 1-continued
| No. | Structure |
|---|---|
| 10 | 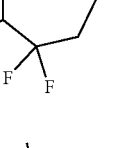 |
| 11 | 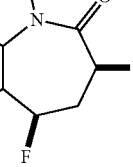 |
| 11A | 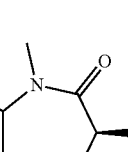 |
| 11B | 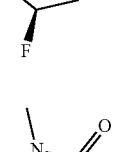 |
| 12 | 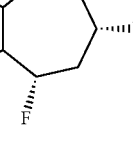 |
| 12A | 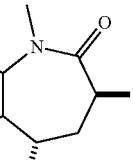 |
| 12B | 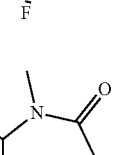 |

TABLE 1-continued
| No. | Structure |
|---|---|
| 13 | 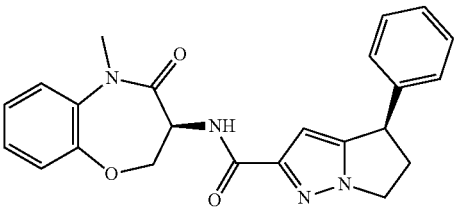 [SMILES: CN1C(=O)[C@@H](NC(=O)c2cc3n(n2)CC[C@@H]3c2ccccc2)COc2ccccc21] |
| 14 | 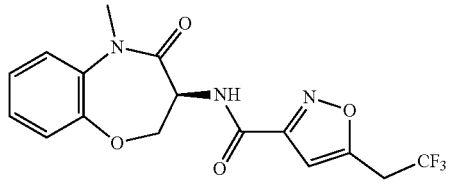 [SMILES: CN1C(=O)[C@@H](NC(=O)c2cc(CC(F)(F)F)on2)COc2ccccc21] |
| 15 | 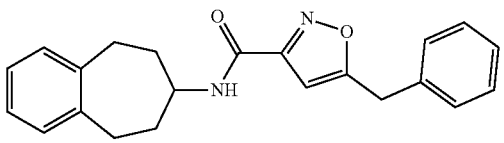 [SMILES: O=C(NC1CCc2ccccc2CC1)c1cc(Cc2ccccc2)on1] |
| 16 | 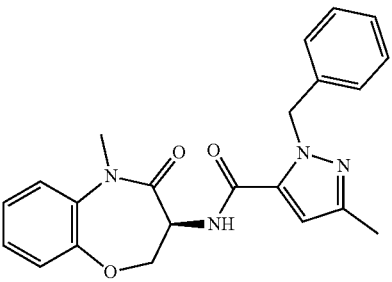 [SMILES: Cc1cc(C(=O)N[C@H]2COc3ccccc3N(C)C2=O)n(Cc2ccccc2)n1] |
| 17 | 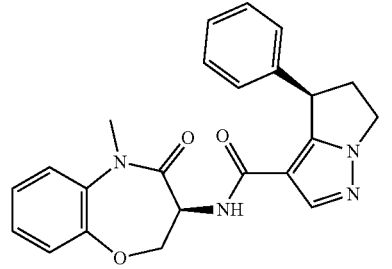 [SMILES: CN1C(=O)[C@@H](NC(=O)c2cnn3c2[C@@H](c2ccccc2)CC3)COc2ccccc21] |
| 18 | 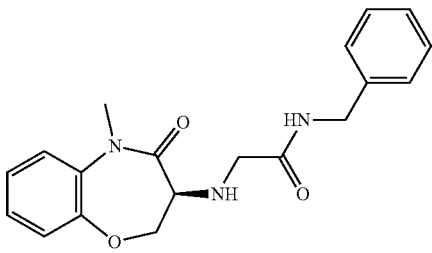 [SMILES: CN1C(=O)[C@@H](NCC(=O)NCc2ccccc2)COc2ccccc21] |

TABLE 1-continued

| No. | Structure |
|---|---|
| 19 | 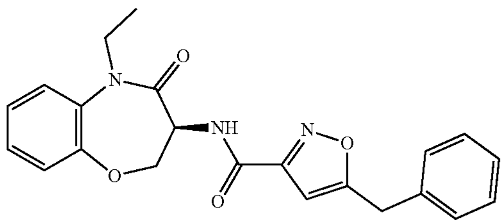 [SMILES: CCN1C(=O)[C@@H](NC(=O)c2cc(Cc3ccccc3)on2)COc2ccccc21] |
| 20 | 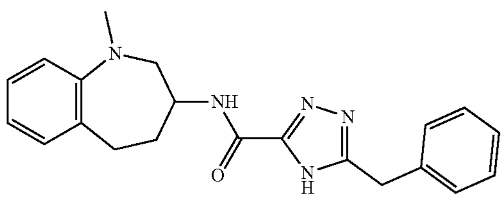 [SMILES: CN1CC(NC(=O)c2nnc(Cc3ccccc3)[nH]2)CCc2ccccc21] |
| 21 | 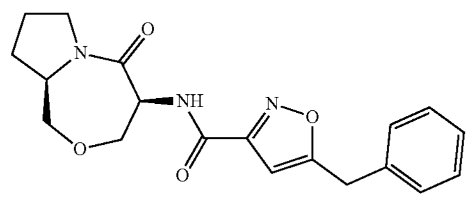 [SMILES: O=C(N[C@H]1COC[C@H]2CCCN2C1=O)c1cc(Cc2ccccc2)on1] |
| 22 | 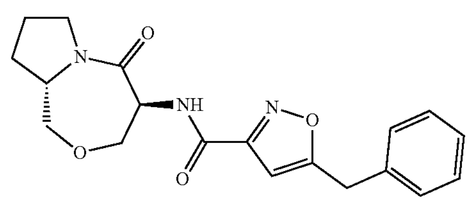 [SMILES: O=C(N[C@H]1COC[C@@H]2CCCN2C1=O)c1cc(Cc2ccccc2)on1] |
| 23 | 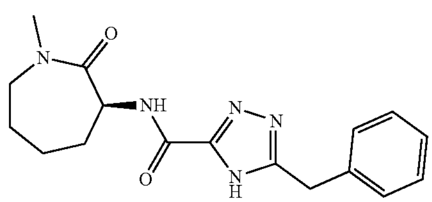 [SMILES: CN1CCCC[C@H](NC(=O)c2nnc(Cc3ccccc3)[nH]2)C1=O] |
| 24 | 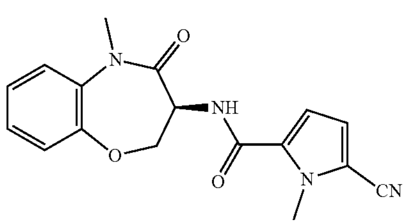 [SMILES: CN1C(=O)[C@@H](NC(=O)c2ccc(C#N)n2C)COc2ccccc21] |
| 25 | 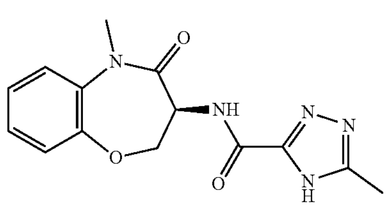 [SMILES: Cc1nnc(C(=O)N[C@H]2COc3ccccc3N(C)C2=O)[nH]1] |

TABLE 1-continued

| No. | Structure |
|---|---|
| 26 | 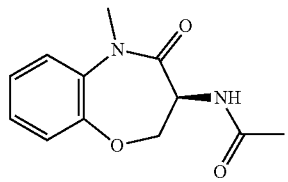 [SMILES: CC(=O)N[C@H]1COc2ccccc2N(C)C1=O] |
| 27 | 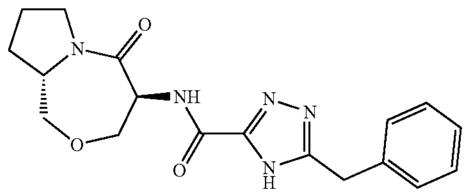 [SMILES: O=C(N[C@H]1COC[C@@H]2CCCN2C1=O)c1nnc(Cc2ccccc2)[nH]1] |
| 28 | 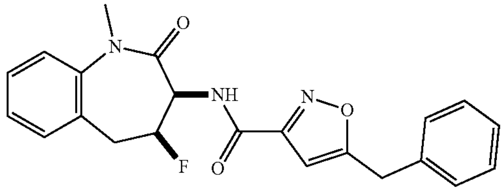 [SMILES: CN1C(=O)[C@@H](NC(=O)c2cc(Cc3ccccc3)on2)[C@@H](F)Cc2ccccc21] |
| 29 | 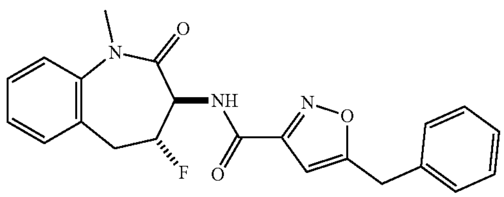 [SMILES: CN1C(=O)[C@@H](NC(=O)c2cc(Cc3ccccc3)on2)[C@H](F)Cc2ccccc21] |
| 30 | 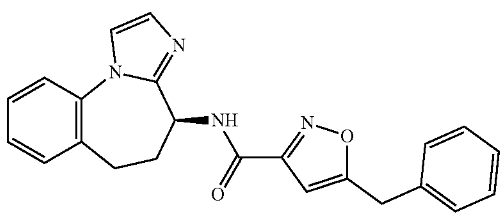 [SMILES: O=C(N[C@H]1CCc2ccccc2-n2ccnc21)c1cc(Cc2ccccc2)on1] |
| 31 | 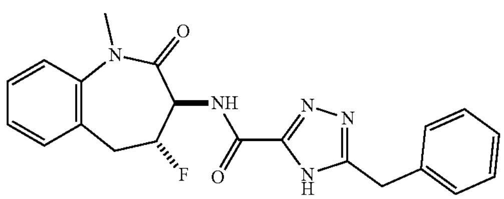 [SMILES: CN1C(=O)[C@@H](NC(=O)c2nnc(Cc3ccccc3)[nH]2)[C@H](F)Cc2ccccc21] |
| 32 | 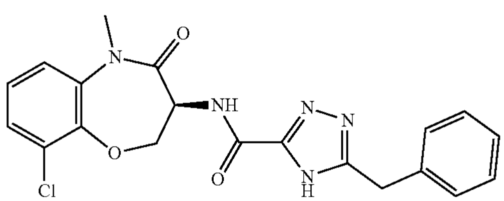 [SMILES: CN1C(=O)[C@@H](NC(=O)c2nnc(Cc3ccccc3)[nH]2)COc2c(Cl)cccc21] |
| 33 | 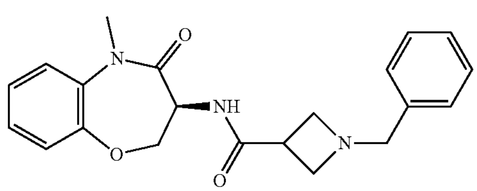 |

TABLE 1-continued

| No. | Structure |
|---|---|
| 34 | 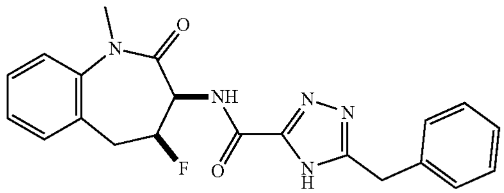 [SMILES: CN1C(=O)[C@@H](NC(=O)c2nnc(Cc3ccccc3)[nH]2)[C@@H](F)Cc2ccccc21] |
| 35 | 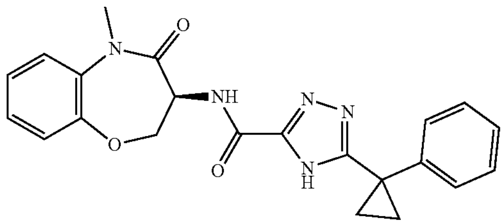 [SMILES: CN1C(=O)[C@@H](NC(=O)c2nnc(C3(c4ccccc4)CC3)[nH]2)COc2ccccc21] |
| 36 | 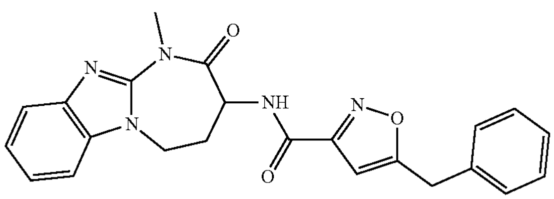 [SMILES: CN1C(=O)C(NC(=O)c2cc(Cc3ccccc3)on2)CCn2c1nc1ccccc12] |
| 37 | 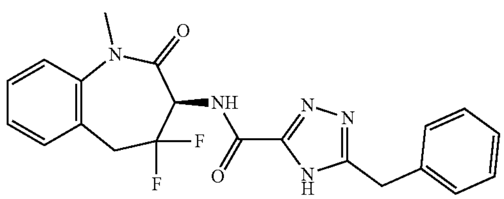 [SMILES: CN1C(=O)[C@@H](NC(=O)c2nnc(Cc3ccccc3)[nH]2)C(F)(F)Cc2ccccc21] |
| 38A | 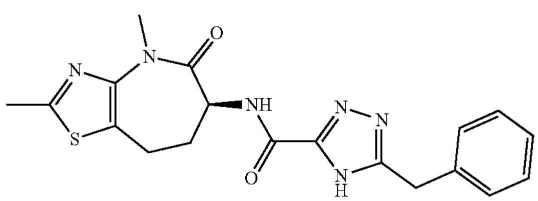 [SMILES: Cc1nc2c(s1)CC[C@H](NC(=O)c1nnc(Cc3ccccc3)[nH]1)C(=O)N2C] |
| 38B | 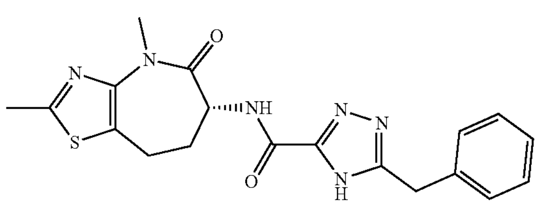 [SMILES: Cc1nc2c(s1)CC[C@@H](NC(=O)c1nnc(Cc3ccccc3)[nH]1)C(=O)N2C] |
| 39 | 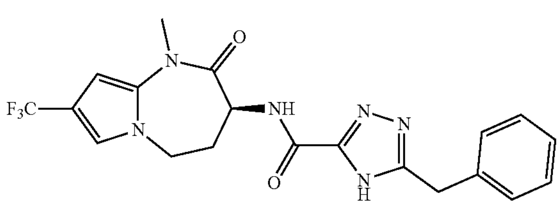 [SMILES: CN1C(=O)[C@@H](NC(=O)c2nnc(Cc3ccccc3)[nH]2)CCn2cc(C(F)(F)F)cc21] |

TABLE 1-continued
| No. | Structure |
|---|---|
| 40 | 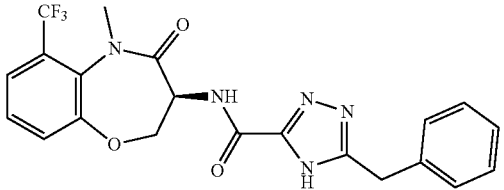 [SMILES: CN1C(=O)[C@@H](NC(=O)c2nnc(Cc3ccccc3)[nH]2)COc2cccc(C(F)(F)F)c21] |
| 41 | 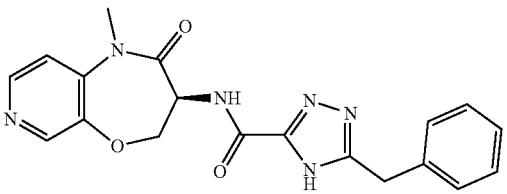 [SMILES: CN1C(=O)[C@@H](NC(=O)c2nnc(Cc3ccccc3)[nH]2)COc2cnccc21] |
| 42 | 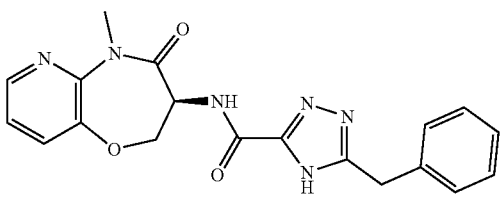 |
| 43 | 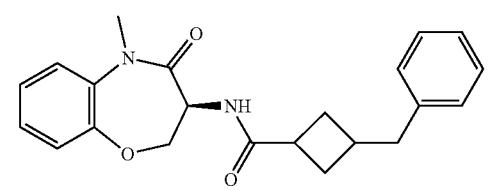 [SMILES: CN1C(=O)[C@@H](NC(=O)C2CC(Cc3ccccc3)C2)COc2ccccc21] |
| 43A | 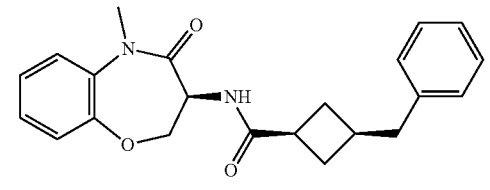 [SMILES: CN1C(=O)[C@@H](NC(=O)[C@H]2C[C@@H](Cc3ccccc3)C2)COc2ccccc21] |
| 44 | 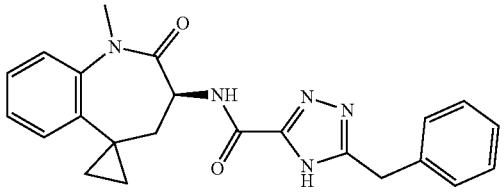 [SMILES: CN1C(=O)[C@@H](NC(=O)c2nnc(Cc3ccccc3)[nH]2)CC2(CC2)c2ccccc21] |
| 45 | 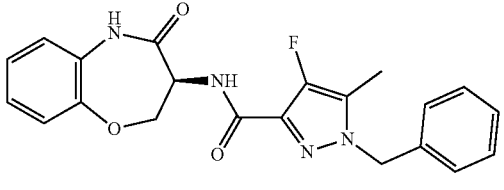 [SMILES: Cc1c(F)c(C(=O)N[C@H]2COc3ccccc3NC2=O)nn1Cc1ccccc1] |
| 46 | 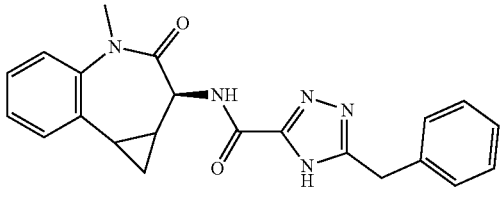 [SMILES: CN1C(=O)[C@@H](NC(=O)c2nnc(Cc3ccccc3)[nH]2)C2CC2c2ccccc21] |

TABLE 1-continued

| No. | Structure |
|---|---|
| 46A | 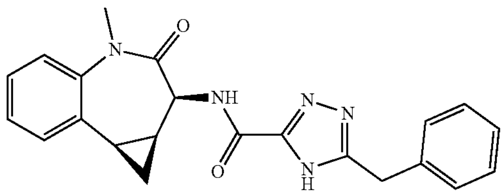 [SMILES: CN1C(=O)[C@@H](NC(=O)c2nnc(Cc3ccccc3)[nH]2)[C@H]2C[C@H]2c2ccccc21] |
| 46B | 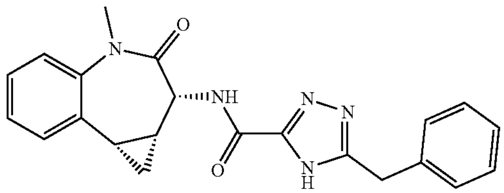 [SMILES: CN1C(=O)[C@H](NC(=O)c2nnc(Cc3ccccc3)[nH]2)[C@@H]2C[C@@H]2c2ccccc21] |
| 47 | 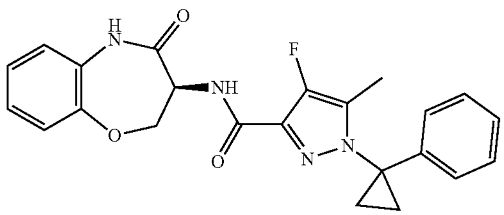 [SMILES: Cc1c(F)c(C(=O)N[C@H]2COc3ccccc3NC2=O)nn1C1(c2ccccc2)CC1] |
| 48 | 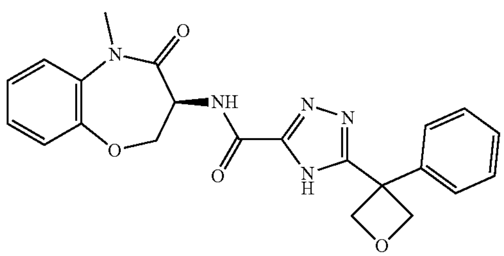 [SMILES: CN1C(=O)[C@@H](NC(=O)c2nnc(C3(c4ccccc4)COC3)[nH]2)COc2ccccc21] |
| 49 | 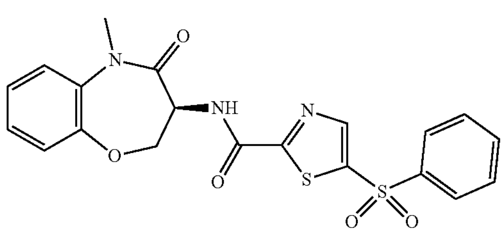 [SMILES: CN1C(=O)[C@@H](NC(=O)c2ncc(S(=O)(=O)c3ccccc3)s2)COc2ccccc21] |
| 50 | 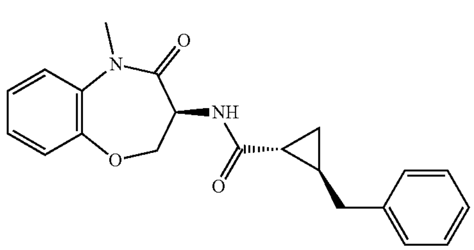 [SMILES: CN1C(=O)[C@@H](NC(=O)[C@@H]2C[C@H]2Cc2ccccc2)COc2ccccc21] |

TABLE 1-continued
| No. | Structure |
|---|---|
| 50A | 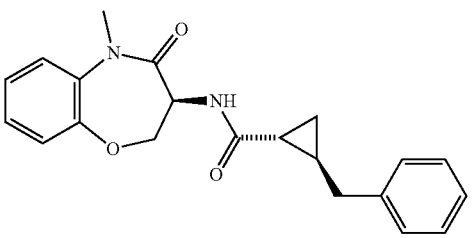<br>First eluting isomer |
| 50B | 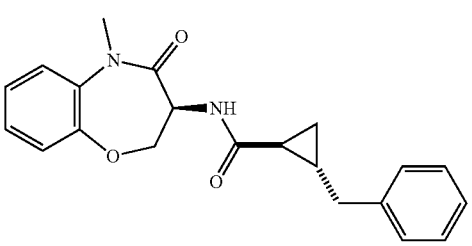<br>Second eluting isomer |
| 51 | 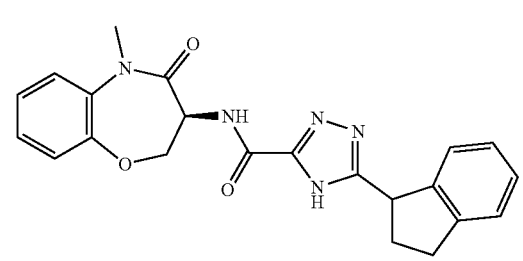 [SMILES: CN1C(=O)[C@@H](NC(=O)c2nnc(C3CCc4ccccc43)[nH]2)COc2ccccc21] |
| 52 | 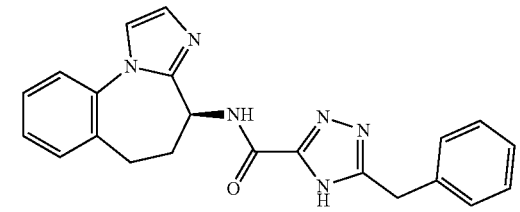 [SMILES: O=C(N[C@H]1CCc2ccccc2-n2ccnc21)c1nnc(Cc2ccccc2)[nH]1] |
| 53 | 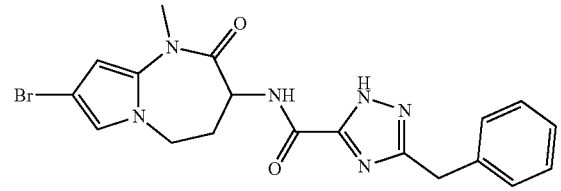 [SMILES: CN1C(=O)C(NC(=O)c2nc(Cc3ccccc3)n[nH]2)CCn2cc(Br)cc21] |
| 54A | 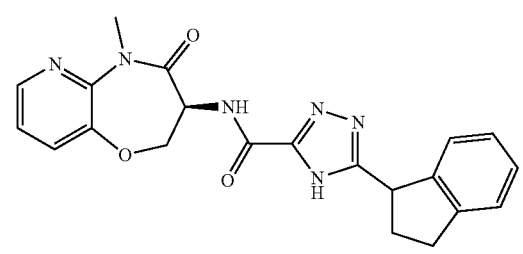<br>Diastereoisomer 1 |

TABLE 1-continued
| No. | Structure |
|---|---|
| 54B | 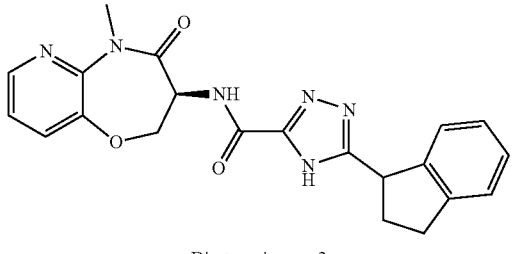<br>Diastereoisomer 2 |
| 55 | 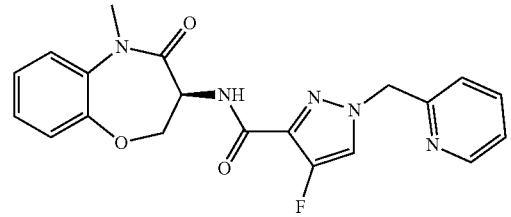 |
| 56 | 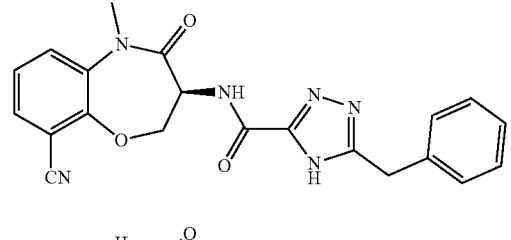 |
| 57 | 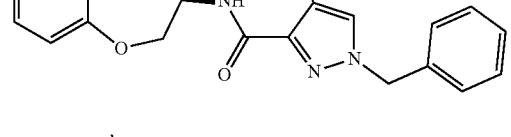 |
| 58 | 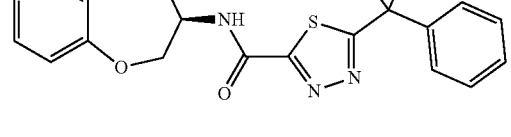 |
| 59 | 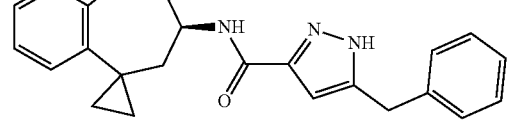 |
| 60 | 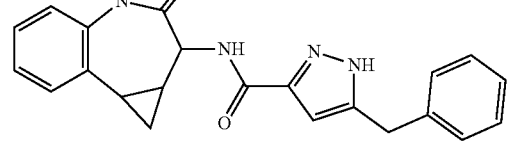 |

TABLE 1-continued

| No. | Structure |
|---|---|
| 60A | 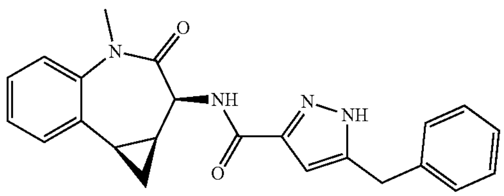 [SMILES: CN1C(=O)[C@@H](NC(=O)c2cc(Cc3ccccc3)[nH]n2)[C@H]2C[C@H]2c2ccccc21] |
| 60B | 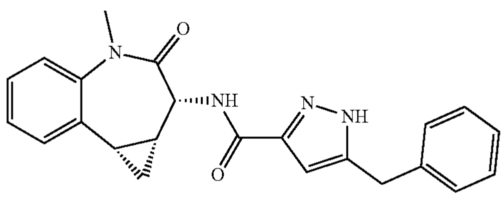 [SMILES: CN1C(=O)[C@H](NC(=O)c2cc(Cc3ccccc3)[nH]n2)[C@@H]2C[C@@H]2c2ccccc21] |
| 61 | 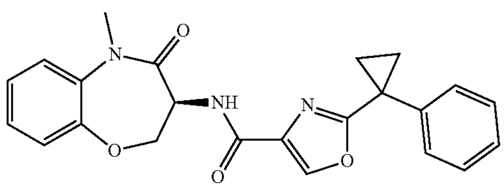 [SMILES: CN1C(=O)[C@@H](NC(=O)c2coc(C3(c4ccccc4)CC3)n2)COc2ccccc21] |
| 62 | 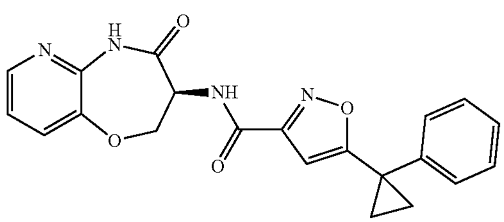 [SMILES: O=C(N[C@H]1COc2cccnc2NC1=O)c1cc(C2(c3ccccc3)CC2)on1] |
| 63 | 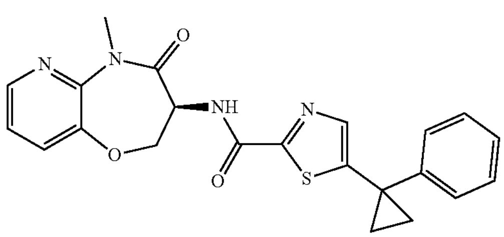 [SMILES: CN1C(=O)[C@@H](NC(=O)c2ncc(C3(c4ccccc4)CC3)s2)COc2cccnc21] |
| 64 | 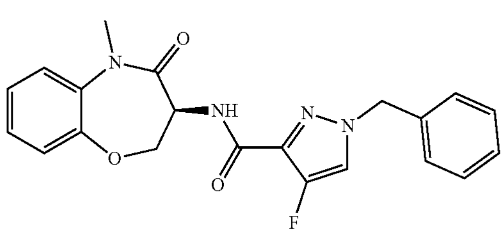 |
| 65 | 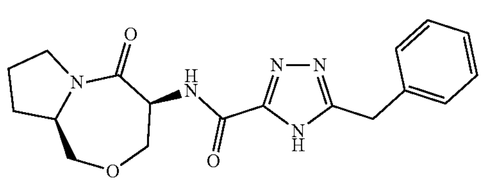 [SMILES: O=C(N[C@H]1COC[C@H]2CCCN2C1=O)c1nnc(Cc2ccccc2)[nH]1] |

TABLE 1-continued

| No. | Structure |
|---|---|
| 66 | 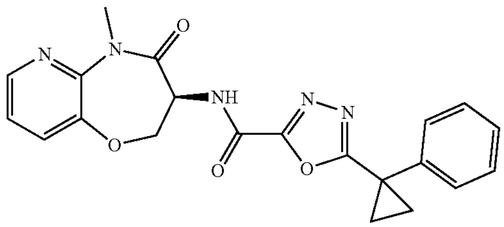 [SMILES: CN1C(=O)[C@@H](NC(=O)c2nnc(C3(c4ccccc4)CC3)o2)COc2cccnc21] |
| 67A | 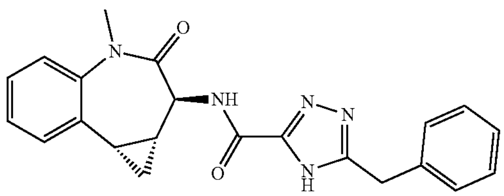 [SMILES: CN1C(=O)[C@@H](NC(=O)c2nnc(Cc3ccccc3)[nH]2)[C@@H]2C[C@@H]2c2ccccc21] |
| 67B | 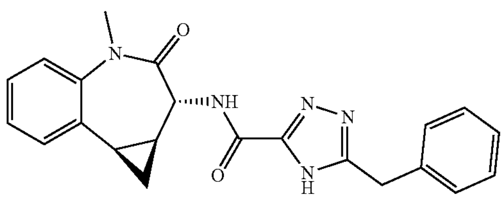 [SMILES: CN1C(=O)[C@H](NC(=O)c2nnc(Cc3ccccc3)[nH]2)[C@H]2C[C@H]2c2ccccc21] |
| 68A | 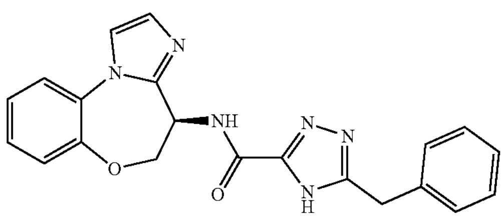 [SMILES: O=C(N[C@H]1COc2ccccc2-n2ccnc21)c1nnc(Cc2ccccc2)[nH]1] |
| 68B | 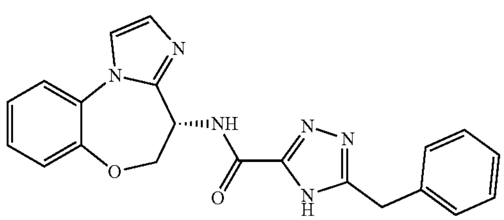 [SMILES: O=C(N[C@@H]1COc2ccccc2-n2ccnc21)c1nnc(Cc2ccccc2)[nH]1] |
| 69A | 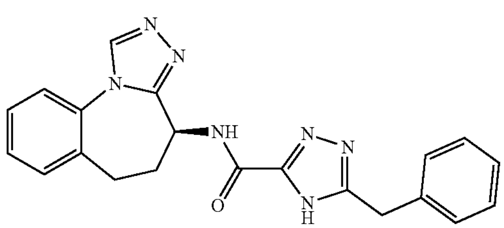 [SMILES: O=C(N[C@H]1CCc2ccccc2-n2cnnc21)c1nnc(Cc2ccccc2)[nH]1] |
| 69B | 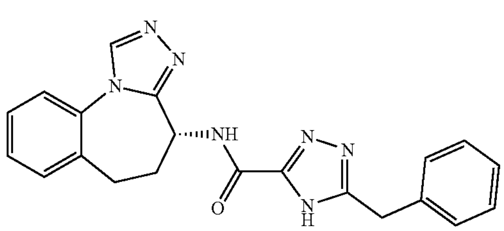 [SMILES: O=C(N[C@@H]1CCc2ccccc2-n2cnnc21)c1nnc(Cc2ccccc2)[nH]1] |

TABLE 1-continued
| No. | Structure |
|---|---|
| 70A | 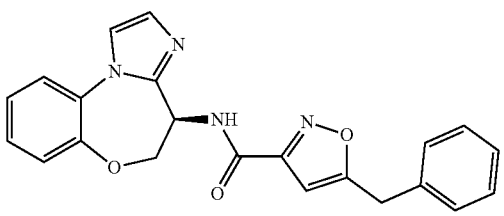 |
| 70B | 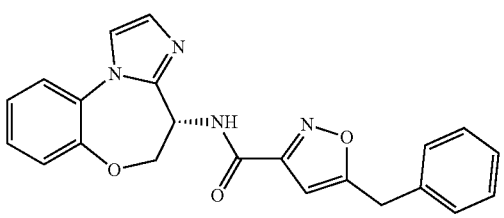 [SMILES: O=C(N[C@@H]1COc2ccccc2-n2ccnc21)c1cc(Cc2ccccc2)on1] |
| 71A | 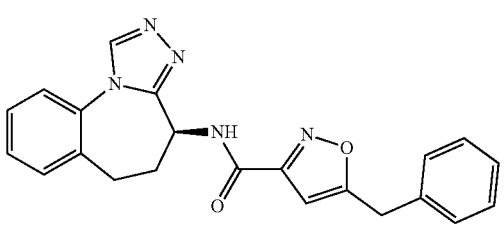 [SMILES: O=C(N[C@H]1CCc2ccccc2-n2cnnc21)c1cc(Cc2ccccc2)on1] |
| 71B | 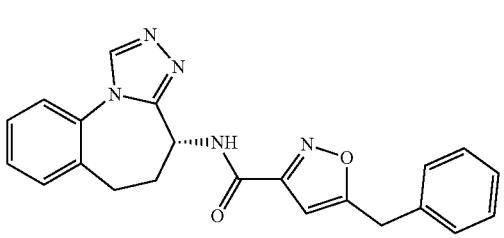 [SMILES: O=C(N[C@@H]1CCc2ccccc2-n2cnnc21)c1cc(Cc2ccccc2)on1] |
| 72 | 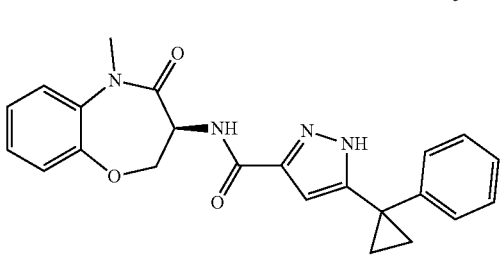 |
| 73 | 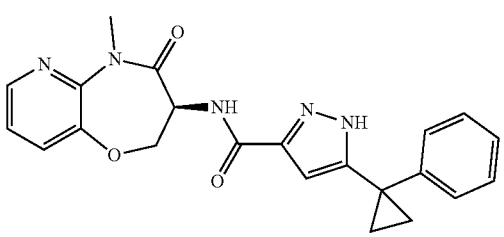 [SMILES: CN1C(=O)[C@@H](NC(=O)c2cc(C3(c4ccccc4)CC3)[nH]n2)COc2cccnc21] |
| 74 | 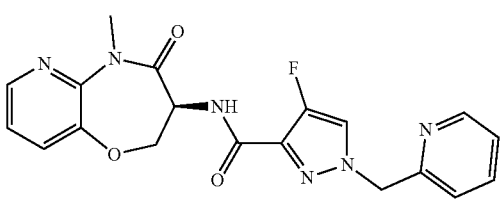 [SMILES: CN1C(=O)[C@@H](NC(=O)c2nn(Cc3ccccn3)cc2F)COc2cccnc21] |

TABLE 1-continued

| No. | Structure |
|---|---|
| 75A | 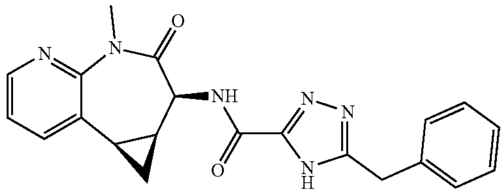 [SMILES: CN1C(=O)[C@@H](NC(=O)c2nnc(Cc3ccccc3)[nH]2)[C@H]2C[C@H]2c2cccnc21] |
| 75B | 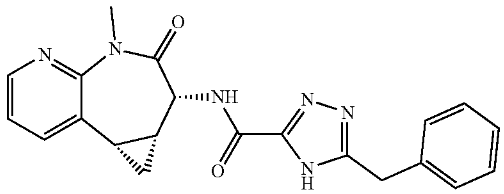 [SMILES: CN1C(=O)[C@H](NC(=O)c2nnc(Cc3ccccc3)[nH]2)[C@@H]2C[C@@H]2c2cccnc21] |
| 76 | 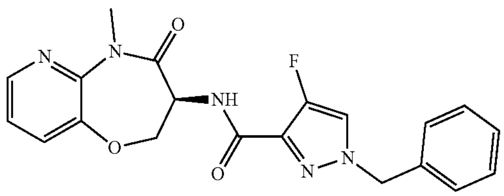 [SMILES: CN1C(=O)[C@@H](NC(=O)c2nn(Cc3ccccc3)cc2F)COc2cccnc21] |
| 77 | 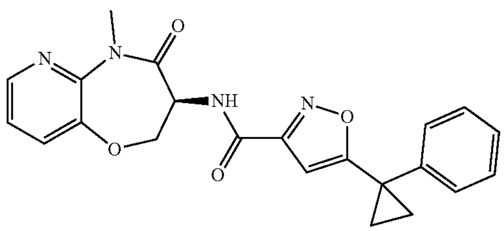 [SMILES: CN1C(=O)[C@@H](NC(=O)c2cc(C3(c4ccccc4)CC3)on2)COc2cccnc21] |
| 78 | 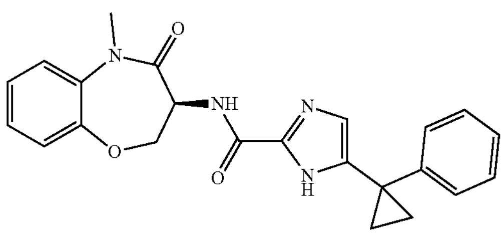 [SMILES: CN1C(=O)[C@@H](NC(=O)c2ncc(C3(c4ccccc4)CC3)[nH]2)COc2ccccc21] |
| 79 | 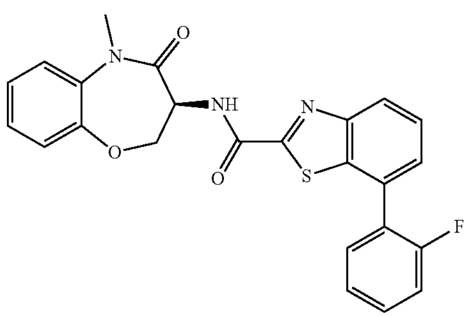 [SMILES: CN1C(=O)[C@@H](NC(=O)c2nc3cccc(-c4ccccc4F)c3s2)COc2ccccc21] |
| 80A | 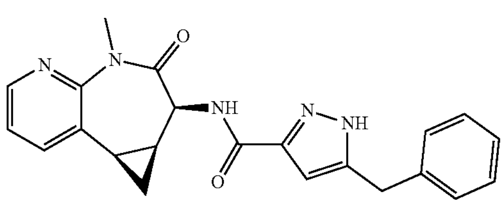 [SMILES: CN1C(=O)[C@@H](NC(=O)c2cc(Cc3ccccc3)[nH]n2)[C@H]2C[C@H]2c2cccnc21] |

TABLE 1-continued

| No. | Structure |
|---|---|
| 80B | 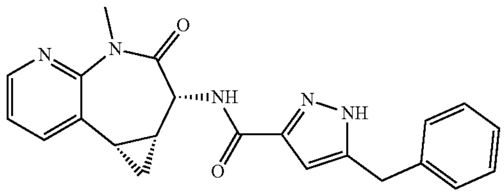 |
| 81A | 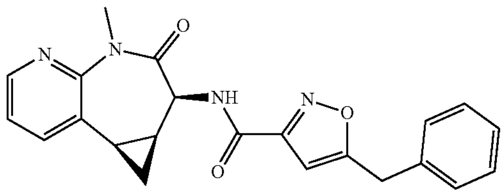 [SMILES: CN1C(=O)[C@@H](NC(=O)c2cc(Cc3ccccc3)on2)[C@H]2C[C@H]2c2cccnc21] |
| 81B | 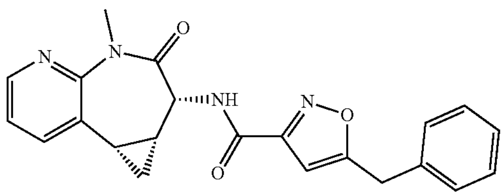 [SMILES: CN1C(=O)[C@H](NC(=O)c2cc(Cc3ccccc3)on2)[C@@H]2C[C@@H]2c2cccnc21] |
| 82A | 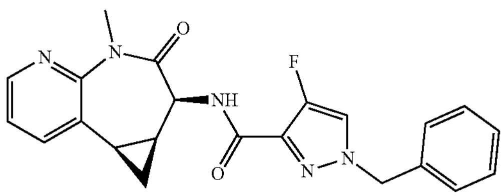 [SMILES: CN1C(=O)[C@@H](NC(=O)c2nn(Cc3ccccc3)cc2F)[C@H]2C[C@H]2c2cccnc21] |
| 82B | 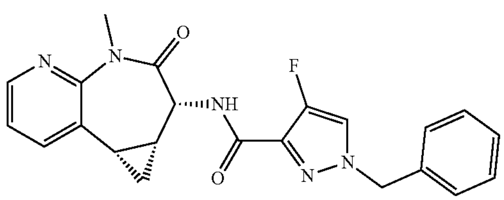 [SMILES: CN1C(=O)[C@H](NC(=O)c2nn(Cc3ccccc3)cc2F)[C@@H]2C[C@@H]2c2cccnc21] |
| 83A | 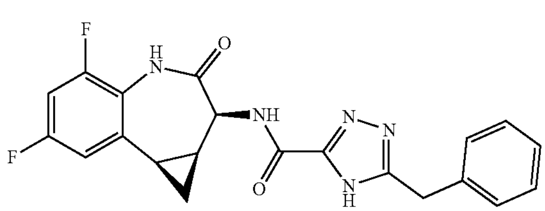 [SMILES: O=C(N[C@@H]1C(=O)Nc2c(F)cc(F)cc2[C@@H]2C[C@H]12)c1nnc(Cc2ccccc2)[nH]1] |
| 83B | 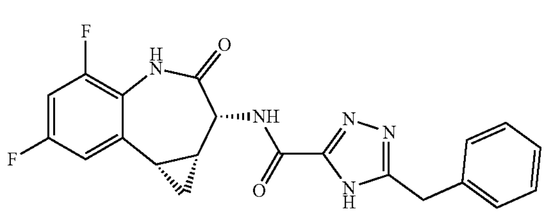 |

TABLE 1-continued

| No. | Structure |
|---|---|
| 84 | 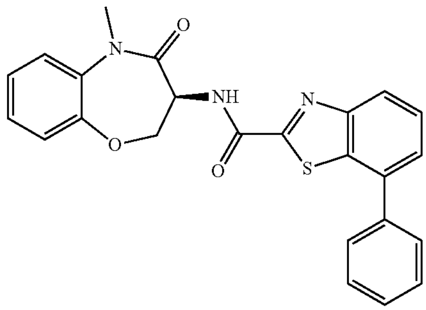 [SMILES: CN1C(=O)[C@@H](NC(=O)c2nc3cccc(-c4ccccc4)c3s2)COc2ccccc21] |
| 85 | 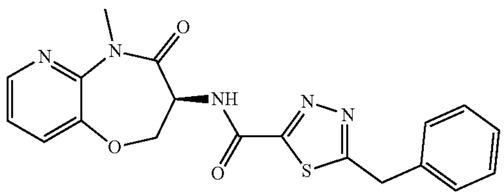 [SMILES: CN1C(=O)[C@@H](NC(=O)c2nnc(Cc3ccccc3)s2)COc2cccnc21] |
| 86 | 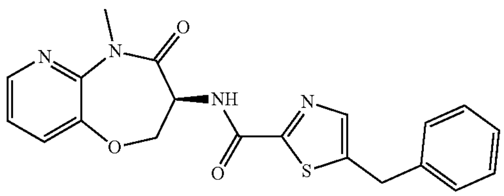 [SMILES: CN1C(=O)[C@@H](NC(=O)c2ncc(Cc3ccccc3)s2)COc2cccnc21] |
| 87 | 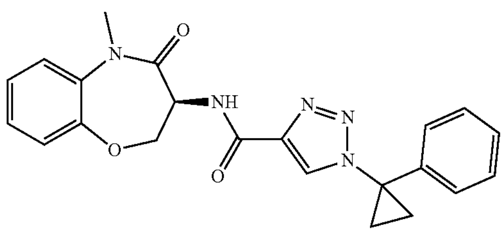 [SMILES: CN1C(=O)[C@@H](NC(=O)c2cn(C3(c4ccccc4)CC3)nn2)COc2ccccc21] |
| 88 | 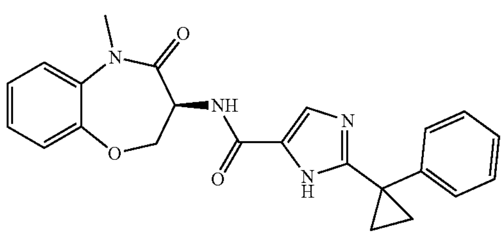 [SMILES: CN1C(=O)[C@@H](NC(=O)c2cnc(C3(c4ccccc4)CC3)[nH]2)COc2ccccc21] |
| 89A | 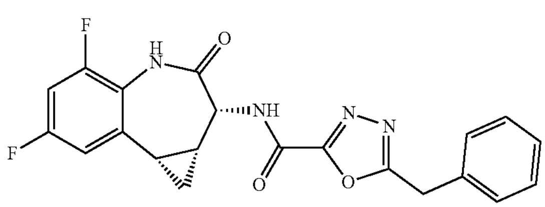 [SMILES: O=C(N[C@H]1C(=O)Nc2c(F)cc(F)cc2[C@H]2C[C@H]21)c1nnc(Cc2ccccc2)o1] |
| 89B | 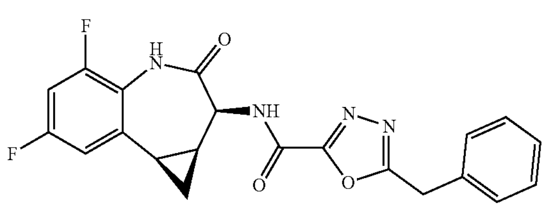 [SMILES: O=C(N[C@@H]1C(=O)Nc2c(F)cc(F)cc2[C@@H]2C[C@H]12)c1nnc(Cc2ccccc2)o1] |

TABLE 1-continued

| No. | Structure |
| --- | --- |
| 90A | 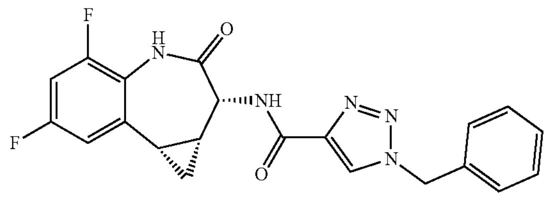 [SMILES: O=C(N[C@H]1C(=O)Nc2c(F)cc(F)cc2[C@H]2C[C@H]21)c1cn(Cc2ccccc2)nn1] |
| 90B | 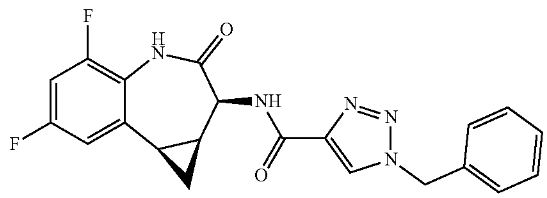 [SMILES: O=C(N[C@@H]1C(=O)Nc2c(F)cc(F)cc2[C@@H]2C[C@H]12)c1cn(Cc2ccccc2)nn1] |
| 91 | 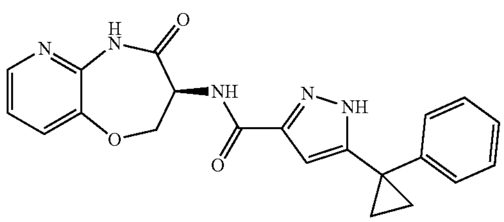 [SMILES: O=C(N[C@H]1COc2cccnc2NC1=O)c1cc(C2(c3ccccc3)CC2)[nH]n1] |
| 92 | 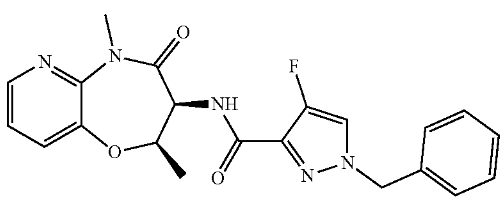 [SMILES: C[C@H]1Oc2cccnc2N(C)C(=O)[C@H]1NC(=O)c1nn(Cc2ccccc2)cc1F] |
| 93 | 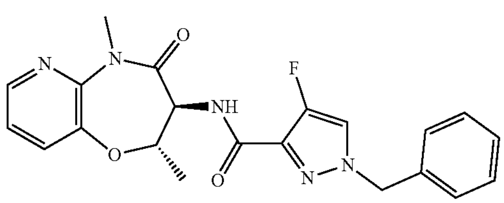 [SMILES: C[C@@H]1Oc2cccnc2N(C)C(=O)[C@H]1NC(=O)c1nn(Cc2ccccc2)cc1F] |
| 94 | 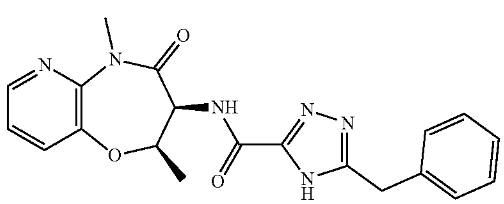 [SMILES: C[C@H]1Oc2cccnc2N(C)C(=O)[C@H]1NC(=O)c1nnc(Cc2ccccc2)[nH]1] |
| 95 | 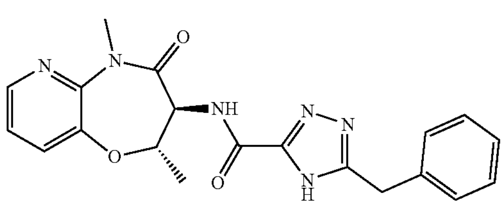 [SMILES: C[C@@H]1Oc2cccnc2N(C)C(=O)[C@H]1NC(=O)c1nnc(Cc2ccccc2)[nH]1] |

TABLE 1-continued

| No. | Structure |
|---|---|
| 96 | 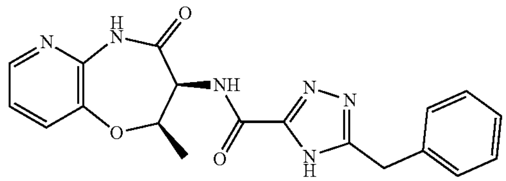 [SMILES: C[C@H]1Oc2cccnc2NC(=O)[C@H]1NC(=O)c1nnc(Cc2ccccc2)[nH]1] |
| 97 | 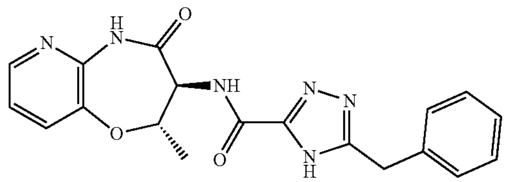 [SMILES: C[C@@H]1Oc2cccnc2NC(=O)[C@H]1NC(=O)c1nnc(Cc2ccccc2)[nH]1] |
| 98A | 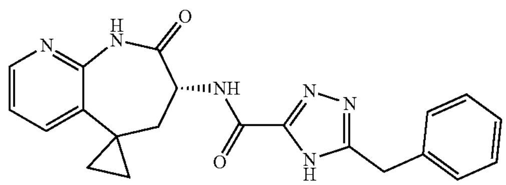 [SMILES: O=C(N[C@@H]1CC2(CC2)c2cccnc2NC1=O)c1nnc(Cc2ccccc2)[nH]1] |
| 98B | 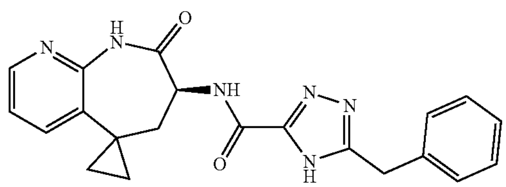 [SMILES: O=C(N[C@H]1CC2(CC2)c2cccnc2NC1=O)c1nnc(Cc2ccccc2)[nH]1] |
| 99 | 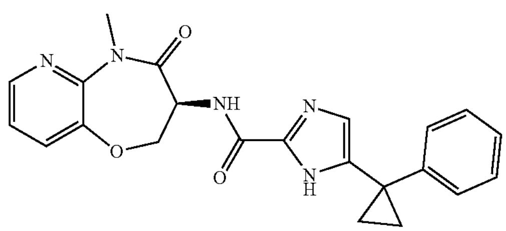 [SMILES: CN1C(=O)[C@@H](NC(=O)c2ncc(C3(c4ccccc4)CC3)[nH]2)COc2cccnc21] |
| 100A | 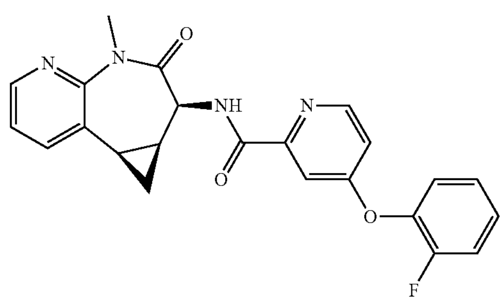 [SMILES: CN1C(=O)[C@@H](NC(=O)c2cc(Oc3ccccc3F)ccn2)[C@H]2C[C@H]2c2cccnc21] |
| 100B | 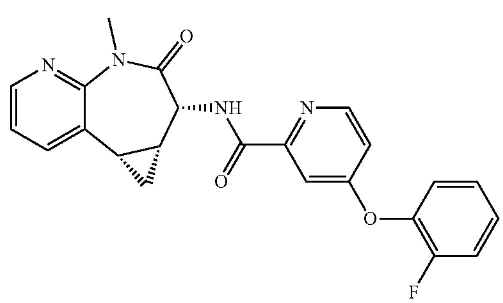 [SMILES: CN1C(=O)[C@H](NC(=O)c2cc(Oc3ccccc3F)ccn2)[C@@H]2C[C@@H]2c2cccnc21] |

TABLE 1-continued

| No. | Structure |
|---|---|
| 101A | (structure) |
| 101B | (structure) |
| 102A | (structure) First eluting isomer |
| 102B | (structure) Second eluting isomer |
| 103A | (structure) |
| 103B | (structure) |
| 104A | (structure) |

TABLE 1-continued

| No. | Structure |
|---|---|
| 104B | 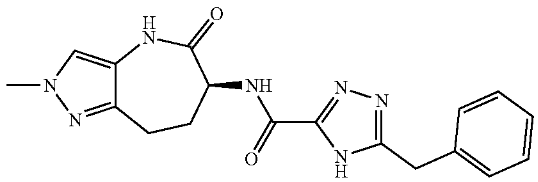 [SMILES: Cn1cc2c(n1)CC[C@H](NC(=O)c1nnc(Cc3ccccc3)[nH]1)C(=O)N2] |
| 105A | 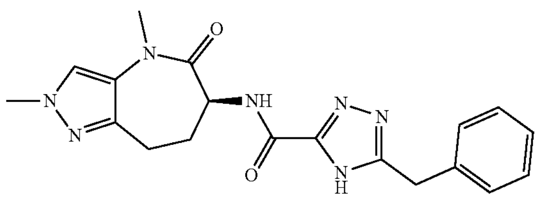 [SMILES: CN1C(=O)[C@@H](NC(=O)c2nnc(Cc3ccccc3)[nH]2)CCc2nn(C)cc21] |
| 105B | 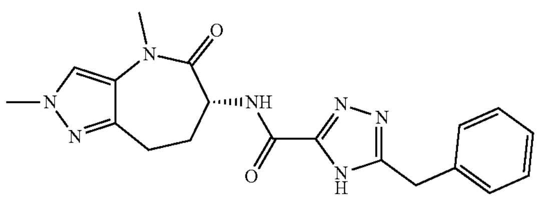 [SMILES: CN1C(=O)[C@H](NC(=O)c2nnc(Cc3ccccc3)[nH]2)CCc2nn(C)cc21] |
| 106 | 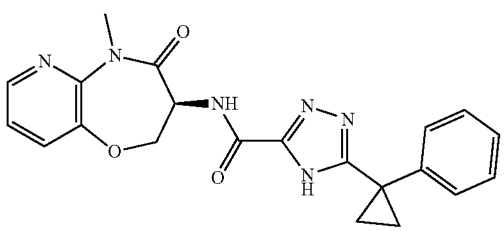 [SMILES: CN1C(=O)[C@@H](NC(=O)c2nnc(C3(c4ccccc4)CC3)[nH]2)COc2cccnc21] |
| 107A | 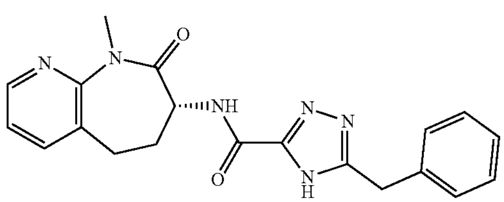 [SMILES: CN1C(=O)[C@H](NC(=O)c2nnc(Cc3ccccc3)[nH]2)CCc2cccnc21] |
| 107B | 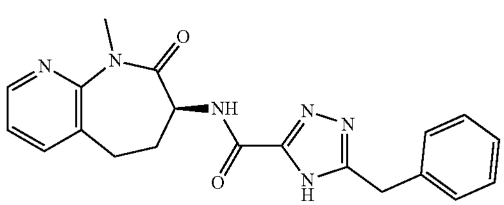 [SMILES: CN1C(=O)[C@@H](NC(=O)c2nnc(Cc3ccccc3)[nH]2)CCc2cccnc21] |
| 108 | 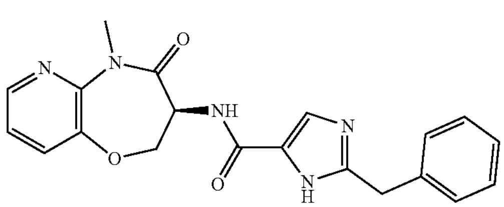 [SMILES: CN1C(=O)[C@@H](NC(=O)c2cnc(Cc3ccccc3)[nH]2)COc2cccnc21] |

TABLE 1-continued

| No. | Structure |
|---|---|
| 109A | 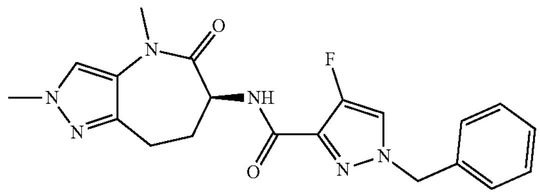 [SMILES: CN1C(=O)[C@@H](NC(=O)c2nn(Cc3ccccc3)cc2F)CCc2nn(C)cc21] |
| 109B | 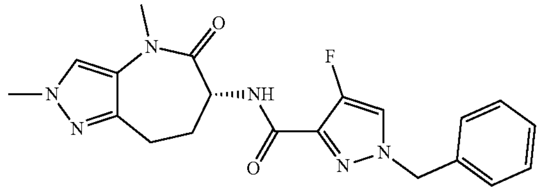 [SMILES: CN1C(=O)[C@H](NC(=O)c2nn(Cc3ccccc3)cc2F)CCc2nn(C)cc21] |
| 110A | 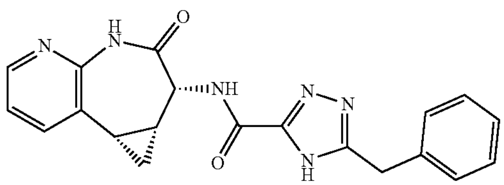 [SMILES: O=C(N[C@H]1C(=O)Nc2ncccc2[C@H]2C[C@H]21)c1nnc(Cc2ccccc2)[nH]1] |
| 110B | 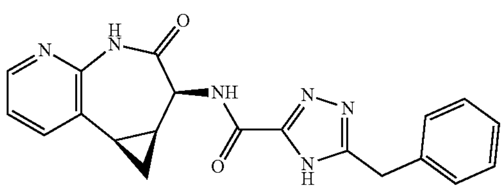 [SMILES: O=C(N[C@@H]1C(=O)Nc2ncccc2[C@@H]2C[C@H]12)c1nnc(Cc2ccccc2)[nH]1] |
| 111A | 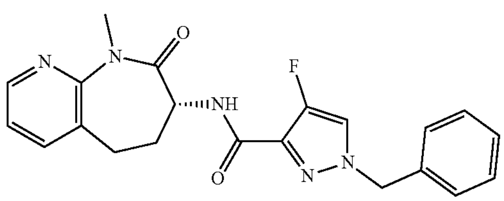 [SMILES: CN1C(=O)[C@H](NC(=O)c2nn(Cc3ccccc3)cc2F)CCc2cccnc21] |
| 111B | 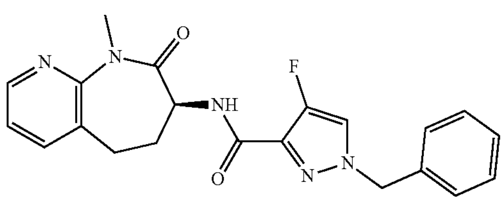 [SMILES: CN1C(=O)[C@@H](NC(=O)c2nn(Cc3ccccc3)cc2F)CCc2cccnc21] |
| 112 | 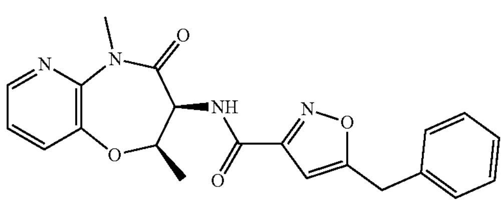 [SMILES: C[C@H]1Oc2cccnc2N(C)C(=O)[C@H]1NC(=O)c1cc(Cc2ccccc2)on1] |

TABLE 1-continued

| No. | Structure |
|---|---|
| 113 | 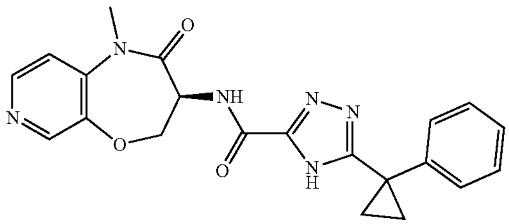 [SMILES: CN1C(=O)[C@@H](NC(=O)c2nnc(C3(c4ccccc4)CC3)[nH]2)COc2cnccc21] |
| 114A | 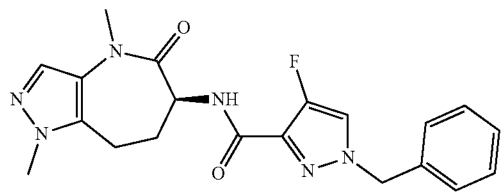 [SMILES: CN1C(=O)[C@@H](NC(=O)c2nn(Cc3ccccc3)cc2F)CCc2c1cnn2C] |
| 114B | 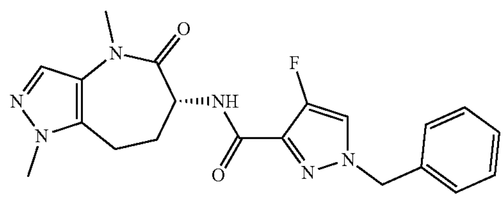 [SMILES: CN1C(=O)[C@H](NC(=O)c2nn(Cc3ccccc3)cc2F)CCc2c1cnn2C] |
| 115 | 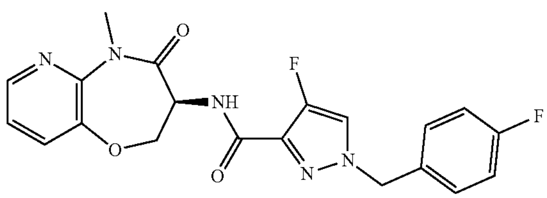 [SMILES: CN1C(=O)[C@@H](NC(=O)c2nn(Cc3ccc(F)cc3)cc2F)COc2cccnc21] |
| 116 | 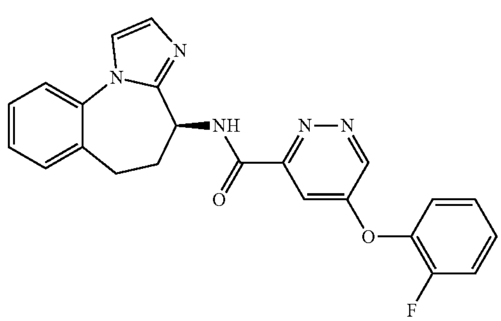 [SMILES: O=C(N[C@H]1CCc2ccccc2-n2ccnc21)c1cc(Oc2ccccc2F)cnn1] |
| 117 | 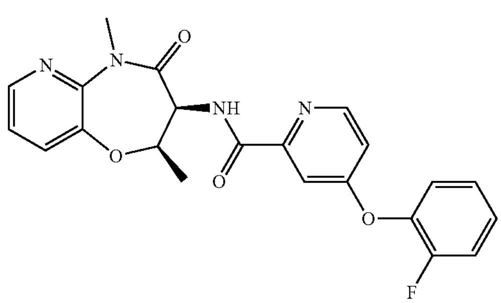 [SMILES: C[C@H]1Oc2cccnc2N(C)C(=O)[C@H]1NC(=O)c1cc(Oc2ccccc2F)ccn1] |

TABLE 1-continued

| No. | Structure |
|---|---|
| 118A | 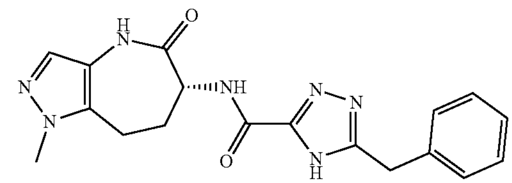 [SMILES: Cn1ncc2c1CC[C@@H](NC(=O)c1nnc(Cc3ccccc3)[nH]1)C(=O)N2] |
| 118B | 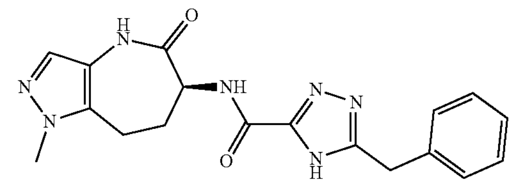 [SMILES: Cn1ncc2c1CC[C@H](NC(=O)c1nnc(Cc3ccccc3)[nH]1)C(=O)N2] |
| 119A | 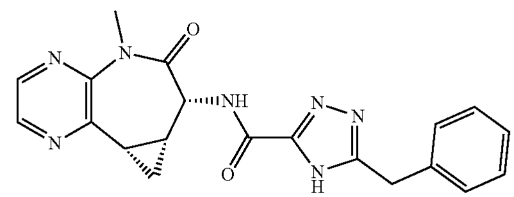 [SMILES: CN1C(=O)[C@H](NC(=O)c2nnc(Cc3ccccc3)[nH]2)[C@@H]2C[C@@H]2c2nccnc21] |
| 119B | 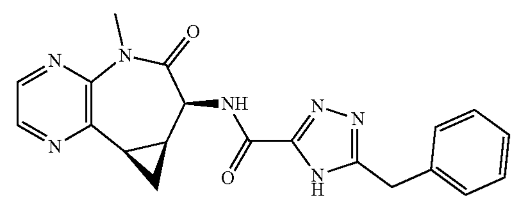 [SMILES: CN1C(=O)[C@@H](NC(=O)c2nnc(Cc3ccccc3)[nH]2)[C@H]2C[C@H]2c2nccnc21] |
| 120A | 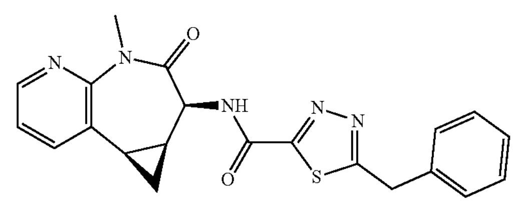 [SMILES: CN1C(=O)[C@@H](NC(=O)c2nnc(Cc3ccccc3)s2)[C@H]2C[C@H]2c2cccnc21] |
| 120B | 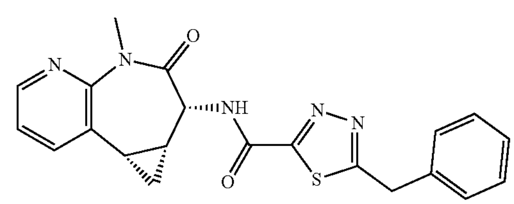 [SMILES: CN1C(=O)[C@H](NC(=O)c2nnc(Cc3ccccc3)s2)[C@@H]2C[C@@H]2c2cccnc21] |
| 121A | 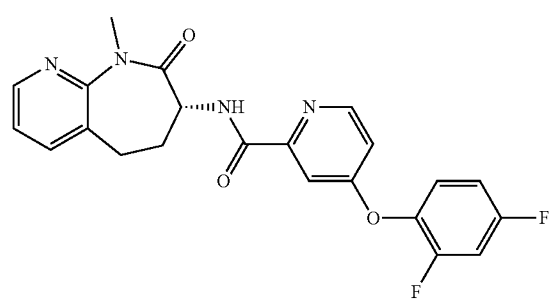 [SMILES: CN1C(=O)[C@H](NC(=O)c2cc(Oc3ccc(F)cc3F)ccn2)CCc2cccnc21] |

TABLE 1-continued

| No. | Structure |
|---|---|
| 121B | 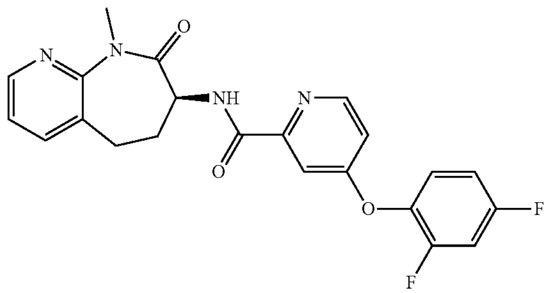 [SMILES: CN1C(=O)[C@@H](NC(=O)c2cc(Oc3ccc(F)cc3F)ccn2)CCc2cccnc21] |
| 122 | 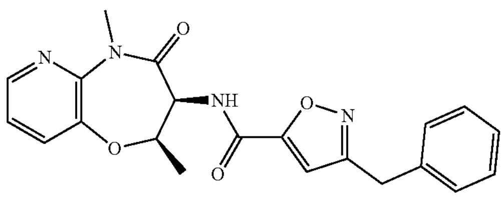 [SMILES: C[C@H]1Oc2cccnc2N(C)C(=O)[C@H]1NC(=O)c1cc(Cc2ccccc2)no1] |
| 123 | 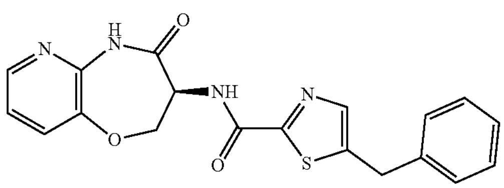 [SMILES: O=C(N[C@H]1COc2cccnc2NC1=O)c1ncc(Cc2ccccc2)s1] |
| 124 | 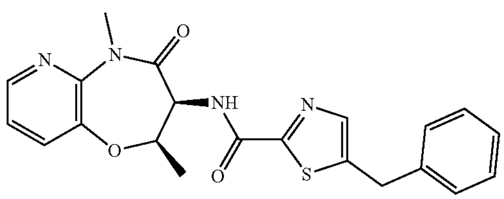 [SMILES: C[C@H]1Oc2cccnc2N(C)C(=O)[C@H]1NC(=O)c1ncc(Cc2ccccc2)s1] |
| 125A | 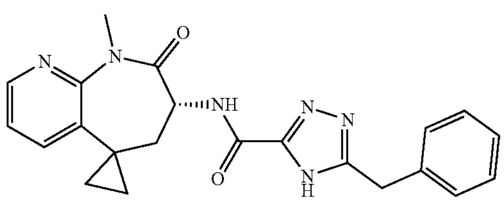 [SMILES: CN1C(=O)[C@H](NC(=O)c2nnc(Cc3ccccc3)[nH]2)CC2(CC2)c2cccnc21] |
| 125B | 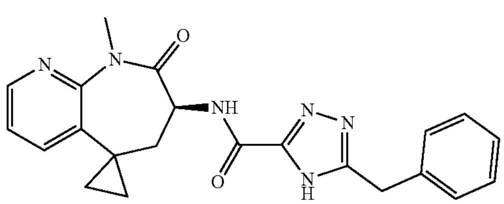 |
| 126 | 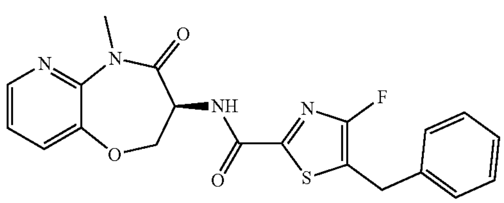 |

TABLE 1-continued

| No. | Structure |
|---|---|
| 127 | 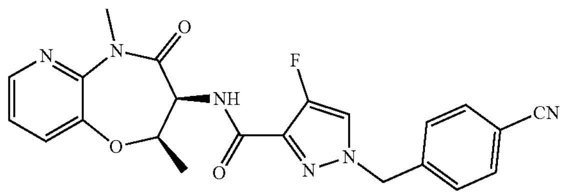 [SMILES: C[C@H]1Oc2cccnc2N(C)C(=O)[C@H]1NC(=O)c1nn(Cc2ccc(C#N)cc2)cc1F] |
| 128 | 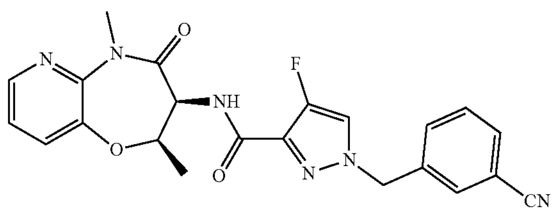 [SMILES: C[C@H]1Oc2cccnc2N(C)C(=O)[C@H]1NC(=O)c1nn(Cc2cccc(C#N)c2)cc1F] |
| 129A | 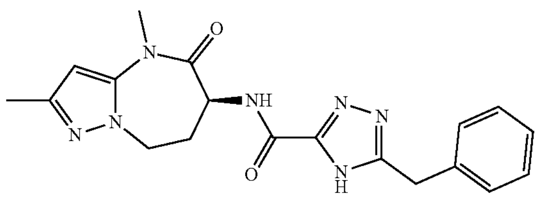 [SMILES: Cc1cc2n(n1)CC[C@H](NC(=O)c1nnc(Cc3ccccc3)[nH]1)C(=O)N2C] |
| 129B | 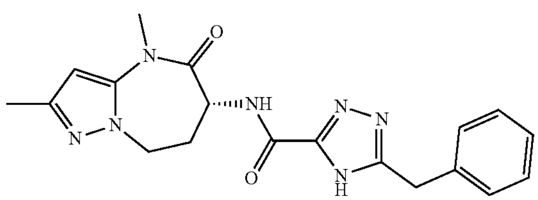 [SMILES: Cc1cc2n(n1)CC[C@@H](NC(=O)c1nnc(Cc3ccccc3)[nH]1)C(=O)N2C] |
| 130 | 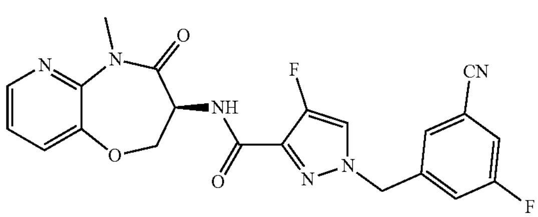 [SMILES: CN1C(=O)[C@@H](NC(=O)c2nn(Cc3cc(F)cc(C#N)c3)cc2F)COc2cccnc21] |
| 131A | 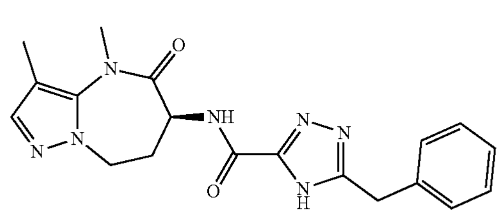 [SMILES: Cc1cnn2c1N(C)C(=O)[C@@H](NC(=O)c1nnc(Cc3ccccc3)[nH]1)CC2] |
| 131B | 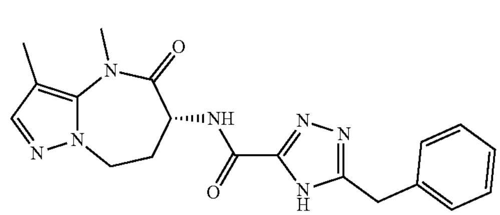 [SMILES: Cc1cnn2c1N(C)C(=O)[C@H](NC(=O)c1nnc(Cc3ccccc3)[nH]1)CC2] |

TABLE 1-continued

| No. | Structure |
|---|---|
| 132 | 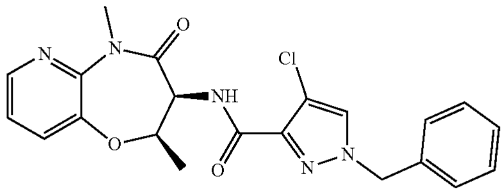 |
| 133 | 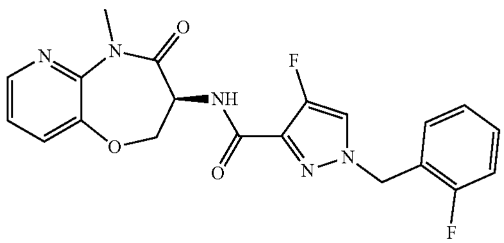 [SMILES: CN1C(=O)[C@@H](NC(=O)c2nn(Cc3ccccc3F)cc2F)COc2cccnc21] |
| 134 | 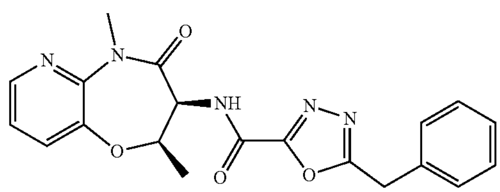 [SMILES: C[C@H]1Oc2cccnc2N(C)C(=O)[C@H]1NC(=O)c1nnc(Cc2ccccc2)o1] |
| 135 | 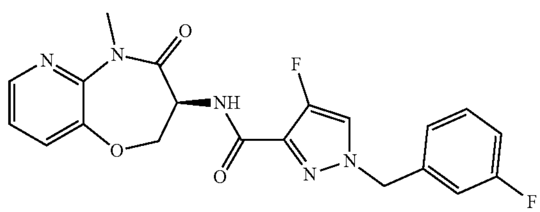 [SMILES: CN1C(=O)[C@@H](NC(=O)c2nn(Cc3cccc(F)c3)cc2F)COc2cccnc21] |
| 136 | 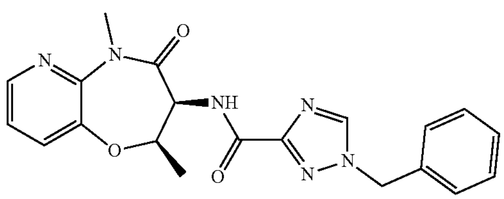 |
| 137 | 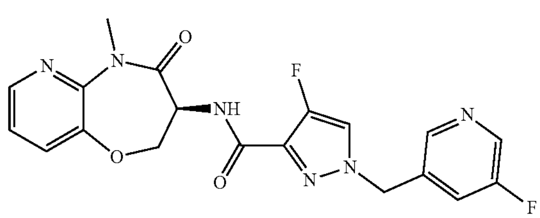 [SMILES: CN1C(=O)[C@@H](NC(=O)c2nn(Cc3cncc(F)c3)cc2F)COc2cccnc21] |
| 138 | 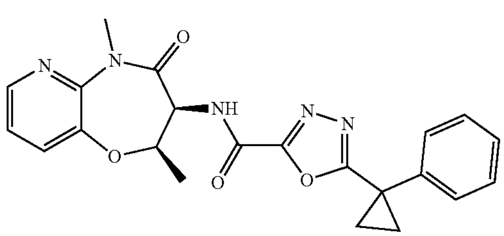 [SMILES: C[C@H]1Oc2cccnc2N(C)C(=O)[C@H]1NC(=O)c1nnc(C2(c3ccccc3)CC2)o1] |

TABLE 1-continued

| No. | Structure |
|---|---|
| 139 | 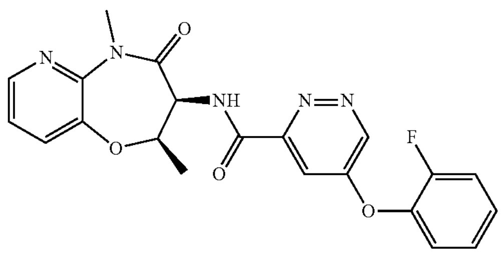 [SMILES: C[C@H]1Oc2cccnc2N(C)C(=O)[C@H]1NC(=O)c1cc(Oc2ccccc2F)cnn1] |
| 140 | 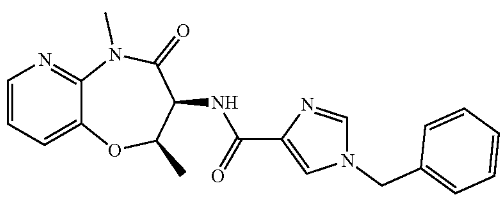 |
| 141A | 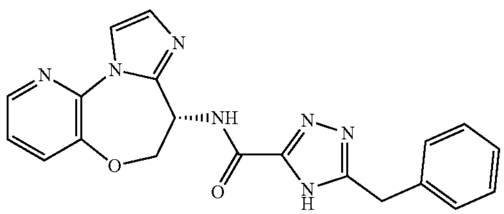 [SMILES: O=C(N[C@@H]1COc2cccnc2-n2ccnc21)c1nnc(Cc2ccccc2)[nH]1] |
| 141B | 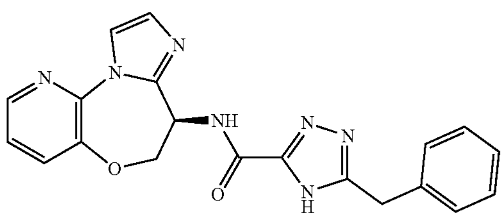 [SMILES: O=C(N[C@H]1COc2cccnc2-n2ccnc21)c1nnc(Cc2ccccc2)[nH]1] |
| 142 | 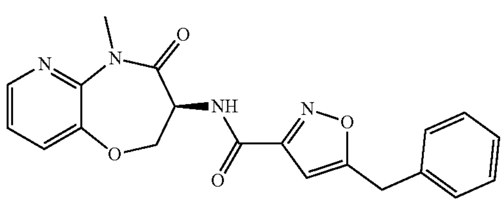 |
| 143 | 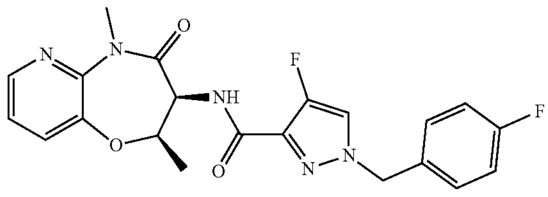 [SMILES: C[C@H]1Oc2cccnc2N(C)C(=O)[C@H]1NC(=O)c1nn(Cc2ccc(F)cc2)cc1F] |
| 144 | 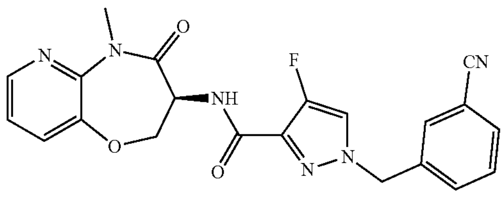 [SMILES: CN1C(=O)[C@@H](NC(=O)c2nn(Cc3cccc(C#N)c3)cc2F)COc2cccnc21] |

TABLE 1-continued

| No. | Structure |
|---|---|
| 145A | 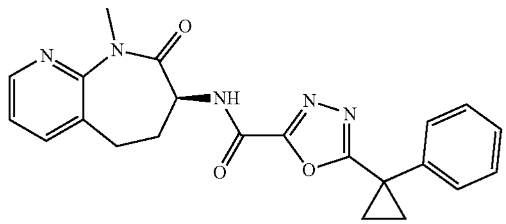 [SMILES: CN1C(=O)[C@@H](NC(=O)c2nnc(C3(c4ccccc4)CC3)o2)CCc2cccnc21] |
| 145B | 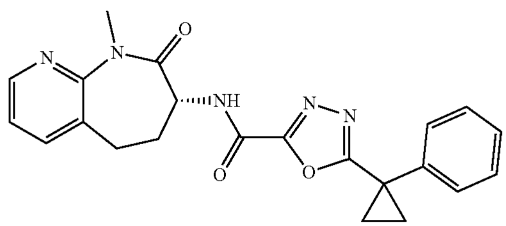 [SMILES: CN1C(=O)[C@H](NC(=O)c2nnc(C3(c4ccccc4)CC3)o2)CCc2cccnc21] |
| 146 | 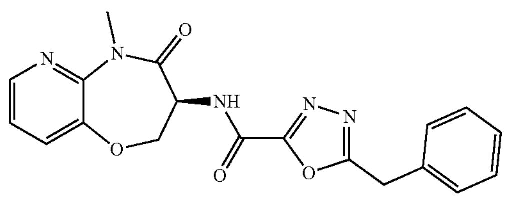 |
| 147 | 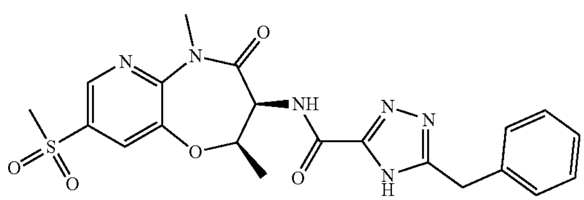 [SMILES: C[C@H]1Oc2cc(S(C)(=O)=O)cnc2N(C)C(=O)[C@H]1NC(=O)c1nnc(Cc2ccccc2)[nH]1] |
| 148A | 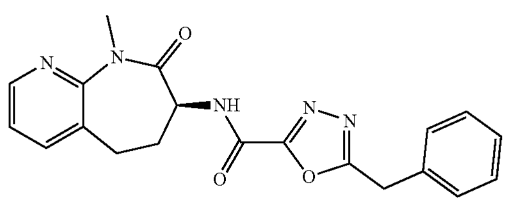 |
| 148B | 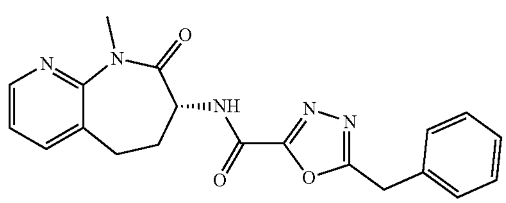 [SMILES: CN1C(=O)[C@H](NC(=O)c2nnc(Cc3ccccc3)o2)CCc2cccnc21] |
| 149 | 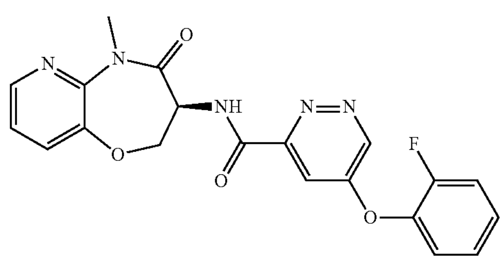 [SMILES: CN1C(=O)[C@@H](NC(=O)c2cc(Oc3ccccc3F)cnn2)COc2cccnc21] |

TABLE 1-continued

| No. | Structure |
|---|---|
| 150 | 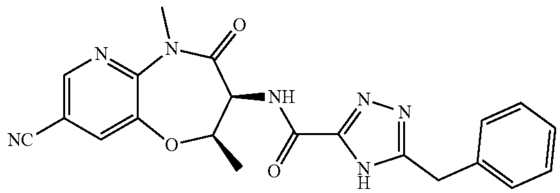 [SMILES: C[C@H]1Oc2cc(C#N)cnc2N(C)C(=O)[C@H]1NC(=O)c1nnc(Cc2ccccc2)[nH]1] |
| 151 | 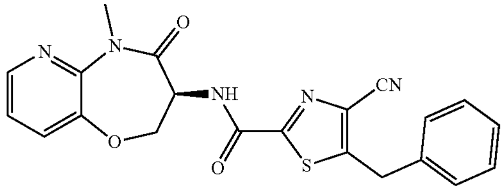 [SMILES: CN1C(=O)[C@@H](NC(=O)c2nc(C#N)c(Cc3ccccc3)s2)COc2cccnc21] |
| 152A | 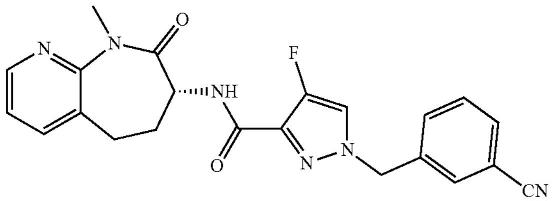 [SMILES: CN1C(=O)[C@H](NC(=O)c2nn(Cc3cccc(C#N)c3)cc2F)CCc2cccnc21] |
| 152B | 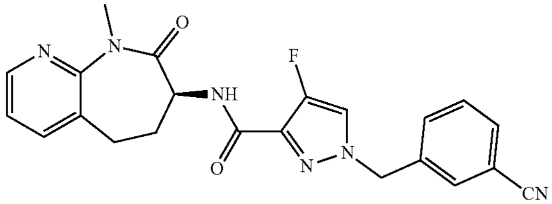 [SMILES: CN1C(=O)[C@@H](NC(=O)c2nn(Cc3cccc(C#N)c3)cc2F)CCc2cccnc21] |
| 153 | 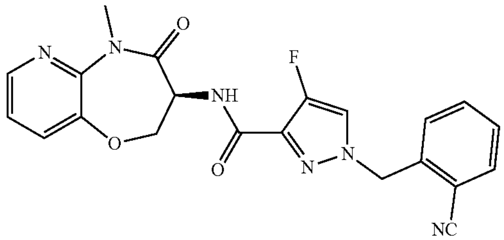 [SMILES: CN1C(=O)[C@@H](NC(=O)c2nn(Cc3ccccc3C#N)cc2F)COc2cccnc21] |
| 154A | 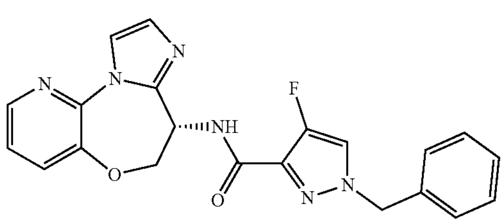 [SMILES: O=C(N[C@@H]1COc2cccnc2-n2ccnc21)c1nn(Cc2ccccc2)cc1F] |
| 154B | 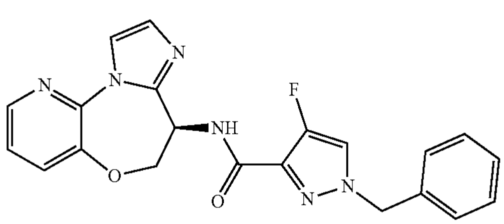 [SMILES: O=C(N[C@H]1COc2cccnc2-n2ccnc21)c1nn(Cc2ccccc2)cc1F] |

TABLE 1-continued

| No. | Structure |
|---|---|
| 155 | 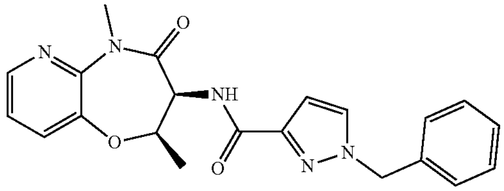 [SMILES: C[C@H]1Oc2cccnc2N(C)C(=O)[C@H]1NC(=O)c1ccn(Cc2ccccc2)n1] |
| 156A | 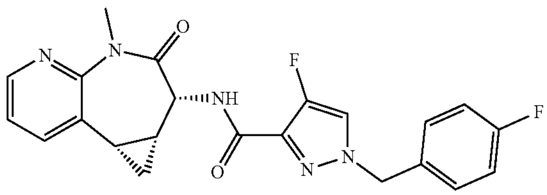 [SMILES: CN1C(=O)[C@H](NC(=O)c2nn(Cc3ccc(F)cc3)cc2F)[C@@H]2C[C@@H]2c2cccnc21] |
| 156B | 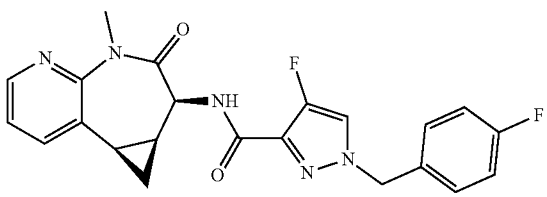 [SMILES: CN1C(=O)[C@@H](NC(=O)c2nn(Cc3ccc(F)cc3)cc2F)[C@H]2C[C@H]2c2cccnc21] |
| 157A | 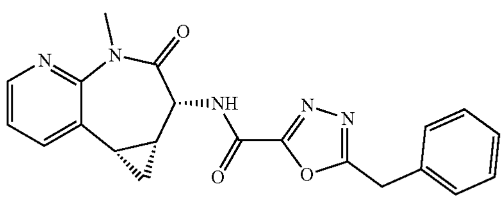 [SMILES: CN1C(=O)[C@H](NC(=O)c2nnc(Cc3ccccc3)o2)[C@@H]2C[C@@H]2c2cccnc21] |
| 157B | 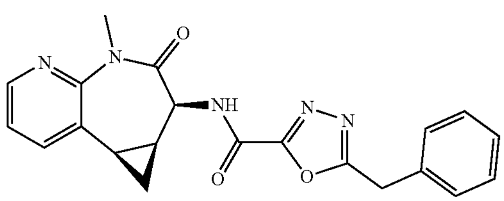 |
| 158 | 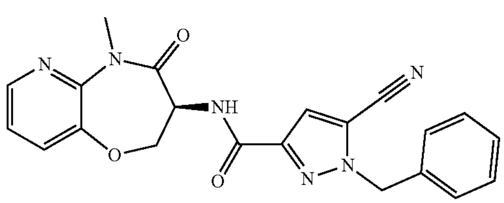 [SMILES: CN1C(=O)[C@@H](NC(=O)c2cc(C#N)n(Cc3ccccc3)n2)COc2cccnc21] |
| 159 | 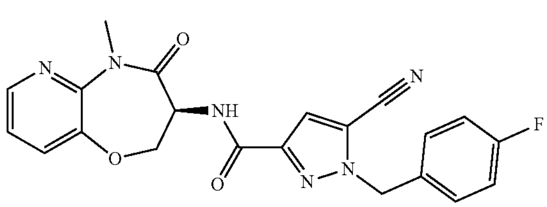 [SMILES: CN1C(=O)[C@@H](NC(=O)c2cc(C#N)n(Cc3ccc(F)cc3)n2)COc2cccnc21] |

TABLE 1-continued

| No. | Structure |
|---|---|
| 160A | (structure) |
| 160B | (structure) |
| 161 | (structure) |
| 162 | (structure) |
| 163 | (structure) |
| 164 | (structure) |
| 165 | (structure) |

TABLE 1-continued

| No. | Structure |
|---|---|
| 166 | 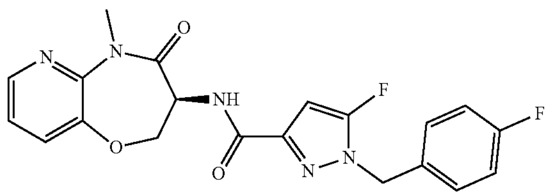 [SMILES: CN1C(=O)[C@@H](NC(=O)c2cc(F)n(Cc3ccc(F)cc3)n2)COc2cccnc21] |
| 167 | 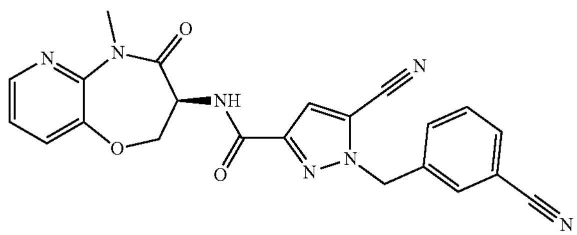 [SMILES: CN1C(=O)[C@@H](NC(=O)c2cc(C#N)n(Cc3cccc(C#N)c3)n2)COc2cccnc21] |
| 168 | 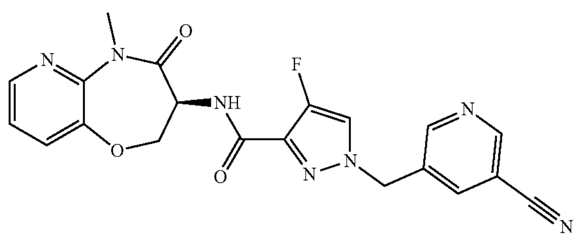 [SMILES: CN1C(=O)[C@@H](NC(=O)c2nn(Cc3cncc(C#N)c3)cc2F)COc2cccnc21] |
| 169 | 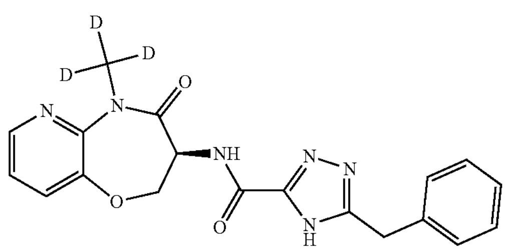 [SMILES: [2H]C([2H])([2H])N1C(=O)[C@@H](NC(=O)c2nnc(Cc3ccccc3)[nH]2)COc2cccnc21] |
| 170A | 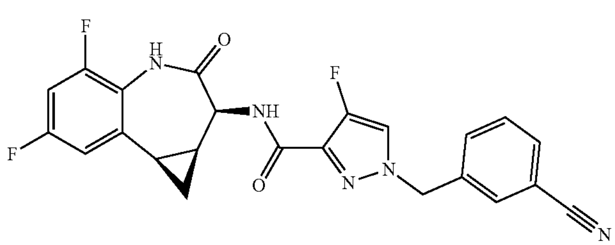 [SMILES: N#Cc1cccc(Cn2cc(F)c(C(=O)N[C@@H]3C(=O)Nc4c(F)cc(F)cc4[C@@H]4C[C@H]34)n2)c1] |
| 170B | 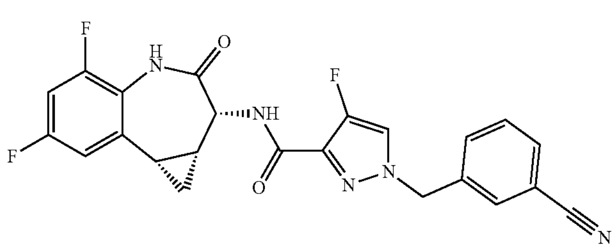 [SMILES: N#Cc1cccc(Cn2cc(F)c(C(=O)N[C@H]3C(=O)Nc4c(F)cc(F)cc4[C@H]4C[C@H]43)n2)c1] |

TABLE 1-continued
| No. | Structure |
|---|---|
| 171 | 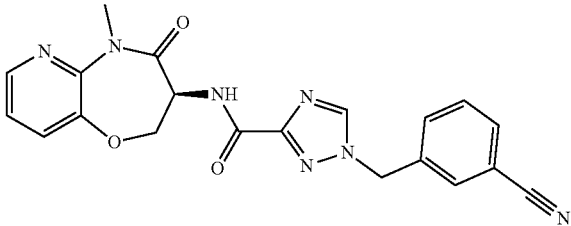 [SMILES: CN1C(=O)[C@@H](NC(=O)c2ncn(Cc3cccc(C#N)c3)n2)COc2cccnc21] |
| 172 | 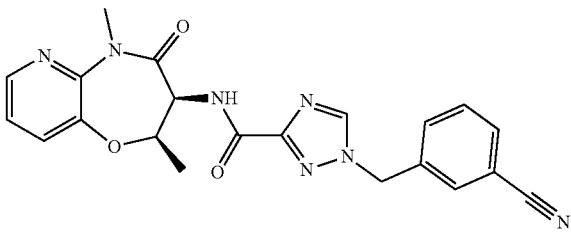 [SMILES: C[C@H]1Oc2cccnc2N(C)C(=O)[C@H]1NC(=O)c1ncn(Cc2cccc(C#N)c2)n1] |
| 173 | 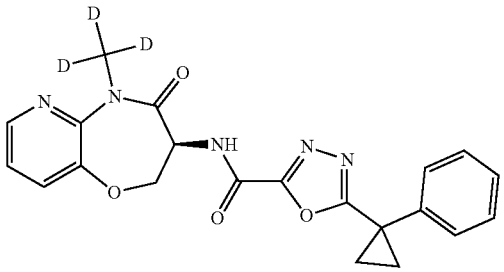 [SMILES: [2H]C([2H])([2H])N1C(=O)[C@@H](NC(=O)c2nnc(C3(c4ccccc4)CC3)o2)COc2cccnc21] |
| 174 | 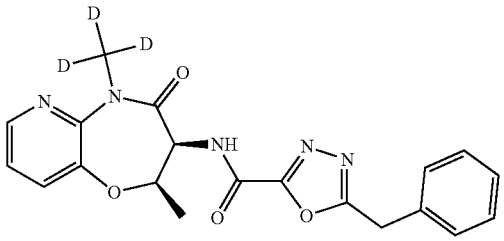 [SMILES: [2H]C([2H])([2H])N1C(=O)[C@@H](NC(=O)c2nnc(Cc3ccccc3)o2)[C@@H](C)Oc2cccnc21] |
| 175 | 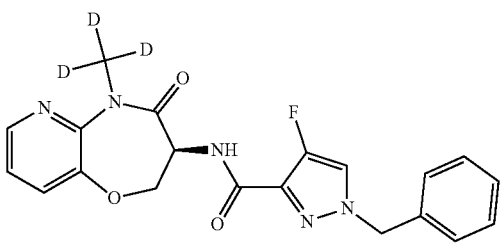 [SMILES: [2H]C([2H])([2H])N1C(=O)[C@@H](NC(=O)c2nn(Cc3ccccc3)cc2F)COc2cccnc21] |
| 176 | 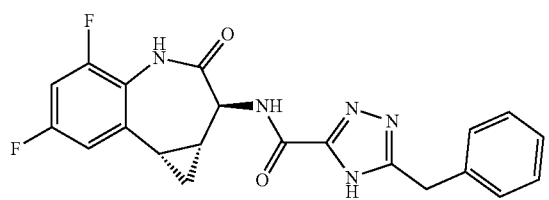 [SMILES: O=C(N[C@@H]1C(=O)Nc2c(F)cc(F)cc2[C@H]2C[C@@H]12)c1nnc(Cc2ccccc2)[nH]1] |

TABLE 1-continued

| No. | Structure |
|---|---|
| 177A | (structure) |
| 177B | (structure) |
| 178A | (structure) |
| 178B | (structure) |
| 179A | (structure) |
| 179B | (structure) |

TABLE 1-continued

| No. | Structure |
| --- | --- |
| 180A | 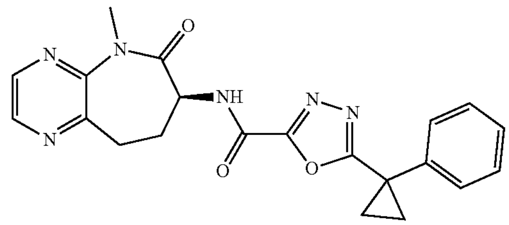 [SMILES: CN1C(=O)[C@@H](NC(=O)c2nnc(C3(c4ccccc4)CC3)o2)CCc2nccnc21] |
| 180B | 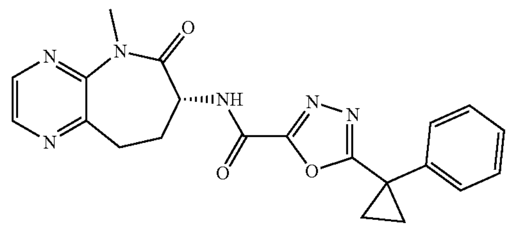 [SMILES: CN1C(=O)[C@H](NC(=O)c2nnc(C3(c4ccccc4)CC3)o2)CCc2nccnc21] |
| 181A | 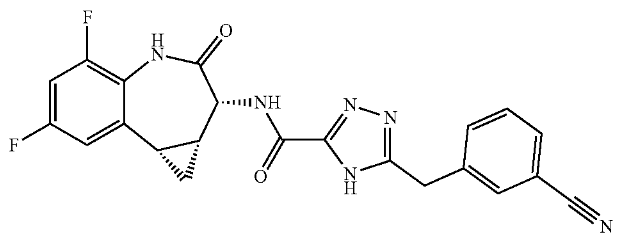 [SMILES: N#Cc1cccc(Cc2nnc(C(=O)N[C@H]3C(=O)Nc4c(F)cc(F)cc4[C@H]4C[C@H]43)[nH]2)c1] |
| 181B | 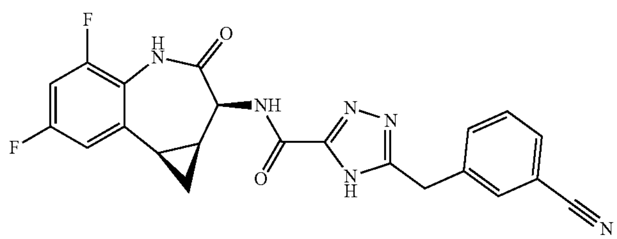 [SMILES: N#Cc1cccc(Cc2nnc(C(=O)N[C@@H]3C(=O)Nc4c(F)cc(F)cc4[C@@H]4C[C@H]34)[nH]2)c1] |
| 182A | 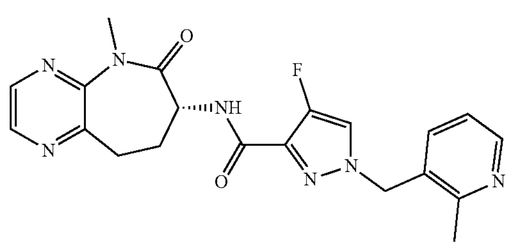 [SMILES: Cc1ncccc1Cn1cc(F)c(C(=O)N[C@@H]2CCc3nccnc3N(C)C2=O)n1] |
| 182B | 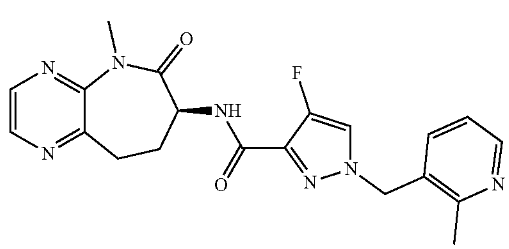 [SMILES: Cc1ncccc1Cn1cc(F)c(C(=O)N[C@H]2CCc3nccnc3N(C)C2=O)n1] |

TABLE 1-continued

| No. | Structure |
|---|---|
| 183A | 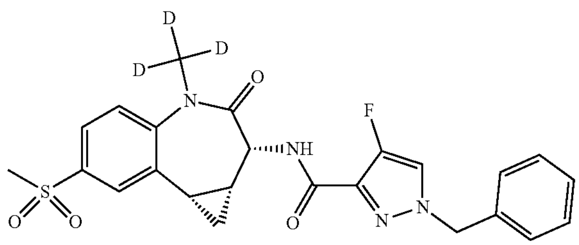 [SMILES: [2H]C([2H])([2H])N1C(=O)[C@H](NC(=O)c2nn(Cc3ccccc3)cc2F)[C@@H]2C[C@@H]2c2cc(S(C)(=O)=O)ccc21] |
| 183B | 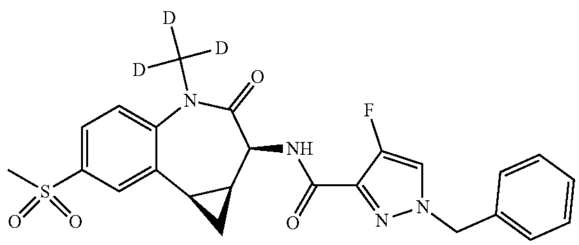 [SMILES: [2H]C([2H])([2H])N1C(=O)[C@@H](NC(=O)c2nn(Cc3ccccc3)cc2F)[C@H]2C[C@H]2c2cc(S(C)(=O)=O)ccc21] |
| 184 | 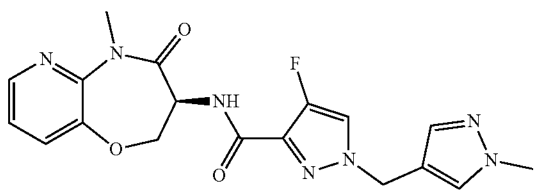 [SMILES: CN1C(=O)[C@@H](NC(=O)c2nn(Cc3cnn(C)c3)cc2F)COc2cccnc21] |
| 185 | 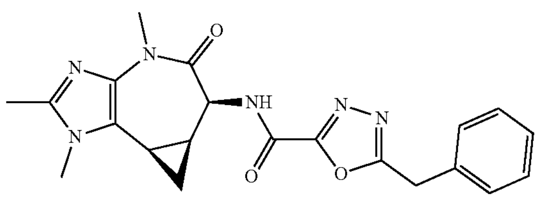 [SMILES: Cc1nc2c(n1C)[C@@H]1C[C@@H]1[C@H](NC(=O)c1nnc(Cc3ccccc3)o1)C(=O)N2C] |
| 186 | 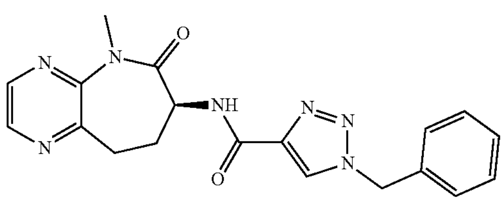 [SMILES: CN1C(=O)[C@@H](NC(=O)c2cn(Cc3ccccc3)nn2)CCc2nccnc21] |
| 187 | 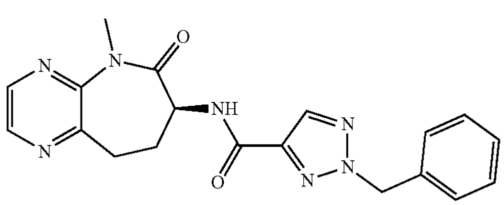 |
| 188 | 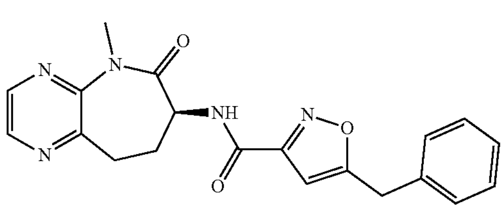 [SMILES: CN1C(=O)[C@@H](NC(=O)c2cc(Cc3ccccc3)on2)CCc2nccnc21] |

TABLE 1-continued

| No. | Structure |
|---|---|
| 189 | 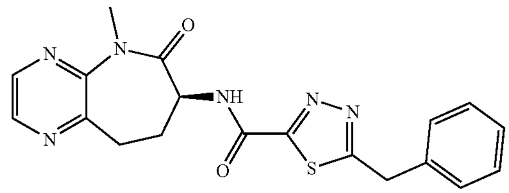 [SMILES: CN1C(=O)[C@@H](NC(=O)c2nnc(Cc3ccccc3)o2)CCc2nccnc21] |
| 190 | 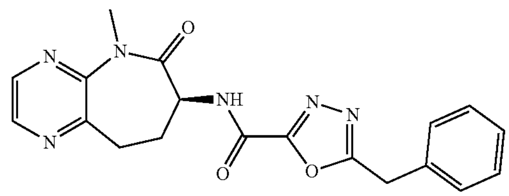 |
| 191 | 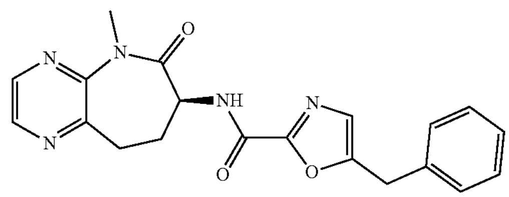 |
| 192 | 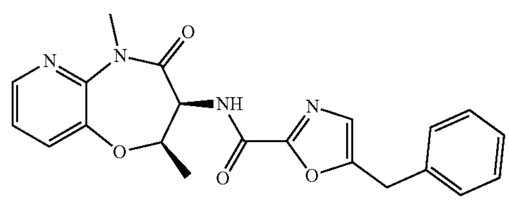 [SMILES: C[C@H]1Oc2cccnc2N(C)C(=O)[C@H]1NC(=O)c1ncc(Cc2ccccc2)o1] |
| 193 | 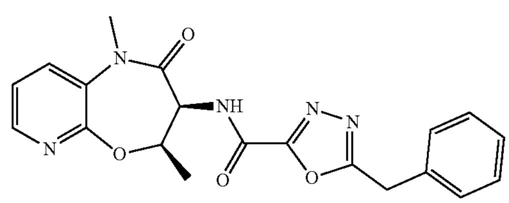 [SMILES: C[C@H]1Oc2ncccc2N(C)C(=O)[C@H]1NC(=O)c1nnc(Cc2ccccc2)o1] |
| 194 | 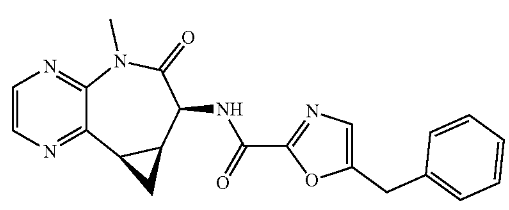 [SMILES: CN1C(=O)[C@@H](NC(=O)c2ncc(Cc3ccccc3)o2)[C@H]2C[C@H]2c2nccnc21] |
| 195 | 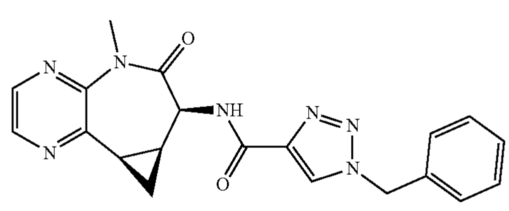 [SMILES: CN1C(=O)[C@@H](NC(=O)c2cn(Cc3ccccc3)nn2)[C@H]2C[C@H]2c2nccnc21] |

TABLE 1-continued

| No. | Structure |
|---|---|
| 196 | 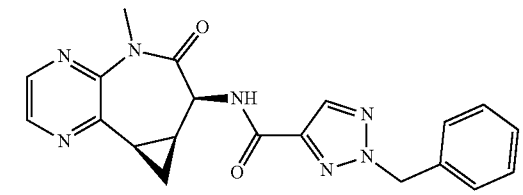 [SMILES: CN1C(=O)[C@@H](NC(=O)c2cnn(Cc3ccccc3)n2)[C@H]2C[C@H]2c2nccnc21] |
| 197 | 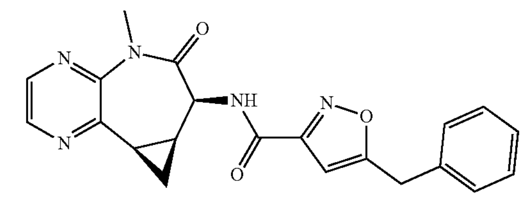 [SMILES: CN1C(=O)[C@@H](NC(=O)c2cc(Cc3ccccc3)on2)[C@H]2C[C@H]2c2nccnc21] |
| 198 | 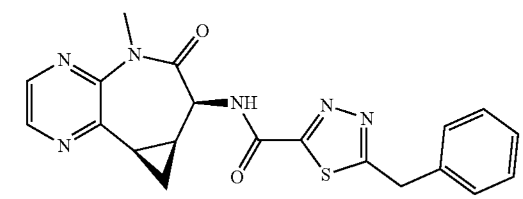 |
| 199 | 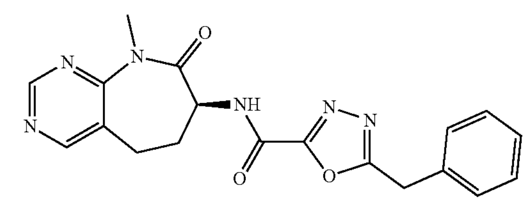 [SMILES: CN1C(=O)[C@@H](NC(=O)c2nnc(Cc3ccccc3)o2)CCc2cncnc21] |
| 200 | 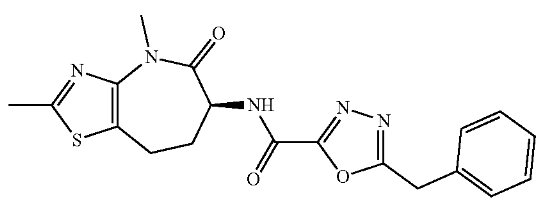 [SMILES: Cc1nc2c(s1)CC[C@H](NC(=O)c1nnc(Cc3ccccc3)o1)C(=O)N2C] |
| 201 | 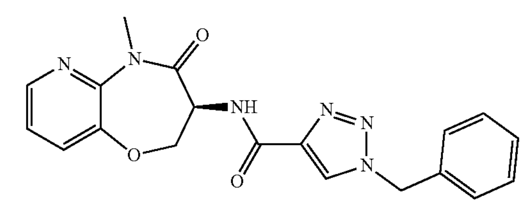 |
| 202 | 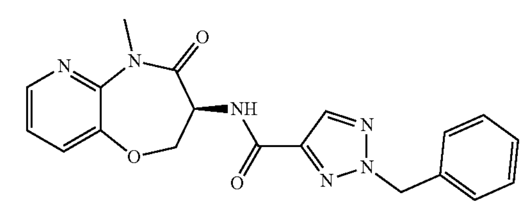 [SMILES: CN1C(=O)[C@@H](NC(=O)c2cnn(Cc3ccccc3)n2)COc2cccnc21] |
| 203 | 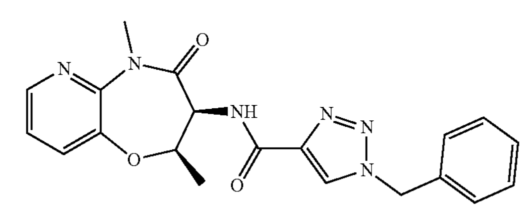 [SMILES: C[C@H]1Oc2cccnc2N(C)C(=O)[C@H]1NC(=O)c1cn(Cc2ccccc2)nn1] |

TABLE 1-continued

| No. | Structure |
|---|---|
| 204 | 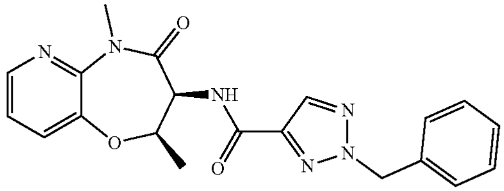 |
| 205 | 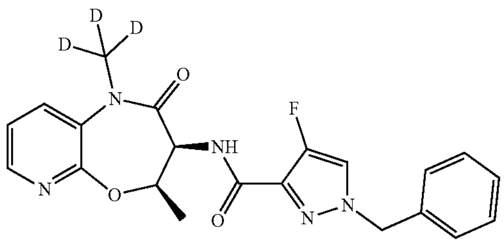 [SMILES: [2H]C([2H])([2H])N1C(=O)[C@@H](NC(=O)c2nn(Cc3ccccc3)cc2F)[C@@H](C)Oc2ncccc21] |
| 206 | 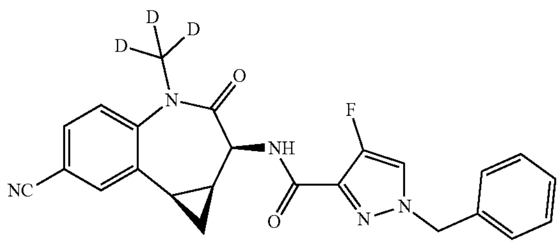 [SMILES: [2H]C([2H])([2H])N1C(=O)[C@@H](NC(=O)c2nn(Cc3ccccc3)cc2F)[C@H]2C[C@H]2c2cc(C#N)ccc21] |
| 207 | 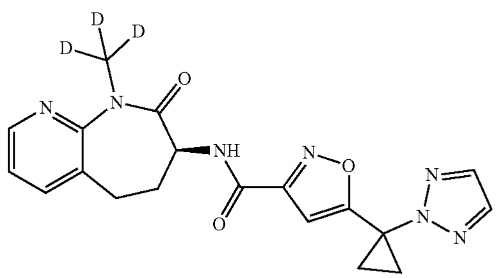 [SMILES: [2H]C([2H])([2H])N1C(=O)[C@@H](NC(=O)c2cc(C3(n4nccn4)CC3)on2)CCc2cccnc21] |
| 208 | 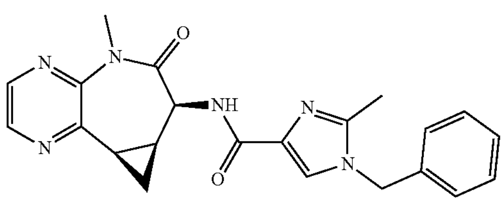 [SMILES: Cc1nc(C(=O)N[C@@H]2C(=O)N(C)c3nccnc3[C@@H]3C[C@H]23)cn1Cc1ccccc1] |
| 209 | 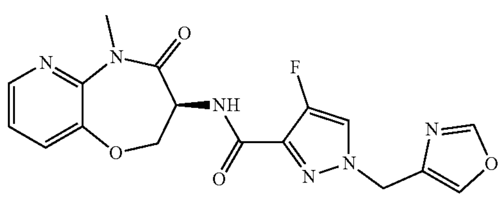 [SMILES: CN1C(=O)[C@@H](NC(=O)c2nn(Cc3cocn3)cc2F)COc2cccnc21] |
| 210 | 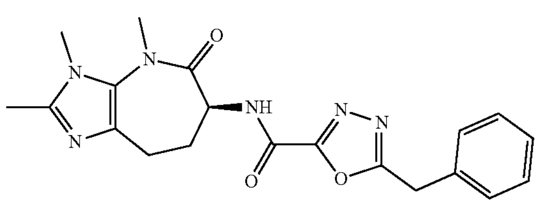 [SMILES: Cc1nc2c(n1C)N(C)C(=O)[C@@H](NC(=O)c1nnc(Cc3ccccc3)o1)CC2] |

TABLE 1-continued

| No. | Structure |
|---|---|
| 211 | 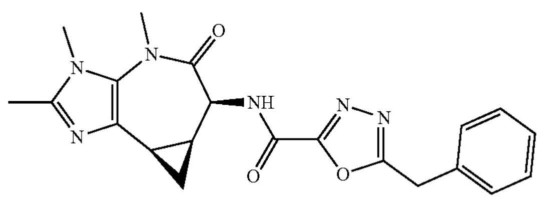 [SMILES: Cc1nc2c(n1C)N(C)C(=O)[C@@H](NC(=O)c1nnc(Cc3ccccc3)o1)[C@H]1C[C@@H]21] |
| 212 | 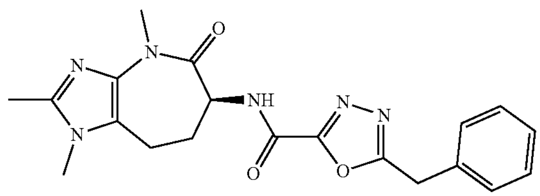 |
| 213 | 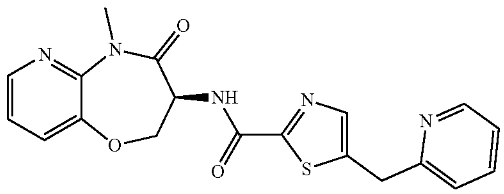 |
| 214 | 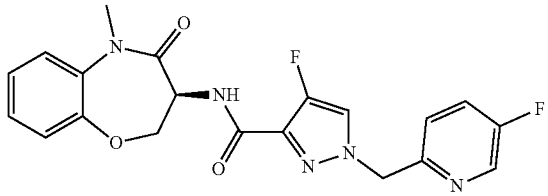 [SMILES: CN1C(=O)[C@@H](NC(=O)c2nn(Cc3ccc(F)cn3)cc2F)COc2ccccc21] |
| 215 | 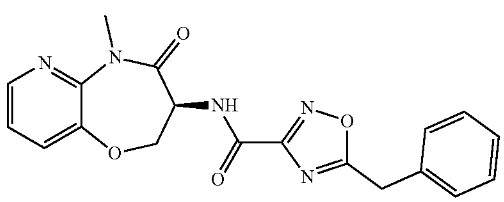 [SMILES: CN1C(=O)[C@@H](NC(=O)c2noc(Cc3ccccc3)n2)COc2cccnc21] |
| 216 | 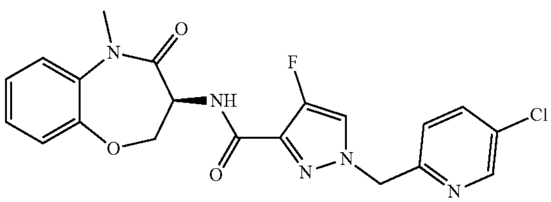 [SMILES: CN1C(=O)[C@@H](NC(=O)c2nn(Cc3ccc(Cl)cn3)cc2F)COc2ccccc21] |
| 217 | 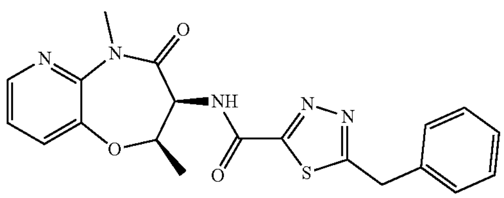 [SMILES: C[C@H]1Oc2cccnc2N(C)C(=O)[C@H]1NC(=O)c1nnc(Cc2ccccc2)s1] |

TABLE 1-continued

| No. | Structure |
|-----|-----------|
| 218 | 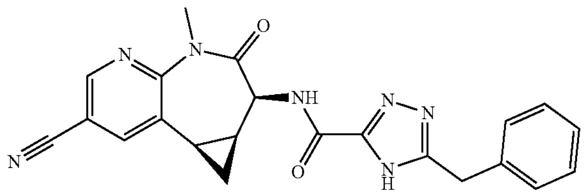 [SMILES: CN1C(=O)[C@@H](NC(=O)c2nnc(Cc3ccccc3)[nH]2)[C@H]2C[C@H]2c2cc(C#N)cnc21] |
| 219 | 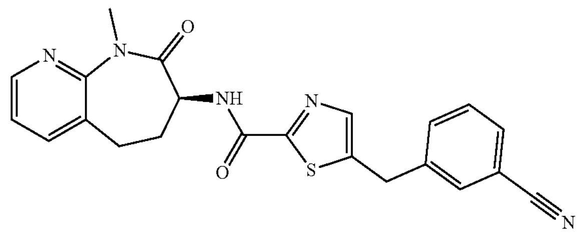 [SMILES: CN1C(=O)[C@@H](NC(=O)c2ncc(Cc3cccc(C#N)c3)s2)CCc2cccnc21] |
| 220 | 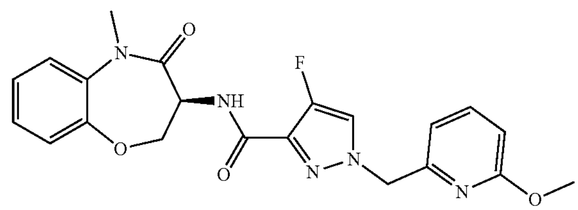 [SMILES: COc1cccc(Cn2cc(F)c(C(=O)N[C@H]3COc4ccccc4N(C)C3=O)n2)n1] |
| 221 | 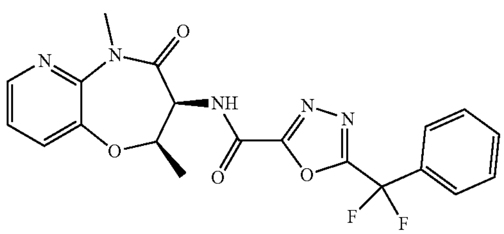 [SMILES: C[C@H]1Oc2cccnc2N(C)C(=O)[C@H]1NC(=O)c1nnc(C(F)(F)c2ccccc2)o1] |
| 222 | 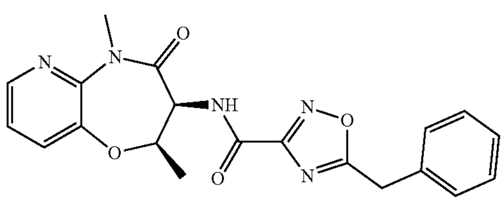 [SMILES: C[C@H]1Oc2cccnc2N(C)C(=O)[C@H]1NC(=O)c1noc(Cc2ccccc2)n1] |
| 223 | 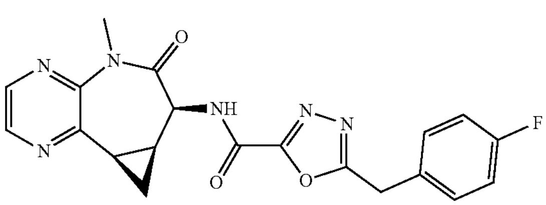 [SMILES: CN1C(=O)[C@@H](NC(=O)c2nnc(Cc3ccc(F)cc3)o2)[C@H]2C[C@H]2c2nccnc21] |
| 224 | 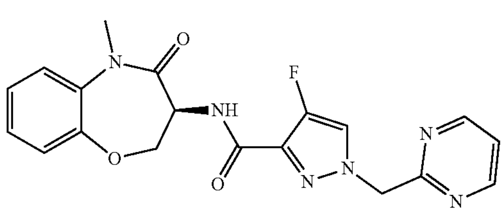 [SMILES: CN1C(=O)[C@@H](NC(=O)c2nn(Cc3ncccn3)cc2F)COc2ccccc21] |

TABLE 1-continued

| No. | Structure |
|-----|-----------|
| 225 | 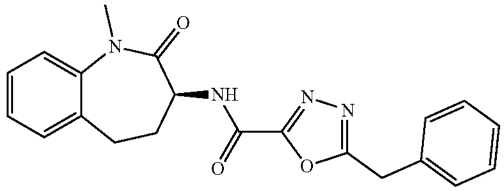 [SMILES: CN1C(=O)[C@@H](NC(=O)c2nnc(Cc3ccccc3)o2)CCc2ccccc21] |
| 226 | 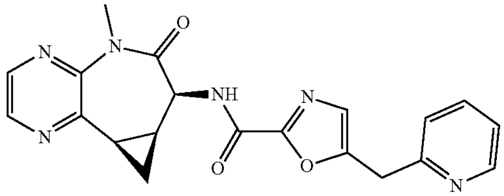 [SMILES: CN1C(=O)[C@@H](NC(=O)c2ncc(Cc3ccccn3)o2)[C@H]2C[C@H]2c2nccnc21] |
| 227 | 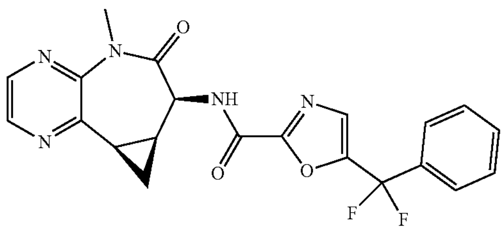 [SMILES: CN1C(=O)[C@@H](NC(=O)c2ncc(C(F)(F)c3ccccc3)o2)[C@H]2C[C@H]2c2nccnc21] |

TABLE 2

| No. | Structure |
|-----|-----------|
| 1 | 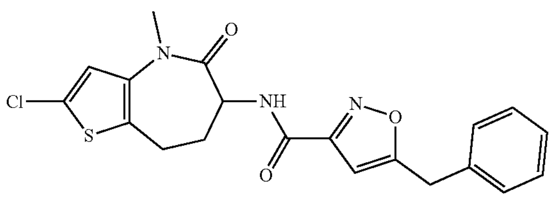 |
| 2 | 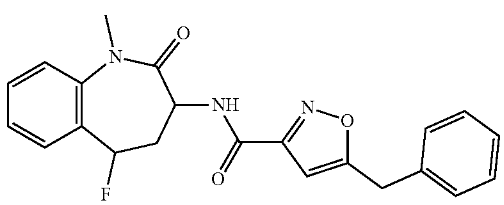 [SMILES: CN1C(=O)C(NC(=O)c2cc(Cc3ccccc3)on2)CC(F)c2ccccc21] |
| 3 | 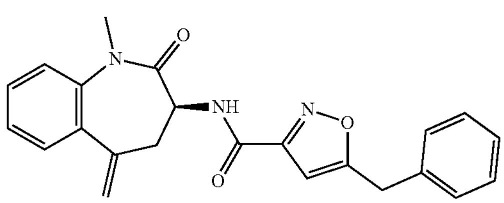 [SMILES: C=C1C[C@H](NC(=O)c2cc(Cc3ccccc3)on2)C(=O)N(C)c2ccccc21] |
| 4 | 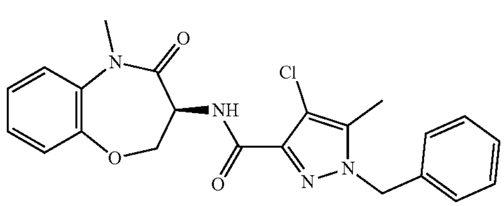 |
| 5 | |
| 6 | |
| 7 | |
| 8 | |

TABLE 2-continued

| No. | Structure |
|---|---|
| 9 | 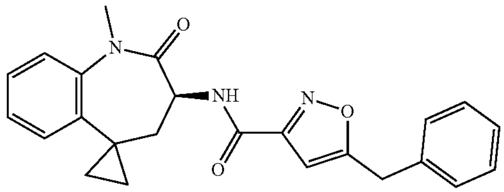 [SMILES: CN1C(=O)[C@@H](NC(=O)c2cc(Cc3ccccc3)on2)CC2(CC2)c2ccccc21] |
| 10 | 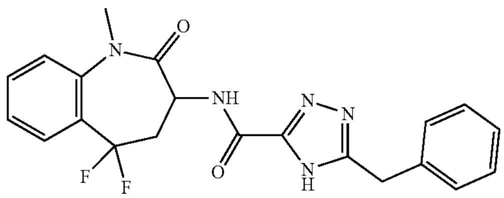 [SMILES: CN1C(=O)C(NC(=O)c2nnc(Cc3ccccc3)[nH]2)CC(F)(F)c2ccccc21] |
| 11 | 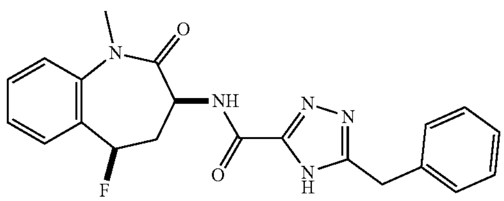 [SMILES: CN1C(=O)[C@@H](NC(=O)c2nnc(Cc3ccccc3)[nH]2)C[C@@H](F)c2ccccc21] |
| 12 | 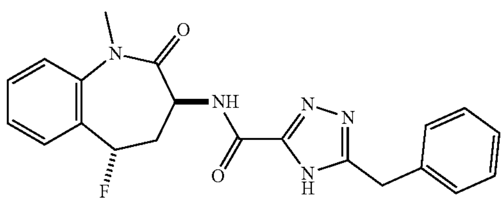 [SMILES: CN1C(=O)[C@@H](NC(=O)c2nnc(Cc3ccccc3)[nH]2)C[C@H](F)c2ccccc21] |
| 13 | 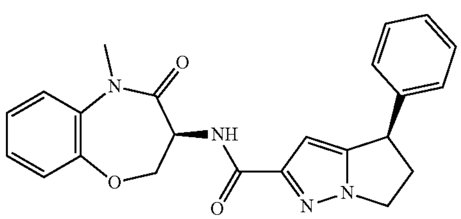 [SMILES: CN1C(=O)[C@@H](NC(=O)c2cc3n(n2)CC[C@@H]3c2ccccc2)COc2ccccc21] |
| 14 | 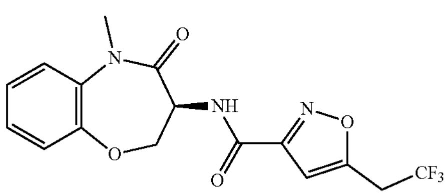 [SMILES: CN1C(=O)[C@@H](NC(=O)c2cc(CC(F)(F)F)on2)COc2ccccc21] |
| 19 | 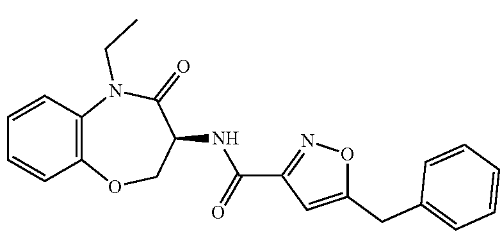 [SMILES: CCN1C(=O)[C@@H](NC(=O)c2cc(Cc3ccccc3)on2)COc2ccccc21] |

TABLE 2-continued

| No. | Structure |
|---|---|
| 20 | 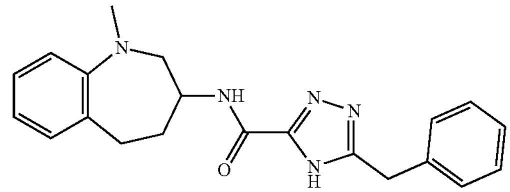 [SMILES: CN1CC(NC(=O)c2nnc(Cc3ccccc3)[nH]2)CCc2ccccc21] |
| 23 | 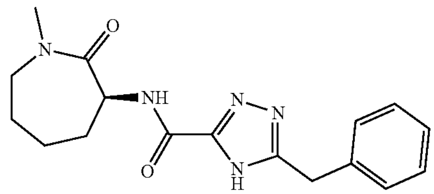 [SMILES: CN1CCCC[C@H](NC(=O)c2nnc(Cc3ccccc3)[nH]2)C1=O] |

TABLE 3

| No. | Structure |
|---|---|
| 14 | 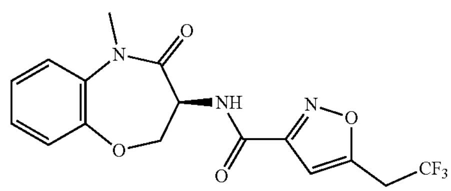 [SMILES: CN1C(=O)[C@@H](NC(=O)c2cc(CC(F)(F)F)on2)COc2ccccc21] |
| 15 | 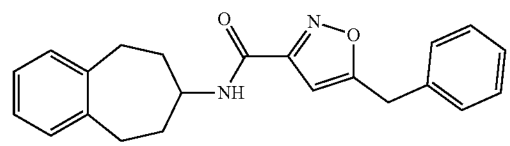 [SMILES: O=C(NC1CCc2ccccc2CC1)c1cc(Cc2ccccc2)on1] |
| 18 | 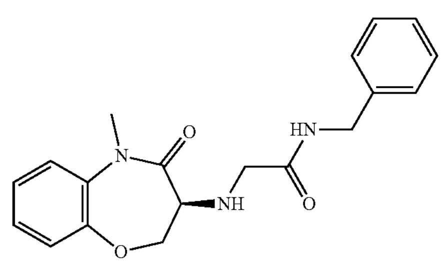 [SMILES: CN1C(=O)[C@@H](NCC(=O)NCc2ccccc2)COc2ccccc21] |
| 20 | 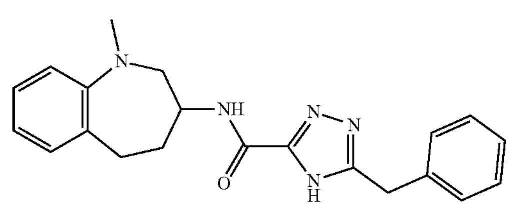 [SMILES: CN1CC(NC(=O)c2nnc(Cc3ccccc3)[nH]2)CCc2ccccc21] |

TABLE 3-continued

| No. | Structure |
|---|---|
| 23 | 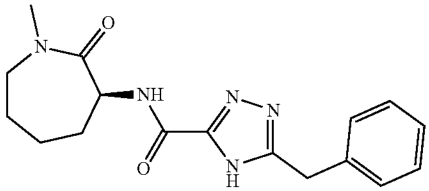 [SMILES: CN1CCCC[C@H](NC(=O)c2nnc(Cc3ccccc3)[nH]2)C1=O] |
| 24 | 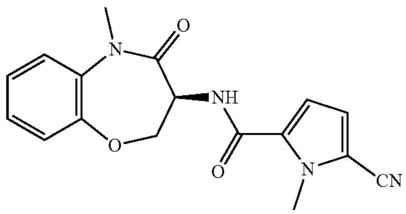 [SMILES: CN1C(=O)[C@@H](NC(=O)c2ccc(C#N)n2C)COc2ccccc21] |
| 25 | |
| 26 | |

TABLE 4

| No. | Structure |
|---|---|
| 1 | 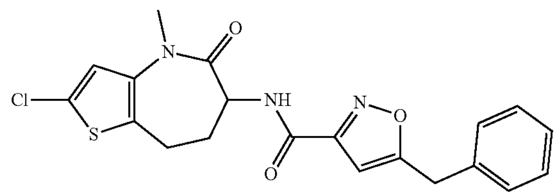 |
| 2 | 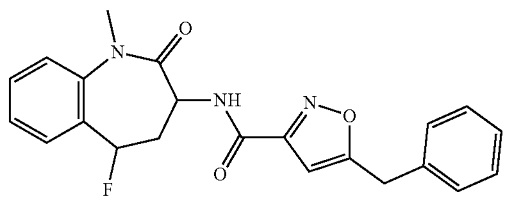 [SMILES: CN1C(=O)C(NC(=O)c2cc(Cc3ccccc3)on2)CC(F)c2ccccc21] |
| 3 | 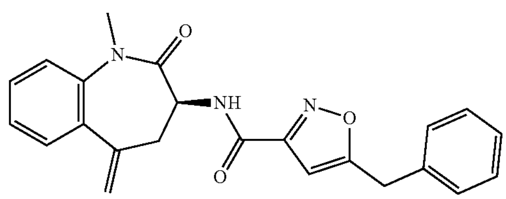 [SMILES: C=C1C[C@H](NC(=O)c2cc(Cc3ccccc3)on2)C(=O)N(C)c2ccccc21] |
| 4 | 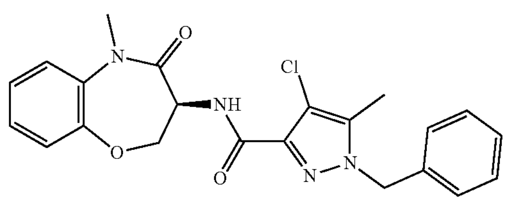 |
| 5 | 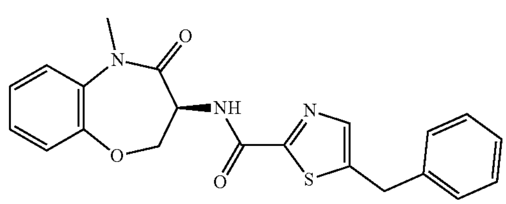 [SMILES: CN1C(=O)[C@@H](NC(=O)c2ncc(Cc3ccccc3)s2)COc2ccccc21] |

TABLE 4-continued

| No. | Structure |
|---|---|
| 6 | 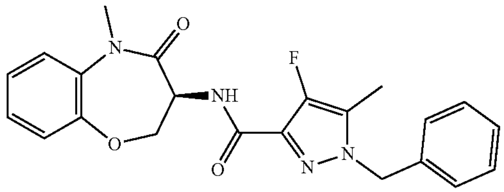 |
| 7 | 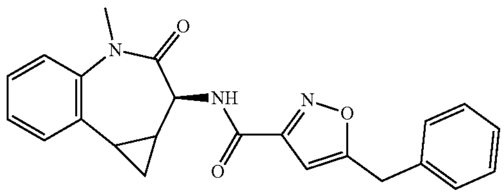 [SMILES: CN1C(=O)[C@@H](NC(=O)c2cc(Cc3ccccc3)on2)C2CC2c2ccccc21] |
| 8 | 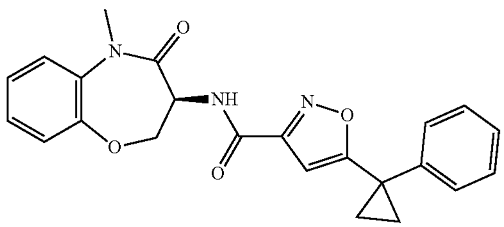 [SMILES: CN1C(=O)[C@@H](NC(=O)c2cc(C3(c4ccccc4)CC3)on2)COc2ccccc21] |
| 9 | 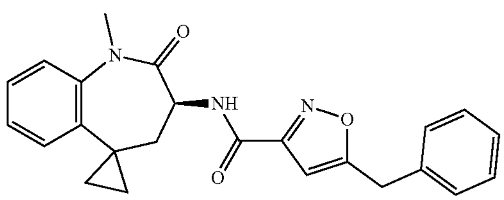 [SMILES: CN1C(=O)[C@@H](NC(=O)c2cc(Cc3ccccc3)on2)CC2(CC2)c2ccccc21] |
| 10 | 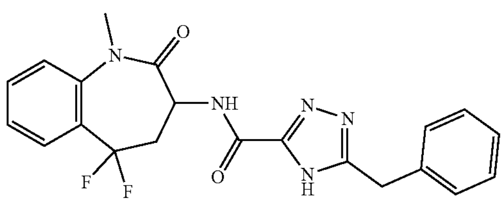 [SMILES: CN1C(=O)C(NC(=O)c2nnc(Cc3ccccc3)[nH]2)CC(F)(F)c2ccccc21] |
| 11 | 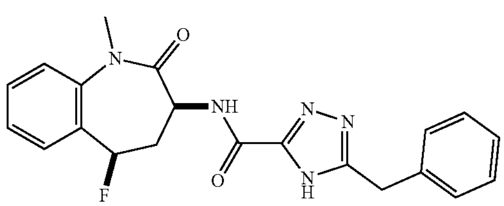 [SMILES: CN1C(=O)[C@@H](NC(=O)c2nnc(Cc3ccccc3)[nH]2)C[C@@H](F)c2ccccc21] |
| 12 | 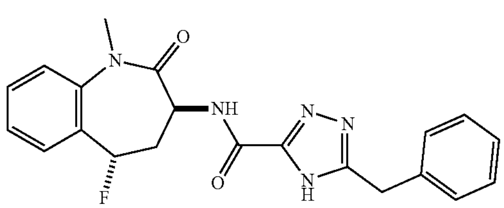 [SMILES: CN1C(=O)[C@@H](NC(=O)c2nnc(Cc3ccccc3)[nH]2)C[C@H](F)c2ccccc21] |

TABLE 4-continued

| No. | Structure |
|---|---|
| 13 | 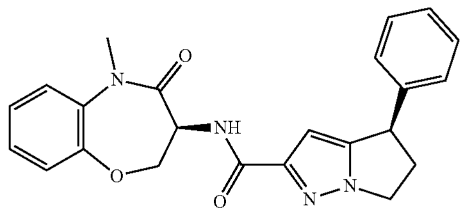 [SMILES: CN1C(=O)[C@@H](NC(=O)c2cc3n(n2)CC[C@@H]3c2ccccc2)COc2ccccc21] |
| 19 | 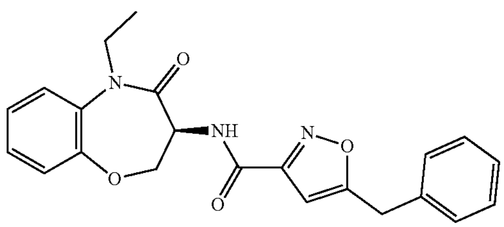 [SMILES: CCN1C(=O)[C@@H](NC(=O)c2cc(Cc3ccccc3)on2)COc2ccccc21] |
| 30 | 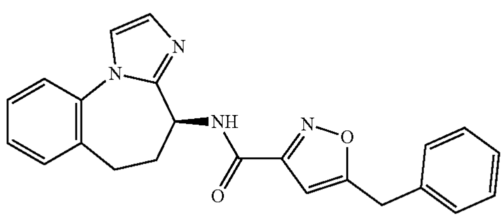 [SMILES: O=C(N[C@H]1CCc2ccccc2-n2ccnc21)c1cc(Cc2ccccc2)on1] |
| 32 | 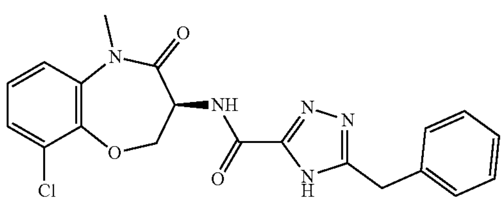 [SMILES: CN1C(=O)[C@@H](NC(=O)c2nnc(Cc3ccccc3)[nH]2)COc2c(Cl)cccc21] |
| 35 | 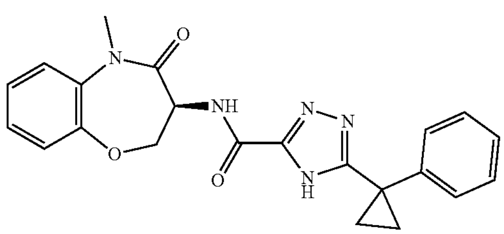 [SMILES: CN1C(=O)[C@@H](NC(=O)c2nnc(C3(c4ccccc4)CC3)[nH]2)COc2ccccc21] |
| 38A | 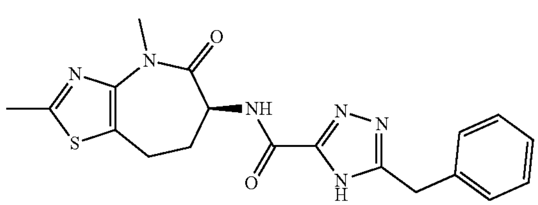 |
| 38B | 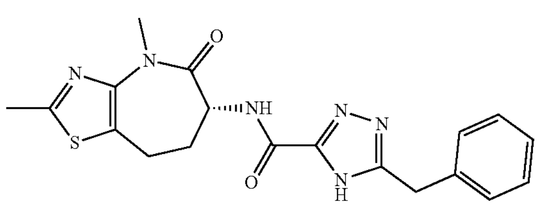 [SMILES: Cc1nc2c(s1)CC[C@@H](NC(=O)c1nnc(Cc3ccccc3)[nH]1)C(=O)N2C] |

TABLE 4-continued
| No. | Structure |
|---|---|
| 40 | 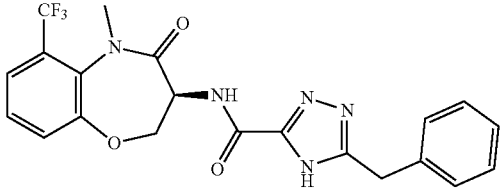 [SMILES: CN1C(=O)[C@@H](NC(=O)c2nnc(Cc3ccccc3)[nH]2)COc2cccc(C(F)(F)F)c21] |
| 41 | 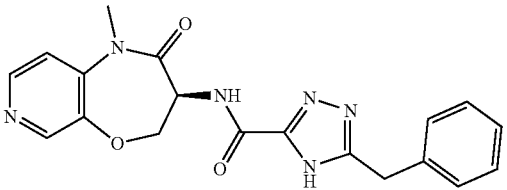 [SMILES: CN1C(=O)[C@@H](NC(=O)c2nnc(Cc3ccccc3)[nH]2)COc2cnccc21] |
| 42 | 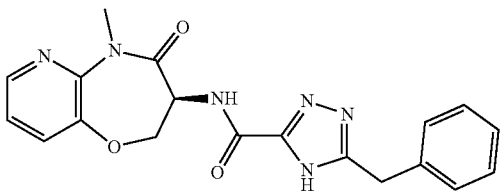 [SMILES: CN1C(=O)[C@@H](NC(=O)c2nnc(Cc3ccccc3)[nH]2)COc2cccnc21] |
| 43 | 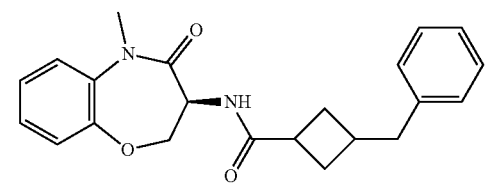 [SMILES: CN1C(=O)[C@@H](NC(=O)C2CC(Cc3ccccc3)C2)COc2ccccc21] |
| 44 | 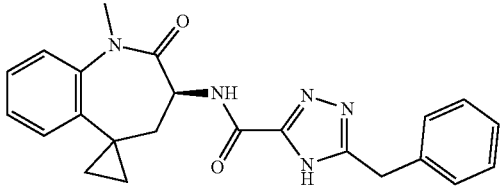 [SMILES: CN1C(=O)[C@@H](NC(=O)c2nnc(Cc3ccccc3)[nH]2)CC2(CC2)c2ccccc21] |
| 45 | 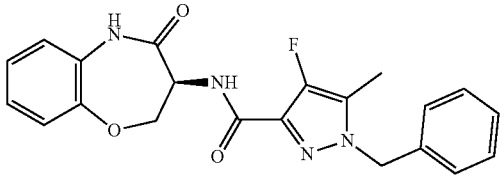 [SMILES: Cc1c(F)c(C(=O)N[C@H]2COc3ccccc3NC2=O)nn1Cc1ccccc1] |
| 46A | 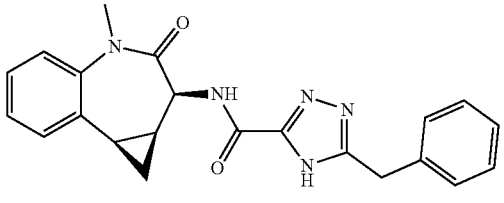 |
| 46B | 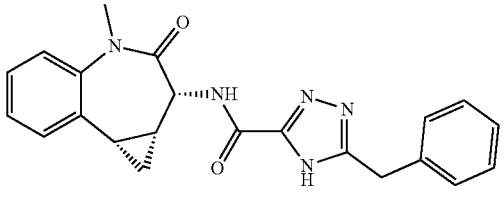 [SMILES: CN1C(=O)[C@H](NC(=O)c2nnc(Cc3ccccc3)[nH]2)[C@@H]2C[C@@H]2c2ccccc21] |

TABLE 4-continued
| No. | Structure |
|---|---|
| 49 | 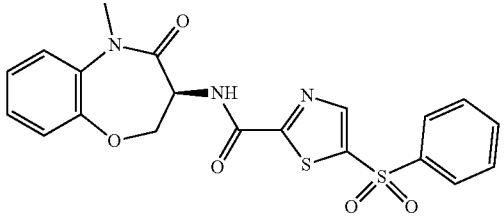 [SMILES: CN1C(=O)[C@@H](NC(=O)c2ncc(S(=O)(=O)c3ccccc3)s2)COc2ccccc21] |
| 50A | 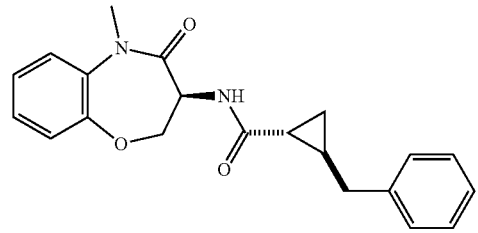<br>First eluting isomer |
| 50B | 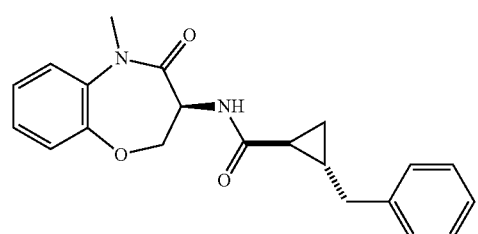<br>Second eluting isomer |
| 51 | 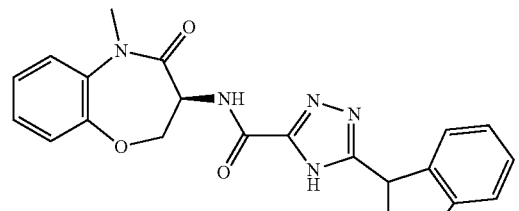 |
| 52 | 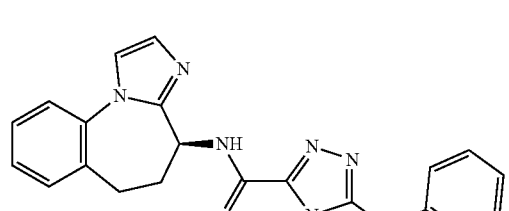 |
| 54A | 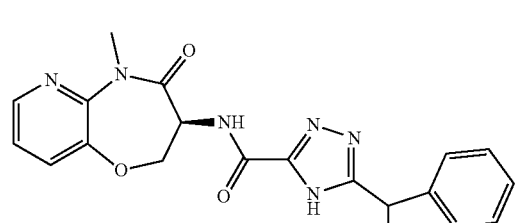<br>Diastereomer 1 |

TABLE 4-continued

| No. | Structure |
|---|---|
| 54B | (structure; Diastereomer 2) |
| 55 | (structure) |
| 56 | (structure) |
| 57 | (structure) |
| 58 | (structure) |
| 59 | (structure) |
| 60A | (structure) |

TABLE 4-continued

| No. | Structure |
|---|---|
| 60B | 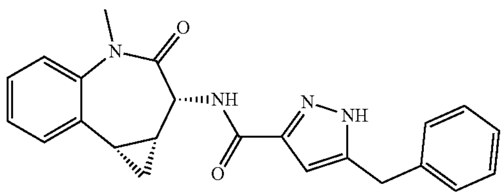 [SMILES: CN1C(=O)[C@H](NC(=O)c2cc(Cc3ccccc3)[nH]n2)[C@@H]2C[C@@H]2c2ccccc21] |
| 61 | 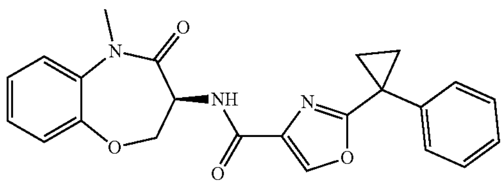 [SMILES: CN1C(=O)[C@@H](NC(=O)c2coc(C3(c4ccccc4)CC3)n2)COc2ccccc21] |
| 62 | 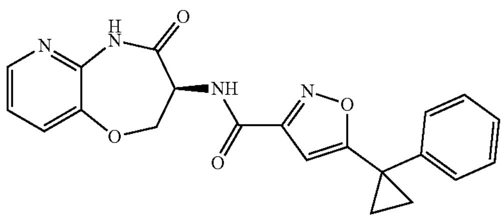 [SMILES: O=C(N[C@H]1COc2cccnc2NC1=O)c1cc(C2(c3ccccc3)CC2)on1] |
| 63 | 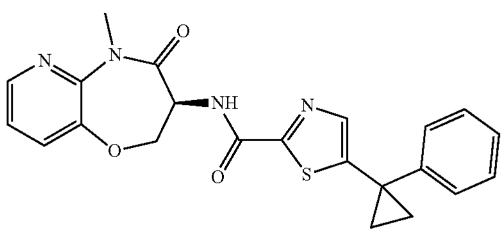 [SMILES: CN1C(=O)[C@@H](NC(=O)c2ncc(C3(c4ccccc4)CC3)s2)COc2cccnc21] |
| 64 | 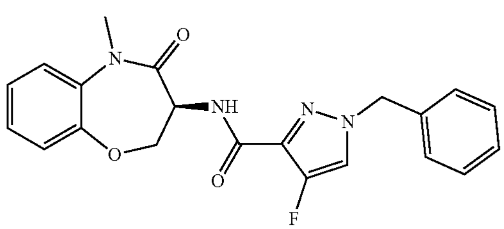 [SMILES: CN1C(=O)[C@@H](NC(=O)c2nn(Cc3ccccc3)cc2F)COc2ccccc21] |
| 66 | 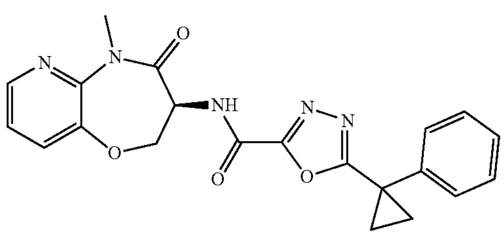 [SMILES: CN1C(=O)[C@@H](NC(=O)c2nnc(C3(c4ccccc4)CC3)o2)COc2cccnc21] |
| 67A | 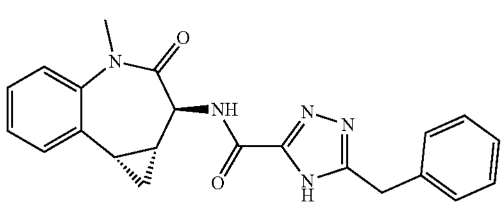 [SMILES: CN1C(=O)[C@@H](NC(=O)c2nnc(Cc3ccccc3)[nH]2)[C@@H]2C[C@@H]2c2ccccc21] |

TABLE 4-continued

| No. | Structure |
|---|---|
| 67B | 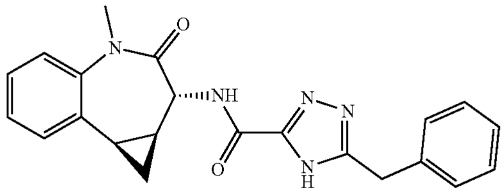 [SMILES: CN1C(=O)[C@H](NC(=O)c2nnc(Cc3ccccc3)[nH]2)[C@H]2C[C@H]2c2ccccc21] |
| 68A | 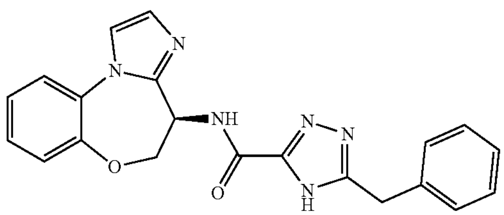 [SMILES: O=C(N[C@H]1COc2ccccc2-n2ccnc21)c1nnc(Cc2ccccc2)[nH]1] |
| 68B | 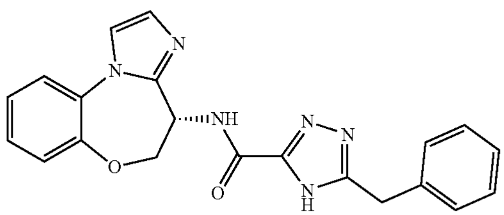 [SMILES: O=C(N[C@@H]1COc2ccccc2-n2ccnc21)c1nnc(Cc2ccccc2)[nH]1] |
| 69A | 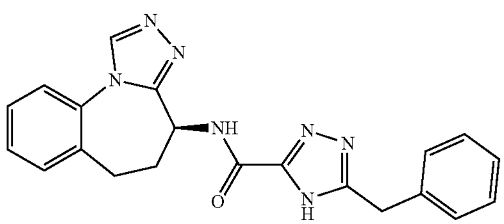 [SMILES: O=C(N[C@H]1CCc2ccccc2-n2cnnc21)c1nnc(Cc2ccccc2)[nH]1] |
| 69B | 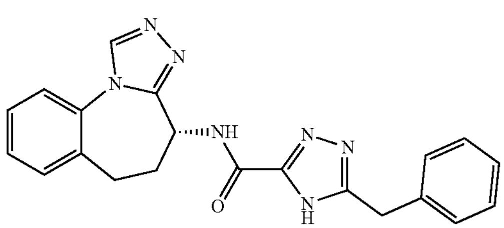 [SMILES: O=C(N[C@@H]1CCc2ccccc2-n2cnnc21)c1nnc(Cc2ccccc2)[nH]1] |
| 70A | 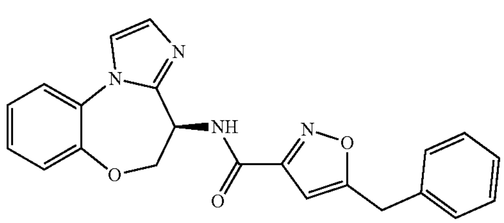 [SMILES: O=C(N[C@H]1COc2ccccc2-n2ccnc21)c1cc(Cc2ccccc2)on1] |
| 70B | 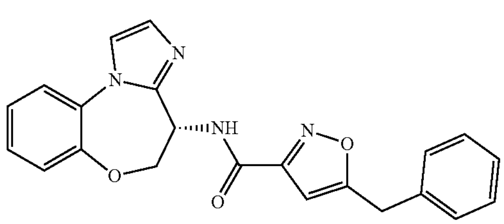 [SMILES: O=C(N[C@@H]1COc2ccccc2-n2ccnc21)c1cc(Cc2ccccc2)on1] |

TABLE 4-continued

| No. | Structure |
|---|---|
| 71A | 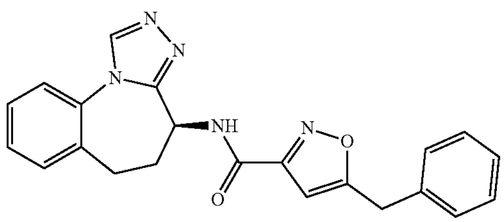 [SMILES: O=C(N[C@H]1CCc2ccccc2-n2cnnc21)c1cc(Cc2ccccc2)on1] |
| 71B | 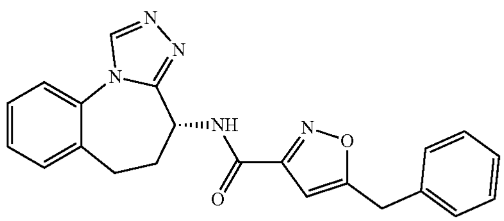 [SMILES: O=C(N[C@@H]1CCc2ccccc2-n2cnnc21)c1cc(Cc2ccccc2)on1] |
| 72 | 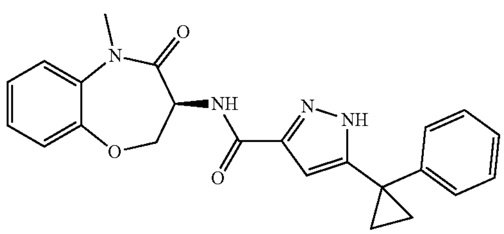 [SMILES: CN1C(=O)[C@@H](NC(=O)c2cc(C3(c4ccccc4)CC3)[nH]n2)COc2ccccc21] |
| 73 | 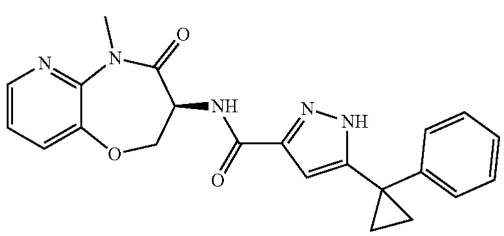 [SMILES: CN1C(=O)[C@@H](NC(=O)c2cc(C3(c4ccccc4)CC3)[nH]n2)COc2cccnc21] |
| 74 | 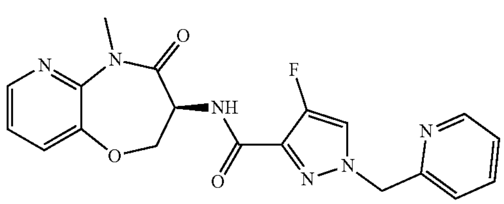 [SMILES: CN1C(=O)[C@@H](NC(=O)c2nn(Cc3ccccn3)cc2F)COc2cccnc21] |
| 75A | 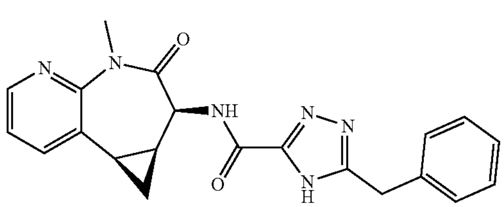 |
| 75B | 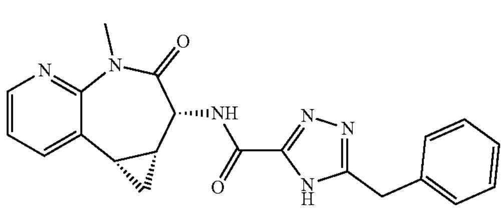 |

TABLE 4-continued
| No. | Structure |
|---|---|
| 76 | 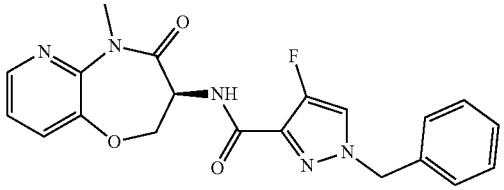 [SMILES: CN1C(=O)[C@@H](NC(=O)c2nn(Cc3ccccc3)cc2F)COc2cccnc21] |
| 77 | 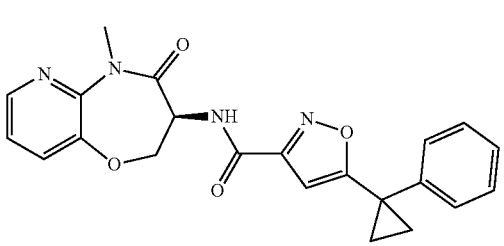 [SMILES: CN1C(=O)[C@@H](NC(=O)c2cc(C3(c4ccccc4)CC3)on2)COc2cccnc21] |
| 78 | 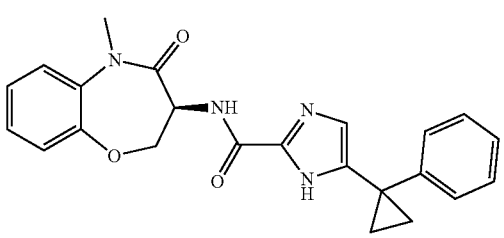 [SMILES: CN1C(=O)[C@@H](NC(=O)c2ncc(C3(c4ccccc4)CC3)[nH]2)COc2ccccc21] |
| 79 | 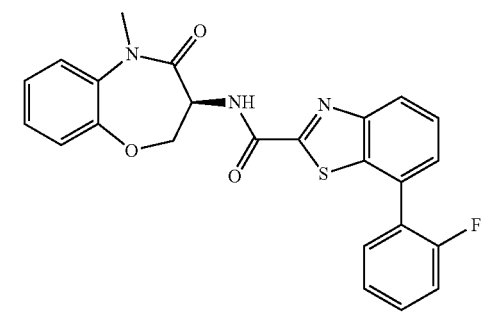 [SMILES: CN1C(=O)[C@@H](NC(=O)c2nc3cccc(-c4ccccc4F)c3s2)COc2ccccc21] |
| 80A | 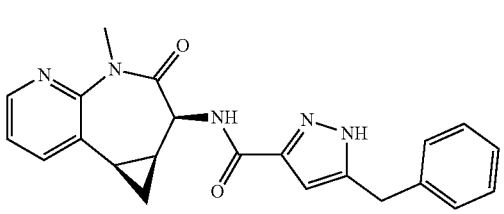 [SMILES: CN1C(=O)[C@@H](NC(=O)c2cc(Cc3ccccc3)[nH]n2)[C@H]2C[C@H]2c2cccnc21] |
| 80B | 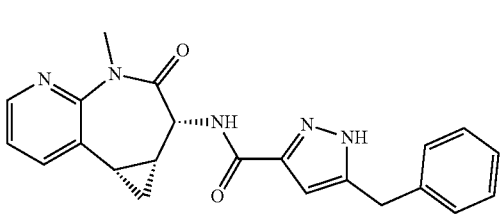 [SMILES: CN1C(=O)[C@H](NC(=O)c2cc(Cc3ccccc3)[nH]n2)[C@@H]2C[C@@H]2c2cccnc21] |
| 81A | 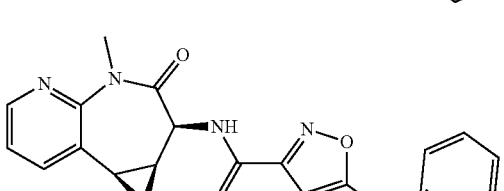 |

TABLE 4-continued

| No. | Structure |
|---|---|
| 81B | 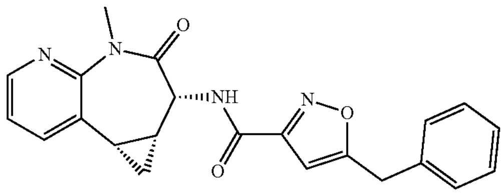 [SMILES: CN1C(=O)[C@H](NC(=O)c2cc(Cc3ccccc3)on2)[C@@H]2C[C@@H]2c2cccnc21] |
| 82A | 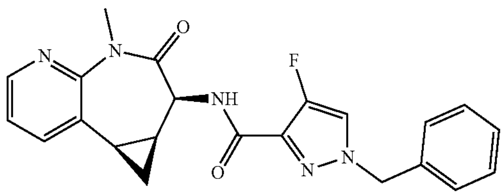 [SMILES: CN1C(=O)[C@@H](NC(=O)c2nn(Cc3ccccc3)cc2F)[C@H]2C[C@H]2c2cccnc21] |
| 82B | 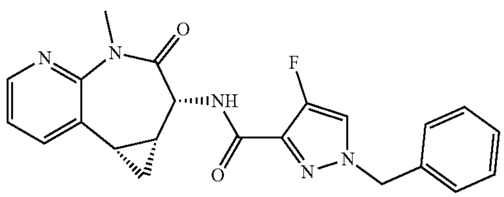 [SMILES: CN1C(=O)[C@H](NC(=O)c2nn(Cc3ccccc3)cc2F)[C@@H]2C[C@@H]2c2cccnc21] |
| 83A | 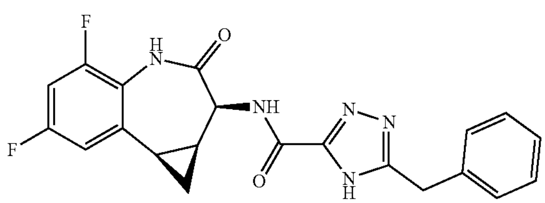 [SMILES: O=C(N[C@@H]1C(=O)Nc2c(F)cc(F)cc2[C@@H]2C[C@H]12)c1nnc(Cc2ccccc2)[nH]1] |
| 83B | 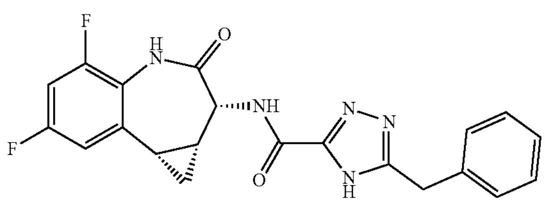 [SMILES: O=C(N[C@H]1C(=O)Nc2c(F)cc(F)cc2[C@H]2C[C@H]21)c1nnc(Cc2ccccc2)[nH]1] |
| 84 | 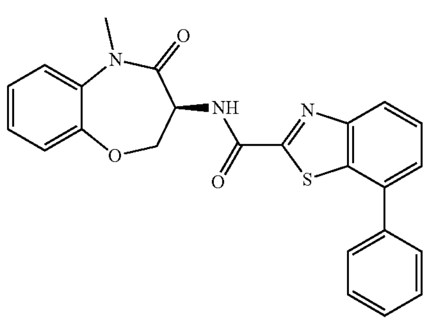 [SMILES: CN1C(=O)[C@@H](NC(=O)c2nc3cccc(-c4ccccc4)c3s2)COc2ccccc21] |
| 85 | 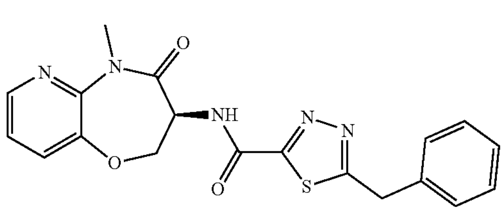 |

189
190
TABLE 4-continued
| No. | Structure |
|---|---|
| 86 | 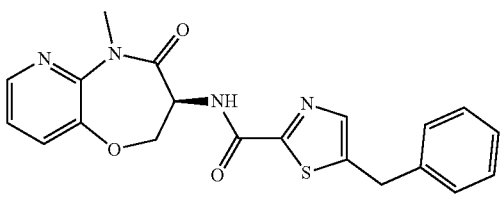 |
| 87 | 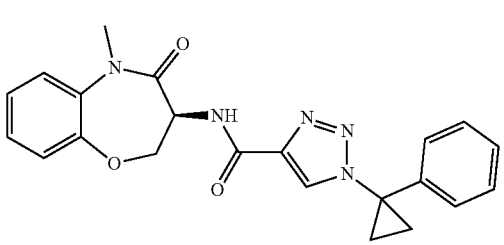 [SMILES: CN1C(=O)[C@@H](NC(=O)c2cn(C3(c4ccccc4)CC3)nn2)COc2ccccc21] |
| 88 | 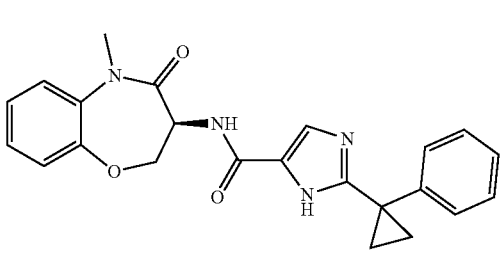 [SMILES: CN1C(=O)[C@@H](NC(=O)c2cnc(C3(c4ccccc4)CC3)[nH]2)COc2ccccc21] |
| 89A | 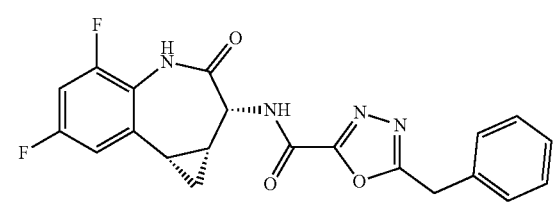 [SMILES: O=C(N[C@H]1C(=O)Nc2c(F)cc(F)cc2[C@H]2C[C@H]21)c1nnc(Cc2ccccc2)o1] |
| 89B | 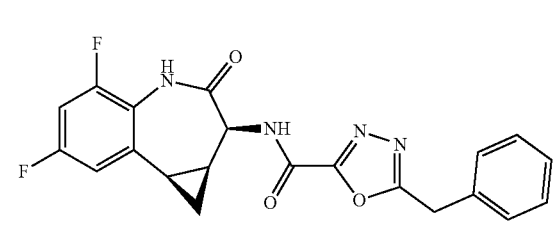 [SMILES: O=C(N[C@@H]1C(=O)Nc2c(F)cc(F)cc2[C@@H]2C[C@H]12)c1nnc(Cc2ccccc2)o1] |
| 90A | 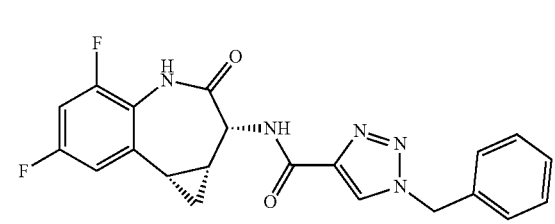 [SMILES: O=C(N[C@H]1C(=O)Nc2c(F)cc(F)cc2[C@H]2C[C@H]21)c1cn(Cc2ccccc2)nn1] |
| 90B | 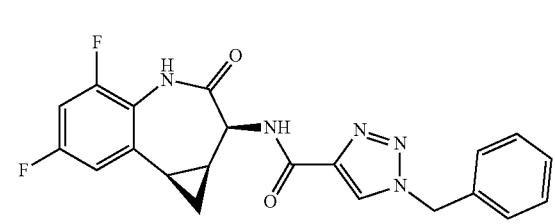 [SMILES: O=C(N[C@@H]1C(=O)Nc2c(F)cc(F)cc2[C@@H]2C[C@H]12)c1cn(Cc2ccccc2)nn1] |

TABLE 4-continued

| No. | Structure |
|---|---|
| 91 | 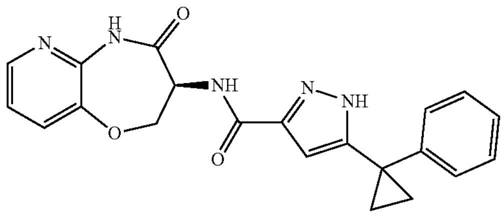 [SMILES: O=C(N[C@H]1COc2cccnc2NC1=O)c1cc(C2(c3ccccc3)CC2)[nH]n1] |
| 92 | 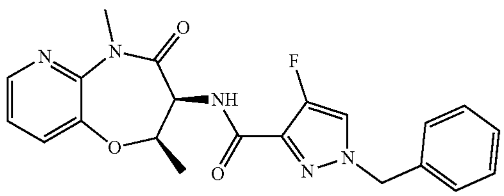 [SMILES: C[C@H]1Oc2cccnc2N(C)C(=O)[C@H]1NC(=O)c1nn(Cc2ccccc2)cc1F] |
| 93 | 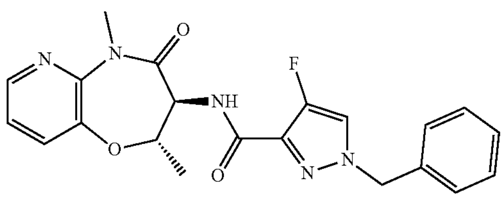 [SMILES: C[C@@H]1Oc2cccnc2N(C)C(=O)[C@H]1NC(=O)c1nn(Cc2ccccc2)cc1F] |
| 94 | 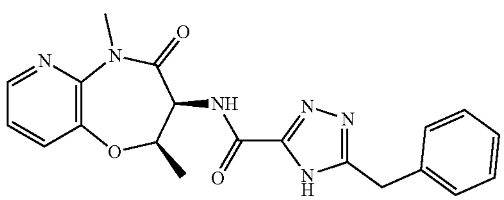 [SMILES: C[C@H]1Oc2cccnc2N(C)C(=O)[C@H]1NC(=O)c1nnc(Cc2ccccc2)[nH]1] |
| 96 | 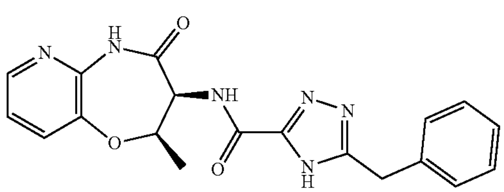 [SMILES: C[C@H]1Oc2cccnc2NC(=O)[C@H]1NC(=O)c1nnc(Cc2ccccc2)[nH]1] |
| 97 | 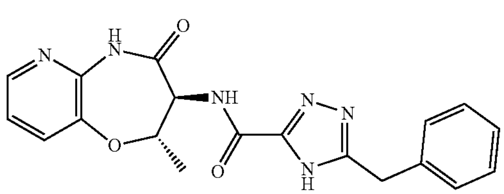 [SMILES: C[C@@H]1Oc2cccnc2NC(=O)[C@H]1NC(=O)c1nnc(Cc2ccccc2)[nH]1] |
| 98B | 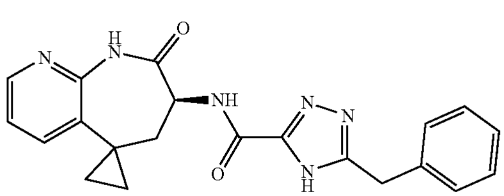 [SMILES: O=C(N[C@H]1CC2(CC2)c2cccnc2NC1=O)c1nnc(Cc2ccccc2)[nH]1] |

TABLE 4-continued

| No. | Structure |
| --- | --- |
| 100A | 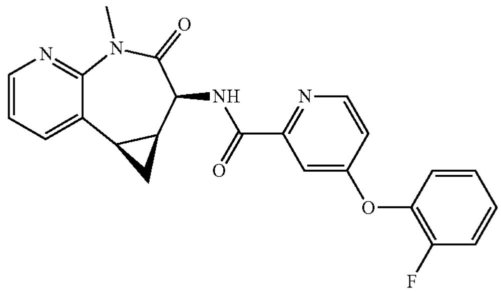 [SMILES: CN1C(=O)[C@@H](NC(=O)c2cc(Oc3ccccc3F)ccn2)[C@H]2C[C@H]2c2cccnc21] |
| 100B | 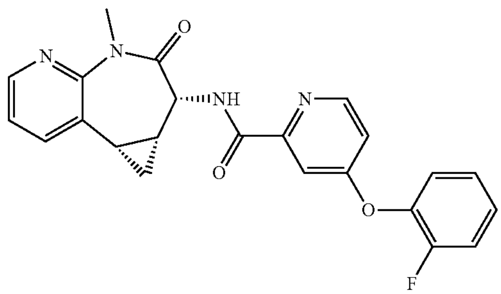 [SMILES: CN1C(=O)[C@H](NC(=O)c2cc(Oc3ccccc3F)ccn2)[C@@H]2C[C@@H]2c2cccnc21] |
| 101B | 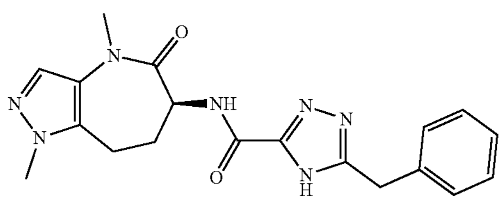 [SMILES: CN1C(=O)[C@@H](NC(=O)c2nnc(Cc3ccccc3)[nH]2)CCc2c1cnn2C] |
| 102B | Second eluting isomer |
| 103B | 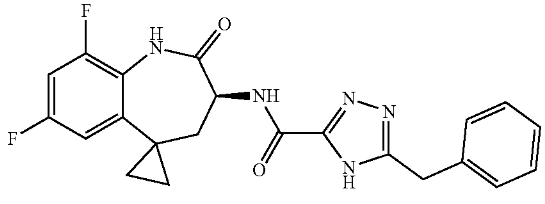 [SMILES: O=C(N[C@H]1CC2(CC2)c2cc(F)cc(F)c2NC1=O)c1nnc(Cc2ccccc2)[nH]1] |
| 104B | 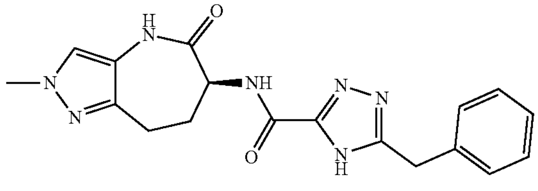 [SMILES: Cn1cc2c(n1)CC[C@H](NC(=O)c1nnc(Cc3ccccc3)[nH]1)C(=O)N2] |

TABLE 4-continued

| No. | Structure |
|---|---|
| 105A | 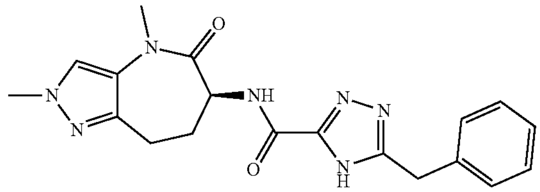 [SMILES: CN1C(=O)[C@@H](NC(=O)c2nnc(Cc3ccccc3)[nH]2)CCc2nn(C)cc21] |
| 106 | 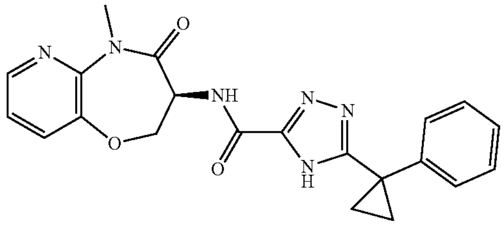 [SMILES: CN1C(=O)[C@@H](NC(=O)c2nnc(C3(c4ccccc4)CC3)[nH]2)COc2cccnc21] |
| 107B | 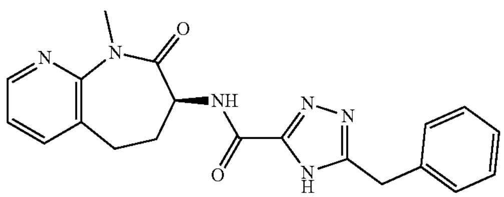 |
| 108 | 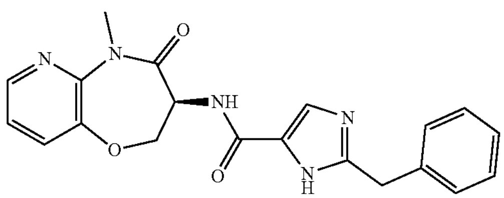 [SMILES: CN1C(=O)[C@@H](NC(=O)c2cnc(Cc3ccccc3)[nH]2)COc2cccnc21] |
| 109A | 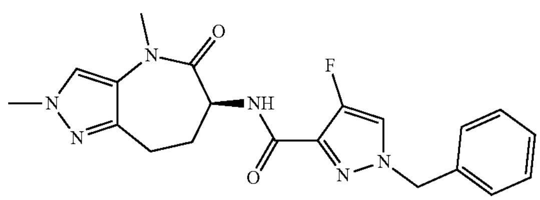 [SMILES: CN1C(=O)[C@@H](NC(=O)c2nn(Cc3ccccc3)cc2F)CCc2nn(C)cc21] |
| 110B | 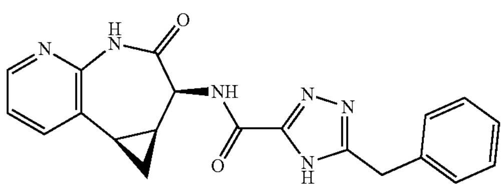 [SMILES: O=C(N[C@@H]1C(=O)Nc2ncccc2[C@@H]2C[C@H]12)c1nnc(Cc2ccccc2)[nH]1] |
| 111B | 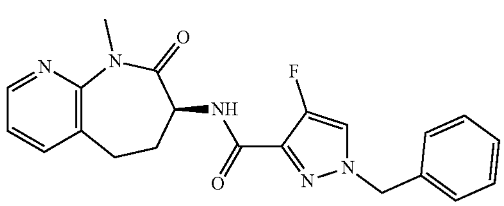 [SMILES: CN1C(=O)[C@@H](NC(=O)c2nn(Cc3ccccc3)cc2F)CCc2cccnc21] |

TABLE 4-continued

| No. | Structure |
|---|---|
| 112 | 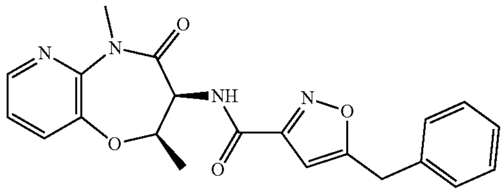 [SMILES: C[C@H]1Oc2cccnc2N(C)C(=O)[C@H]1NC(=O)c1cc(Cc2ccccc2)on1] |
| 113 | 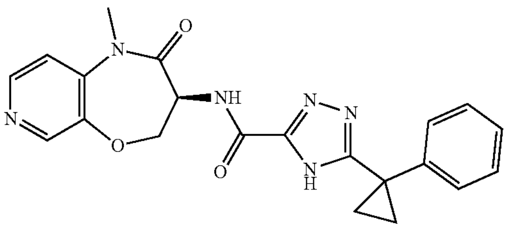 [SMILES: CN1C(=O)[C@@H](NC(=O)c2nnc(C3(c4ccccc4)CC3)[nH]2)COc2cnccc21] |
| 114A | 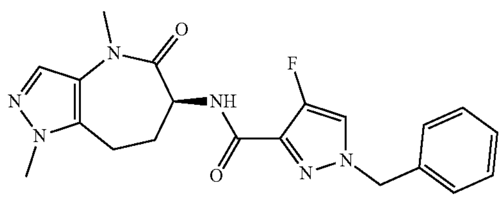 [SMILES: CN1C(=O)[C@@H](NC(=O)c2nn(Cc3ccccc3)cc2F)CCc2c1cnn2C] |
| 115 | 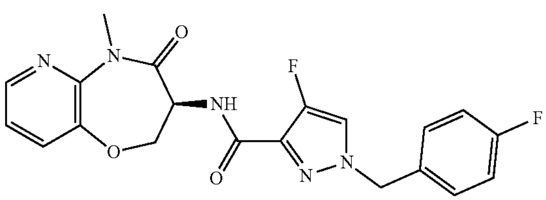 [SMILES: CN1C(=O)[C@@H](NC(=O)c2nn(Cc3ccc(F)cc3)cc2F)COc2cccnc21] |
| 116 | 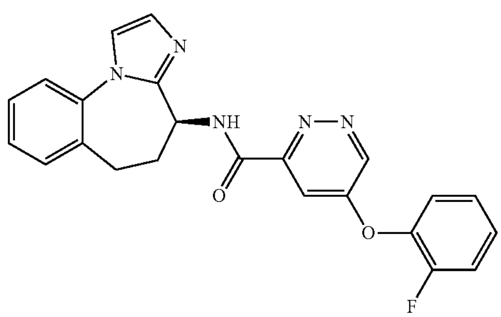 [SMILES: O=C(N[C@H]1CCc2ccccc2-n2ccnc21)c1cc(Oc2ccccc2F)cnn1] |
| 117 | 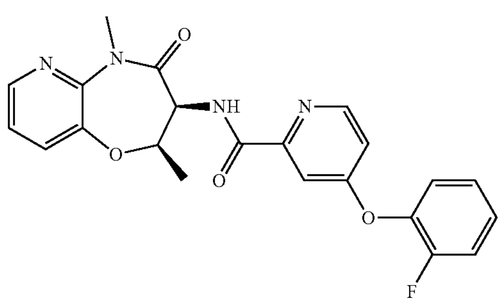 [SMILES: C[C@H]1Oc2cccnc2N(C)C(=O)[C@H]1NC(=O)c1cc(Oc2ccccc2F)ccn1] |

TABLE 4-continued

| No. | Structure |
|---|---|
| 119B | (structure) |
| 120A | (structure) |
| 121B | (structure) |
| 122 | (structure) |
| 123 | (structure) |
| 124 | (structure) |
| 125B | (structure) |

TABLE 4-continued

| No. | Structure |
|---|---|
| 126 | 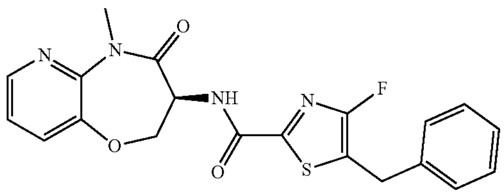 [SMILES: CN1C(=O)[C@@H](NC(=O)c2nc(F)c(Cc3ccccc3)s2)COc2cccnc21] |
| 127 | 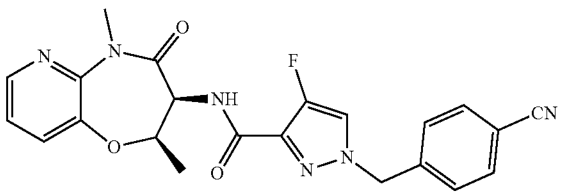 [SMILES: C[C@H]1Oc2cccnc2N(C)C(=O)[C@H]1NC(=O)c1nn(Cc2ccc(C#N)cc2)cc1F] |
| 128 | 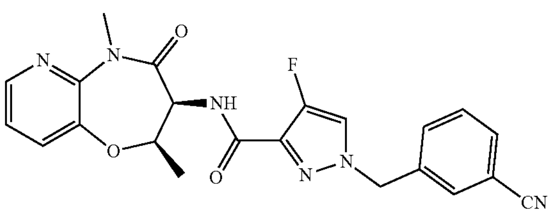 [SMILES: C[C@H]1Oc2cccnc2N(C)C(=O)[C@H]1NC(=O)c1nn(Cc2cccc(C#N)c2)cc1F] |
| 129A | 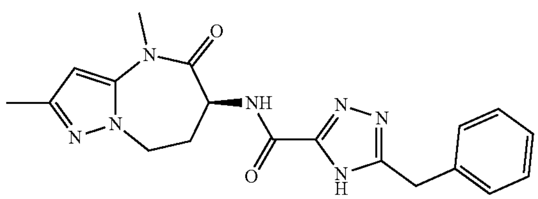 [SMILES: Cc1cc2n(n1)CC[C@H](NC(=O)c1nnc(Cc3ccccc3)[nH]1)C(=O)N2C] |
| 130 | 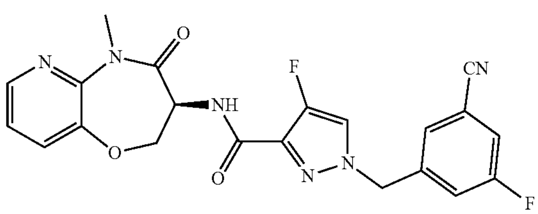 [SMILES: CN1C(=O)[C@@H](NC(=O)c2nn(Cc3cc(F)cc(C#N)c3)cc2F)COc2cccnc21] |
| 131A | 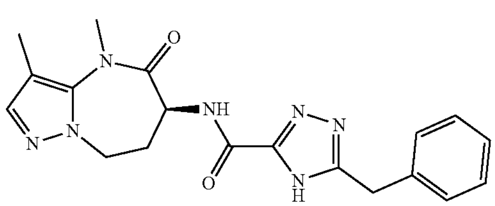 [SMILES: Cc1cnn2c1N(C)C(=O)[C@@H](NC(=O)c1nnc(Cc3ccccc3)[nH]1)CC2] |
| 132 | 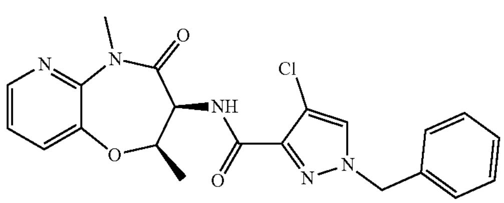 |

TABLE 4-continued

| No. | Structure |
|---|---|
| 133 | 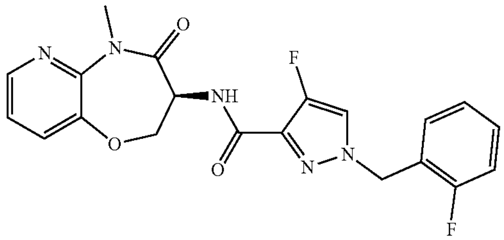 [SMILES: CN1C(=O)[C@@H](NC(=O)c2nn(Cc3ccccc3F)cc2F)COc2cccnc21] |
| 134 | 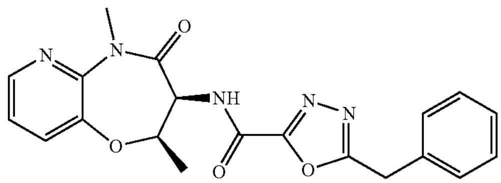 [SMILES: C[C@H]1Oc2cccnc2N(C)C(=O)[C@H]1NC(=O)c1nnc(Cc2ccccc2)o1] |
| 135 | 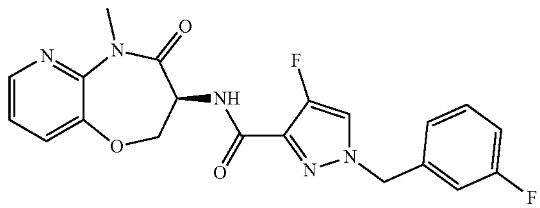 |
| 136 | 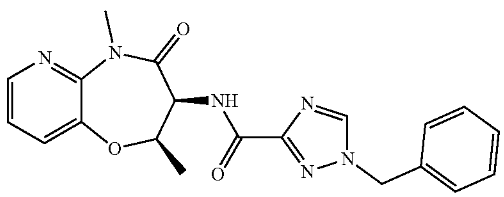 |
| 137 | 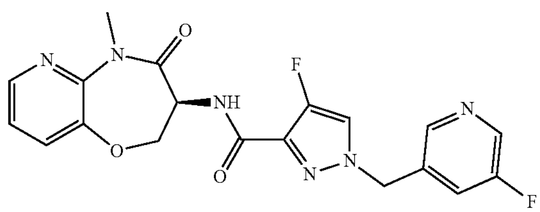 [SMILES: CN1C(=O)[C@@H](NC(=O)c2nn(Cc3cncc(F)c3)cc2F)COc2cccnc21] |
| 138 | 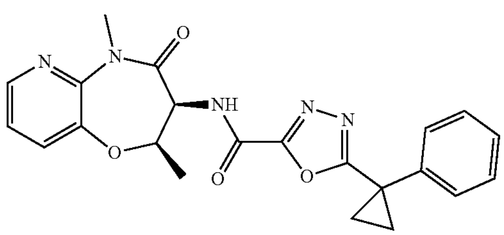 [SMILES: C[C@H]1Oc2cccnc2N(C)C(=O)[C@H]1NC(=O)c1nnc(C2(c3ccccc3)CC2)o1] |
| 139 | 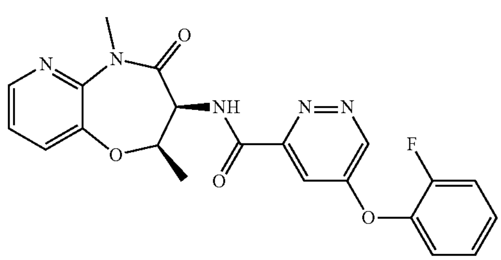 [SMILES: C[C@H]1Oc2cccnc2N(C)C(=O)[C@H]1NC(=O)c1cc(Oc2ccccc2F)cnn1] |

TABLE 4-continued

| No. | Structure |
|---|---|
| 140 | 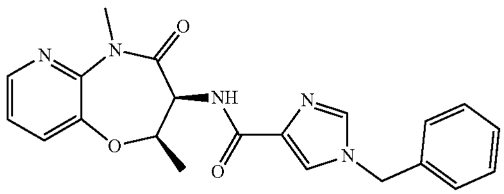 |
| 141B | 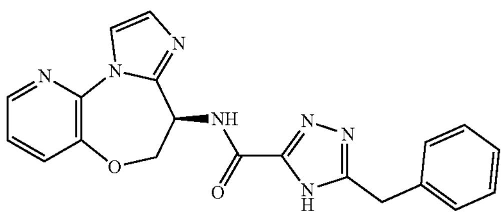 [SMILES: O=C(N[C@H]1COc2cccnc2-n2ccnc21)c1nnc(Cc2ccccc2)[nH]1] |
| 142 | 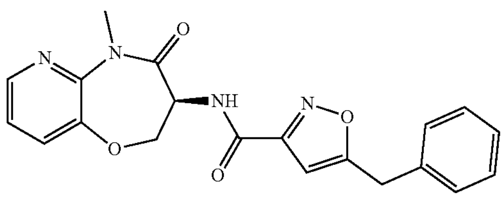 |
| 143 | 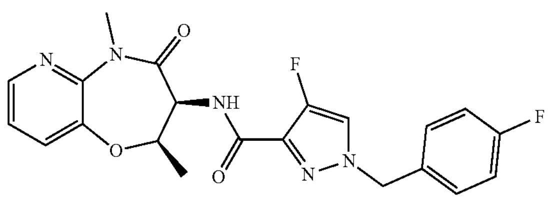 [SMILES: C[C@H]1Oc2cccnc2N(C)C(=O)[C@H]1NC(=O)c1nn(Cc2ccc(F)cc2)cc1F] |
| 144 | 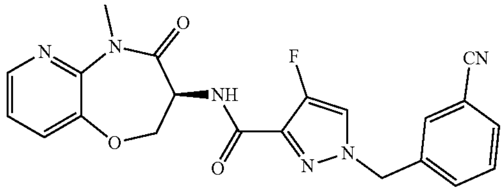 [SMILES: CN1C(=O)[C@@H](NC(=O)c2nn(Cc3cccc(C#N)c3)cc2F)COc2cccnc21] |
| 145A | 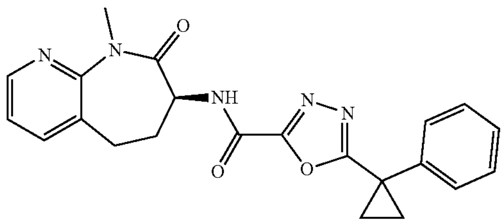 [SMILES: CN1C(=O)[C@@H](NC(=O)c2nnc(C3(c4ccccc4)CC3)o2)CCc2cccnc21] |
| 146 | 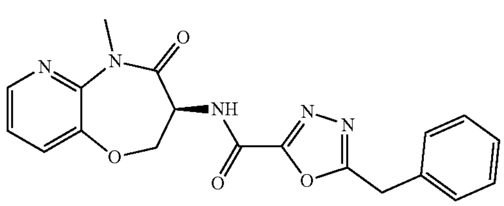 |

TABLE 4-continued

| No. | Structure |
|---|---|
| 147 | 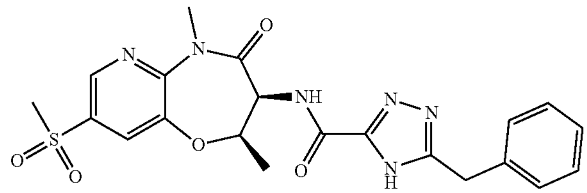 [SMILES: C[C@H]1Oc2cc(S(C)(=O)=O)cnc2N(C)C(=O)[C@H]1NC(=O)c1nnc(Cc2ccccc2)[nH]1] |
| 148A | 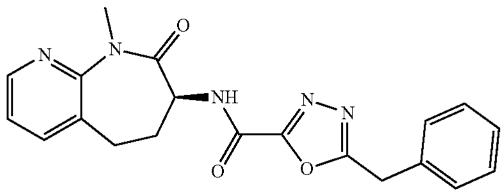 |
| 148B | 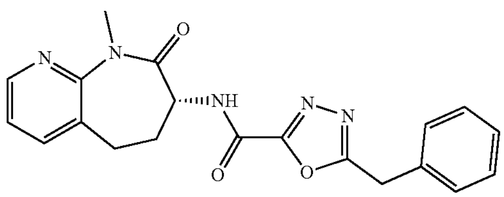 [SMILES: CN1C(=O)[C@H](NC(=O)c2nnc(Cc3ccccc3)o2)CCc2cccnc21] |
| 149 | 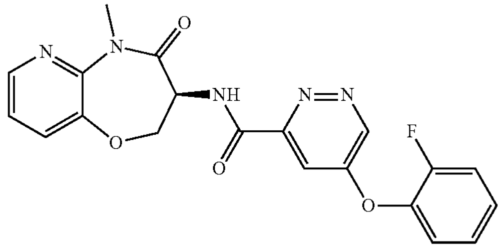 [SMILES: CN1C(=O)[C@@H](NC(=O)c2cc(Oc3ccccc3F)cnn2)COc2cccnc21] |
| 150 | 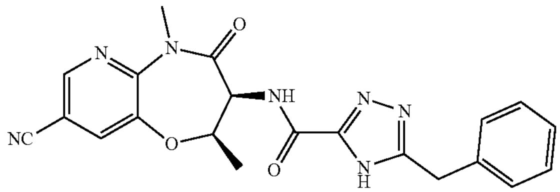 [SMILES: C[C@H]1Oc2cc(C#N)cnc2N(C)C(=O)[C@H]1NC(=O)c1nnc(Cc2ccccc2)[nH]1] |
| 151 | 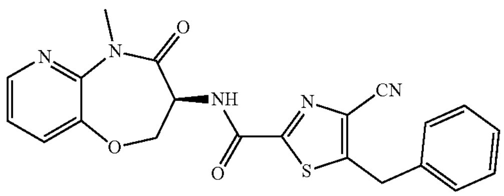 [SMILES: CN1C(=O)[C@@H](NC(=O)c2nc(C#N)c(Cc3ccccc3)s2)COc2cccnc21] |
| 152B | 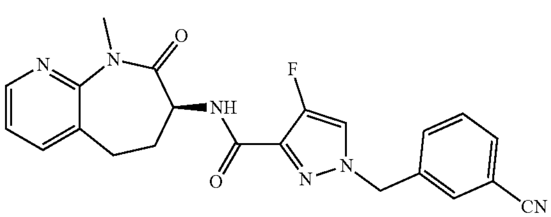 [SMILES: CN1C(=O)[C@@H](NC(=O)c2nn(Cc3cccc(C#N)c3)cc2F)CCc2cccnc21] |

TABLE 4-continued
| No. | Structure |
|---|---|
| 153 | 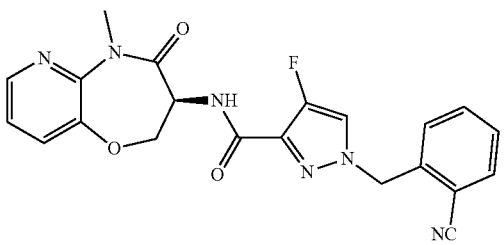 |
| 154B | 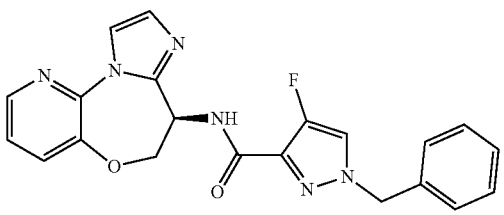 [SMILES: O=C(N[C@H]1COc2cccnc2-n2ccnc21)c1nn(Cc2ccccc2)cc1F] |
| 155 | 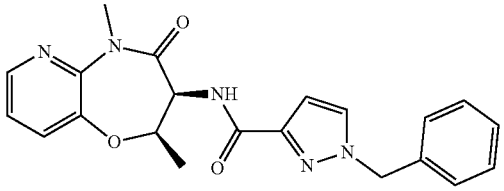 [SMILES: C[C@H]1Oc2cccnc2N(C)C(=O)[C@H]1NC(=O)c1ccn(Cc2ccccc2)n1] |
| 156B | 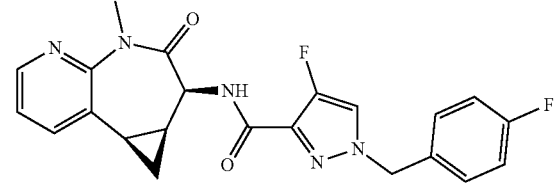 [SMILES: CN1C(=O)[C@@H](NC(=O)c2nn(Cc3ccc(F)cc3)cc2F)[C@H]2C[C@H]2c2cccnc21] |
| 157B | 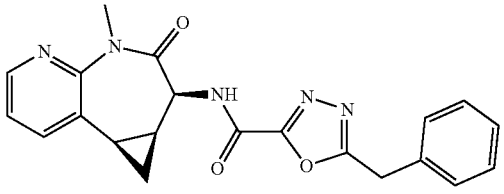 [SMILES: CN1C(=O)[C@@H](NC(=O)c2nnc(Cc3ccccc3)o2)[C@H]2C[C@H]2c2cccnc21] |
| 158 | 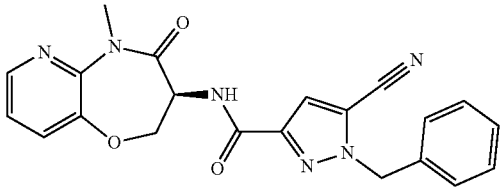 [SMILES: CN1C(=O)[C@@H](NC(=O)c2cc(C#N)n(Cc3ccccc3)n2)COc2cccnc21] |
| 159 | 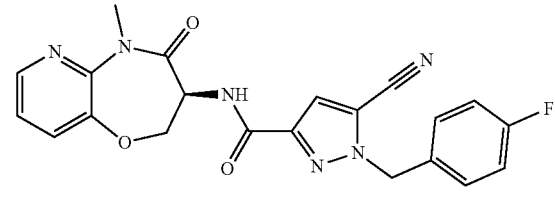 [SMILES: CN1C(=O)[C@@H](NC(=O)c2cc(C#N)n(Cc3ccc(F)cc3)n2)COc2cccnc21] |

TABLE 4-continued
| No. | Structure |
|---|---|
| 160A | 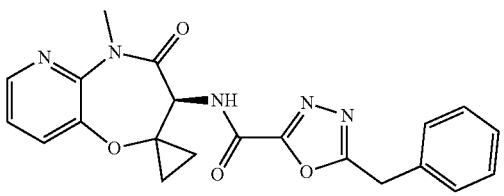 |
| 161 | 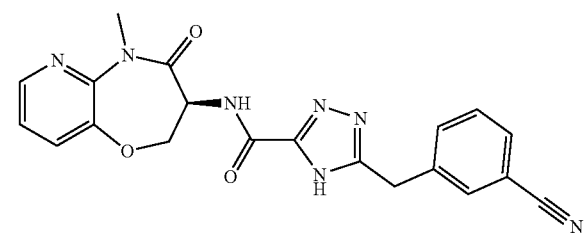 |
| 162 | 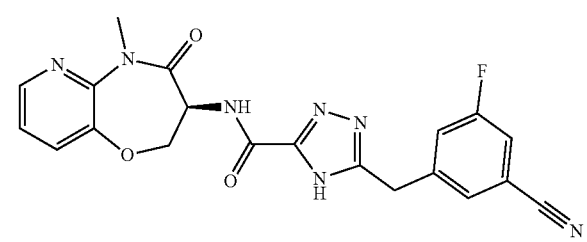 [SMILES: CN1C(=O)[C@@H](NC(=O)c2nnc(Cc3cc(F)cc(C#N)c3)[nH]2)COc2cccnc21] |
| 163 | 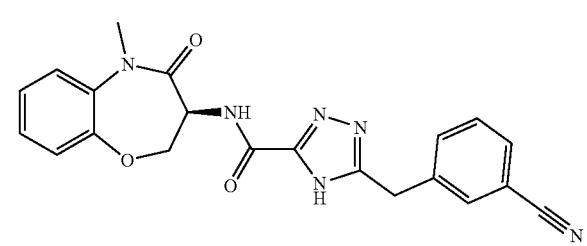 |
| 164 | 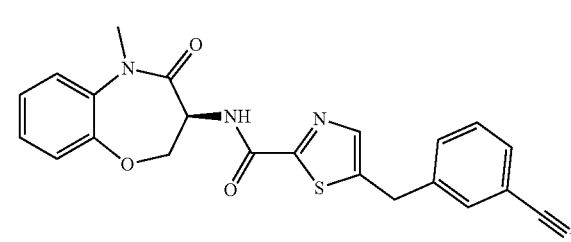 |
| 165 | 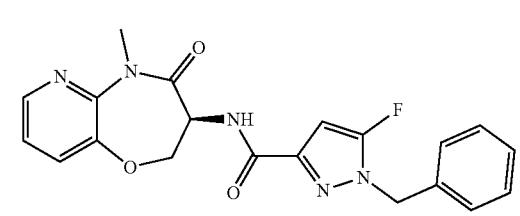 [SMILES: CN1C(=O)[C@@H](NC(=O)c2cc(F)n(Cc3ccccc3)n2)COc2cccnc21] |
| 166 | 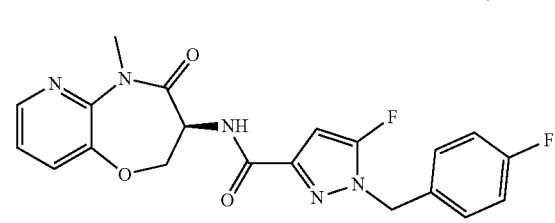 [SMILES: CN1C(=O)[C@@H](NC(=O)c2cc(F)n(Cc3ccc(F)cc3)n2)COc2cccnc21] |

TABLE 4-continued

| No. | Structure |
|---|---|
| 167 | 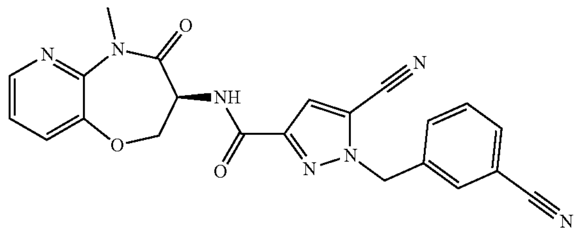 [SMILES: CN1C(=O)[C@@H](NC(=O)c2cc(C#N)n(Cc3cccc(C#N)c3)n2)COc2cccnc21] |
| 168 | 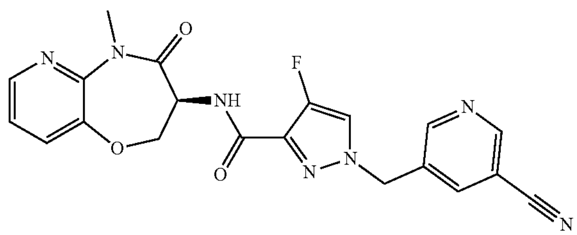 [SMILES: CN1C(=O)[C@@H](NC(=O)c2nn(Cc3cncc(C#N)c3)cc2F)COc2cccnc21] |
| 169 | 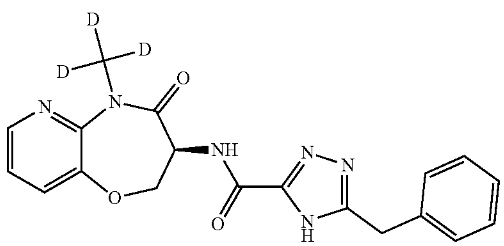 [SMILES: [2H]C([2H])([2H])N1C(=O)[C@@H](NC(=O)c2nnc(Cc3ccccc3)[nH]2)COc2cccnc21] |
| 170A | 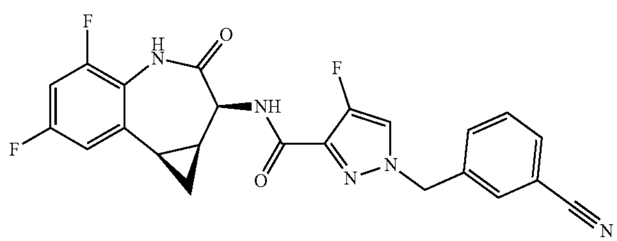 [SMILES: N#Cc1cccc(Cn2cc(F)c(C(=O)N[C@@H]3C(=O)Nc4c(F)cc(F)cc4[C@@H]4C[C@H]34)n2)c1] |
| 171 | 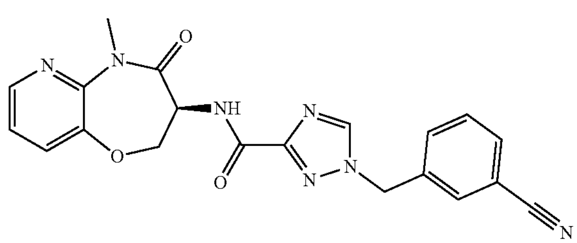 [SMILES: CN1C(=O)[C@@H](NC(=O)c2ncn(Cc3cccc(C#N)c3)n2)COc2cccnc21] |
| 172 | 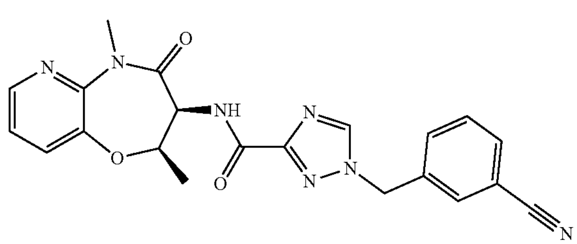 [SMILES: C[C@H]1Oc2cccnc2N(C)C(=O)[C@H]1NC(=O)c1ncn(Cc2cccc(C#N)c2)n1] |

TABLE 4-continued
| No. | Structure |
|---|---|
| 173 | 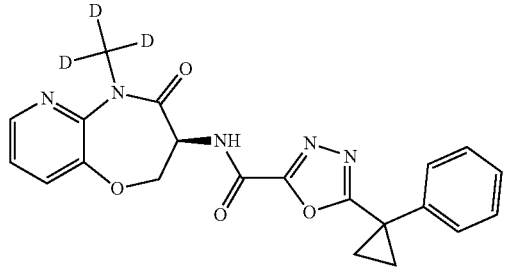 [SMILES: [2H]C([2H])([2H])N1C(=O)[C@@H](NC(=O)c2nnc(C3(c4ccccc4)CC3)o2)COc2cccnc21] |
| 174 | 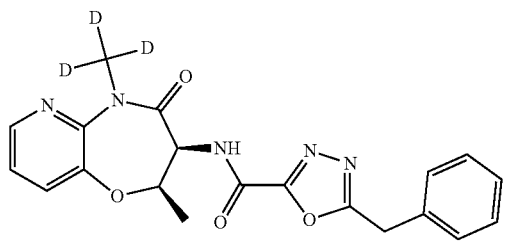 [SMILES: [2H]C([2H])([2H])N1C(=O)[C@@H](NC(=O)c2nnc(Cc3ccccc3)o2)[C@@H](C)Oc2cccnc21] |
| 175 | 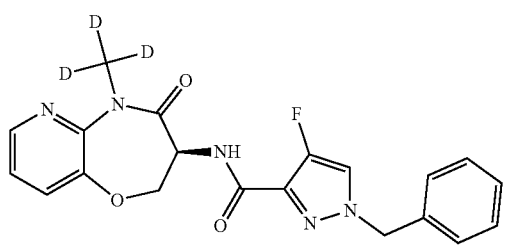 [SMILES: [2H]C([2H])([2H])N1C(=O)[C@@H](NC(=O)c2nn(Cc3ccccc3)cc2F)COc2cccnc21] |
| 176 | 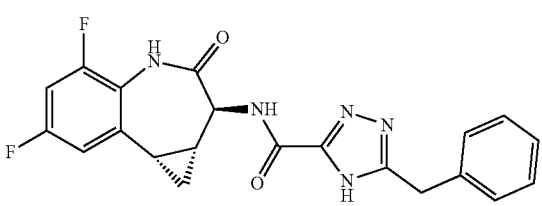 [SMILES: O=C(N[C@@H]1C(=O)Nc2c(F)cc(F)cc2[C@H]2C[C@@H]12)c1nnc(Cc2ccccc2)[nH]1] |
| 177A | 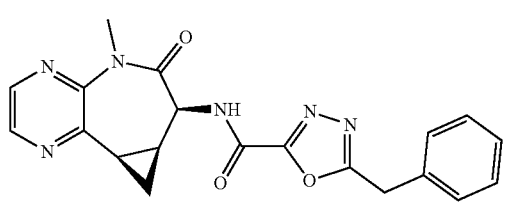 |
| 178A | 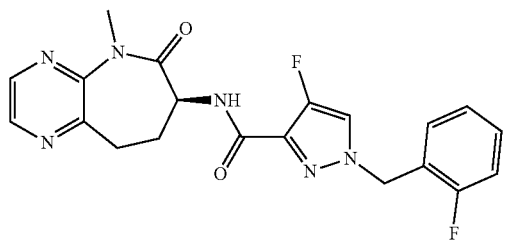 [SMILES: CN1C(=O)[C@@H](NC(=O)c2nn(Cc3ccccc3F)cc2F)CCc2nccnc21] |

TABLE 4-continued

| No. | Structure |
|---|---|
| 179A | 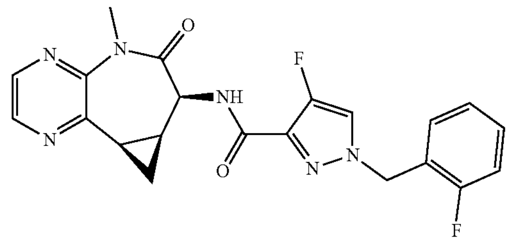 [SMILES: CN1C(=O)[C@@H](NC(=O)c2nn(Cc3ccccc3F)cc2F)[C@H]2C[C@H]2c2nccnc21] |
| 180A | 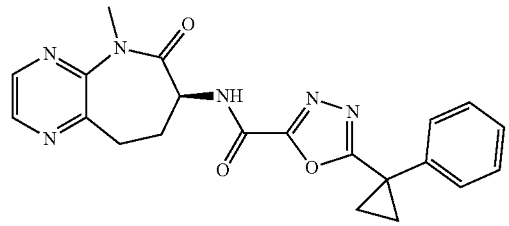 [SMILES: CN1C(=O)[C@@H](NC(=O)c2nnc(C3(c4ccccc4)CC3)o2)CCc2nccnc21] |
| 181B | 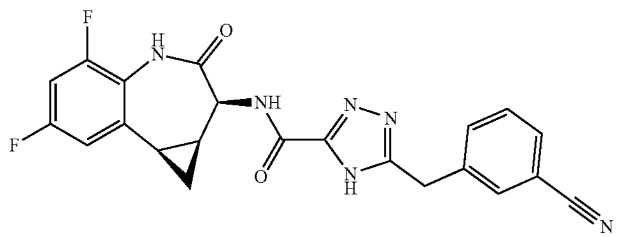 [SMILES: N#Cc1cccc(Cc2nnc(C(=O)N[C@@H]3C(=O)Nc4c(F)cc(F)cc4[C@@H]4C[C@H]34)[nH]2)c1] |
| 182B | 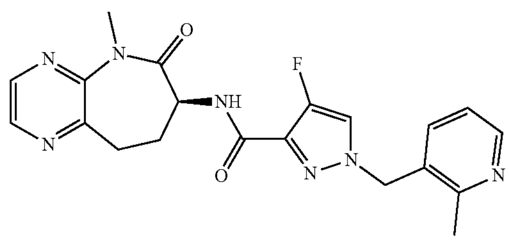 [SMILES: Cc1ncccc1Cn1cc(F)c(C(=O)N[C@H]2CCc3nccnc3N(C)C2=O)n1] |
| 183B | 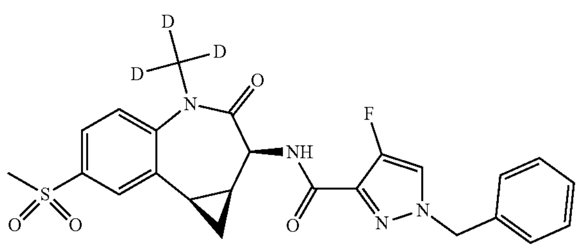 [SMILES: [2H]C([2H])([2H])N1C(=O)[C@@H](NC(=O)c2nn(Cc3ccccc3)cc2F)[C@H]2C[C@H]2c2cc(S(C)(=O)=O)ccc21] |
| 184 | 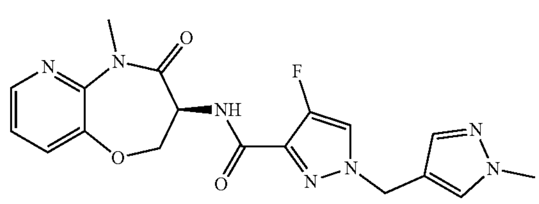 [SMILES: CN1C(=O)[C@@H](NC(=O)c2nn(Cc3cnn(C)c3)cc2F)COc2cccnc21] |
| 188 | 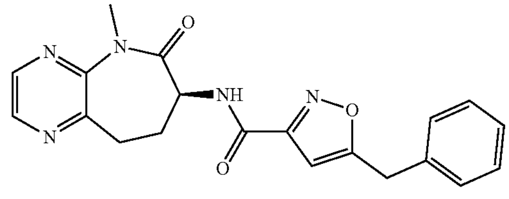 [SMILES: CN1C(=O)[C@@H](NC(=O)c2cc(Cc3ccccc3)on2)CCc2nccnc21] |

TABLE 4-continued

| No. | Structure |
|---|---|
| 190 | 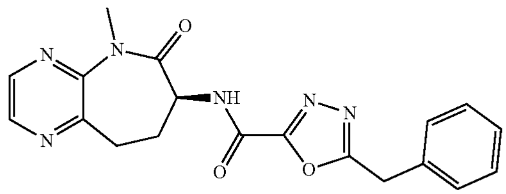 [SMILES: CN1C(=O)[C@@H](NC(=O)c2nnc(Cc3ccccc3)o2)CCc2nccnc21] |
| 192 | 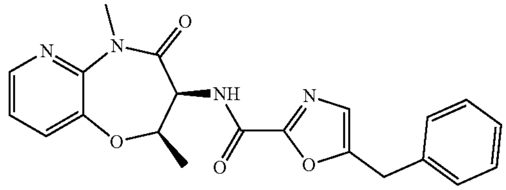 [SMILES: C[C@H]1Oc2cccnc2N(C)C(=O)[C@H]1NC(=O)c1ncc(Cc2ccccc2)o1] |
| 193 | 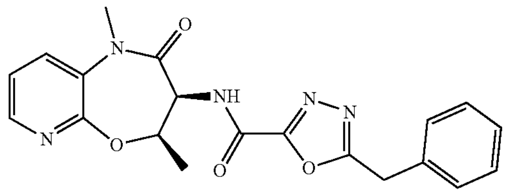 [SMILES: C[C@H]1Oc2ncccc2N(C)C(=O)[C@H]1NC(=O)c1nnc(Cc2ccccc2)o1] |
| 194 | 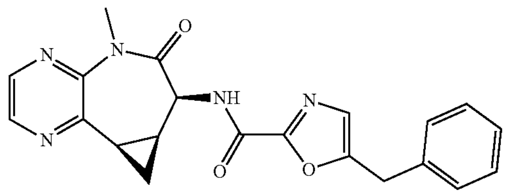 |
| 195 | 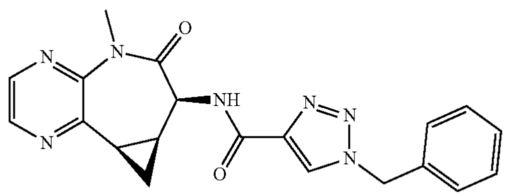 [SMILES: CN1C(=O)[C@@H](NC(=O)c2cn(Cc3ccccc3)nn2)[C@H]2C[C@H]2c2nccnc21] |
| 197 | 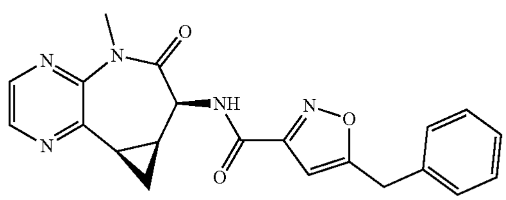 [SMILES: CN1C(=O)[C@@H](NC(=O)c2cc(Cc3ccccc3)on2)[C@H]2C[C@H]2c2nccnc21] |
| 198 | 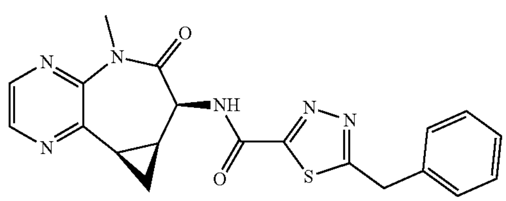 |
| 200 | 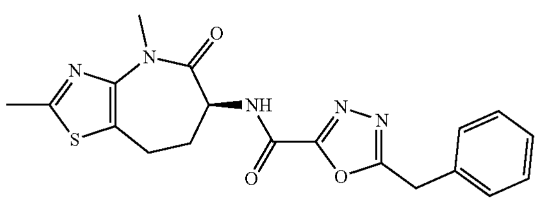 [SMILES: Cc1nc2c(s1)CC[C@H](NC(=O)c1nnc(Cc3ccccc3)o1)C(=O)N2C] |

TABLE 4-continued

| No. | Structure |
|---|---|
| 201 | 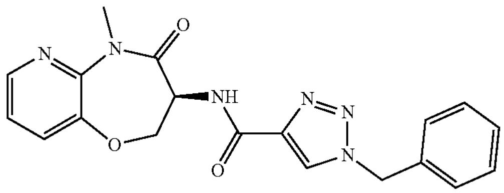 [SMILES: CN1C(=O)[C@@H](NC(=O)c2cn(Cc3ccccc3)nn2)COc2cccnc21] |
| 203 | 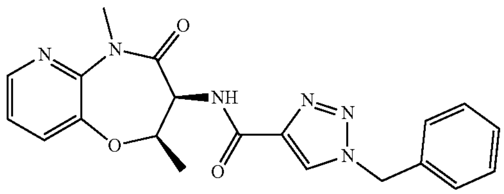 [SMILES: C[C@H]1Oc2cccnc2N(C)C(=O)[C@H]1NC(=O)c1cn(Cc2ccccc2)nn1] |
| 204 | 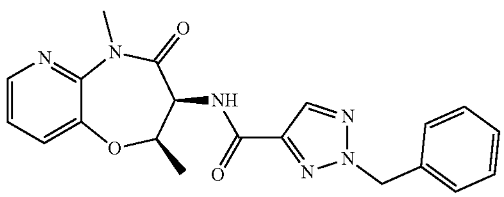 |
| 205 | 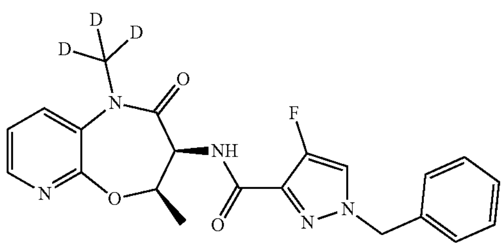 [SMILES: [2H]C([2H])([2H])N1C(=O)[C@@H](NC(=O)c2nn(Cc3ccccc3)cc2F)[C@@H](C)Oc2ncccc21] |
| 206 | 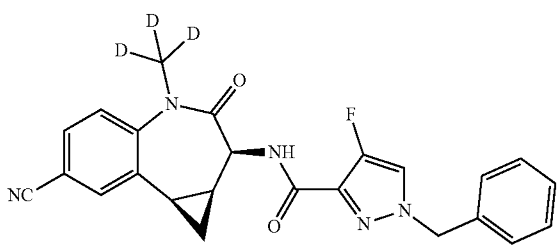 [SMILES: [2H]C([2H])([2H])N1C(=O)[C@@H](NC(=O)c2nn(Cc3ccccc3)cc2F)[C@H]2C[C@H]2c2cc(C#N)ccc21] |
| 207 | 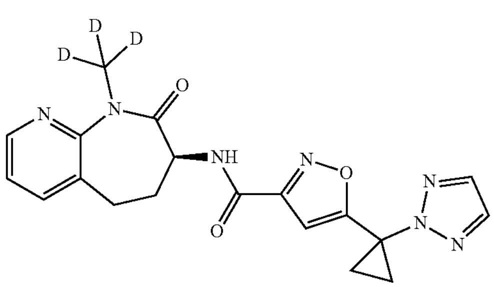 [SMILES: [2H]C([2H])([2H])N1C(=O)[C@@H](NC(=O)c2cc(C3(n4nccn4)CC3)on2)CCc2cccnc21] |
| 208 | 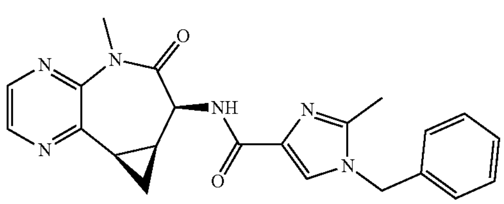 [SMILES: Cc1nc(C(=O)N[C@@H]2C(=O)N(C)c3nccnc3[C@@H]3C[C@H]23)cn1Cc1ccccc1] |

TABLE 4-continued

| No. | Structure |
| --- | --- |
| 209 | 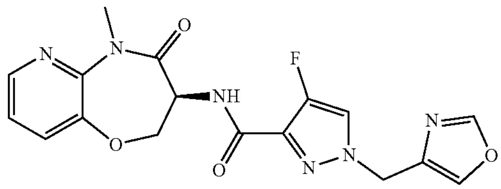 [SMILES: CN1C(=O)[C@@H](NC(=O)c2nn(Cc3cocn3)cc2F)COc2cccnc21] |
| 213 | 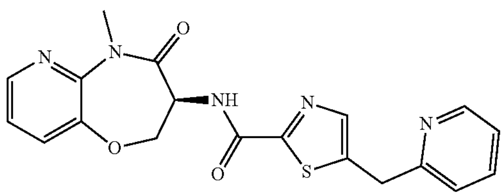 |
| 214 | 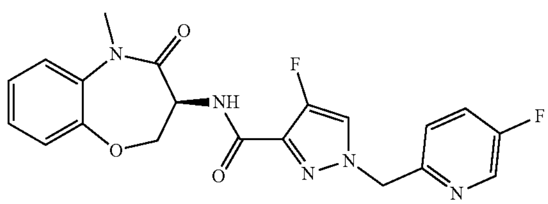 [SMILES: CN1C(=O)[C@@H](NC(=O)c2nn(Cc3ccc(F)cn3)cc2F)COc2ccccc21] |
| 215 | 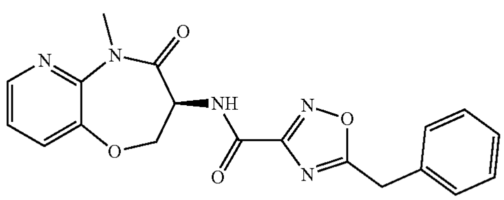 [SMILES: CN1C(=O)[C@@H](NC(=O)c2noc(Cc3ccccc3)n2)COc2cccnc21] |
| 216 | 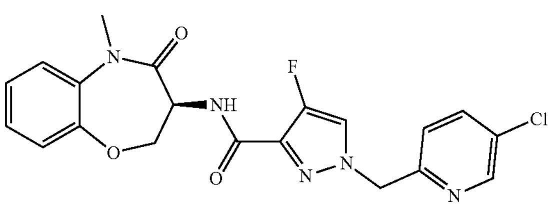 [SMILES: CN1C(=O)[C@@H](NC(=O)c2nn(Cc3ccc(Cl)cn3)cc2F)COc2ccccc21] |
| 217 | 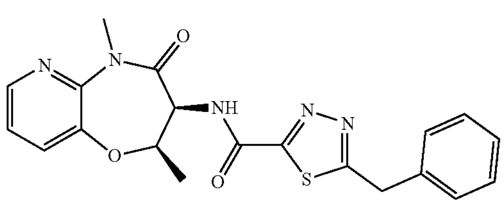 |
| 218 | 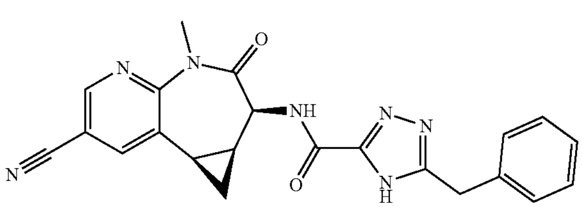 [SMILES: CN1C(=O)[C@@H](NC(=O)c2nnc(Cc3ccccc3)[nH]2)[C@H]2C[C@H]2c2cc(C#N)cnc21] |

TABLE 4-continued

| No. | Structure |
|---|---|
| 219 | 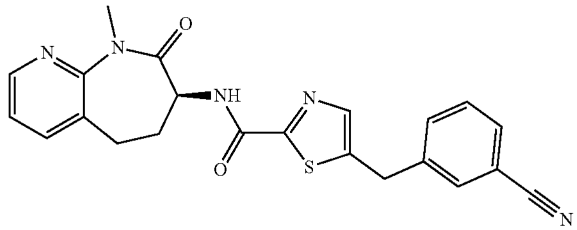 [SMILES: CN1C(=O)[C@@H](NC(=O)c2ncc(Cc3cccc(C#N)c3)s2)CCc2cccnc21] |
| 220 | 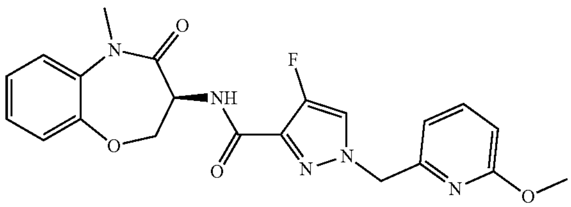 [SMILES: COc1cccc(Cn2cc(F)c(C(=O)N[C@H]3COc4ccccc4N(C)C3=O)n2)n1] |
| 221 | 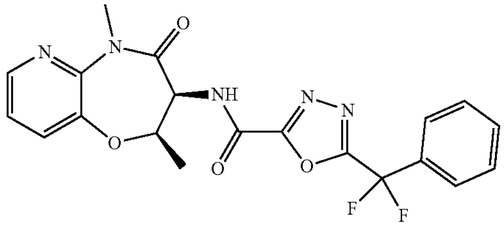 [SMILES: C[C@H]1Oc2cccnc2N(C)C(=O)[C@H]1NC(=O)c1nnc(C(F)(F)c2ccccc2)o1] |
| 222 | 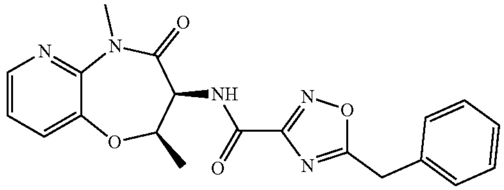 [SMILES: C[C@H]1Oc2cccnc2N(C)C(=O)[C@H]1NC(=O)c1noc(Cc2ccccc2)n1] |
| 223 | 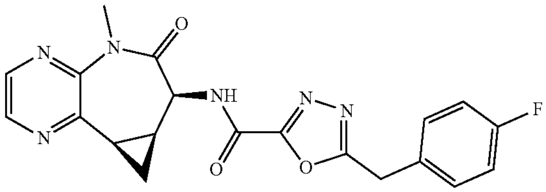 [SMILES: CN1C(=O)[C@@H](NC(=O)c2nnc(Cc3ccc(F)cc3)o2)[C@H]2C[C@H]2c2nccnc21] |
| 224 | 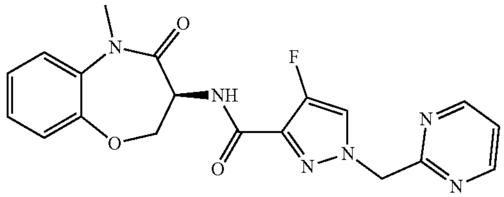 [SMILES: CN1C(=O)[C@@H](NC(=O)c2nn(Cc3ncccn3)cc2F)COc2ccccc21] |
| 226 | 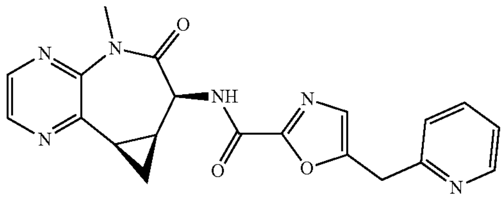 [SMILES: CN1C(=O)[C@@H](NC(=O)c2ncc(Cc3ccccn3)o2)[C@H]2C[C@H]2c2nccnc21] |

TABLE 4-continued

| No. | Structure |
|-----|-----------|
| 227 | 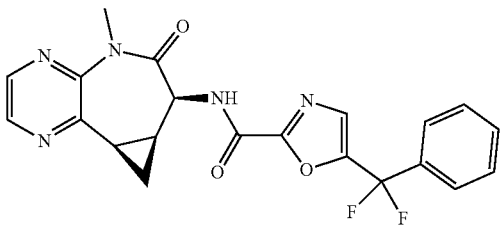 [SMILES: CN1C(=O)[C@@H](NC(=O)c2ncc(C(F)(F)c3ccccc3)o2)[C@H]2C[C@H]2c2nccnc21] |

4. Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Experiments with knockout animal models and Necrostatin 1, a receptor-interacting protein kinase 1 inhibitor, have demonstrated the effectiveness of receptor-interacting protein kinase 1 inhibition in protecting tissues from inflammatory bowel diseases (e.g., ulcerative colitis and Crohn's disease), psoriasis, retinal-detachment-induced photoreceptor necrosis, retinitis pigmentosa, cerulein-induced acute pancreatitis, and sepsis/systemic inflammatory response syndrome (SIRS), and alleviating ischemic brain injury, retinal ischemia/reperfusion injury, Huntington's disease, renal ischemia reperfusion injury, cisplatin induced kidney injury, traumatic brain injury, hematological and solid organ malignancies, bacterial infections and viral infections (e.g., tuberculosis and influenza) and lysosomal storage diseases.

The receptor-interacting protein kinase 1 inhibitors of the present disclosure are therefore useful for treating diseases and conditions mediated by receptor-interacting protein kinase 1, including but not limited to inflammatory diseases or disorders, necrotic cell diseases, neurodegenerative diseases, central nervous system (CNS) diseases, ocular diseases, infections, and malignancies. In certain embodiments, the receptor-interacting protein kinase 1 inhibitors described herein can inhibit inflammation, protect tissue or cell from damage or undesired cell death (e.g., necrosis or apoptosis), ameliorate symptoms, and improve immune response or neuronal function in a patient suffering from any of the prescribed diseases or conditions. Moreover, the compounds may be suitable for treatment of immune-mediated disease, such as but not limited to, allergic diseases, autoimmune diseases, and prevention of transplant rejection.

Provided herein are compounds and compositions for use in medicine. In certain embodiments, the compounds and compositions are for use in the treatment of a receptor-interacting protein kinase 1-mediated disease or disorder. Also provided is a method of treating a receptor-interacting protein kinase 1-mediated disease or disorder comprising administering a therapeutically effective amount of a compound or pharmaceutical composition disclosed herein to a subject in need thereof. In certain embodiments, the disease or disorder is an inflammatory disease associated with A20 SNPs.

Various specific diseases and disorders are described below. In certain embodiments, the disease or disorder is necrotizing enterocolitis, tuberous sclerosis, Tangier's Disease, Wohlman's Syndrome, inflammatory bowel disease, Crohn's disease, ulcerative colitis, psoriasis, retinal detachment, retinitis pigmentosa, macular degeneration, pancreatitis (e.g., acute pancreatitis), atopic dermatitis, rheumatoid arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, periodontitis, bacterial infection, staphylococcus infection, mycobacterium infection, ofretinitis pigmentosa, influenza, transplant rejection, burns or hypoxia. In certain embodiments, the disease or disorder is trauma, ischemia, stroke, cardiac infarction, infection, lysosomal storage disease, Niemann-Pick disease, Gaucher's disease, Krabbe disease, sepsis, Parkinson's disease, Alzheimer's disease, amyotrophic lateral sclerosis (ALS/Lou Gehrig's Disease), Huntington's disease, HIV-associated dementia, encephalopathy, retinal degenerative disease, glaucoma, age-related macular degeneration, rheumatoid arthritis, psoriasis, psoriatic arthritis or inflammatory bowel disease. In certain embodiments, the disease or disorder is Alzheimer's disease, ALS, Friedreich's ataxia, Huntington's disease, Lewy body disease, Parkinson's disease, Huntington's disease, multiple sclerosis, diabetic neuropathy, polyglutamine (polyQ) diseases, stroke, Fahr disease, Menke's disease, Wilson's disease, cerebral ischemia, lysosomal storage disease or a prion disorder. In certain embodiments, the disease is ALS. In certain embodiments, the disease is Alzheimer's disease. In certain embodiments, the disease is lysosomal storage disease. In certain embodiments, the disease is Parkinson's disease. In certain embodiments the disorder is an ischemic disease of organs including but not limited to brain, heart, kidney and liver. In some different embodiments, the disorder is an ocular disorder such as retinal degenerative disease, glaucoma or age-related macular degeneration. In some different embodiments, the disorder is a central nervous system (CNS) disorder.

In certain embodiments, the compounds and compositions are useful for treating psoriasis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

In certain embodiments, provided is a method of treating a disease or disorder selected from the group consisting of rheumatoid arthritis, systemic onset juvenile idiopathic arthritis (SoJIA), spondyloarthritis, osteoarthritis, psoriasis, Crohn's disease, ulcerative colitis, and multiple sclerosis, comprising administering a therapeutically effective amount of a compound as provided herein to a subject in need thereof. In certain embodiments, provided is a method of treating a disease or disorder selected from the group consisting of autoimmune hepatitis, atherosclerosis, neutrophilic dermatoses, or a rare disease driven by A20, NEMO, and/or LUBAC mutations, comprising administering a therapeutically effective amount of a compound as provided herein to a subject in need thereof. In certain embodiments, the compound is of Formula I (or any Formula described herein or tautomer thereof), wherein A is triazole. In certain embodiments, the compound is of Formula V or Va. In certain embodiments, the method comprises administering Compound 42 or tautomer thereof.

Inflammatory Diseases or Disorders

The receptor-interacting protein kinase 1 inhibitors described herein may be used to treat inflammatory diseases and disorders. Inflammatory diseases and disorders typically exhibit high levels of inflammation in the connective tissues, or degeneration of these tissues.

Non-limiting examples of inflammatory diseases and disorders include Alzheimer's, ankylosing spondylitis, arthritis including osteoarthritis, rheumatoid arthritis (RA), psoriasis, asthma, atherosclerosis, Crohn's disease, colitis, dermatitis, diverticulitis, fibromyalgia, hepatitis, irritable bowel syndrome (IBS), inflammatory bowel disease (IBD), systemic lupus erythematous (SLE), nephritis, Parkinson's disease, and ulcerative colitis.

In certain embodiments, the compounds and compositions of the present disclosure are useful for treating rheumatoid arthritis (RA). In certain embodiments, the compounds and compositions of the present disclosure are useful for treating ulcerative colitis. I In certain embodiments, the compounds and compositions of the present disclosure are useful for treating psoriasis. In certain embodiments, the compounds and compositions of the present disclosure are useful for treating psoriasis or psoriatic arthritis. In certain embodiments, the disease is spondyloarthritis.

Necrotic Cell Diseases

The compounds described herein may be used for the treatment of diseases/disorders caused or otherwise associated with necrosis. The term "necrotic cell disease" refers to diseases associated with or caused by cellular necrosis, for example trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis or inflammatory bowel disease.

The necrotic cell diseases can be acute diseases such as trauma, ischemia, stroke, cardiac infarction, anthrax lethal toxin induced septic shock, sepsis, cell death induced by LPS, and HIV induced T-cell death leading to immunodeficiency. The necrotic cell diseases also include chronic neurodegenerative diseases, such as Parkinson's disease, Huntington's disease, amyotrophic lateral sclerosis, Alzheimer's disease, infectious encelopathies, and dementia such as HIV associated dementia.

Neurodegenerative and CNS Diseases

The receptor-interacting protein kinase 1 inhibitors described herein may also be used to treat neurodegenerative diseases. Neurodegenerative diseases can affect many of the body's activities, such as balance, movement, talking, breathing, and heart function. Neurodegenerative diseases can be genetic or caused by medical conditions such as alcoholism, tumors, strokes, toxins, chemicals, and viruses.

Non-limiting examples of neurodegenerative diseases include Alzheimer's disease, amyotrophic lateral sclerosis (ALS), Friedreich's ataxia, Huntington's disease, Lewy body disease, Parkinson's disease, and spinal muscular atrophy. In certain embodiments, neurodegenerative diseases and CNS diseases include Niemann-Pick disease, type C1 (NPC1), Alzheimer's disease, amyotrophic lateral sclerosis (ALS), Friedreich's ataxia, Huntington's disease, Lewy body disease, Parkinson's disease and spinal muscular atrophy.

In certain embodiments, the receptor interacting protein kinase 1 inhibitors described herein may be used to treat NPC1 via inhibiting necroptosis that causes neuronal loss. In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS).

More generally, the receptor-interacting protein kinase 1 inhibitors described herein can be used to preserve neuron viability and promote axon growth and nerve functions within the central nervous system (CNS). Accordingly, the compounds may be used to reduce or even reverse the loss of cognitive, motor, and sensory functions associated with a CNS disease or disorder, by preserving neuron viability and/or promoting axon regeneration and/or nerve functions.

The receptor-interacting protein kinase 1 inhibitors described herein can be used in a method for promoting axon regeneration in a CNS neuron, such as a CNS sensory neuron, a motor neuron, a cortical neuron, a cerebellar neuron, a hippocampal neuron, and a midbrain neuron. The receptor-interacting protein kinase 1 inhibitors described herein can be used in a method for promoting nerve function or preserving the viability following injury to a CNS neuron. In another embodiments, these compounds can be used to promote regeneration of an axon in a CNS neuron that is degenerated in the CNS disease or disorder. The RIP receptor-interacting protein kinase 1 inhibitors may be administered by any conventional means, such as locally to the neuron or applied ex vivo before re-implantation.

Accordingly, in one aspect, the disclosure provides a method of treating a CNS disorder in a subject in need thereof, wherein a symptom of the CNS disorder is axon degeneration or injury within a CNS neuron. The method comprises administering to the subject an effective amount of a compound or composition disclosed herein thereby to promote regeneration of an axon in a CNS neuron affected by the CNS disorder. Following administration, neural functions may be measured, for example, as an indication of axon regeneration. It is also contemplated that, following administration of the compound or composition, the neuron function of the CNS neuron is preserved or improved relative to the neuron function prior to administration.

Non-limiting examples of CNS diseases or disorders include brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, poly glutamine (polyQ) diseases, stroke, Fahr disease, Menke's disease, Wilson's disease, cerebral ischemia, and a prion disorder.

In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, poly glutamine (polyQ) diseases, stroke, Fahr disease, Menke's disease, Wilson's disease, cerebral ischemia, prion disorder (e.g., Creutzfeldt-Jakob disease). In certain embodiments, the CNS disorder is brain injury (e.g., traumatic brain injury) or spinal cord injury (e.g., chronic, acute or traumatic spinal cord injury). In certain embodiments, the CNS disorder affects a subject's basic vital life functions such as breathing, heart beat and blood pressure, e.g., an injury to or aneurysm in the brain stem.

In certain embodiments, the CNS disease or disorder affects a subject's cognitive ability. In certain embodiments, the CNS disease or disorder affects a subject's movement and/or strength. In certain embodiments, the CNS disease or disorder affects a subject's coordination.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy and prion disorders.

In certain embodiments, the CNS disorder affects a subject's movement and/or strength, such as injury to the brain or spinal cord or a neurodegenerative CNS disorder such as Parkinson's disease, frontotemporal dementia, dementia with Lewy bodies, corticobasal degeneration, progress supranuclear palsy, Huntington's disease, multiple system atrophy, amyotrophic lateral sclerosis and hereditary spastic paresis.

In certain embodiments, the CNS disorder affects a subject's coordination, such as brain injury to the cerebellum or a neurodegenerative CNS disorder such as spinocerebellar atrophies, Friedreich's ataxia and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis and spinocerebellar atrophies.

Non-limiting examples of neurodegenerative diseases include Alzheimer's disease, lysomal storage diseases, amyotrophic lateral sclerosis (ALS), Friedreich's ataxia, Huntington's disease, Lewy body disease, Parkinson's disease, and spinal muscular atrophy.

In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS). In certain embodiments, the compounds and compositions of the present disclosure are useful for treating lysosomal storage diseases.

In certain embodiments, the disorder is a brain disorders, such as, but not limited to, Alzheimer's disease, ALS, frontotemporal dementias, vascular dementia, Huntington's disease, Parkinson's disease, Lewy Body dementia, Progressive Supranuclear Palsy, multiple sclerosis, neuromyelitis optica, ischemic brain damage (stroke), hypoxic brain damage, traumatic brain injury, spinal cord injury, sepsis-induced brain damage, CNS infections, CNS abscesses, glioblastoma multiforme, epilepsy, neuropathic pain, major depression, bipolar depression, schizophrenia, autism, Niemann-Pick disease, neuro-Behçet's disease.

In certain embodiments, provided is a method of treating a CNS disease or disorder, comprising administering a therapeutically effective amount of a compound as provided herein to a subject in need thereof. In certain embodiments, the disease or disorder is Alzheimer's disease or amyotrophic lateral sclerosis (ALS). In certain embodiments, the compound is of Formula I (or any Formula described herein), wherein A is other than triazole. In certain embodiments, the compound is of Formula VI.

Ocular Conditions

The receptor-interacting protein kinase 1 inhibitors described herein can also be used to treat ocular conditions, for example to reduce or prevent the loss of photoreceptor and/or retinal pigment epithelial cell viability.

In certain embodiments, the disclosure provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound or composition described herein, thereby preserving the viability of the photoreceptor cells disposed within the retina of the eye. After administration, the visual function (e.g., visual acuity) of the eye may be preserved or improved relative to the visual function of the eye prior to administration.

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. AMD may be the neovascular or the dry form of AMD. Retinal detachment may be a rhegmatogenous, a serous, and a tractional retinal detachment. In certain embodiments, the ocular condition may be a condition selected from the group consisting of geographic atrophy, glaucoma, and other ischemic eye diseases.

In certain embodiments, the disclosure provides a method of preserving the viability of retinal pigment epithelial (RPE) cells within the retina of a subject with an ocular condition with administration of a compound of the present disclosure. The subject being treated may have a loss of retinal pigment epithelial cells in the retina of the eye with the condition and the ocular condition may be selected from the group consisting of age-related macular degeneration (AMD), BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE), and other uveitis disorders. In certain embodiments, the method comprises administering to the eye of the subject an effective amount of a compound or composition described herein, thereby preserving the viability of the retinal pigment epithelial cells.

Provided in another embodiment is a method of preserving the viability of photoreceptor cells disposed within a retina of a subject with an ocular condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. Therefore, in certain embodiments, the method comprises administering to the eye an effective amount of a compound or composition described herein, thereby preserving the viability of the photoreceptor cells disposed within the retina of the subject with a condition.

Provided in another embodiment is a method of preserving the viability of photoreceptor cells disposed within a retina of a mammalian eye following retinal detachment. The retinal detachment may be a rhegmatogenous retinal detachment, tractional retinal detachment, or serous retinal detachment. In other embodiments, the retinal detachment may occur as a result of a retinal tear, retinoblastoma, melanoma or other cancers, diabetic retinopathy, uveitis, choroidal neovascularization, retinal ischemia, pathologic myopia, or trauma. In certain embodiments, the method comprises administering a compound or composition described herein to the eye in which a region of the retina has been detached in amounts sufficient to preserve the viability of photoreceptor cells disposed within the region of the detached retina.

Provided in another embodiment is a method of preserving visual function of an eye of a subject with an ocular condition selected from the group consisting of age-related macular degeneration (AMD), retinosis pigmentosa (RP), macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity, wherein a symptom of the ocular condition is the loss of photoreceptor cells viability in the retina of the eye, wherein the method comprises treating the subject with a compound or composition described herein to the subject.

In another aspect, the disclosure provides a method of preserving the visual function of an eye of a subject with an ocular condition, wherein a symptom of the ocular condition is the loss of photoreceptor cell viability and/or RPE viability in the retina of the eye wherein the method comprises treating the subject with a compound or composition described herein to the subject.

In certain embodiments, provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound or composition, thereby preserving the viability of the retinal ganglion cells disposed within the retina of the eye. After administration of the compound or composition, the visual function of the eye may be preserved or improved relative to the visual function of the eye prior to administration. Further, after the administration, the preserved retinal ganglion cell is capable of supporting axonal regeneration.

Non-limiting examples of symptoms associated with the ocular conditions include the loss of retinal ganglion cell viability in the retina of the eye, glaucoma, optic nerve injury, optic neuritis, optic neuropathies, diabetic retinopathy, central retinal artery occlusion, and central retinal vein occlusion.

The compounds described herein may also be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy, and hereditary optic neuropathy (e.g., Leber's optic neuropathy, Dominant Optic Atrophy, Behr's syndrome).

Also disclosed is a method of preserving the visual function of an eye of a subject with an ocular condition selected from the group consisting of glaucoma, optic nerve injury, optic neuropathies, diabetic retinopathy, central retinal artery occlusion and central retinal vein occlusion. The method comprises administering to the eye of the subject an effective amount of a compound or composition described herein, thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion and central retinal vein occlusion. The method comprises administering a compound or composition described herein to the eye in which a region of the retina has been affected in amounts sufficient to preserve the viability of retinal ganglion cells disposed within the region of the affected retina. The preserved retinal ganglion cell is capable of supporting axonal regeneration.

Also disclosed is a method for promoting axon regeneration in an eye of a subject with an ocular condition, wherein a symptom of the ocular condition is the loss of retinal ganglion cell viability in the retina of the eye with the condition. The method comprises administering to the eye of the subject an effective amount of a compound or composition described herein, thereby promoting axon regeneration of the retinal ganglion cell within the retina of the eye.

In each of the foregoing embodiments, it is understood that the methods and compositions described herein can be used to preserve the viability and/or promote axon regeneration of retinal ganglion cells during treatment of the underlying conditions including, but not limited to, glaucoma, optic nerve injury, optic neuritis, optic neuropathies, diabetic retinopathy, central retinal artery occlusion and central retinal vein occlusion.

Tissue Injuries or Damages

The ability of the compounds described herein to inhibit inflammation and cell death makes them suitable for ameliorating tissue injuries or damages. The tissue injuries or damages may be a result of any of the diseases or conditions described above. For example, the compounds may be used for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis, or for the amelioration of liver tissue injury or damage associated with overdose of acetaminophen, or for amelioration of kidney tissue injury or damage following renal transplant or the administration of nephrotoxic drugs or substances. In certain embodiments, the For example, the compounds may be used for amelioration of brain tissue injury or damage following pulmonary injury or damage.

Non-limiting examples of brain injury or damage include stroke (e.g., hemorrhagic and non-hemorrhagic), traumatic brain injury (TBI), cerebral hemorrhage, subarachnoid hemorrhage, intracranial hemorrhage secondary to cerebral arterial malformation, cerebral infarction, perinatal brain injury, non-traumatic brain injury, Alzheimer's disease, Parkinson's disease, Huntington's disease, multiple sclerosis, amyotrophic lateral sclerosis, brain hemorrhage, brain infections, brain tumor, subclinical brain injury, spinal cord injury, anoxic-ischemic brain injury, focal cerebral ischemia, global cerebral ischemia, and hypoxic hypoxia.

In an embodiment, the compounds and compositions of the present disclosure may be used to treat peritoneal tissue injury. Non-limiting examples of peritoneal tissue injury include peritoneal deterioration, peritoneal sclerosis, and peritoneal cancer. For example, the receptor interacting protein kinase 1 inhibitors described herein may be used to treat peritoneal damage caused by peritoneal dialysis fluid (PDF) and PD-related side effects.

Liver Injury and Diseases

In an embodiment, the compounds and compositions of the present disclosure may be used to treat liver injury and diseases. Non-limiting examples of liver injury or damage include not only degeneration or necrosis of liver parenchyma cells which results from injury caused by a certain factor, but also undesirable phenomena caused by biological reactions to the injury, such as mobilization, infiltration, activation of Kupffer cells, leukocytes and the like, fibrosis of the liver tissue, etc., which reactions occur alone or in combination. In certain embodiments, the receptor interacting protein kinase 1 inhibitors described herein may be used to treat steatohepatitis and hepatocellular carcinoma via inhibiting receptor interacting protein kinase 1 activity-dependent apoptosis of hepatocytes and hepatocarcinogenesis. In an embodiment, the receptor interacting protein kinase 1 inhibitors described herein may be used to treat alcoholic hepatitis, autoimmune hepatitis, fulminent hepatic failure, acute cholestasis and liver injury.

Kidney Injury and Diseases

In an embodiment, the compounds and compositions of the present disclosure may be used to treat kidney injury and diseases. Non-limiting examples of kidney diseases include chronic kidney disease (CKD) (e.g., glomerular diseases, tubulointerstitial diseases, obstruction, polycystic kidney disease), acute kidney injury (AKI), diabetic nephropathy, fibrosis, glomerulonephritis, focal glomerulosclerosis, immune complex nephropathy, crystalline nephropathy, or lupus nephritis. Kidney disease may be caused by drug-induced renal injury or kidney graft rejection. Kidney disease may be characterized as nephrotic syndrome or renal insufficiency. In an embodiment, the receptor interacting protein kinase 1 inhibitors described herein may be used to treat kidney diseases (e.g., AKI) via inhibiting cell death pathway in kidney diseases. In an embodiment, the receptor interacting protein kinase 1 inhibitors described herein may be used to treat patient with kidney stones and to prevent crystal-induced cytotoxicity and acute kidney injury via inhibiting receptor interacting protein kinase 3-MLKL-mediated necroptosis.

Skin Diseases

In an embodiment, the compounds and compositions of the present disclosure may be used to treat dermal (or skin) diseases, including but not limited to, inflammatory skin diseases or neutrophilic dermatosis.

Malignancies

In an embodiment, the compounds and compositions of the present disclosure are useful for treating malignancies/cancers such as carcinoma, sarcoma, melanoma, lymphoma or leukemia. Non-limiting examples of malignancies suitably treated by the receptor interacting protein kinase 1 inhibitors described herein include lung cancer (e.g. non-small cell lung cancer, small-cell lung cancer), hepatocellular cancer, melanoma, pancreatic cancer, urological cancer, bladder cancer, colorectal cancer, colon cancer, breast cancer, prostate cancer, renal cancer, thyroid cancer, gall bladder cancer, peritoneal cancer, ovarian cancer, cervical cancer, gastric cancer, endometrial cancer, esophageal cancer, head and neck cancer, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, vulval cancer, cancers of the adrenal cortex, ACTH producing tumors, lymphoma, and leukemia.

Infectious Diseases

In an embodiment, the compounds and compositions of the present disclosure are useful for treating infectious diseases resulting from the presence of pathogenic agents, including pathogenic viruses, pathogenic bacteria, fungi, protozoa, multicellular parasites and aberrant proteins known as prions. Non-limiting examples of infectious diseases suitably treated by the receptor interacting protein kinase 1 inhibitors described herein include virus infectious diseases and bacterial infectious diseases. The virus infectious disease is not particularly limited and includes, for example, infectious diseases with respiratory infectious viruses (e.g., infectious diseases due to respiratory infectious viruses such as influenza virus, rhino virus, corona virus, parainfluenza virus, RS virus, adeno virus, reo virus and the like), *Staphylococcus aureus* (MRSA) pneumonia, *Serratia marcescens* hemorrhagic pneumonia, herpes zoster caused by herpes virus, diarrhea caused by rotavirus, viral hepatitis, AIDS and the like. The bacterial infectious disease is not particularly limited and includes, for example, infectious diseases caused by *Bacillus cereus, Vibrio parahaemolyticus*, Enterohemorrhagic *Escherichia coli, Staphylococcus aureus*, MRSA, *Salmonella, Botulinus, Candida* and the like.

Bone Diseases

In an embodiment, the compounds and compositions of the present disclosure are useful for treating bone diseases that may result from a bone remodeling disorder whereby the balance between bone formation and bone resorption is shifted. Non-limiting examples of bone remodeling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. Additional examples of bone diseases suitably treated by the receptor interacting protein kinase 1 inhibitors described herein include bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment. Additional examples of diseases affecting bone or bone joints suitably treated by the receptor interacting protein kinase 1 inhibitors described herein include metastatic bone cancer, rheumatic diseases such as rheumatoid arthritis, osteoarthritis and other inflammatory arthropathies. In an embodiment, the receptor interacting protein kinase 1 inhibitors described herein may be used to treat postmenopausal osteoporosis via inhibiting osteocyte necroptosis and trabecular deterioration.

Cardiovascular Diseases

In an embodiment, the compounds and compositions of the present disclosure are useful for treating cardiovascular diseases that may be relate to the cardiovascular disorders of fragile plaque disorder, occlusive disorder and stenosis. Non-limiting cardiovascular diseases include coronary artery disorders and peripheral arterial disorders, including, among others, atherosclerosis, arterial occlusion, aneurysm formation, thrombosis, post-traumatic aneurysm formation, restenosis, and post-operative graft occlusion. It is believed that atherosclerosis results from maladaptive inflammation driven primarily by macrophages. Thus, the compounds and compositions of the present disclosure may be used to treat atherosclerosis via inhibiting macrophage necroptosis.

Transplantation

In an embodiment, the compounds and compositions of the present disclosure are useful for treating transplant patients. Non-limiting examples of transplant patient suitably treated by the receptor interacting protein kinase 1 inhibitors described herein include patients with solid and non-solid organ and tissue transplantations and transplants, such as liver, heart, kidney, and heterologous and autologous bone marrow transplantations/transplants. Typically, immunosuppressive therapy is used to avoid graft rejection in recipients of solid organ transplants. Recipients of bone marrow transplants are usually subjected to extensive irradiation and chemotherapy prior to transplantation. It is believed that receptor interacting protein kinase 1 and NF-κB signaling in dying cells determines cross-priming of CD8+ T cells. Thus, the receptor interacting protein kinase 1 inhibitors described herein may be used to treat transplant patient and avoid graft rejection by modulating cross-priming of CD8+ T cells.

Other Diseases and Conditions

Additional examples of diseases and disorders suitably treated by the receptor-interacting protein kinase 1 inhibitors described herein include pancreatitis, atopic dermatitis, spondyloarthritis, gout, systemic onset juvenile idiopathic arthritis (SoJIA), systemic lupus erythematosus (SLE), Sjogren's syndrome, systemic scleroderma, anti-phospholipid syndrome (APS), vasculitis, primary sclerosing cholangitis (PSC), acetaminophen toxicity, kidney damage/injury (nephritis, renal transplant, surgery, administration of nephrotoxic drugs e.g. cisplatin, acute kidney injury(AKI)), Celiac disease, autoimmune idiopathic thrombocytopenic purpura (autoimmune ITP), cerebrovascular accident (CVA, stroke), myocardial infarction (MI), allergic diseases (including asthma), diabetes, Wegener's granulomatosis, pulmonary sarcoidosis, Behçet's disease, interleukin-1 converting enzyme (ICE/caspase-1) associated fever syndrome, chronic obstructive pulmonary disease (COPD), tumor necrosis factor receptor-associated periodic syndrome (TRAPS), peridontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (e.g., tuberculosis and influenza), and lysosomal storage diseases. Additional examples of diseases and disorders suitably treated by the receptor-interacting protein kinase 1 inhibitors described herein include Gaucher disease or organ failure.

Non-limiting examples of lysosomal storage diseases include Gaucher disease, GM2 Gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs and Wolman disease.

5. Kits

Provided herein are also kits that include a compound of the disclosure, or a pharmaceutically acceptable salt, tautomer, stereoisomer, mixture of stereoisomers, prodrug, or deuterated analog thereof, and suitable packaging. In certain embodiments, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

6. Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts and may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In certain embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

7. Combination Therapy

In certain embodiments, the compounds described herein may be administered in combination with at least one other therapeutically active agent. The two or more agents can be coadministered, co-formulated, or administered separately. In certain embodiments, the other therapeutically active agent is selected from a thrombolytic agent, a tissue plasminogen activator, an anticoagulant, a platelet aggregation inhibitor, an antimicrobial agent (an antibiotic, a broad-spectrum antibiotic, a lactam, an antimycobacterial agent, a bactericidal antibiotic, anti-MRSA therapy), a long acting beta agonist, a combination of an inhaled corticosteroid and a long acting beta agonist, a short acting beta agonist, a leukotriene modifier, an anti-IgE, a methylxanthine bronchodilator, a mast cell inhibitor, a protein tyrosine kinase inhibitor, a CRTH2/Dprostanoid receptor antagonist, an epinephrine inhalation aerosol, a phosphodiesterase inhibitor, a combination of a phosphodiesterase-3 inhibitor and a phosphodiesterase-4 inhibitor, a long-acting inhaled anticholinergic, a muscarinic antagonist, a long-acting muscarinic antagonist, a low dose steroid, an inhaled corticosteroid, an oral corticosteroid, a topical corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor, a cystic fibrosis transmembrane conductance regulator potentiator, a mucolytic agent, pancreatic enzymes, a bronchodilator, an opthalmalic intravitreal injection, an anti-vascular endothelial growth factor inhibitor, a ciliary neurotrophic growth factor agent, a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, inactivated influenza vaccine, a ciliary neurotrophic growth factor, a gene transfer agent, a topical immunomodulator, calcineurin inhibitor, an interferon gamma, an antihistamine, a monoclonal antibody, a polyclonal anti-T-cell antibody, an anti-thymocyte gamma globulin-equine antibody, an antithymocyte globulin-rabbit antibody, an anti-CD40 antagonist, a JAK inhibitor, and an anti-TCR murine mAb.

Exemplary other therapeutically active agents include heparin, coumadin, clopidrogel, dipyridamole, ticlopidine HCL, eptifibatide, aspirin, vancomycin, cefeprime, a combination of piperacillin and tazobactam, imipenem, meropenem, doripenem, ciprofloxacin, levofloxacin, ofloxacin, moxifloxacin, hydrocortisone, vedolizumab, alicaforsen, remestemcel-L, ixekizumab, tildrakizumab, secukinumab, chlorhexidine, doxycycline, minocycline, fluticasone (fluticasone proprionate, fluticasone furoate), beclomethasone dipropionate, budesonide, trimcinolone acetonide, flunisolide, mometasone fuorate, ciclesonide, arformoterol tartrate, formoterol fumarate, salmeterol xinafoate, albuterol (albuterol sulfate), levalbuterol tartrate, ipratropium bromide, montelukast sodium, zafirlukast, zileuton, omalizumab, theophylline, cromulyn sodium, nedocromil sodium, masitinib, AMG 853, indacaterol, E004, reslizumab, salbutamol, tiotropium bromide, VR506, lebrikizumab, RPL554, afibercept, umeclidinium, indacterol maleate, aclidinium bromide, roflumilast, SCH527123, glycoprronium bromide, olodaterol, a combination of fluticasone furoate and vilanterol vilanterol, a combination of fluticasone propionate and salmeterol, a combination of fluticasone furoate and fluticasone proprionate, a combination of fluticasone propionate and eformoterol fumarate dihydrate, a combination of formoterol and budesonide, a combination of beclomethasone dipropionate and formoterol, a combination of mometasone furoate and formoterol fumarate dihydrate, a combination of umeclidinium and vilanterol, a combination of ipratropium bromide and albuterol sulfate, a combination of glycopyrronium bromide and indacaterol maleate, a combination of glycopyrrolate and formoterol fumarate, a combination of aclidinium and formoterol, isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, delamanid, imatinib, ARG201, tocilizumab, muromonab-CD3, basiliximab, daclizumab, rituximab, prednisolone, anti-thymocyte globulin, FK506 (tacrolimus), methotrexate, cyclosporine, sirolimus, everolimus, mycophenolate sodium, mycophenolate mofetil, cyclophosphamide, azathioprine, thalidomide, chlorambucil, nifedipine, nicardipine, nitroglycerin, lisinopril, diltaizem, fluoxetine, bosentan, epoprostenol, colchicine, para-aminobenzoic acid, dimethyl sulfoxide, D-penicillamine, interferon alpha, interferon gamma (INF-g)), omeprazole, metoclopramide, lansoprazole, esomeprazole, pantoprazole, rabeprazole, imatinib, belimumab, ARG201, tocilizumab, ivacftor, dornase alpha, pancrelipase, tobramycin, aztreonam, colistimethate sodium, cefadroxil monohydrate, cefazolin, cephalexin, cefazolin, moxifloxacin, levofloxacin, gemifloxacin, azithromycin, gentamicin, ceftazidime, a combination of trimethoprim and sulfamethoxazole, chloramphenicol, a combination of ivacftor and lumacaftor, ataluren, NT-501-CNTF, a gene transfer agent encoding myosin VIIA (MY07A), ranibizumab, pegaptanib sodium, NT501, humanized sphingomab, bevacizumab, oseltamivir, zanamivir, rimantadine, amantadine, nafcillin, sulfamethoxazolem, trimethoprim, sulfasalazine, acetyl sulfisoxazole, vancomycin, muromonab-CD3, ASKP-1240, ASP015K, TOL101, pimecrolimus, hydrocortizone, betamethasone, flurandrenolide, triamcinolone, fluocinonide, clobetasol, hydrocortisone, methylprednisolone, prednisolone, a recombinant synthetic type I interferon, interferon alpha-2a, interferon alpha-2b, hydroxyzine, diphenhydramine, flucloxacillin, dicloxacillin, and erythromycin.

A compound described herein may be administered in combination with other anti-inflammatory agents for any of the indications above, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologics, anti-IL1 agents, anti-IL1 7 biologics, anti-CD22, anti-integrin agents, anti-IFNa, anti-CD20 or CD4 biologics and other cytokine inhibitors or biologics to T-cell or B-cell receptors or interleukins.

In the treatment of ALS, a compound described herein may be administered in combination with riluzole.

In the treatment of Parkinson's disease, a compound described herein may be administered in combination with levodopa, carbodopa or a combination thereof, pramipexole, ropinirole, rotigotine, selegiline, rasagiline, entacapone, tolcapone, benztropine, trihexyphenidyl, or amantadine.

In the treatment of Alzheimer's disease, a compound described herein may be administered in combination with donepezil, galantamine, memantine, rivastigmine, anti-ABeta (amyloid beta) therapies including aducanumab, crenezumab, solanezumab, and gantenerumab, small molecule inhibitors of BACE1 including verubecestat, AZD3293 (LY3314814), elenbecestat (E2609), LY2886721, PF-05297909, JNJ-54861911, TAK-070, VTP-37948, HPP854, CTS-21166, or anti-tau therapies such as LMTM (leuco-methylthioninium-bis(hydromethanesulfonate)).

In the treatment of rheumatoid arthritis, a compound described herein may be administered in combination with ibuprofen, naproxen, prednisone, methotrexate, leflunomide, hydroxychloroquine, sulfasalazine, abatacept, adalimumab, anakinra, certolizumab, etanercept, golimumab, infliximab, rituximab, tocilizumab or tofacitinib.

In the treatment of CVA, a compound described herein may be administered to in combination with a thrombolytic agent (such as tissue plasminogen activator (TPA®), Activase®, Lanoteplase®, Reteplase®, Staphylokinase®, Streptokinase®, Tenecteplase®, Urokinase®), an anticoagulant (such as heparin, coumadin, clopidrogel (Plavix®)), and a platelet aggregation inhibitor (such as dipyridamole (Persantine®), ticlopidine HCL (Ticlid®), eptifibatide (Integrillin®), and/or aspirin).

In the treatment of SIRS, a compound described herein may be administered in combination with a broad-spectrum antibiotic (such as vacomycin) or other anti-MRSA therapy (cefeprime (Maxipime®), piperacillin/tazobactam (Zosyn®), carbapenem (imipenem, meropenem, doripenem), quinolones (ciprofloxacin, levofloxacin, ofloxacin, moxifloxacin, etc.), and low dose steroids such as hydrocortisones.

In the treatment of inflammatory bowel disease (particularly, Crohn's disease and/or ulcerative colitis), a compound of any formula described herein, may be administered in combination with vedolizumab (Entyvio®), alicaforsen, or remestemcel-L (Prochymal®). Specifically, in the treatment of inflammatory bowel disease (particularly, Crohn's disease and/or ulcerative colitis), a compound described herein may be administered in combination with alicaforsen, or remestemcel-L (Prochymal®). In the treatment of psoriasis, a compound described herein may be administered in combination with ixekizumab, tildrakizumab (MK-3222), or secukinumab (AIN457).

Specifically, in the treatment of psoriasis, a compound described herein may be administered in combination with ixekizumab, or tildrakizumab (MK-3222). In the treatment of periodonitis, a compound of any formula described herein may be administered in combination with an antimicrobial agent, (such as chlorhexidine (Peridex®, PerioChip®, PerioGard®, etc.)) or an antibiotic (such as doxycycline (Vibrox®, Periostat®, Monodox®, Oracea®, Doryx®, etc.) or minocycline (Dynacin®, Minocin®, Arestin®, Dynacin®, etc.).

In the treatment of asthma, a compound of any formula described herein may be administered in combination with an inhaled corticosteroid ((ICS) such as fluticasone proprionate (Flovent®), beclomethasone dipropionate (QVAR®), budesonide (Pulmicort), triamcinolone acetonide (Azmacort®), flunisolide (Aerobid®), mometasone fuorate (Asmanex® Twisthaler®), or Ciclesonide (Alvesco®)), a long acting beta agonist ((LABA) such as formoterol fumarate (Foradil®), salmeterol xinafoate (Serevent®)), a combination of an ICS and LABA (such as fluticasone furoate and vilanterol (Breo Ellipta®), formoterol/budesonide inhalation (Symbicort®), beclomethasone dipropionate/formoterol (Inuvair®), and fluticasone propionate/salmeterol (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Labid®, Lanophyllin®, Quibron-T®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Unidur®, Uniphyl®), a mast cell inhibitor (such as cromulyn sodium (Nasalcrom®) and nedocromil sodium (Tilade®)), a long-acting muscarinic antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptorantagonist (AMG 853), indacaterol (Arcapta® Neohaler®), an epinephrine inhalation aerosol (E004), fluticasone furoate/fluticasone proprionate, vilanterol inhalation/ fluticasone furoate powder (Relovair™), fluticasone propionate/eformoterol fumarate dihydrate (Flutiform®), reslizumab, salbutamol dry-powder inhalation, tiotropium bromide (Spiriva® HandiHaler®), formoterol/budesonide (Symbicort® SMART®), fluticasone furoate (Veramyst®), Vectura's VR506, lebrikizumab (RG3637), a combination phosphodiesterase (PDE)-3 and (PDE)-4 inhibitor (RPL554).

In the treatment of COPD, a compound of any formula described herein, may be administered in combination with a LABA (such as salmeterol xinafoate (Serevent), umeclidinium/vilanterol (Anuro Ellipta®), umeclidinium (Incruse Ellipta®), arformoterol tartrate (Brovana®), formoterol fumarate inhalation powder (Foradil®), indacterol maleate (Arcapta® Neohaler®), or fluticasone propionate/eformoterol fumarate dehydrate (Flutiform®)), a long-acting inhaled anticholinergic (or muscarinic antagonist, such as tiotropium bromide (Spiriva®), and aclidinium bromide (Tudorza® Pressair®), a phosphodiesterase (PDE-r) inhibitor (such as roflumilast, Daliresp®), a combination ICS/ LABA (such as fluticasone furoate and vilanterol (Breo Ellipta®), fluticasone propionate/salmeterol (Advair®), budesonide/formoterol (Symbicort®), mometasone/formoterol (Dulera®), ipratropium bromide/albuterol sulfate (Duoneb®, Atrovent®), albuterol/ipratropium (Combivent Respimat®)), a SABA (such as ipratropium bromide (Atrovent®), and albuterol sulfate(ProAir®, Proventil®)), and an ICS (such as budesonide (Pulmicort®) and fluticasone propionate (Flovent®), beclometasone dipropionate (QVAR®).

Other agents that may be suitable for use in combination therapy in the treatment of COPD include SCH527123 (a CXCR2 antagonist), glycoprronium bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In the treatment of a mycobacterium infection (tuberculosis), a compound of any formula described herein may be administered in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (capreomycin), a fluorquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturo®), oxazolidinone (Sutezolid®), or delamanid (OPC-67683).

Specifically, in the treatment of a mycobacterium infection (tuberculosis), a compound described herein may be administered in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluorquinolone (levofloxacin, moxifloxicin, ofloxacin), thioamide (ehionamide), cycloserine (Seromycin®), kanamycin (Kantrex®), streptomycin, viomycin, capreomycin (Capastat®)), bedaquiline fumarate (Sirturo®), oxazolidinone (Sutezolid®), or delamanid (OPC-67683).

In the treatment of systemic scleroderma, a compound of any formula described herein may be administered in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, diltaizem (Cardizem®, Cardizem SR®, Cardizem CD®, Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (KMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumab (Actema®).

Specifically, in the treatment of systemic scleroderma, a compound of any formula described herein may be administered in combination with an oral corticosteroid (such as prednisolone (Delatsone®, Orapred, Millipred, Omnipred, Econopred, Flo-Pred), anti-thymocyte globulin (Atgam®), FK506 (tacrolimus), thalidomide (Thalomid®), chlorambucil (Leukeran®), a calcium channel blocker (such as nifedipine (Procardia®, Adalat®) or nicardipine (Cardene®), a topical emollient (nitroglycerin ointment), an ACE inhibitor (such as lisinopril (Zestril®, diltaizem (Cardizem®, Cardizem SR®), Cardizem CD®), Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (KMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), or tocilizumab (Actema®).

In the treatment of cystic fibrosis, a compound as described herein may be administered in combination with a cystic fibrosis transmembrane conductance regulator (CFTR) potentiator (ivacftor (Kalydeco®)) a mucolytic agent (such as dornase alpha (Pulmozyme®)), pancreatic enzymes (such as Pancrelipase (Creon®, Pancreaze®, Ultresa®, Zenpep®)), a bronchodilator (such as albuterol (AccuNeb®, ProAir®, Proventil HFA®), VoSpire ER®, Ventolin HFA®)), an antibiotic (including inhaled, oral or parenteral, such as tobramycin solution for inhalation (TOBI®, Bethkis®, TOBI Podhaler®), aztreonam inhalation (Azactam®, Cayston®), colistimethate sodium (Coly-Mycin®), cephalosporins (cefadroxil monohydrate (Duricef®), cefazolin (Kefzol®), cephalexin (Keflex®), cefazolin (Ancef®, etc.), fluoroquinolones (moxifloxacin, levofloxacin, gemifloxacin, etc), azithromycin (Zithromax®), gentamicin (Garamycin®), piperacillin/tazobacam (Zosyn®), cephalexin (Keflex®), ceftazidime (Fortaz, Tazicef), ciprofloxin (Cipro XR, Proquin XR), trimethoprim/sulfamethoxazole (Bactrim DS, Septra DS), chloramphenicol)), or ivacftor (Kalydeco®)/lumacaftor (VX-809), ataluren (Translarna®), or with tiopropium bromide (Spiriva® Handihaler®) as add on to standard therapy.

In the treatment ofretinitis pigmentosa, a compound as described herein may be administered in combination with a ciliary neurotrophic growth factor (NT-501-CNTF) or gene transfer agent, UshStat®.

In the treatment of macular degeneration, a compound of any formula described herein, may be administered in combination with opthalmalic intravitreal injections (afibercept (Eylea®)) or with an anti-vascular endothelial growth factor (VEGF) inhibitor (such as ranibizumab (Lucentis®) or pegaptanib sodium (Macugen®)), a ciliary neurotrophic growth factor agent (NT501), iSONEP®, or bevacizumab (Avastin®).

In the treatment of influenza, a compound as described herein may be administered in combination with a trivalent (IIV3) inactivated influenza vaccine (such as Afluria®, Fluarix®, Flucelvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as FluMist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®.

In the treatment of a staphylococcus infection, a compound of any formula described herein may be administered in combination with an antibiotic (such as a-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In the treatment of transplant rejection, a compound of any formula described herein may be administered in combination with a high-dose corticosteroid (such as prednisone (Deltasone®), methylprednisolone (SoluMedrol®) etc.) a calcineurin inhibitor (such as cyclosporine (Sandimmune®, Neoral®, Gengraf®), tacrolimus (Prograf®, Astragraf XL®)), an mTor inhibitor (such as sirolimus (Rapamune®) or everolimus (Afinitor®)), an anti-proliferative agent (such as azathioprine (Imuran®, Azasan®), mycophenolate mofetil (CellCept®), or mycophenolate sodium (Myfortic®)), a monoclonal antibody (such as muromonab-CD3 (Orthoclone OKT3®)), an interleukine-2 receptor antagonist ((Basiliximab®, Simulect®), daclizumab (Zenapax®), or rituximab (Rituxan®)), a polyclonal anti-T-cell antibody (such as anti-thymocyte gamma globulin-equine (Atgam®), or antithymocyte globulin-rabbit (Thymoglobulin®)) an anti-CD40 antagonist (ASKP-1240), a JAK inhibitor (ASP015K), or an anti-TCR murine mAb (TOL101).

Specifically, in the treatment of transplant rejection, a compound of any formula described herein may be administered in combination with a monoclonal antibody (such as muromonab-CD3 (Orthoclone OKT3®)), a polyclonal anti-T-cell antibody (such as anti-thymocyte gamma globulin-equine (Atgam®), or antithymocyte globulin-rabbit (Thymoglobulin®)) an anti-CD40 antagonist (ASKP-1240), a JAK inhibitor (ASP015K), or an anti-TCR murine mAb (TOL101).

In the treatment of atopic dermatitis, a compound of any formula described herein may be administered in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methylprednisolone (Medrol®), or prednisolone (Pediapred®, Prelone®), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (Eryc®, T-Stat®, Erythra-Derm®, etc.)), anon-steroidal immunosuppressive agent (such as azathioprine (Imuran®, Azasan®), methotrexate (Rhuematrex®, Trexall®), cyclosporine (Sandimmune®), or mycophenolate mofetil (CellCept®)).

Specifically, in the treatment of atopic dermatitis, a compound of any formula described herein may be administered in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methylprednisolone (Medrol®), or prednisolone (Pediapred®, Prelone®), an interferon gamma (Alferon N®, Infergen®, Intron A, Roferon-A®)), an antihistamine (for itching such as Atarax®, Vistaril®, Benadryl®), or an antibiotic (such as penicillin derivatives flucloxacillin (Floxapen®) or dicloxacillin (Dynapen®), erythromycin (Eryc®, T-Stat®, Erythra-Derm®, etc.)).

In the treatment of burns, e.g. a burn injury or burn shock, a compound of any formula described herein may be administered alone, or in combination with an antimicrobial agent, typically a topical antibiotic (mafenide acetate cream, silver sulfadiazine cream) and/or a analgesic (opioid analgesics, e.g., morphine, oxycodone). Other therapeutic agents that may be useful for the treatment of burns include retinoids and pirfenidone.

In certain embodiments, the at least one other therapeutically active agent is selected from a thrombolytic agent, a tissue plasminogen activator, an anticoagulant, and a platelet aggregation inhibitor. In certain embodiments, the at least one other therapeutically active agent is selected from heparin, coumadin, clopidrogel, dipyridamole, ticlopidine HCL, eptifibatide, and aspirin. In certain embodiments, the kinase-mediated disease or disorder treated with these agents is a cerebrovascular accident.

In certain embodiments, the at least one other therapeutically active agent is selected from broad-spectrum antibiotic, anti-MRSA therapy and a low dose steroid. In certain embodiments, the at least one other therapeutically active agent is selected from vacomycin, cefeprime, a combination of piperacillin and tazobactam, imipenem, meropenem, doripenem, ciprofloxacin, levofloxacin, ofloxacin, moxifloxacin, and hydrocortisone. In certain embodiments, the disease or disorder treated with these agents is systemic inflammatory response syndrome.

In certain embodiments, the at least one other therapeutically active agent is alicaforsen or remestemcel-L. In certain embodiments, the disease or disorder treated with these agents is Crohn's disease or ulcerative colitis.

In certain embodiments, the at least one other therapeutically active agent is ixekizumab, or tildrakizumab. In certain embodiments, the kinase-mediated disease or disorder treated with these agents is psoriasis.

In certain embodiments, the at least one other therapeutically active agent is an antimicrobial agent or an antibiotic. In certain embodiments, the at least one other therapeutically active agent is selected from chlorhexidine, doxycycline and minocycline. In certain embodiments, the disease or disorder treated with these agents is periodonitis.

In certain embodiments, the at least one other therapeutically active agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. In certain embodiments, the at least one other therapeutically active agent is selected from fluticasone proprionate, beclomethasone dipropionate, budesonide, trimcinolone acetonide, flunisolide, mometasone fuorate, or ciclesonide, formoterol fumarate, salmeterol xinafoate, a combination of fluticasone furoate and vilanterol, a combination of formoterol and budesonide inhalation, a combination of beclomethasone dipropionate and formoterol, a combination of fluticasone propionate and salmeterol, albuterol sulfate, levalbuterol tartrate, a combination of ipratropium bromide and albuterol, ipratropium bromide, montelukast sodium, zafirlukast, zileuton, omalizumab theophylline, cromulyn sodium, nedocromil sodium, and a combination of mometasone furoate and formoterol fumarate dihydrate. In certain embodiments, the at least one other therapeutically active agent is selected from protein tyrosine kinase inhibitor, a CRTH2/D-prostanoid receptor antagonist, an epinephrine inhalation aerosol, and a combination of a phosphodiesterase-3 inhibitor and a phosphodiesterase-4 inhibitor. In certain embodiments, the at least one other therapeutically active agent is selected from masitinib, AMG 853, indacaterol, E004, a combination of fluticasone furoate and fluticasone proprionate, a combination of vinanterol fluticasone furoate, a combination of fluticasone propionate and eformoterol fumarate dihydrate, reslizumab, salbutamol, tiotropium bromide, a combination of formoterol and budesonide, fluticasone furoate, VR506, lebrikizumab, and RPL554. In certain embodiments, the kinase-mediated disease or disorder treated with these agents is asthma.

In certain embodiments, the at least one other therapeutically active agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. In certain embodiments, the at least one other therapeutically active agent is selected from salmeterol xinafoate, a combination of umeclidinium and vilanterol, umeclidinium, arformoterol tartrate, formoterol fumarate, indacterol maleate, a combination of fluticasone propionate and eformoterol fumarate dihydrate, tiotropium bromide, aclidinium bromide, roflumilast, a combination of fluticasone furoate and vilanterol, a combination of fluticasone propionate and salmeterol, a combination of budesonide and formoterol, a combination of mometasone and formoterol, a combination of ipratropium bromide and albuterol sulfate, a combination of albuterol and ipratropium, ipratropium bromide, albuterol sulfate, budesonide, fluticasone propionate, and beclometasone dipropionate. In certain embodiments, the at least one other therapeutically active agent is selected from SCH527123, glycoprronium bromide, a combination of glycopyrronium bromide and indacaterol maleate, a combination of glycopyrrolate and formoterol fumarate, indacaterol maleate, olodaterol, tiotropium, olodaterol, and a combination of aclidinium and formoterol. In certain embodiments, the disease or disorder treated with these agents is COPD.

In certain embodiments, the at least one other therapeutically active agent is an antimycobacterial agent or a bactericidal antibiotic. In certain embodiments, the at least one other therapeutically active agent is selected from isoniazid, ehambutol, rifampin, pyrazinamide, rifabutin, rifapentine, capreomycin, levofloxacin, moxifloxicin, ofloxacin, ehionamide, cycloserine, kanamycin, streptomycin, viomycin, bedaquiline fumarate, PNU-100480, and delamanid. In certain embodiments, the kinase-mediated disease or disorder treated with these agents is a mycobacterium infection.

In certain embodiments, the at least one other therapeutically active agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. In certain embodiments, the at least one active agent is selected from prednisolone, anti-thymocyte globulin, FK506 (tacrolimus), thalidomide, chlorambucil, nifedipine, nicardipine, nitroglycerin ointment, lisinopril, diltaizem, fluoxetine, bosentan, epoprostenol, colchicines, para-aminobenzoic acid, dimethyl sulfoxide, D-penicillamine, interferon alpha, interferon gamma (INF-g)), omeprazole, metoclopramide, lansoprazole, esomeprazole, pantoprazole, rabeprazole, imatinib, ARG201, and tocilizumab. In certain embodiments, the disease or disorder treated with these agents is systemic scleroderma.

In certain embodiments, the at least one other therapeutically active agent is selected from a cystic fibrosis transmembrane conductance regulator potentiator, amucolytic agent, pancreatic enzymes, a bronchodilator, an antibiotic, or ivacftor/lumacaftor, ataluren, and tiopropium bromide. In certain embodiments, the at least one other therapeutically active agent is selected from ivacftor, dornase alpha, pancrelipase, albuterol, tobramycin, aztreonam, colistimethate sodium, cefadroxil monohydrate, cefazolin, cephalexin, cefazolin, moxifloxacin, levofloxacin, gemifloxacin, azithromycin, gentamicin, piperacillin/tazobacam, ceftazidime, ciprofloxin, trimethoprim/sulfamethoxazole, chloramphenicol, or ivacftor/lumacaftor, ataluren, and tiopropium bromide. In certain embodiments, the disease or disorder treated with these agents is cystic fibrosis.

In certain embodiments, the at least one other therapeutically active agent is a ciliary neurotrophic growth factor or a gene transfer agent. In certain embodiments, the at least one other therapeutically active agent is NT-501-CNTF or a gene transfer agent encoding myosin VIIA (MY07A). In certain embodiments, the disease or disorder treated with these agents is retinitis pigmentosa.

In certain embodiments, the at least one other therapeutically active agent is selected from opthalmalic intravitreal injections, an anti-vascular endothelial growth factor inhibitor, and a ciliary neurotrophic growth factor agent. In certain embodiments, the at least one other therapeutically active agent is selected from afibercept, ranibizumab, pegaptanib sodium, NT501, humanized sphingomab, and bevacizumab. In certain embodiments, the disease or disorder treated with these agents is macular degeneration.

In certain embodiments, the at least one other therapeutically active agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. In certain embodiments, the at least one other therapeutically active agent is selected from oseltamivir, zanamivir, rimantadine, or amantadine. In certain embodiments, the kinase-mediated disease or disorder treated with these agents is influenza.

In certain embodiments, the at least one other therapeutically active agent is selected from a beta-Lactam, nafcillin, sulfamethoxazolem, trimethoprim, sulfasalazine, acetyl sulfisoxazole, and vancomycin. In certain embodiments, disease or disorder treated with these agents is a staphylococcus infection.

In certain embodiments, the at least one other therapeutically active agent is selected from a monoclonal antibody, a polyclonal anti-T-cell antibody, an anti-thymocyte gamma globulin-equine antibody, an antithymocyte globulin-rabbit antibody, an anti-CD40 antagonist, a JAK inhibitor, and an anti-TCR murine mAb.

In certain embodiments, the at least one other therapeutically active agent is selected from muromonab-CD3, ASKP-1240, ASP015K, and TOL101. In certain embodiments, the disease or disorder treated with these agents is transplant rejection.

In certain embodiments, the at least one other therapeutically active agent is selected from a topical immunomodulator or calcineurin inhibitor, a topical corticosteroid, an oral corticosteroid, an interferon gamma, an antihistamine, or an antibiotic. In certain embodiments, the at least one other therapeutically active agent is selected from pimecrolimus, tacrolimus, hydrocortizone, betamethasone, flurandrenolide, fluticasone, triamcinolone, fluocinonide, clobetasol, hydrocortisone, methylprednisolone, prednisolone, an interferon alpha protein, a recombinant synthetic type I interferon, interferon alpha-2a, interferon alpha-2b, hydroxyzine, diphenhydramine, flucloxacillin, dicloxacillin, and erythromycin. In certain embodiments, the disease or disorder treated with these agents is atopic dermatitis.

8. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In certain embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound disclosed herein administered per dose or per day. Daily dosage of a compound disclosed herein may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In certain embodiments, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

9. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more formulas or compounds disclosed herein, may be accomplished as described in the following examples. If available, reagents may be purchased commercially, e.g. from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). *Greene's protective groups in organic synthesis*. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Scheme 1 shows the synthesis of compounds of Formula I, wherein LG is a leaving group and $X^1$, $X^2$, $Y^1$, $Y^2$, A, L, $R^2$, $R^3$, $R^4$, and $R^9$, are as defined herein.

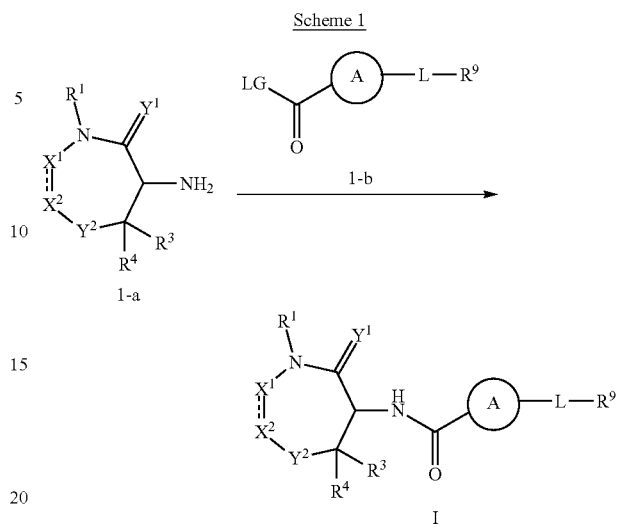

As depicted in Scheme 1, the compounds of Formula I may be prepared by contacting a suitably substituted 1-a with compound 1-b, under standard amide bond forming reaction conditions. As is typical in peptide coupling reactions, an activating agent may be used to facilitate the reaction. Suitable coupling agents (or activating agents) are known in the art and include for example, carbodiimides (e.g., N,N'-dicyclohexylcarbodiimide (DCC), N,N'-dicyclopenty lcarbodiimide, N,N'-diisopropylcarbodiimide (DIC), 1-ethyl-3-(3-dimethylaminopropyl)carbodiimide (EDC), N-t-butyl-N-methylcarbodiimide (BMC), N-t-butyl-N-ethylcarbodiimide (BEC), 1,3-bis(2,2-dimethyl-1,3-dioxolan-4-ylmethyl)carbodiimide (BDDC), etc.), anhydrides (e.g., symmetric, mixed, or cyclic anhydrides), activated esters (e.g., phenyl activated ester derivatives, p-hydroxamic activated ester, hexafluoroacetone (HFA), etc.), acylazoles (acylimidazoles using CDI, acylbenzotriazoles, etc.), acyl azides, acid halides, phosphonium salts (HOBt, PyBOP, HOAt, etc), aminium/uronium salts (e.g., tetramethyl aminium salts, bispyrrolidino aminium salts, bispiperidino aminium salts, imidazolium uronium salts, pyrimidinium uronium salts, uronium salts derived from N,N,N'-trimethyl-N'-phenylurea, morpholino-based aminium/uronium coupling reagents, antimoniate uronium salts, etc.), organophosphorus reagents (e.g., phosphinic and phosphoric acid derivatives), organosulfur reagents (e.g., sulfonic acid derivatives), triazine coupling reagents (e.g., 2-chloro-4,6-dimethoxy-1,3,5-triazine, 4-(4,6-dimethoxy-1,3,5-triazin-2-yl)-4 methylmorpholinium chloride, 4-(4,6-dimethoxy-1,3,5-triazin-2-yl)-4 methylmorpholinium tetrafluoroborate, etc.), pyridinium coupling reagents (e.g., Mukaiyama's reagent, pyridinium tetrafluoroborate coupling reagents, etc.), polymer-supported reagents (e.g., polymer-bound carbodiimide, polymer-bound TBTU, polymer-bound 2,4,6-trichloro-1,3,5-triazine, polymer-bound HOBt, polymer-bound HOSu, polymer-bound IIDQ, polymer-bound EEDQ, etc.), and the like (see, e.g., El-Faham, et al. Chem. Rev., 2011, 111(11): 6557-6602; Han, et al. Tetrahedron, 2004, 60:2447-2467). Compounds of formula 1-a and 1-b for use in Scheme 1 may be obtained as described in the schemes and Examples provided herein or from conventional synthetic methods known in the art using appropriate starting materials.

Scheme 2 shows an exemplary synthesis for compounds which contain a 6,7-fused ring and where $Y^1$ is O. In Scheme 2, PG is a protecting group (e.g., BOC) and $X^6$, $X^7$, $X^8$, $X^9$, $Y^2$, q, $R^1$, $R^3$, $R^4$, and $R^{10}$ are as defined herein.

Scheme 2

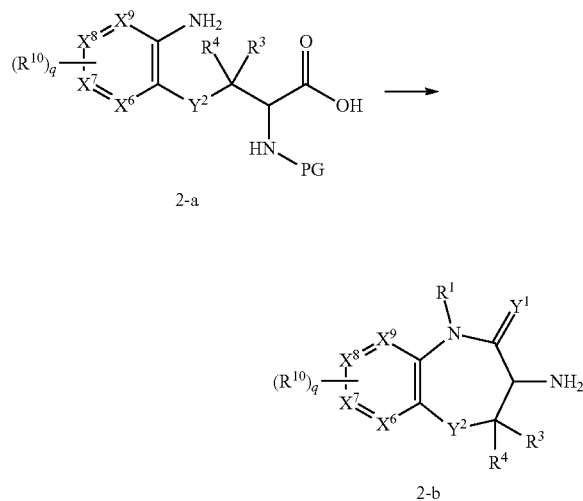

2-a 2-b

In Scheme 2, appropriately substituted 2-a can be cyclized under standard amide bond forming reaction conditions (e.g., as described above). Compounds of formula 2-a may be obtained from commercial sources, or prepared as described in the Examples provided herein or from conventional synthetic methods known in the art using appropriate starting materials. Further, the desired functional groups at $Y^2$, $R^1$, $R^3$, $R^4$ and $R^{10}$ may be installed prior to, or after, cyclization by employing conventional synthetic methods known in the art (e.g., halogenation, reduction, oxidation, olefination, alkylation, etc.).

Scheme 3 shows an exemplary synthesis for compounds which contain a 5,7-fused ring and where $Y^1$ is O. In Scheme 3, Z is halo and $X^1$, $X^2$, $X^3$, $X^4$, $X^5$, $Y^2$, q, $R^1$, $R^3$, $R^4$, and $R^{10}$ are as defined herein.

In Scheme 3, appropriately substituted 3-a can be contacted with hydroxylamine hydrochloride under reaction conditions sufficient to provide 3-b. Ring expansion of 3-b to provide lactam 3-c can be performed by contacting oxime 3-b with phosphorus pentoxide. Alternatively, lactam 3-c can be provided by contacting 3-a with sodium azide in the presence of sulfuric acid. α-Halogenation of 3-c using a suitable reagent (e.g., NBS, iodotrimethylsilane, etc.) and optional N-alkylation of the azapanone nitrogen with a compound of formula $R^1$-LG, where LG is a suitable leaving group (e.g., halo) provides 3-d. Contacting 3-d with sodium azide yields 3-e. Reduction of the azide in 3-e (e.g., hydrogenation, triphenylphosphine, etc.) provides 3-f. Compounds of formula 3-a may be obtained from commercial sources, or prepared as described in the Examples provided herein or from conventional synthetic methods known in the art using appropriate starting materials. Further, alternative functional groups may be installed at any point prior to, during, or after, the steps shown in Scheme 3 by employing conventional synthetic methods known in the art (e.g., halogenation, reduction, oxidation, olefination, alkylation, etc.).

Also provided herein is a process for preparing a compound of Formula II:

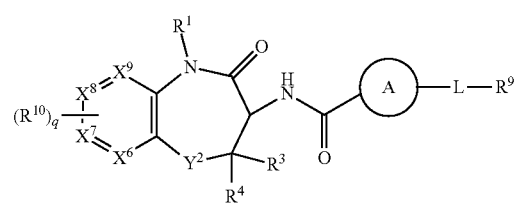

II or a salt, tautomer, stereoisomer or mixture of stereoisomers thereof, comprising contacting a compound of Formula XVI or a salt, tautomer, stereoisomer or mixture of stereoisomers thereof:

Scheme 3

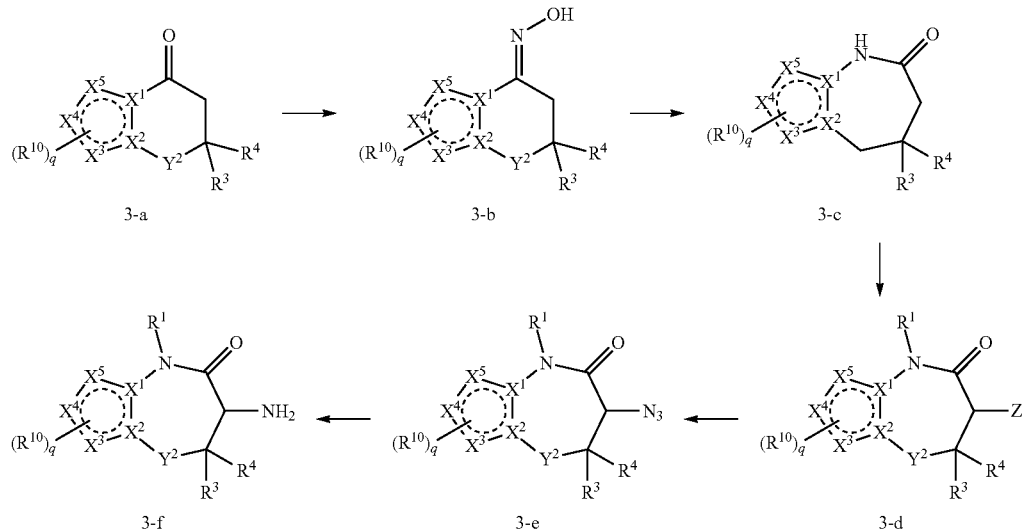

3-a 3-b 3-c 3-f 3-e 3-d

XVI

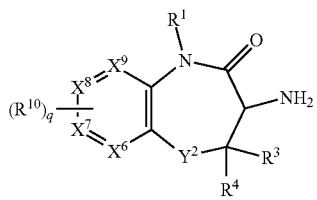

and contacting a compound of Formula XVI or a salt, tautomer, stereoisomer or mixture of stereoisomers thereof, with a compound of Formula XVII:

XVII

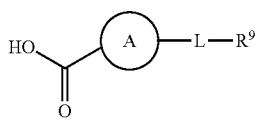

under reaction conditions sufficient to provide the compound of Formula II or a salt, tautomer, stereoisomer or mixture of stereoisomers thereof, wherein
$Y^2$ is —O—, —S—, or —NR$^5$—;
$R^5$ is H or optionally substituted $C_1$-$C_6$ alkyl; and
L, ring A, q, $R^1$, $R^3$, $R^4$, $R^9$, $R^{10}$, $X^6$, $X^7$, $X^8$ and $X^9$ are as defined herein.

In certain embodiments, provided is a process for preparing a compound of Formula II:

II

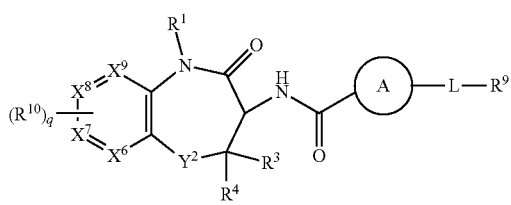

or a salt, tautomer, stereoisomer or mixture of stereoisomers thereof, comprising:
(a) contacting a compound of Formula X:

X

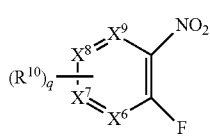

or a salt, tautomer, stereoisomer or mixture of stereoisomers thereof, with a compound of Formula XI:

XI

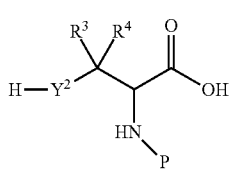

under reaction conditions sufficient to provide the compound of Formula XII or a salt, tautomer, stereoisomer or mixture of stereoisomers thereof:

XII

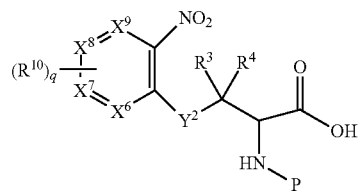

(b) contacting a compound of Formula XII or a salt, tautomer, stereoisomer or mixture of stereoisomers thereof, under reaction conditions sufficient to provide the compound of Formula (XIII) or a salt, tautomer, stereoisomer or mixture of stereoisomers thereof:

XIII

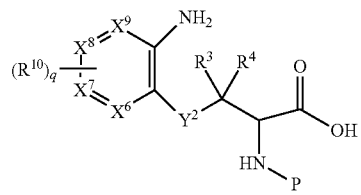

(c) contacting a compound of Formula XIII or a salt, tautomer, stereoisomer or mixture of stereoisomers thereof, under reaction conditions sufficient to provide the compound of Formula XIV or a salt, tautomer, stereoisomer or mixture of stereoisomers thereof:

XIV

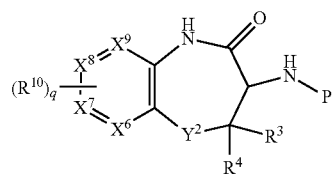

(d) optionally contacting a compound of Formula XIV or a salt, tautomer, stereoisomer or mixture of stereoisomers thereof, with an alkylating agent, under reaction conditions sufficient to provide the compound of Formula XV or a salt, tautomer, stereoisomer or mixture of stereoisomers thereof:

XV

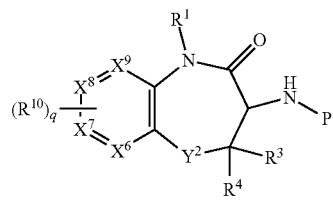

(e) deprotecting the compound of Formula XV or a salt, tautomer, stereoisomer or mixture of stereoisomers thereof, under reaction conditions sufficient to provide the compound of Formula XVI or a salt, tautomer, stereoisomer or mixture of stereoisomers thereof:

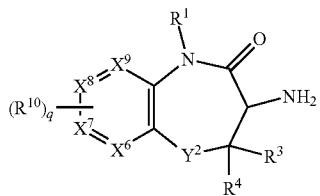

and contacting a compound of Formula XVI or a salt, tautomer, stereoisomer or mixture of stereoisomers thereof, with a compound of Formula XVII:

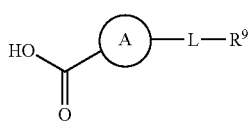

under reaction conditions sufficient to provide the compound of Formula II or a salt, tautomer, stereoisomer or mixture of stereoisomers thereof, wherein
P is a protecting group;
$Y^2$ is —O—, —S—, or —$NR^5$—;
$R^5$ is H or optionally substituted $C_1$-$C_6$ alkyl; and
L, ring A, q, $R^1$, $R^3$, $R^4$, $R^9$, $R^{10}$, $X^6$, $X^7$, $X^8$ and $X^9$ are as defined herein.

In certain embodiments of the processes described above, at least one of $X^7$ or $X^9$ is N. In certain embodiments of the processes described above, $X^7$ is N and $X^6$, $X^8$ and $X^9$ are CH. In certain embodiments of the processes described above, $X^9$ is N and $X^6$, $X^7$ and $X^8$ are CH. In certain embodiments of the processes described above, $R^1$ is methyl. In certain embodiments of the processes described above, $Y^2$ is —O—.

In certain embodiments of the processes described above, P is tert-butoxycarbonyl. In certain embodiments of the processes described above, the reaction conditions of step (b) comprise hydrogen gas. In certain embodiments of the processes described above, the reaction conditions of step (c) comprise a peptide coupling agent. In certain embodiments of the processes described above, the alkylating agent of step (d) is methyliodide.

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Procedures

Liquid Chromatography-Mass Spectrometry Method A:

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, C18 column (50×2.1 mm, 1.7 μm particle size), column temperature 40° C., mobile phase: A—water+0.1% HCOOH/B—$CH_3CN$+0.1% HCOOH, flow rate: 1.0 mL/min, run time=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method B:

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ BEH, C18 column (50×2.1 mm, 1.7 μm particle size), column temperature 40° C., mobile phase: A-0.1% v/v aqueous ammonia solution pH 10/B—$CH_3CN$, flow rate: 1.0 mL/min, run time=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method C:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.2 min with a total run time of 2.6 min. The column temperature was at 40° C. with a flow rate of 1.0 mL/min.

Liquid Chromatography-Mass Spectrometry Method D:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 3.2 min with a total run time of 3.6 min. The column temperature was at 40° C. with a flow rate of 1.0 mL/min.

Liquid Chromatography-Mass Spectrometry Method E:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 3.0×50 mm. A linear gradient was applied, starting at 95% A (A: 0.05% TFA in water) and ending at 100% B (B: 0.05% TFA in MeCN) over 1.8 min with a total run time of 2.0 min. The column temperature was at 45° C. with a flow rate of 1.5 mL/min.

Liquid Chromatography-Mass Spectrometry Method F:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 3.0×50 mm. A linear gradient was applied, starting at 95% A (A: 0.05% TFA in water) and ending at 100% B (B: 0.05% TFA in MeCN) over 2.8 min with a total run time of 3.0 min. The column temperature was at 45° C. with a flow rate of 1.5 mL/min.

Liquid Chromatography-Mass Spectrometry Method G:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Kinetex EVO, 2.6 µm, 3.0×50 mm. A linear gradient was applied, starting at 90% A (A: 0.05% $NH_4HCO_3$ in water) and ending at 95% B (B: MeCN) over 1.7 min with a total run time of 2.0 min. The column temperature was at 40° C. with a flow rate of 1.3 mL/min.

Liquid Chromatography-Mass Spectrometry Method H:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Kinetex EVO, 2.6 µm, 3.0×50 mm. A linear gradient was applied, starting at 90% A (A: 0.05% $NH_4HCO_3$ in water) and ending at 95% B (B: MeCN) over 2.7 min with a total run time of 3.0 min. The column temperature was at 40° C. with a flow rate of 1.3 mL/min.

Liquid Chromatography-Mass Spectrometry Method I:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 2.1×50 mm. A linear gradient was applied, starting at 90% A (A: 0.10% formic acid in water) and ending at 100% B (B: 0.10% formic acid in MeCN) over 1.70 min with a total run time of 2.0 min. The column temperature was at 45° C. with a flow rate of 1.0 mL/min.

Liquid Chromatography-Mass Spectrometry Method J:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 2.1×50 mm. A linear gradient was applied, starting at 90% A (A: 0.10% formic acid in water) and ending at 95% B (B: 0.10% formic acid in MeCN) over 2.70 min with a total run time of 3.0 min. The column temperature was at 45° C. with a flow rate of 1.0 mL/min.

Liquid Chromatography-Mass Spectrometry Method K:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 3.0×50 mm. A linear gradient was applied, starting at 95% A (A: 0.05% TFA in water) and ending at 100% B (B: 0.05% TFA in MeCN) over 1.6 min with a total run time of 2.0 min. The column temperature was at 40° C. with a flow rate of 1.5 mL/min.

Liquid Chromatography-Mass Spectrometry Method L:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 3.0×50 mm. A linear gradient was applied, starting at 95% A (A: 0.05% TFA in water) and ending at 100% B (B: 0.05% TFA in MeCN) over 2.6 min with a total run time of 3.0 min. The column temperature was at 40° C. with a flow rate of 1.5 mL/min.

Liquid Chromatography-Mass Spectrometry Method M:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Kinetex XB—C18, 2.6 µm, 3.0×50 mm. A linear gradient was applied, starting at 95% A (A: 0.05% TFA in water) and ending at 100% B (B: 0.05% TFA in MeCN) over 2.8 min with a total run time of 3.0 min. The column temperature was at 40° C. with a flow rate of 1.5 mL/min.

Liquid Chromatography-Mass Spectrometry Method N:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 3.0×50 mm. A linear gradient was applied, starting at 95% A (A: 0.05% TFA in water) and ending at 100% B (B: 0.05% TFA in MeCN) over 1.7 min with a total run time of 2.0 min. The column temperature was at 40° C. with a flow rate of 1.5 mL/min.

Liquid Chromatography-Mass Spectrometry Method O:
The column used was an Agilent Poroshell HPH-C18, 2.7 µm, 3.0×50 mm. A linear gradient was applied, starting at 95% A (A: 0.05% NH$_4$HCO$_3$ in water) and ending at 95% B (B: 0.05% NH$_4$HCO$_3$ in MeCN) over 2.7 min with a total run time of 3 min. The column temperature was at 45° C. with a flow rate of 1.5 mL/min.

Liquid Chromatography-Mass Spectrometry Method P:
The column used was an Ascentis Express C18, 3.5 µm, 4.6×50 mm. A linear gradient was applied, starting at 90% A (A: 0.05% NH$_4$HCO$_3$ in water) and ending at 95% B (B: 0.05% NH$_4$HCO$_3$ in MeCN) over 5.2 min with a total run time of 5.6 min. The column temperature was at 40° C. with a flow rate of 1.5 mL/min.

Liquid Chromatography-Mass Spectrometry Method Q:
The column used was an Agilent Poroshell HPH-C18, 2.7 µm, 3.0×50 mm. A linear gradient was applied, starting at 95% A (A: 0.05% NH$_4$HCO$_3$ in water) and ending at 95% B (B: 0.05% NH$_4$HCO$_3$ in MeCN) over 4.7 min with a total run time of 5.0 min. The column temperature was at 40° C. with a flow rate of 1.5 mL/min.

Liquid Chromatography-Mass Spectrometry Method R:
The column used was an Agilent Poroshell HPH-C18, 2.7 µm, 3.0×50 mm. A linear gradient was applied, starting at 95% A (A: 0.05% NH$_4$HCO$_3$ in water) and ending at 95% B (B: 0.05% NH$_4$HCO$_3$ in MeCN) over 1.8 min with a total run time of 2.0 min. The column temperature was at 40° C. with a flow rate of 1.5 mL/min.

Liquid Chromatography-Mass Spectrometry Method S:
The column used was an Ascentis Express C18, 2.7 µm, 3.0×50 mm. A linear gradient was applied, starting at 95% A (A: 0.05% TFA in water) and ending at 100% B (B: 0.05% TFA in MeCN) over 1.8 min with a total run time of 2.0 min. The column temperature was at 40° C. with a flow rate of 1.5 mL/min.

Liquid Chromatography-Mass Spectrometry Method T:
The column used was an Ascentis Express C18, 2.7 µm, 3.0×50 mm. A linear gradient was applied, starting at 95% A (A: 0.05% TFA in water) and ending at 100% B (B: 0.05% TFA in MeCN) over 2.7 min with a total run time of 3.0 min. The column temperature was at 40° C. with a flow rate of 1.5 mL/min.

Liquid Chromatography-Mass Spectrometry Method U:
The column used was an Acquity UPLCTM BEH, C18 column (50×2.1 mm, 1.7 µm particle size), column temperature 40° C., mobile phase: A-10 mM aqueous ammonium bicarbonate solution adjusted to pH 10 with aqueous ammonia solution/B—CH$_3$CN, flow rate: 1.0 mL/min, run-time=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method V:
The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 4.2 min with a total run time of 5.3 min. The column temperature was at 40° C. with a flow rate of 1.0 mL/min.

Liquid Chromatography-Mass Spectrometry Method W:
The column used was an Shim-pack XR-ODS, 2.2 µm, 3.0×50 mm. A linear gradient was applied, starting at 95% A (A: 0.05% TFA in water) and ending at 100% B (B: 0.05% TFA in MeCN) over 4.2 min with a total run time of 5.3 min. The column temperature was at 40° C. with the flow rate of 1.0 mL/min.

Liquid Chromatography-Mass Spectrometry Method X:
The column used was an Ascentis Express C18, 2.7 µm, 3.0×50 mm. A linear gradient was applied, starting at 95% A (A: 0.05% TFA in water) and ending at 95% B (B: 0.05% TFA in MeCN) over 4.1 min with a total run time of 5.3 min. The column temperature was at 40° C. with the flow rate of 1.5 mL/min.

Liquid Chromatography-Mass Spectrometry Method Y:
The column used was an Poroshell HPH-C18, 2.7 µm, 3.0×50 mm. A linear gradient was applied, starting at 95% A (A: 0.05% NH$_4$HCO$_3$ in water) and ending at 95% B (B: 0.05% NH$_4$HCO$_3$ in MeCN) over 1.8 min with a total run time of 2 min. The column temperature was at 45° C. with the flow rate of 1.5 mL/min.

HPLC analyses were performed on a SHIMADZU UFLC with two LC20 AD pump and a SPD-M20A Photodiiode Array Detector. The column used was an XBridge C18, 3.5 µm, 4.6×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Thin layer chromatography (TLC) was performed on Alugram® (Silica gel 60 F254) from Mancherey-Nagel and UV was typically used to visualize the spots. Additional visualization methods were also employed in some cases. In these cases the TLC plate was developed with iodine (generated by adding approximately 1 g of I$_2$ to 10 g silica gel and thoroughly mixing), ninhydrin (available commercially from Aldrich), or Magic Stain (generated by thoroughly mixing 25 g (NH$_4$)$_6$Mo$_7$O$_{24}$.4H$_2$O, 5 g (NH$_4$)$_2$Ce(IV)(NO$_3$)$_6$ in 450 mL water and 50 mL concentrated H$_2$SO$_4$) to visualize the compound. Flash chromatography was performed using 40-63 µm (230-400 mesh) silica gel from Silicycle following analogous techniques to those disclosed in Still, W. C.; Kahn, M.; and Mitra, M. Journal of Organic Chemistry, 1978, 43, 2923. Typical solvents used for flash chromatography or thin layer chromatography were mixtures of chloroform/methanol, dichloromethane/methanol, ethyl acetate/methanol and hexanes/ethyl acetate.

Analytical Methods $^1$H Nuclear magnetic resonance (NMR) spectroscopy was carried out using a Bruker Avance III equipped with a BBFO 300 MHz probe operating at 300 MHz or one of the following instruments: a Bruker Avance 400 instrument equipped with probe DUAL 400 MHz S1, a Bruker Avance 400 instrument equipped with probe 6 S1 400 MHz 5 mm $^1$H—$^{13}$C ID, a Bruker Avance III 400 instrument with nanobay equipped with probe Broadband BBFO 5 mm direct, a Bruker Mercury Plus 400 NMR Spectrometer equipped with a Bruker 400 BBO probe all operating at 400 MHz. The spectra were acquired in the stated solvent at around room temperature unless otherwise stated. In all cases, NMR data were consistent with the proposed structures. Flash chromatography was performed using 40-63 µm (230-400 mesh) silica gel from Silicycle following analogous techniques to those disclosed in Still, W. C.; Kahn, M.; and Mitra, M. Journal of Organic Chemistry, 1978, 43, 2923.

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

Example 1: 5-Benzyl-N-(2-chloro-4-methyl-5-oxo-4H,5H,6H,7H,8H-thieno[3,2-b]azepin-6-yl)-1,2-oxazole-3-carboxamide

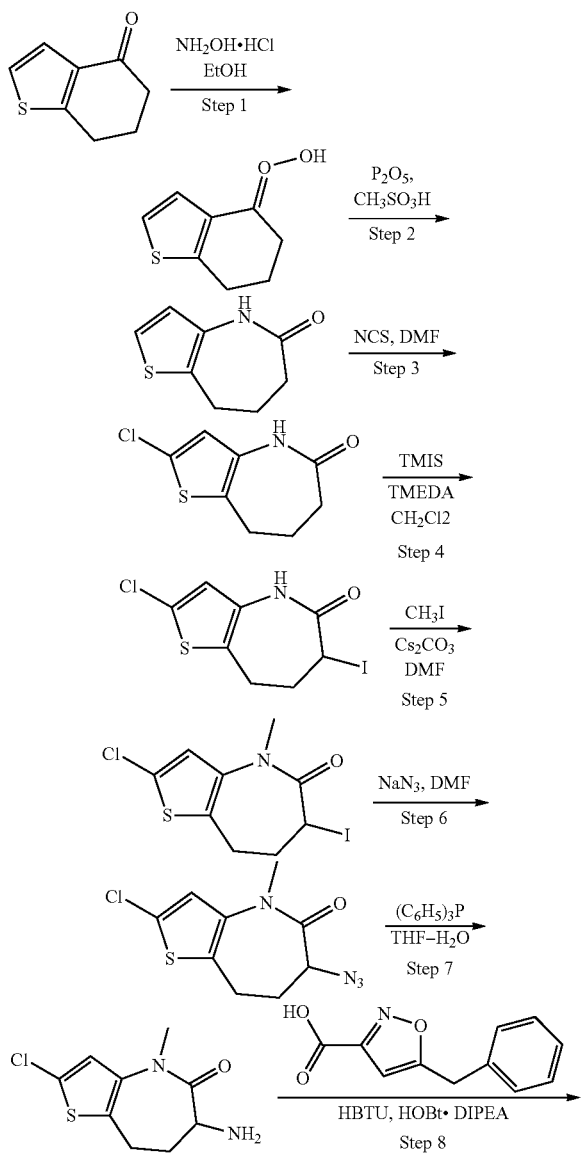

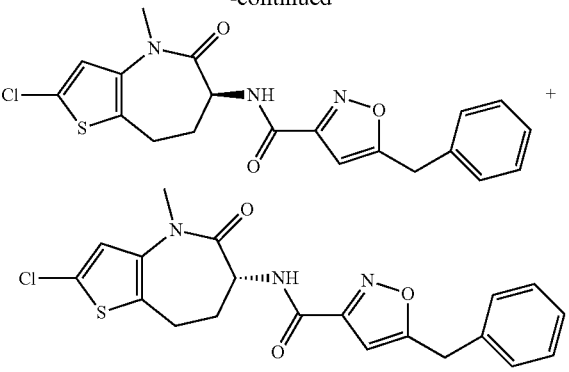

Step 1: Preparation of N-[4,5,6,7-Tetrahydro-1-benzothiophen-4-ylidene]hydroxylamine A solution of hydroxylamine hydrochloride (4.56 g, 65.7 mmol) in 5 N sodium acetate solution (120 mL) was added to a solution of 6,7-dihydro-1-benzothiophen-4(5H)-one (2.00 g, 13.1 mmol) in EtOH (200 mL). The reaction mixture was heated to 100° C. and stirred for 2 h. Volatiles were removed under reduced pressure and the crude product was dissolved in water and extracted with EtOAc. The organic portion was washed with brine, dried over $Na_2SO_4$, filtered and concentrated under reduced pressure. The crude product was purified by column chromatography (cyclohexane-EtOAc, 100:0 to 50:50) to give the title compound (1.10 g, 51%). $^1$H NMR (400 MHz, $CDCl_3$) δ 7.76-7.42 (m, 1H), 7.30 (d, J=5.3 Hz, 1H), 7.09 (d, J=5.3 Hz, 1H), 2.89 (t, J=6.1 Hz, 2H), 2.82-2.77 (m, 2H), 2.02 (quin, J=6.3 Hz, 2H). LC-MS (Method A): m/z=168.0 $[M+H]^+$, 0.83 min.

Step 2: Preparation of 4H,5H,6H,7H,8H-Thieno[3,2-b]azepin-5-one

Phosphorus pentoxide (11.3 g, 79.5 mmol) was added to methanesulfonic acid (10.9 g, 113.6 mmol) and the mixture was stirred for 2 h. N-[4,5,6,7-Tetrahydro-1-benzothiophen-4-ylidene]hydroxylamine (1.10 g, 6.58 mmol) was then added to the above stirred solution, which had been previously warmed to 100° C. After stirring for 4 h at 110° C., the reaction was cooled and quenched carefully by adding sat. $NaHCO_3$ solution. The mixture was extracted with chloroform. The combined organic portions were washed with sat. $NaHCO_3$ solution and water, dried over $Na_2SO_4$, filtered and concentrated under reduced pressure. The crude product was purified by column chromatography (cyclohexane-EtOAc, 80:20 to 0:100) to give the desired compound (450 mg, 41%). $^1$H NMR (400 MHz, $CDCl_3$) δ 7.90-7.69 (m, 1H), 7.08 (d, J=5.3 Hz, 1H), 6.64 (d, J=5.3 Hz, 1H), 3.00 (t, J=6.9 Hz, 2H), 2.67-2.60 (m, 2H), 2.26-2.14 (m, 2H).

Step 3: Preparation of 2-Chloro-4H,5H,6H,7H,8H-thieno[3,2-b]azepin-5-one

N-Chlorosuccinimide (356 mg, 2.68 mmol) was added to a solution of 4H,5H,6H,7H,8H-thieno[3,2-b]azepin-5-one (450 mg, 2.69 mmol) in DMF (10 mL). The reaction was warmed to 50° C. and stirred at that temperature for 16 h. The reaction was diluted with EtOAc, washed twice with sat. $NH_4Cl$ solution, dried over $Na_2SO_4$, filtered and concentrated under reduced pressure. The crude product was purified by column chromatography (cyclohexane/EtOAc, 100:0 to 0:100) to give the title compound (190 mg, 35%). $^1$H NMR (400 MHz, CDCl$_3$) δ 7.73 (br.s, 1H), 6.50 (s, 1H), 2.89 (t, J=6.9 Hz, 2H), 2.66-2.59 (m, 2H), 2.23-2.13 (m, 2H). LC-MS (Method A): m/z=202.1 [M+H]$^+$, 0.84 min.

Step 4: Preparation of 2-Chloro-6-iodo-4H,5H,6H, 7H,8H-thieno[3,2-b]azepin-5-one Iodotrimethylsilane (264 μL, 0.189 mmol) was added to a solution of 2-chloro-4H,5H,6H,7H,8H-thieno[3,2-b]azepin-5-one (190 mg, 0.945 mmol) and TMEDA (430 μL, 22.8 mmol) in CH$_2$Cl$_2$ (3 mL) which had been pre-cooled to −10° C. The reaction was stirred at −10° C. for 30 min. Powdered iodine (360 mg, 1.42 mmol) was added. The mixture was stirred at −10° C. for 1 h, allowed to reach room temperature over 1.5 h, stirred for a further 30 min and quenched with 1 M Na$_2$S$_2$O$_3$ solution. The layers were separated and the aqueous portion was extracted twice with CH$_2$Cl$_2$. The combined organic portions were dried over Na$_2$SO$_4$, filtered and concentrated under reduced pressure. The crude product was triturated with CH$_2$Cl$_2$ to yield the title compound (135 mg, 44%). $^1$H NMR (400 MHz, DMSO-d$_6$) δ 10.03 (s, 1H), 6.69 (s, 1H), 4.99-4.91 (m, 1H), 3.15-3.06 (m, 1H), 2.95 (ddd, J=17.4, 11.9, 5.5 Hz, 1H), 2.19-208 (m, 1H), 1.88 (dddd, J=14.9, 11.9, 5.1, 2.0 Hz, 1H).

Step 5: Preparation of 2-Chloro-6-iodo-4-methyl-4H,5H,6H,7H,8H-thieno[3,2-b]azepin-5-one Iodomethane (29 μL, 0.460 mmol) was added to a mixture of 2-chloro-6-iodo-4H,5H,6H,7H,8H-thieno[3,2-b]azepin-5-one (135 mg, 0.418 mmol) and Cs$_2$CO$_3$ (205 mg, 0.627 mmol) in DMF (6 mL). The reaction was stirred at room temperature for 4 h, cooled to 4° C. and stirred at that temperature for 36 h. Further iodomethane (29 μL, 0.460 mmol) was added and the mixture was stirred at room temperature for 5 h. EtOAc was added and the organic portion was washed twice with 0.5 M HCl solution, dried over Na$_2$SO$_4$, filtered and concentrated under reduced pressure. The crude product was purified by column chromatography (cyclohexane/EtOAc, 100:0 to 50:50) to give the title compound (72 mg, 51%). $^1$H NMR (400 MHz, DMSO-d$_6$) δ 7.28 (s, 1H), 4.82 (dd, J=9.2, 6.7 Hz, 1H), 3.17 (s, 3H), 2.90-2.56 (m, 4H). LC-MS (Method A): m/z=342.0 [M+H]$^+$, 1.10 min.

Step 6: Preparation of 6-Azido-2-chloro-4-methyl-4H,5H,6H,7H,8H-thieno[3,2-b]azepin-5-one A mixture of 2-chloro-6-iodo-4-methyl-4H,5H,6H,7H, 8H-thieno[3,2-b]azepin-5-one (70 mg, 0.205 mmol) and NaN$_3$ (20 mg, 0.307 mmol) in DMF (2 mL) was stirred at 33° C. for 2 h. EtOAc was added and the organic portion was washed twice with 0.5 M HCl solution, dried over Na$_2$SO$_4$, filtered and concentrated under reduced pressure to afford the title compound (52 mg), which was directly progressed to the next step. $^1$H NMR (400 MHz, DMSO-d$_6$) δ 7.28 (s, 1H), 4.11 (dd, J=11.7, 7.4 Hz, 1H), 3.20 (s, 3H), 2.88-2.77 (m, 2H), 2.53-2.40 (m, 1H), 2.28-2.13 (m, 1H). LC-MS (Method A): m/z=257.1 [M+H]$^+$, 1.04 min.

Step 7: Preparation of 6-Amino-2-chloro-4-methyl-4H, 5H, 6H, 7H, 8H-thieno[3,2-b]azepin-5-one A mixture of 6-azido-2-chloro-4-methyl-4H,5H,6H,7H, 8H-thieno[3,2-b]azepin-5-one (52 mg) and triphenylphosphine (60 mg, 0.229 mg) in 3:1 THF-H$_2$O (2 mL) was stirred at room temperature for 18 h. The reaction was diluted with EtOAc and washed twice with water. The organic portion was dried over Na$_2$SO$_4$, filtered and concentrated under reduced pressure. The crude product was purified by column chromatography (cyclohexane/EtOAc, 60:40) to afford the title compound (37 mg, 85% purity). $^1$H NMR (400 MHz, DMSO-d$_6$) δ 7.25 (s, 1H), 3.37-3.28 (m, 1H), 3.16 (s, 3H), 2.71-2.64 (m, 2H), 2.37-2.26 (m, 1H), 1.90-1.77 (m, 1H), 1.66 (br. s, 2H). LC-MS (Method A): m/z=231.1 [M+H]$^+$, 0.41 min.

Amide Coupling Procedure A

Step 8: Preparation and Separation of 5-Benzyl-N-(2-chloro-4-methyl-5-oxo-4H,5H,6H,7H,8H-thieno[3,2-b]azepin-6-yl)-1,2-oxazole-3-carboxamide A solution of 6-amino-2-chloro-4-methyl-4H,5H,6H,7H, 8H-thieno[3,2-b]azepin-5-one (27 mg, ~85% purity), HBTU (39.6 mg, 0.104 mmol), 1-hydroxybenzotriazole (14 mg, 0.104 mmol), DIPEA (45 μL, 0.261 mmol) and 5-benzyl-1, 2-oxazole-3-carboxylic acid (19 mg, 0.092 mmol) in DMF (3.5 mL) was stirred at room temperature for 4 h. EtOAc was added and the organic portion was washed twice with sat. NH$_4$Cl solution, dried over Na$_2$SO$_4$, filtered and concentrated under reduced pressure. The crude product was purified by column chromatography (cyclohexane/EtOAc, 100:0 to 50:50) to give the title compound as a mixture of enantiomers. This mixture was resolved by chiral HPLC on a Whelk O-1 (R,R) (25×2.0 cm), 10 μm column using a mobile phase of n-hexane/(EtOH/MeOH/CH$_2$Cl$_2$ 45/45/10+ 0.1% isopropylamine) 20/80% v/v to afford the two title compounds as separated enantiomers.

First eluting enantiomer, Enantiomer 1: $^1$H NMR (400 MHz, CDCl$_3$) δ 7.76 (d, J=7.5 Hz, 1H), 7.42-7.20 (m, 5H), 6.80 (s, 1H), 6.34 (s, 1H), 4.81 (dt, J=11.2, 7.2 Hz, 1H), 4.13 (s, 2H), 3.31 (s, 3H), 3.02-2.78 (m, 2H), 2.77-2.66 (m, 1H), 2.23-2.09 (m, 1H). LC-MS (Method A): m/z=416.2 [M+H]$^+$, 1.16 min. e.e. >99.5% as determined on a Whelk O-1 (R,R) (25×2.0 cm), 10 μm column using a mobile phase of n-hexane/(EtOH/MeOH/CH$_2$Cl$_2$ 45/45/10+0.1% isopropylamine) 20/80% v/v.

Second eluting enantiomer, Enantiomer 2: $^1$H NMR (400 MHz, CDCl$_3$) δ 7.82-7.71 (m, 1H), 7.39-7.23 (m, 5H), 6.80 (s, 1H), 6.34 (s, 1H), 4.81 (dt, J=11.2, 7.1 Hz, 1H), 4.13 (s, 2H), 3.31 (s, 3H), 3.00-2.78 (m, 2H), 2.76-2.66 (m, 1H), 2.21-2.10 (m, 1H). LC-MS (Method A): m/z=416.2 [M+H]$^+$, 1.16 min. e.e.=98.4% as determined on a Whelk O-1 (R,R) (25×2.0 cm), 10 μm column using a mobile phase of n-hexane/(EtOH/MeOH/CH$_2$Cl$_2$ 45/45/10+0.1% isopropylamine) 20/80% v/v.

Example 2: 5-benzyl-N-(5-fluoro-1-methyl-2-oxo-2, 3,4,5-tetrahydro-1H-benzo[b]azepin-3-yl)isoxazole-3-carboxamide

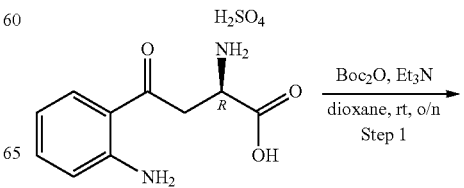

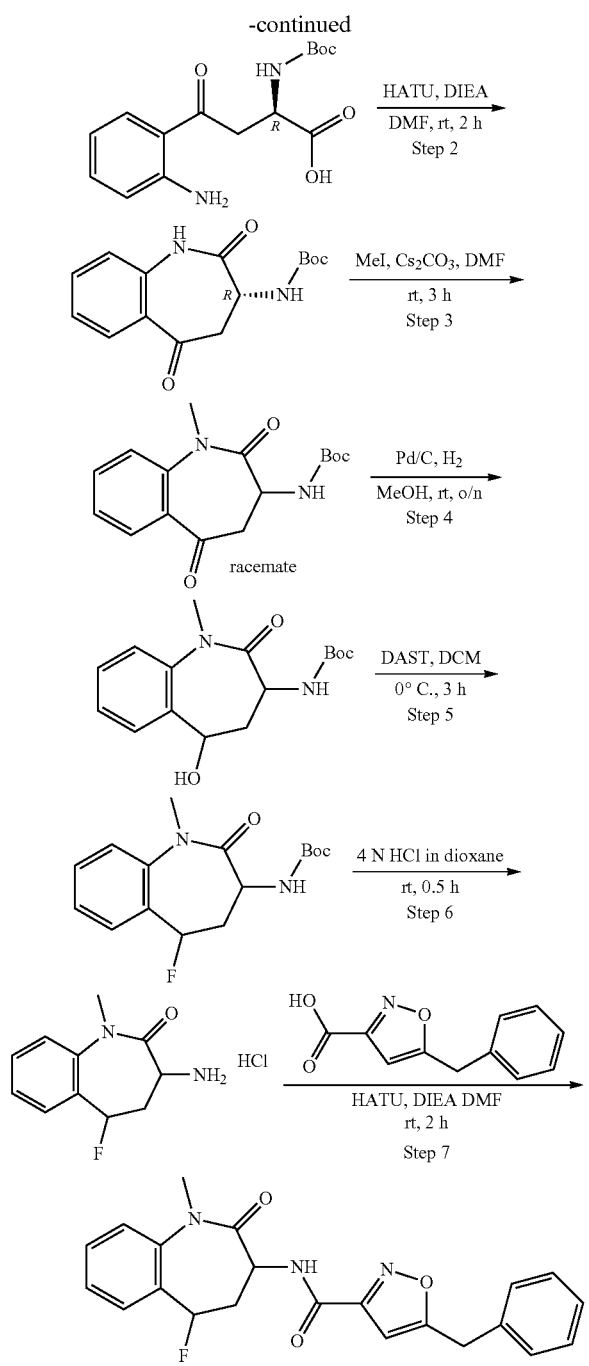

Step 1: Preparation of (2R)-4-(2-aminophenyl)-2-[[(tert-butoxy)carbonyl]amino]-4-oxobutanoic acid Di-tert-butyl dicarbonate (7.19 g, 32.9 mmol) was added to a solution of the sulphate of (2R)-2-amino-4-(2-aminophenyl)-4-oxobutanoic acid (9.18 g, 29.9 mmol) and triethylamine (12.1 g, 119.6 mmol) in dioxane (50 mL) under nitrogen atmosphere with stirring. The resulting mixture was stirred overnight at room temperature. The reaction mixture was concentrated under vacuum to afford the title compound (9.18 g crude). LC-MS (Method C): m/z=309.1 [M+H]$^+$, 1.307 min.

Step 2: Preparation of (R)-tert-butyl (2,5-dioxo-2,3,4,5-tetrahydro-1H-benzo[b]azepin-3-yl)carbamate 2-(7-Aza-1H-benzotriazole-1-yl)-1,1,3,3-tetramethyluronium hexafluorophosphate (13.6 g, 35.9 mmol) and ethyldiisopropylamine (11.6 g, 89.7 mmol) were added to a stirred solution of (2R)-4-(2-aminophenyl)-2-[[(tert-butoxy)carbonyl]amino]-4-oxobutanoic acid (9.21 g, 29.8 mmol) in N,N-dimethylformamide (50 mL). The resulting solution was stirred for 2 hours at room temperature. The reaction mixture was diluted with water (50 mL), and extracted with ethyl acetate (3×40 mL). The combined organic layers were dried over anhydrous sodium sulfate, filtered and concentrated under vacuum. The residue was purified by column chromatography (ethyl acetate/petroleum ether, 1/6) to afford the title compound (2.2 g, 25%). LC-MS (Method C): m/z=291.1 [M+H]$^+$, 1.298 min.

Step 3: Preparation of tert-butyl (1-methyl-2,5-dioxo-2,3,4,5-tetrahydro-1H-benzo[b]azepin-3-yl)carbamate Iodomethane (1.08 g, 7.60 mmol) was added dropwise to a stirred solution of (R)-tert-butyl (2,5-dioxo-2,3,4,5-tetrahydro-1H-benzo[b]azepin-3-yl)carbamate (2.01 g, 6.89 mmol) and cesium carbonate (2.47 g, 7.58 mmol) in N,N-dimethylformamide (20 mL) with stirring. The resulting solution was stirred for 3 hours at room temperature. Water (10 mL) was added to quench the reaction. The reaction mixture was extracted with ethyl acetate (3×50 mL). The combined organic layers were concentrated under vacuum. The residue was purified by column chromatography (ethyl acetate/petroleum ether, 1/10) to afford the title compound (1.20 g, 57%). LC-MS (Method G): m/z=305.0 [M+H]$^+$, 1.004 min.

Step 4: Preparation of tert-butyl (5-hydroxy-1-methyl-2-oxo-2,3,4,5-tetrahydro-1H-benzo[b]azepin-3-yl)carbamate tert-Butyl (1-methyl-2,5-dioxo-2,3,4,5-tetrahydro-1H-benzo[b]azepin-3-yl)carbamate (506.0 mg, 1.66 mmol) in methanol (20 mL) was hydrogenated in the presence of 10% palladium on carbon (50.0 mg) under hydrogen atmosphere (2-3 atmospheres). The resulting solution was stirred overnight at room temperature. The solids were removed by filtration and the filtrate was evaporated under vacuum to afford the title compound (0.5 g crude). LC-MS (Method C): m/z=307.2 [M+H]$^+$, 1.273 min.

Step 5: Preparation of tert-butyl N-[5-fluoro-1-methyl-2-oxo-2,3,4,5-tetrahydro-1H-1-benzazepin-3-yl]carbamate Diethylaminosulfur trifluoride (40.3 mg, 0.25 mmol) was added to a solution of tert-butyl (5-hydroxy-1-methyl-2-oxo-2,3,4,5-tetrahydro-1H-benzo[b]azepin-3-yl)carbamate (30.6 mg, 0.10 mmol) in dichloromethane (2 mL) under nitrogen atmosphere at 0° C. The resulting solution was stirred for 3 hours at 0° C. The reaction was quenched with saturated aqueous sodium bicarbonate (2 mL) and extracted with ethyl acetate (3×5 mL). The combined organic layers were dried over anhydrous sodium sulfate, filtered and concentrated under vacuum. The residue was purified by column chromatography (ethyl acetate/petroleum ether, 1/4)

to afford the title compound (25 mg, 81%). LC-MS (Method K): m/z=208.9 [M−Boc+H]⁺, 0.946 min.

Step 6: Preparation of 3-amino-5-fluoro-1-methyl-2,3,4,5-tetrahydro-1H-1-benzazepin-2-one hydrochloride A solution of tert-butyl N-[5-fluoro-1-methyl-2-oxo-2,3,4,5-tetrahydro-1H-1-benzazepin-3-yl]carbamate (25.0 mg, 0.08 mmol) in 4 N hydrogen chloride in dioxane (2 mL) was stirred for 0.5 hour at room temperature. The resulting mixture was concentrated under vacuum to afford the title compound (20 mg crude). LC-MS (Method K): m/z=208.9 [M+H]⁺, 0.555 min.

Step 7: Preparation of 5-benzyl-N-(5-fluoro-1-methyl-2-oxo-2,3,4,5-tetrahydro-1H-benzo[b]azepin-3-yl)isoxazole-3-carboxamide A solution of 5-benzyl-1,2-oxazole-3-carboxylic acid (16.0 mg, 0.08 mmol) in N,N-dimethylformamide (2 mL) was added to a stirred solution of 2-(7-aza-1H-benzotriazole-1-yl)-1,1,3,3-tetramethyluronium hexafluorophosphate (45.6 mg, 0.12 mmol), ethyldiisopropylamine (38.7 mg, 0.30 mmol), 3-amino-5-fluoro-1-methyl-2,3,4,5-tetrahydro-1H-1-benzazepin-2-one hydrochloride (20.0 mg, 0.08 mmol) in N,N-dimethylformamide (10 mL). The resulting solution was stirred for 2 hours at room temperature and then diluted with water (10 mL). The reaction mixture was extracted with ethyl acetate (3×20 mL). The combined organic layers were dried over anhydrous sodium sulfate, filtered and concentrated under vacuum. The crude product was purified by reverse phase chromatography using an Xbridge Phenyl OBD 5 μm, 19×150 mm column; mobile phase, water (10 mmol/L NH₄HCO₃) and ACN (50.0% ACN to 70.0% in 7 min) to afford the title compound. ¹H NMR (400 MHz, DMSO-d₆) δ 8.85 (d, J=7.6 Hz, 1H), 7.59-7.52 (m, 2H), 7.44-7.26 (m, 7H), 6.54 (s, 1H), 5.76 (dd, J=4.4, 48.8 Hz, 1H), 4.52-4.45 (m, 1H), 4.22 (s, 2H), 3.25 (s, 3H), 2.74-2.71 (m, 1H), 2.66-2.61 (m, 1H). LC-MS (Method L): m/z=394.1 [M+H]⁺, 1.482 min.

Amide Coupling Procedure B

Step 8: Preparation of 5-benzyl-N-(5-fluoro-1-methyl-2-oxo-2,3,4,5-tetrahydro-1H-benzo[b]azepin-3-yl)isoxazole-3-carboxamide (First Eluting Isomer, Example 2A) and 5-benzyl-N-(5-fluoro-1-methyl-2-oxo-2,3,4,5-tetrahydro-1H-benzo[b]azepin-3-yl)isoxazole-3-carboxamide (Second Eluting Isomer Example 2B)

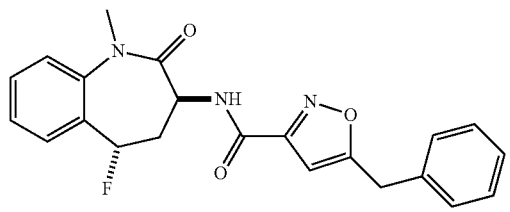

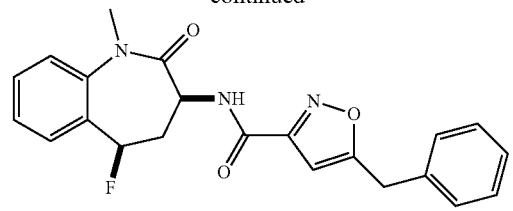

3-Amino-5-fluoro-1-methyl-2,3,4,5-tetrahydro-1H-1-benzazepin-2-one (30 mg, 0.140 mmol) was added to a stirring solution of 5-benzyl-1,2-oxazole-3-carboxylic acid (32.3 mg, 0.159 mmol), N,N,N',N'-tetramethyl-O-(7-azabenzotriazol-1-yl)uronium hexafluorophosphate (65.7 mg, 0.173 mmol) and N,N-diisopropylethylamine (55.7 mg, 0.432 mmol) in N,N-dimethylformamide (5 mL). After stirring for 3 hours at room temperature, the reaction mixture was diluted with water (10 mL) and extracted with ethyl acetate (3×10 mL). The combined organic layers were washed with brine, dried over anhydrous sodium sulfate, filtered and concentrated under reduced pressure. The crude product was purified by Prep-HPLC with the following conditions: Column, XBridge Prep C18 OBD Column, 5 μm, 19×150 mm; mobile phase, water (0.05% TFA) and ACN (45.0% ACN to 70.0% over 7 min); Detector, UV 254/220 nm to afford the title compounds:

Example 2A, first eluting isomer: ¹H NMR (300 MHz, CD₃OD) δ 8.53 (d, J=6.9 Hz, 1H), 7.55-7.50 (m, 1H), 7.50-7.42 (m, 1H), 7.40-7.14 (m, 7H), 6.36 (s, 1H), 5.79-5.28 (m, 1H), 4.73-4.48 (m, 1H), 4.13 (s, 2H), 3.32 (s, 3H), 2.91-2.72 (m, 1H), 2.64-2.40 (m, 1H). LC-MS (Method D): m/z=394.1 [M+H]⁺, 2.075 min.

Example 2B, second eluting isomer: ¹H NMR (300 MHz, DMSO-d₆) δ 8.84 (d, J=7.5 Hz, 1H), 7.51-7.39 (m, 4H), 7.38-7.25 (m, 5H), 6.52 (s, 1H), 5.98-5.28 (m, 1H), 4.34-4.25 (m, 1H), 4.21 (s, 2H), 3.29 (s, 3H), 2.91-2.83 (m, 1H), 2.42-2.32 (m, 1H). LC-MS (Method D): m/z=394.1 [M+H]⁺, 2.164 min.

Example 3: (S)-5-benzyl-N-(1-methyl-5-methylene-2-oxo-2,3,4,5-tetrahydro-1H-benzo[b]azepin-3-yl)isoxazole-3-carboxamide

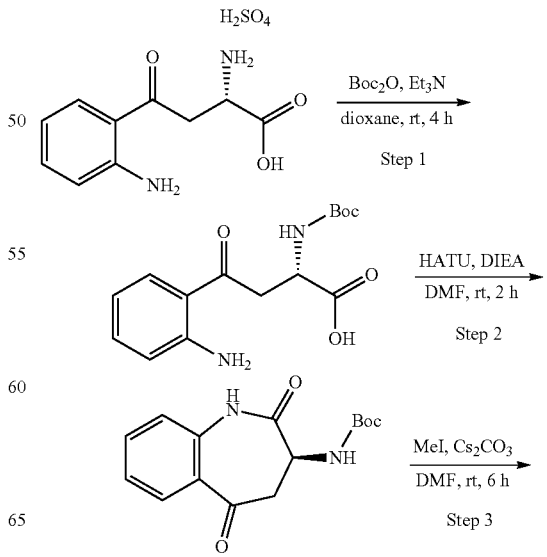

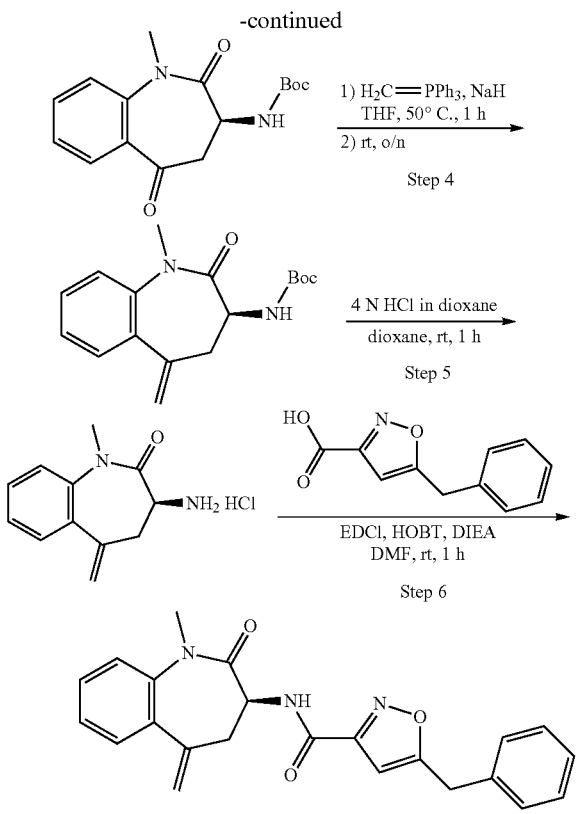

Step 1: Preparation of (2S)-4-(2-aminophenyl)-2-[[(tert-butoxy)carbonyl]amino]-4-oxobutanoic acid Di-tert-butyl dicarbonate (0.96 g, 4.39 mmol) was added to a solution of the sulphate of (2S)-2-amino-4-(2-aminophenyl)-4-oxobutanoic acid (1.22 g, 4.00 mmol) and triethylamine (1.21 g, 11.98 mmol) in dioxane (10 mL) under nitrogen atmosphere with stirring. The resulting mixture was stirred for 4 hours at room temperature. The reaction mixture was concentrated under vacuum to afford the title compound (1.22 g crude). LC-MS (Method K): m/z=309.1 [M+H]$^+$, 1.549 min.

Step 2: Preparation of tert-butyl N-[(3S)-2,5-dioxo-2,3,4,5-tetrahydro-1H-1-benzazepin-3-yl]carbamate 2-(7-Aza-1H-benzotriazole-1-yl)-1,1,3,3-tetramethyluronium hexafluorophosphate (1.82 g, 4.80 mmol) and ethyldiisopropylamine (1.55 g, 11.99 mmol) were added to a stirred solution of (2S)-4-(2-aminophenyl)-2-[[(tert-butoxy)carbonyl]amino]-4-oxobutanoic acid (1.23 g, 4.00 mmol) in N,N-dimethylformamide (10 mL). The resulting solution was stirred for 2 hours at room temperature. The reaction mixture was diluted with water (10 mL) and extracted with ethyl acetate (3×20 mL). The combined organic portions were dried over anhydrous sodium sulfate, filtered and concentrated under reduced pressure to afford the title compound (850 mg). LC-MS (Method K): m/z=291.1 [M+H]$^+$, 0.850 min.

Step 3: Preparation of tert-butyl N-[(3S)-1-methyl-2,5-dioxo-2,3,4,5-tetrahydro-1H-1-benzazepin-3-yl]carbamate Iodomethane (118 mg, 0.83 mmol) was added dropwise to a stirred mixture of tert-butyl N-[(3S)-2,5-dioxo-2,3,4,5-tetrahydro-1H-1-benzazepin-3-yl]carbamate (220.0 mg, 0.76 mmol) and cesium carbonate (272 mg, 0.83 mmol) in N,N-dimethylformamide (20 mL). The resulting mixture was stirred for 6 hours at room temperature before water (10 mL) was added to quench the reaction. The reaction mixture was extracted with ethyl acetate (3×20 mL). The combined organic layers were dried over anhydrous sodium sulfate, filtered and concentrated under vacuum. The residue was purified by column chromatography (ethyl acetate/petroleum ether, 1/4) to provide the title compound (130 mg, 56%). LC-MS (Method K): m/z=305.0 [M+H]$^+$, 0.907 min.

Step 4: Preparation of tert-butyl N-[(3S)-1-methyl-5-methylidene-2-oxo-2,3,4,5-tetrahydro-1H-1-benzazepin-3-yl]carbamate A suspension of methyltriphenylphosphonium bromide (382 mg, 1.07 mmol) and sodium hydride (20.0 mg, 0.83 mmol) in tetrahydrofuran (2 mL) was stirred for 1 h at 50° C. under nitrogen atmosphere. Then a solution of tert-butyl N-[(3S)-1-methyl-2,5-dioxo-2,3,4,5-tetrahydro-1H-1-benzazepin-3-yl]carbamate (101.0 mg, 0.33 mmol) in tetrahydrofuran (2 mL) was added drop-wise to the reaction mixture with stirring. The resulting solution was stirred overnight at room temperature. The reaction was then quenched by the addition of saturated aqueous ammonium chloride (5 mL). The resulting solution was extracted with ethyl acetate (3×10 mL) and the organic layers were combined, dried over anhydrous sodium sulfate, filtered and concentrated under vacuum. The residue was purified by column chromatography (ethyl acetate/petroleum ether, 1/10) to provide the title compound (75 mg, 75%). LC-MS (Method C): m/z=303.2 [M+H]$^+$, 1.531 min.

Step 5: Preparation of (S)-3-amino-1-methyl-5-methylene-4,5-dihydro-1H-benzo[b]azepin-2(3H)-one hydrochloride A solution of tert-butyl N-[(3S)-1-methyl-5-methylidene-2-oxo-2,3,4,5-tetrahydro-1H-1-benzazepin-3-yl]carbamate (40.0 mg, 0.13 mmol) in hydrogen chloride in dioxane (4 N, 6 mL) was stirred for 1 hour at room temperature. The reaction mixture was concentrated under vacuum to afford the title compound (25.2 mg crude). LC-MS (Method C): m/z=203.2 [M+H]$^+$, 0.635 min.

Amide Coupling Procedure C

Step 6: Preparation of (S)-5-benzyl-N-(1-methyl-5-methylene-2-oxo-2,3,4,5-tetrahydro-1H-benzo[b]azepin-3-yl)isoxazole-3-carboxamide A solution of (S)-3-amino-1-methyl-5-methylene-4,5-dihydro-1H-benzo[b]azepin-2(3H)-one hydrochloride (25.4 mg, 0.10 mmol) in N,N-dimethylformamide (2 mL) was added to a stirred solution of 5-benzyl-1,2-oxazole-3-carboxylic acid (20 mg, 0.10 mmol), 1-hydroxybenzotriazole (16 mg, 0.12 mmol), 1-(3-dimethylaminopropyl)-3-ethylcarbodiimide (23 mg, 0.12 mmol), ethyldiisopropylamine (39 mg, 0.30 mmol) in N,N-dimethylformamide (8 mL). The resulting solution was stirred for 1 hour at room temperature. The reaction mixture was diluted with water (5 mL) and extracted with ethyl acetate (3×10 mL). The combined organic layers were dried over anhydrous sodium sulfate, filtered and concentrated under vacuum. The crude product was purified by reverse phase chromatography using an Xbridge Phenyl OBD 5 μm, 19×150 mm column; mobile phase, water (10 mmol/L NH$_4$HCO$_3$) and ACN (50.0% ACN to 70.0% in 7 min) to afford the title compound (17.8 mg, 44%) as a white solid. This compound was further purified by chiral HPLC on a Chiralpak AS-H (25×2.0 cm), 5 µm column using a mobile phase of n-hexane/(2-propanol/MeOH 1/1+0.1% isopropylamine) 60/40% v/v to afford the title compound. $^1$H NMR (400 MHz, CDCl$_3$) δ 7.87 (d, J=6.8 Hz, 1H), 7.44-7.22 (m, 8H), 7.18 (d, J=7.8 Hz, 1H), 6.33 (s, 1H), 5.25-5.20 (m, 1H), 5.14-5.08 (m, 1H), 4.91 (td, J=6.9, 12.1 Hz, 1H), 4.13 (s, 2H), 3.55 (tdd, J=2.9, 6.5, 15.7 Hz, 1H), 3.39 (s, 3H), 2.84 (dd, J=12.0, 15.6 Hz, 1H). LC-MS (Method A): m/z=388.1 [M+H]$^+$, 1.21 min. e.e. >99.5% as determined on a Chiralpak AS-H (25×0.46 cm), 5 µm column using a mobile phase of n-hexane/(2-propanol/MeOH 1/1+0.1 isopropylamine) 60/40% v/v.

Example 4: (S)-1-benzyl-4-chloro-5-methyl-N-(5-methyl-4-oxo-2,3,4,5-tetrahydrobenzo[b][1,4]oxazepin-3-yl)-1H-pyrazole-3-carboxamide

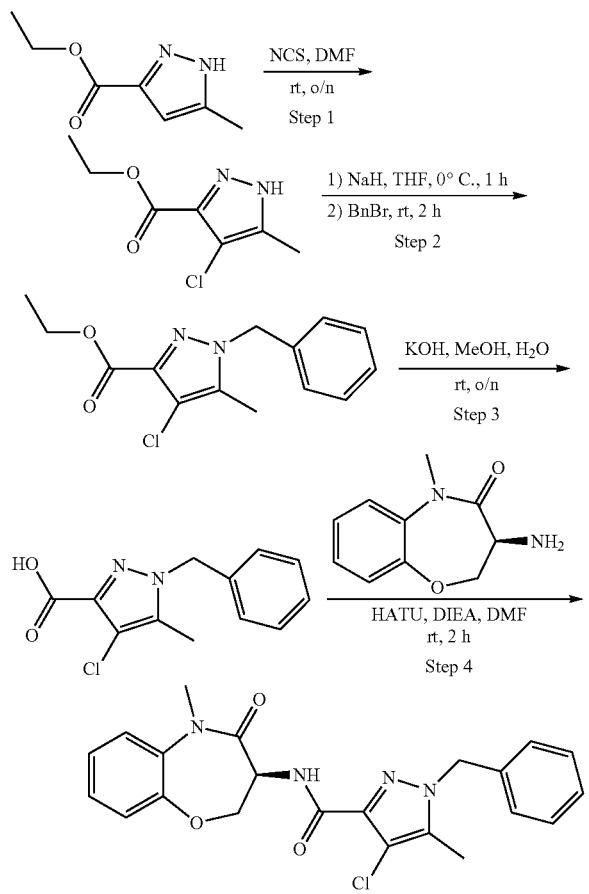

Step 1: Preparation of ethyl 4-chloro-5-methyl-1H-pyrazole-3-carboxylate

N-Chlorosuccinimide (0.81 g, 5.99 mmol) was added to a solution of ethyl 5-methyl-1H-pyrazole-3-carboxylate (1.01 g, 6.49 mmol) in N,N-dimethylformamide (5 mL). The resulting solution was stirred overnight at room temperature. The reaction mixture was diluted with water (20 mL) and extracted with ethyl acetate (3×20 mL). The combined organic layers were dried over anhydrous sodium sulfate, filtered and concentrated under vacuum. The residue was purified by column chromatography (ethyl acetate/petroleum ether, 1/5) to afford the title compound (0.81 g, 65%). LC-MS (Method C): m/z=230.1 [M+CH$_3$CN+H]$^+$, 1.240 min.

Step 2: Preparation of ethyl 1-benzyl-4-chloro-5-methyl-1H-pyrazole-3-carboxylate Sodium hydride (108 mg, 4.50 mmol) was added to a solution of ethyl 4-chloro-5-methyl-1H-pyrazole-3-carboxylate (600 mg, 3.18 mmol) in tetrahydrofuran (3 mL). After stirring for 1 h at 0° C., benzyl bromide (550 mg, 3.22 mmol) was added. The resulting mixture was stirred for 2 hours at room temperature. After quenching with water (3 mL), the reaction mixture was extracted with ethyl acetate (2×3 mL). The combined organic layers were dried over anhydrous sodium sulfate, filtered and concentrated under vacuum. The residue was purified by column chromatography (ethyl acetate/petroleum ether, 1/1) to afford the title compound (500 mg, 56%). LC-MS (Method E): m/z=278.9 [M+H]$^+$, 0.986 min.

Step 3: Preparation of 1-benzyl-4-chloro-5-methyl-1H-pyrazole-3-carboxylic acid

Potassium hydroxide (80 mg, 1.43 mmol) was added to a solution of ethyl 1-benzyl-4-chloro-5-methyl-1H-pyrazole-3-carboxylate (120 mg, 0.43 mmol) in methanol (1.5 mL) and water (0.5 mL). The resulting solution was stirred overnight at room temperature. The reaction mixture was concentrated under vacuum and diluted with water (5 mL). 3 N Hydrochloride acid was added to adjust the pH to 3. The resulting solid was collected by filtration to afford the title compound (110 mg). LC-MS (Method F): m/z=251.0 [M+H]$^+$, 1.323 min.

Step 4: Preparation of (S)-1-benzyl-4-chloro-5-methyl-N-(5-methyl-4-oxo-2,3,4,5-tetrahydrobenzo[b][1,4]oxazepin-3-yl)-1H-pyrazole-3-carboxamide The crude material obtained using Amide Coupling Procedure B was purified by reverse phase chromatography using an Xbridge Prep C18 5 µm, 19×150 mm column; Mobile phase: Phase A: aqueous ammonium bicarbonate (0.05%); Phase B: acetonitrile; (20% to 80% in 12 min) to afford the title compound. $^1$H-NMR (400 MHz, DMSO-d$_6$) δ 8.18 (d, J=7.9 Hz, 1H), 7.50 (dd, J=7.6, 1.9 Hz, 1H), 7.43-7.14 (m, 8H), 5.46 (s, 2H), 4.83 (dt, J=11.5, 7.8 Hz, 1H), 4.56 (dd, J=11.5, 9.8 Hz, 1H), 4.42 (dd, J=9.8, 7.7 Hz, 1H), 3.32 (s, 3H), 2.20 (s, 3H). LC-MS (Method E): m/z=425.0 [M+H]$^+$, 1.488 min.

Example 5: (S)-5-benzyl-N-(5-methyl-4-oxo-2,3,4,5-tetrahydrobenzo[b][1,4]oxazepin-3-yl)thiazole-2-carboxamide

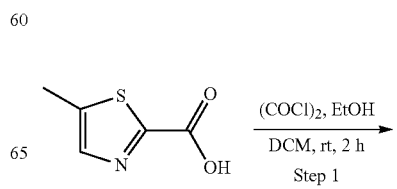

Step 1

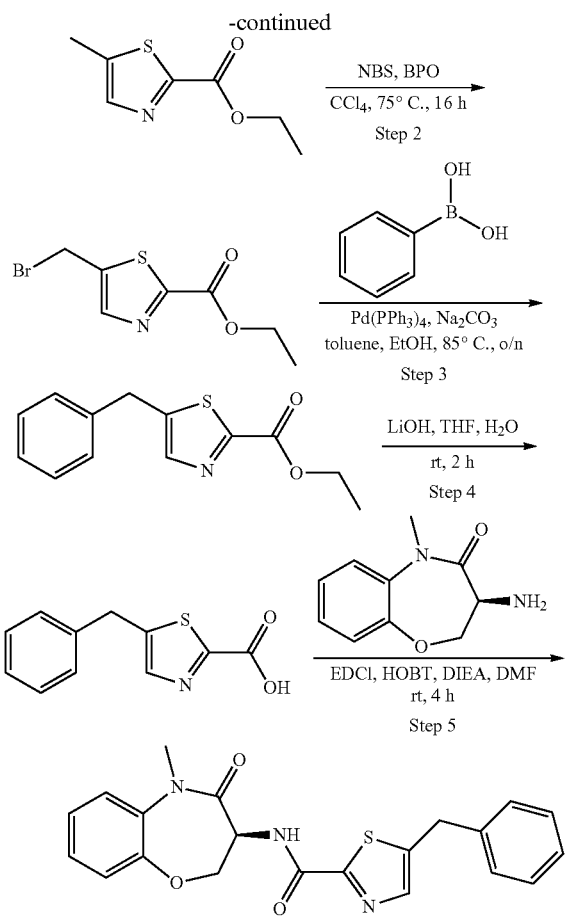

Step 1: Preparation of ethyl 5-methylthiazole-2-carboxylate

Oxalyl chloride (5 mL, 50.0 mmol) was added to a stirring solution of 5-methylthiazole-2-carboxylic acid (1.43 g, 10.0 mmol) in dichloromethane (10 mL). The resulting solution was stirred for 2 hours at room temperature and concentrated under vacuum. The residue was quenched by the addition of ethanol (50 mL) and concentrated under vacuum. The residue was diluted with water (20 mL), and extracted with ethyl acetate (3×20 mL). The combined organic layers were dried over anhydrous sodium sulfate, filtered and concentrated under vacuum to afford the title compound (1.6 g, 90%) as a white solid. LC-MS (Method E): m/z=172 [M+H]+, 0.607 min.

Step 2: Preparation of ethyl 5-(bromomethyl)thiazole-2-carboxylate

N-Bromosuccinimide (900 mg, 5.0 mmol) was added to a solution of ethyl 5-methylthiazole-2-carboxylate (850 mg, 5.0 mmol) in carbon tetrachloride (20 mL). The reaction was initiated by benzoyl peroxide (1 mg) and then heated at 75° C. and stirred for 16 hours. The reaction mixture was cooled to 0° C. and the solid was removed by filtration. The filtrate was diluted with water (20 mL) and then extracted with ethyl acetate (3×20 mL). The combined organic layers were washed with saturated aqueous sodium carbonate and brine, dried over sodium sulfate, filtered and concentrated under vacuum. The residue was purified by column chromatography (ethyl acetate/hexane, 1/20) to afford the title compound (1.0 g, 80%). LC-MS (Method F): m/z=250, 252 [M+H]+, 1.490 min.

Step 3: Preparation of ethyl 5-benzylthiazole-2-carboxylate

A 50-mL round-bottomed flask was charged with ethyl 5-(bromomethyl)thiazole-2-carboxylate (300 mg, 1.38 mmol), toluene (10 mL), ethanol (5 mL), phenylboronic acid (100 mg, 2.00 mmol) and sodium carbonate (372 mg, 5.52 mmol). The reaction mixture was placed under a nitrogen atmosphere and tetrakis(triphenylphosphine)palladium (147 mg, 0.13 mmol) was added. The resulting solution was stirred at 85° C. overnight under nitrogen atmosphere and was then quenched by the addition of water (20 mL). The resulting solution was extracted with ethyl acetate (3×40 mL). The combined organic layers were washed with saturated aqueous sodium carbonate and brine, dried over anhydrous sodium sulfate, filtered and concentrated under vacuum. The residue was purified by column chromatography (ethyl acetate/hexane, 1/15) to afford the title compound (250 mg, 56%). LC-MS (Method C): m/z=248 [M+H]+, 1.971 min.

Step 4: Preparation of 5-benzylthiazole-2-carboxylic acid

A solution of lithium hydroxide (5.4 mg, 2.02 mmol) in water (3 mL) was added to a solution of ethyl 5-benzylthiazole-2-carboxylate (100 mg, 0.405 mmol) in tetrahydrofuran (9 mL). The resulting solution was stirred for 2 hours at room temperature and diluted with water (10 mL). The pH value of the solution was adjusted to 3-4 with 1N aqueous hydrogen chloride. The resulting solution was extracted with ethyl acetate (3×20 mL) and the combined organic layers were dried over anhydrous sodium sulfate, filtered and concentrated under vacuum to afford the title compound (80 mg, 76%). LC-MS (Method F): m/z=220 [M+H]+, 0.790 min.

Step 5: Preparation of (S)-5-benzyl-N-(5-methyl-4-oxo-2,3,4,5-tetrahydrobenzo[b][1,4]oxazepin-3-yl)thiazole-2-carboxamide The crude material obtained using Amide Coupling Procedure C was purified by reverse phase chromatography using an Xbridge Prep C18 5 μm, 19×150 mm column; Mobile phase: Phase A: aqueous ammonium bicarbonate (0.05%); Phase B: acetonitrile; (20% to 80% in 12 min) to afford the title compound. 1H NMR (300 MHz, Chloroform-d) δ 8.12 (d, J=7.3 Hz, 1H), 7.62 (s, 1H), 7.41-7.16 (m, 9H), 5.12-4.95 (m, 1H), 4.81-4.69 (m, 1H), 4.37-4.21 (m, 1H), 4.19 (s, 2H), 3.46 (s, 3H). LC-MS (Method D): m/z=394 [M+H]+, 2.232 min.

Example 6: (S)-1-benzyl-4-fluoro-5-methyl-N-(5-methyl-4-oxo-2,3,4,5-tetrahydrobenzo[b][1,4]oxazepin-3-yl)-1H-pyrazole-3-carboxamide

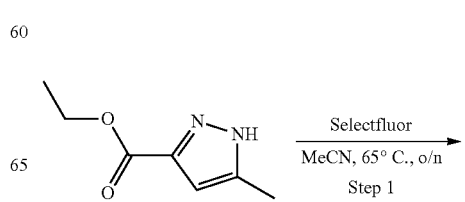

Step 1

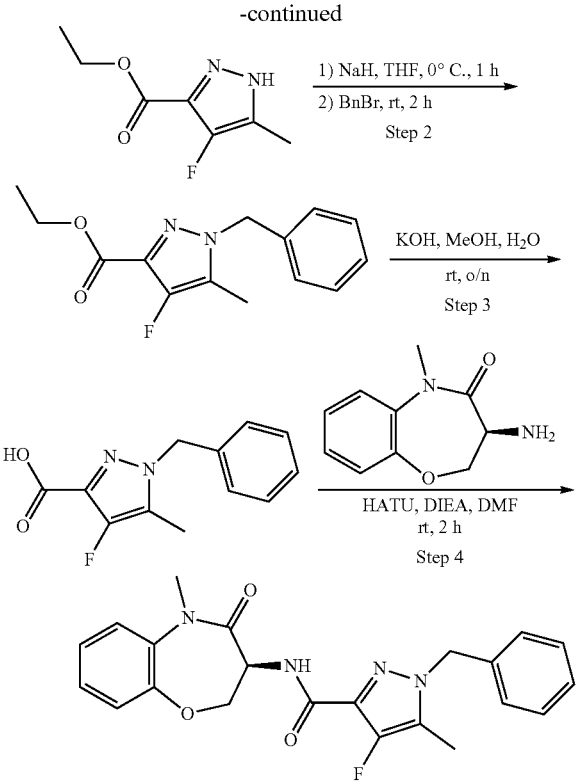

Step 1: Preparation of ethyl 4-fluoro-5-methyl-1H-pyrazole-3-carboxylate

Selectfluor (3.5 g, 9.9 mmol) was added to a solution of ethyl 5-methyl-1H-pyrazole-3-carboxylate (1.01 g, 6.49 mmol) in acetonitrile (10 mL). The resulting solution was stirred overnight at 65° C. in an oil bath. The reaction mixture was cooled to room temperature and concentrated under vacuum. The residue was diluted with water (10 mL) and extracted with ethyl acetate (2×10 mL). The combined organic layers were dried over sodium sulfate, filtered and concentrated under vacuum. The residue was purified by column chromatography (ethyl acetate/petroleum ether, 1/1) to afford the title compound (660 mg, 59%). LC-MS (Method E): m/z=172.9 [M+H]$^+$, 0.607 min.

Step 2: Preparation of ethyl 1-benzyl-4-fluoro-5-methyl-1H-pyrazole-3-carboxylate Sodium hydride (118 mg, 4.92 mmol) was added to a solution of ethyl 4-fluoro-5-methyl-1H-pyrazole-3-carboxylate (600 mg, 3.49 mmol) in tetrahydrofuran (3 mL). After stirring for 1 hour at 0° C., benzyl bromide (595 mg, 3.48 mmol) was added. The resulting mixture was stirred for 2 hours at room temperature. The reaction mixture was then quenched with water (20 mL) and extracted with ethyl acetate (2×20 mL). The combined organic layers were dried over anhydrous sodium sulfate, filtered and concentrated under vacuum. The residue was purified by column chromatography (ethyl acetate/petroleum ether, 1/1) to afford the title compound (240 mg, 26%). LC-MS (Method C): m/z=263.1 [M+H]$^+$, 1.490 min.

Step 3: Preparation of 1-benzyl-4-fluoro-5-methyl-1H-pyrazole-3-carboxylic acid Potassium hydroxide (80 mg, 1.43 mmol) was added to a solution of ethyl 1-benzyl-4-fluoro-5-methyl-1H-pyrazole-3-carboxylate (113 mg, 0.43 mmol) in methanol (1.5 mL), and water (0.5 mL). The resulting solution was stirred 2 hours at room temperature. The resulting mixture was concentrated under vacuum and the residue was diluted with water (1.5 mL). Hydrochloric acid (3N) was added to adjust the pH to 3. The resulting solid was collected by filtration to afford the title compound (110 mg). LC-MS (Method E): m/z=235.1 [M+H]$^+$, 1.257 min.

Step 4: Preparation of (S)-1-benzyl-4-fluoro-5-methyl-N-(5-methyl-4-oxo-2,3,4,5-tetrahydrobenzo[b][1,4]oxazepin-3-yl)-1H-pyrazole-3-carboxamide The crude material obtained using Amide Coupling Procedure B was purified by reverse phase chromatography using an Xbridge Prep C18 5 μm 19×150 mm column; Mobile phase: Phase A: aqueous ammonium bicarbonate (0.05%); Phase B: acetonitrile; (20% to 80% in 12 min) to afford the title compound. $^1$H-NMR (400 MHz, DMSO-d$_6$) δ 8.10 (d, J=8.0 Hz, 1H), 7.50 (dd, J=7.6, 2.0 Hz, 1H), 7.43-7.20 (m, 6H), 7.20-7.13 (m, 2H), 5.39 (s, 2H), 4.83 (dt, J=11.4, 7.8 Hz, 1H), 4.56 (dd, J=11.5, 9.8 Hz, 1H), 4.42 (dd, J=9.8, 7.7 Hz, 1H), 3.32 (s, 3H), 2.16 (d, J=1.4 Hz, 3H). LC-MS (Method F): m/z=409.1 [M+H]$^+$, 1.412 min.

Example 7: 5-benzyl-N-((2S)-4-methyl-3-oxo-1,1a,2,3,4,8b-hexahydrobenzo[b]cyclopropa[d]azepin-2-yl)isoxazole-3-carboxamide

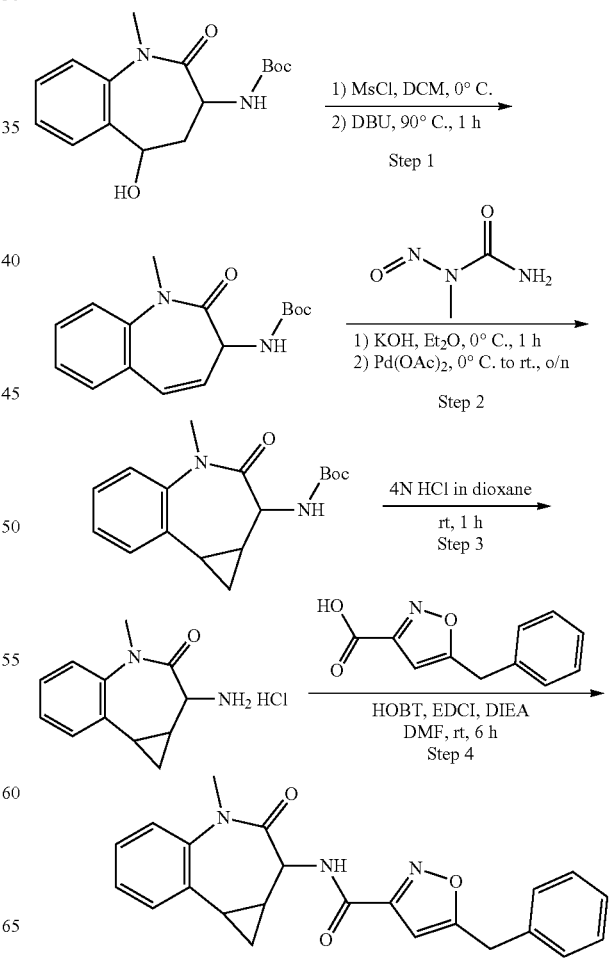

Step 1: Preparation of (Z)-tert-butyl (1-methyl-2-oxo-2,3-dihydro-1H-benzo[b]azepin-3-yl)carbamate To a solution of tert-butyl (5-hydroxy-1-methyl-2-oxo-2,3,4,5-tetrahydro-1H-benzo[b]azepin-3-yl)carbamate (918.0 mg, 3.00 mmol) and triethylamine (909.0 mg, 9.00 mmol) in dichloromethane (20 mL) was added dropwise a solution of methanesulfonyl chloride (687 mg, 6.00 mmol) in dichloromethane (2 mL) at 0° C. After stirring overnight at room temperature, the reaction mixture was quenched by the addition of water (10 mL) and extracted with ethyl acetate (3×20 mL). The combined organic layers were dried over anhydrous sodium sulfate and concentrated under vacuum. 1,8-Diazabicyclo[5.4.0]undec-7-ene was added to the crude solid with stirring. The resulting solution was stirred for 1 hour at 90° C. Water (20 mL) was added to quench the reaction. The reaction mixture was extracted with ethyl acetate (3×40 mL). The combined organic layers were dried over anhydrous sodium sulfate, filtered and concentrated under vacuum to afford the title compound (0.3 g crude). LC-MS (Method C): m/z=289.0 [M+H]$^+$, 1.494 min.

Step 2: Preparation of tert-butyl N-[7-methyl-6-oxo-7-azatricyclo[6.4.0.0-[2,4]]dodeca-1(8),9,11-trien-5-yl]carbamate A solution of 1-methyl-1-nitrosourea (1.073 g, 10.41 mmol) in ether (10 mL) was added to a solution of potassium hydroxide (1.166 g, 20.78 mmol) in water (1.75 mL) dropwise with stirring at 0° C. After stirring for 1 hour at 0° C., the organic phase was separated to provide a solution of diazomethane (10 mL). To a solution of (Z)-tert-butyl (1-methyl-2-oxo-2,3-dihydro-1H-benzo[b]azepin-3-yl)carbamate (300.0 mg, 1.04 mmol) in tetrahydrofuran (4 mL) was added the solution of diazomethane (10 ml) with stirring at 0° C. To this mixture was added a solution of palladium diacetate (23.3 mg, 0.10 mmol) in tetrahydrofuran (1 mL) dropwise with stirring at 0° C. The resulting mixture was stirred overnight at room temperature. The solids were removed by filtration and the filtrate was concentrated under vacuum. The residue was purified by column chromatography (ethyl acetate/petroleum ether, 1/5) to afford the title compound (50 mg, 16%). LC-MS (Method N): m/z=303.1 [M+H]$^+$, 1.043 min.

Step 3: Preparation of 5-amino-7-methyl-7-azatricyclo[6.4.0.0-[2,4]]dodeca-1(8),9,11-trien-6-one hydrochloride A solution of tert-butyl N-[7-methyl-6-oxo-7-azatricyclo[6.4.0.0-[2,4]]dodeca-1(8),9,11-trien-5-yl]carbamate (151.0 mg, 0.50 mmol) was treated with 4N hydrogen chloride in dioxane (10 mL) for 1 hour at room temperature. The reaction mixture was concentrated under vacuum to provide the title compound (50 mg crude). LC-MS (Method C): m/z=203.1 [M+H]$^+$, 1.043 min.

Step 4: Preparation of 5-benzyl-N-((2S)-4-methyl-3-oxo-1,1a,2,3,4,8b-hexahydrobenzo[b]cyclopropa[d]azepin-2-yl)isoxazole-3-carboxamide The crude product obtained using Amide Coupling Procedure C was purified by reverse phase chromatography using an Xbridge Phenyl OBD 5 µm, 19×150 mm column; mobile phase, water (10 mmol/L NH$_4$HCO$_3$) and ACN (50.0% ACN to 70.0% in 7 min) to afford the title compound. $^1$H NMR (300 MHz, DMSO-d$_6$) δ 8.82 (d, J=7.5 Hz, 1H), 7.47 (d, J=7.5 Hz, 1H), 7.39-7.20 (m, 8H), 6.60 (s, 1H), 4.45 (d, J=7.5 Hz, 1H), 4.22 (s, 2H), 3.22 (s, 3H), 2.30-2.21 (m, 1H), 1.92-1.84 (m, 1H), 1.08-1.01 (m, 2H). LC-MS (Method H): m/z=388.1 [M+H]$^+$, 1.700 min.

This mixture was resolved by chiral HPLC on a Chiralpak IB (25×2.0 cm), 5 µm column using a mobile phase of n-hexane/(ethanol/methanol/dichloromethane 45/45/10+0.1% isopropylamine) 60/40% v/v with a flow rate of 18 mL/min to afford the two separated enantiomers.

First eluting enantiomer (6.3 min), Enantiomer 1: $^1$H NMR (400 MHz, CDCl$_3$) δ 8.13 (d, J=7.0 Hz, 1H), 7.40-7.16 (m, 8H), 7.10 (dd, J=7.8, 1.4 Hz, 1H), 6.35 (s, 1H), 4.76 (d, J=7.2 Hz, 1H), 4.12 (s, 2H), 3.35 (s, 3H), 2.17-2.08 (m, 1H), 2.02 (td, J=8.7, 4.9 Hz, 1H), 1.22 (q, J=5.3 Hz, 1H), 1.05 (td, J=8.5, 6.5 Hz, 1H). LC-MS (Method A): m/z=388.3 [M+H]$^+$, 1.17 min. e.e.>99.9% as determined on a Chiralpak IB (25×0.46 cm), 5 µm column using a mobile phase of n-hexane/(ethanol/methanol/dichloromethane 45/45/10+0.1% isopropylamine) 60/40% v/v with a flow rate of 1 mL/min.

Second eluting enantiomer (7.9 min), Enantiomer 2: $^1$H NMR (400 MHz, CDCl$_3$) δ 8.14 (d, J=7.3 Hz, 1H), 7.41-7.17 (m, 8H), 7.12 (dd, J=7.7, 1.6 Hz, 1H), 6.37 (s, 1H), 4.78 (d, J=7.0 Hz, 1H), 4.14 (s, 2H), 3.36 (s, 3H), 2.14 (td, J=9.2, 5.4 Hz, 1H), 2.03 (td, J=8.7, 5.0 Hz, 1H), 1.23 (q, J=5.3 Hz, 1H), 1.07 (td, J=8.5, 6.3 Hz, 1H). LC-MS (Method A): m/z=388.3 [M+H]$^+$, 1.17 min. e.e.>99.9% as determined on a Chiralpak IB (25×0.46 cm), 5 µm column using a mobile phase of n-hexane/(ethanol/methanol/dichloromethane 45/45/10+0.1% isopropylamine) 60/40% v/v with a flow rate of 1 mL/min.

Example 8: (S)—N-(5-methyl-4-oxo-2,3,4,5-tetrahydrobenzo[b][1,4]oxazepin-3-yl)-5-(1-phenylcyclopropyl)isoxazole-3-carboxamide

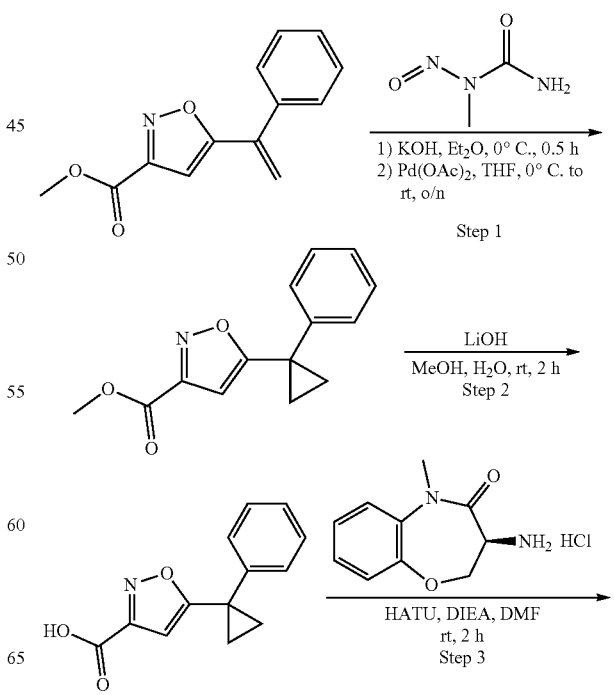

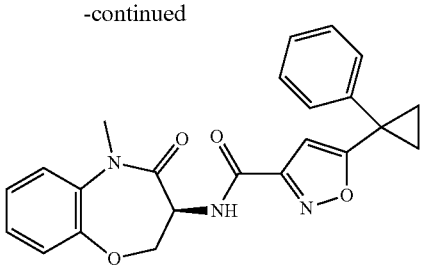

Step 1: Preparation of methyl 5-(1-phenylcyclopropyl)-1,2-oxazole-3-carboxylate A solution of 1-methyl-1-nitrosourea (449.8 mg, 4.36 mmol) in ether (10 mL) was added dropwise to a solution of potassium hydroxide (359.1 mg, 6.40 mmol) in water (0.54 mL) with stirring at 0° C. After stirring for 0.5 hour at 0° C., the organic phase was separated to provide a solution of diazomethane (10 mL). To a solution of ethyl 5-(1-phenylethenyl)-1,2-oxazole-3-carboxylate (50.0 mg, 0.21 mmol) in tetrahydrofuran (3 mL) was added the solution of diazomethane (10 mL) with stirring at 0° C. followed by the addition of a solution of palladium diacetate (4.7 mg, 0.02 mmol) in tetrahydrofuran (1 mL) dropwise with stirring at 0° C. The resulting solution was stirred overnight at room temperature. The solids were removed by filtration and the filtrate was concentrated under vacuum. The residue was purified by column chromatography (ethyl acetate/petroleum ether, 1/5) to afford the title compound (30 mg, 57%) as a yellow solid. LC-MS (Method C): m/z=244.0 [M+H]+, 1.519 min.

Step 2: Preparation of 5-(1-phenylcyclopropyl)-1,2-oxazole-3-carboxylic acid A solution of methyl 5-(1-phenylcyclopropyl)-1,2-oxazole-3-carboxylate (25.0 mg, 0.10 mmol) and lithium hydroxide (4.8 mg, 0.20 mmol) in methanol/water=3/1 (2 mL) was stirred for 2 hours at room temperature. The pH value of the solution was adjusted to 6-7 with 1N hydrochloric acid. The resulting solution was extracted with ethyl acetate (3×10 mL) and the combined organic layers were dried over anhydrous sodium sulfate, filtered and concentrated under vacuum to afford the title compound (20 mg crude). LC-MS (Method G): m/z=230 [M+H]+, 0.700 min.

Step 3: Preparation of (S)—N-(5-methyl-4-oxo-2,3,4,5-tetrahydrobenzo[b][1,4]oxazepin-3-yl)-5-(1-phenylcyclopropyl)isoxazole-3-carboxamide The crude product obtained using Amide Coupling Procedure B was purified by reverse phase chromatography using an Xbridge Phenyl OBD 5 μm, 19×150 mm column; mobile phase, water (10 mmol/L NH$_4$HCO$_3$) and ACN (50.0% ACN to 70.0% in 7 min) to afford the title compound. $^1$H NMR (300 MHz, DMSO-d$_6$) δ 8.82 (d, J=8.1 Hz, 1H), 7.52-7.48 (m, 1H), 7.38-7.25 (m, 7H), 7.24-7.20 (m, 1H), 6.36 (s, 1H), 4.87-4.77 (m, 1H), 4.55 (dd, J=9.9, 11.7 Hz, 1H), 4.38 (dd, J=8.1, 9.9 Hz, 1H), 3.30 (s, 3H), 1.57-1.52 (m, 2H), 1.45-1.41 (m, 2H). LC-MS (Method H): m/z=404.2 [M+H]+, 1.766 min.

Example 9: (S)-5-benzyl-N-(1-methyl-2-oxo-1,2,3,4-tetrahydrospiro[benzo[b]azepine-5,1'-cyclopropan]-3-yl)isoxazole-3-carboxamide

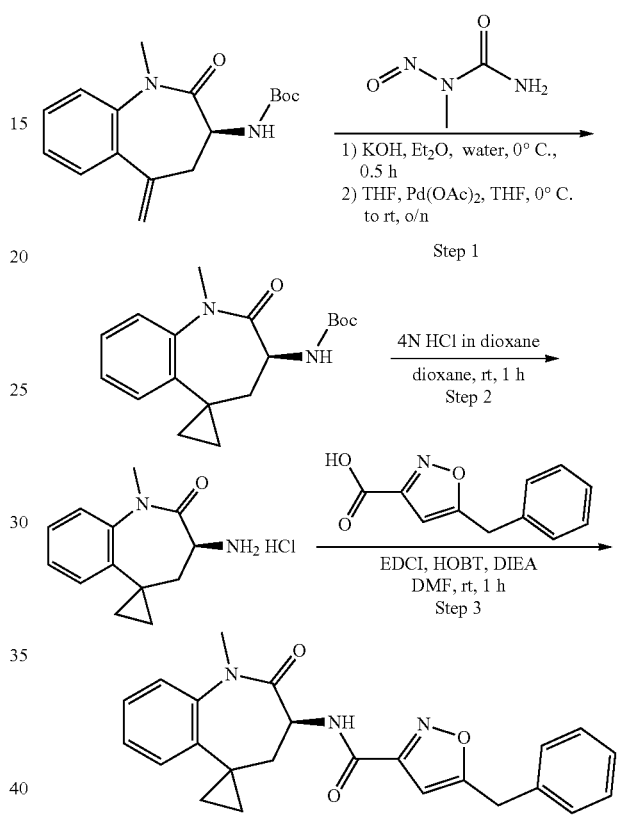

Step 1: Preparation of tert-butyl N-[(3S)-1-methyl-2-oxo-1,2,3,4-tetrahydrospiro[1-benzazepine-5,1-cyclopropane]-3-yl]carbamate A solution of 1-methyl-1-nitrosourea (255.8 mg, 2.48 mmol) in ether (10 mL) was added dropwise to a solution of potassium hydroxide (278 mg, 4.96 mmol) in water (0.4 mL) with stirring at 0° C. After stirring for 0.5 hour at 0° C., the organic phase was separated to provide a solution of diazomethane (10 mL). To a solution of tert-butyl N-[(3R)-1-methyl-2-oxo-2,3-dihydro-1H-1-benzazepin-3-yl]carbamate (75.0 mg, 0.25 mmol) in tetrahydrofuran (1.5 mL) was added the solution of diazomethane (10 mL) dropwise followed by the addition of a solution of palladium diacetate (5.5 mg, 0.02 mmol) in tetrahydrofuran (0.5 mL) dropwise with stirring at 0° C. The resulting solution was stirred overnight at room temperature. The solids were removed by filtration and the filtrate was concentrated under vacuum. The residue was purified by column chromatography (ethyl acetate/petroleum ether, 1/5) to afford the title compound (55 mg, 70%). LC-MS (Method C): m/z=317.2 [M+H]+, 1.531 min.

Step 2: Preparation of (3S)-3-amino-1-methyl-1,2,3,4-tetrahydrospiro[1-benzazepine-5,1-cyclopropane]-2-one hydrochloride tert-Butyl N-[(3S)-1-methyl-2-oxo-1,2,3,4-tetrahydrospiro[1-benzazepine-5,1-cyclopropane]-3-yl]carbamate (40.0 mg, 0.13 mmol) was treated with 4N hydrogen chloride in dioxane (6 mL) for 1 hour at room temperature. The resulting mixture was concentrated under vacuum to afford the title compound (25.2 mg) as a yellow solid. LC-MS (Method K): m/z=217.2 [M+H]$^+$, 0.635 min.

Step 3: Preparation of (S)-5-benzyl-N-(1-methyl-2-oxo-1,2,3,4-tetrahydrospiro[benzo[b]azepine-5,1'-cyclopropan]-3-yl)isoxazole-3-carboxamide The crude product obtained using Amide Coupling Procedure C was purified by reverse phase chromatography using an Xbridge Phenyl OBD 5 μm, 19×150 mm column; mobile phase, water (10 mmol/L NH$_4$HCO$_3$) and ACN (50% to 70% in 7 min) to afford the title compound (17.8 mg, 44%) as a white solid. This compound was further purified by chiral HPLC on a Chiralpak AS-H (25×2.0 cm), 5 μm column using a mobile phase of n-hexane/(2-propanol/MeOH 1/1+0.1% isopropylamine) 60/40% v/v to afford the title compound. $^1$H NMR (400 MHz, CDCl$_3$) δ 7.78 (d, J=7.0 Hz, 1H), 7.39-7.19 (m, 9H), 6.31 (s, 1H), 4.69 (td, J=7.6, 10.9 Hz, 1H), 4.11 (s, 2H), 3.43 (s, 3H), 3.13 (dd, J=12.3, 8.3 Hz, 1H), 1.33 (dd, J=12.5, 11.0 Hz, 1H), 1.16-1.08 (m, 1H), 0.88 (ddd, J=9.3, 5.5, 4.3 Hz, 1H), 0.71 (td, J=5.5, 9.3 Hz, 1H), 0.51-0.42 (m, 1H). LC-MS (Method A): m/z=402.2 [M+H]$^+$, 1.21 min. e.e. >99.5% as determined on a Chiralpak AS-H (25×0.46 cm), 5 μm column using a mobile phase of n-hexane/(2-propanol/MeOH 1/1+0.1% isopropylamine) 60/40% v/v.

Example 10: 5-benzyl-N-(5,5-difluoro-1-methyl-2-oxo-2,3,4,5-tetrahydro-1H-benzo[b]azepin-3-yl)-4H-1,2,4-triazole-3-carboxamide

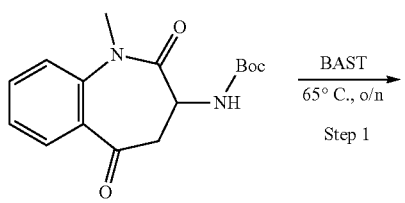

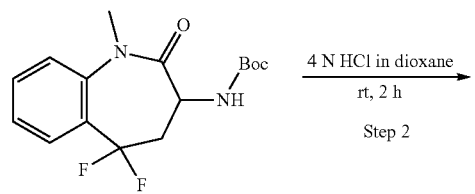

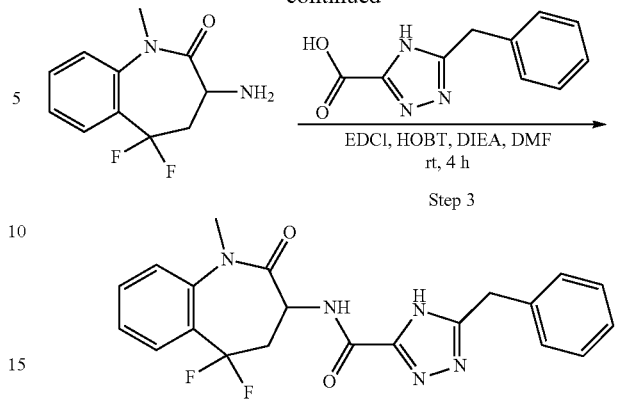

Step 1: Preparation of tert-butyl(5,5-difluoro-1-methyl-2-oxo-2,3,4,5-tetrahydro-1H-1-benzazepin-3-yl)carbamate A solution of tert-butyl (1-methyl-2,5-dioxo-2,3,4,5-tetrahydro-1H-benzo[b]azepin-3-yl)carbamate (200 mg, 0.658 mmol) in bis(2-methoxyethyl)aminosulfur trifluoride (6 mL) was heated to 65° C. and stirred overnight. The reaction mixture was allowed to cool to ambient temperature, quenched with water (30 mL) and extracted with ethyl acetate (3×40 mL). The combined organic layers were washed with saturated aqueous sodium carbonate and brine, dried over anhydrous sodium sulfate and concentrated under vacuum. The residue was purified by column chromatography (ethyl acetate/hexane, 1/20) to afford the title compound (60 mg, 30%). LC-MS (Method E): m/z=327 [M+H]$^+$, 1.035 min.

Step 2: Preparation of 3-amino-5,5-difluoro-1-methyl-4,5-dihydro-1H-benzo[b]azepin-2(3H)-one tert-Butyl (5,5-difluoro-1-methyl-2-oxo-2,3,4,5-tetrahydro-1H-benzo[b]azepin-3-yl)carbamate (40 mg, 0.184 mmol) was added to a solution of (4N) hydrogen chloride in 1,4-dioxane (30 mL). The resulting solution was stirred for 2 hours at ambient temperature and concentrated under vacuum to afford the title compound (50 mg crude) as a yellow solid. LC-MS (Method N): m/z=227 [M+H]$^+$, 0.995 min.

Step 3: Preparation of 5-benzyl-N-(5,5-difluoro-1-methyl-2-oxo-2,3,4,5-tetrahydro-1H-benzo[b]azepin-3-yl)-4H-1,2,4-triazole-3-carboxamide The crude product obtained using Amide Coupling Procedure C was purified by reverse phase chromatography using an Xbridge Prep C18 5 μm, 19×150 mm column; Mobile phase: Phase A: aqueous ammonium bicarbonate (0.05%); Phase B: acetonitrile; (20% to 80% in 12 min) to afford the title compound. $^1$H NMR (400 MHz, DMSO-d$_6$) δ 14.25 (s, 1H), 8.59 (s, 1H), 7.63 (m 3H), 7.44 (t, J=7.5 Hz, 1H), 7.35-7.18 (m, 5H), 4.52 (dt, J=11.8, 7.8 Hz, 1H), 4.10 (s, 2H), 3.26 (s, 3H), 3.15-2.81 (m, 2H). LC-MS (Method L): m/z=412.1 [M+H]$^+$, 1.309 min.

287

Example 11 and 12: 5-benzyl-N-((3S,5R)-5-fluoro-1-methyl-2-oxo-2,3,4,5-tetrahydro-1H-benzo[b]azepin-3-yl)-4H-1,2,4-triazole-3-carboxamide and 5-benzyl-N-((3R,5S)-5-fluoro-1-methyl-2-oxo-2,3,4,5-tetrahydro-1H-benzo[b]azepin-3-yl)-4H-1,2,4-triazole-3-carboxamide (Example 11) and 5-benzyl-N-((3S,5S)-5-fluoro-1-methyl-2-oxo-2,3,4,5-tetrahydro-1H-benzo[b]azepin-3-yl)-4H-1,2,4-triazole-3-carboxamide and 5-benzyl-N-((3R,5R)-5-fluoro-1-methyl-2-oxo-2,3,4,5-tetrahydro-1H-benzo[b]azepin-3-yl)-4H-1,2,4-triazole-3-carboxamide (Example 12)

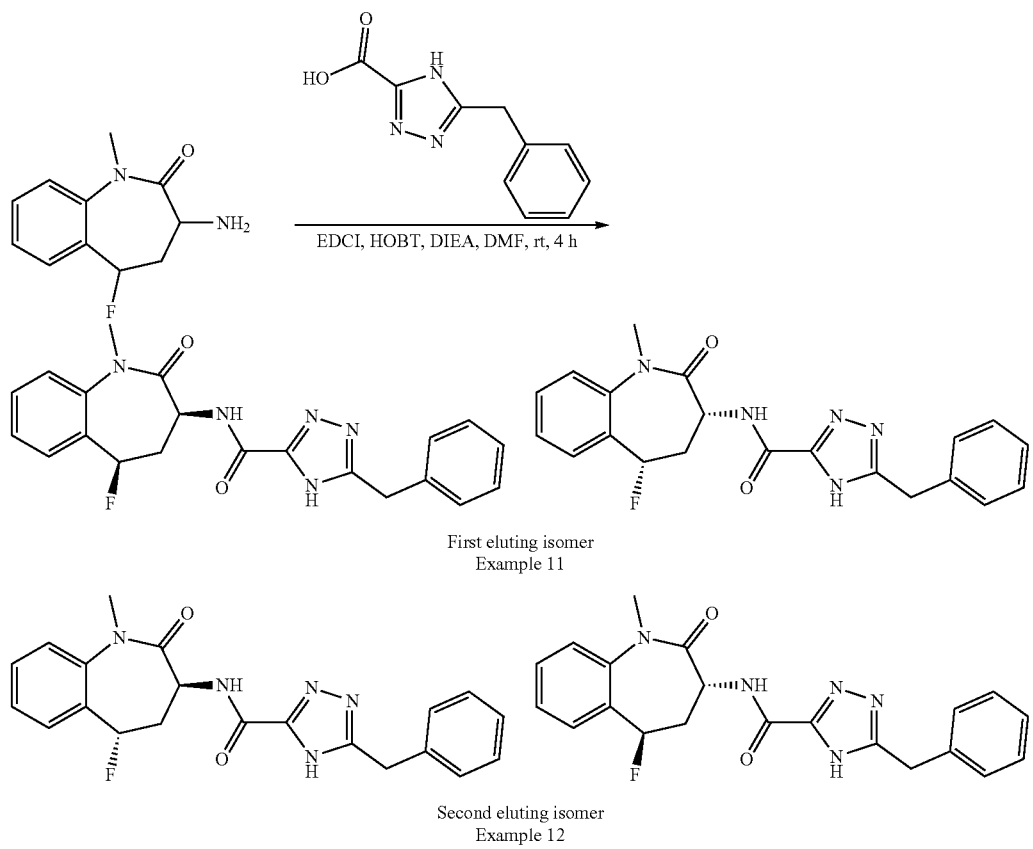

First eluting isomer
Example 11

Second eluting isomer
Example 12

The crude product obtained using Amide Coupling Procedure A was purified by reverse phase column chromatography using an Xbridge Phenyl OBD 5 μm, 19×150 mm column; mobile phase, water (10 mmol/L NH$_4$HCO$_3$) and ACN (25.0% to 55.0% in 7 min) to afford the title compounds:

Example 11, first eluting isomer: $^1$H NMR (400 MHz, DMSO-d$_6$) δ 14.41 (s, 1H), 8.41 (s, 1H), 7.65-7.49 (m, 2H), 7.45 (dt, J=7.7, 1.7 Hz, 1H), 7.40-7.20 (m, 6H), 5.76 (dd, J=47.0, 4.8 Hz, 1H), 4.47 (dt, J=11.4, 7.5 Hz, 1H), 4.12 (s, 2H), 3.27 (s, 3H), 2.94-2.56 (m, 2H). LC-MS (Method F): m/z=394.1 [M+H]$^+$, 1.085 min.

Example 12, second eluting isomer: $^1$H NMR (400 MHz, DMSO-d$_6$) δ 14.37 (s, 1H), 8.41 (s, 1H), 7.58-7.38 (m, 4H), 7.38-7.20 (m, 5H), 5.92 (ddd, J=46.6, 10.5, 8.1 Hz, 1H), 4.30 (dt, J=11.4, 7.9 Hz, 1H), 4.12 (s, 2H), 3.31 (s, 3H), 2.96-2.78 (m, 1H), 2.41-2.30 (m, 1H). LC-MS (Method F): m/z=394.1 [M+H]$^+$, 1.156 min.

288

Example 11: Chiral Separation

This mixture was resolved by chiral HPLC on a Whelk O-1 (R,R) (25×2.0 cm), 10 μm column using a mobile phase of n-hexane/(ethanol+0.1% isopropylamine) 30/70% v/v with a flow rate of 18 mL/min to afford the two separated enantiomers.

First eluting enantiomer (6.8 min), Enantiomer 1: $^1$H NMR (400 MHz, CDCl$_3$) δ 8.27 (d, J=6.8 Hz, 1H), 7.35 (m, 9H), 5.51 (m, 1H), 4.74 (dt, J=11.0, 7.1 Hz, 1H), 4.15 (s, 2H), 3.41 (s, 3H), 3.07 (m, 1H), 2.44 (m, 1H). LC-MS (Method A): m/z=394.3 [M+H]$^+$, 0.87 min. e.e.>99.9% as determined on a Whelk O-1 (R,R) (25×0.46 cm), 5 μm column using a mobile phase of n-hexane/(ethanol+0.1% isopropylamine) 30/70% v/v with a flow rate of 1 mL/min.

Second eluting enantiomer (8.9 min), Enantiomer 2: $^1$H NMR (400 MHz, CDCl$_3$) δ 8.27 (d, J=6.8 Hz, 1H), 7.35 (m, 9H), 5.51 (m, 1H), 4.74 (dt, J=11.0, 7.1 Hz, 1H), 4.15 (s, 2H), 3.41 (s, 3H), 3.07 (m, 1H), 2.44 (m, 1H). LC-MS (Method A): m/z=394.3 [M+H]$^+$, 0.86 min. e.e.>99.9% as determined on a Whelk O-1 (R,R) (25×0.46 cm), 5 μm column using a mobile phase of n-hexane/(ethanol+0.1% isopropylamine) 30/70% v/v with a flow rate of 1 mL/min.

Example 12: Chiral Separation

This mixture was resolved by chiral HPLC on a Chiralcel OJ-H (25×2.0 cm), 5 μm column using a mobile phase of n-hexane/(ethanol/methanol 1/1+0.1% isopropylamine) 30/70% v/v with a flow rate of 18 mL/min to afford the two separated enantiomers.

First eluting enantiomer (4.8 min), Enantiomer 1: $^1$H NMR (400 MHz, CDCl$_3$) δ 8.14 (d, J=6.1 Hz, 1H), 7.62-7.14 (m, 9H), 5.87-5.64 (m, 1H), 4.67-4.54 (m, 1H), 4.17 (s, 2H), 3.44 (s, 3H), 3.03-2.85 (m, 1H), 2.66-2.53 (m, 1H). LC-MS (Method U): m/z=394.2 [M+H]$^+$, 0.75 min. e.e.>99.9% as determined on a Chiralcel OJ-H (25×0.46 cm), 5 μm column using a mobile phase of n-hexane/(ethanol/methanol 1/1+0.1% isopropylamine) 50/50% v/v with a flow rate of 1 mL/min.

Second eluting enantiomer (7.0 min), Enantiomer 2: $^1$H NMR (400 MHz, CDCl$_3$) δ 8.14 (d, J=6.3 Hz, 1H), 7.62-7.15 (m, 10H), 5.86-5.63 (m, 1H), 4.66-4.53 (m, 1H), 4.12 (s, 2H), 3.42 (s, 3H), 3.00-2.82 (m, 1H), 2.64-2.52 (m, 1H). LC-MS (Method U): m/z=394.2 [M+H]$^+$, 0.74 min. e.e.>99.9% as determined on a Chiralcel OJ-H (25×0.46 cm), 5 μm column using a mobile phase of n-hexane/(ethanol/methanol 1/1+0.1% isopropylamine) 50/50% v/v with a flow rate of 1 mL/min.

Example 13: (R)—N—((S)-5-methyl-4-oxo-2,3,4,5-tetrahydrobenzo[b][1,4]oxazepin-3-yl)-4-phenyl-5,6-dihydro-4H-pyrrolo[1,2-b]pyrazole-2-carboxamide

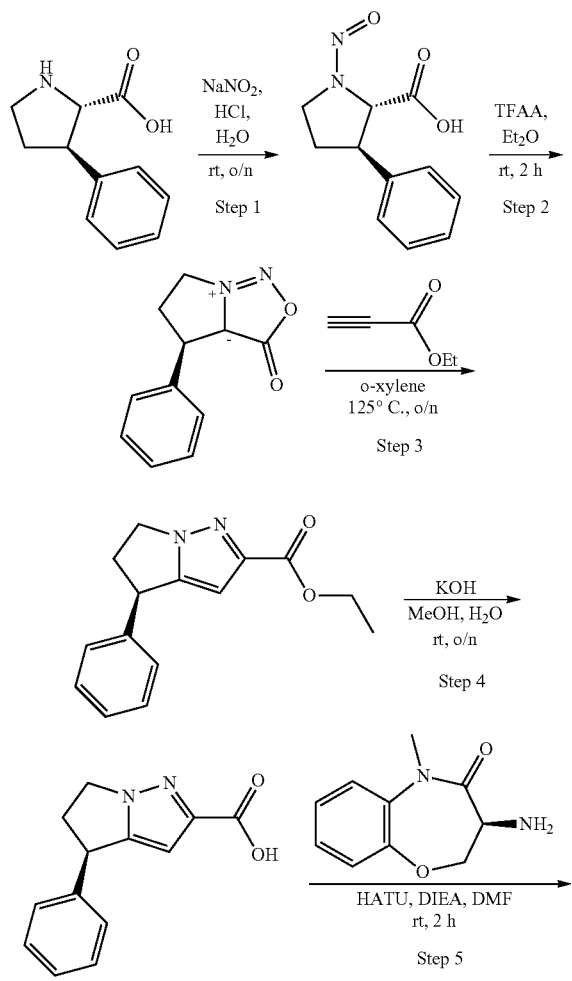

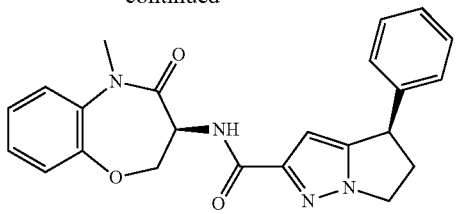

Step 1: Preparation of (2S,3R)-1-nitroso-3-phenylpyrrolidine-2-carboxylic acid (2S,3R)-3-phenylpyrrolidine-2-carboxylic acid (1.01 g, 5.23 mmol) was added to a solution of sodium nitrite (800 mg, 11.59 mmol) in water (5 mL). Concentrated hydrochloric acid (5 mL) was added at 0° C. The reaction mixture was stirred overnight at room temperature, diluted with water (50 mL) and extracted with ethyl acetate (3×50 mL). The combined organic phases were dried over sodium sulfate, filtered and concentrated under reduced pressure to afford the title compound (700 mg crude). LC-MS (Method I): m/z=220.95[M+H]$^+$, 0.741 min.

Step 2: Preparation of (R)-3-oxo-4-phenyl-3,4,5,6-tetrahydropyrrolo[1,2c][1,2,3]oxadiazol-7-ium-3a-ide To a solution of (2S,3R)-1-nitroso-3-phenylpyrrolidine-2-carboxylic acid (700 mg, 3.18 mmol) in ether (7 mL) at 0° C. was added trifluoroacetic anhydride (1.01 g, 4.76 mmol) dropwise. The resulting solution was stirred for 2 hours at room temperature. The reaction mixture was concentrated under vacuum and diluted with water (50 mL). The pH value of the solution was adjusted to 8 with potassium carbonate (0.5 M). The resulting solution was extracted with dichloromethane (3×50 mL). The combined organic layers were dried over sodium sulfate, filtered and concentrated under vacuum. The residue was purified by column chromatography (ethyl acetate/petroleum ether, 1:1) to afford the title compound (380 mg, 59%) d. LC-MS (Method I): m/z=202.9 [M+H]$^+$, 0.725 min.

Step 3: Preparation of ethyl (4R)-4-phenyl-4H,5H,6H-pyrrolo[1,2-b]pyrazole-3-carboxylate To a solution of (R)-3-oxo-4-phenyl-3,4,5,6-tetrahydropyrrolo[1,2-c][1,2,3]oxadiazol-7-ium-3a-ide (380 mg, 1.88 mmol) in o-xylene (6 mL), purged and maintained with an inert atmosphere of nitrogen, was added ethyl prop-2-ynoate (240 mg, 2.45 mmol) dropwise. The resulting solution was stirred overnight at 125° C. in an oil bath. The resulting mixture was concentrated under vacuum. The residue was purified by column chromatography (ethyl acetate/petroleum ether, 1:1) to afford the title compound (100 mg, 21%). LC-MS (Method J): m/z=257.1 [M+H]$^+$, 1.367 min.

Step 4: Preparation of (4R)-4-phenyl-4H,5H,6H-pyrrolo[1,2-b]pyrazole-2-carboxylic acid To a solution of ethyl (4R)-4-phenyl-4H,5H,6H-pyrrolo[1,2-b]pyrazole-2-carboxylate (100 mg, 0.39 mmol) in methanol (2.1 mL) and water (0.7 mL) was added potassium hydroxide (67 mg, 1.19 mmol). The resulting solution was stirred overnight at room temperature, concentrated under vacuum and the resulting residue was diluted with water. The pH value of the solution was adjusted to 3 with 3N hydrochloric acid. The resulting solid was collected by filtration to afford the title compound (80 mg, 90%). LC-MS (Method I): m/z=228.9 [M+H]$^+$, 0.804 min.

Step 5: Preparation of (R)—N—((S)-5-methyl-4-oxo-2,3,4,5-tetrahydrobenzo[b][1,4]oxazepin-3-yl)-4-phenyl-5,6-dihydro-4H-pyrrolo[1,2-b]pyrazole-2-carboxamide The crude product obtained using Amide Coupling Procedure B was purified by reverse phase chromatography using an Xbridge Phenyl OBD 5 μm, 19×150 mm column; mobile phase, water (10 mmol/L NH$_4$HCO$_3$) and ACN (25.0% to 55.0% in 7 min) to afford the title compound. $^1$H-NMR (400 MHz, DMSO-d$_6$) δ 8.12 (d, J=8.1 Hz, 1H), 7.51 (dd, J=7.5, 1.9 Hz, 1H), 7.39-7.20 (m, 8H), 6.32 (d, J=0.9 Hz, 1H), 4.84 (dt, J=11.5, 7.9 Hz, 1H), 4.61-4.48 (m, 2H), 4.45-4.31 (m, 2H), 4.22 (dt, J=11.0, 7.7 Hz, 1H), 3.32 (s, 3H), 3.09 (dtd, J=12.7, 8.3, 4.2 Hz, 1H), 2.51-2.41 (m, 1H). LC-MS (Method J): m/z=403.2 [M+H]$^+$, 1.499 min.

Example 14: (S)—N-(5-methyl-4-oxo-2,3,4,5-tetrahydrobenzo[b][1,4]oxazepin-3-yl)-5-(2,2,2-trifluoroethyl)isoxazole-3-carboxamide

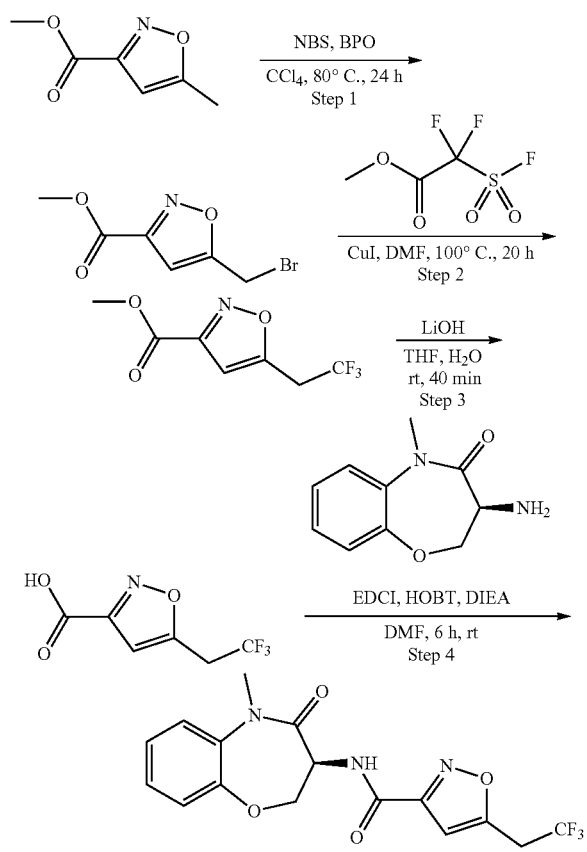

Step 1: Preparation of methyl 5-(bromomethyl)isoxazole-3-carboxylate

To a solution of methyl 5-methylisoxazole-3-carboxylate (4.65 g, 30 mmol) and N-bromosuccinimide in carbon tetrachloride (250 mL) was added benzoyl peroxide (2 mg, 0.1 mol %). The resulting mixture was refluxed at 80° C. for 24 hours. The solids were removed by filtration and the filtrate was concentrated under vacuum. The residue was purified by column chromatography (ethyl acetate/hexane, 1/5) to afford the title compound (1.6 g, 23%) as a white solid. LC-MS (Method C): m/z=221.7 [M+H]$^+$, 0.746 min.

Step 2: Preparation of methyl 5-(2,2,2-trifluoroethyl)isoxazole-3-carboxylate

To a mixture of methyl 5-(bromomethyl)isoxazole-3-carboxylate (350 mg, 1.59 mmol) and cuprous iodide (570 mg, 3.00 mmol) in N,N-dimethylformamide (10 mL) was added methyl 2,2-difluoro-2-(fluorosulfonyl)acetate (1.44 g, 7.50 mmol). The resulting mixture was heated at 100° C. for 20 hours. After cooling to room temperature, the reaction mixture was diluted with water (25 mL) and extracted with ethyl acetate (3×25 mL). The combined organic phases were dried over sodium sulfate, filtered and concentrated under reduced pressure. The residue was purified by column chromatography (ethyl acetate/hexane, 1/5) to afford the title compound (125 mg, 37%) as a yellow solid. LC-MS (Method C): m/z=209.9 [M+H]$^+$, 0.788 min.

Step 3: Preparation of 5-(2,2,2-trifluoroethyl)isoxazole-3-carboxylic acid

To a solution of methyl 5-(2,2,2-trifluoroethyl)isoxazole-3-carboxylate (90 mg, 0.43 mmol) in 4:1 THF:H$_2$O (2.5 mL) was added lithium hydroxide (72 mg, 3 mmol). The resulting solution was stirred for 40 min at room temperature. After completion of the reaction the solvent was evaporated under reduced pressure and to the resulting residue was added water (25 mL). This solution was washed with ethyl acetate (3×50 mL). The aqueous layer was acidified with 1N hydrochloric acid to pH~3-4, and extracted with ethyl acetate (3×20 mL). The combined organic phases from this extraction were dried over sodium sulfate, filtered and concentrated under reduced pressure to afford the title compound (43 mg crude), which was used directly for the next step without further purification. LC-MS (Method D): m/z=196.9 [M+H]$^+$, 0.290 min.

Step 4: Preparation of (S)—N-(5-methyl-4-oxo-2,3,4,5-tetrahydrobenzo[b][1,4]oxazepin-3-yl)-5-(2,2,2-trifluoroethyl)isoxazole-3-carboxamide The crude product obtained using Amide Coupling Procedure C was purified by crystallization (ethanol/n-hexane) to afford the title compound. $^1$H NMR (300 MHz, Chloroform-d) δ 7.80 (d, J=7.0 Hz, 1H), 7.26-7.19 (m, 4H), 6.71 (s, 1H), 5.04 (dt, J=11.1, 7.1 Hz, 1H), 4.76 (dd, J=9.8, 7.4 Hz, 1H), 4.28 (dd, J=11.1, 9.7 Hz, 1H), 3.69 (q, J=9.7 Hz, 2H), 3.46 (s, 3H). LC-MS (Method E): m/z=370.2 [M+H]$^+$, 2.462 min.

Example 15: 5-benzyl-N-(6,7,8,9-tetrahydro-5H-benzo[7]annulen-7-yl)isoxazole-3-carboxamide

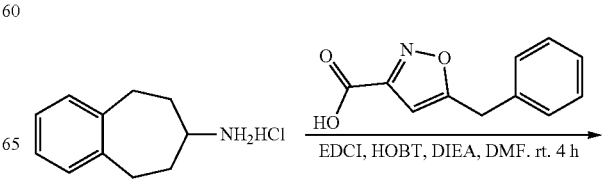

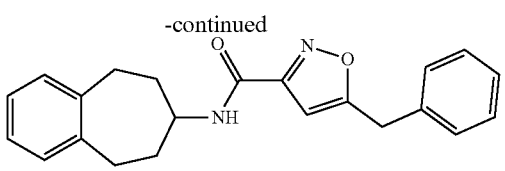

The crude product obtained using Amide Coupling Procedure C was purified by Prep-HPLC with the following conditions: Column, Xbridge Phenyl OBD Column, 5 μm, 19×150 mm; mobile phase, water (10 mmol/L NH₄HCO₃) and ACN (50.0% ACN to 70.0% over 7 min); Detector, UV 254 & 220 nm to afford the title compound. ¹H NMR (300 MHz, DMSO-d₆) δ 8.63 (d, J=8.4 Hz, 1H), 7.25-7.14 (m, 5H), 7.15-7.07 (m, 4H), 6.52 (s, 1H), 4.19 (s, 2H), 4.17-4.04 (m, 1H), 2.89-2.69 (m, 4H), 2.02-1.97 (m, 2H), 1.43-1.23 (m, 2H). LC-MS (Method F): m/z=347.1 [M+H]⁺, 1.652 min.

Example 16: (S)-1-benzyl-3-methyl-N-(5-methyl-4-oxo-2,3,4,5-tetrahydrobenzo[b][1,4]oxazepin-3-yl)-1H-pyrazole-5-carboxamide

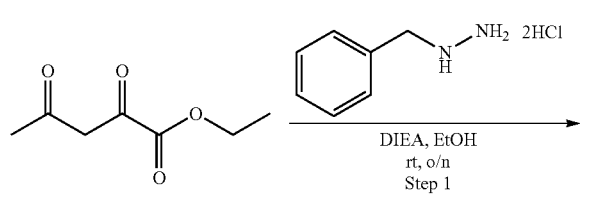

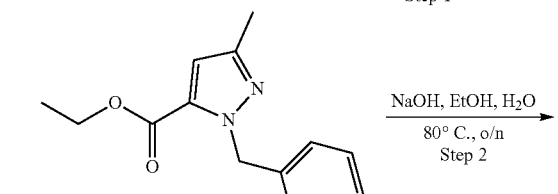

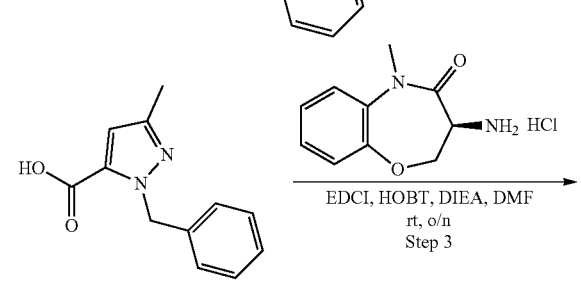

Step 1: Preparation of ethyl 1-benzyl-3-methyl-1H-pyrazole-5-carboxylate

To a solution of ethyl 2,4-dioxopentanoate (0.5 g, 3.20 mmol) and benzylhydrazine hydrochloride (0.75 g, 3.84 mmol) in ethanol (10 mL) was added N,N-diisopropylethylamine (1.2 g, 9.60 mmol). After stirring overnight at room temperature, the reaction mixture was diluted with water (20 mL) and extracted with ethyl acetate (3×50 mL). The combined organic layers were washed with brine, dried over anhydrous sodium sulfate, filtered and concentrated under reduced pressure. The residue was purified by column chromatography (ethyl acetate/petroleum ether, 1/1) to afford the title compound (0.5 g, 65%) as a yellow oil. LC-MS (Method S): m/z=245.2 [M+H]⁺, 1.070 min.

Step 2: Preparation of 1-benzyl-3-methyl-1H-pyrazole-5-carboxylic acid

A solution of sodium hydroxide (0.25 g, 6.02 mmol) in water (1 mL) was added to a stirred solution of ethyl 1-benzyl-3-methyl-1H-pyrazole-5-carboxylate (0.5 g, 2.01 mmol) in ethanol (2 mL). The resulting mixture was stirred overnight at 80° C. After cooling to room temperature, the reaction mixture was adjusted to pH=3-4 with aqueous hydrochloric acid (1 N, 20 mL) and extracted with ethyl acetate (3×50 mL). The combined organic layers were washed with brine, dried over anhydrous sodium sulfate, filtered and concentrated under reduced pressure to afford the title compound (0.4 g, 90%) as a white solid, which was used directly in the next step without further purification. LC-MS (Method C): m/z=217.2 [M+H]⁺, 1.219 min.

Step 3: Preparation of (S)-1-benzyl-3-methyl-N-(5-methyl-4-oxo-2,3,4,5-tetrahydrobenzo[b][1,4]oxazepin-3-yl)-1H-pyrazole-5-carboxamide The crude product obtained using Amide Coupling Procedure C was purified by Prep-HPLC with the following conditions: Column, Xbridge Phenyl OBD Column, 5 μm, 19×150 mm; mobile phase, water (10 mmol/L NH₄HCO₃) and ACN (50.0% ACN to 70.0% over 7 min); Detector, UV 254 & 220 nm to afford the title compound. ¹H NMR (400 MHz, DMSO-d₆) δ 8.68 (d, J=8.4 Hz, 1H), 7.53-7.47 (m, 1H), 7.35-7.19 (m, 6H), 7.11-7.07 (m, 2H), 6.82 (s, 1H), 5.64-5.51 (m, 2H), 4.88-4.81 (m, 1H), 4.55-4.49 (m, 1H), 4.40-4.35 (m, 1H), 3.30 (s, 3H), 2.20 (s, 3H). LC-MS (Method L): m/z=391.1 [M+H]⁺, 1.437 min.

Example 17: (R)—N—((S)-5-methyl-4-oxo-2,3,4,5-tetrahydrobenzo[b][1,4]oxazepin-3-yl)-4-phenyl-5,6-dihydro-4H-pyrrolo[1,2-b]pyrazole-3-carboxamide

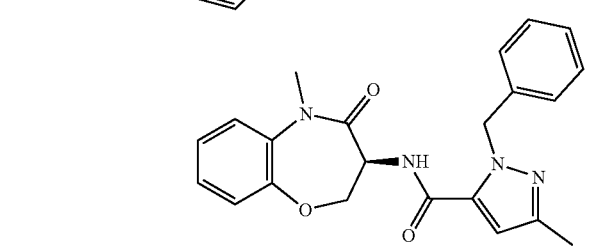

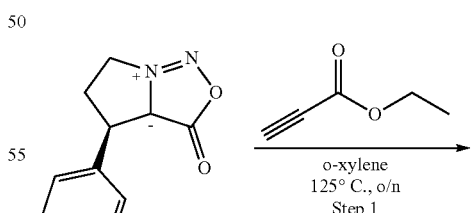

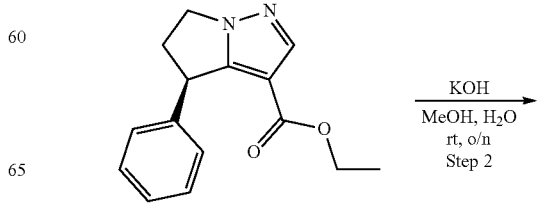

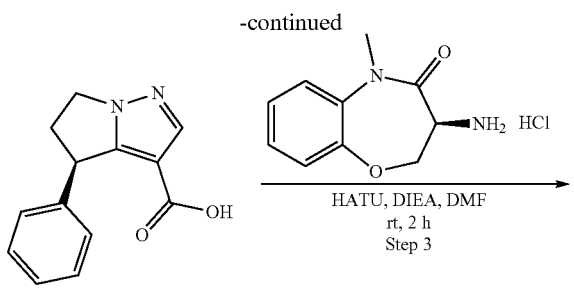

4.22-4.03 (m, 3H), 3.26 (s, 3H), 3.19-3.05 (m, 1H), 2.39 (dq, J=8.8, 4.3 Hz, 1H). LC-MS (Method O): m/z=403.0 [M+H]⁺, 1.334 min.

Example 18: (S)—N-benzyl-2-((5-methyl-4-oxo-2,3,4,5-tetrahydrobenzo[b][1,4]oxazepin-3-yl)amino)acetamide

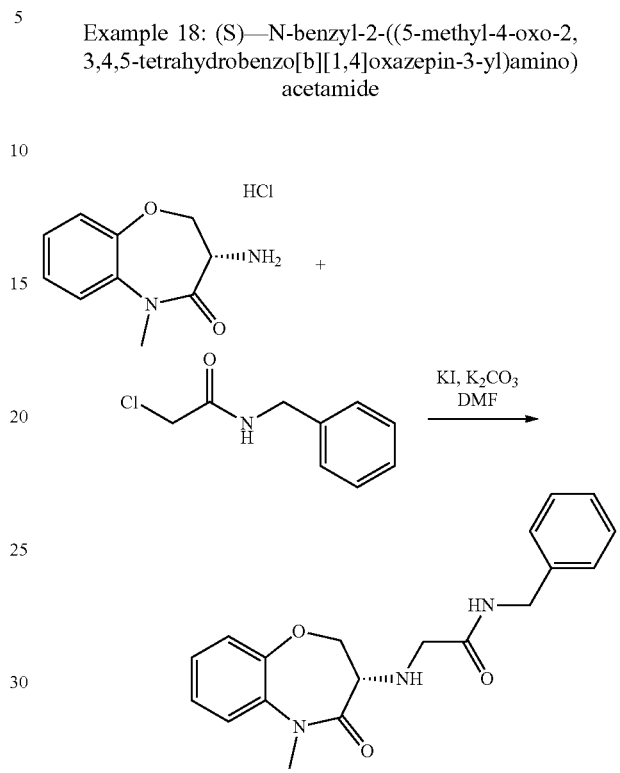

Step 1: Preparation of ethyl(4R)-4-phenyl-4H,5H,6H-pyrrolo[1,2-b]pyrazole-3-carboxylate

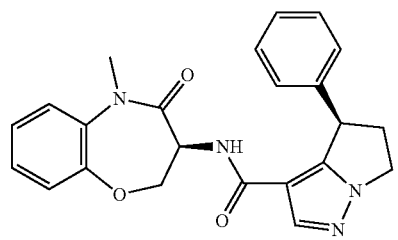

To a stirring solution of (R)-3-oxo-4-phenyl-3,4,5,6-tetrahydropyrrolo[1,2-c][1,2,3]oxadiazol-7-ium-3a-ide (380 mg, 1.88 mmol) in o-xylene (6 mL) under nitrogen atmosphere was added ethyl prop-2-ynoate (240 mg, 2.45 mmol). The resulting mixture was heated to 125° C. and stirred overnight in an oil bath. The reaction mixture was cooled to rt, concentrated under reduced pressure and the resulting residue was purified by column chromatography (ethyl acetate/petroleum ether, 1/1) to afford the title compound (120 mg, 25%) as a light yellow oil. LC-MS (Method J): m/z=257.0 [M+H]⁺, 1.323 min.

Step 2: Preparation of (4R)-4-phenyl-4H,5H,6H-pyrrolo[1,2-b]pyrazole-3-carboxylic acid A solution of potassium hydroxide (67 mg, 1.19 mmol) in water (7 mL) was added to a solution of ethyl (4R)-4-phenyl-4H,5H,6H-pyrrolo[1,2-b]pyrazole-3-carboxylate (100 mg, 0.39 mmol) in methanol (2.1 mL). After stirring overnight at room temperature, the reaction mixture was concentrated under reduced pressure and diluted with water. The pH value of the solution was adjusted to 3 with hydrochloric acid (3 N, 20 mL). The precipitate was collected by filtration to afford the title compound (50 mg, 47%) as a yellow solid. LC-MS (Method I): m/z=228.9 [M+H]⁺, 0.738 min.

Step 3: Preparation of (R)—N—((S)-5-methyl-4-oxo-2,3,4,5-tetrahydrobenzo[b][1,4]oxazepin-3-yl)-4-phenyl-5,6-dihydro-4H-pyrrolo[1,2-b]pyrazole-3-carboxamide The crude product obtained using Amide Coupling Procedure B was purified by preparative HPLC with the following conditions: Column, Xbridge Phenyl OBD Column, 5 μm, 19×150 mm; mobile phase, water (10 mmol/L NH₄HCO₃) and ACN (25.0% ACN to 55.0% over 7 min); Detector, UV 254 & 220 nm to afford the title compound. ¹H NMR (400 MHz, DMSO-d₆) δ 8.02 (s, 1H), 7.79 (d, J=8.8 Hz, 1H), 7.44 (dd, J=7.6, 2.0 Hz, 1H), 7.34-7.14 (m, 6H), 7.10-7.02 (m, 2H), 4.77-4.58 (m, 2H), 4.35-4.23 (m, 1H), A mixture of (3S)-3-amino-5-methyl-2,3,4,5-tetrahydro-1,5-benzoxazepin-4-one hydrochloride (40 mg, 0.175 mmol, e.e.=90%), N-benzyl-2-chloroacetamide (18 mg, 0.097 mmol), K₂CO₃ (27 mg, 0.195 mmol), and KI (32 mg, 0.195 mmol) in DMF (3 mL) was stirred at 30° C. for 16 h. The mixture was diluted with EtOAc and washed twice with sat. NH₄Cl solution. The aqueous portion was extracted with EtOAc. The combined organic portions were dried over Na₂SO₄, filtered and concentrated under reduced pressure. The crude product was purified by column chromatography (cyclohexane-EtOAc, 80:20 to 0:100) to afford the title compound. ¹H NMR (400 MHz, CDCl₃) δ 7.46-7.08 (m, 10H), 4.51-4.37 (m, 2H), 4.33 (dd, J=10.2, 7.4 Hz, 1H), 4.12 (t, J=10.8 Hz, 1H), 3.61-3.43 (m, 3H), 3.41 (s, 3H), 3.06-2.97 (m, 1H). LC-MS (Method A): m/z=340.0 [M+H]⁺, 0.70 min. e.e.=88% as determined on a Chiralcel OD-H (25×0.46 cm), 5 μm column using a mobile phase of n-hexane/(ethanol+0.1% isopropylamine) 35/65% v/v.

Example 19: (S)-5-benzyl-N-(5-ethyl-4-oxo-2,3,4,5-tetrahydrobenzo[b][1,4]oxazepin-3-yl)isoxazole-3-carboxamide

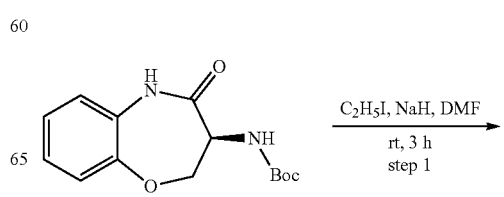

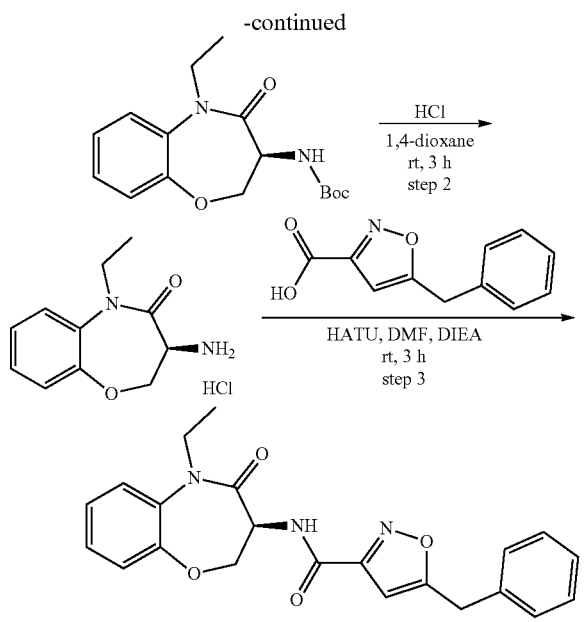

Step 1: Preparation of tert-butyl N-((3S)-5-ethyl-4-oxo-2,3,4,5-tetrahydro-1,5-benzoxazepin-3-yl)carbamate Sodium hydride (8.64 mg, 0.22 mmol) was added to a stirring solution of tert-butyl N-((3S)-4-oxo-2,3,4,5-tetrahydro-1,5-benzoxazepin-3-yl)carbamate (50 mg, 0.18 mmol) in N,N-dimethylformamide (5 mL). The resulting mixture was stirred for 1 hour at room temperature. Iodoethane (33.7 mg, 0.21 mmol) was added dropwise. After stirring for 3 hours at room temperature, the reaction mixture was quenched with water (10 mL) and extracted with ethyl acetate (3×10 mL). The combined organic layers were washed with brine, dried over anhydrous sodium sulfate, filtered and concentrated under reduced pressure. The resulting residue was purified by column chromatography (ethyl acetate/petroleum ether, 1/3) to afford the title compound (40 mg, 73%) as a yellow solid. LC-MS (Method S): m/z=307.2 [M+H]$^+$, 1.021 min.

Step 2: Preparation of (3S)-3-amino-5-ethyl-2,3,4,5-tetrahydro-1,5-benzoxazepin-4-one hydrochloride tert-Butyl N-((3S)-5-ethyl-4-oxo-2,3,4,5-tetrahydro-1,5-benzoxazepin-3-yl)carbamate (40 mg, 0.13 mmol) was added to a solution of hydrogen chloride in dioxane (4 M, 10 mL). The reaction mixture was stirred for 3 hours at room temperature and concentrated under reduced pressure to afford the title compound (30 mg) as a white solid, which was used directly in the next step without further purification. LC-MS (Method D): m/z=207.1 [M+H]$^+$, 0.930 min.

Step 3: Preparation of (S)-5-benzyl-N-(5-ethyl-4-oxo-2,3,4,5-tetrahydrobenzo[b][1,4]oxazepin-3-yl)isoxazole-3-carboxamide The crude product obtained using Amide Coupling Procedure B was purified by Prep-HPLC with the following conditions: Column, XBridge Prep C18 OBD Column, 5 μm, 19×150 mm; mobile phase, water (0.05% TFA) and ACN (45.0% ACN to 70.0% over 7 min); Detector, UV 254 & 220 nm to afford the title compounds. $^1$H NMR (300 MHz, DMSO-d$_6$) δ 8.82 (d, J=7.8 Hz, 1H), 7.54-7.51 (m, 1H), 7.38-7.21 (m, 8H), 6.54 (s, 1H), 4.84-4.75 (m, 1H), 4.56 (t, J=11.4 Hz, 1H), 4.39-4.33 (m, 1H), 4.21 (s, 2H), 4.10-4.03 (m, 1H), 3.67-3.60 (m, 1H), 1.02 (t, J=7.2 Hz, 3H). LC-MS (Method D): m/z=392.2 [M+H]$^+$, 2.181 min.

Example 20: 5-benzyl-N-(1-methyl-2,3,4,5-tetrahydro-1H-benzo[b]azepin-3-yl)-4H-1,2,4-triazole-3-carboxamide

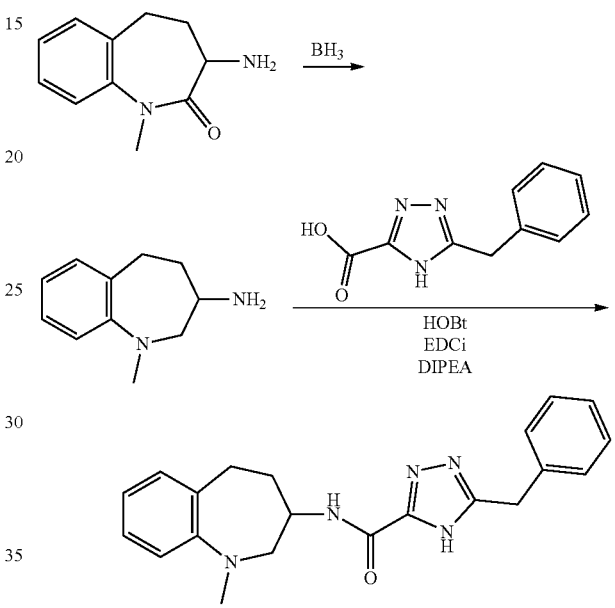

Borane tetrahydrofuran complex (1M solution in THF, 570 μL, 0.570 mmol) was added dropwise to a solution of 3-amino-1-methyl-2,3,4,5-tetrahydro-1H-1-benzazepin-2-one (50 mg, 0.26 mmol) in THF (1 mL) which had been pre-cooled to 0° C. The reaction was allowed to gradually warm to room temperature and stirred for 18 h before being quenched with 1M HCl solution. The resulting mixture was stirred at room temperature for 3 h. Volatiles were removed under reduced pressure. The crude product was purified by ion exchange chromatography on an SCX cartridge (MeOH then 7M NH$_3$ in MeOH) to afford the title compound. $^1$H NMR (400 MHz, DMSO-d$_6$) δ 7.14-7.02 (m, 2H), 6.93-6.85 (m, 1H), 6.84-6.74 (m, 1H), 3.10-2.85 (m, 2H), 2.84-2.68 (m, 4H), 2.66-2.54 (m, 1H), 2.48-2.36 (m, 1H), 1.89-1.77 (m, 1H), 1.75-1.55 (m, 2H), 1.33-1.06 (m, 1H). LC-MS (Method A): m/z=177.2 [M+H]$^+$, 0.40 min.

The crude product obtained using Amide Coupling Procedure C was purified by column chromatography (CH$_2$Cl$_2$-MeOH, 95:5 to 80:20) and then by reverse phase chromatography (water-CH$_3$CN, 100:0 to 50:50) to afford the title compound as a mixture of enantiomers. $^1$H NMR (400 MHz, DMSO-d$_6$) δ 14.61-14.37 (m, 1H), 8.37-8.25 (m, 1H), 7.35-7.10 (m, 7H), 6.99-6.93 (m, 1H), 6.85 (td, J=7.3, 1.1 Hz, 1H), 4.19-4.11 (m, 1H), 4.08 (s, 2H), 3.05-2.98 (m, 1H), 2.84 (s, 3H), 2.81-2.73 (m, 2H), 2.65-2.58 (m, 1H), 1.89-1.78 (m, 1H), 1.68-1.55 (m, 1H). LC-MS (Method A): m/z=362.4 [M+H]$^+$, 1.02 min.

Example 21: 5-benzyl-N-((4S,9aR)-5-oxohexa-hydro-1H,3H-pyrrolo[2,1-c][1,4]oxazepin-4-yl)isoxazole-3-carboxamide

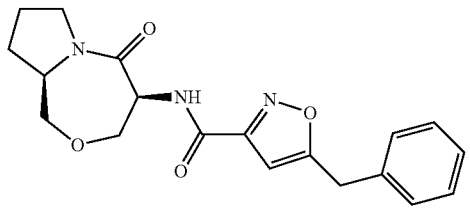 [SMILES: O=C(N[C@H]1COC[C@H]2CCCN2C1=O)c1cc(Cc2ccccc2)on1]

Example 22: 5-benzyl-N-((4S,9aS)-5-oxohexa-hydro-1H,3H-pyrrolo[2,1-c][1,4]oxazepin-4-yl)isoxazole-3-carboxamide

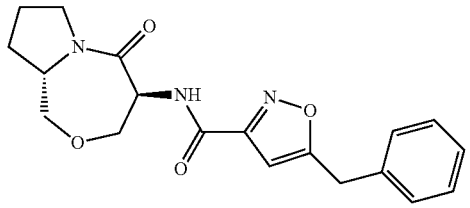 [SMILES: O=C(N[C@H]1COC[C@@H]2CCCN2C1=O)c1cc(Cc2ccccc2)on1]

Example 23: (S)-5-benzyl-N-(1-methyl-2-oxoazepan-3-yl)-4H-1,2,4-triazole-3-carboxamide

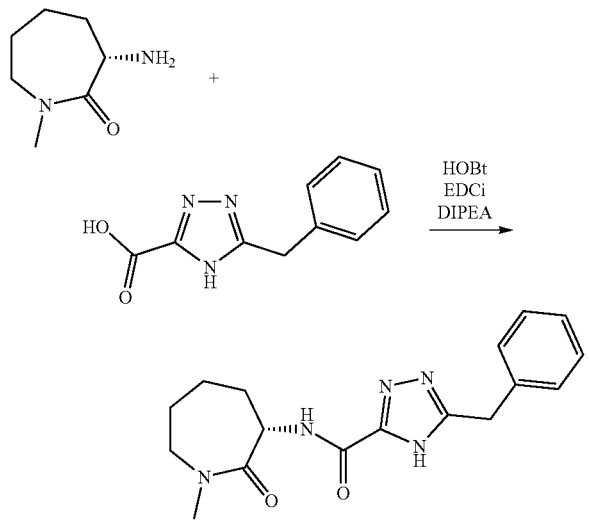

The crude product obtained using Amide Coupling Procedure C was purified by column chromatography (CH$_2$Cl$_2$/MeOH 9:1), then by column chromatography on KP-NH modified silica gel (EtOAc/MeOH 9:1) and then by reverse phase chromatography (water-CH$_3$CN, 70:30) to afford the title compound. $^1$H NMR (400 MHz, DMSO-d$_6$) δ 14.44 (s, 1H), 8.34 (d, J=6.2 Hz, 1H), 7.37-7.20 (m, 5H), 4.75-4.65 (m, 1H), 4.11 (s, 2H), 3.68 (dd, J=15.4, 11.4 Hz, 1H), 3.23 (dd, J=15.3, 5.2 Hz, 1H), 2.94 (s, 3H), 2.01-1.93 (m, 1H), 1.92-1.82 (m, 1H), 1.81-1.67 (m, 2H), 1.45-1.28 (m, 2H). LC-MS (Method A): m/z=328.3 [M+H]$^+$, 0.74 min.

Example 24: (S)-5-cyano-1-methyl-N-(5-methyl-4-oxo-2,3,4,5-tetrahydrobenzo[b][1,4]oxazepin-3-yl)-1H-pyrrole-2-carboxamide

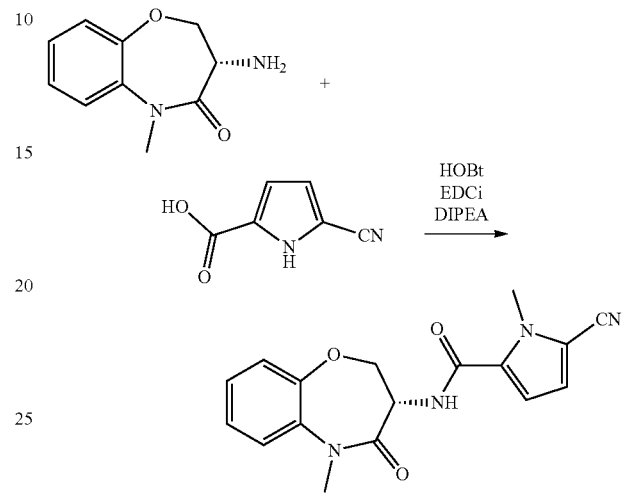

The crude product obtained using Amide Coupling Procedure C was purified by column chromatography (cyclohexane-EtOAc, 100:0 to 70:30) to afford the title compound. $^1$H NMR (400 MHz, CDCl$_3$) δ 7.32-7.19 (m, 4H), 7.11 (d, J=6.6 Hz, 1H), 6.77 (d, J=4.3 Hz, 1H), 6.69 (d, J=4.3 Hz, 1H), 5.00 (dt, J=11.2, 6.9 Hz, 1H), 4.77 (dd, J=9.7, 7.4 Hz, 1H), 4.25 (dd, J=11.1, 9.7 Hz, 1H), 4.00 (s, 3H), 3.47 (s, 3H). LC-MS (Method A): m/z=325.0 [M+H]$^+$, 0.93 min.

Example 25: (S)-5-methyl-N-(5-methyl-4-oxo-2,3,4,5-tetrahydrobenzo[b][1,4]oxazepin-3-yl)-4H-1,2,4-triazole-3-carboxamide

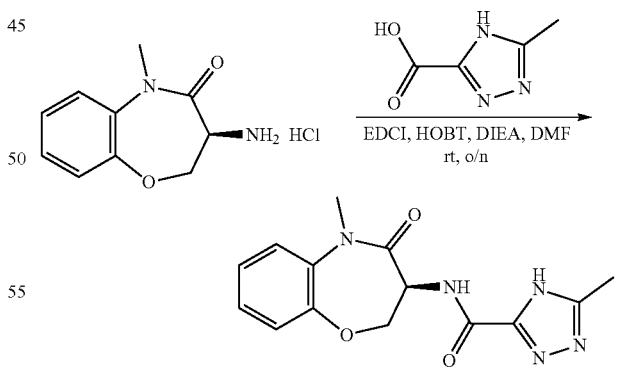

The crude product obtained using Amide Coupling Procedure C was purified by Prep-HPLC with the following conditions: Column, Xbridge Phenyl OBD Column, 5 μm, 19×150 mm; mobile phase, water (10 mmol/L NH$_4$HCO$_3$) and ACN (50.0% ACN to 70.0% over 7 min); Detector, UV 254 & 220 nm to afford the title compound. $^1$H NMR (400 MHz, DMSO-d$_6$) δ 14.2 (br. s, 1H), 8.43 (d, J=6.8 Hz, 1H), 7.54-7.45 (m, 1H), 7.22-7.18 (m, 3H), 4.90-4.75 (m, 1H), 4.58 (t, J=10.0 Hz, 1H), 4.47-4.35 (m, 1H), 4.39 (s, 3H), 2.39 (s, 3H). LC-MS (Method L): m/z=302.0 [M+H]+, 0.885 min.

Example 26: (S)—N-(5-methyl-4-oxo-2,3,4,5-tetrahydrobenzo[b][1,4]oxazepin-3-yl)acetamide

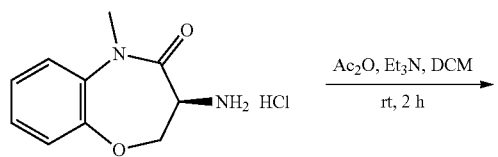

Acetic anhydride (20.5 mg, 0.20 mmol) was added to a solution of (3S)-3-amino-5-methyl-2,3,4,5-tetrahydro-1,5-benzoxazepin-4-one hydrochloride (45.6 mg, 0.20 mmol) and triethylamine (40 mg, 0.40 mmol) in dichloromethane (5 mL). After stirring at room temperature for 2 hours, the reaction mixture was diluted with water (5 mL), and extracted with dichloromethane (3×10 mL). The combined organic layers were washed with brine, dried over anhydrous sodium sulfate, filtered and concentrated under reduced pressure. The residue was purified by Prep-HPLC with the following conditions: Column, Xbridge Phenyl OBD Column, 5 μm, 19×150 mm; mobile phase, water (10 mmol/L NH4HCO3) and ACN (50.0% ACN to 70.0% over 7 min); Detector, UV 254 & 220 nm to afford the title compound. 1H NMR (400 MHz, DMSO-d6) δ 8.25 (d, J=8.4 Hz, 1H), 7.50-7.45 (m, 1H), 7.36-7.15 (m, 3H), 4.76-4.65 (m, 1H), 4.38-4.15 (m, 2H), 3.29 (s, 3H), 1.84 (s, 3H). LC-MS (Method D): m/z=235.1 [M+H]+, 1.340 min.

Example 27: 5-benzyl-N-((4S,9aS)-5-oxohexahydro-1H,3H-pyrrolo[2,1-c][1,4]oxazepin-4-yl)-4H-1,2,4-triazole-3-carboxamide

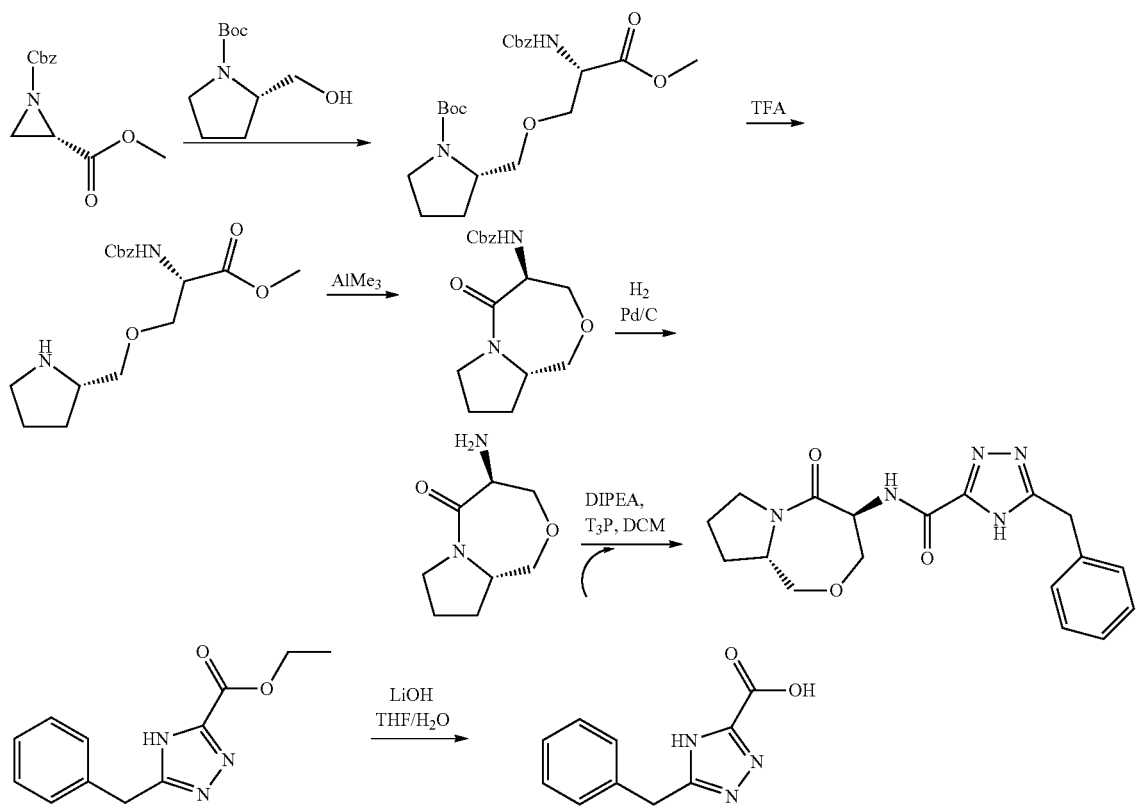

Step 1: Preparation of tert-butyl (2S)-2-{[(2S)-2-{[(benzyloxy)carbonyl]amino}-3-methoxy-3-oxopropoxy]methyl}pyrrolidine-1-carboxylate Boron trifluoride diethyl etherate (0.52 mL, 4.25 mmol) was added to a solution of 1-benzyl 2-methyl (2S)-aziridine-1,2-dicarboxylate (2.00 g, 8.50 mmol) and N-Boc-L-prolinol (6.85 g, 34.03 mmol) in dry CHCl3 (20 mL) at −30° C. under a nitrogen atmosphere. The solution was left to stir overnight at room temperature, then diluted with CH2Cl2 (20 mL) and washed with water (3×10 mL) with back-extraction. The combined organic extracts were dried over Na2SO4, filtered and concentrated under reduced pressure. The crude product was purified by column chromatography (cyclohexane-diethyl ether, 50:50) to afford the title product (3.30 g, 89%) as a colorless oil. $^1$H NMR (400 MHz, CDCl$_3$) δ 7.47-7.30 (m, 5H), 5.97-5.50 (m, 1H), 5.23-5.08 (m, 2H), 4.49 (br. s., 1H), 4.07-3.21 (m, 10H), 1.97-1.73 (m, 4H), 1.49-1.38 (m, 9H). LC-MS (Method A): m/z=437.5 [M+H]$^+$, 1.18 min.

Step 2: Preparation of methyl (2S)-2-{[(benzyloxy)carbonyl]amino}-3-[(2S)-pyrrolidin-2-ylmethoxy]propanoate A solution of tert-butyl (2S)-2-{[(2S)-2-{[(benzyloxy)carbonyl](methyl)amino}-3-methoxy-3-oxopropoxy]methyl}pyrrolidine-1-carboxylate (450 mg, 1.03 mmol) in CH$_2$Cl$_2$ (5 mL) and TFA (5 mL) was stirred at 0° C. for 3 h. The reaction mixture was concentrated under reduced pressure and the crude product was purified by column chromatography on KP-NH modified silica (cyclohexane-EtOAc, 80:20 to 60:40 then neat MeOH) to afford the title compound (313 mg, 90%) as a colorless oil. $^1$H NMR (400 MHz, CDCl$_3$) δ 7.48-7.29 (m, 5H), 6.23 (br. s., 1H), 5.22-5.10 (m, 2H), 4.50 (br. s., 1H), 3.96 (dd, J=9.9, 3.1 Hz, 1H), 3.78 (s, 3H), 3.72 (dd, J=9.8, 3.3 Hz, 1H), 3.51-3.44 (m, 1H), 3.39-3.32 (m, 1H), 3.25 (dq, J=4.5, 7.0 Hz, 1H), 3.02-2.93 (m, 1H), 2.91-2.81 (m, 1H), 1.87-1.63 (m, 3H), 1.44-1.32 (m, 1H). LC-MS (Method A): m/z=337.3 [M+H]$^+$, 0.49 min.

Step 3: Preparation of benzyl N-[(4S,9aS)-5-oxo-octahydropyrrolo[2,1-c][1,4]oxazepin-4-yl]carbamate Trimethylaluminum solution (2M in heptane, 0.56 mL, 1.12 mmol) was added dropwise to a stirred solution of methyl (2S)-2-{[(benzyloxy)carbonyl]amino}-3-[(2S)-pyrrolidin-2-ylmethoxy]propanoate (313 mg, 0.93 mmol) in CH$_2$Cl$_2$ (5 mL) at −30° C. The solution was left to warm to room temperature and left to stir at room temperature for 1 h. The reaction was cooled to 0° C. and 1N HCl aqueous solution (4.63 mL, 4.63 mmol) and water (5 mL) were added. The phases were separated and the aqueous fraction was extracted twice with CH$_2$Cl$_2$, filtered through a hydrophobic frit (Phase Separator) and concentrated under reduced pressure. The crude product was purified by column chromatography (CH$_2$Cl$_2$-MeOH, 95:5) to give the title compound (217 mg, 77%) as a colorless oil. $^1$H NMR (400 MHz, CDCl$_3$) δ 7.45-7.29 (m, 5H), 5.73 (br. s., 1H), 5.14 (br. s., 2H), 4.41 (br. s., 1H), 4.18-3.89 (m, 3H), 3.82-3.58 (m, 2H), 3.54-3.19 (m, 2H), 2.18-2.04 (m, 1H), 1.97-1.83 (m, 1H), 1.81-1.64 (m, 1H), 1.56-1.39 (m, 1H). LC-MS (Method A): m/z=305.3 [M+H]$^+$, 0.74 min.

Step 4: Preparation of (4S,9aS)-4-amino-octahydro-pyrrolo[2,1-c][1,4]oxazepin-5-one Palladium on carbon (10%, 75 mg) was added to a solution of benzyl N-[(4S,9aS)-5-oxo-octahydropyrrolo[2,1-c][1,4]oxazepin-4-yl]carbamate (215 mg, 0.71 mmol) in MeOH (5 mL) under a nitrogen atmosphere. The atmosphere of nitrogen was replaced with an atmosphere of hydrogen and the reaction was stirred for 15 h. The reaction was quenched by filtration through a Celite plug, washing with abundant MeOH. The filtrate was concentrated under reduced pressure to give the title compound (116 mg, 96%) which was used directly in the next step. $^1$H NMR (400 MHz, CDCl$_3$) δ 4.23-4.11 (m, 1H), 4.02 (dd, J=12.5, 1.3 Hz, 1H), 3.93 (dd, J=12.8, 4.5 Hz, 1H), 3.80-3.68 (m, 2H), 3.64 (dd, J=4.4, 0.9 Hz, 1H), 3.41 (ddd, J=11.9, 10.4, 6.8 Hz, 1H), 3.23 (dd, J=12.7, 9.4 Hz, 1H), 2.18-2.08 (m, 1H), 2.00-1.87 (m, 1H), 1.86-1.68 (m, 1H), 1.57-1.44 (m, 1H). LC-MS (Method B): m/z=171.1 [M+H]$^+$, 0.35 min.

Step 5: Preparation of 5-benzyl-N-((4S,9aS)-5-oxo-hexahydro-1H,3H-pyrrolo[2,1-c][1,4]oxazepin-4-yl)-4H-1,2,4-triazole-3-carboxamide To a suspension of 5-benzyl-4H-1,2,4-triazole-3-carboxylic acid (50 mg, 0.246 mmol) and (4S,9aS)-4-amino-octahydropyrrolo[2,1-c][1,4]oxazepin-5-one (42 mg, 0.246 mmol), in CH$_2$Cl$_2$ (2 mL) was added N,N-diisopropylethylamine (0.107 mL, 0.49 mmol). The reaction mixture was stirred for 10 minutes, and then T3P solution (50 wt % in EtOAc, 0.22 mL, 0.37 mmol) was added. After 40 minutes the reaction mixture was quenched by adding water, and the two phases were separated. The organic phase was washed with 0.5 N HCl solution, sat. NaHCO$_3$ solution, and brine, and concentrated under reduced pressure. The crude product was purified by column chromatography (CH$_2$Cl$_2$-MeOH, 90:10 to 70:30) to afford the title compound. $^1$H NMR (400 MHz, CDCl$_3$) δ 8.05 (d, J=6.3 Hz, 1H), 7.40-7.17 (m, 5H), 4.72 (dd, J=6.9, 4.9 Hz, 1H), 4.33-4.03 (m, 5H), 3.84 (d, J=12.8 Hz, 1H), 3.75-3.62 (m, 1H), 3.43 (dt, J=6.8, 11.2 Hz, 1H), 3.31 (dd, J=12.8, 9.5 Hz, 1H), 2.21-2.08 (m, 1H), 1.95-1.83 (m, 1H), 1.81-1.64 (m, 1H), 1.58-1.43 (m, 1H). LC-MS (Method A): m/z=356.3 [M+H]$^+$, 0.67 min.

Example 28 and 29: 5-benzyl-N-((3R,4S)-4-fluoro-1-methyl-2-oxo-2,3,4,5-tetrahydro-1H-benzo[b]azepin-3-yl)isoxazole-3-carboxamide and 5-benzyl-N-((3S,4R)-4-fluoro-1-methyl-2-oxo-2,3,4,5-tetrahydro-1H-benzo[b]isoxazole-3-carboxamide (28); and 5-benzyl-N-((3R,4R)-4-fluoro-1-methyl-2-oxo-2,3,4,5-tetrahydro-1H-benzo[b]azepin-3-yl)isoxazole-3-carboxamide and 5-benzyl-N-((3S,4S)-4-fluoro-1-methyl-2-oxo-2,3,4,5-tetrahydro-1H-benzo[b]azepin-3-yl)isoxazole-3-carboxamide (29)

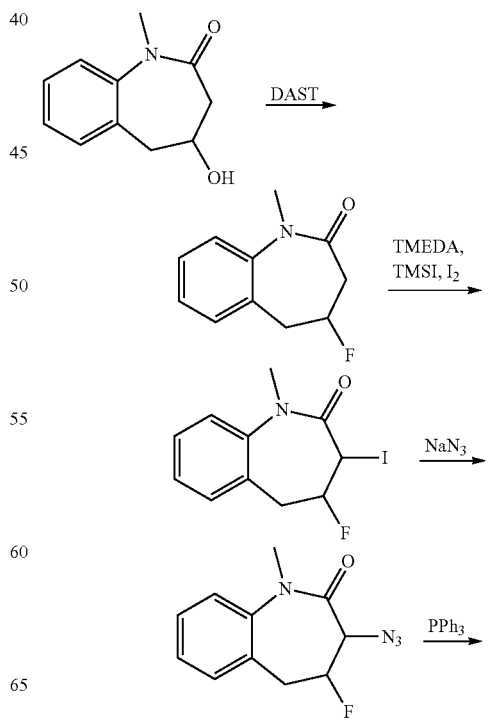

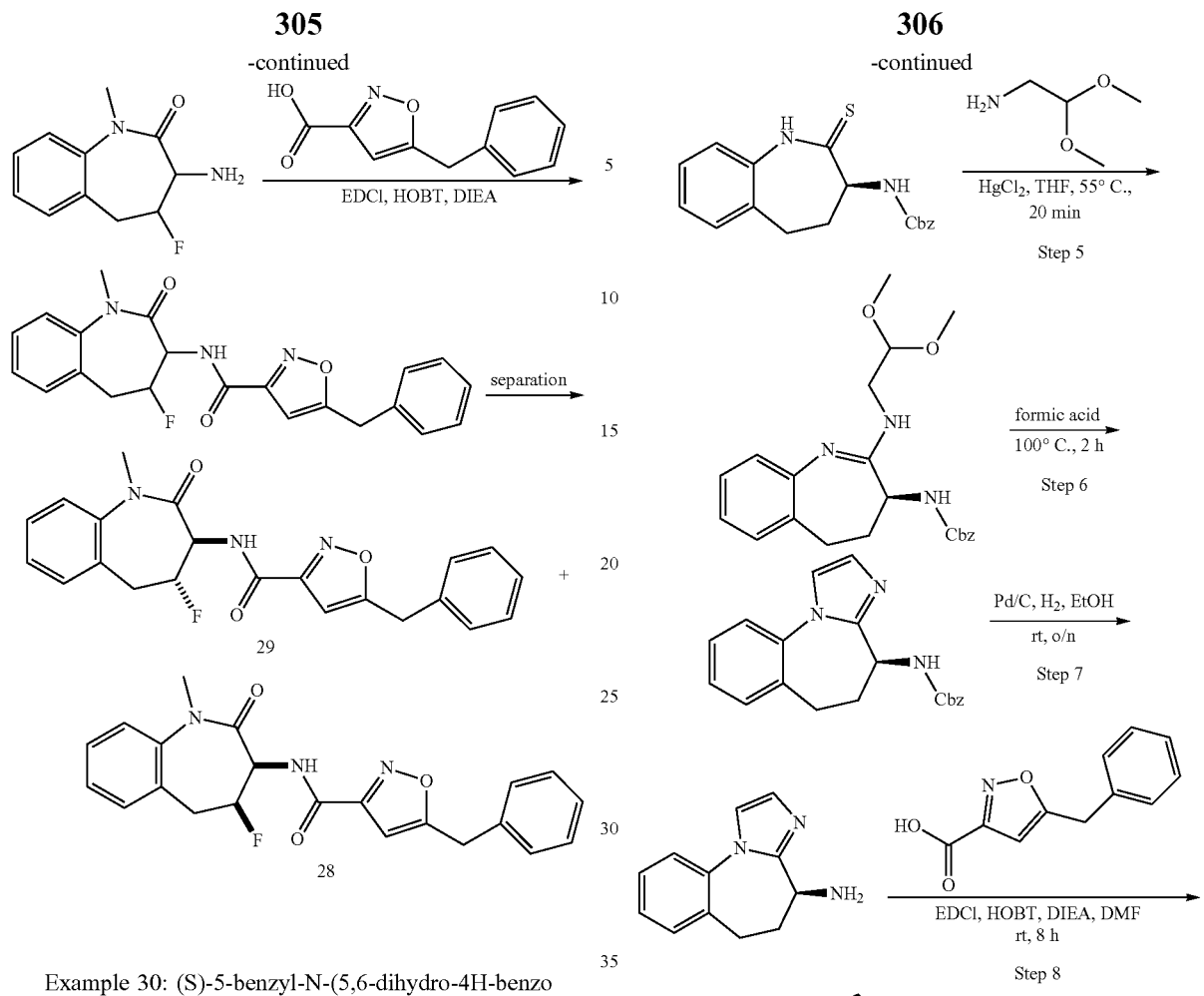

Example 30: (S)-5-benzyl-N-(5,6-dihydro-4H-benzo[f]imidazo[1,2-a]azepin-4-yl)isoxazole-3-carboxamide

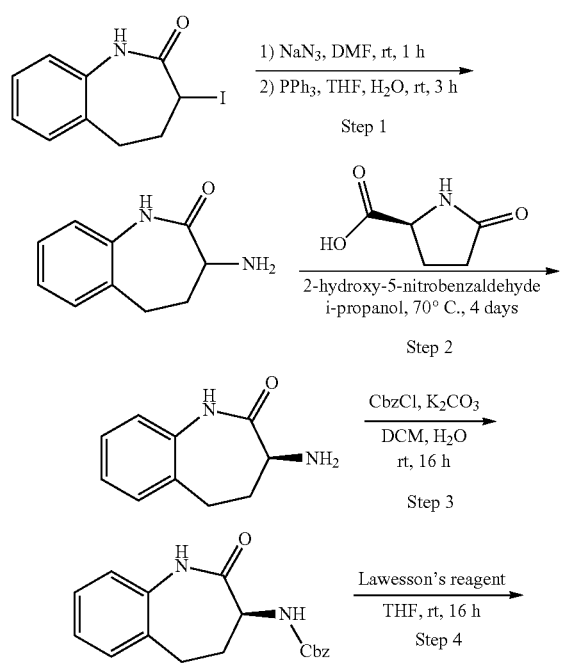

Step 1: Preparation of 3-amino-2,3,4,5-tetrahydro-1H-1-benzazepin-2-one

To a solution of 3-iodo-2,3,4,5-tetrahydro-1H-1-benzazepin-2-one (4.50 g, 15.7 mmol) in N,N-dimethylformamide (20 mL) was added sodium azide (1.23 g, 18.8 mmol) and the reaction mixture was stirred at room temperature. Precipitate formed after 30 minutes. The reaction mixture was diluted with water (300 mL). More solids precipitated and the mixture was stirred for an additional 10 minutes. The solid was collected by filtration, washed with water (20 mL), and dried in vacuo. The crude product was dissolved in tetrahydrofuran (30 mL) and water (0.5 mL). Triphenylphosphine (4.50 g, 17.2 mmol) was added and the reaction mixture was stirred at room temperature for 3 hours. Solids were removed by filtration. The filtrate was dried over anhydrous sodium sulfate and concentrated to afford the title compound (2.00 g, 72%) as a white solid. LC-MS (Method E): m/z=177.0 [M+H]$^+$, 0.413 min.

Step 2: Preparation of (3S)-3-amino-2,3,4,5-tetrahydro-1H-1-benzazepin-2-one To a solution of 3-amino-2,3,4,5-tetrahydro-1H-1-benzazepin-2-one (1.85 g, 11.0 mmol) in isopropanol (200 mL) at 70° C. was added L-pyroglutamic acid (1.42 g, 11.0 mmol) followed by 2-hydroxy-5-nitrobenzaldehyde (0.06 g, 0.33 mmol). The reaction mixture was stirred at 70° C. for 4 days. After cooling to room temperature, the solid was collected by filtration, rinsed with isopropanol and the filtrate was basified with ammonium hydroxide (28%, 10 mL). The resulting solution was extracted with dichloromethane (4×100 mL). The combined organic layers were washed with brine, dried over anhydrous sodium sulfate and concentrated to afford the title compound (0.91 g, 49%) as a white solid. LC-MS (Method E): m/z=177.0 [M+H]$^+$, 0.421 min.

Step 3: Preparation of benzyl N-((3S)-2-oxo-2,3,4,5-tetrahydro-1H-1-benzazepin-3-yl)carbamate A solution of potassium carbonate (2.00 g, 15 mmol) in water (4 mL) was added to a solution of (3S)-3-amino-2,3,4,5-tetrahydro-1H-1-benzazepin-2-one (0.5 g, 3 mmol) in dichloromethane (30 mL) and then benzyl chloroformate (0.77 g, 4.5 mmol) was added. The reaction mixture was stirred at room temperature for 16 hours. The organic layer was separated, washed with brine, dried over anhydrous sodium sulfate, filtered and concentrated under vacuum to afford the title compound (0.87 g, 99%) as a white solid. LC-MS (Method E): m/z=311.0 [M+H]$^+$, 0.838 min.

Step 4: Preparation of benzyl N-((3S)-2-sulfanylidene-2,3,4,5-tetrahydro-1H-1-benzazepin-3-yl)carbamate Lawesson's reagent (1.05 g, 2.6 mmol) was added to a solution of benzyl N-((3S)-2-oxo-2,3,4,5-tetrahydro-1H-1-benzazepin-3-yl)carbamate (0.80 g, 2.6 mmol) in tetrahydrofuran (40 mL) and the reaction mixture was stirred under a nitrogen atmosphere for 16 hours at room temperature. The precipitate was removed by filtration. The filtrate was concentrated under reduced pressure. The resulting residue was diluted with water (50 mL) and extracted with ethyl acetate (3×50 mL). The combined organic layers were washed with brine, dried over sodium sulfate, filtered and concentrated under reduced pressure to give the crude title compound (0.82 g, 98%) as a white solid. LC-MS (Method E): m/z=349.1 [M+Na]$^+$, 0.946 min.

Step 5: Preparation of benzyl N-((3S)-2-((2,2-dimethoxyethyl)amino)-4,5-dihydro-3H-1-benzazepin-3-yl)carbamate 2,2-Dimethoxyethanamine (1.06 g, 10.1 mmol) was added to a mixture of benzyl N-((3S)-2-sulfanylidene-2,3,4,5-tetrahydro-1H-1-benzazepin-3-yl)carbamate (0.81 g, 2.5 mmol) and mercury dichloride (0.89 g, 3.3 mmol) in tetrahydrofuran (25 mL). The resulting mixture was heated for 20 minutes at 55° C. After cooling to room temperature, the solids were removed by filtration and the filtrate was concentrated under reduced pressure. The resulting residue was diluted with water (20 mL) and extracted with dichloromethane (3×100 mL). The combined organic layers were washed with brine, dried over anhydrous sodium sulfate and concentrated under reduced pressure to give the title compound (0.89 g, 90%) as a light yellow solid. LC-MS (Method C): m/z=398.2 [M+H]$^+$, 1.182 min.

Step 6: Preparation of (S)-benzyl (5,6-dihydro-4H-benzo[f]imidazo[1,2-a]azepin-4-yl)carbamate A solution of benzyl N-((3S)-2-((2,2-dimethoxyethyl)amino)-4,5-dihydro-3H-1-benzazepin-3-yl)carbamate (0.85 g, 3 mmol) in formic acid (8 mL, 96%) was heated for 2 hours at 100° C. The black sediment was removed by filtration and the filtrate was concentrated under reduced pressure. The resulting residue was diluted with water (50 mL), basified with aqueous sodium hydroxide (1 N, 30 mL) and extracted with ethyl acetate (3×50 mL). The combined organic layers were washed with brine, dried over anhydrous sodium sulfate, filtered and concentrated under reduced pressure. The residue was purified by column chromatography (ethyl acetate/petroleum ether, 1/3) to afford the title compound (0.68 g, 95%) as a white solid. LC-MS (Method E): m/z=334.0 [M+H]$^+$, 0.671 min.

Step 7: Preparation of (S)-5,6-dihydro-4H-benzo[f]imidazo[1,2-a]azepin-4-amine A solution of (S)-benzyl (5,6-dihydro-4H-benzo[f]imidazo[1,2-a]azepin-4-yl)carbamate (0.68 g, 2 mmol) in ethanol (20 mL) was aged overnight in the presence of palladium on carbon (10%, 0.5 g) under an hydrogen atmosphere (2-3 atm). The reaction mixture was filtered through Celite and the filtrate was concentrated under reduced pressure to afford the title compound (0.40 g, 99%) as a yellow oil. LC-MS (Method C): m/z=200.1 [M+H]$^+$, 0.915 min.

Step 8: Preparation of (S)-5-benzyl-N-(5,6-dihydro-4H-benzo[f]imidazo[1,2-a]azepin-4-yl)isoxazole-3-carboxamide The crude product obtained using Amide Coupling Procedure C was purified by Prep-HPLC with the following conditions: Column, XBridge Prep C18 OBD Column, 5 µm, 19×150 mm; mobile phase, water (0.1% formic acid) and ACN (45.0% ACN to 70.0% over 7 min); Detector, UV 254/220 nm to afford the title compound. $^1$H NMR (300 MHz, DMSO-d$_6$) δ 9.00 (d, J=7.8 Hz, 1H), 7.49 (d, J=1.5 Hz, 1H), 7.46-7.41 (m, 3H), 7.40-7.21 (m, 6H), 6.96 (d, J=1.5 Hz, 1H), 6.53 (s, 1H), 4.80 (dd, J=10.2, 7.5 Hz, 1H), 4.18 (s, 2H), 2.72 (dd, J=11.7, 6.0 Hz, 1H), 2.45-2.27 (m, 3H). LC-MS (Method O): m/z=385.0 [M+H]$^+$, 1.587 min.

Example 31 and 34: 5-benzyl-N-((3R,4R)-4-fluoro-1-methyl-2-oxo-2,3,4,5-tetrahydro-1H-benzo[b]azepin-3-yl)-4H-1,2,4-triazole-3-carboxamide and 5-benzyl-N-((3S,4S)-4-fluoro-1-methyl-2-oxo-2,3,4,5-tetrahydro-1H-benzo[b]azepin-3-yl)-4H-1,2,4-triazole-3-carboxamide (31); and 5-benzyl-N-((3R,4S)-4-fluoro-1-methyl-2-oxo-2,3,4,5-tetrahydro-1H-benzo[b]azepin-3-yl)-4H-1,2,4-triazole-3-carboxamide and 5-benzyl-N-((3S,4R)-4-fluoro-1-methyl-2-oxo-2,3,4,5-tetrahydro-1H-benzo[b]azepin-3-yl)-4H-1,2,4-triazole-3-carboxamide (34)

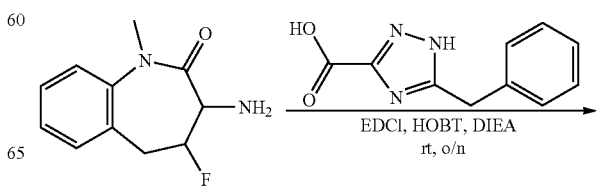

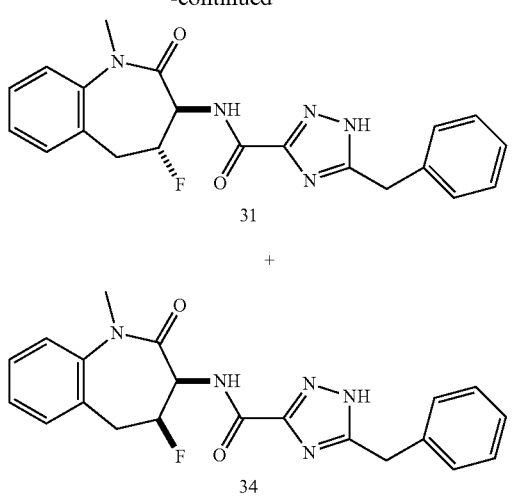

31

+

34

Example 32: (S)-5-benzyl-N-(9-chloro-5-methyl-4-oxo-2,3,4,5-tetrahydrobenzo[b][1,4]oxazepin-3-yl)-4H-1,2,4-triazole-3-carboxamide

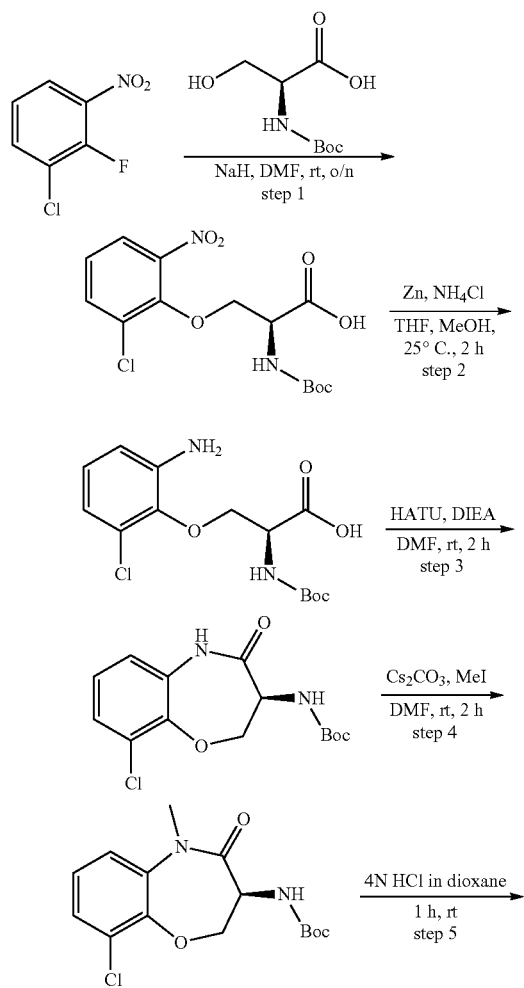

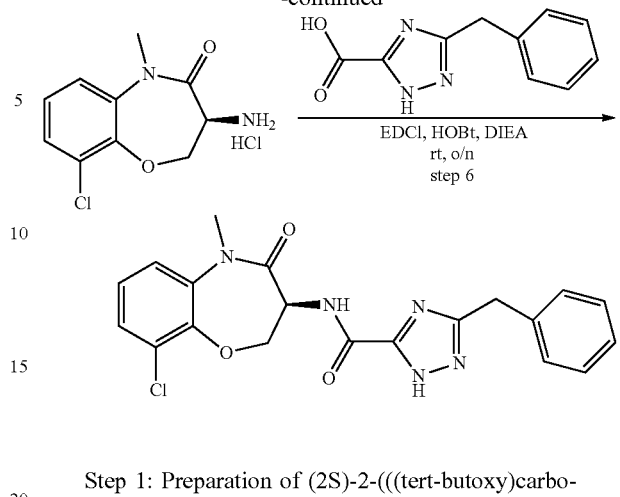

Step 1: Preparation of (2S)-2-(((tert-butoxy)carbonyl)amino)-3-(2-chloro-6-nitrophenoxy)propanoic acid Sodium hydride (60%, 0.39 g, 97.6 mmol) was added to a solution of (S)-2-(tert-butoxycarbonylamino)-3-hydroxypropanoic acid (10.0 g, 48.8 mmol) in N,N-dimethylformamide (50 mL) under nitrogen atmosphere. After stirring for 2 hours at 0° C., 1-chloro-2-fluoro-3-nitrobenzene (8.6 g, 48.8 mmol) was added. The reaction mixture was stirred overnight at room temperature, quenched with hydrochloric acid (0.5 M, 50 mL) and extracted with ethyl acetate (3×50 mL). The combined organic layers were washed with brine, dried over anhydrous sodium sulfate, filtered and concentrated under reduced pressure. The resulting residue was purified by reverse phase column chromatography using an RP-C18 column (acetonitrile/water, 7/3) to afford the title compound (5.5 g, 31%) as a yellow solid. LC-MS (Method G): m/z=361.0 [M+H]$^+$, 0.665 min.

Step 2: Preparation of (2S)-3-(2-amino-6-chlorophenoxy)-2-(((tert-butoxy)carbonyl)amino)propanoic acid Zinc (8.13 g, 125 mmol) and ammonium chloride (6.70 g, 125 mmol) were added to a stirred solution of (2S)-2-(((tert-butoxy)carbonyl)amino)-3-(2-chloro-6-nitrophenoxy)propanoic acid (4.5 g, 12.5 mmol) in methanol/tetrahydrofuran (100 mL, 1/1). The resulting mixture was stirred for 2 hours at 25° C. Solids were removed by filtration and the filtrate was concentrated under reduced pressure to afford the title compound (4 g crude) as a white solid, which was used directly in the next step without further purification. LC-MS (Method G): m/z=331.0 [M+H]$^+$, 0.704 min.

Step 3: Preparation of tert-butyl N-((3S)-9-chloro-4-oxo-2,3,4,5-tetrahydro-1,5-benzoxazepin-3-yl)carbamate 2-(7-Aza-1H-benzotriazole-1-yl)-1,1,3,3-tetramethyluronium hexafluorophosphate (1.1 g, 2.91 mmol) and ethyldiisopropylamine (0.94 g, 7.26 mmol) were added to a stirred solution of (2S)-3-(2-amino-6-chlorophenoxy)-2-(((tert-butoxy)carbonyl)amino)propanoic acid (0.80 g, 2.42 mmol) in N,N-dimethylformamide (10 mL). After stirring for 2 hours at room temperature, the reaction mixture was diluted with water (50 mL) and extracted with ethyl acetate (3×40 mL). The combined organic layers were washed with brine, dried over anhydrous sodium sulfate, filtered and concentrated under reduced pressure. The residue was purified by column chromatography (ethyl acetate/petroleum ether, 1/6) to afford the title compound (0.18 g, 24%) as a yellow solid. LC-MS (Method G): m/z=313.0 [M+H]⁺, 1.006 min.

Step 4: Preparation of tert-butyl N-((3S)-9-chloro-5-methyl-4-oxo-2,3,4,5-tetrahydro-1,5-benzoxazepin-3-yl)carbamate Iodomethane (82 mg, 0.58 mmol) was added dropwise to a stirred mixture of tert-butyl N-((3S)-9-chloro-4-oxo-2,3,4,5-tetrahydro-1,5-benzoxazepin-3-yl)carbamate (180 mg, 0.58 mmol) and cesium carbonate (188 mg, 0.58 mmol) in N,N-dimethylformamide (10 mL). After stirring for 2 hours at room temperature, the reaction mixture was quenched with water (50 mL) and extracted with ethyl acetate (3×50 mL). The combined organic layers were washed with brine, dried over anhydrous sodium sulfate, filtered and concentrated under reduced pressure. The residue was purified by column chromatography (ethyl acetate/petroleum ether, 1/6) to afford the title compound (120 mg, 64%) as a white solid. LC-MS (Method G): m/z=327.0 [M+H]⁺, 1.045 min.

Step 5: Preparation of (3S)-3-amino-9-chloro-5-methyl-2,3,4,5-tetrahydro-1,5-benzoxazepin-4-one hydrochloride tert-butyl N-((3S)-9-chloro-5-methyl-4-oxo-2,3,4,5-tetrahydro-1,5-benzoxazepin-3-yl)carbamate (120 mg, 0.37 mmol) was added to a solution of hydrogen chloride in dioxane (4 M, 10 mL). The reaction mixture was stirred for 1 hour at room temperature and concentrated under reduced pressure to afford the title compound (83 mg crude) as a white solid. LC-MS (Method G): m/z=227.0 [M+H]⁺, 0.772 min.

Step 6: Preparation of (S)-5-benzyl-N-(9-chloro-5-methyl-4-oxo-2,3,4,5-tetrahydrobenzo[b][1,4]oxazepin-3-yl)-4H-1,2,4-triazole-3-carboxamide The crude product obtained using Amide Coupling Procedure C was purified by Prep-HPLC with the following conditions: Column, Xbridge Phenyl OBD Column, 5 μm, 19×150 mm; mobile phase, water (10 mmol/L NH₄HCO₃) and ACN (50.0% ACN to 70.0% over 7 min); Detector, UV 254 & 220 nm to afford the title compound. ¹H NMR (400 MHz, CD₃OD) δ 7.44-7.20 (m, 8H), 4.98 (dd, J=15.2, 10.0 Hz, 1H), 4.68 (dd, J=13.2, 10.0 Hz, 1H), 4.46 (dd, J=15.2, 13.2 Hz, 1H), 4.17 (s, 2H), 3.42 (s, 3H). LC-MS (Method Q): m/z=412.2 [M+H]⁺, 1.336 min.

Example 33: (S)-1-benzyl-N-(5-methyl-4-oxo-2,3,4,5-tetrahydrobenzo[b][1,4]oxazepin-3-yl)azetidine-3-carboxamide

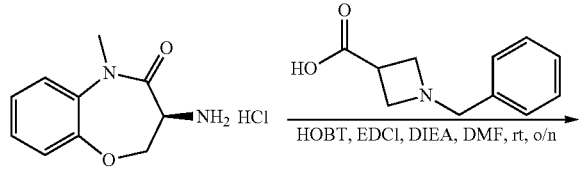

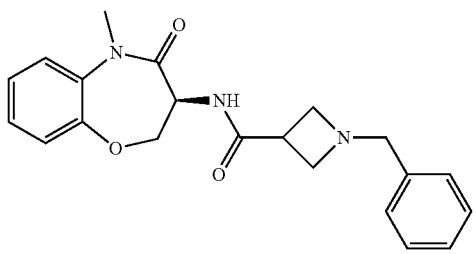

The crude product obtained using Amide Coupling Procedure C was purified by Prep-HPLC with the following conditions: Column, Xbridge Prep C18 OBD Column, 5 μm, 19×150 mm; mobile phase, water (10 mmol/L NH₄HCO₃) and ACN (30.0% ACN to 60.0% over 7 min); Detector, UV 254 & 220 nm to afford the title compound. ¹H NMR (300 MHz, CDCl₃) δ 7.29 (s, 4H), 7.19 (m, 4H), 7.06 (d, J=6.9 Hz, 1H), 4.95-4.80 (m, 1H), 4.67 (dd, J=9.6, 7.5 Hz, 1H), 4.14 (dd, J=11.1, 9.6 Hz, 1H), 3.65 (s, 2H), 3.57 (s, 2H), 3.51 (s, 3H), 3.34 (m, 2H), 3.22-3.02 (m, 1H). LC-MS (Method O): m/z=365.9 [M+H]⁺, 1.215 min.

Example 35: (S)—N-(5-methyl-4-oxo-2,3,4,5-tetrahydrobenzo[b][1,4]oxazepin-3-yl)-5-(1-phenylcyclopropyl)-4H-1,2,4-triazole-3-carboxamide

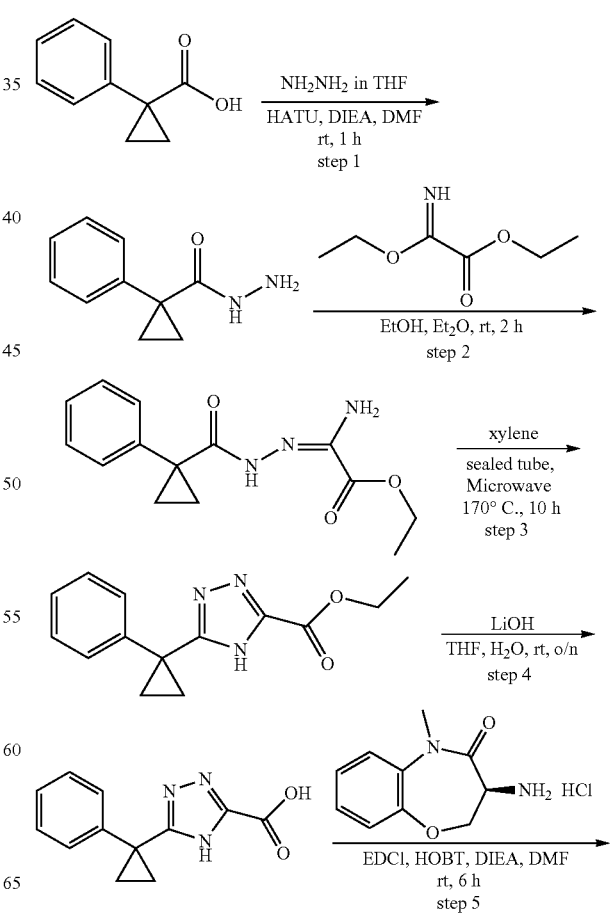

-continued

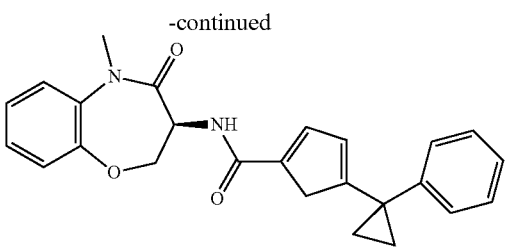

Step 1: Preparation of 1-phenylcyclopropane-1-carbohydrazide

A solution of hydrazine in tetrahydrofuran (1 M, 30 mL) was added to a solution of 1-phenylcyclopropane-1-carboxylic acid (0.48 g, 3.00 mmol), 2-(7-aza-1H-benzotriazole-1-yl)-1,1,3,3-tetramethyluronium hexafluorophosphate (1.37 g, 3.60 mmol) and ethyldiisopropylamine (1.16 g, 8.98 mmol) in N,N-dimethylformamide (10 mL). After stirring for 1 hour at room temperature, the reaction mixture was diluted with water (20 mL), and extracted with ethyl acetate (3×20 mL). The combined organic layers were washed with brine, dried over anhydrous sodium sulfate, filtered and concentrated under reduced pressure. The residue was purified by column chromatography (ethyl acetate/petroleum ether, 1/2) to afford the title compound (0.53 g, 98%) as a yellow oil. LC-MS (Method R: m/z=177.2 [M+H]$^+$, 0.670 min.

Step 2: Preparation of ethyl 2-amino-2-(((1-phenylcyclopropyl)formamido)imino)acetate Ethyl 2-ethoxy-2-iminoacetate (452 mg, 3.11 mmol) was added to a stirred solution of 1-phenylcyclopropane-1-carbohydrazide (528 mg, 3.00 mmol) in ethanol/ether (12 mL, 1/3). The reaction mixture was stirred for 2 hours at room temperature. The yellow solid was collected by filtration to afford the title compound (300 mg, 36%). LC-MS (Method S: m/z=276.2 [M+H]$^+$, 0.663 min.

Step 3: Preparation of ethyl 5-(1-phenylcyclopropyl)-4H-1,2,4-triazole-3-carboxylate A solution of ethyl 2-amino-2-(((1-phenylcyclopropyl)formamido)imino)acetate (275 mg, 1.00 mmol) in xylene (10 mL) was irradiated with microwave radiation for 10 hours at 170° C. The reaction mixture was concentrated under reduced pressure. The residue was purified by column chromatography (ethyl acetate/petroleum ether, 1/4) to afford the title compound (100 mg, 39%) as a yellow solid. LC-MS (Method C): m/z=258.1 [M+H]$^+$, 1.641 min.

Step 4: Preparation of 5-(1-phenylcyclopropyl)-4H-1,2,4-triazole-3-carboxylic acid A solution of lithium hydroxide (28 mg, 1.17 mmol) in water (1 mL) was added into a solution of ethyl 5-(1-phenylcyclopropyl)-4H-1,2,4-triazole-3-carboxylate (100 mg, 0.39 mmol) in tetrahydrofuran (3 mL) and the resulting mixture was stirred overnight at room temperature. After adjusting the pH to 6-7 with aqueous hydrochloride acid (1 N, 20 mL), the reaction mixture was extracted with ethyl acetate (3×10 mL). The combined organic layers were washed with brine, dried over anhydrous sodium sulfate, filtered and concentrated under reduced pressure to afford the title compound (90 mg crude) as a yellow solid, which was used directly in the next step without further purification. LC-MS (Method R): m/z=230.2 [M+H]$^+$, 0.530 min.

Step 5: Preparation of (S)—N-(5-methyl-4-oxo-2,3,4,5-tetrahydrobenzo[b][1,4]oxazepin-3-yl)-5-(1-phenylcyclopropyl)-4H-1,2,4-triazole-3-carboxamide The crude product obtained using Amide Coupling Procedure C was purified by Prep-HPLC with the following conditions: Column, Xbridge Phenyl OBD Column, 5 μm, 19×150 mm; mobile phase, water (10 mmol/L NH$_4$HCO$_3$) and ACN (50.0% ACN to 70.0% over 7 min); Detector, UV 254 & 220 nm to afford the title compound. $^1$H NMR (400 MHz, CD$_3$OD) δ 7.44-7.20 (m, 9H), 4.99 (dd, J=11.6, 7.6 Hz, 1H), 4.58 (dd, J=9.6, 7.6 Hz, 1H), 4.39 (dd, J=11.6, 10.0 Hz, 1H), 3.57 (s, 3H), 1.67-1.56 (m, 2H), 1.46-1.29 (m, 2H). LC-MS (Method D): m/z=404.1 [M+H]$^+$, 1.966 min.

Example 36: 5-benzyl-N-(1-methyl-2-oxo-2,3,4,5-tetrahydro-1H-benzo[4,5]imidazo[1,2-a][1,3]diazepin-3-yl)isoxazole-3-carboxamide

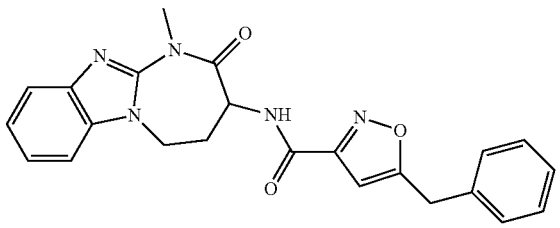 [SMILES: CN1C(=O)C(NC(=O)c2cc(Cc3ccccc3)on2)CCn2c1nc1ccccc12]

Example 37: (R)-5-benzyl-N-(4,4-difluoro-1-methyl-2-oxo-2,3,4,5-tetrahydro-1H-benzo[b]azepin-3-yl)-4H-1,2,4-triazole-3-carboxamide

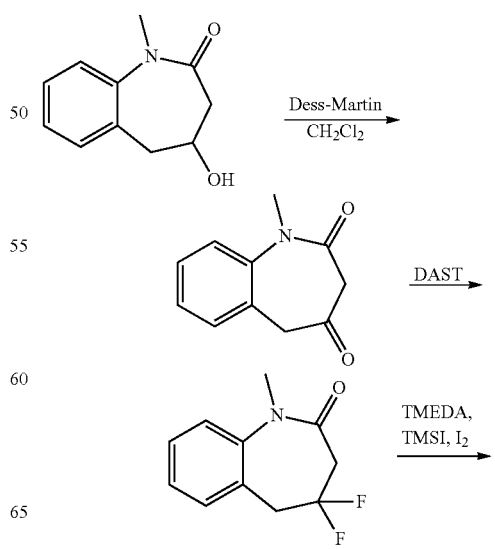

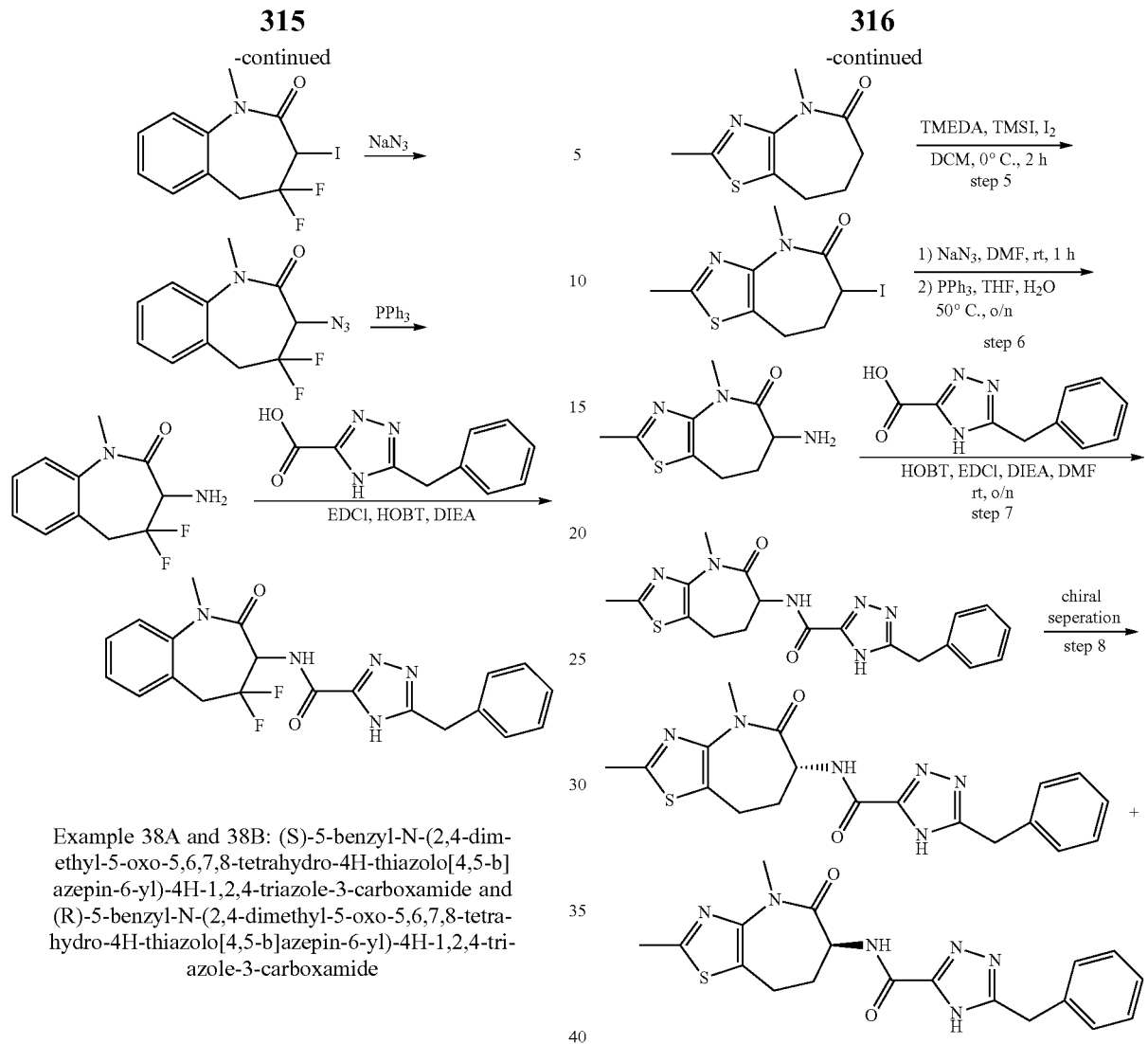

Example 38A and 38B: (S)-5-benzyl-N-(2,4-dimethyl-5-oxo-5,6,7,8-tetrahydro-4H-thiazolo[4,5-b]azepin-6-yl)-4H-1,2,4-triazole-3-carboxamide and (R)-5-benzyl-N-(2,4-dimethyl-5-oxo-5,6,7,8-tetrahydro-4H-thiazolo[4,5-b]azepin-6-yl)-4H-1,2,4-triazole-3-carboxamide

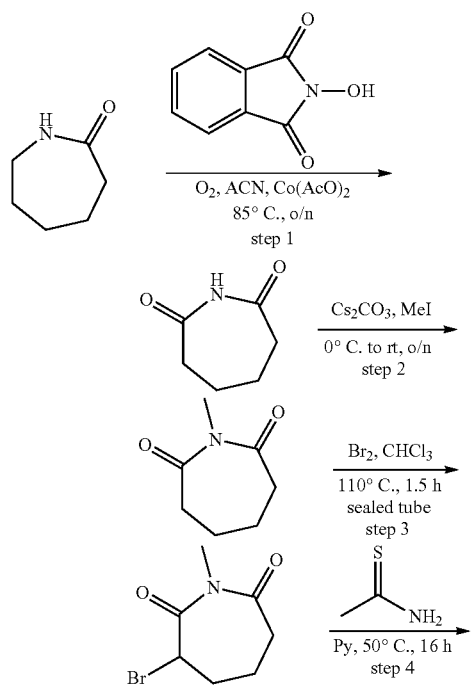

Step 1: Preparation of azepane-2,7-dione

A stirring solution of azepan-2-one (11.3 g, 100 mmol), 2-hydroxyisoindoline-1,3-dione (1.63 g, 10 mmol), and cobalt acetate (88.5 mg, 0.5 mmol) in acetonitrile (100 mL) was flushed with oxygen (balloon). The reaction mixture was heated overnight at 85° C. under an oxygen atmosphere. The solids were removed by filtration and the filtrate was concentrated under vacuum. The residue was purified by column chromatography (ethyl acetate/petroleum ether, 1/3) to afford the title compound (3.70 g, 29.1%) as a white solid. LC-MS (Method C): m/z=128.2 [M+H]$^+$, 0.683 min.

Step 2: Preparation of 1-methylazepane-2,7-dione

Iodomethane (1.68 g, 11.8 mmol) was added dropwise to a stirring mixture of azepane-2,7-dione (1.50 g, 11.8 mmol) and cesium carbonate (3.85 g, 5.0 mmol) in N,N-dimethylformamide (25 mL) at 0° C. The reaction mixture was stirred overnight at room temperature, quenched by the addition of water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (1.1 g, 66.1%) as a yellow oil. LC-MS (Method C): m/z=142.1 [M+H]+, 0.863 min.

Step 3: Preparation of 3-bromo-1-methylazepane-2,7-dione

Bromine (632 mg, 4.00 mmol) was added to a stirring solution of 1-methylazepane-2,7-dione (564 mg, 4.0 mmol) in chloroform (10 mL). The reaction mixture was stirred at 110° C. for 1.5 hours in a sealed tube. The reaction mixture was concentrated under high vacuum to afford the title compound (600 mg crude) as a brown oil. LC-MS (Method C): m/z=220.1 [M+H]+, 0.940 min.

Step 4: Preparation of 2,4-dimethyl-7,8-dihydro-4H-thiazolo[4,5-b]azepin-5(6H)-one Ethanethioamide (300 mg, 4.0 mmol) was added to a solution of 3-bromo-1-methylazepane-2,7-dione (600 mg, 4.0 mmol) in pyridine (10 mL). The reaction mixture was stirred at 50° C. for 16 hours, quenched by the addition of water (20 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (70 mg, 9%) as a yellow solid. LC-MS (Method C): m/z=197.1 [M+H]+, 0.981 min.

Step 5: Preparation of 6-iodo-2,4-dimethyl-7,8-dihydro-4H-thiazolo[4,5-b]azepin-5(6H)-one $N^1,N^1,N^2,N^2$-tetramethylethane-1,2-diamine (124 mg, 1.07 mmol) was added to a stirring solution of 2,4-dimethyl-7,8-dihydro-4H-thiazolo[4,5-b]azepin-5(6H)-one (70 mg, 0.36 mmol) in dichloromethane (5 mL) at 0° C. followed by the addition of iodotrimethylsilane (214 mg, 1.07 mmol). The reaction mixture was stirred for 1 hour at 0° C. After adding iodine (137.2 mg, 0.54 mmol), the reaction mixture was stirred for another 2 hours at 0° C. and quenched with aqueous sodium thiosulfate (5%, 15 mL). The resulting solution was stirred for an additional 15 minutes and extracted with ethyl acetate (3×20 mL). The combined organic layers were washed with brine, dried over anhydrous sodium sulfate, filtered and concentrated under vacuum to afford the title compound (61 mg crude) as a yellow solid, which was used directly in the next step without further purification. LC-MS (Method R): m/z=323.2 [M+H]+, 0.820 min.

Step 6: Preparation of 6-amino-2,4-dimethyl-7,8-dihydro-4H-thiazolo[4,5-b]azepin-5(6H)-one To a solution of 6-iodo-2,4-dimethyl-7,8-dihydro-4H-thiazolo[4,5-b]azepin-5(6H)-one (61 mg, 0.19 mmol) in N,N-dimethylformamide (2 mL) was added sodium azide (37.1 mg, 0.57 mmol). The reaction mixture was stirred for 1 hour at room temperature and concentrated under reduced pressure. The residue was dissolved in tetrahydrofuran (3 mL) and water (1 mL) and triphenylphosphine (149.3 mg, 0.57 mmol) was added in one portion. The reaction mixture was stirred at 50° C. overnight, diluted with water (10 mL) and extracted with ethyl acetate (3×20 mL). The combined organic layers were washed with brine, dried over anhydrous sodium sulfate, filtered and concentrated under vacuum. The residue was purified by column chromatography (methanol/dichloromethane, 1/10) to afford the title compound (33 mg, 83%) as a yellow solid. LC-MS (Method C): m/z=212.1 [M+H]+, 0.735 min.

Step 7: Preparation of 5-benzyl-N-(2,4-dimethyl-5-oxo-5,6,7,8-tetrahydro-4H-thiazolo[4,5-b]azepin-6-yl)-4H-1,2,4-triazole-3-carboxamide The crude product obtained using Amide Coupling Procedure C was purified by Prep-HPLC with the following conditions: column: X bridge Prep C18, 19×150 mm, 5 μm; Mobile phase: Phase A: water (10 mmol/L NH$_4$HCO$_3$); Phase B: ACN (20% to 80% over 12 min); Detector, UV 220 & 254 nm to afford the title compound. LC-MS (Method R): m/z=397.1 [M+H]+, 1.095 min.

Step 8: Preparation of (R)-5-benzyl-N-(2,4-dimethyl-5-oxo-5,6,7,8-tetrahydro-4H-thiazolo[4,5-k]azepin-6-yl)-4H-1,2,4-triazole-3-carboxamide (First Eluting Isomer) and (S)-5-benzyl-N-(2,4-dimethyl-5-oxo-5,6,7,8-tetrahydro-4H-thiazolo[4,5-k]azepin-6-yl)-4H-1,2,4-triazole-3-carboxamide (Second Eluting Isomer)

The enantiomers of 5-benzyl-N-(2,4-dimethyl-5-oxo-5,6,7,8-tetrahydro-4H-thiazolo[4,5-b]azepin-6-yl)-4H-1,2,4-triazole-3-carboxamide (24 mg, 0.06 mmol) were separated by Prep-Chiral-HPLC with the following conditions: Column: Chiralpak IA, 2×25 cm, 5 μm; Mobile Phase A: hexanes, Mobile Phase B: EtOH; Flow rate: 15 mL/min; Gradient: 50% B to 50% B over 17.5 min; UV 220 & 254 nm; RT 1:10.18 min; RT 2: 15.13 min to afford the title compounds:

Example 38B (first eluting isomer): $^1$H NMR (400 MHz, Methanol-d$_4$) δ 7.36-7.25 (m, 5H), 4.73-4.69 (m, 1H), 4.18 (s, 2H), 3.39 (s, 3H), 3.05-2.88 (m, 2H), 2.73-2.64 (m, 4H), 2.36-2.27 (m, 1H). LC-MS (Method D): m/z=397.1 [M+H]+, 1.623 min.

Example 38A (second eluting isomer): $^1$H NMR (400 MHz, Methanol-d$_4$) δ 7.36-7.24 (m, 5H), 4.73-4.68 (m, 1H), 4.18 (s, 2H), 3.39 (s, 3H), 3.06-2.87 (m, 2H), 2.73-2.63 (m, 4H), 2.36-2.27 (m, 1H). LC-MS (Method D): m/z=397.1 [M+H]+, 1.623 min.

Example 39: (S)-5-benzyl-N-(1-methyl-2-oxo-8-(trifluoromethyl)-2,3,4,5-tetrahydro-1H-pyrrolo[1,2-a][1,3]diazepin-3-yl)-4H-1,2,4-triazole-3-carboxamide

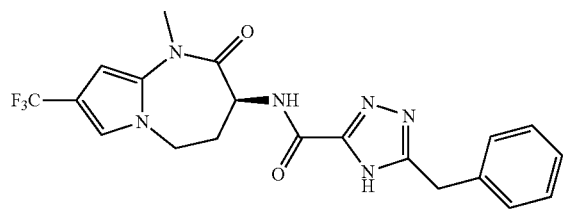 [SMILES: CN1C(=O)[C@@H](NC(=O)c2nnc(Cc3ccccc3)[nH]2)CCn2cc(C(F)(F)F)cc21]

Example 40: (S)-5-benzyl-N-(5-methyl-4-oxo-6-(trifluoromethyl)-2,3,4,5-tetrahydrobenzo[b][1,4]oxazepin-3-yl)-4H-1,2,4-triazole-3-carboxamide

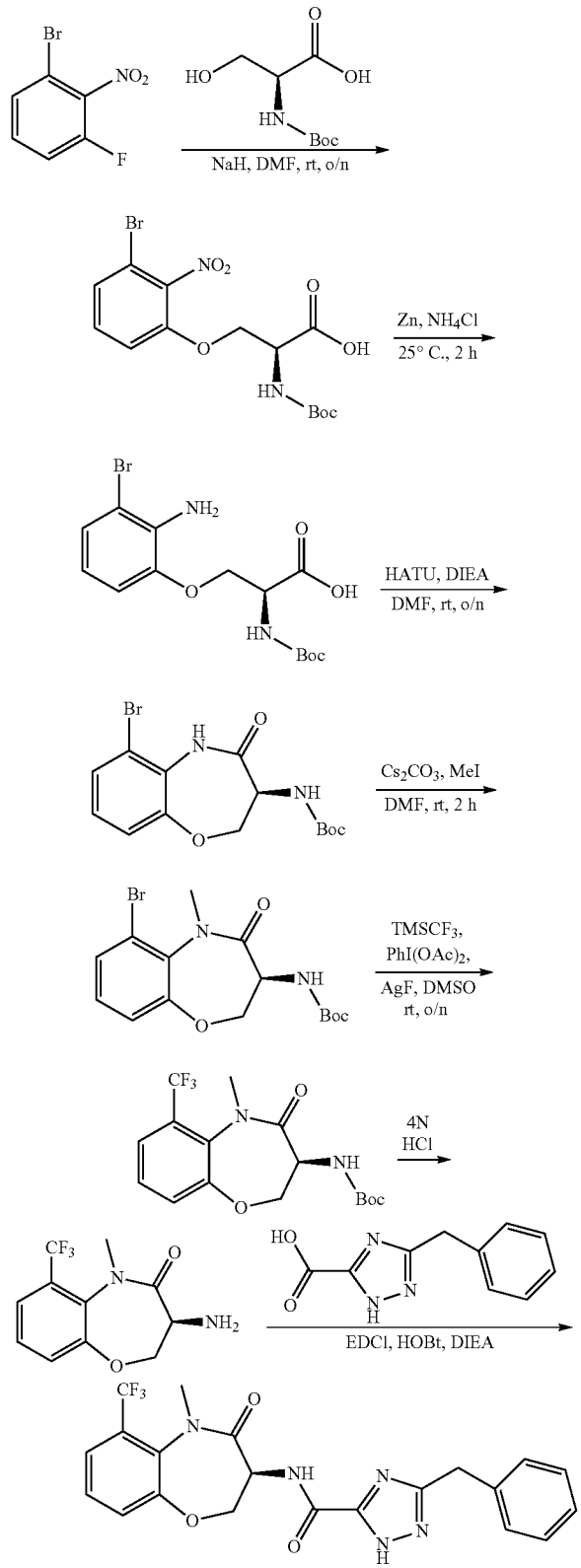

Example 41: (S)-5-benzyl-N-(1-methyl-2-oxo-1,2,3,4-tetrahydropyrido[3,4-b][1,4]oxazepin-3-yl)-4H-1,2,4-triazole-3-carboxamide

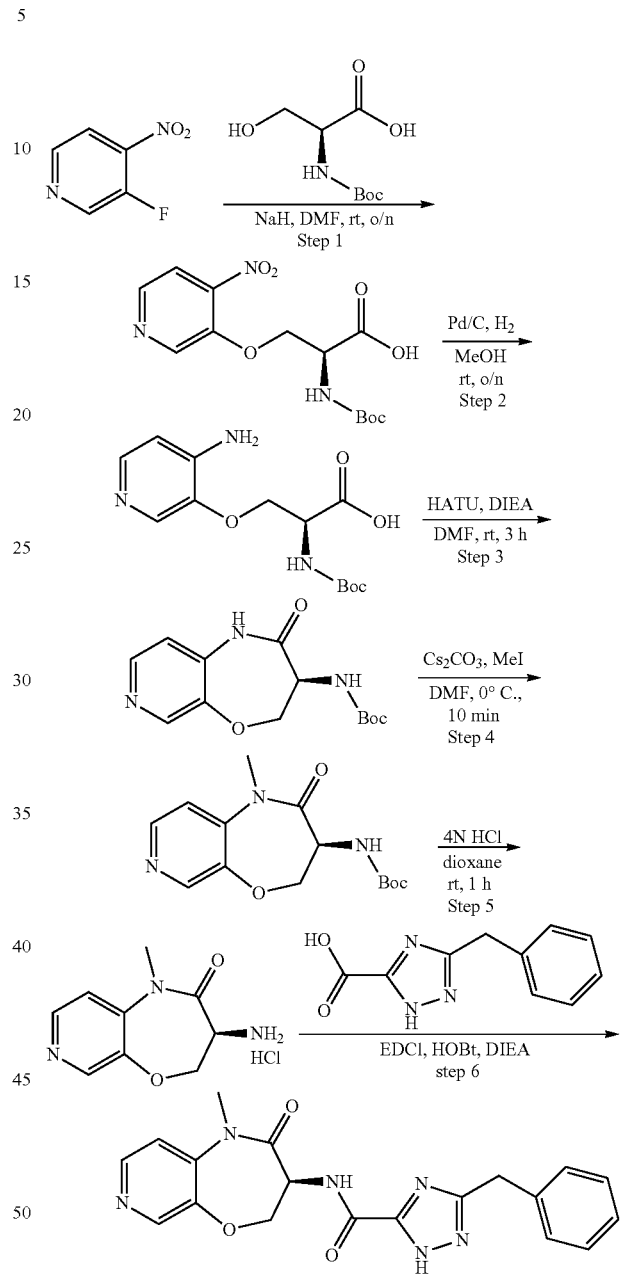

Step 1: Preparation of (2S)-2-(((tert-butoxy)carbonyl)amino)-3-((4-nitropyridin-3-yl)oxy)propanoic acid Sodium hydride (60%, 1.92 g, 80.1 mmol) was added to a stirred solution of (2S)-2-(tert-butoxycarbonylamino)-3-hydroxypropanoic acid (8.21 g, 40.0 mmol) in dimethyl formamide (30 mL) under nitrogen atmosphere at 0° C. After stirring for 2 hours at 0° C., a solution of 3-fluoro-4-nitropyridine (5.52 g, 40.0 mmol) in dimethyl formamide (10 mL) was added dropwise. The reaction mixture was stirred overnight at room temperature, quenched by the addition of water (10 mL), and extracted with ethyl acetate (3×20 mL). The combined organic layers were washed with brine, dried over anhydrous sodium sulfate, filtered and concentrated under reduced pressure. The residue was purified by reverse phase CombiFlash using a RP-C18 column (acetonitrile/water, 1/4) to afford the title compound (2.41 g, 18%) as a yellow solid. LC-MS (Method S): m/z=328.1 [M+H]$^+$, 0.829 min.

Step 2: Preparation of (2S)-34(4-aminopyridin-3-yl)oxy)-2-(((tert-butoxy)carbonyl)amino)propanoic acid (2S)-2-(((tert-butoxy)carbonyl)amino)-3-((4-nitropyridin-3-yl)oxy)propanoic acid (2.41 g, 7.34 mmol) in methanol (20 mL) was aged overnight at room temperature in the presence of palladium on carbon (10%, 345 mg) under a hydrogen atmosphere (2-3 atm). The reaction mixture was filtered through Celite and the filtrate was concentrated under reduced pressure to afford the title compound (1.8 g, 83%) as a yellow solid, which was used directly in the next step without further purification. LC-MS (Method S): m/z=298.1 [M+H]$^+$, 0.601 min.

Step 3: Preparation of tert-butyl N-((3S)-2-oxo-1H,2H,3H,4H-pyrido[3,4-b][1,4]oxazepin-3-yl)carbamate 2-(7-Aza-1H-benzotriazole-1-yl)-1,1,3,3-tetramethyluronium hexafluorophosphate (1.5 g, 4.04 mmol) and ethyldiisopropylamine (1.30 g, 10.1 mmol) were added to a stirred solution of (2S)-3-((4-aminopyridin-3-yl)oxy)-2-(((tert-butoxy)carbonyl)amino)propanoic acid (1.01 g, 3.37 mmol) in N,N-dimethylformamide (13 mL). After stirring for 3 hours at room temperature, the reaction mixture was diluted with water (15 mL), and extracted with ethyl acetate (3×15 mL). The combined organic layers were washed with brine, dried over anhydrous sodium sulfate, filtered and concentrated under reduced pressure. The resulting residue was purified by column chromatography (methanol/dichloromethane, 1/10) to afford the title compound (0.4 g, 83%) as a yellow solid. LC-MS (Method S): m/z=280.1 [M+H]$^+$, 0.604 min.

Step 4: Preparation of tert-butyl N-((3S)-1-methyl-2-oxo-1H,2H,3H,4H-pyrido[3,4-b][1,4]oxazepin-3-yl)carbamate Iodomethane (203 mg, 1.43 mmol) was added dropwise to a mixture of tert-butyl N-((3S)-2-oxo-1H,2H,3H,4H-pyrido[3,4-b][1,4]oxazepin-3-yl)carbamate (400 mg, 1.43 mmol) and cesium carbonate (467 mg, 1.43 mmol) in N,N-dimethylformamide (7 mL). After stirring for 10 minutes at 0° C., the reaction mixture was diluted with water (15 mL), and extracted with ethyl acetate (3×15 mL). The combined organic layers were washed with brine, dried over anhydrous sodium sulfate, filtered and concentrated under reduced pressure. The residue was purified by column chromatography (ethyl acetate/petroleum ether, 1/3) to afford the title compound (300 mg, 72%) as a yellow solid. LC-MS (Method S): m/z=294.1 [M+H]$^+$, 0.650 min.

Step 5: Preparation of (3S)-3-amino-1-methyl-1H,2H,3H,4H-pyrido[3,4-b][1,4]oxazepin-2-one hydrochloride A solution of hydrogen chloride in 1,4-dioxane (4 M, 5 mL, 20 mmol) was added to a solution of tert-butyl N-((3S)-1-methyl-2-oxo-1H,2H,3H,4H-pyrido[3,4-b][1,4]oxazepin-3-yl)carbamate (300 mg, 1.02 mmol) in 1,4-dioxane (7 mL). The reaction mixture was stirred for 1 hour at room temperature and concentrated to afford the title compound (215 mg, 92%) as a white solid. LC-MS (Method S): m/z=194.1 [M+H]$^+$, 0.184 min.

Step 6: Preparation of (S)-5-benzyl-N-(1-methyl-2-oxo-1,2,3,4-tetrahydropyrido[3,4-b][1,4]oxazepin-3-yl)-4H-1,2,4-triazole-3-carboxamide A solution of (3S)-3-amino-1-methyl-1H,2H,3H,4H-pyrido[3,4-b][1,4]oxazepin-2-one hydrochloride (115 mg, 0.50 mmol) in N,N-dimethylformamide (1 mL) was added to a stirring solution of 5-benzyl-2H-1,2,4-triazole-3-carboxylic acid (102 mg, 0.50 mmol), ethyldiisopropylamine (129 mg, 1.00 mmol), N$^1$-((ethylimino)methylene)-N$^3$,N$^3$-dimethylpropane-1,3-diamine hydrochloride (115 mg, 0.60 mmol) and 1-hydroxybenzotriazole (92 mg, 0.60 mmol) in N,N-dimethylformamide (5 mL). The reaction mixture was stirred overnight at room temperature and concentrated under reduced pressure. The residue was purified by Prep-HPLC with the following conditions: Column: XBridge Prep C18 OBD Column 19×150 mm 5 µm; Mobile Phase A: water (10 mmol/L NH$_4$HCO$_3$), Mobile Phase B: ACN; Flow rate: 30 mL/min; Gradient: 15% B to 45% B over 10 min; 254 nm. The collected fractions were combined and concentrated under reduced pressure to afford the title compound. $^1$H NMR (400 MHz, CDCl$_3$) δ 12.34 (s, 1H), 8.54-8.46 (m, 2H), 8.06 (d, J=7.3 Hz, 1H), 7.36-7.29 (m, 5H), 7.16 (d, J=5.2 Hz, 1H), 5.09 (m, 1H), 4.77 (dd, J=10.0, 3.2 Hz, 1H), 4.41 (dd, J=11.6, 10.0 Hz, 1H), 4.20 (s, 2H), 3.46 (s, 3H). LC-MS (Method T): m/z=379.2 [M+H]$^+$, 0.888 min.

Example 42: (S)-5-benzyl-N-(5-methyl-4-oxo-2,3,4,5-tetrahydropyrido[3,2-b][1,4]oxazepin-3-yl)-4H-1,2,4-triazole-3-carboxamide

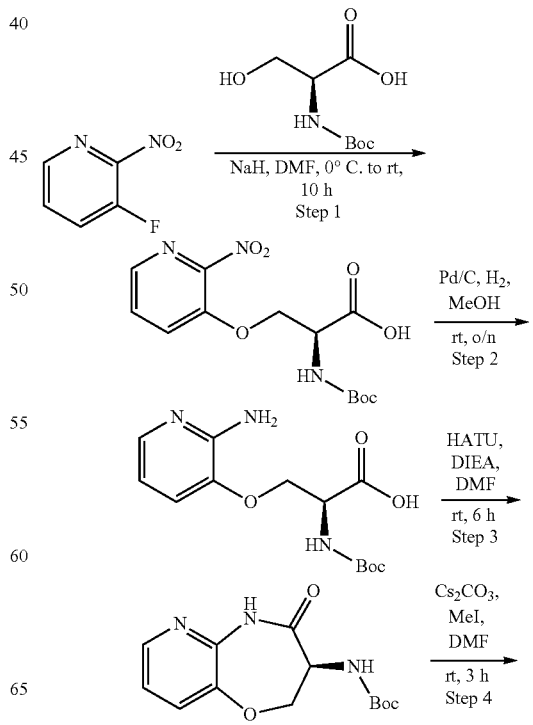

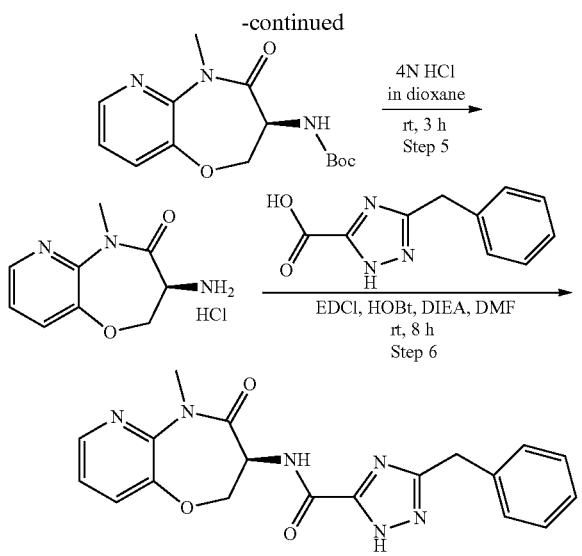

Step 1: Preparation of (2S)-2-(((tert-butoxy)carbonyl)amino)-3-((2-nitropyridin-3-yl)oxy)propanoic acid Sodium hydride (60%, 2 g, 50 mmol) was added into a stirring solution of (2S)-2-(tert-butoxycarbonylamino)-3-hydroxypropanoic acid (5 g, 25.0 mmol) in N,N-dimethylformamide (100 mL). The resulting mixture was stirred at 0° C. for 2 hours. 3-Fluoro-2-nitropyridine (3.6 g, 25.3 mmol) was added and the reaction mixture was stirred at room temperature for an additional 8 hours before quenching with hydrochloric acid (3 N, 5 mL). After adjusting the pH to 3-4 with hydrochloric acid (3 N, 20 mL), the resulting mixture was extracted with ethyl acetate (3×100 mL). The combined organic layers were washed with brine, dried over anhydrous sodium sulfate and concentrated under reduced pressure. The residue was purified by reversed phase chromatography with a RP-C18 column (acetonitrile/water, 1/2) to afford the title compound (3.2 g, 39%) as a light yellow oil. LC-MS (Method C): m/z=272.1 [M+H−(t-BuO)]$^+$, 1.269 min.

Step 2: Preparation of (2S)-3-((2-aminopyridin-3-yl)oxy)-2-(((tert-butoxy)carbonyl)amino)propanoic acid (2S)-2-(((tert-butoxy)carbonyl)amino)-3-((2-nitropyridin-3-yl)oxy)propanoic acid (0.45 g, 1.4 mmol) in methanol (20 mL) was aged overnight at room temperature in the presence of palladium on carbon (10%, 0.5 g) under hydrogen atmosphere (2-3 atm). The reaction mixture was filtered through Celite and the filtrate was concentrated under reduced pressure to afford the title compound (0.32 g, 78%) as a yellow oil. LC-MS (Method C): m/z=298.1 [M+H]$^+$, 0.982 min.

Step 3: Preparation of tert-butyl N-((3S)-4-oxo-2H,3H,4H,5H-pyrido[3,2-b][1,4]oxazepin-3-yl)carbamate N,N,N',N'-tetramethyl-O-(7-azabenzotriazol-1-yl)uronium hexafluorophosphate (0.73 g, 1.92 mmol) and N,N-diisopropylethylamine (0.25 g, 1.93 mmol) were added to a stirring solution of (2S)-3-((2-aminopyridin-3-yl)oxy)-2-(((tert-butoxy)carbonyl)amino)propanoic acid (0.45 g, 1.51 mmol) in N,N-dimethylformamide (5 mL). After stirring for 6 hours at room temperature, the reaction mixture was quenched by the addition of water (20 mL), and extracted with ethyl acetate (3×100 mL). The combined organic layers were washed with brine, dried over anhydrous sodium sulfate and concentrated under reduced pressure. The resulting residue was purified by column chromatography (methanol/dichloromethane, 1/10) to afford the title compound (0.11 g, 26%) as a white solid. LC-MS (Method C): m/z=280.1 [M+H]$^+$, 1.248 min.

Step 4: Preparation of tert-butyl N-((3S)-5-methyl-4-oxo-2H,3H,4H,5H-pyrido[3,2-b][1,4]oxazepin-3-yl)carbamate Iodomethane (50 mg, 0.35 mmol) was added dropwise to a stirring solution of tert-butyl N-((3S)-4-oxo-2H,3H,4H,5H-pyrido[3,2-b][1,4]oxazepin-3-yl)carbamate (100 mg, 0.36 mmol) and cesium carbonate (120 mg, 0.36 mmol) in N,N-dimethylformamide (5 mL). After stirring for 3 hours at room temperature, the reaction mixture was diluted with water (20 mL), and extracted with ethyl acetate (3×100 mL). The combined organic layers were washed with brine, dried over anhydrous sodium sulfate, filtered and concentrated under reduced pressure. The residue was purified by column chromatography (methanol/dichloromethane, 1/10) to afford the title compound (90 mg, 86%) as a white solid. LC-MS (Method C): m/z=294.1 [M+H]$^+$, 1.333 min.

Step 5: Preparation of (3S)-3-amino-5-methyl-2H,3H,4H,5H-pyrido-[3,2-b][1,4]oxazepin-4-one hydrochloride tert-butyl N-((3S)-5-methyl-4-oxo-2H,3H,4H,5H-pyrido[3,2-b][1,4]oxazepin-3-yl)carbamate (90 mg, 0.31 mmol) was added to a solution of hydrogen chloride in dioxane (4 M, 10 mL). The reaction mixture was stirred for 3 hours at room temperature and concentrated under reduced pressure to afford the title compound (65 mg, 93%) as a white solid, which was used directly in the next step without further purification. LC-MS (Method C): m/z=194.1 [M+H]$^+$, 0.847 min.

Step 6: Preparation of (S)-5-benzyl-N-(5-methyl-4-oxo-2,3,4,5-tetrahydropyrido[3,2-b][1,4]oxazepin-3-yl)-4H-1,2,4-triazole-3-carboxamide A solution of (3S)-3-amino-5-methyl-2H,3H,4H,5H-pyrido-[3,2-b][1,4]oxazepin-4-one hydrochloride (55 mg, 0.24 mmol) in N,N-dimethylformamide (1 mL) was added to a stirring solution of 5-benzyl-2H-1,2,4-triazole-3-carboxylic acid (80 mg, 0.40 mmol), 1-hydroxy-benzotriazole (70 mg, 0.53 mmol), N-(3-dimethylaminopropyl)-N'-ethylcarbodiimide hydrochloride (100 mg, 0.52 mmol) and N,N-diisopropylethylamine (160 mg, 1.21 mmol) in N,N-dimethylformamide (2 mL). After stirring for 8 hours at room temperature, the reaction mixture was quenched by the addition of water (20 mL), and extracted with ethyl acetate (3×50 mL). The combined organic layers were washed with brine, dried over anhydrous sodium sulfate, filtered and concentrated under reduced pressure. The resulting residue was purified by Prep-HPLC with the following conditions: Column, XBridge Shield RP18 OBD Column, 5 μm, 19×150 mm; mobile phase, water (0.1% formic acid) and ACN (30.0% ACN to 60.0% over 7 min); Detector, UV 254 & 220 nm to afford the title compound. $^1$H NMR (300 MHz, DMSO-$d_6$) δ 14.45 (s, 1H), 8.67 (d, J=7.2 Hz, 1H), 8.37 (dd, J=4.8, 1.8 Hz, 1H), 7.71 (dd, J=7.8, 1.5 Hz, 1H), 7.37-7.21 (m, 6H), 4.92-4.82 (m, 1H), 4.73 (dd, J=11.4, 9.6 Hz, 1H), 4.53 (dd, J=9.6, 7.5 Hz, 1H), 4.14 (s, 2H), 3.37 (s, 3H). LC-MS (Method D): m/z=379.1 [M+H]⁺, 1.611 min.

Example 43: 3-benzyl-N—((S)-5-methyl-4-oxo-2,3,4,5-tetrahydrobenzo[b][1,4]oxazepin-3-yl)cyclobutane-1-carboxamide

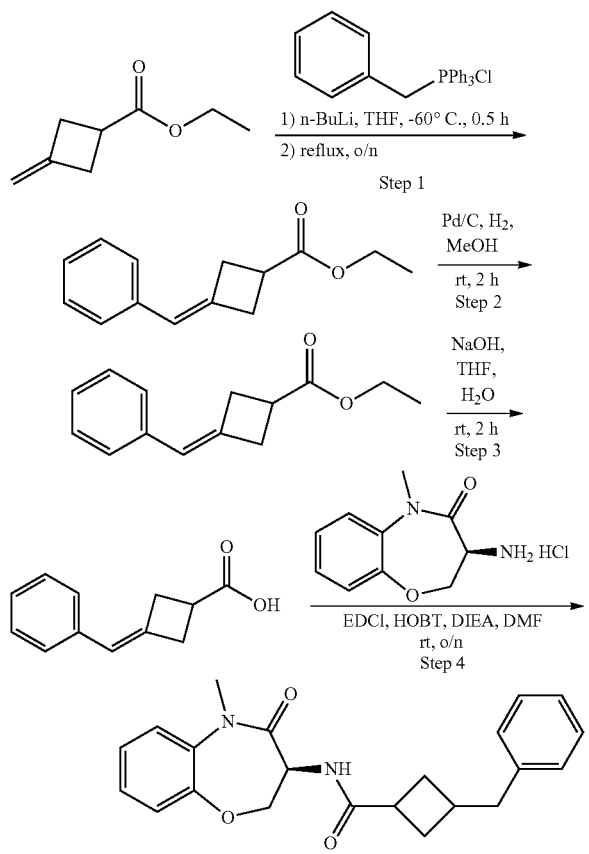

Step 1: Preparation of ethyl 3-(phenylmethylidene)cyclobutane-1-carboxylate

A solution of n-butyllithium in hexane (2.5 M, 3.4 mL, 8.5 mmol) was added dropwise to a suspension of benzyltriphenylphosphonium chloride (3.3 g, 8.5 mmol) in anhydrous tetrahydrofuran (50 mL) at −60° C. The resulting mixture was stirred at −60° C. for 0.5 hour and then allowed to warm to room temperature. Ethyl 3-oxocyclobutanecarboxylate (1.2 g, 8.5 mmol) was added and the reaction mixture was heated at reflux and stirred overnight. After cooling to room temperature, the reaction mixture was quenched with water (50 mL), and extracted with ethyl acetate (3×50 mL). The combined organic layers were washed with brine, dried over anhydrous sodium sulfate, filtered and concentrated under reduced pressure. The resulting residue was purified by column chromatography (ethyl acetate/petroleum ether, 1/20) to afford the title compound (0.14 g, 8%) as a light yellow oil. LC-MS (Method S): m/z=217.2 [M+H]⁺, 1.144 min.

Step 2: Preparation of ethyl 3-benzylcyclobutane-1-carboxylate

Ethyl 3-(phenylmethylidene)cyclobutane-1-carboxylate (130 mg, 0.6 mmol) in ethanol (5 mL) was hydrogenated in the presence of palladium on carbon (10%, 15 mg) under a hydrogen atmosphere. After stirring for 2 hours at room temperature, the reaction mixture was filtered through Celite and the filtrate was concentrated under reduced pressure to afford the title compound (100 mg crude) as a yellow oil, which was used directly in the next step without further purification. LC-MS (Method S): m/z=219.3 [M+H]⁺, 1.160 min.

Step 3: Preparation of 3-benzylcyclobutane-1-carboxylic acid

A solution of sodium hydroxide (60 mg, 1.5 mmol) in water (1 mL) was added into a solution of ethyl 3-benzylcyclobutane-1-carboxylate (100 mg, 0.5 mmol) in tetrahydrofuran (3 mL). After stirring for 2 hours at room temperature, the reaction mixture was diluted with water (10 mL), adjusted to pH=3 with aqueous hydrochloric acid (3 N, 10 mL) and extracted with ethyl acetate (3×10 mL). The combined organic layers were washed with brine, dried over anhydrous sodium sulfate and concentrated under reduced pressure to afford the crude title compound (85 mg, 97%) as a yellow oil. LC-MS (Method I): m/z=190.9 [M+H]⁺, 0.954 min.

Step 4: Preparation of 3-benzyl-N—((S)-5-methyl-4-oxo-2,3,4,5-tetrahydrobenzo[b][1,4]oxazepin-3-yl)cyclobutane-1-carboxamide The crude product obtained using Amide Coupling Procedure C was purified by Prep-HPLC with the following conditions: Column, Xbridge Prep C18 OBD Column, 5 μm, 19×150 mm; mobile phase, water (0.05% NH₃H₂O), ACN (25% ACN to 55% B over 7 min); detector, UV 254 & 220 nm to afford the title compound. ¹H NMR (400 MHz, CDCl₃) δ 7.29-7.13 (m, 9H), 6.41 (d, J=6.0 Hz, 1H), 4.93-4.86 (m, 1H), 4.69 (t, J=7.6 Hz, 1H), 4.12 (t, J=10.0 Hz, 1H), 3.44 (s, 3H), 2.88-2.69 (m, 3H), 2.48 (q, J=7.6 Hz, 1H), 2.35-2.24 (m, 2H), 2.09-1.91 (m, 2H). LC-MS (Method O): m/z=365.0 [M+H]⁺, 1.585 min.

Example 44: (S)-5-benzyl-N-(1-methyl-2-oxo-1,2,3,4-tetrahydrospiro[benzo[b]azepine-5,1'-cyclopropan]-3-yl)-4H-1,2,4-triazole-3-carboxamide

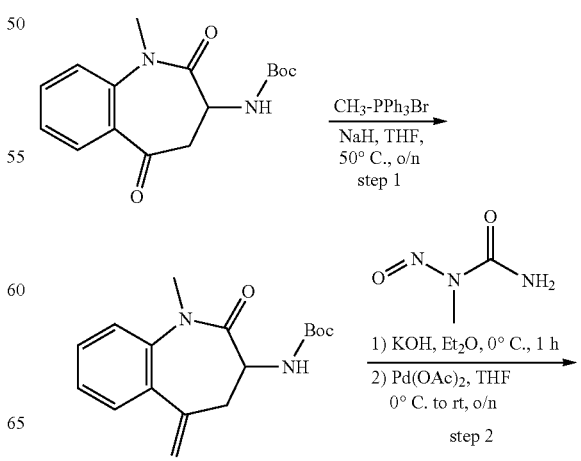

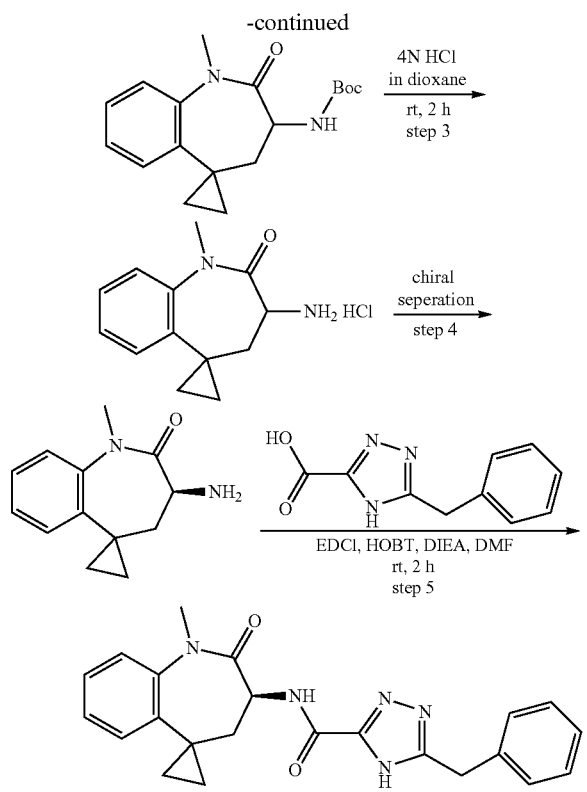

Step 1: Preparation of tert-butyl 1-methyl-5-methyl-ene-2-oxo-2,3,4,5-tetrahydro-1H-benzo[b]azepin-3-ylcarbamate To a mixture of methyltriphenylphosphonium bromide (4.4 g, 12.3 mmol) in tetrahydrofuran (10 mL) was added sodium hydride (60%, 0.30 g, 12.3 mmol). The resulting mixture was stirred for 1 hour at 50° C. under a nitrogen atmosphere. To this mixture a solution of tert-butyl 1-methyl-2,5-dioxo-2,3,4,5-tetrahydro-1H-benzo[b]azepin-3-ylcarbamate (1.50 g, 4.93 mmol) in tetrahydrofuran (20 mL) was added dropwise at 50° C. After stirring overnight at 50° C., the reaction mixture was quenched with saturated aqueous ammonium chloride (30 mL), and extracted with ethyl acetate (3×40 mL). The combined organic layers were washed with brine, dried over anhydrous sodium sulfate, filtered and concentrated under vacuum. The residue was purified by column chromatography (ethyl acetate/petroleum ether, 1/10) to afford the title compound (600 mg, 40%) as a yellow solid. LC-MS (Method C): m/z=303.2 [M+H]$^+$, 1.531 min.

Step 2: Preparation of tert-butyl N-[7-methyl-6-oxo-7-azatricyclo[6.4.0.0-[2,4]]dodeca-1(8),9,11-trien-5-yl]carbamate To a solution of potassium hydroxide (2.23 g, 39.7 mmol) in water (3.3 mL) was added a solution of 1-methyl-1-nitrosourea (2.05 g, 19.7 mmol) in ether (100 mL) dropwise at 0° C. The resulting mixture was stirred for 1 hour at 0° C. and then the organic phase was separated to get the solution of diazomethane (100 mL). To a solution of tert-butyl 1-methyl-5-methylene-2-oxo-2,3,4,5-tetrahydro-1H-benzo[b]azepin-3-ylcarbamate (0.6 g, 1.99 mmol) in tetrahydrofuran (5 mL) was added the solution of diazomethane (100 mL) dropwise, followed by adding a mixture of palladium diacetate (45 mg, 0.20 mmol) in tetrahydrofuran (1 mL) dropwise at 0° C. The reaction mixture was stirred overnight at room temperature. The solids were removed by filtration and the filtrate was concentrated under vacuum. The residue was purified by column chromatography (ethyl acetate/petroleum ether, 1/10) to afford the title compound (0.15 g, 24%) as a yellow solid. LC-MS (Method C): m/z=317.2 [M+H]$^+$, 1.531 min.

Step 3: Preparation of 3-amino-1-methyl-1,2,3,4-tetrahydrospiro[1-benzazepine-5,1-cyclopropane]-2-one hydrochloride A solution of hydrogen chloride in 1,4-dioxane (4 N, 10 mL) was added to a solution of tert-butyl N-[7-methyl-6-oxo-7-azatricyclo[6.4.0.0-[2,4]]dodeca-1(8),9,11-trien-5-yl] carbamate (150 mg, 0.60 mmol) in 1,4-dioxane (2 mL). The reaction mixture was stirred at room temperature for 2 hours and concentrated under vacuum to afford the title compound (95 mg crude) as a yellow solid. LC-MS (Method K): m/z=217.2 [M+H]$^+$, 0.635 min.

Step 4: Preparation of (3S)-3-amino-1-methyl-1,2,3,4-tetrahydrospiro[1-benzazepine-5,1-cyclopropane]-2-one (First Eluting Isomer) and (3R)-3-amino-1-methyl-1,2,3,4-tetrahydrospiro[1-benzazepine-5,1-cyclopropane]-2-one (Second Eluting Isomer)

3-Amino-1-methyl-1,2,3,4-tetrahydrospiro[1-benzazepine-5,1-cyclopropane]-2-one hydrochloride (90 mg crude) was separated by Prep-Chiral-HPLC with the following conditions: Column: Phenomenex Lux Cellulose-4, AXIA Packed, 2.12×25 cm, 5 μm; Mobile Phase A: hexanes (0.1% DEA), Mobile Phase B: EtOH; Flow rate: 20 mL/min; Gradient: 35% B to 35% B over 17.5 min; 220/254 nm; RT1: 11.24 min; RT2: 13.82 min to afford the title compounds.
First eluting isomer: (36 mg, 38%) as a white solid. LC-MS (Method D): m/z=217.2 [M+H]$^+$, 1.096 min.
Second eluting isomer: (46 mg, 48%) as a white solid. LC-MS (Method D): m/z=217.2 [M+H]$^+$, 1.089 min.

Step 5: Preparation of (S)-5-benzyl-N-(1-methyl-2-oxo-1,2,3,4-tetrahydrospiro[benzo[b]azepine-5,1'-cyclopropan]-3-yl)-4H-1,2,4-triazole-3-carboxamide The crude product obtained using Amide Coupling Procedure C was purified by Prep-HPLC with the following conditions: Column, Xbridge Phenyl OBD Column, 5 μm, 19×150 mm; mobile phase, water (10 mmol/L NH$_4$HCO$_3$) and ACN (50.0% ACN to 70.0% in 7 min); Detector, UV 254 & 220 nm to afford the title compound. $^1$H NMR (300 MHz, DMSO-d$_6$) δ 8.20 (d, J=7.5 Hz, 1H), 7.45-7.32 (m, 2H), 7.35-7.20 (m, 7H), 4.46-4.36 (m, 1H), 4.07 (s, 2H), 3.30 (s, 3H), 2.71-2.65 (m, 1H), 1.57 (t, J=12.6 Hz, 1H), 1.10-1.07 (m, 1H), 0.75-0.63 (m, 2H), 0.42-0.37 (m, 1H). LC-MS (Method D): m/z=402.2 [M+H]$^+$, 1.871 min.

Example 45: (S)-1-benzyl-4-fluoro-5-methyl-N-(4-oxo-2,3,4,5-tetrahydrobenzo[b][1,4]oxazepin-3-yl)-1H-pyrazole-3-carboxamide

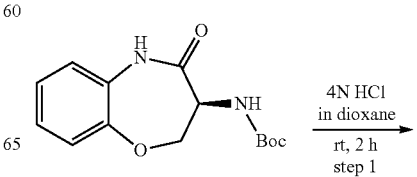

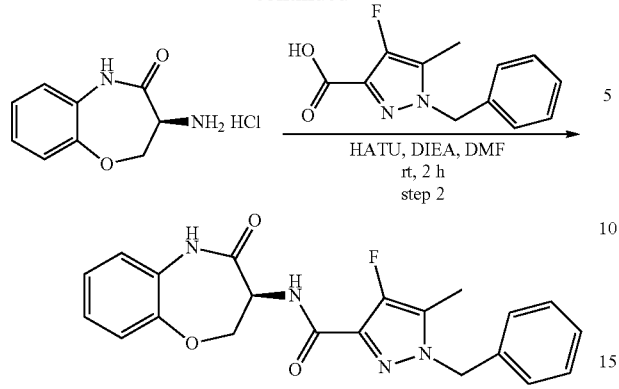

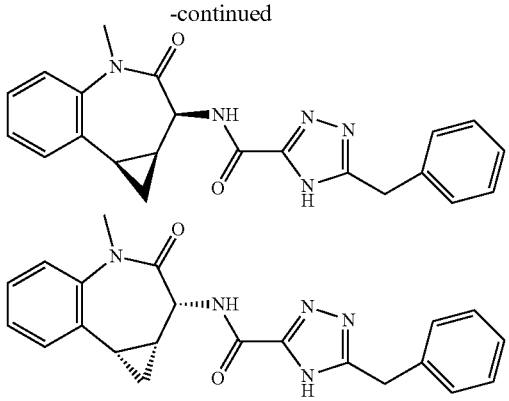

Step 1: Preparation of (3S)-3-amino-2,3,4,5-tetrahydro-1,5-benzoxazepin-4-one hydrochloride tert-Butyl N-((3S)-4-oxo-2,3,4,5-tetrahydro-1,5-benzoxazepin-3-yl)carbamate (100 mg, 0.36 mmol) was added to a solution of hydrogen chloride in 1,4-dioxane (4 M, 5 mL). The reaction mixture was stirred for 2 hours at room temperature and concentrated under reduced pressure to afford the title compound (100 mg crude) as a white solid, which was used directly in the next step without further purification. LC-MS (Method E): m/z=178.9 [M+H]+, 0.397 min.

Step 2: Preparation of (S)-1-benzyl-4-fluoro-5-methyl-N-(4-oxo-2,3,4,5-tetrahydrobenzo[b][1,4]oxazepin-3-yl)-1H-pyrazole-3-carboxamide The crude product obtained using Amide Coupling Procedure B was purified by Prep-HPLC with the following conditions: Column: XBridge Prep C18 OBD Column 19×150 mm 5 μm; Mobile Phase A: water (10 mmol/L NH4HCO3), Mobile Phase B: ACN; Flow rate: 30 mL/min; Gradient: 15% B to 45% B in 10 min; 254 nm. The collected fractions were combined and concentrated under reduced pressure to afford the title compound. 1H NMR (400 MHz, DMSO-d6) δ 10.15 (s, 1H), 8.09 (d, J=7.6 Hz, 1H), 7.43-7.28 (m, 3H), 7.20-7.09 (m, 6H), 5.39 (s, 2H), 4.80 (dt, J=10.0, 7.3 Hz, 1H), 4.53-4.39 (m, 2H), 2.17 (d, J=1.4 Hz, 3H). LC-MS (Method F): m/z=395.0 [M+H]+, 2.860 min.

Example 46: 5-benzyl-N-((2S)-4-methyl-3-oxo-1,1a,2,3,4,8b-hexahydrobenzo[b]cyclopropa[d]azepin-2-yl)-4H-1,2,4-triazole-3-carboxamide The crude product obtained using Amide Coupling Procedure C was purified by Prep-HPLC with the following conditions: Column: XBridge Prep C18 OBD Column, 5 μm, 19×150 mm; Mobile Phase A: water (0.05% TFA), Mobile Phase B: ACN; Flow rate: 20 mL/min; Gradient: 35% B to 65% B over 7 min; 254/220 nm to afford the title compound. LC-MS (Method J): m/z=388.2 [M+H]+, 1.305 min.

The enantiomers of 5-benzyl-N-{7-methyl-6-oxo-7-azatricyclo[6.4.0.0^{2,4}]dodeca-1(8),9,11-trien-5-yl}-4H-1,2,4-triazole-3-carboxamide were separated by Prep-Chiral-HPLC with the following conditions: Column: CHIRALPAK IC, 2.0 cm×25 cm (5 μm); Mobile Phase A: hexanes, Mobile Phase B: EtOH; Flow rate: 20 mL/min; Gradient: 50% B to 50% B over 30 min; 254/220 nm; RT1: 10.478 min; RT2: 13.826 min to afford the title compounds:

Example 46A (first eluting isomer): 1H NMR (400 MHz, Chloroform-d) δ 8.54 (d, J=7.1 Hz, 1H), 7.39-7.17 (m, 8H), 7.11 (d, J=7.5 Hz, 1H), 4.80 (d, J=7.0 Hz, 1H), 4.22 (s, 2H), 3.35 (s, 3H), 2.28-1.80 (m, 2H), 1.21 (m, 1H), 1.04 (m, 1H). LC-MS (Method J): m/z=388.2 [M+H]+, 1.302 min.

Example 46B (second eluting isomer): 1H NMR (400 MHz, Chloroform-d) δ 8.53 (d, J=7.1 Hz, 1H), 7.39-7.18 (m, 8H), 7.12 (d, J=7.7 Hz, 1H), 4.80 (d, J=7.0 Hz, 1H), 4.23 (s, 2H), 3.35 (s, 3H), 2.09 (m, 1H), 2.02 (m, 1H), 1.21 (m, 1H), 1.05 (m, 1H). LC-MS (Method J): m/z=388.2 [M+H]+, 1.306 min.

Example 47: (S)-4-fluoro-5-methyl-N-(4-oxo-2,3,4,5-tetrahydrobenzo[b][1,4]oxazepin-3-yl)-1-(1-phenylcyclopropyl)-1H-pyrazole-3-carboxamide

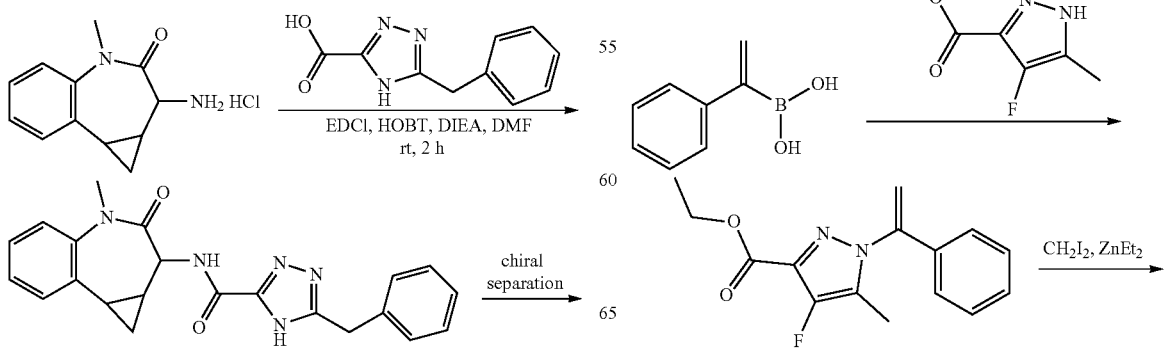

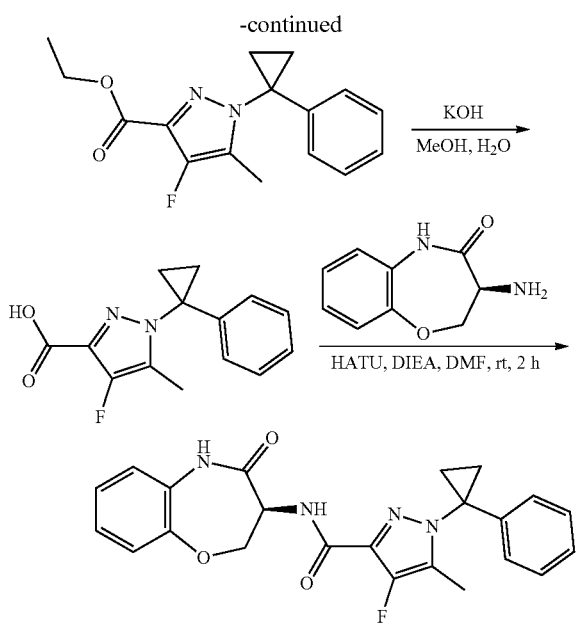

Example 48: (S)—N-(5-methyl-4-oxo-2,3,4,5-tetra-hydrobenzo[b][1,4]oxazepin-3-yl)-5-(3-phenylox-etan-3-yl)-4H-1,2,4-triazole-3-carboxamide

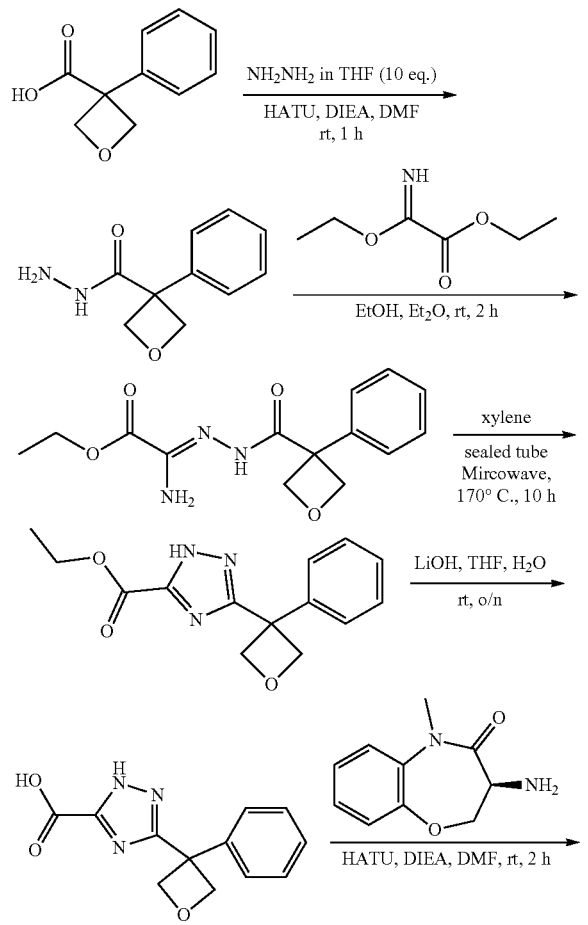

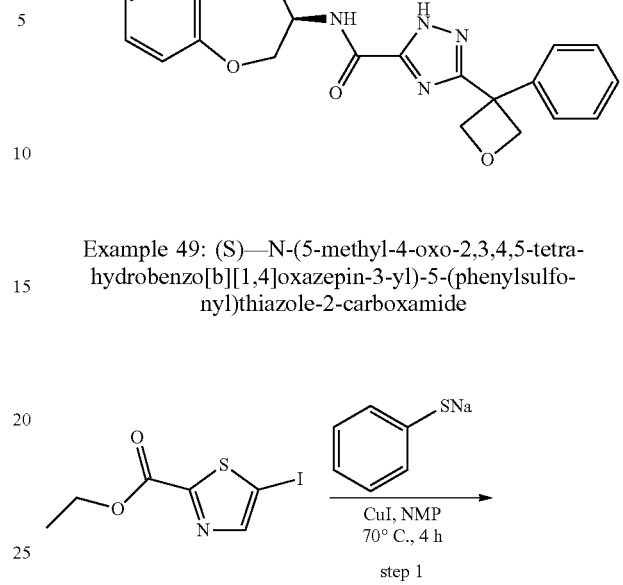

Example 49: (S)—N-(5-methyl-4-oxo-2,3,4,5-tetra-hydrobenzo[b][1,4]oxazepin-3-yl)-5-(phenylsulfo-nyl)thiazole-2-carboxamide Step 1: Preparation of ethyl 5-(phenylthio)thiazole-2-carboxylate To a stirring mixture of ethyl 5-iodo-1,3-thiazole-2-carboxylate (300 mg, 1.06 mmol), sodium benzenethiolate (220 mg, 1.66 mmol) in 1-methyl-2-pyrrolidinone (10 mL) was added cuprous iodide (40 mg, 0.21 mmol) under an argon atmosphere. The resulting solution was stirred for 4 hours at 70° C., quenched with water (20 mL) and extracted with ethyl acetate (4×20 mL). The combined organic layers were washed with brine, dried over anhydrous sodium sulfate, filtered and concentrated under vacuum. The residue was purified by Prep-TLC (ethyl acetate/petroleum ether, 5/1) to afford the title compound (120 mg, 43%) as a yellow oil. LC-MS (Method S): m/z=266.0 [M+H]$^+$, 1.040 min.

Step 2: Preparation of ethyl 5-(phenylsulfonyl)thiazole-2-carboxylate

To a stirring mixture of ethyl 5-(phenylthio)thiazole-2-carboxylate (100 mg, 0.38 mmol) in dichloromethane (4 mL) was added 3-chloroperoxybenzoic acid (167 mg, 0.97 mmol). The reaction mixture was stirred for 2 hours at room temperature and concentrated under vacuum. The residue was purified by column chromatography (ethyl acetate/petroleum ether, 1/5) to afford the title compound (100 mg, 88%) as a yellow oil. LC-MS (Method S): m/z=298.0 [M+H]$^+$, 0.931 min.

Step 3: Preparation of 5-(phenylsulfonyl)thiazole-2-carboxylic acid

To a stirring mixture of ethyl 5-(phenylsulfonyl)thiazole-2-carboxylate (100 mg, 0.34 mmol) in tetrahydrofuran (3 mL) and water (1 mL) was added lithium hydroxide (12 mg, 0.50 mmol). The resulting mixture was stirred for 2 hours at room temperature and concentrated under vacuum. The residue was diluted with water (10 mL) and adjusted to pH=6 with aqueous hydrochloric acid (1 N, 10 mL). The resulting solution was extracted with ethyl acetate (3×20 mL). The combined organic layers were washed with brine, dried over anhydrous sodium sulfate, and filtered. The filtrate was concentrated under vacuum to afford the title compound (90 mg crude) as a white oil, which was used directly in the next step without further purification. LC-MS (Method E): m/z=270.0 [M+H]$^+$, 0.635 min.

Step 4: Preparation of (S)—N-(5-methyl-4-oxo-2,3,4,5-tetrahydrobenzo[b][1,4]oxazepin-3-yl)-5-(phenylsulfonyl)thiazole-2-carboxamide The crude product obtained using Amide Coupling Procedure B was purified by Prep-HPLC with the following conditions: column: Xbridge Prep C18, 19×150 mm, 5 μm; Mobile phase: Phase A: water (10 mmol/L NH$_4$HCO$_3$); Phase B: ACN (20% to 80% over 12 min); Detector, UV 220 & 254 nm to afford the title compound. $^1$H NMR (300 MHz, DMSO-d$_6$) δ 9.24 (br. s, 1H), 8.76 (s, 1H), 8.10-8.01 (m, 2H), 7.82-7.63 (m, 3H), 7.52-7.44 (m, 1H), 7.38-7.17 (m, 3H), 4.83-4.70 (m, 1H), 4.71-4.59 (m, 1H), 4.45-4.32 (m, 1H), 3.30 (s, 3H). LC-MS (Method O): m/z=443.9 [M+H]$^+$, 1.594 min.

Example 50: (1R,2S)-2-benzyl-N—((S)-5-methyl-4-oxo-2,3,4,5-tetrahydrobenzo[b][1,4]oxazepin-3-yl)cyclopropane-1-carboxamide

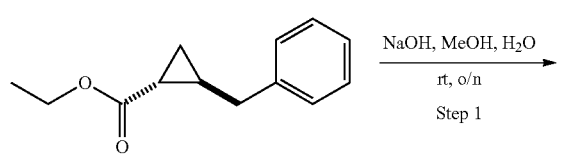

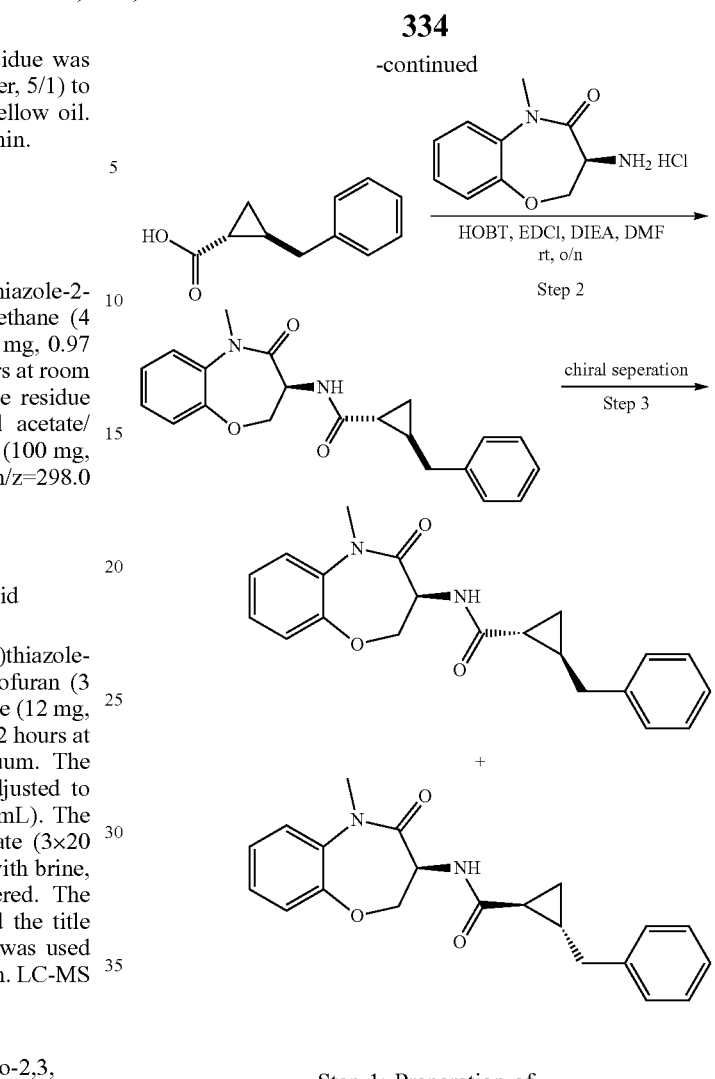

Step 1: Preparation of (+)-trans-2-benzylcyclopropanecarboxylic acid

Sodium hydroxide (60%, 74 mg, 1.84 mmol) was added to a solution of (±)-trans-ethyl 2-benzylcyclopropanecarboxylate (200 mg, 0.74 mmol) in methanol (12 mL) and water (6 mL). The reaction mixture was stirred overnight at room temperature. After removal of methanol under reduced pressure, the pH value of the solution was adjusted to 6 with aqueous hydrochloric acid (1 N, 10 mL). The resulting mixture was extracted with ethyl acetate (3×10 mL). The combined organic layers were washed with brine, dried over anhydrous sodium sulfate, filtered and concentrated under vacuum to afford the title compound (95 mg, 73%) as a yellow oil. LC-MS (Method I): m/z=177.0 [M+H]$^+$, 0.877 min.

Step 2: Preparation of trans-2-benzyl-N—((S)-5-methyl-4-oxo-2,3,4,5-tetrahydrobenzo[b][1,4]oxazepin-3-yl)cyclopropanecarboxamide The crude product obtained using Amide Coupling Procedure C was purified by Prep-HPLC with the following conditions: Column, Xbridge Prep C18 OBD Column, 5 μm, 19×150 mm; mobile phase, water (10 mmol/L NH$_4$HCO$_3$) and ACN (40.0% ACN to 65.0% over 8 min); Detector, UV 254 nm to afford the title compound. LC-MS (Method J): m/z=351.1 [M+H]$^+$, 2.116 min.

Step 3: Preparation of (1R,2S)-2-benzyl-N—((S)-5-methyl-4-oxo-2,3,4,5-tetrahydrobenzo[b][1,4]oxazepin-3-yl)cyclopropanecarboxamide and (1S,2R)-2-benzyl-N—((S)-5-methyl-4-oxo-2,3,4,5-tetrahydrobenzo[b][1,4]oxazepin-3-yl)cyclopropanecarboxamide The diastereomers of trans 2-benzyl-N—((S)-5-methyl-4-oxo-2,3,4,5-tetrahydrobenzo[b][1,4]oxazepin-3-yl)cyclopropanecarboxamide were separated by Prep-Chiral-HPLC with the following conditions: Column: Phenomenex Lux Cellulose-4, AXIA Packed, 2.12×25 cm, 5 µm; Mobile Phase A:hexanes, Mobile Phase B: EtOH; Flow rate: 20 mL/min; Gradient: 30% B to 30% B over 12 min; 254/220 nm; RT1: 7.474 min; RT2: 8.916 min to afford the title compounds:

Example 50A (first eluting isomer): ¹H NMR (400 MHz, Chloroform-d) δ 7.31-7.23 (m, 2H), 7.24-7.11 (m, 7H), 6.65 (d, J=6.4 Hz, 1H), 4.94-4.85 (m, 1H), 4.69-4.61 (m, 1H), 4.18-4.09 (m, 1H), 3.44 (s, 3H), 2.79-2.71 (m, 1H), 2.58-2.50 (m, 1H), 1.57 (s, 1H), 1.37-1.33 (m, 1H), 1.20-1.16 (m, 1H), 0.80-0.75 (m, 1H). LC-MS (Method J): m/z=351.1 [M+H]⁺, 2.116 min.

Example 50B (second eluting isomer): ¹H NMR (400 MHz, Chloroform-d) δ 7.31-7.26 (m, 2H), 7.21-7.13 (m, 7H), 6.59 (d, J=6.4 Hz, 1H), 4.95-4.84 (m, 1H), 4.69-4.58 (m, 1H), 4.16-4.09 (m, 1H), 3.43 (s, 3H), 2.79-2.70 (m, 1H), 2.63-2.54 (m, 1H), 1.67-1.57 (m, 1H), 1.37-1.32 (m, 1H), 1.17-1.13 (m, 1H), 0.78-0.73 (m, 1H). LC-MS (Method J): m/z=351.1 [M+H]⁺, 1.451 min.

Example 51: 5-(2,3-dihydro-1H-inden-1-yl)-N—((S)-5-methyl-4-oxo-2,3,4,5-tetrahydrobenzo[b][1,4]oxazepin-3-yl)-4H-1,2,4-triazole-3-carboxamide

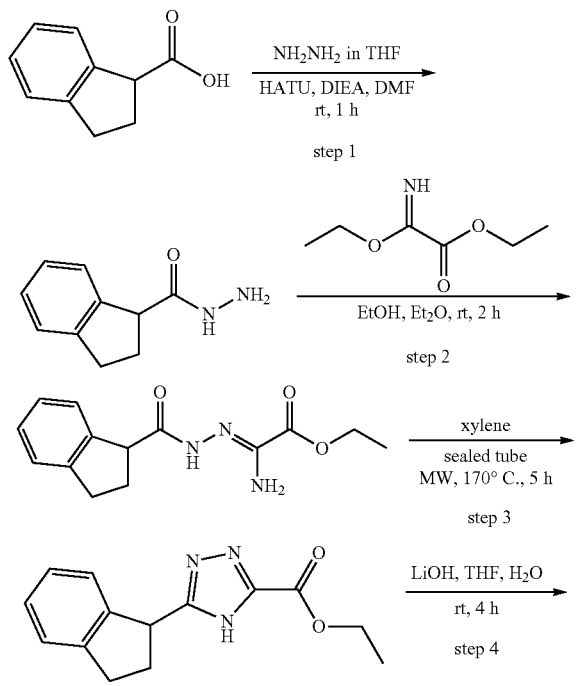

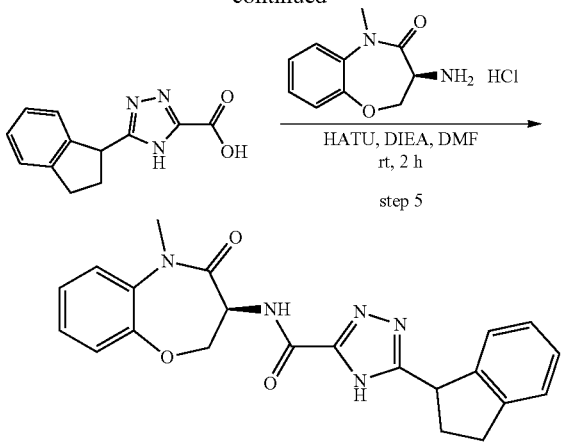

Step 1: Preparation of 2,3-dihydro-1H-indene-1-carbohydrazide

A solution of hydrazine in tetrahydrofuran (1 M, 31 mL, 31 mmol) was added to a solution of 2,3-dihydro-1H-indene-1-carboxylic acid (1.0 g, 6.2 mmol), 2-(7-aza-1H-benzotriazole-1-yl)-1,1,3,3-tetramethyluronium hexafluorophosphate (2.8 g, 7.4 mmol) and ethyldiisopropylamine (2.4 g, 18.6 mmol) in N,N-dimethylformamide (20 mL). After stirring for 1 hour at room temperature, the reaction mixture was diluted with water (20 mL) and extracted with ethyl acetate (3×50 mL). The combined organic layers were washed with brine, dried over anhydrous sodium sulfate, filtered and concentrated under vacuum. The residue was purified by column chromatography (methanol/dichloromethane, 1/10) to afford the title compound (0.87 g, 80%) as a white solid. LC-MS (Method E): m/z=177.0 [M+H]⁺, 0.506 min.

Step 2: Preparation of ethyl 2-amino-2-(2-(2,3-dihydro-1H-indene-1-carbonyl)hydrazono)acetate Ethyl 2-ethoxy-2-iminoacetate (412 mg, 2.8 mmol) was added to a solution of 2,3-dihydro-1H-indene-1-carbohydrazide (500 mg, 2.8 mmol) in ethanol (5 mL) and diethyl ether (5 mL). The resulting suspension was stirred at room temperature for 2 hours. The solids were removed by filtration and the filtrate was concentrated under vacuum to afford the title compound (600 mg, 78%) as a yellow solid. LC-MS (Method S): m/z=276.2 [M+H]⁺, 0.709 min.

Step 3: Preparation of ethyl 5-(2,3-dihydro-1H-inden-1-yl)-4H-1,2,4-triazole-3-carboxylate Ethyl 2-amino-2-(2-(2,3-dihydro-1H-indene-1-carbonyl)hydrazono)acetate (600 mg, 2.2 mmol) was added to xylene (10 mL) in a sealed tube. The reaction mixture was heated for 5 hours at 170° C. irradiated by microwave. After concentration under high vacuum, the residue was purified by column chromatography (methanol/dichloromethane, 1/10) to afford the title compound (340 mg, 60%) as a yellow oil. LC-MS (Method I): m/z=258.1 [M+H]⁺, 0.848 min.

Step 4: Preparation of 5-(2,3-dihydro-1H-inden-1-yl)-4H-1,2,4-triazole-3-carboxylic acid Lithium hydroxide (95.3 mg, 4.0 mmol) was added to a solution of ethyl 5-(2,3-dihydro-1H-inden-1-yl)-4H-1,2,4- triazole-3-carboxylate (340 mg, 1.3 mmol) in tetrahydrofuran (6 mL) and water (3 mL). After stirring at room temperature for 4 hours and removing tetrahydrofuran under reduced pressure, the reaction mixture was diluted with water (20 mL), the pH was adjusted to 2 with aqueous hydrochloric acid (1 N, 20 mL), and extracted with ethyl acetate (3×50 mL). The combined organic layers were washed with brine, dried over anhydrous sodium sulfate, filtered and concentrated under vacuum to afford the title compound (140 mg, 47%) as a yellow solid. LC-MS (Method E): m/z=229.9 [M+H]$^+$, 0.642 min.

Step 5: Preparation of 5-(2,3-dihydro-1H-inden-1-yl)-N—((S)-5-methyl-4-oxo-2,3,4,5-tetrahydrobenzo[b][1,4]oxazepin-3-yl)-4H-1,2,4-triazole-3-carboxamide The crude product obtained using Amide Coupling Procedure B was purified by Prep-HPLC with the following conditions: Column: XBridge Shield RP18 OBD Column, 5 µm, 19×150 mm; Mobile Phase A: water (10 mmol/L NH$_4$HCO$_3$), Mobile Phase B: ACN; Flow rate: 20 mL/min; Gradient: 25% B to 50% B over 10 min; 254 nm to afford the title compound. $^1$H NMR (400 MHz, Chloroform-d) δ 8.12 (d, J=7.2 Hz, 1H), 7.33 (d, J=7.2, 1H), 7.29-7.19 (m, 6H), 5.17-5.06 (m, 1H), 4.77-4.67 (m, 2H), 4.34-4.27 (m, 1H), 3.45 (s, 3H), 3.16-3.01 (m, 2H), 2.68-2.63 (m, 1H), 2.46-2.39 (m, 1H). LC-MS (Method J): m/z=404.3 [M+H]$^+$, 1.332 min.

Example 52: (S)-5-benzyl-N-(5,6-dihydro-4H-benzo[f]imidazo[1,2-a]azepin-4-yl)-4H-1,2,4-triazole-3-carboxamide

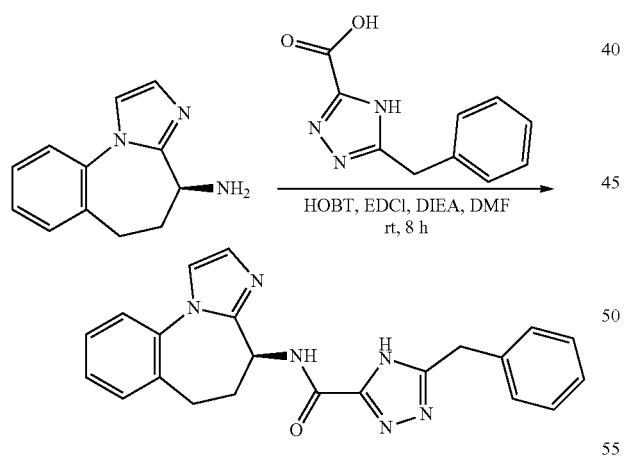

The crude product obtained using Amide Coupling Procedure C was purified by Prep-HPLC with the following conditions: Column, XBridge Shield RP18 OBD Column, 5 µm, 19×150 mm; mobile phase, water (0.05% TFA) and ACN (10.0% ACN to 40.0% over 7 min); Detector, UV 220 & 254 nm to afford the title compound. $^1$H NMR (300 MHz, DMSO-d$_6$) δ 14.43 (s, 1H), 8.67 (s, 1H), 7.56 (d, J=1.5 Hz, 1H), 7.53-7.47 (m, 3H), 7.46-7.22 (m, 6H), 7.04 (d, J=1.5 Hz, 1H), 4.87-4.77 (m, 1H), 4.14 (s, 2H), 2.80-2.73 (m, 1H), 2.67-2.56 (m, 1H), 2.46-2.32 (m, 2H). LC-MS (Method O): m/z=385.0 [M+H]$^+$, 1.229 min.

Example 53: 3-benzyl-N-(8-bromo-1-methyl-2-oxo-2,3,4,5-tetrahydro-1H-pyrrolo[1,2-a][1,3]diazepin-3-yl)-1H-1,2,4-triazole-5-carboxamide

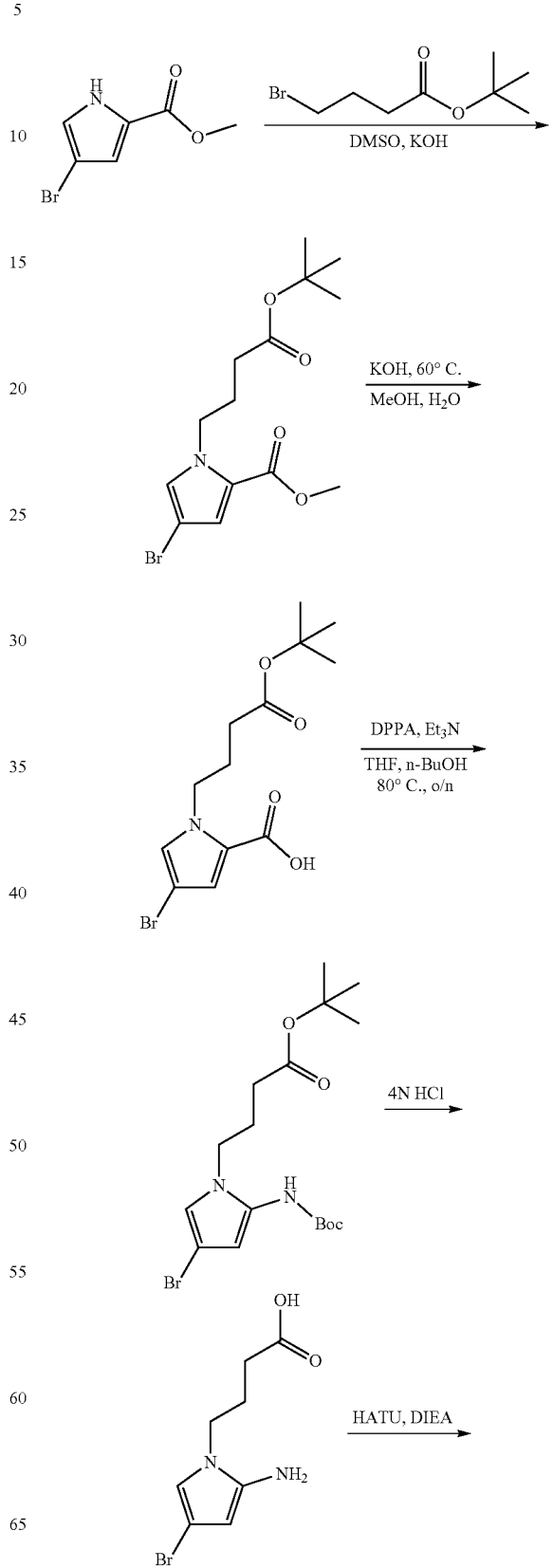

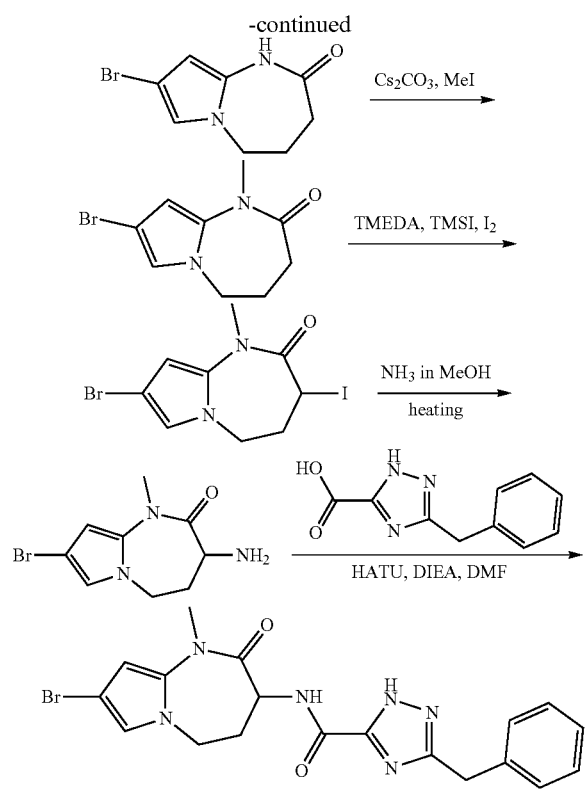

Example 54A and 54B: 5-((R)-2,3-dihydro-1H-inden-1-yl)-N—((S)-5-methyl-4-oxo-2,3,4,5-tetrahydropyrido[3,2-b][1,4]oxazepin-3-yl)-4H-1,2,4-triazole-3-carboxamide and 5-((S)-2,3-dihydro-1H-inden-1-yl)-N—((S)-5-methyl-4-oxo-2,3,4,5-tetrahydropyrido[3,2-b][1,4]oxazepin-3-yl)-4H-1,2,4-triazole-3-carboxamide

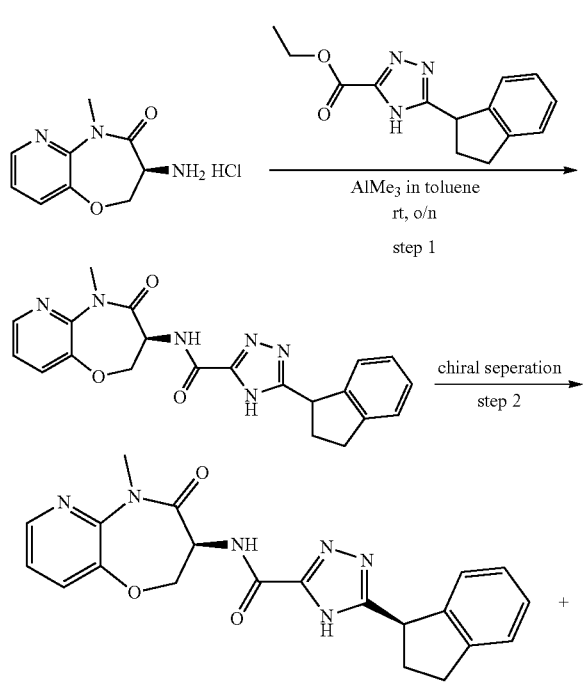

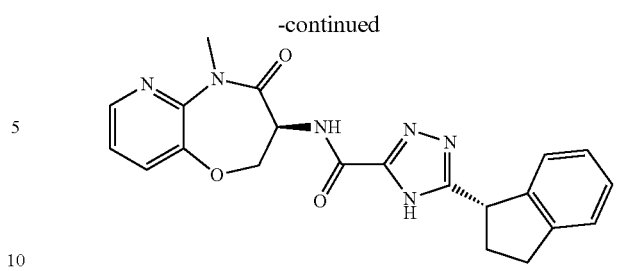

Step 1: Preparation of 5-(2,3-dihydro-1H-inden-1-yl)-N—((S)-5-methyl-4-oxo-2,3,4,5-tetrahydropyrido[3,2-b][1,4]oxazepin-3-yl)-4H-1,2,4-triazole-3-carboxamide A solution of trimethylaluminum in toluene (2 M, 0.6 mL, 1.2 mmol) was added to a mixture of (S)-3-amino-5-methyl-2,3-dihydropyrido[3,2-b][1,4]oxazepin-4(5H)-one hydrochloride (60 mg, 0.26 mmol) in toluene (2 mL) dropwise at 0° C. The resulting solution was warmed to room temperature and stirred for 30 minutes. A solution of ethyl 5-(2,3-dihydro-1H-inden-1-yl)-4H-1,2,4-triazole-3-carboxylate (108 mg, 0.42 mmol) in toluene (2 mL) was added to the resulting solution dropwise. The resulting solution was stirred overnight at room temperature. The solution was then quenched with water (10 mL) and extracted with ethyl acetate (3×50 mL). The organic layers were combined and concentrated under vacuum. The residue was purified by Prep-HPLC with the following conditions: Column: XBridge Prep Phenyl OBD Column 19×150 mm, 5 mm; Mobile Phase A: water (0.05% $NH_3H_2O$), Mobile Phase B: ACN; Flow rate: 20 mL/min; Gradient: 25% B to 50% B over 7 min; 254 nm; Rt: 6 min to afford the title compound (25 mg, 23.8%) as a white solid. LC-MS (Method D): m/z=405.1 $[M+H]^+$, 1.759 min.

Step 2: Preparation of 5-((R)-2,3-dihydro-1H-inden-1-yl)-N—((S)-5-methyl-4-oxo-2,3,4,5-tetrahydropyrido[3,2-b][1,4]oxazepin-3-yl)-4H-1,2,4-triazole-3-carboxamide and 5-((S)-2,3-dihydro-1H-inden-1-yl)-N—((S)-5-methyl-4-oxo-2,3,4,5-tetrahydropyrido[3,2-b][1,4]oxazepin-3-yl)-4H-1,2,4-triazole-3-carboxamide 5-(2,3-dihydro-1H-inden-1-yl)-N—((S)-5-methyl-4-oxo-2,3,4,5-tetrahydropyrido[3,2-b][1,4]oxazepin-3-yl)-4H-1,2,4-triazole-3-carboxamide (25 mg) was separated by Prep-Chiral-HPLC with the following conditions: Column: Chiralpak IA, 2×25 cm, 5 μm; Mobile Phase A:hexane, Mobile Phase B: EtOH; Flow rate: 16 mL/min; Gradient: 50% B to 50% B over 40 min; 220/254 nm; RT1: 9.716 min; RT2: 29.084 min to afford the title compounds:

54A (first eluting isomer): $^1$H NMR (400 MHz, Methanol-$d_4$) δ 8.36-8.35 (m, 1H), 7.70-7.68 (m, 1H), 7.34-7.31 (m, 2H), 7.25-7.24 (m, 1H), 7.22-7.19 (m, 1H), 7.16-7.07 (m, 1H), 5.07-5.02 (m, 1H), 4.72-4.65 (m, 2H), 4.55-4.50 (m, 1H), 3.49 (s, 3H), 3.18-3.15 (m, 1H), 3.07-3.05 (m, 1H), 2.65-2.62 (m, 1H), 2.43-2.38 (m, 1H). LC-MS (Method T): m/z=405.3 $[M+H]^+$, 1.296 min.

54B (second eluting isomer): $^1$H NMR (400 MHz, Methanol-$d_4$) δ 8.36-8.35 (m, 1H), 7.70-7.68 (m, 1H), 7.34-7.31 (m, 2H), 7.25-7.24 (m, 1H), 7.22-7.19 (m, 1H), 7.16-7.07 (m, 1H), 5.07-5.02 (m, 1H), 4.72-4.65 (m, 2H), 4.55-4.50 (m, 1H), 3.49 (s, 3H), 3.18-3.15 (m, 1H), 3.07-3.05 (m, 1H), 2.65-2.62 (m, 1H), 2.43-2.38 (m, 1H). LC-MS (Method T): m/z=405.3 [M+H]$^+$, 1.301 min.

Example 55: (S)-4-fluoro-N-(5-methyl-4-oxo-2,3,4,5-tetrahydrobenzo[b][1,4]oxazepin-3-yl)-1-(pyridin-2-ylmethyl)-1H-pyrazole-3-carboxamide

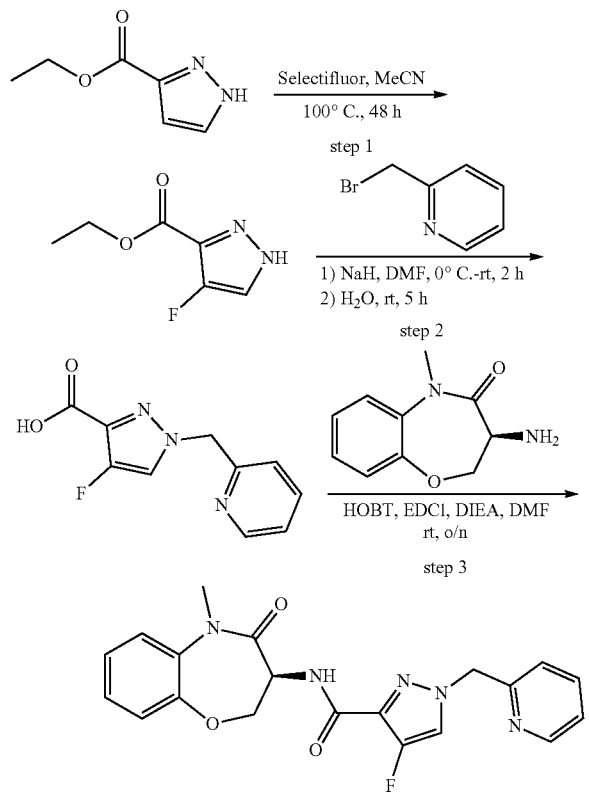

Step 1: Preparation of ethyl 4-fluoro-1H-pyrazole-3-carboxylate 1-(Chloromethyl)-4-fluoro-1,4-diazonia-bicyclo[2.2.2]octane tetrafluoroborate (14 g, 39.5 mmol) was added to a mixture of ethyl 1H-pyrazole-3-carboxylate (5 g, 35.7 mmol) in acetonitrile (50 mL). The resulting mixture was stirred for 48 hours at 100° C. After cooling to room temperature, the solids were removed by filtration and the filtrate was concentrated under vacuum to afford the title compound (2.4 g) as a yellow solid. LC-MS (Method S): m/z=159.2 [M+H]$^+$, 0.639 min.

Step 2: Preparation of 4-fluoro-1-(pyridin-2-ylmethyl)-1H-pyrazole-3-carboxylic acid Sodium hydride (60%, 506 mg, 12.7 mmol) was added to a solution of ethyl 4-fluoro-1H-pyrazole-3-carboxylate (500 mg, 3.2 mmol) in N,N-dimethylformamide (10 mL) at 0° C. The resulting mixture was stirred at room temperature for 0.5 hour before adding 2-(bromomethyl)pyridine (600 mg, 3.5 mmol). The reaction mixture was stirred at room temperature for 1.5 hours and quenched by adding water (10 mL). The resulting solution was stirred at room temperature for 5 hours. The pH was adjusted to 7 with aqueous hydrochloric acid (1 N, 10 mL). The resulting solution was extracted with ethyl acetate (3×50 mL). The combined organic layers were washed with brine, dried over anhydrous sodium sulfate, filtered and concentrated under vacuum to afford the title compound (360 mg, 72%). LC-MS (Method I): m/z=221.9 [M+H]$^+$, 0.320 min.

Step 3: Preparation of (S)-4-fluoro-N-(5-methyl-4-oxo-2,3,4,5-tetrahydrobenzo[b][1,4]oxazepin-3-yl)-1-(pyridin-2-ylmethyl)-1H-pyrazole-3-carboxamide The crude product obtained using Amide Coupling Procedure C was purified by Prep-HPLC with the following conditions: Column: XBridge Prep C18 OBD Column, 5 µm, 19×150 mm; Mobile Phase A: water (10 mmol/L NH$_4$HCO$_3$), Mobile Phase B: ACN; Flow rate: 20 mL/min; Gradient: 30% B to 45% B over 7 min; 254/220 nm to afford the title compound. $^1$H NMR (400 MHz, DMSO-d$_6$) δ 8.56-8.55 (m, 1H), 8.16-8.15 (d, J=4.4 Hz, 1H), 8.11-8.09 (m, 1H), 7.83-7.82 (m, 1H), 7.51-7.49 (m, 1H), 7.34-7.28 (m, 3H), 7.24-7.20 (m, 2H), 5.46 (s, 2H), 4.91-4.78 (m, 1H), 4.58-4.53 (m, 1H), 4.41-4.37 (m, 1H), 3.33 (s, 3H). LC-MS (Method F): m/z=396.1 [M+H]$^+$, 0.924 min.

Example 56: (S)-5-benzyl-N-(9-cyano-5-methyl-4-oxo-2,3,4,5-tetrahydrobenzo[b][1,4]oxazepin-3-yl)-2H-1,2,4-triazole-3-carboxamide

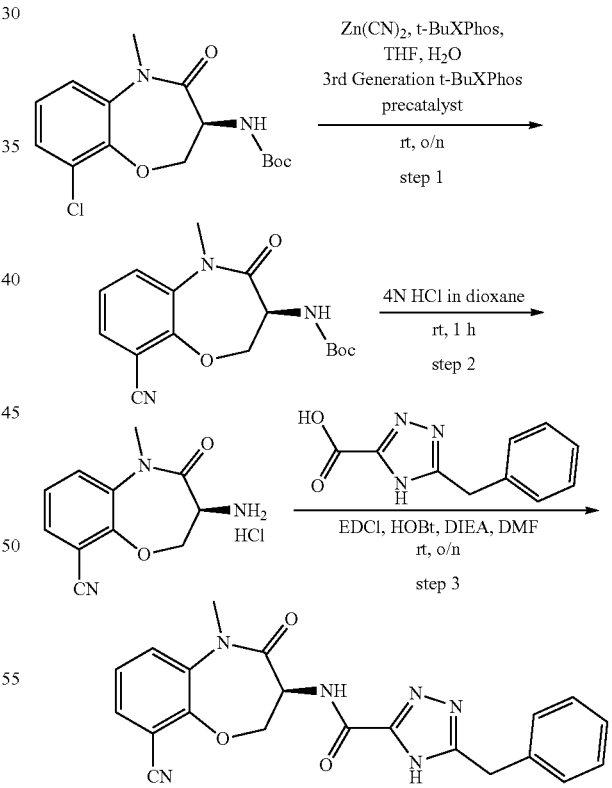

Step 1: (S)-tert-butyl 9-cyano-5-methyl-4-oxo-2,3,4,5-tetrahydrobenzo[b][1,4]oxazepin-3-ylcarbamate To a mixture of (S)-tert-butyl 9-chloro-5-methyl-4-oxo-2,3,4,5-tetrahydrobenzo[b][1,4]oxazepin-3-ylcarbamate (200 mg, 0.61 mmol) and zinc cyanide (300 mg, 2.59 mmol)

in tetrahydrofuran (2 mL) and water (10 mL) were added 3rd generation t-BuXPhos precatalyst (244 mg, 0.31 mmol) and t-BuXPhos (130 mg, 0.31 mmol) under a nitrogen atmosphere. The reaction mixture was stirred overnight at room temperature and diluted with water (50 mL). The resulting mixture was extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/6) to afford the title compound (150 mg, 78%) as a white solid. LC-MS (Method E): m/z=262.0 [M+H−56]+, 0.853 min.

Step 2: Preparation of (S)-3-amino-5-methyl-4-oxo-2,3,4,5-tetrahydrobenzo[b][1,4]oxazepine-9-carbonitrile hydrochloride A solution of hydrogen chloride in 1,4-dioxane (4 N, 10 mL) was added to a solution of (S)-tert-butyl 9-cyano-5-methyl-4-oxo-2,3,4,5-tetrahydrobenzo[b][1,4]oxazepin-3-ylcarbamate (90 mg, 0.28 mmol) in 1,4-dioxane (2 mL). The reaction mixture was stirred for 1 hour at room temperature and concentrated under vacuum to afford the title compound (55 mg) as a white solid. LC-MS (Method E): m/z=218.0 [M+H]+, 0.551 min.

Step 3: Preparation of (S)-5-benzyl-N-(9-cyano-5-methyl-4-oxo-2,3,4,5-tetrahydrobenzo[b][1,4]oxazepin-3-yl)-4H-1,2,4-triazole-3-carboxamide The crude product obtained using Amide Coupling Procedure C was purified by Prep-HPLC with the following conditions: Column, Xbridge Phenyl OBD Column, 5 μm, 19×150 mm; mobile phase, water (10 mmol/L NH4HCO3) and ACN (50.0% ACN to 70.0% over 7 min); Detector, UV 254 & 220 nm to afford the title compound. 1H NMR (400 MHz, DMSO-d6) δ 14.20 (s, 1H), 8.55 (s, 1H), 7.81 (dd, J=8.2, 1.5 Hz, 1H), 7.72 (dd, J=7.8, 1.5 Hz, 1H), 7.44 (t, J=8.0 Hz, 1H), 7.35-7.14 (m, 5H), 4.94-4.74 (m, 2H), 4.58-4.47 (m, 1H), 4.10 (s, 2H), 3.30 (s, 3H). LC-MS (Method F): m/z=403.0 [M+H]+, 1.069 min.

Example 57: (S)-1-benzyl-4-fluoro-N-(4-oxo-2,3,4,5-tetrahydropyrido[3,2-b][1,4]oxazepin-3-yl)-1H-pyrazole-3-carboxamide

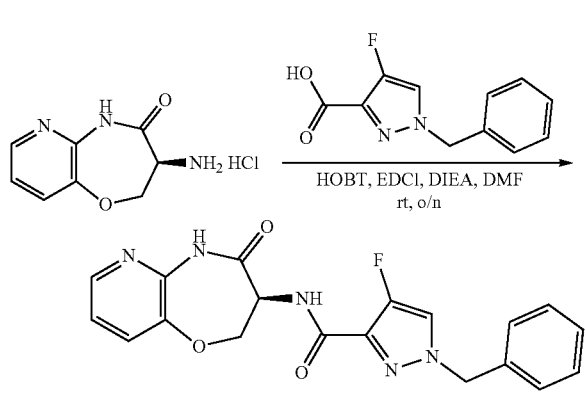

The crude product obtained using Amide Coupling Procedure C was purified by Prep-HPLC with the following conditions: Column: X Bridge Shield RP18 OBD Column, 5 μm, 19×150 mm; Mobile Phase A: water (0.1% formic acid), Mobile Phase B: ACN; Flow rate: 20 mL/min; Gradient: 25% B to 60% B over 7 min; UV 254 & 220 nm to afford the title compound. 1H NMR (400 MHz, DMSO-d6) δ 10.55 (s, 1H), 8.23 (d, J=7.6 Hz, 1H), 8.17-8.13 (m, 2H), 7.56 (dd, J=7.6, 1.2 Hz, 1H), 7.41-7.31 (m, 3H), 7.30-7.27 (m, 2H), 7.19-7.15 (m, 1H), 5.35 (s, 2H), 4.83-4.77 (m, 1H), 4.53-4.42 (m, 2H). LC-MS (Method V): m/z=382.1 [M+H]+, 2.321 min.

Example 58: (S)—N-(5-methyl-4-oxo-2,3,4,5-tetrahydrobenzo[b][1,4]oxazepin-3-yl)-5-(1-phenylcyclopropyl)-1,3,4-thiadiazole-2-carboxamide

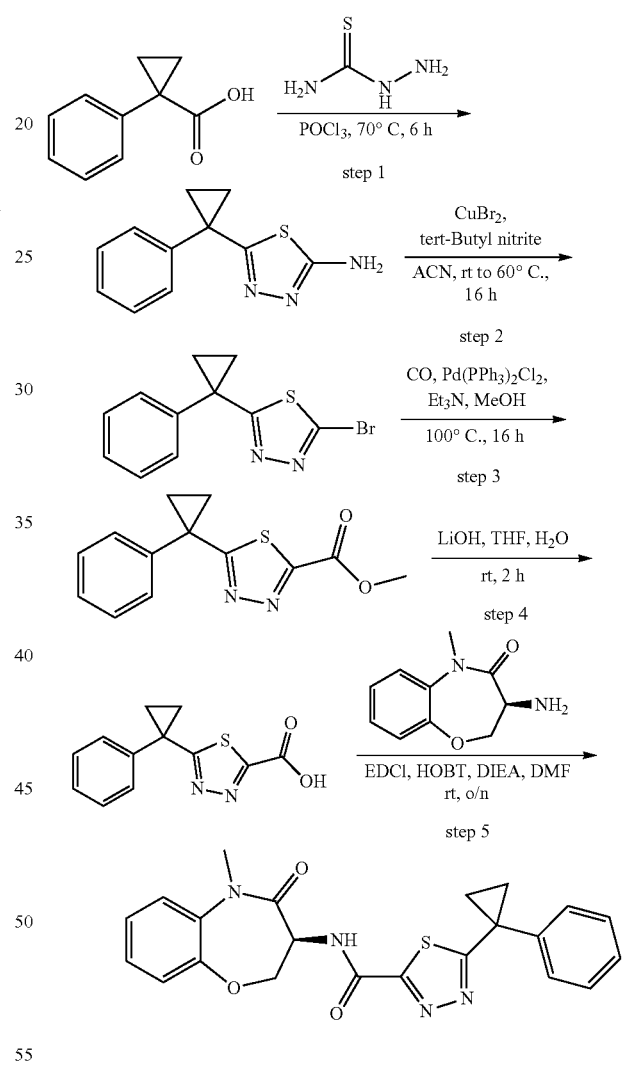

Step 1: Preparation of 5-(1-phenylcyclopropyl)-1,3,4-thiadiazol-2-amine

A mixture of 1-phenylcyclopropanecarboxylic acid (1.6 g, 10 mmol) and N-aminothiourea (0.91 g, 10 mmol) in phosphoryl trichloride (10 mL) was heated for 1 hour at 70° C. and then cooled to room temperature. Water (100 mL) was added. The reaction mixture was heated to 70° C. and stirred for 5 hours. The pH value of the resulting solution was adjusted to 8 with saturated aqueous sodium hydroxide (30 mL). The solids were collected by filtration to afford the title compound (1.9 g, 87%) as a white solid. LC-MS (Method Q): m/z=218.1 [M+H]+, 0.817 min.

Step 2: Preparation of 2-bromo-5-(1-phenylcyclopropyl)-1,3,4-thiadiazole

To a mixture of 5-(1-phenylcyclopropyl)-1,3,4-thiadiazol-2-amine (1.1 g, 5.0 mmol) in acetonitrile (20 mL) was added cupric bromide (2.2 g, 10 mmol). The resulting mixture was stirred at room temperature for 15 minutes before adding tert-butyl nitrite (1.5 mL, 10 mmol) to the mixture dropwise over a period of 15 minutes at room temperature. The reaction mixture was heated at 60° C. and stirred for 16 hours before adding water (50 mL). The solids were removed by filtration and the filtrate was extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/10) to afford the title compound (1.0 g, 70%) as a yellow solid. LC-MS (Method K): m/z=281.0 [M+H]+, 1.107 min.

Step 3: Preparation of ethyl 5-(1-phenylcyclopropyl)-1,3,4-thiadiazole-2-carboxylate Bis(triphenylphosphine)palladium(II) chloride (277 mg, 0.395 mmol) was added to a mixture of 2-bromo-5-(1-phenylcyclopropyl)-1,3,4-thiadiazole (1.0 g, 3.57 mmol) and triethylamine (879 mg, 8.70 mmol) in methanol (20 mL). After stirring for 16 hours at 100° C. under a carbon monoxide atmosphere (50 atm), the reaction mixture was diluted with water (20 mL) and extracted with ethyl acetate (3×20 mL). The combined organic layers were washed with brine, dried over anhydrous sodium sulfate, filtered and concentrated under vacuum. The residue was purified by column chromatography (ethyl acetate/petroleum ether, 1/20) to afford the title compound (600 mg, 61%) as a yellow solid. LC-MS (Method E): m/z=261.1 [M+H]+, 0.923 min.

Step 4: Preparation of 5-(1-phenylcyclopropyl)-1,3,4-thiadiazole-2-carboxylic acid Lithium hydroxide (5.4 mg, 2.0 mmol) was added to a solution of ethyl 5-(1-phenylcyclopropyl)-1,3,4-thiadiazole-2-carboxylate (100 mg, 0.41 mmol) in tetrahydrofuran (9 mL) and water (3 mL). The resulting mixture was stirred for 2 hours at room temperature. After removal of tetrahydrofuran under reduced pressure, the pH value of the solution was adjusted to 3-4 with aqueous hydrochloric acid (1 N, 20 mL). The resulting mixture was extracted with ethyl acetate (3×10 mL). The combined organic layers were washed with brine, dried over anhydrous sodium sulfate, filtered and concentrated under vacuum to afford the title compound (80 mg, 76%) as a yellow oil. LC-MS (Method C): m/z=247.0 [M+H]+, 1.288 min.

Step 5: Preparation of (S)—N-(5-methyl-4-oxo-2,3,4,5-tetrahydrobenzo[b][1,4]oxazepin-3-yl)-5-(1-phenylcyclopropyl)-1,3,4-thiadiazole-2-carboxamide The crude product obtained using Amide Coupling Procedure C was purified by Prep-HPLC with the following conditions: column: Xbridge Prep C18, 19×150 mm 5 μm; Mobile phase: water (10 mmol/L NH4HCO3) and ACN (20% to 80% over 12 min); Detector, UV220 & 254 nm to afford the title compound. 1H NMR (300 MHz, DMSO-d6) δ 9.20 (s, 1H), 7.49-7.18 (m, 9H), 4.77-4.75 (m, 1H), 4.69-4.62 (m, 1H), 4.41-4.35 (m, 1H), 3.27 (s, 3H), 1.82-1.76 (m, 2H), 1.66-1.57 (m, 2H). LC-MS (Method V): m/z=421.1 [M+H]+, 3.918 min.

Example 59: 5-benzyl-N-[(3S)-1-methyl-2-oxo-1,2,3,4-tetrahydrospiro[1-benzazepine-5,1-cyclopropane]-3-yl]-1H-pyrazole-3-carboxamide

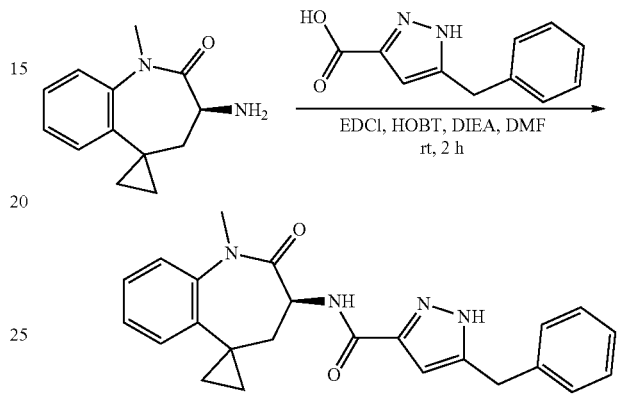

The crude product obtained using Amide Coupling Procedure C was purified by Prep-HPLC with the following conditions: Column, Xbridge Phenyl OBD Column, 5 μm, 19×150 mm; mobile phase, water (10 mmol/L NH4HCO3) and ACN (50.0% ACN to 70.0% over 7 min); Detector, UV 254 & 220 nm to afford the title compound. 1H NMR (300 MHz, DMSO-d6) δ 13.15 (s, 1H), 7.88 (d, J=8.1 Hz, 1H), 7.45-7.36 (m, 2H), 7.35-7.18 (m, 7H), 6.34 (s, 1H), 4.46-4.36 (m, 1H), 3.97 (s, 2H), 3.29 (s, 3H), 2.72-2.64 (m, 1H), 1.51 (t, J=12.0 Hz, 1H), 1.10-1.04 (m, 1H), 0.74-0.66 (m, 2H), 0.43-0.37 (m, 1H). LC-MS (Method D): m/z=401.2 [M+H]+, 1.994 min.

Examples 60A and 60B: 5-benzyl-N-((1aS,2S,8bR)-4-methyl-3-oxo-1,1a,2,3,4,8b-hexahydrobenzo[b]cyclopropa[d]azepin-2-yl)-1H-pyrazole-3-carboxamide (60A) and 5-benzyl-N-((1aR,2R,8bS)-4-methyl-3-oxo-1,1a,2,3,4,8b-hexahydrobenzo[b]cyclopropa[d]azepin-2-yl)-1H-pyrazole-3-carboxamide (60B)

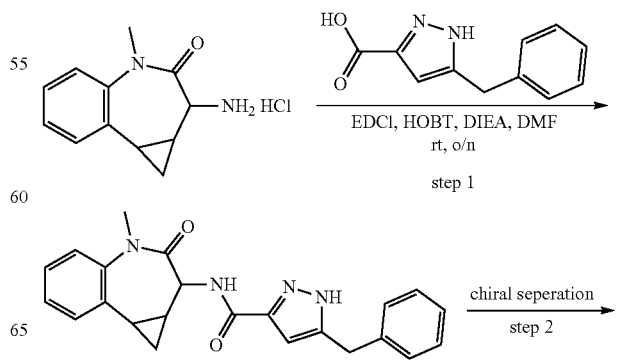

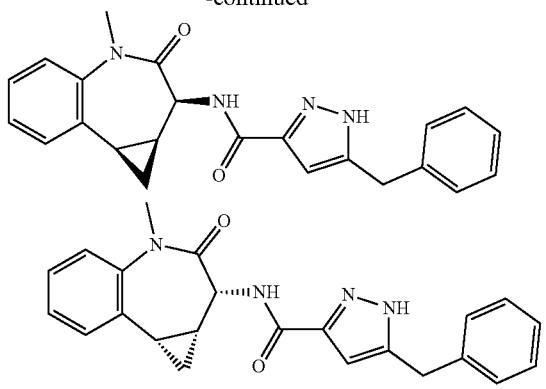

Step 1: Preparation of 5-benzyl-N-(4-methyl-3-oxo-1,1a,2,3,4,8b-hexahydrobenzo[b]cyclopropa[d]azepin-2-yl)-1H-pyrazole-3-carboxamide The crude product obtained using Amide Coupling Procedure C was purified by Prep-HPLC with the following conditions: Column: XBridge Prep C18 OBD Column, 5 μm, 19×150 mm; Mobile Phase A: water (0.05% TFA), Mobile Phase B: ACN; Flow rate: 20 mL/min; Gradient: 35% B to 65% B over 7 min; 254/220 nm to afford the title compound. LC-MS (Method I): m/z=387.2 [M+H]$^+$, 1.405 min.

Step 2: Preparation of 5-benzyl-N-((1aS,2S,8bR)-4-methyl-3-oxo-1,1a,2,3,4,8b-hexahydrobenzo[b]cyclopropa[d]azepin-2-yl)-1H-pyrazole-3-carboxamide (First Eluting Isomer) and 5-benzyl-N-((1aR,2R,8bS)-4-methyl-3-oxo-1,1a,2,3,4,8b-hexahydrobenzo[b]cyclopropa[d]azepin-2-yl)-1H-pyrazole-3-carboxamide (Second Eluting Isomer)

5-Benzyl-N-{7-methyl-6-oxo-7-azatricyclo[6.4.0.0^{2,4}]dodeca-1(8),9,11-trien-5-yl}-1H-pyrazole-3-carboxamide (30 mg, 0.077 mmol) was separated by Prep-Chiral-HPLC with the following conditions: Column: CHIRALPAK IC, 2.0 cm×25 cm (5 μm); Mobile Phase A: hexanes, Mobile Phase B: EtOH; Flow rate: 20 mL/min; Gradient: 50% B to 50% B over 30 min; 254/220 nm; RT1: 10.478 min; RT2: 13.826 min to afford the title compounds:

Example 60A (first eluting isomer): $^1$H NMR (300 MHz, Chloroform-d) δ 8.47 (d, J=7.7 Hz, 1H), 7.41-7.08 (m, 9H), 6.57 (s, 1H), 4.85 (d, J=7.6 Hz, 1H), 4.04 (s, 2H), 3.32 (s, 3H), 2.18-1.92 (m, 2H), 1.16-0.88 (m, 2H). LC-MS (Method J): m/z=387.2 [M+H]$^+$, 2.043 min.

Example 60B (second eluting isomer): $^1$H NMR (300 MHz, Chloroform-d) δ 8.29 (s, 1H), 7.39-7.05 (m, 9H), 6.53 (s, 1H), 4.85 (d, J=7.6 Hz, 1H), 4.04 (s, 2H), 3.31 (s, 3H), 2.18-1.92 (m, 2H), 1.16-1.07 (m, 1H), 1.02-0.89 (m, 1H). LC-MS (Method J): m/z=387.2 [M+H]$^+$, 1.409 min.

Example 61: (S)—N-(5-methyl-4-oxo-2,3,4,5-tetrahydrobenzo[b][1,4]oxazepin-3-yl)-2-(1-phenylcyclopropyl)oxazole-4-carboxamide

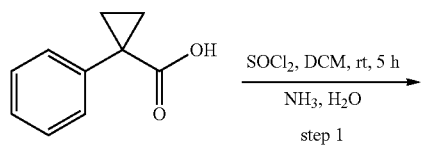

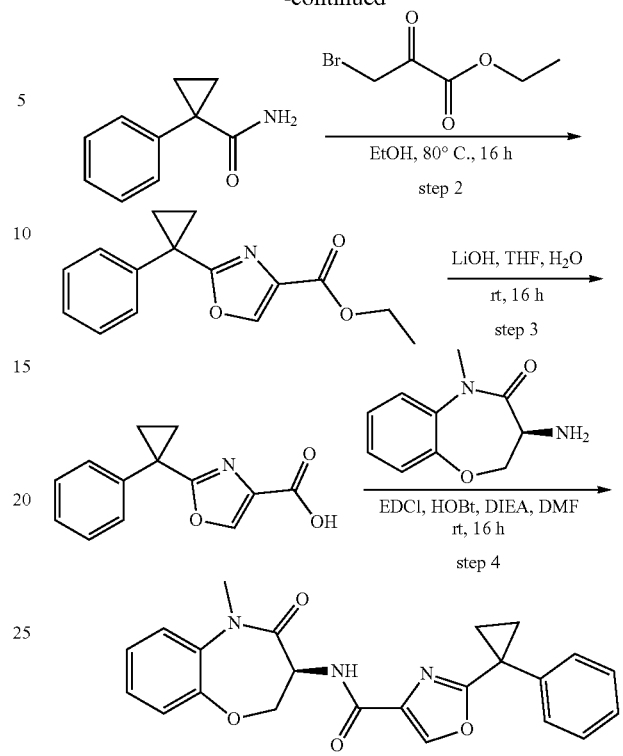

Step 1: Preparation of 1-phenylcyclopropanecarboxamide

To a stirring solution of 1-phenylcyclopropanecarboxylic acid (1.62 g, 10.0 mmol) in dichloromethane (10 mL) was added thionyl chloride (6 g, 50.0 mmol) dropwise at 0° C. The resulting solution was stirred for 5 hours at room temperature and the reaction mixture was concentrated under high vacuum. The residue was then added to ammonium hydroxide (28%, 50 mL) dropwise at 0° C. The resulting solution was diluted with water (50 mL) and extracted with ethyl acetate (3×100 mL). The combined organic layers were washed with brine, dried over anhydrous sodium sulfate, filtered and concentrated under vacuum to afford the title compound (1.50 g, 93%) as a yellow solid. LC-MS (Method I): m/z=162.1 [M+H]$^+$, 0.725 min.

Step 2: Preparation of ethyl 2-(1-phenylcyclopropyl)oxazole-4-carboxylate

A mixture of ethyl 3-bromo-2-oxopropanoate (970 mg, 5.0 mmol) and 1-phenylcyclopropanecarboxamide (810 mg, 5.0 mmol) in ethanol (10 mL) was heated for 16 hours at 80° C. under a nitrogen atmosphere. After cooling to room temperature, the reaction mixture was quenched by the addition of water (50 mL) and extracted with ethyl acetate (3×50 mL). The combined organic layers were washed with saturated aqueous sodium carbonate (30 mL) and brine (30 mL), dried over anhydrous sodium sulfate, filtered and concentrated under vacuum. The residue was purified by column chromatography (ethyl acetate/petroleum ether, 1/10) to afford the title compound (420 mg, 33%) as a white solid. LC-MS (Method C): m/z=258.1 [M+H]$^+$, 1.527 min.

Step 3: Preparation of 2-(1-phenylcyclopropyl)oxazole-4-carboxylic acid

Lithium hydroxide (5.4 mg, 2.02 mmol) was added to a mixture of ethyl 2-(1-phenylcyclopropyl) oxazole-4-carboxylate (100 mg, 0.39 mmol) in tetrahydrofuran (9 mL) and water (3 mL). The reaction mixture was stirred for 16 hours at room temperature. After removal of tetrahydrofuran under reduced pressure, the pH value of the solution was adjusted to 6 with aqueous hydrochloric acid (1 N, 5 mL). The resulting mixture was extracted with ethyl acetate (3×10 mL). The combined organic layers were washed with brine, dried over anhydrous sodium sulfate, filtered and concentrated under vacuum to afford the title compound (67 mg, 76%) as a yellow oil. LC-MS (Method C): m/z=230.1 $[M+H]^+$, 1.291 min.

Step 4: Preparation of (S)—N-(5-methyl-4-oxo-2,3,4,5-tetrahydrobenzo[b][1,4]oxazepin-3-yl)-2-(1-phenylcyclopropyl)oxazole-4-carboxamide The crude product obtained using Amide Coupling Procedure C was purified by Prep-HPLC with the following conditions: column: Xbridge Prep C18, 19×150 mm, 5 µm; Mobile phase: Phase A: water (10 mmol/L $NH_4HCO_3$); Phase B: ACN (20% to 80% over 12 min); Detector, UV220 & 254 nm to afford the title compound. $^1$H NMR (300 MHz, DMSO-$d_6$) δ 8.45 (s, 1H), 8.11 (d, J=7.8 Hz, 1H), 7.49-7.19 (m, 9H), 4.85-4.76 (m, 1H), 4.57-4.50 (m, 1H), 4.39-4.33 (m, 1H), 3.29 (s, 3H), 1.61-1.58 (m, 2H), 1.42-1.38 (m, 2H). LC-MS (Method D): m/z=404.2 $[M+H]^+$, 2.148 min.

Example 62: (S)—N-(4-oxo-2,3,4,5-tetrahydropyrido[3,2-b][1,4]oxazepin-3-yl)-5-(1-phenylcyclopropyl)isoxazole-3-carboxamide

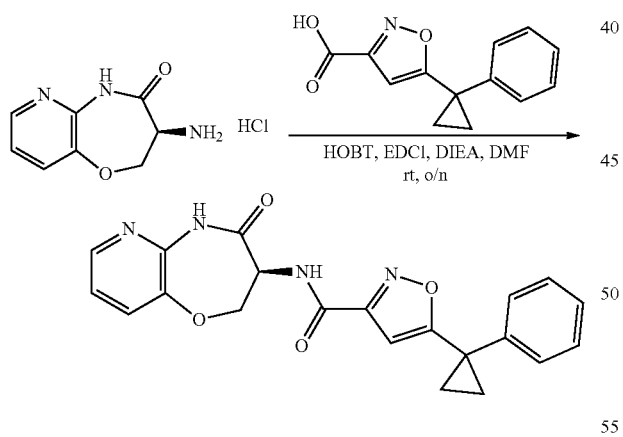

The crude product obtained using Amide Coupling Procedure C was purified by Prep-HPLC with the following conditions: Column: X Select CSH Prep C18 OBD Column, 5 µm, 19×150 mm; Mobile Phase A: water (0.05% TFA), Mobile Phase B: ACN; Flow rate: 20 mL/min; Gradient: 35% B to 70% B over 7 min; UV 254 & 220 nm to afford the title compound. $^1$H NMR (400 MHz, DMSO-$d_6$) δ 10.54 (s, 1H), 8.93 (d, J=8.0 Hz, 1H), 8.15 (dd, J=4.4, 1.2 Hz, 1H), 7.55 (dd, J=8.0, 1.2 Hz, 1H), 7.41-7.29 (m, 5H), 7.17 (dd, J=8.0, 4.8 Hz, 1H), 6.41 (s, 1H), 4.85-4.78 (m, 1H), 4.53-4.42 (m, 2H), 1.58-1.43 (m, 4H). LC-MS (Method D): m/z=391.1 $[M+H]^+$, 1.981 min.

Example 63: (S)—N-(5-methyl-4-oxo-2,3,4,5-tetrahydropyrido[3,2-b][1,4]oxazepin-3-yl)-5-(1-phenylcyclopropyl)thiazole-2-carboxamide

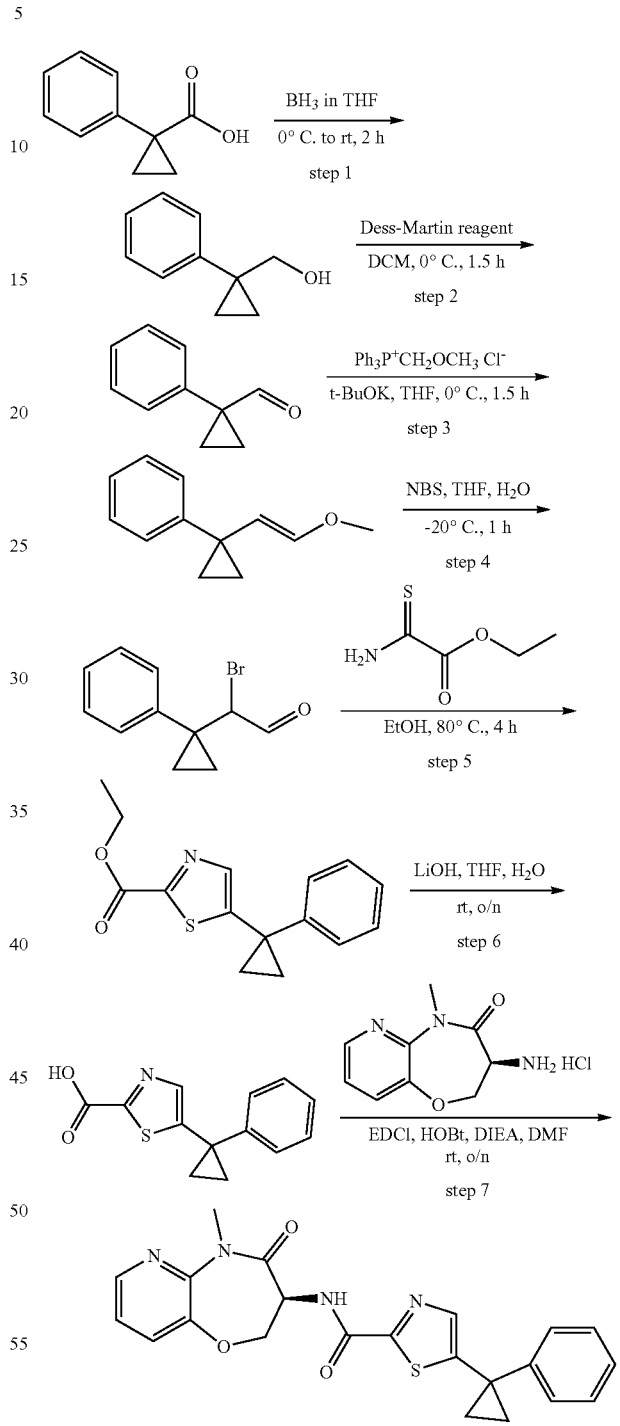

Step 1: Preparation of (1-phenylcyclopropyl)methanol

A solution of borane in tetrahydrofuran (1 M, 60 mL, 60 mmol) was slowly added to a solution of 1-phenylcyclopropanecarboxylic acid (6.5 g, 40 mmol) in tetrahydrofuran (40 mL) at 0° C. The reaction mixture was stirred for 2 hours at room temperature, quenched with water (50 mL) and extracted with ethyl acetate (3×60 mL). The combined organic layers were washed with brine, dried over anhydrous sodium sulfate, filtered and concentrated under vacuum to afford the title compound (5.5 g, 93%) as a colorless oil. LC-MS (Method C): m/z=131.2 [M−H$_2$O+H]$^+$, 1.125 min.

Step 2: Preparation of 1-phenylcyclopropanecarbaldehyde

Dess-Martin periodinane (35.6 g, 84 mmol) was added to a solution of (1-phenylcyclopropyl)methanol (5.4 g, 42 mmol) in dichloromethane (40 mL) at 0° C. The resulting mixture was stirred at 0° C. for 1.5 hours. The solids were removed by filtration and the filtrate was concentrated under vacuum. The resulting residue was purified by column chromatography (ethyl acetate/petroleum ether, 1/10) to afford the title compound (4.4 g, 72%) as a colorless oil. LC-MS (Method C): m/z=147.2 [M+H]$^+$, 1.215 min.

Step 3: Preparation of (E)-(1-(2-methoxyvinyl)cyclopropyl)benzene

To a solution of methoxymethyl)triphenylphosphonium chloride (22.4 g, 65 mmol) in tetrahydrofuran (30 mL) was added a solution of potassium 2-methylpropan-2-olate in tetrahydrofuran (1 M, 65 mL, 65 mmol) at 0° C. The resulting mixture was stirred at 0° C. for 0.5 hour followed by the addition of 1-phenylcyclopropanecarbaldehyde (4.2 g, 29 mmol). The reaction mixture was stirred at room temperature for 1 hour, quenched by the addition of water (100 mL) and extracted with ethyl acetate (3×100 mL). The combined organic phases were washed with brine, dried over anhydrous sodium sulfate, filtered and concentrated under reduced pressure to afford the title compound (20 g crude) as a yellow oil, which was used directly in the next step without further purification.

Step 4: Preparation of 2-bromo-2-(1-phenylcyclopropyl)acetaldehyde

To a solution of (E)-(1-(2-methoxyvinyl)cyclopropyl) benzene (3.8 g, 22 mmol) in tetrahydrofuran (20 mL) and water (2 mL) was added N-bromosuccinimide (4.3 g, 24 mmol) at −20° C. The solution was stirred at −20° C. for 1 hour and concentrated to afford the title compound (8 g crude) as a yellow oil, which was used directly in the next step without further purification.

Step 5: Preparation of ethyl 5-(1-phenylcyclopropyl)thiazole-2-carboxylate

To a solution of 2-bromo-2-(1-phenylcyclopropyl)acetaldehyde (2 g, 8 mmol) in ethanol (20 mL) was added ethyl 2-amino-2-thioxoacetate (1.1 g, 8 mmol). The reaction mixture was stirred at 80° C. for 4 hours and concentrated under vacuum. The residue was purified by column chromatography (ethyl acetate/petroleum ether, 1/5) to afford the title compound (310 mg, 14%) as a yellow oil. LC-MS (Method I): m/z=274.0 [M+H]$^+$, 1.034 min.

Step 6: Preparation of 5-(1-phenylcyclopropyl)thiazole-2-carboxylic acid

Lithium hydroxide (52.8 mg, 2.2 mmol) was added to a solution of ethyl 5-(1-phenylcyclopropyl)thiazole-2-carboxylate (100 mg, 0.36 mmol) in tetrahydrofuran (2 mL) and water (1 mL). The reaction mixture was stirred at room temperature overnight, concentrated under reduced pressure and diluted with water (10 mL). The resulting mixture was adjusted to pH=5 with aqueous hydrochloric acid (1 N, 10 mL) and extracted with ethyl acetate (3×10 mL). The combined organic layers were washed with brine, dried over anhydrous sodium sulfate, filtered and concentrated under vacuum to afford the title compound (49 mg, 56%) as a yellow oil, which was used directly in the next step without further purification. LC-MS (Method C): m/z=246.1 [M+H]$^+$, 1.200 min.

Step 7: S)—N-(5-methyl-4-oxo-2,3,4,5-tetrahydropyrido[3,2-b][1,4]oxazepin-3-yl)-5-(1-phenylcyclopropyl)thiazole-2-carboxamide The crude product obtained using Amide Coupling Procedure C was purified by Prep-HPLC with the following conditions: column: Xbridge Prep C18, 19×250 mm, 5 μm; Mobile phase: Phase A: water (10 mmol/L NH$_4$HCO$_3$); Phase B: ACN (45% to 65% over 7 min); Detector, UV220 & 254 nm to afford the title compound. $^1$H NMR (400 MHz, DMSO-d$_6$) δ 8.95 (d, J=7.5 Hz, 1H), 8.36 (dd, J=4.7, 1.6 Hz, 1H), 7.74 (s, 1H), 7.70 (dd, J=7.9, 1.6 Hz, 1H), 7.40-7.23 (m, 6H), 4.88-4.71 (m, 2H), 4.52 (dd, J=9.1, 6.7 Hz, 1H), 3.35 (s, 3H), 1.47 (s, 4H). LC-MS (Method T): m/z=421.3 [M+H]$^+$, 1.729 min.

Example 64: (S)-1-benzyl-4-fluoro-N-(5-methyl-4-oxo-2,3,4,5-tetrahydrobenzo[b][1,4]oxazepin-3-yl)-1H-pyrazole-3-carboxamide

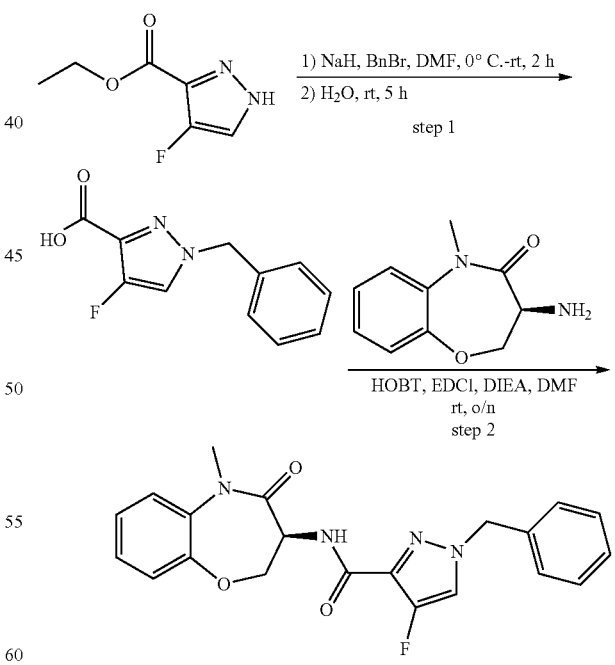

Step 1: Preparation of 1-benzyl-4-fluoro-1H-pyrazole-3-carboxylic acid

Sodium hydride (60%, 1 g, 25 mmol) was added to a solution of ethyl 4-fluoro-1H-pyrazole-3-carboxylate (1.2 g, 7.6 mmol) in N,N-dimethylformamide (20 mL) at 0° C. The resulting mixture was stirred for 0.5 hour at room temperature followed by adding benzyl bromide (1.36 g, 8.0 mmol). The resulting mixture was stirred for 2 hours at room temperature. Water (20 mL) was added dropwise. The resulting solution was then stirred at room temperature for 5 hours. The pH value of the solution was adjusted to 7 with aqueous hydrochloric acid (1 N, 20 mL). The resulting solution was extracted with ethyl acetate (3×50 mL). The combined organic layers were washed with brine, dried over anhydrous sodium sulfate, filtered and concentrated under vacuum. The residue was then purified by Prep-HPLC with the following conditions: Column: XBridge C18 OBD Prep Column, 5 μm, 19 mm×250 mm; Mobile Phase A: water (0.1% formic acid), Mobile Phase B: ACN; Flow rate: 20 mL/min; Gradient: 30% B to 60% B over 7 min; 254 nm to afford the title compound (370 mg, 22%) as a white solid. LC-MS (Method D): m/z=221.1 [M+H]$^+$, 1.206 min.

Step 2: Preparation of (S)-1-benzyl-4-fluoro-N-(5-methyl-4-oxo-2,3,4,5tetrahydrobenzo[b][1,4]oxazepin-3-yl)-1H-pyrazole-3-carboxamide The crude product obtained using Amide Coupling Procedure C was purified by Prep-HPLC with the following conditions: Column: XBridge Prep C18 OBD Column 19×150 mm, 5 μm; Mobile Phase A: water (0.05% NH$_3$H$_2$O), Mobile Phase B: ACN; Flow rate: 20 mL/min; Gradient: 25% B to 55% B over 7 min; Detector, UV220 & 254 nm to afford the title compound. $^1$H NMR (400 MHz, Chloroform-d) δ 7.66 (d, J=6.8 Hz, 1H), 7.43-7.40 (m, 3H), 7.39-7.21 (m, 6H), 5.26 (s, 2H), 5.13-5.07 (m, 1H), 4.83-4.81 (m, 1H), 4.31-4.26 (m, 1H), 3.47 (s, 3H). LC-MS (Method J): m/z=395.2 [M+H]$^+$, 1.474 min.

Example 65: N-[(4S,9aR)-5-oxo-octahydropyrrolo[2,1-c][1,4]oxazepin-4-yl]-5-benzyl-4H-1,2,4-triazole-3-carboxamide

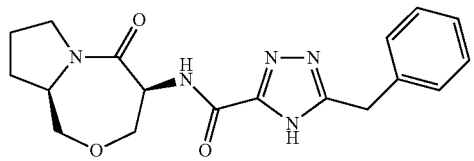 [SMILES: O=C(N[C@H]1COC[C@H]2CCCN2C1=O)c1nnc(Cc2ccccc2)[nH]1]

The title compound was prepared from N-Boc-D-prolinol using the procedure described in Example 27.

The crude product was purified by column chromatography on KP-NH modified silica gel (CH$_2$Cl$_2$-MeOH, 97:3 to 90:10) to afford the title compound. $^1$H NMR (400 MHz, CDCl$_3$) δ 8.31 (d, J=6.3 Hz, 1H), 7.37-7.23 (m, 5H), 4.90 (ddd, J=9.3, 6.3, 2.8 Hz, 1H), 4.21 (s, 2H), 4.17 (dd, J=11.7, 2.6 Hz, 1H), 4.09 (q, J=8.8 Hz, 1H), 3.98 (d, J=12.5 Hz, 1H), 3.93-3.82 (m, 1H), 3.52-3.39 (m, 2H), 3.24 (dd, J=12.8, 9.3 Hz, 1H), 2.33-2.17 (m, 1H), 2.01-1.90 (m, 1H), 1.87-1.70 (m, 1H), 1.66-1.51 (m, 1H). LC-MS (Method A): m/z=356.4 [M+H]$^+$, 0.71 min.

Example 66: (S)—N-(5-methyl-4-oxo-2,3,4,5-tetrahydropyrido[3,2-b][1,4]oxazepin-3-yl)-5-(1-phenylcyclopropyl)-1,3,4-oxadiazole-2-carboxamide

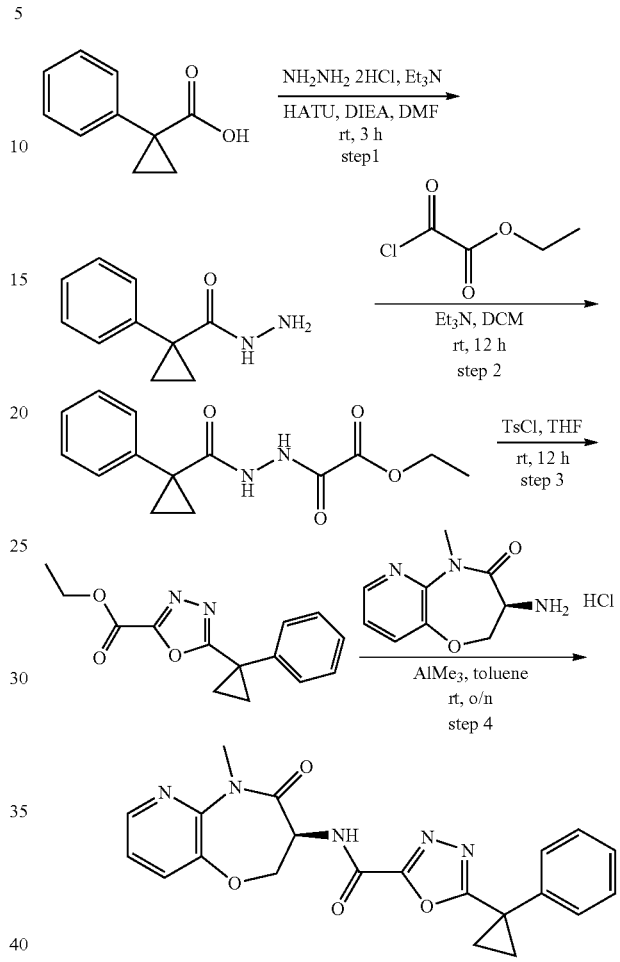

Step 1: Preparation of 1-phenylcyclopropanecarbohydrazide

Triethylamine (93.5 g, 925.5 mmol) was added to a stirring mixture of hydrazine dihydrochloride (32.1 g, 308.6 mmol) in N,N-dimethylformamide (300 mL). The resulting mixture was added to a mixture of 1-phenylcyclopropanecarboxylic acid (10.0 g, 61.7 mmol), O-(7-azabenzotriazol-1-yl)-N,N,N',N'-tetramethyluronium hexafluorophosphate (28.2 g, 74.0 mmol) and N,N-diisopropylethylamine (23.9 g, 185.1 mmol) in N,N-dimethylformamide (100 mL). The reaction mixture was stirred at room temperature for 2 hours, diluted with water (500 mL) and extracted with ethyl acetate (5×100 mL). The combined organic layers were washed with brine, dried over anhydrous sodium sulfate, filtered and concentrated under vacuum. The residue was purified by column chromatography (ethyl acetate/petroleum ether, 1/3) to afford the title compound (6 g, 55.2%) as a white solid. LC-MS (Method E): m/z=177.0 [M+H]$^+$, 1.139 min.

Step 2: Preparation of ethyl 2-oxo-2-(2-(1-phenylcyclopropanecarbonyl)hydrazinyl)acetate Ethyl 2-chloro-2-oxoacetate (1.56 g, 11.4 mmol) was added to a stirring solution of 1-phenylcyclopropane carbohydrazide (2.00 g, 11.4 mmol) and triethylamine (3.44 g, 34.1 mmol) in dichloromethane (40 mL) at room temperature. The reaction mixture was stirred for 12 hours at room temperature, quenched by the addition of water (40 mL) and extracted with dichloromethane (3×50 mL). The combined organic layers were washed with brine, dried over anhydrous sodium sulfate, filtered and concentrated under vacuum. The residue was purified by column chromatography (ethyl acetate/petroleum ether, 1/3) to afford the title compound (3 g, 96.7%) as a yellow oil. LC-MS (Method E): m/z=277.0 [M+H]$^+$, 0.676 min.

Step 3: Preparation of ethyl 5-(1-phenylcyclopropyl)-1,3,4-oxadiazole-2-carboxylate Tosyl chloride (0.80 g, 3.62 mmol) was added to a stirring solution of ethyl 2-oxo-2-(2-(1-phenylcyclopropanecarbonyl)hydrazinyl)acetate (1.0 g, 3.62 mmol) and triethylamine (1.1 g, 6.6 mmol) in dichloromethane (25 mL). The reaction mixture was stirred for 12 hours at room temperature, quenched by the addition of water (20 mL) and extracted with dichloromethane (3×25 mL). The combined organic layers were washed with brine, dried over anhydrous sodium sulfate, filtered and concentrated under vacuum. The residue was purified by column chromatography (ethyl acetate/petroleum ether, 1/3) to afford the title compound (0.80 g, 85.6%) as a yellow oil. LC-MS (Method C): m/z=259.0 [M+H]$^+$, 1.457 min.

Step 4: Preparation of (S)—N-(5-methyl-4-oxo-2,3,4,5-tetrahydropyrido[3,2-b][1,4]oxazepin-3-yl)-5-(1-phenylcyclopropyl)-1,3,4-oxadiazole-2-carboxamide The crude product obtained using the procedure described in Example 54 was purified by Prep-HPLC with the following conditions: Column: XBridge Prep C18 OBD Column, 5 μm, 19×150 mm; mobile phase, water (10 mmol/L NH$_4$HCO$_3$), ACN (40% ACN to 70% B over 7 min); detector, UV 254 & 220 nm to afford the title compound. $^1$H NMR (400 MHz, DMSO-d$_6$) δ 9.49 (s, 1H), 8.37-8.35 (m, 1H), 7.71-7.69 (m, 1H), 7.42-7.30 (m, 6H), 4.82-4.80 (m, 1H), 4.75-4.73 (m, 1H), 4.54-4.50 (m, 1H), 3.33 (s, 3H), 1.70-1.69 (m, 2H), 1.54-1.50 (m, 2H). LC-MS (Method T): m/z=406.3 [M+H]$^+$, 2.463 min.

Example 67A and 67B: 5-benzyl-N-((1aR,2S,8bS)-4-methyl-3-oxo-1,1a,2,3,4,8b-hexahydrobenzo[b]cyclopropa[d]azepin-2-yl)-4H-1,2,4-triazole-3-carboxamide (67A) and 5-benzyl-N-((1aS,2R,8bR)-4-methyl-3-oxo-1,1a,2,3,4,8b-hexahydrobenzo[b]cyclopropa[d]azepin-2-yl)-4H-1,2,4-triazole-3-carboxamide (67B)

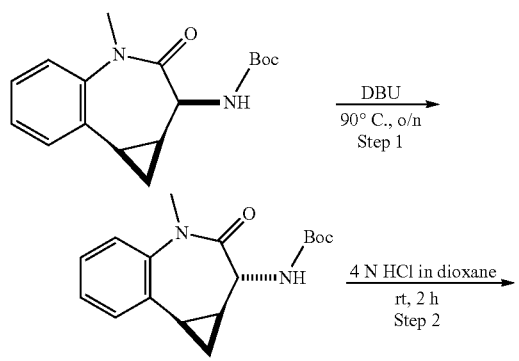

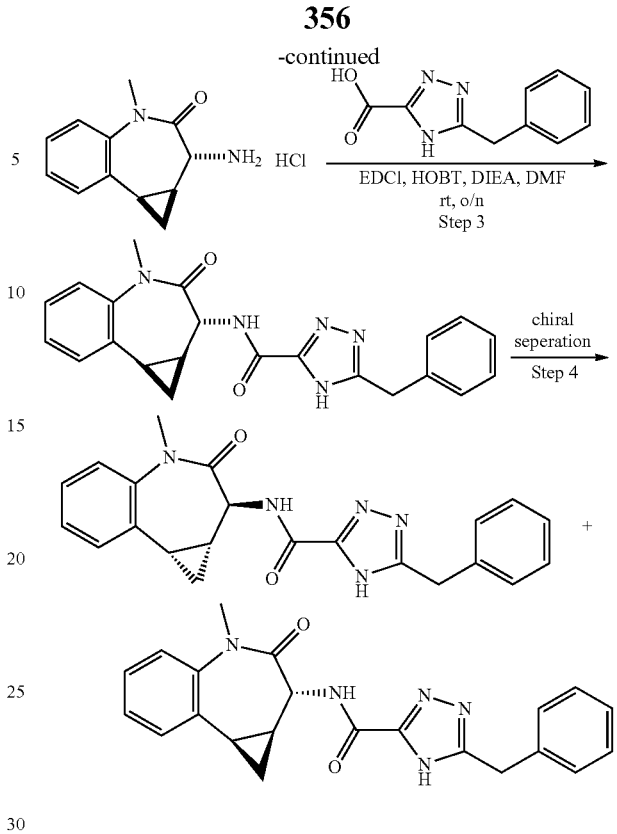

Step 1: Preparation of tert-butyl (trans-4-methyl-3-oxo-1,1a,2,3,4,8b-hexahydrobenzo[b]cyclopropa[d]azepin-2-yl)carbamate A solution of tert-butyl (cis-4-methyl-3-oxo-1,1a,2,3,4,8b-hexahydrobenzo[b]cyclopropa[d]azepin-2-yl)carbamate (100 mg, 0.33 mmol) in 1,8-diazabicyclo[5.4.0]undec-7-ene was stirred at 90° C. overnight. The solution was purified by TLC (ethyl acetate/petroleum ether, 1/8) to afford the title compound (60 mg, 60%) as a yellow solid. LC-MS (Method E): m/z=325.0 [M+Na]$^+$, 0.930 min.

Step 2: Preparation of trans-2-amino-4-methyl-1,1a,2,8b-tetrahydrobenzo[b]cyclopropa[d]azepin-3(4H)-one hydrochloride To a solution of tert-butyl (trans-4-methyl-3-oxo-1,1a,2,3,4,8b-hexahydrobenzo[b]cyclopropa[d]azepin-2-yl)carbamate (60 mg, 0.20 mmol) in 1,4-dioxane (2 mL) was added a solution of hydrogen chloride in 1,4-dioxane (4 M, 5 mL, 20 mmol). The reaction mixture was stirred for 2 hours at room temperature and concentrated under high vacuum to afford the title compound (40 mg crude) as a yellow solid, which was used directly in the next step without further purification. LC-MS (Method S): m/z=203.3 [M+H]$^+$, 0.592 min.

Step 3: Preparation of trans-5-benzyl-N-(4-methyl-3-oxo-1,1a,2,3,4,8b-hexahydrobenzo[b]cyclopropa[d]azepin-2-yl)-4H-1,2,4-triazole-3-carboxamide The crude product obtained using Amide Coupling Procedure C was purified by Prep-HPLC with the following conditions: Column: XBridge Prep C18 OBD Column, 5 μm, 19×150 mm; Mobile Phase A: water (0.05% TFA), Mobile Phase B: ACN; Flow rate: 20 mL/min; Gradient:

35% B to 65% B over 7 min; 254/220 nm to afford the title compound. LC-MS (Method J): m/z=388.2 [M+H]⁺, 1.305 min.

Step 7: Preparation of 5-benzyl-N-((1aR,2S,8bS)-4-methyl-3-oxo-1,1a,2,3,4,8b-hexahydrobenzo[b]cyclopropa[d]azepin-2-yl)-4H-1,2,4-triazole-3-carboxamide (First Eluting Isomer) and 5-benzyl-N-((1aS,2R,8bR)-4-methyl-3-oxo-1,1a,2,3,4,8b-hexahydrobenzo[b]cyclopropa[d]azepin-2-yl)-4H-1,2,4-triazole-3-carboxamide (Second Eluting Isomer)

The enantiomers of trans-5-benzyl-N-(4-methyl-3-oxo-1,1a,2,3,4,8b-hexahydrobenzo[b]cyclopropa[d]azepin-2-yl)-4H-1,2,4-triazole-3-carboxamide (25 mg, 0.065 mmol) were separated by Prep-Chiral-HPLC with the following conditions: Column: Chiralpak ID-2, 2×25 cm, 5 μm; Mobile Phase A: hexane, Mobile Phase B: EtOH; Flow rate: 17 mL/min; Gradient: 50% B to 50% B over 22 min; UV 254 & 220 nm; RT 1: 11.72 min; RT 2: 18.02 min to afford the title compounds.

Example 67A (first eluting isomer): ¹H NMR (300 MHz, Methanol-d₄) δ 7.56 (d, J=7.5 Hz, 1H), 7.42-7.19 (m, 9H), 4.23-4.13 (m, 3H), 3.43 (s, 3H), 2.25-2.15 (m, 1H), 1.72-1.58 (m, 1H), 1.25-1.13 (m, 1H), 0.79-0.65 (m, 1H). LC-MS (Method D): m/z=388.2 [M+H]⁺, 1.806 min.

Example 67B (second eluting isomer): ¹H NMR (300 MHz, Methanol-d₄) δ 7.56 (d, J=7.5 Hz, 1H), 7.42-7.19 (m, 9H), 4.23-4.13 (m, 3H), 3.43 (s, 3H), 2.25-2.15 (m, 1H), 1.72-1.58 (m, 1H), 1.25-1.13 (m, 1H), 0.79-0.65 (m, 1H). LC-MS (Method D): m/z=388.2 [M+H]⁺, 1.812 min.

Example 68A: (R)-5-benzyl-N-(4,5-dihydrobenzo[b]imidazo[1,2-d][1,4]oxazepin-4-yl)-4H-1,2,4-triazole-3-carboxamide

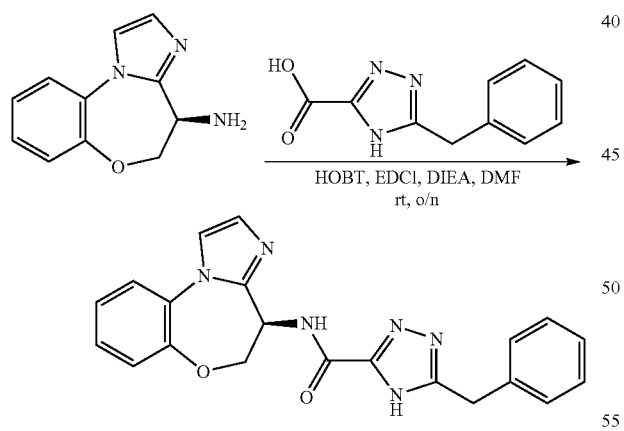

The crude product obtained using Amide Coupling Procedure C was purified by Prep-HPLC with the following conditions: Column: X Bridge Prep C18 OBD Column 19×150 mm 5 μm; Mobile Phase A: water (10 mmol/L NH₄HCO₃), Mobile Phase B: ACN; Flow rate: 30 mL/min; Gradient: 25% B to 55% B over 7 min; UV 254 & 220 nm to afford the title compound. ¹H NMR (300 MHz, DMSO-d₆) δ 14.42 (s, 1H), 8.80 (br. s, 1H), 7.70-7.64 (m, 2H), 7.43-7.25 (m, 8H), 7.07 (d, J=1.2 Hz, 1H), 5.40-5.31 (m, 1H), 4.64-4.49 (m, 2H), 4.14 (s, 2H). LC-MS (Method D): m/z=387.1 [M+H]⁺, 1.322 min.

Example 68B: (S)-5-benzyl-N-(4,5-dihydrobenzo[b]imidazo[1,2-d][1,4]oxazepin-4-yl)-4H-1,2,4-triazole-3-carboxamide

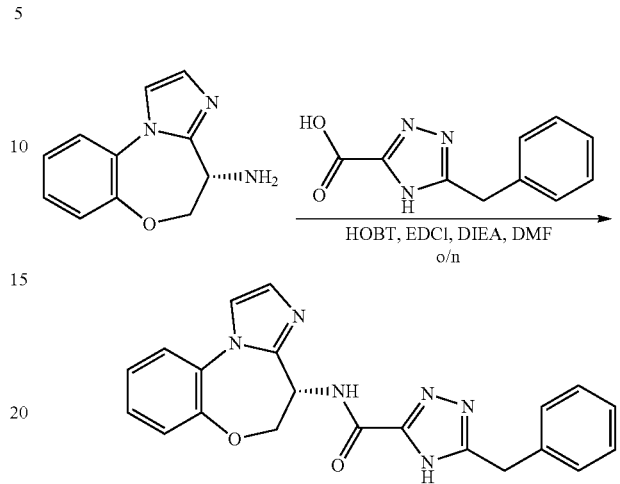

The crude product obtained using Amide Coupling Procedure C was purified by Prep-HPLC with the following conditions: Column: X Bridge Prep C18 OBD Column 19×150 mm 5 μm; Mobile Phase A: water (10 mmol/L NH₄HCO₃), Mobile Phase B: ACN; Flow rate: 30 mL/min; Gradient: 25% B to 55% B over 7 min; UV 254 & 220 nm to afford the title compound ¹H NMR (300 MHz, DMSO-d₆) δ 14.39 (s, 1H), 8.80 (s, 1H), 7.70-7.65 (m, 2H), 7.41-7.22 (m, 8H), 7.07 (d, J=1.2 Hz, 1H), 5.40-5.31 (m, 1H), 4.64-4.49 (m, 2H), 4.14 (s, 2H). LC-MS (Method D): m/z=387.1 [M+H]⁺, 1.325 min.

Example 69A and 69B: (S)-5-benzyl-N-(5,6-dihydro-4H-benzo[f][1,2,4]triazolo[4,3-a]azepin-4-yl)-4H-1,2,4-triazole-3-carboxamide (69A) and (R)-5-benzyl-N-(5,6-dihydro-4H-benzo[f][1,2,4]triazolo[4,3-a]azepin-4-yl)-4H-1,2,4-triazole-3-carboxamide (69B)

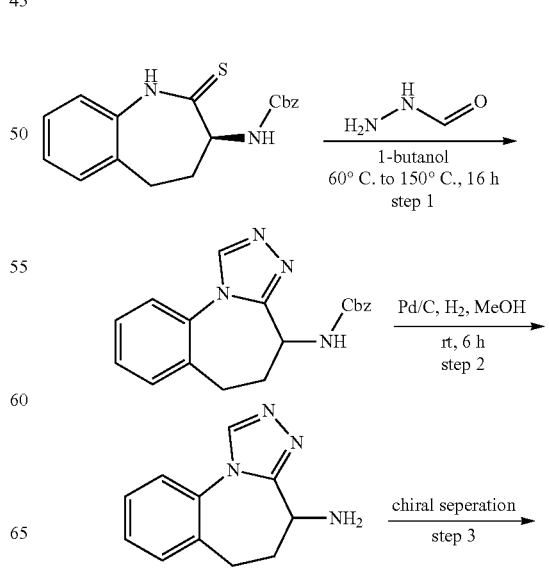

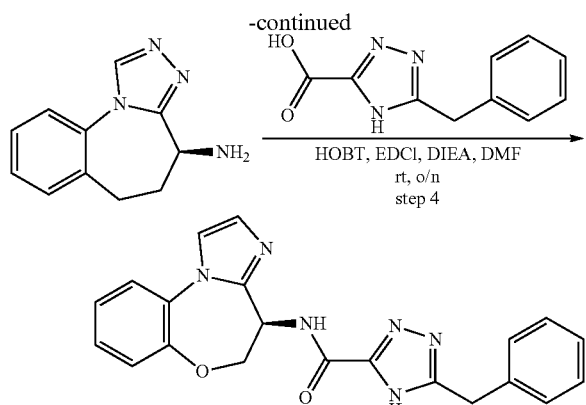

Step 1: Preparation of benzyl (5,6-dihydro-4H-benzo[f][1,2,4]triazolo[4,3-a]azepin-4-yl)carbamate Formylhydrazine (0.54 g, 9 mmol) was added to a stirring solution of (S)-benzyl (2-thioxo-2,3,4,5-tetrahydro-1H-benzo[b]azepin-3-ylcarbamate (1.00 g, 3 mmol) in 1-butanol (15 mL). After stirring at 60° C. for 1 hour and at 150° C. for 15 hours, the reaction mixture was concentrated under high vacuum, diluted with water (50 mL) and extracted with ethyl acetate (3×100 mL). The combined organic layers were washed with brine, dried over anhydrous sodium sulfate, filtered and concentrated under vacuum. The residue was purified by column chromatography (ethyl acetate/petroleum ether, 1/3) to afford the title compound (0.64 g, 63%) as a white solid. LC-MS (Method E): m/z=335.1 [M+H]+, 0.746 min.

Step 2: Preparation of 5,6-dihydro-4H-benzo[f][1,2,4]triazolo[4,3-a]azepin-4-amine Benzyl (5,6-dihydro-4H-benzo[f][1,2,4]triazolo[4,3-a]azepin-4-yl)carbamate (0.63 g, 1.9 mmol) in methanol (20 mL) was hydrogenated in the presence of palladium on carbon (10%, 0.2 g) under a hydrogen atmosphere (2-3 atm). The reaction mixture was stirred at room temperature for 6 hours under a hydrogen atmosphere. The solids were removed by filtration and the filtrate was concentrated under high vacuum to afford the title compound (0.36 g, 95%) as a colorless oil. LC-MS (Method C): m/z=201.1 [M+H]+, 0.848 min.

Step 3: Preparation of (S)-5,6-dihydro-4H-benzo[f][1,2,4]triazolo[4,3-a]azepin-4-amine and (R)-5,6-dihydro-4H-benzo[f][1,2,4]triazolo[4,3-a]azepin-4-amine The enantiomers of 5,6-dihydro-4H-benzo[f][1,2,4]triazolo[4,3-a]azepin-4-amine (0.36 g, 1.8 mmol) were separated by Prep-Chiral-HPLC with the following conditions: Column: Chiralpak IC, 2×25 cm, 5 μm; Mobile Phase A: MTBE, Mobile Phase B: EtOH; Flow rate: 15 mL/min; Gradient: 60% B to 60% B over 23 min; 220/254 nm; RT 1: 12.04 min; RT 2: 20.81 min to afford the title compounds.
(S)-5,6-dihydro-4H-benzo[f][1,2,4]triazolo[4,3-a]azepin-4-amine (first eluting isomer): 110 mg (62%) as a white solid. LC-MS (Method C): m/z=201.1 [M+H]+, 0.848 min.
(R)-5,6-dihydro-4H-benzo[f][1,2,4]triazolo[4,3-a]azepin-4-amine (second eluting isomer): 110 mg (62%) as a white solid. LC-MS (Method C): m/z=201.1 [M+H]+, 0.848 min.

Step 4: Preparation of (S)-5-benzyl-N-(5,6-dihydro-4H-benzo[f][1,2,4]triazolo[4,3-a]azepin-4-yl)-4H-1,2,4-triazole-3-carboxamide The crude product obtained using Amide Coupling Procedure C was purified by Prep-HPLC with the following conditions: Column: XBridge C18 OBD Prep Column, 100 Å, 5 μm, 19 mm×250 mm; Mobile Phase A: water (10 mmol/L NH4HCO3), Mobile Phase B: ACN; Flow rate: 20 mL/min; Gradient: 20% B to 40% B over 7 min; UV 254 & 220 nm to afford the title compound. 1H NMR (300 MHz, DMSO-d6) δ 14.39 (s, 1H), 8.93 (m, 2H), 7.62-7.59 (m, 1H), 7.56-7.43 (m, 3H), 7.38-7.23 (m, 5H), 5.02-4.92 (m, 1H), 4.14 (s, 2H), 2.84-2.77 (m, 1H), 2.60-2.55 (m, 1H), 2.48-2.40 (m, 2H). LC-MS (Method D): m/z=386.2 [M+H]+, 1.489 min.

Example 69B: (R)-5-benzyl-N-(5,6-dihydro-4H-benzo[f][1,2,4]triazolo[4,3-a]azepin-4-yl)-4H-1,2,4-triazole-3-carboxamide

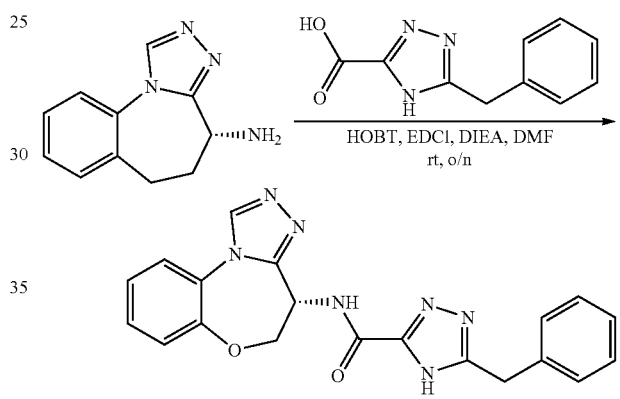

The crude product obtained using Amide Coupling Procedure C was purified by Prep-HPLC with the following conditions: Column: X Bridge C18 OBD Prep Column, 100 Å, 5 μm, 19 mm×250 mm; Mobile Phase A: water (10 mmol/L NH4HCO3), Mobile Phase B: ACN; Flow rate: 20 mL/min; Gradient: 20% B to 40% B over 7 min; UV 254 & 220 nm to afford the title compound 1H NMR (300 MHz, DMSO-d6) δ 14.39 (s, 1H), 8.93 (m, 2H), 7.62-7.59 (m, 1H), 7.56-7.43 (m, 3H), 7.37-7.22 (m, 5H), 5.02-4.92 (m, 1H), 4.14 (s, 2H), 2.84-2.73 (m, 1H), 2.58-2.54 (m, 1H), 2.48-2.41 (m, 2H). LC-MS (Method D): m/z=386.2 [M+H]+, 1.486 min.

Example 70A: (R)-5-benzyl-N-(4,5-dihydrobenzo[b]imidazo[1,2-d][1,4]oxazepin-4-yl)isoxazole-3-carboxamide

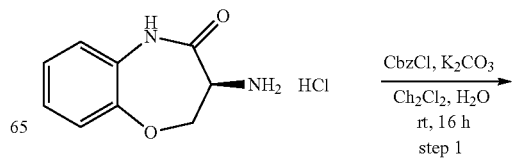

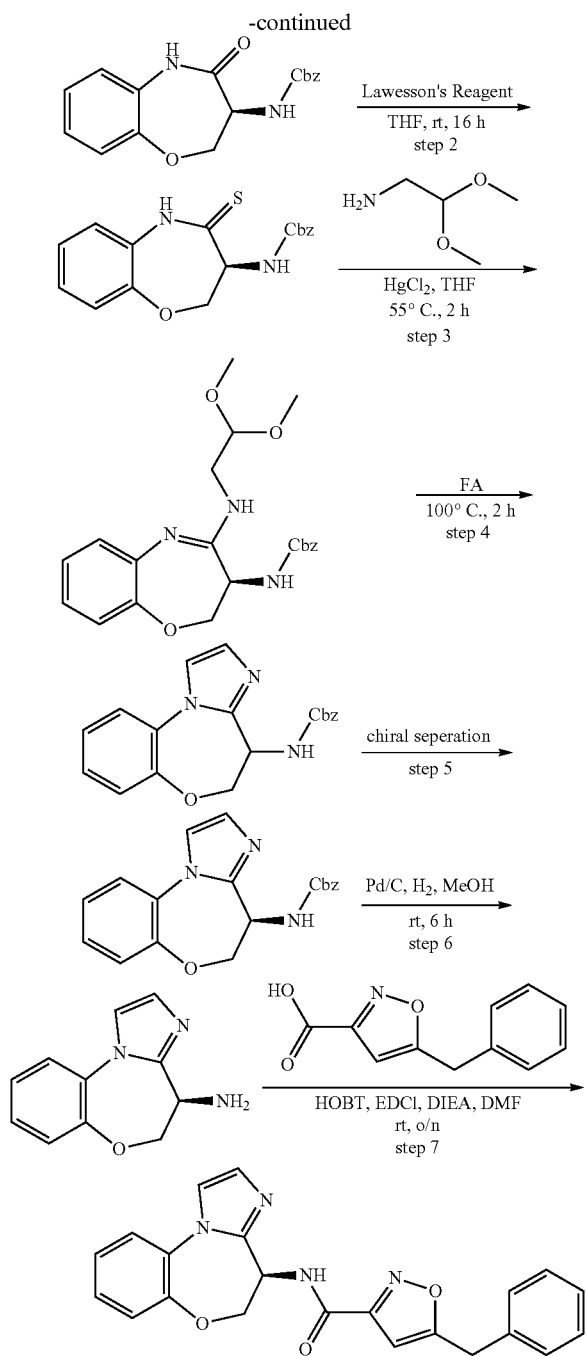

Step 1: Preparation of (S)-benzyl(4-oxo-2,3,4,5-tetrahydrobenzo[b][1,4]oxazepin-3-yl)carbamate A solution of potassium carbonate (4.8 g, 35 mmol) in water (9 mL) was added to a solution of (S)-3-amino-2,3-dihydrobenzo[b][1,4]oxazepin-4(5H)-one hydrochloride (1.5 g, 7 mmol) in dichloromethane (70 mL) and then benzyl chloroformate (1.8 g, 10.5 mmol) was added. The reaction mixture was stirred at room temperature for 16 hours. The precipitate was collected by filtration, washed with water (20 mL) and dried under high vacuum to afford the title compound (1.44 g, 66%) as a white solid. LC-MS (Method C): m/z=313.1 [M+H]$^+$, 1.365 min.

Step 2: Preparation of (S)-benzyl 4-thioxo-2,3,4,5-tetrahydrobenzo[b][1,4]oxazepin-3-ylcarbamate Lawesson's reagent (2.43 g, 6 mmol) was added to a solution of (S)-benzyl 4-oxo-2,3,4,5-tetrahydrobenzo[b][1,4]oxazepin-3-ylcarbamate (1.9 g, 6 mmol) in tetrahydrofuran (50 mL) and the reaction mixture was stirred under a nitrogen atmosphere for 16 hours at room temperature. The precipitate was removed by filtration and the filtrate was concentrated under reduced pressure. The resulting residue was diluted with water (50 mL) and extracted with ethyl acetate (3×100 mL). The combined organic layers were washed with brine, dried over sodium sulfate and concentrated under reduced pressure to give the title compound (1.85 g crude) as a light yellow solid. LC-MS (Method E): m/z=351.0 [M+Na]$^+$, 0.946 min.

Step 3: Preparation of (R)-benzyl 4-(2,2-dimethoxyethylamino)-2,3-dihydrobenzo[b][1,4]-oxazepin-3-ylcarbamate 2,2-Dimethoxyethanamine (2.37 g, 22.6 mmol) was added to a solution of (S)-benzyl 4-thioxo-2,3,4,5-tetrahydrobenzo[b][1,4]oxazepin-3-ylcarbamate (1.85 g, 5.65 mmol) and mercury dichloride (2.0 g, 7.35 mmol) in tetrahydrofuran (50 mL). The reaction mixture was stirred at 55° C. for 2 hours and cooled to room temperature. Solids were removed by filtration and the filtrate was concentrated under reduced pressure. The residue was diluted with water (100 mL) and extracted with dichloromethane (3×100 mL). The combined organic layers were washed with brine, dried over anhydrous sodium sulfate and concentrated under reduced pressure to give the title compound (2.20 g, 98%) as a light yellow oil. LC-MS (Method C): m/z=400.2 [M+H]$^+$, 1.157 min.

Step 4: Preparation of benzyl (4,5-dihydrobenzo[b]imidazo[1,2-d]1-[1,4]oxazepin-4-yl)carbamate A solution of (R)-benzyl 4-(2,2-dimethoxyethylamino)-2,3-dihydrobenzo[b][1,4]-oxazepin-3-ylcarbamate (2.2 g, 5.5 mmol) in formic acid (15 mL, 96%) was stirred at 100° C. for 2 hours. The black sediment was removed by filtration and the filtrate was concentrated under reduced pressure. The resulting residue was diluted with water (50 mL), basified with aqueous sodium hydroxide (1 N, 30 mL) to pH=6 and extracted with ethyl acetate (3×100 mL). The combined organic layers were washed with brine, dried over anhydrous sodium sulfate, filtered and concentrated under reduced pressure. The residue was purified by column chromatography (ethyl acetate/petroleum ether, 1/3) to afford the title compound (0.45 g, 24%) as a white solid. LC-MS (Method E): m/z=336.0 [M+H]$^+$, 0.655 min.

Step 5: Preparation of (S)-benzyl (4,5-dihydrobenzo[b]imidazo[1,2-d][1,4]oxazepin-4-yl)carbamate (First Eluting Isomer) and (R)-benzyl (4,5-dihydrobenzo[b]imidazo[1,2-d][1,4]oxazepin-4-yl)carbamate (Second Eluting Isomer)

The enantiomers of benzyl (4,5-dihydrobenzo[b]imidazo[1,2-d][1,4]oxazepin-4-yl)carbamate (450 mg, 1.35 mmol) were separated by SFC with the following conditions: Column: CHIRALPAK-IC-SFC, 5 cm×25 cm (5 μm); Mobile Phase A: CO$_2$ 50%, Mobile Phase B: MeOH: 50%; Flow rate: 150 mL/min; 220 nm; RT 1: 5.65 min; RT 2: 6.91 min to afford the title compounds:

(S)-benzyl (4,5-dihydrobenzo[b]imidazo[1,2-d][1,4]oxazepin-4-yl)carbamate: (250 mg, 56%) as a white solid. LC-MS (Method E): m/z=336.0 [M+H]$^+$, 0.655 min.

(R)-benzyl (4,5-dihydrobenzo[b]imidazo[1,2-d][1,4]oxazepin-4-yl)carbamate (second eluting isomer): (200 mg, 45%) as a white solid. LC-MS (Method E): m/z=336.0 [M+H]$^+$, 0.655 min.

Step 6: Preparation of (R)-4,5-dihydrobenzo[b]imidazo[1,2-d][1,4]oxazepin-4-amine (R)-Benzyl (4,5-dihydrobenzo[b]imidazo[1,2-d][1,4]oxazepin-4-yl)carbamate (0.25 g, 0.75 mmol) in methanol (20 mL) was hydrogenated in the presence of palladium on carbon (10%, 0.5 g) under a hydrogen atmosphere (2-3 atm). The reaction mixture was stirred for 6 hours at room temperature under a hydrogen atmosphere. The solids were removed by filtration and the filtrate was concentrated under high vacuum to afford the title compound (0.14 g, 93%) as a white solid. LC-MS (Method C): m/z=202.1 [M+H]$^+$, 0.758 min.

Step 7: Preparation of (R)-5-benzyl-N-(4,5-dihydrobenzo[b]imidazo[1,2-d][1,4]oxazepin-4-yl)isoxazole-3-carboxamide The crude product obtained using Amide Coupling Procedure C was purified by Prep-HPLC with the following conditions: Column: X Bridge Prep C18 OBD Column, 5 μm, 19×150 mm; Mobile Phase A: water (10 mmol/L NH$_4$HCO$_3$), Mobile Phase B: ACN; Flow rate: 20 mL/min; Gradient: 20% B to 65% B over 7 min; UV 254 & 220 nm to afford the title compound. $^1$H NMR (300 MHz, DMSO-d$_6$) δ 9.24 (d, J=8.7 Hz, 1H), 7.71-7.65 (m, 2H), 7.40-7.28 (m, 8H), 7.07 (d, J=1.2 Hz, 1H), 6.59 (s, 1H), 5.43-5.34 (m, 1H), 4.61-4.46 (m, 2H), 4.24 (s, 2H). LC-MS (Method D): m/z=387.1 [M+H]$^+$, 1.579 min.

Example 70B: (S)-5-benzyl-N-(4,5-dihydrobenzo[b]imidazo[1,2-d][1,4]oxazepin-4-yl)isoxazole-3-carboxamide

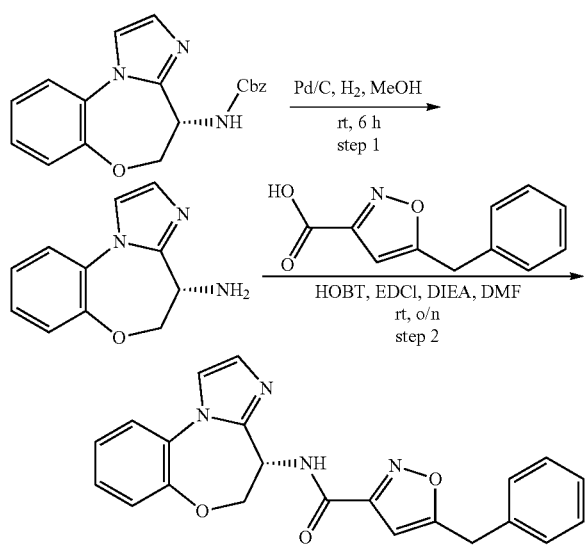

Step 1: Preparation of (S)-4,5-dihydrobenzo[b]imidazo[1,2-d][1,4]oxazepin-4-amine (S)-Benzyl (4,5-dihydrobenzo[b]imidazo[1,2-d][1,4]oxazepin-4-yl)carbamate (0.2 g, 0.6 mmol) in methanol (20 mL) was hydrogenated in the presence of palladium on carbon (10%, 0.2 g) under a hydrogen atmosphere (2-3 atm). The reaction mixture was stirred at room temperature for 6 hours under a hydrogen atmosphere. The solids were removed by filtration and the filtrate was concentrated under high vacuum to afford the title compound (0.11 g, 92%) as a white solid. LC-MS (Method C): m/z=202.1 [M+H]$^+$, 0.758 min.

Step 2: Preparation of (S)-5-benzyl-N-(4,5-dihydrobenzo[b]imidazo[1,2-d][1,4]oxazepin-4-yl)isoxazole-3-carboxamide The crude product obtained using Amide Coupling Procedure C was purified by Prep-HPLC with the following conditions: Column: X Bridge Prep C18 OBD Column, 5 μm, 19×150 mm; Mobile Phase A: water (10 mmol/L NH$_4$HCO$_3$), Mobile Phase B: ACN; Flow rate: 20 mL/min; Gradient: 45% B to 57% B over 7 min; UV 254 & 220 nm to afford the title compound. $^1$H NMR (300 MHz, DMSO-d$_6$) δ 9.24 (d, J=8.4 Hz, 1H), 7.71-7.65 (m, 2H), 7.42-7.28 (m, 8H), 7.07 (d, J=1.5 Hz, 1H), 6.59 (s, 1H), 5.43-5.34 (m, 1H), 4.62-4.45 (m, 2H), 4.24 (s, 2H). LC-MS (Method V): m/z=387.1 [M+H]$^+$, 2.491 min.

Example 71A: (S)-5-benzyl-N-(5,6-dihydro-4H-benzo[f][1,2,4]triazolo[4,3-a]azepin-4-yl)isoxazole-3-carboxamide

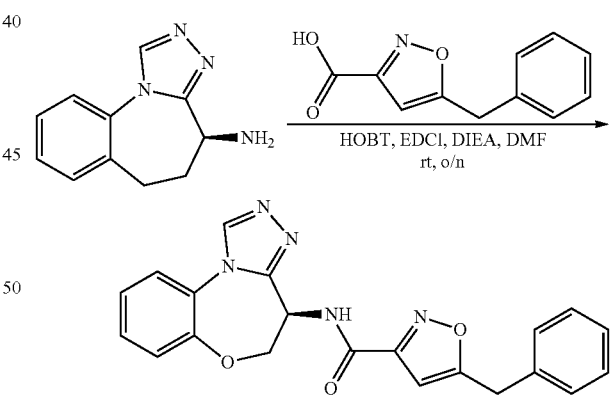

The crude product obtained using Amide Coupling Procedure C was purified by Prep-HPLC with the following conditions: Column: X Bridge Prep C18 OBD Column, 5 μm, 19×150 mm; Mobile Phase A: water (10 mmol/L NH$_4$HCO$_3$), Mobile Phase B: ACN; Flow rate: 20 mL/min; Gradient: 30% B to 58% B over 7 min; UV 254 & 220 nm to afford the title compound. NMR (300 MHz, DMSO-d$_6$) δ 9.36 (d, J=8.4 Hz, 1H), 8.93 (s, 1H), 7.62-7.59 (m, 1H), 7.55-7.43 (m, 3H), 7.40-7.26 (m, 5H), 6.58 (s, 1H), 5.01-4.92 (m, 1H), 4.24 (s, 2H), 2.86-2.77 (m, 1H), 2.49-2.39 (m, 3H). LC-MS (Method D): m/z=386.2 [M+H]$^+$, 1.805 min.

Example 71B: (R)-5-benzyl-N-(5,6-dihydro-4H-benzo[f][1,2,4]triazolo[4,3-a]azepin-4-yl)isoxazole-3-carboxamide

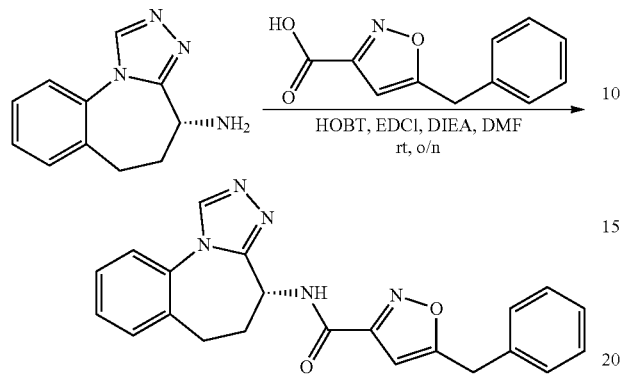

The crude product obtained using Amide Coupling Procedure C was purified by Prep-HPLC with the following conditions: Column: X Bridge Prep C18 OBD Column, 5 µm, 19×150 mm; Mobile Phase A: water (10 mmol/L NH$_4$HCO$_3$), Mobile Phase B: ACN; Flow rate: 20 mL/min; Gradient: 30% B to 60% B over 7 min; UV 254 & 220 nm to afford the title compound. NMR (300 MHz, DMSO-d$_6$) δ 9.36 (d, J=8.1 Hz, 1H), 8.93 (s, 1H), 7.63-7.59 (m, 1H), 7.55-7.43 (m, 3H), 7.40-7.26 (m, 5H), 6.58 (s, 1H), 5.01-4.92 (m, 1H), 4.24 (s, 2H), 2.86-2.77 (m, 1H), 2.49-2.38 (m, 3H). LC-MS (Method D): m/z=386.2 [M+H]$^+$, 1.809 min.

Example 72: (S)—N-(5-methyl-4-oxo-2,3,4,5-tetrahydrobenzo[b][1,4]oxazepin-3-yl)-5-(1-phenylcyclopropyl)-1H-pyrazole-3-carboxamide

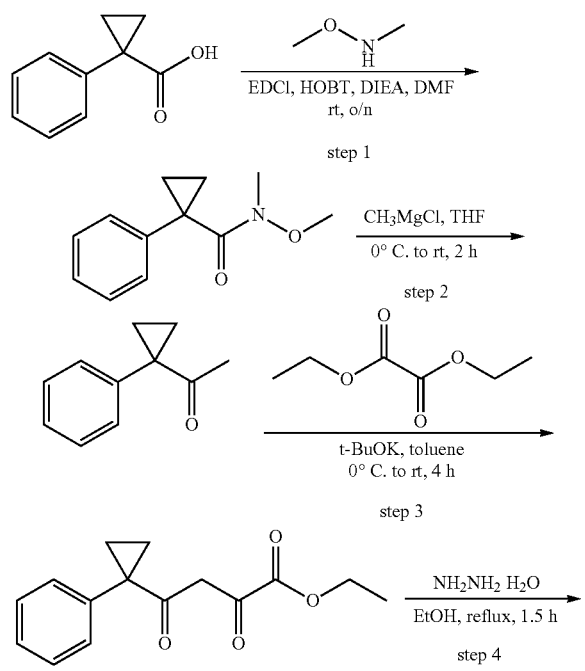

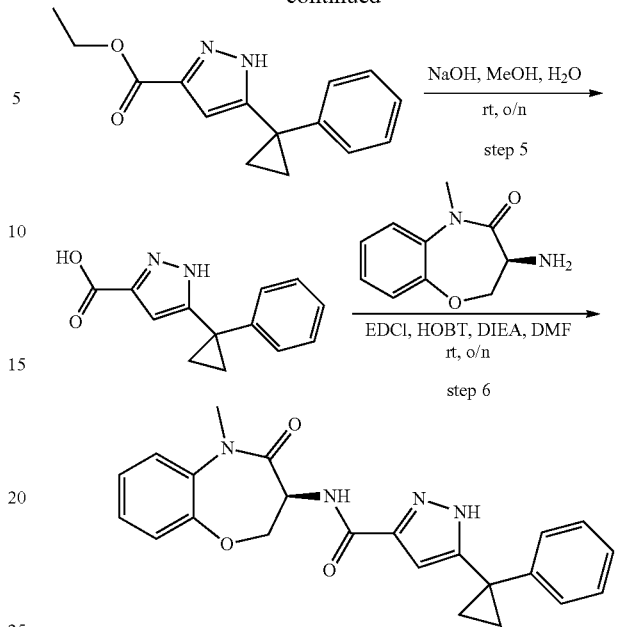

Step 1: Preparation of N-methoxy-N-methyl-1-phenylcyclopropane-carboxamide

N,N-diisopropylethylamine (47.2 g, 219.6 mmol) was added to a mixture of 1-phenylcyclopropanecarboxylic acid (10.0 g, 61.7 mmol), O,N-dimethylhydroxylamine hydrochloride (6.5 g, 67.8 mmol), N-(3-dimethylaminopropyl))-N'-ethylcarbodiimide hydrochloride (14.2 g, 73.9 mmol) and 1-hydroxybenzotriazole (10.0 g, 73.9 mmol) in N,N-dimethylformamide (60 mL). The resulting mixture was stirred overnight at room temperature, diluted with water (300 mL) and extracted ethyl acetate (3×200 mL). The combined organic phases were washed with brine, dried over sodium sulfate, filtered and concentrated under reduced pressure. The residue was purified by column chromatography (ethyl acetate/petroleum ether, 1/20) to afford the title compound (11.2 g, 89.6%) as colorless oil. LC-MS (Method K): m/z=206.0 [M+H]$^+$, 1.489 min.

Step 2: Preparation of 1-(1-phenylcyclopropyl)ethanone

To a solution of methylmagnesium bromide (3 M, 14 mL, 42 mmol) in tetrahydrofuran was added a solution of N-methoxy-N-methyl-1-phenylcyclopropanecarboxamide (11.2 g, 24.4 mmol) in tetrahydrofuran (50 mL) at 0° C. The resulting mixture was stirred overnight at room temperature, quenched with saturated ammonium chloride (50 mL), extracted with ethyl acetate (3×80 mL). The combined organic layers were washed with brine, dried with sodium sulfate and concentrated under reduced pressure. The residue was purified by column chromatography (ethyl acetate/petroleum ether, 1/20) to afford the title compound (7.4 g, 85%) as a colorless oil. LC-MS (Method E): m/z=161.0 [M+H]$^+$, 0.889 min.

Step 3: Preparation of ethyl 2,4-dioxo-4-(1-phenylcyclopropyl)butanoate

To a mixture of 1-(1-phenylcyclopropyl)ethanone (1.92 g, 12 mmol) and diethyl oxalate (2.1 g, 14.4 mmol) in toluene (8 mL) was added potassium 2-methylpropan-2-olate (1.7 g, 15.6 mmol) at 0° C. The resulting mixture was stirred at room temperature for 4 hours and concentrated under vacuum. The residue was diluted with water (20 mL). The resulting mixture was neutralized to pH=6 with aqueous hydrochloric acid (1 N) and extracted with ethyl acetate (3×20 mL). The combined organic layers were washed with brine, dried over anhydrous sodium sulfate, filtered and concentrated under reduced pressure. The residue was purified by column chromatography (ethyl acetate/petroleum ether, 1/10) to afford the title compound (1.95 g, 61%) as a yellow solid. LC-MS (Method S): m/z=261.2 [M+H]+, 1.076 min.

Step 4: Preparation of ethyl 5-(1-phenylcyclopropyl)-1H-pyrazole-3-carboxylate

To a solution of ethyl 2,4-dioxo-4-(1-phenylcyclopropyl) butanoate (800 mg, 3.0 mmol) in ethanol (8 mL) was added hydrazine hydrate (80% aqueous solution, 200 mg, 3.0 mmol). The reaction mixture was stirred at 80° C. for 1.5 hours and concentrated under vacuum. The resulting residue was purified by column chromatography (ethyl acetate/petroleum ether, 1/3) to afford the title compound (550 mg, 70%) as a yellow solid. LC-MS (Method K): m/z=256.7 [M+H]+, 1.640 min.

Step 5: Preparation of 5-(1-phenylcyclopropyl)-1H-pyrazole-3-carboxylic acid

To a solution of ethyl 5-(1-phenylcyclopropyl)-1H-pyrazole-3-carboxylate (470 mg, 1.8 mmol) in methanol (4.5 mL) and water (1.5 mL) was added sodium hydroxide (432 mg, 10.8 mmol). The reaction mixture was stirred overnight at room temperature and concentrated under vacuum. The residue was diluted with water (20 mL) and adjusted to pH=5 using aqueous hydrochloric acid (1 N) and extracted with ethyl acetate (3×10 mL). The combined organic layers were washed with brine, dried over anhydrous sodium sulfate and concentrated under vacuum to afford the title compound (280 mg crude) as a yellow solid, which was used directly in the next step without further purification. LC-MS (Method K): m/z=228.7 [M+H]+, 1.434 min.

Step 6: Preparation of (S)—N-(5-methyl-4-oxo-2,3,4,5-tetrahydrobenzo[b][1,4]oxazepin-3-yl)-5-(1-phenylcyclopropyl)-1H-pyrazole-3-carboxamide The crude product obtained using Amide Coupling Procedure C was purified by Prep-HPLC with the following conditions: Column: XBridge Prep C18 OBD Column, 5 µm, 19×150 mm; mobile phase, water (10 mmol/L NH4HCO3), ACN (40% ACN to 65% B over 7 min); detector, UV 254 & 220 nm to afford the title compound. 1H NMR (300 MHz, DMSO-d6) 13.16 (s, 1H), 8.06 (d, J=8.1 Hz, 1H), 7.55-7.46 (m, 1H), 7.38-7.17 (m, 8H), 6.34 (s, 1H), 4.93-4.75 (m, 1H), 4.60-4.28 (m, 2H), 3.31 (s, 3H), 1.39-1.16 (m, 4H). LC-MS (Method O): m/z=403.05 [M+H]+, 1.511 min.

Example 73: (S)—N-(5-methyl-4-oxo-2,3,4,5-tetrahydropyrido[3,2-b][1,4]oxazepin-3-yl)-5-(1-phenylcyclopropyl)-1H-pyrazole-3-carboxamide

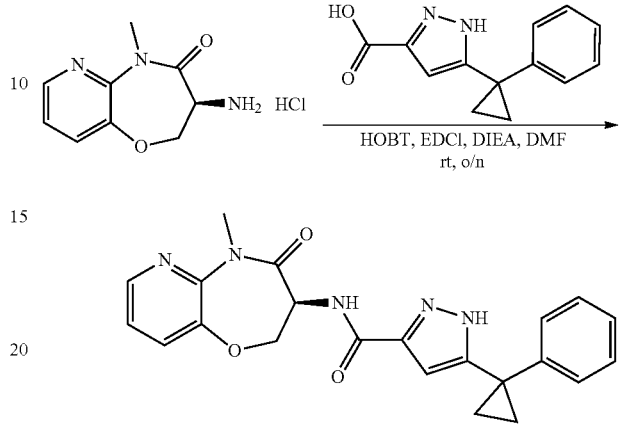

The crude product obtained using Amide Coupling Procedure C was purified by Prep-HPLC with the following conditions: Column: X Bridge C18 OBD Prep Column, 100 Å, 5 µm, 19 mm×250 mm; Mobile Phase A: water (10 mmol/L NH4HCO3), Mobile Phase B: ACN; Flow rate: 20 mL/min; Gradient: 30% B to 50% B over 7 min; UV 254 & 220 nm to afford the title compound. 1H NMR (300 MHz, DMSO-d6) δ 13.18 (s, 1H), 8.38-8.35 (m, 1H), 8.24 (d, J=7.5 Hz, 1H), 7.73-7.69 (m, 1H), 7.36-7.20 (m, 6H), 6.54-6.35 (m, 1H), 4.90-4.80 (m, 1H), 4.70-4.62 (m, 1H), 4.53-4.46 (m, 1H), 3.35 (s, 3H), 1.34-1.30 (m, 4H). LC-MS (Method D): m/z=404.2 [M+H]+, 1.872 min.

Example 74: (S)-4-fluoro-N-(5-methyl-4-oxo-2,3,4,5-tetrahydropyrido[3,2-b][1,4]oxazepin-3-yl)-1-(pyridin-2-ylmethyl)-1H-pyrazole-3-carboxamide

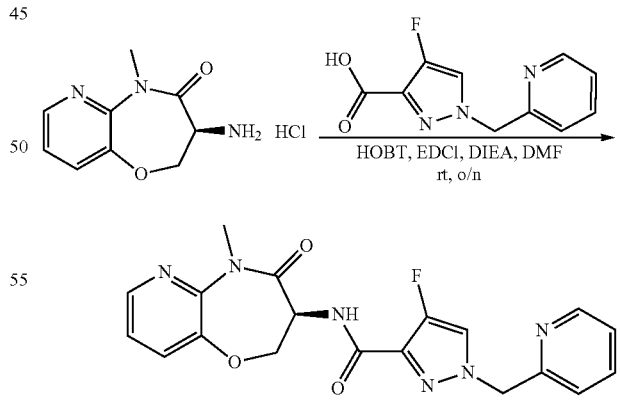

The crude product obtained using Amide Coupling Procedure C was purified by Prep-HPLC with the following conditions: Column: X Bridge Prep C18 OBD Column, 5 µm, 19×150 mm; Mobile Phase A: water (10 mmol/L NH4HCO3), Mobile Phase B: ACN; Flow rate: 20 mL/min; Gradient: 5% B to 57% B over 7 min; UV 254 & 220 nm to afford the title compound. ¹H NMR (400 MHz, DMSO-d₆) δ 8.56 (d, J=4.8 Hz, 1H), 8.36 (dd, J=4.8, 1.6 Hz, 1H), 8.27 (d, J=7.6 Hz, 1H), 8.16 (d, J=4.4 Hz, 1H), 7.87-7.77 (m, 1H), 7.70 (dd, J=8.0, 1.6 Hz, 1H), 7.38-7.31 (m, 2H), 7.21 (d, J=8.0 Hz, 1H), 5.47 (s, 2H), 4.88-4.80 (m, 1H), 4.71-4.64 (m, 1H), 4.52-4.47 (m, 1H), 3.35 (s, 3H). LC-MS (Method V): m/z=397.1 [M+H]⁺, 2.159 min.

Example 75A and 75B: 5-benzyl-N-((1aS,2S,8bR)-4-methyl-3-oxo-1,1a,2,3,4,8b-hexahydrocyclopropa[d]pyrido[2,3-b]azepin-2-yl)-4H-1,2,4-triazole-3-carboxamide (75A) and 5-benzyl-N-((1aR,2R,8bS)-4-methyl-3-oxo-1,1a,2,3,4,8b-hexahydrocyclopropa[d]pyrido[2,3-b]azepin-2-yl)-4H-1,2,4-triazole-3-carboxamide (75B)

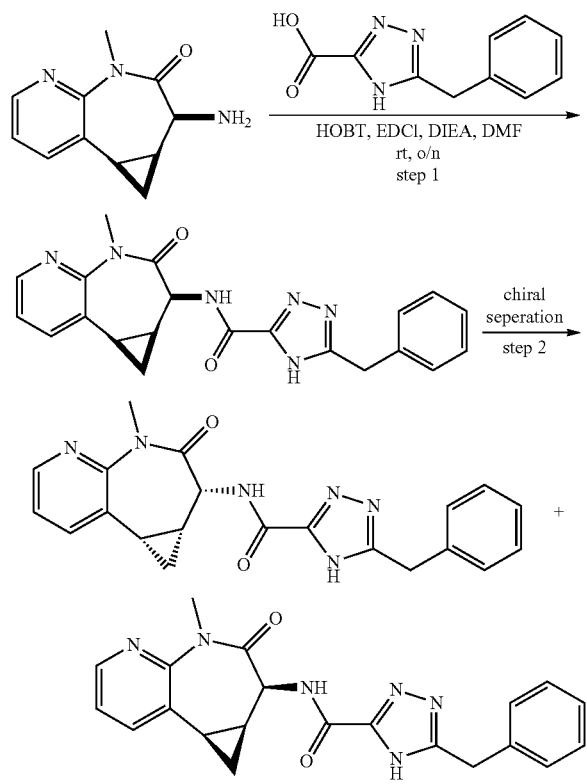

Step 1: Preparation of 5-benzyl-N-(cis-4-methyl-3-oxo-1,1a,2,3,4,8b-hexahydrocyclopropa[d]pyrido[2,3-b]azepin-2-yl)-4H-1,2,4-triazole-3-carboxamide The crude product obtained using Amide Coupling Procedure C was purified by Prep-HPLC with the following conditions: column: X bridge Prep C18, 19×150 mm, 5 μm; Mobile phase: Phase A: water (10 mmol/L NH₄HCO₃); Phase B: ACN (20% to 80% over 12 min); Detector, UV 220 & 254 nm to afford the title compound (55 mg, 44.3%) as a white solid. LC-MS (Method C): m/z=389.2 [M+H]⁺, 1.111 min.

Step 2: Preparation of 5-benzyl-N-((1aR,2R,8bS)-4-methyl-3-oxo-1,1a,2,3,4,8b-hexahydrocyclopropa[d]pyrido[2,3-b]azepin-2-yl)-4H-1,2,4-triazole-3-carboxamide (First Eluting Isomer) and 5-benzyl-N-((1aS,2S,8bR)-4-methyl-3-oxo-1,1a,2,3,4,8b-hexahydrocyclopropa[d]pyrido[2,3-b]azepin-2-yl)-4H-1,2,4-triazole-3-carboxamide (Second Eluting Isomer)

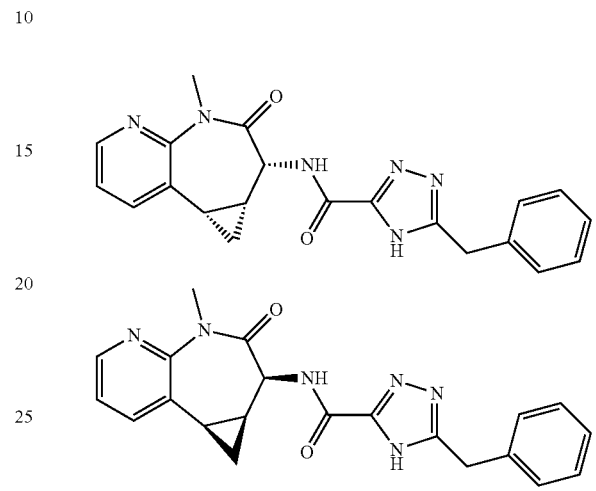

The enantiomers of 5-benzyl-N-(cis-4-methyl-3-oxo-1,1a,2,3,4,8b-hexahydrocyclopropa[d]pyrido[2,3-b]azepin-2-yl)-4H-1,2,4-triazole-3-carboxamide (55 mg, 0.14 mmol) were separated by Prep-Chiral-HPLC with the following conditions: Column: Chiralpak IC, 2×25 cm, 5 μm; Mobile Phase A: hexane, Mobile Phase B: EtOH; Flow rate: 19 mL/min; Gradient: 35% B to 35% B over 18.5 min; UV 220 & 254 nm; RT 1: 13.00 min; RT 2: 15.67 min to afford the title compounds:

Example 75B (first eluting isomer): ¹H NMR (400 MHz, DMSO-d₆) δ 14.37 (s, 1H), 8.46 (d, J=7.2 Hz, 1H), 8.40-8.38 (m, 1H), 8.02-7.98 (m, 1H), 7.35-7.25 (m, 6H), 4.46 (d, J=7.2 Hz, 1H), 4.16 (s, 2H), 3.30 (s, 3H), 2.33-2.26 (m, 1H), 2.05-1.99 (m, 1H), 1.21-1.14 (m, 1H), 1.11-1.04 (m, 1H). LC-MS (Method D): m/z=389.2 [M+H]⁺, 1.651 min.

Example 75A (second eluting isomer): ¹H NMR (400 MHz, DMSO-d₆) δ 8.54 (d, J=7.2 Hz, 1H), 8.40-8.38 (m, 1H), 8.02-7.98 (m, 1H), 7.38-7.23 (m, 6H), 4.46 (d, J=7.2 Hz, 1H), 4.14 (s, 2H), 3.30 (s, 3H), 2.32-2.26 (m, 1H), 2.06-1.99 (m, 1H), 1.20-1.15 (m, 1H), 1.10-1.04 (m, 1H). LC-MS (Method D): m/z=389.2 [M+H]⁺, 1.656 min.

Example 76: (S)-1-benzyl-4-fluoro-N-(5-methyl-4-oxo-2,3,4,5-tetrahydropyrido[3,2-b][1,4]oxazepin-3-yl)-1H-pyrazole-3-carboxamide

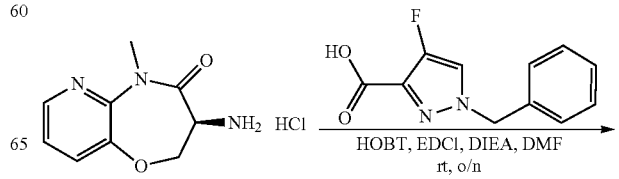

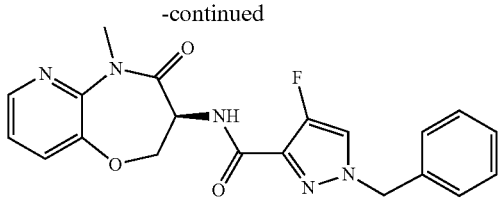

The crude product obtained using Amide Coupling Procedure C was purified by Prep-HPLC with the following conditions: Column: X Bridge Prep C18 OBD Column, 5 µm, 19×150 mm; Mobile Phase A: water (10 mmol/L NH$_4$HCO$_3$), Mobile Phase B: ACN; Flow rate: 20 mL/min; Gradient: 32% B to 54% B over 7 min; UV 254 & 220 nm to afford the title compound. $^1$H NMR (300 MHz, DMSO-d$_6$) δ 8.37 (dd, J=4.5, 1.5 Hz, 1H), 8.26 (d, J=7.5 Hz, 1H), 8.15 (d, J=4.5 Hz, 1H), 7.71 (dd, J=8.1, 1.8 Hz, 1H), 7.43-7.27 (m, 6H), 5.36 (s, 2H), 4.90-4.80 (m, 1H), 4.73-4.65 (m, 1H), 4.55-4.48 (m, 1H), 3.36 (s, 3H). LC-MS (Method D): m/z=396.1 [M+H]$^+$, 1.893 min.

Example 77: (S)—N-(5-methyl-4-oxo-2,3,4,5-tetrahydropyrido[3,2-b][1,4]oxazepin-3-yl)-5-(1-phenylcyclopropyl)isoxazole-3-carboxamide

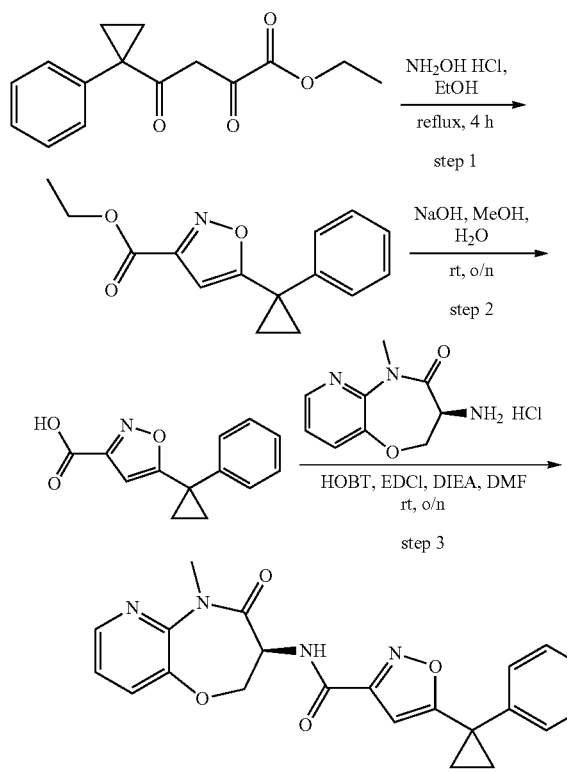

Step 1: Preparation of ethyl 5-(1-phenylcyclopropyl)isoxazole-3-carboxylate

To a mixture of ethyl 2,4-dioxo-4-(1-phenylcyclopropyl)butanoate (970 mg, 3.7 mmol) in ethanol (10 mL) was added hydroxylamine hydrochloride (255 mg, 3.7 mmol). The reaction mixture was heated at reflux and stirred for 4 hours. Upon concentration under reduced pressure, the residue was purified by column chromatography (ethyl acetate/petroleum ether, 1/5) to afford the title compound (260 mg, 27%) as a yellow solid. LC-MS (Method K): m/z=258.1 [M]$^+$, 1.603 min.

Step 2: Preparation of 5-(1-phenylcyclopropyl)isoxazole-3-carboxylic acid

To a solution of ethyl 5-(1-phenylcyclopropyl)isoxazole-3-carboxylate (100 mg, 0.39 mmol) in methanol (3 mL) and water (1 mL) was added sodium hydroxide (93 mg, 2.33 mmol). The resulting mixture was stirred at room temperature overnight, concentrated to dryness and diluted with water (10 mL). The reaction mixture was adjusted to pH=5 with aqueous hydrochloric acid (1 N, 10 mL), and extracted with ethyl acetate (3×10 mL). The combined organic layers were washed with brine, dried over anhydrous sodium sulfate, filtered and concentrated under vacuum to afford the title compound (80 mg crude) as a yellow solid. LC-MS (Method E): m/z=229.9 [M+H]$^+$, 0.840 min.

Step 3: Preparation of (S)—N-(5-methyl-4-oxo-2,3,4,5-tetrahydropyrido[3,2-b][1,4]oxazepin-3-yl)-5-(1-phenylcyclopropyl)isoxazole-3-carboxamide The crude product obtained using Amide Coupling Procedure C was purified by Prep-HPLC with the following conditions: Column: X Bridge Prep C18 OBD Column, 5 µm, 19×150 mm; Mobile Phase A: water (10 mmol/L NH$_4$HCO$_3$), Mobile Phase B: ACN; Flow rate: 20 mL/min; Gradient: 40% B to 75% B over 7 min; UV 254 & 220 nm to afford the title compound. $^1$H NMR (300 MHz, DMSO-d$_6$) δ 8.95 (d, J=8.1 Hz, 1H), 8.37 (dd, J=4.8, 1.5 Hz, 1H), 7.70 (dd, J=7.8, 1.5 Hz, 1H), 7.43-7.29 (m, 6H), 6.38 (s, 1H), 4.90-4.80 (m, 1H), 4.70-4.62 (m, 1H), 4.55-4.48 (m, 1H), 3.35 (s, 3H), 1.58-1.51 (m, 2H), 1.50-1.42 (m, 2H). LC-MS (Method D): m/z=405.1 [M+H]$^+$, 2.134 min.

Example 78: (S)—N-(5-methyl-4-oxo-2,3,4,5-tetrahydrobenzo[b][1,4]oxazepin-3-yl)-5-(1-phenylcyclopropyl)-1H-imidazole-2-carboxamide

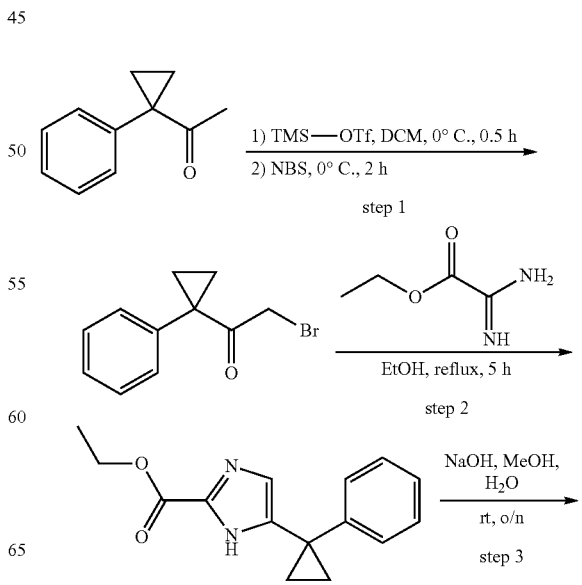

-continued

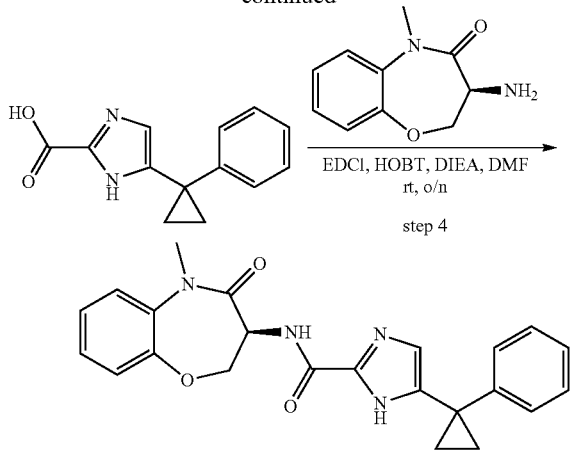

Step 1: Preparation of 2-bromo-1-(1-phenylcyclopropyl)ethanone

To a solution of 1-(1-phenylcyclopropyl)ethanone (4.0 g, 25.0 mmol) and triethylamine (5.0 g, 50 mmol) in dichloromethane (100 mL) was added trimethylsilyl trifluoromethanesulfonate (5.55 g, 25.0 mmol) at 0° C. After stirring for 0.5 hour, 1-bromopyrrolidine-2,5-dione (4.9 g, 27.5 mmol) was added in portions at 0° C. The reaction mixture was stirred for another 2 hours, quenched with 100 mL of water and extracted with dichloromethane (3×80 mL). The combined organic phases were washed with brine, dried over sodium sulfate, filtered and concentrated under vacuum. The residue was purified by column chromatography (ethyl acetate/petroleum ether, 1/20) to afford the title compound (3.4 g, 57%) as a yellow oil. LC-MS (Method E): m/z=238.8 [M+H]$^+$, 0.971 min.

Step 2: Preparation of ethyl 5-(1-phenylcyclopropyl)-1H-imidazole-2-carboxylate

A solution of 2-bromo-1-(1-phenylcyclopropyl)ethanone (3.4 g, 14.2 mmol), ethyl 2-amino-2-iminoacetate (1.65 g, 14.2 mmol) and triethylamine (4.3 g, 42.6 mmol) in ethanol (50 mL) was heated at reflux for 5 hours. Upon concentration under reduced pressure the resulting residue was purified by column chromatography (ethyl acetate/petroleum ether, 1/5) to afford the title compound (520 mg, 14%) as a yellow solid. LC-MS (Method C): m/z=257.0 [M+H]$^+$, 1.000 min.

Step 3: Preparation of 5-(1-phenylcyclopropyl)-1H-imidazole-2-carboxylic acid

To a solution of ethyl 5-(1-phenylcyclopropyl)-1H-imidazole-2-carboxylate (300 mg, 1.2 mmol) in methanol (9 mL) and water (3 mL) was added sodium hydroxide (288 mg, 7.2 mmol). The mixture was stirred at room temperature overnight. The solution was adjusted to pH=5, and extracted with ethyl acetate (3×10 mL). The combined organic layers were washed with brine, dried over anhydrous sodium sulfate and concentrated under vacuum to afford the title compound (130 mg crude) as a yellow solid. LC-MS (Method C): m/z=229.1 [M+H]$^+$, 0.906 min.

Step 4: Preparation of (S)—N-(5-methyl-4-oxo-2,3,4,5-tetrahydrobenzo[b][1,4]oxazepin-3-yl)-5-(1-phenylcyclopropyl)-1H-imidazole-2-carboxamide The crude product obtained using Amide Coupling Procedure C was purified by Prep-HPLC with the following conditions: Column: XBridge Prep C18 OBD Column, 5 μm, 19×150 mm; mobile phase, water (10 mmol/L NH$_4$HCO$_3$), ACN (40% ACN to 70% B over 7 min); detector, UV 254 & 220 nm to afford the title compound. $^1$H NMR (400 MHz, DMSO-d$_6$) δ 13.11-12.79 (m, 1H), 8.32-8.17 (m, 1H), 7.51 (dd, J=7.6, 1.9 Hz, 1H), 7.37-7.16 (m, 8H), 6.85-6.44 (m, 1H), 4.88-4.74 (m, 1H), 4.66-4.50 (m, 1H), 4.45-4.35 (m, 1H), 3.32 (s, 3H), 1.38-1.27 (m, 2H), 1.25-1.12 (m, 2H). LC-MS (Method Q): m/z=403.3 [M+H]$^+$, 1.533 min.

Example 79: (S)-7-(2-fluorophenyl)-N-(5-methyl-4-oxo-2,3,4,5-tetrahydrobenzo[b][1,4]oxazepin-3-yl)benzo[d]thiazole-2-carboxamide

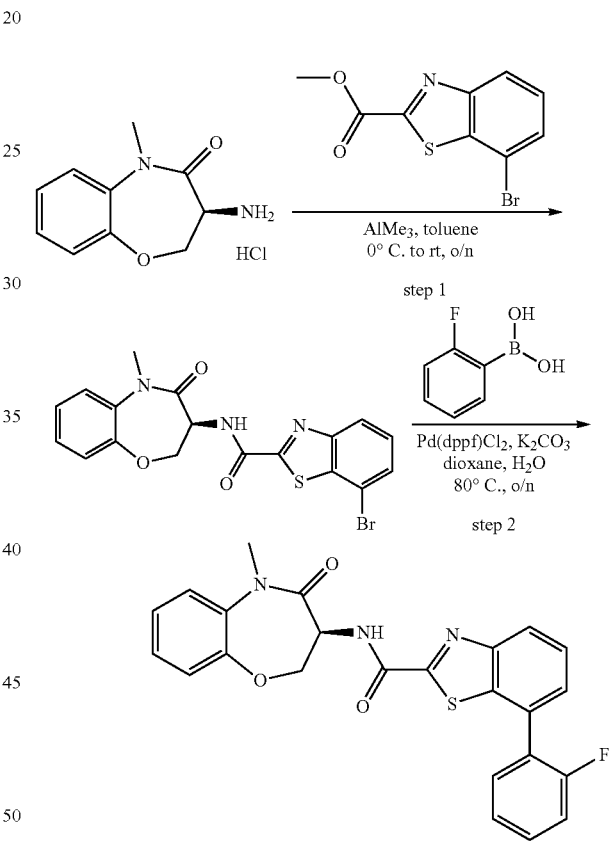

Step 1: Preparation of (S)-7-bromo-N-(5-methyl-4-oxo-2,3,4,5-tetrahydrobenzo[b][1,4]oxazepin-3-yl)benzo[d]thiazole-2-carboxamide Utilizing the procedure described in Example 54 provided title compound (370 mg) as a yellow solid that was used in the next step without purification. LC-MS (Method S): m/z=432.2 [M+H]$^+$, 1.102 min.

Step 2: Preparation of 7-(2-fluorophenyl)-N—((S)-5-methyl-4-oxo-2,3,4,5-tetrahydrobenzo[b][1,4]oxazepin-3-yl)benzo[c]thiazole-2-carboxamide

[1,1'-Bis(diphenylphosphino)ferrocene]dichloropalladium(II) (29 mg, 0.04 mmol) was added to a mixture of (S)-7-bromo-N-(5-methyl-4-oxo-2,3,4,5-tetrahydrobenzo[b][1,4]oxaz-epin-3-yl)benzo[d]thiazole-2-carboxamide (170 mg, 0.39 mmol), 2-fluorophenylboronic acid (85 mg, 0.59 mmol) and potassium carbonate (109 mg, 0.79 mmol) in dioxane (2 mL) and water (0.5 mL) under an atmosphere of nitrogen. The resulting mixture was stirred overnight at 80° C. Solids were removed by filtration and the filtrate was concentrated under reduced pressure. The residue was purified by Prep-HPLC with the following conditions: Column: XBridge Prep C18 OBD Column, 5 µm, 19×150 mm; Mobile Phase A: water (0.05% TFA), Mobile Phase B: ACN; Flow rate: 20 mL/min; Gradient: 3% B to 38% B over 7 min; 254 & 220 nm; Rt: 6.33 min to afford the title compound. $^1$H NMR (300 MHz, DMSO-d$_6$) δ 9.31-9.29 (d, J=7.5 Hz, 1H), 8.29-8.26 (d, J=8.1 Hz, 1H), 7.79-7.77 (m, 1H), 7.68-7.60 (m, 2H), 7.60-7.51 (m, 2H), 7.43-7.26 (m, 5H), 4.89-4.72 (m, 2H), 4.50-4.44 (m, 1H), 3.33 (s, 3H). LC-MS (Method T): m/z=448.3 [M+H]$^+$, 1.884 min.

Example 80A and 80B: 5-benzyl-N-((1aS,2S,8bR)-4-methyl-3-oxo-1,1a,2,3,4,8b-hexahydrocyclopropa[d]pyrido[2,3-b]azepin-2-yl)-1H-pyrazole-3-carboxamide (80A) and 5-benzyl-N-((1aR,2R,8bS)-4-methyl-3-oxo-1,1a,2,3,4,8b-hexahydrocyclopropa[d]pyrido[2,3-b]azepin-2-yl)-1H-pyrazole-3-carboxamide (80B)

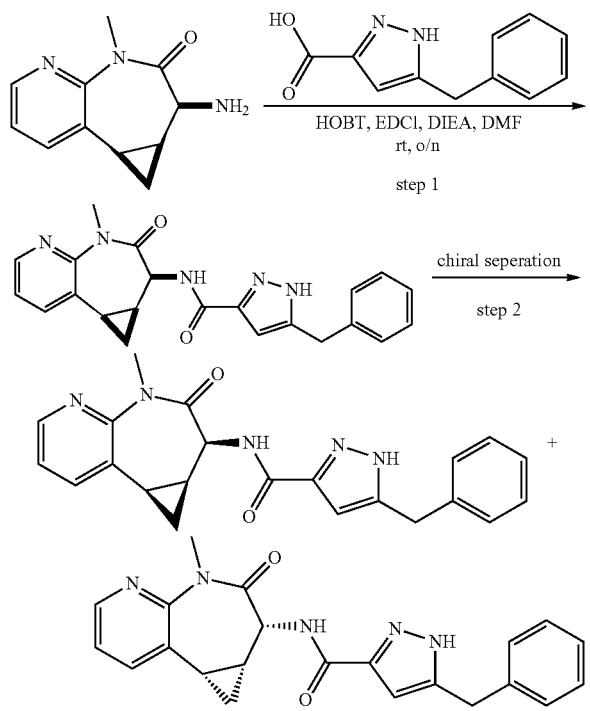

Step 1: Preparation of 5-benzyl-N-(cis-4-methyl-3-oxo-1,1a,2,3,4,8b-hexahydrocyclopropa[d]pyrido[2,3-b]azepin-2-yl)-1H-pyrazole-3-carboxamide The crude product obtained using Amide Coupling Procedure C was purified by Prep-HPLC with the following conditions: Column: X Bridge C18 OBD Prep Column, 100 Å, 5 µm, 19 mm×250 mm; Mobile Phase A: water (10 mmol/L NH$_4$HCO$_3$), Mobile Phase B: ACN; Flow rate: 20 mL/min; Gradient: 30% B to 50% B over 7 min; UV 254 & 220 nm to afford the title compound. LC-MS (Method D): m/z=388.2 [M+H]$^+$, 1.757 min.

Step 2: Preparation of 5-benzyl-N-((1aS,2S,8bR)-4-methyl-3-oxo-1,1a,2,3,4,8b-hexahydro cyclopropa[d]pyrido[2,3-b]azepin-2-yl)-1H-pyrazole-3-carboxamide (First Eluting Isomer) and 5-benzyl-N-((1aR,2R,8bS)-4-methyl-3-oxo-1,1a,2,3,4,8b-hexahydrocyclopropa[d]pyrido[2,3-b]azepin-2-yl)-1H-pyrazole-3-carboxamide (Second Eluting Isomer)

The racemate of 5-benzyl-N-(cis-4-methyl-3-oxo-1,1a,2,3,4,8b-hexahydrocyclopropa[d]pyrido[2,3-b]azepin-2-yl)-1H-pyrazole-3-carboxamide (60 mg, 0.16 mmol) was separated by Prep-Chiral-HPLC with the following conditions: Column: CHIRAL IC, 2×25 cm, 5 µm; Mobile Phase A: hexane, Mobile Phase B: EtOH; Flow rate: 20 mL/min; Gradient: 60% B to 60% B over 16.5 min; UV 254 & 220 nm; RT 1: 8.27 min; RT 2: 13.00 min to afford the title compounds:

Example 80A (first eluting isomer): $^1$H NMR (300 MHz, Methanol-d$_4$) δ 8.38 (dd, J=4.8, 1.8 Hz, 1H), 7.94 (dd, J=7.8, 1.8 Hz, 1H), 7.35-7.21 (m, 6H), 6.52 (s, 1H), 4.65 (s, 1H), 4.05 (s, 2H), 3.40 (s, 3H), 2.31-2.23 (m, 1H), 2.12-2.03 (m, 1H), 1.32-1.26 (m, 1H), 1.22-1.13 (m, 1H). LC-MS (Method D): m/z=388.2 [M+H]$^+$, 1.757 min.

Example 80B (second eluting isomer): $^1$H NMR (300 MHz, Methanol-d$_4$) δ 8.38 (dd, J=4.5, 1.8 Hz, 1H), 7.94 (dd, J=7.8, 1.5 Hz, 1H), 7.35-7.21 (m, 6H), 6.52 (s, 1H), 4.65 (s, 1H), 4.06 (s, 2H), 3.40 (s, 3H), 2.31-2.23 (m, 1H), 2.12-2.04 (m, 1H), 1.33-1.26 (m, 1H), 1.22-1.13 (m, 1H). LC-MS (Method D): m/z=388.2 [M+H]$^+$, 1.757 min.

Example 81A and 81B: 5-benzyl-N-((1aS,2S,8bR)-4-methyl-3-oxo-1,1a,2,3,4,8b-hexahydrocyclopropa[d]pyrido[2,3-b]azepin-2-yl)isoxazole-3-carboxamide (81A) and 5-benzyl-N-((1aR,2R,8bS)-4-methyl-3-oxo-1,1a,2,3,4,8b-hexahydrocyclopropa[d]pyrido[2,3-b]azepin-2-yl)isoxazole-3-carboxamide (81B)

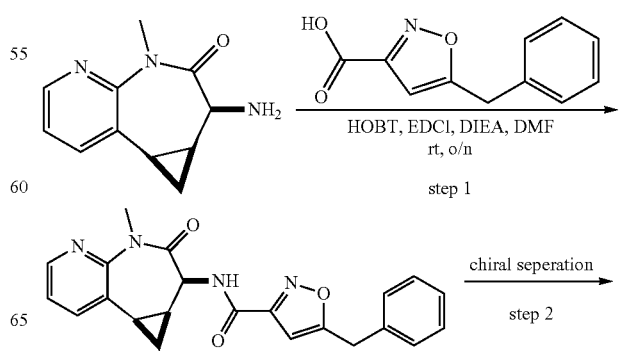

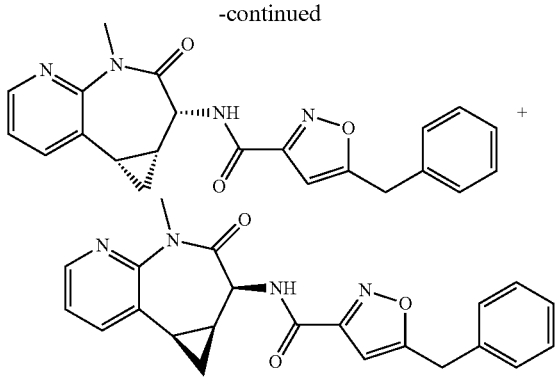

Step 1: Preparation of 5-benzyl-N-(cis-4-methyl-3-oxo-1,1a,2,3,4,8b-hexahydrocyclopropa[d]pyrido[2,3-b]azepin-2-yl)isoxazole-3-carboxamide The crude product obtained using Amide Coupling Procedure C was purified by Prep-HPLC with the following conditions: Column: X Bridge Prep C18 OBD Column, 5 µm, 19×150 mm; Mobile Phase A: water (10 mmol/L NH₄HCO₃), Mobile Phase B: ACN; Flow rate: 20 mL/min; Gradient: 25% B to 55% B over 7 min; UV 254 & 220 nm to afford the title compound. LC-MS (Method D): m/z=389.1 [M+H]⁺, 2.036 min.

Step 2: Preparation of 5-benzyl-N-((1aR,2R,8bS)-4-methyl-3-oxo-1,1a,2,3,4,8b-hexahydrocyclopropa[d]pyrido[2,3-b]azepin-2-yl)isoxazole-3-carboxamide (First Eluting Isomer) and 5-benzyl-N-((1aS,2S,8bR)-4-methyl-3-oxo-1,1a,2,3,4,8b-hexahydrocyclopropa[d]pyrido[2,3-b]azepin-2-yl)isoxazole-3-carboxamide (Second Eluting Isomer)

The racemate of 5-benzyl-N-(cis-4-methyl-3-oxo-1,1a,2,3,4,8b-hexahydrocyclopropa[d]pyrido[2,3-b]azepin-2-yl)isoxazole-3-carboxamide (60 mg, 0.15 mmol) was separated by Prep-Chiral-HPLC with the following conditions: Column: Chiralpak IC, 2×25 cm, 5 µm; Mobile Phase A: hexanes, Mobile Phase B: EtOH; Flow rate: 18 mL/min; Gradient: 50% B to 50% B over 17 min; UV 254 & 220 nm; RT 1:12.098 min; RT 2: 14.358 min to afford the title compounds:

Example 81B (first eluting isomer): ¹H NMR (300 MHz, DMSO-d₆) δ 8.98 (d, J=7.5 Hz, 1H), 8.40 (dd, J=4.5, 1.8 Hz, 1H), 7.98 (dd, J=7.5, 1.8 Hz, 1H), 7.40-7.26 (m, 6H), 6.62 (s, 1H), 4.45 (d, J=7.2 Hz, 1H), 4.24 (s, 2H), 3.29 (s, 3H), 2.34-2.25 (m, 1H), 2.02-1.94 (m, 1H), 1.25-1.06 (m, 2H). LC-MS (Method D): m/z=389.1 [M+H]⁺, 2.036 min.

Example 81A (second eluting isomer): ¹H NMR (300 MHz, DMSO-d₆) δ 8.98 (d, J=7.2 Hz, 1H), 8.40 (dd, J=4.5, 1.8 Hz, 1H), 7.98 (dd, J=7.5, 1.8 Hz, 1H), 7.40-7.26 (m, 6H), 6.62 (s, 1H), 4.45 (d, J=7.2 Hz, 1H), 4.24 (s, 2H), 3.29 (s, 3H), 2.34-2.25 (m, 1H), 2.02-1.94 (m, 1H), 1.22-1.06 (m, 2H). LC-MS (Method D): m/z=389.1 [M+H]⁺, 2.027 min.

Example 82A and 82B: 1-benzyl-4-fluoro-N-((1aS,2S,8bR)-4-methyl-3-oxo-1,1a,2,3,4,8b-hexahydrocyclopropa[d]pyrido[2,3-b]azepin-2-yl)-1H-pyrazole-3-carboxamide (82A) and 1-benzyl-4-fluoro-N-((1aR,2R,8bS)-4-methyl-3-oxo-1,1a,2,3,4,8b-hexahydrocyclopropa[d]pyrido[2,3-b]azepin-2-yl)-1H-pyrazole-3-carboxamide (82B)

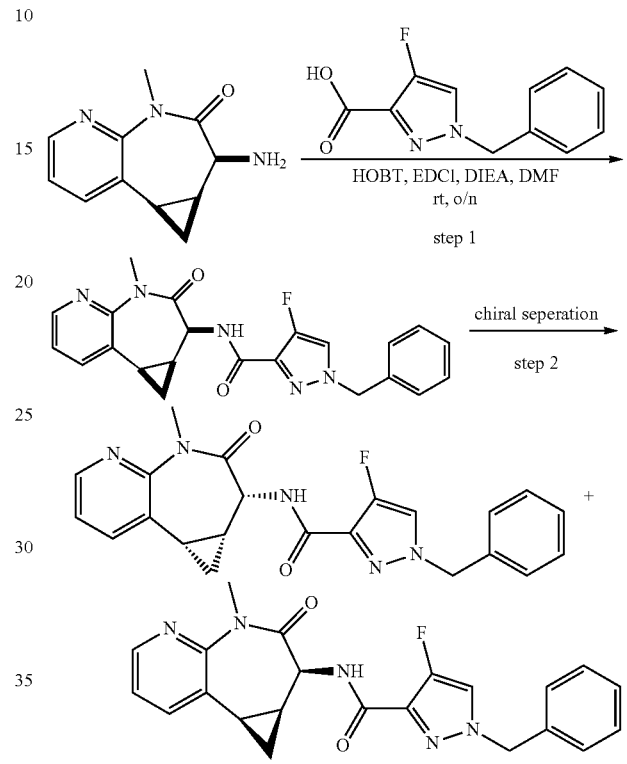

Step 1: Preparation of 1-benzyl-4-fluoro-N-(cis-4-methyl-3-oxo-1,1a,2,3,4,8b-hexahydrocyclopropa[d]pyrido[2,3-b]azepin-2-yl)-1H-pyrazole-3-carboxamide The crude product obtained using Amide Coupling Procedure C was purified by Prep-HPLC with the following conditions: Column: X Bridge C18 OBD Prep Column, 100 Å, 5 µm, 19 mm×250 mm; Mobile Phase A: water (10 mmol/L NH₄HCO₃), Mobile Phase B: ACN; Flow rate: 20 mL/min; Gradient: 35% B to 65% B over 7 min; UV 254 & 220 nm to afford the title compound (58 mg, 50%) as a white solid. LC-MS (Method V): m/z=406.1 [M+H]⁺, 2.852 min.

Step 2: Preparation of 1-benzyl-4-fluoro-N-((1aR,2R,8bS)-4-methyl-3-oxo-1,1a,2,3,4,8b-hexahydrocyclopropa[d]pyrido[2,3-b]azepin-2-yl)-1H-pyrazole-3-carboxamide (First Eluting Isomer) and 1-benzyl-4-fluoro-N-((1aS,2S,8bR)-4-methyl-3-oxo-1,1a,2,3,4,8b-hexahydrocyclopropa[d]pyrido[2,3-b]azepin-2-yl)-1H-pyrazole-3-carboxamide (Second Eluting Isomer)

The racemate of 1-benzyl-4-fluoro-N-(cis-4-methyl-3-oxo-1,1a,2,3,4,8b-hexahydrocyclopropa[d]pyrido[2,3-b]azepin-2-yl)-1H-pyrazole-3-carboxamide (58 mg, 0.15 mmol) was separated by Prep-Chiral-HPLC with the following conditions: Column: Chiralpak IC, 2×25 cm, 5 μm; Mobile Phase A: hexane, Mobile Phase B: EtOH; Flow rate: 18 mL/min; Gradient: 50% B to 50% B over 23 min; UV 254 & 220 nm; RT 1: 10.936 min; RT 2: 16.976 min to afford the title compounds:

Example 82B (first eluting isomer): $^1$H NMR (300 MHz, DMSO-$d_6$) δ 8.39 (dd, J=4.8, 1.8 Hz, 1H), 8.17-8.12 (m, 2H), 8.00 (dd, J=7.8, 1.8 Hz, 1H), 7.44-7.28 (m, 6H), 5.36 (s, 2H), 4.46 (d, J=6.9 Hz, 1H), 3.30 (s, 3H), 2.33-2.24 (m, 1H), 2.06-1.98 (m, 1H), 1.26-1.14 (m, 1H), 1.12-1.03 (m, 1H). LC-MS (Method V): m/z=406.1 [M+H]$^+$, 2.852 min.

Example 82A (second eluting isomer): $^1$H NMR (300 MHz, Methanol-$d_4$) δ 8.38 (dd, J=4.8, 1.8 Hz, 1H), 7.94 (dd, J=7.5, 1.8 Hz, 1H), 7.77 (d, J=4.5 Hz, 1H), 7.44-7.27 (m, 6H), 5.35 (s, 2H), 4.66 (s, 1H), 3.41 (s, 3H), 2.32-2.23 (m, 1H), 2.15-2.03 (m, 1H), 1.33-1.26 (m, 1H), 1.22-1.14 (m, 1H). LC-MS (Method D): m/z=406.1 [M+H]$^+$, 1.932 min.

Example 83A: 5-benzyl-N-((1aS,2S,8bR)-5,7-difluoro-3-oxo-1,1a,2,3,4,8b-hexahydrobenzo[b]cyclopropa[d]azepin-2-yl)-4H-1,2,4-triazole-3-carboxamide

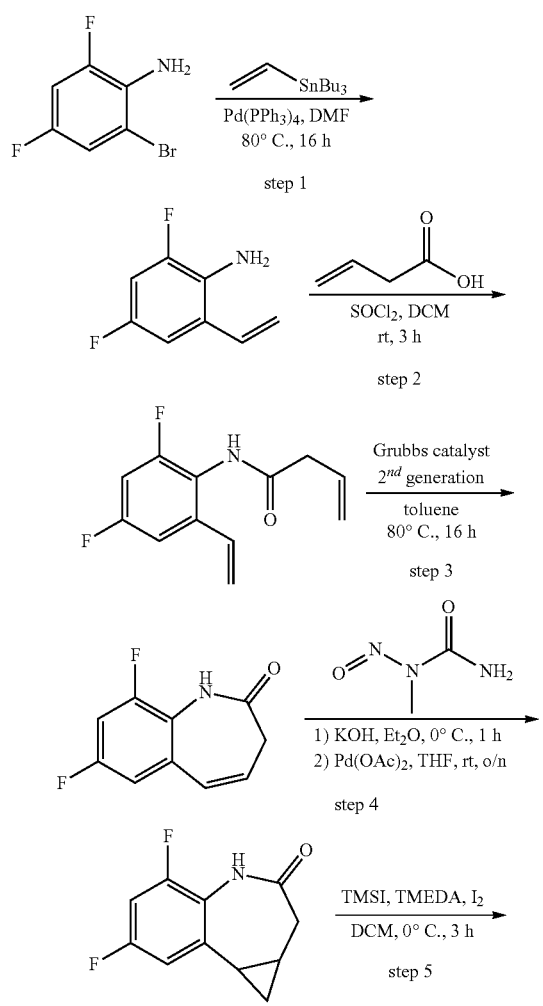
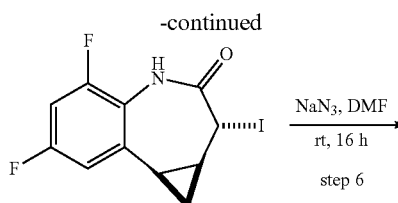
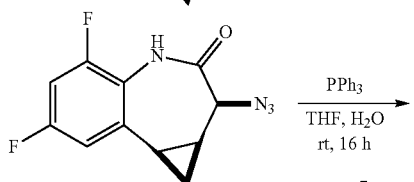
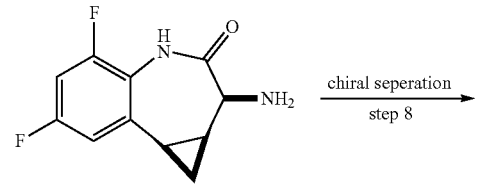
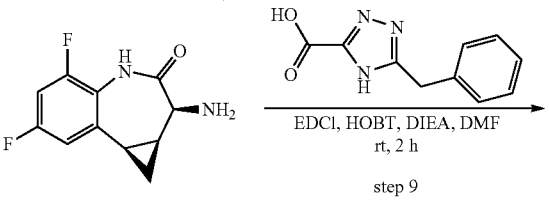
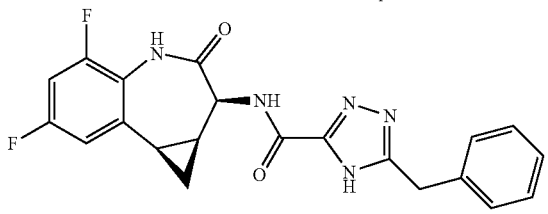

Step 1: Preparation of 2,4-difluoro-6-vinylbenzenamine

To a solution of 2-bromo-4,6-difluoroaniline (10.0 g, 48.0 mmol) in N,N-dimethylformamide (50 mL) was added tributyl(ethenyl)stannane (18.0 g, 56.7 mmol) and tetrakis (triphenylphosphine)palladium (2.2 g, 1.90 mmol) under a nitrogen atmosphere. The resulting mixture was stirred for 16 hours at 80° C. After cooling to room temperature, the reaction mixture was quenched by the addition of water (200 mL) and extracted with dichloromethane (3×200 mL). The combined organic layers were washed with brine, dried over sodium sulfate, filtered and concentrated under vacuum. The residue was purified by column chromatography (ethyl acetate/petroleum ether, 3/17) to afford the title compound (6.0 g, 80%) as a yellow oil. LC-MS (Method C): m/z=156.0 [M+H]$^+$, 1.216 min.

Step 2: Preparation of N-(2,4-difluoro-6-vinylphenyl)but-3-enamide

Thionyl chloride (9.3 g, 46.46 mmol) was added to a solution of but-3-enoic acid (4.0 g, 46.46 mmol) in dichloromethane (20 mL) dropwise. After stirring for 1 hour at room temperature, the resulting mixture was added to a solution of triethylamine (11.8 g, 116.6 mmol) and 2-ethenyl-4,6-difluoroaniline (6.0 g, 38.67 mmol) in dichloromethane (20 mL). The reaction mixture was stirred for 3 hours at room temperature, quenched by the addition of water (50 mL) and extracted with dichloromethane (3×100 mL). The combined organic layers were washed with brine, dried over sodium sulfate, filtered and concentrated under vacuum. The residue was purified by column chromatography (ethyl acetate/petroleum ether, 3/17) to afford the title compound (5.7 g, 66%) as a yellow oil. LC-MS (Method C): m/z=224.0 [M+H]$^+$, 1.145 min.

Step 3: Preparation of (Z)-7,9-difluoro-1H-benzo[b] azepin-2(3H)-one

[1,3-bis(2,4,6-trimethylphenyl)imidazolidin-2-ylidene] dichloro(phenylmethylidene) ruthenium tricyclohexylphosphine (3.4 g, 4.0 mmol) was added to a solution of N-(5-ethenyl-2,4-difluorophenyl)but-3-enamide (4.4 g, 19.9 mmol) in toluene (150 mL). The resulting solution was stirred for 16 hours at 80° C. and then concentrated under vacuum. The residue was purified by column chromatography (ethyl acetate/petroleum ether, 1/4) to afford the title compound (2.8 g, 69%) as a yellow oil. LC-MS (Method S): m/z=196.0 [M+H]$^+$, 0.754 min.

Step 4: Preparation of 5,7-difluoro-1,1a,2,8b-tetrahydrobenzo[b]cyclopropa[d]azepin-3(4H)-one To a solution of potassium hydroxide (40 g, 714 mmol) in water (60 mL) was added a solution of 1-methyl-1-nitrosourea (20.6 g, 199.8 mmol) in ether (150 mL) dropwise at 0° C. under nitrogen atmosphere. The resulting mixture was stirred for 1 hour at 0° C. and then the organic phase was separated to get a solution of diazomethane (150 mL). To a solution of 7,9-difluoro-2,3-dihydro-1H-1-benza-zepin-2-one (2.0 g, 10.25 mmol) in tetrahydrofuran (60 mL) was added the solution of diazomethane (150 mL) dropwise, followed by adding a mixture of palladium diacetate (224.5 mg, 1.00 mmol) in tetrahydrofuran (10 mL) dropwise at 0° C. The reaction mixture was stirred overnight at room temperature. The solids were removed by filtration and the filtrate was concentrated under vacuum to afford the title compound (1.2 g crude) as a yellow oil. LC-MS (Method C): m/z=210.0 [M+H]$^+$, 1.117 min.

Step 5: Preparation of trans-5,7-difluoro-2-iodo-1, 1a,2,8b-tetrahydrobenzo[b]cyclopropa[d]azepin-3 (4H)-one To a mixture of 5,7-difluoro-1,1a,2,8b-tetrahydrobenzo [b]cyclopropa[d]azepin-3(4H)-one (1.2 g, 6.0 mmol) in dichloromethane (60 mL) was added N,N,N',N'-tetramethylethylenediamine (2.1 g, 18.0 mmol) followed by the addition of iodotrimethylsilane (3.6 g, 18.0 mmol) at 0° C. After stirring for 2 hours at 0° C., iodine (2.3 g, 9.0 mmol) was added. The reaction mixture was stirred for 1 hour at 0° C., quenched with aqueous sodium thiosulfate (5%, 40 mL) and extracted with ethyl acetate (3×50 mL). The combined organic layers were washed with brine, dried over anhydrous sodium sulfate, and filtered. The filtrate was concentrated under vacuum to afford the title compound (1.32 g crude) as a yellow oil. LC-MS (Method C): m/z=336.0 [M+H]$^+$, 1.213 min.

Step 6: Preparation of cis-2-azido-5,7-difluoro-1,1a, 2,8b-tetrahydrobenzo[b]cyclopropa[d]azepin-3(4H)-one Sodium azide (250 mg, 3.84 mmol) was added to a solution of trans-5,7-difluoro-2-iodo-1,1a,2,8b-tetrahydrobenzo[b]cyclopropa[d]azepin-3(4H)-one (860 mg, 2.56 mmol) in N,N-dimethylformamide (40 mL). The resulting mixture was stirred for 16 hours at room temperature, quenched by adding water (50 mL) and extracted with ethyl acetate (3×50 mL). The combined organic layers were washed with brine, dried over sodium sulfate, and filtered. The filtrate was concentrated under vacuum to afford the title compound (520 mg crude) as a yellow oil. LC-MS (Method C): m/z=251.0 [M+H]$^+$, 1.176 min.

Step 7: Preparation of cis-2-amino-5,7-difluoro-1, 1a,2,8b-tetrahydrobenzo[b]cyclopropa[d]azepin-3 (4H)-one Triphenylphosphine (629 mg, 2.40 mmol) was added to a solution of cis-2-azido-5,7-difluoro-1,1a,2,8b-tetrahydrobenzo[b]cyclopropa[d]azepin-3(4H)-one (400 mg, 1.60 mmol) in tetrahydrofuran (10 mL) and water (1 mL). The resulting mixture was stirred for 16 hours at room temperature, diluted with water (50 mL) and extracted with dichloromethane (3×50 mL). The combined organic layers were washed with brine, dried over anhydrous sodium sulfate, filtered and concentrated to dryness under vacuum. The residue was purified by column chromatography (methanol/dichloromethane, 3/97) to afford the title compound (310 mg, 86%) as a yellow oil. LC-MS (Method C): m/z=225.0 [M+H]$^+$, 0.776 min.

Step 8: Preparation of (1aR,2R,8bS)-2-amino-5,7-difluoro-1,1a,2,8b-tetrahydrobenzo[b]cyclopropa[d] azepin-3(4H)-one (First Eluting Isomer) and (1aS, 2S,8bR)-2-amino-5,7-difluoro-1,1a,2,8b-tetrahydrobenzo[b]cyclopropa[d]azepin-3(4H)-one (Second Eluting Isomer)

The racemate of cis-2-amino-5,7-difluoro-1,1a,2,8b-tetrahydrobenzo[b]cyclopropa[d]azepin-3(4H)-one (310 mg, 1.38 mmol) was separated by Prep-Chiral-HPLC with the following conditions: Column. Chiralpak IA, 2×25 cm, 5 μm; Mobile Phase A: hexane, Mobile Phase B: EtOH; Flow rate: 15 mL/min; Gradient: 50% B to 50% B over 28 min; 254/220 nm; RT1: 10.247 min; RT2: 20.789 min to afford the title compounds:

(1aR,2R,8bS)-2-amino-5,7-difluoro-1,1a,2,8b-tetrahydrobenzo[b]cyclopropa[d]azepin-3(4H)-one (first eluting isomer): (150 mg, 48%) as a white solid. LC-MS (Method C): m/z=225.0 [M+H]$^+$, 0.776 min.

(1aS,2S,8bR)-2-amino-5,7-difluoro-1,1a,2,8b-tetrahydrobenzo[b]cyclopropa[d]azepin-3(4H)-one (second eluting isomer): (140 mg, 45%) as a white solid. LC-MS (Method C): m/z=225.0 [M+H]$^+$, 0.776 min.

Step 9: 5-benzyl-N-((1aS,2S,8bR)-5,7-difluoro-3-oxo-1,1a,2,3,4,8b-hexahydrobenzo[b]cyclopropa[d] azepin-2-yl)-4H-1,2,4-triazole-3-carboxamide N,N-diisopropylethylamine (50 mg, 0.39 mmol) was added to a mixture of (1aS,2S,8bR)-2-amino-5,7-difluoro-1,1a,2,8b-tetrahydrobenzo[b]cyclopropa[d]azepin-3(4H)-one (30 mg, 0.13 mmol), 5-benzyl-4H-1,2,4-triazole-3-carboxylic acid (32 mg, 0.16 mmol), N-(3-dimethylaminopropyl)-N'-ethylcarbodiimide hydrochloride (31 mg, 0.16 mmol) and 1-hydroxybenzotriazole (22 mg, 0.16 mmol) in N,N-dimethylformamide (5 mL). The resulting mixture was stirred for 2 hours at room temperature, diluted with water (50 mL) and extracted with ethyl acetate (3×50 mL). The combined organic layers were washed with brine, dried over sodium sulfate, filtered and concentrated under vacuum. The residue was purified by Prep-HPLC with the following conditions: Column, XBridge C18 OBD Prep Column, 5 μm, 19 mm×250 mm; mobile phase, water (10 mmoL/L NH$_4$HCO$_3$) and ACN (30.0% ACN to 60.0% over 7 min); Detector, UV 254 nm to afford the title compound. $^1$H NMR (400 MHz, DMSO-d$_6$) δ 14.30 (br. s, 1H), 9.96 (br. s, 1H), 8.43 (d, J=6.8 Hz, 1H), 7.36-7.19 (m, 7H), 4.61 (d, J=6.8 Hz, 1H), 4.14 (s, 2H), 2.32-2.26 (m, 1H), 2.07-2.01 (m, 1H), 1.43-1.39 (m, 1H), 1.12-1.07 (m, 1H). LC-MS (Method Q): m/z=410.3 [M+H]$^+$, 1.144 min.

Example 83B: 5-benzyl-N-((1aR,2R,8bS)-5,7-difluoro-3-oxo-1,1a,2,3,4,8b-hexahydrobenzo[b]cyclopropa[d]azepin-2-yl)-4H-1,2,4-triazole-3-carboxamide

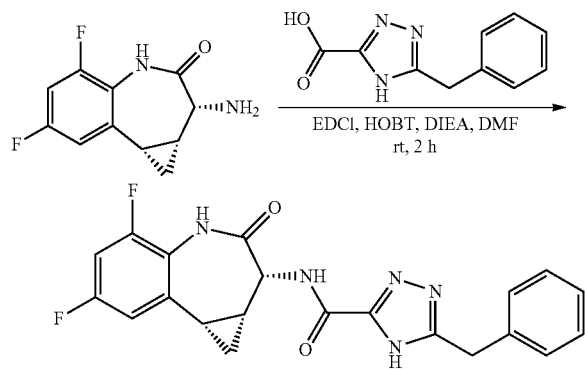

The crude product obtained using Amide Coupling Procedure C was purified by Prep-HPLC with the following conditions: Column, XBridge C18 OBD Prep Column, 5 μm, 19 mm×250 mm; mobile phase, water (10 mmoL/L NH$_4$HCO$_3$) and ACN (30.0% ACN up to 60.0% in 7 min); Detector, UV 254 nm to afford the title compound. $^1$H NMR (400 MHz, DMSO-d$_6$) δ 14.41 (s, 1H), 9.95 (s, 1H), 8.42 (d, J=6.8 Hz, 1H), 7.35-7.19 (m, 7H), 4.61 (d, J=6.8 Hz, 1H), 4.14 (s, 2H), 2.32-2.26 (m, 1H), 2.07-2.01 (m, 1H), 1.43-1.39 (m, 1H), 1.12-1.07 (m, 1H). LC-MS (Method Q): m/z=410.30 [M+H]$^+$, 1.143 min.

Example 84: (S)—N-(5-methyl-4-oxo-2,3,4,5-tetrahydrobenzo[b][1,4]oxazepin-3-yl)-7-phenylbenzo[d]thiazole-2-carboxamide

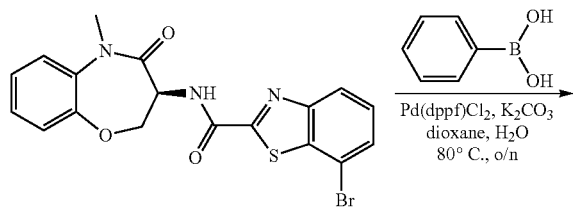

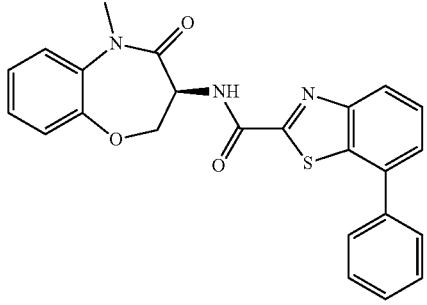

[1,1'-Bis(diphenylphosphino)ferrocene]dichloropalladium(II) (34 mg, 0.05 mmol) was added to a mixture of (S)-7-bromo-N-(5-methyl-4-oxo-2,3,4,5-tetrahydrobenzo[b][1,4]oxaz-epin-3-yl)benzo[d]thiazole-2-carboxamide (200 mg, 0.47 mmol), phenylboronic acid (85 mg, 0.70 mmol) and potassium carbonate (128 mg, 0.93 mmol) in dioxane (2 mL) and water (0.5 mL) under a nitrogen atmosphere. The resulting mixture was stirred overnight at 80° C. Solids were removed by filtration and the filtrate was concentrated under reduced pressure. The residue was purified by Prep-HPLC with the following conditions: Column: XBridge Prep C18 OBD Column, 5 μm, 19×150 mm; Mobile Phase A: water (0.05% TFA), Mobile Phase B: ACN; Flow rate: 20 mL/min; Gradient: 3% B to 38% B over 7 min; 254 & 220 nm; Rt: 6.33 min to afford the title compound. $^1$H NMR (300 MHz, DMSO-d$_6$) δ 9.30 (d, J=7.8 Hz, 1H), 8.23 (d, J=7.8 Hz, 1H), 7.79-7.60 (m, 4H), 7.60-7.49 (m, 4H), 7.34-7.26 (m, 3H), 4.96-4.68 (m, 2H), 4.50-4.45 (m, 1H), 3.33 (s, 3H). LC-MS (Method T): m/z=430.3 [M+H]$^+$, 1.906 min.

Example 85: (S)-5-benzyl-N-(5-methyl-4-oxo-2,3,4,5-tetrahydropyrido[3,2-b][1,4]oxazepin-3-yl)-1,3,4-thiadiazole-2-carboxamide

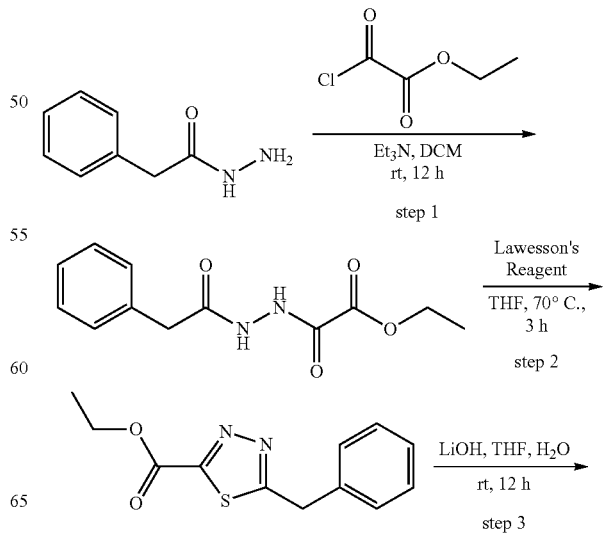

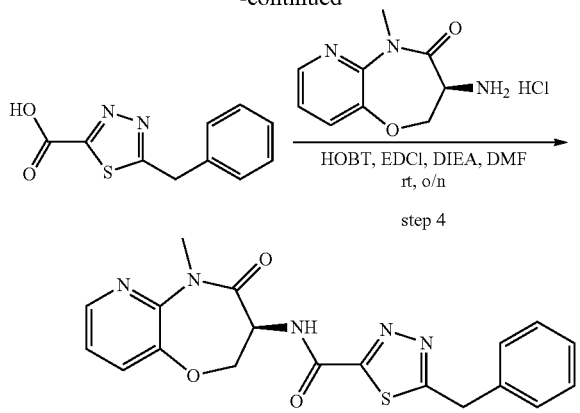

Step 1: Preparation of ethyl 2-oxo-2-(2-(2-phenylacetyl)hydrazinyl)acetate

To a stirring solution of 2-phenylacetohydrazide (2 g, 13.3 mmol) and triethylamine (4.04 g, 39.9 mmol) in dichloromethane (30 mL) was added ethyl 2-chloro-2-oxoacetate (1.8 g, 13.4 mmol) dropwise at 0° C. The resulting solution was stirred for 12 hours at room temperature, diluted with water (20 mL) and extracted with dichloromethane (5×50 mL). The combined organic layers were washed with brine, dried over anhydrous sodium sulfate, filtered and concentrated under vacuum. The residue was purified by column chromatography (ethyl acetate/petroleum ether, 1/3) to afford the title compound (1.2 g, 36%) as a white solid. LC-MS (Method I): m/z=251.0 [M+H]$^+$, 0.944 min.

Step 2: Preparation of ethyl 5-benzyl-1,3,4-thiadiazole-2-carboxylate

To a mixture of ethyl 2-oxo-2-(2-(2-phenylacetyl)hydrazinyl)acetate (0.65 g, 2.6 mmol) in tetrahydrofuran (8 mL) was added Lawesson's reagent (1.89 g, 4.7 mmol). The resulting mixture was stirred for 3 hours at 70° C. After cooling to room temperature, the reaction mixture was diluted with ethyl acetate (30 mL). The phases were separated and the organic layer was washed with aqueous sodium bicarbonate (10%, 3×20 mL) and brine, dried over anhydrous sodium sulfate, filtered and concentrated to dryness under vacuum. The residue was purified by column chromatography (ethyl acetate/petroleum ether, 1/3) to afford the title compound (500 mg, 78%) as a yellow oil. LC-MS (Method I): m/z=249.0 [M+H]$^+$, 0.991 min.

Step 3: Preparation of 5-benzyl-1,3,4-thiadiazole-2-carboxylic acid

To a mixture of ethyl 5-benzyl-1,3,4-thiadiazole-2-carboxylate (500 mg, 2.01 mmol) in tetrahydrofuran (6 mL) and water (2 mL) was added lithium hydroxide (97 mg, 4.04 mmol). The resulting solution was stirred for 12 hours at room temperature and concentrated under vacuum. The residue was diluted with water (10 mL) and the pH value of the solution was adjusted to 6 with aqueous hydrochloric acid (1 N, 10 mL). The resulting solution was extracted with ethyl acetate (3×15 mL). The combined organic layers were washed with brine, dried over anhydrous sodium sulfate, and filtered. The filtrate was concentrated under vacuum to afford the title compound (250 mg crude) as a white solid. LC-MS (Method I): m/z=221.0 [M+H]$^+$, 0.574 min.

Step 4: Preparation of (S)-5-benzyl-N-(5-methyl-4-oxo-2,3,4,5-tetrahydropyrido[3,2-b][1,4]oxazepin-3-yl)-1,3,4-thiadiazole-2-carboxamide The crude product obtained using Amide Coupling Procedure C was purified by Prep-HPLC with the following conditions: Column: X Bridge Prep C18 OBD Column, 5 μm, 19×150 mm; Mobile Phase A: water (10 mmol/L NH$_4$HCO$_3$), Mobile Phase B: ACN; Flow rate: 20 mL/min; Gradient: 38% B to 70% B over 7 min; UV 254 & 220 nm to afford the title compound. $^1$H NMR (300 MHz, DMSO-d$_6$) δ 9.46 (d, J=6.6 Hz, 1H), 8.37 (dd, J=4.8, 1.8 Hz, 1H), 7.71 (dd, J=7.8, 1.5 Hz, 1H), 7.38-7.26 (m, 6H), 4.91-4.75 (m, 2H), 4.58-4.52 (m, 3H), 3.36 (s, 3H). LC-MS (Method D): m/z=396.1 [M+H]$^+$, 1.912 min.

Example 86: (S)-5-benzyl-N-(5-methyl-4-oxo-2,3,4,5-tetrahydropyrido[3,2-b][1,4]oxazepin-3-yl)thiazole-2-carboxamide

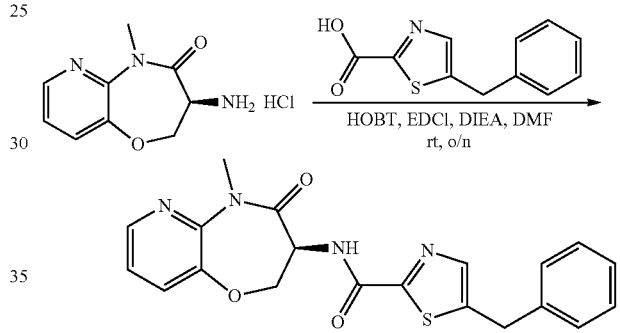

The crude product obtained using Amide Coupling Procedure C was purified by Prep-HPLC with the following conditions: Column: X Bridge Prep C18 OBD Column, 5 μm, 19×150 mm; Mobile Phase A: water (10 mmol/L NH$_4$HCO$_3$), Mobile Phase B: ACN; Flow rate: 20 mL/min; Gradient: 38% B to 70% B over 7 min; UV 254 & 220 nm to afford the title compound. $^1$H NMR (300 MHz, DMSO-d$_6$) δ 8.95 (d, J=7.2 Hz, 1H), 8.37 (dd, J=4.8, 1.5 Hz, 1H), 7.88 (s, 1H), 7.71 (dd, J=8.1, 1.5 Hz, 1H), 7.37-7.23 (m, 6H), 4.89-4.72 (m, 2H), 4.56-4.50 (m, 1H), 4.28 (s, 2H), 3.36 (s, 3H). LC-MS (Method D): m/z=395.1 [M+H]$^+$, 2.096 min.

Example 87: (S)—N-(5-methyl-4-oxo-2,3,4,5-tetrahydrobenzo[b][1,4]oxazepin-3-yl)-1-(1-phenylcyclopropyl)-1H-1,2,3-triazole-4-carboxamide

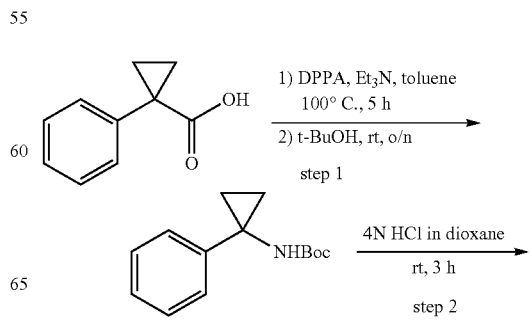

-continued

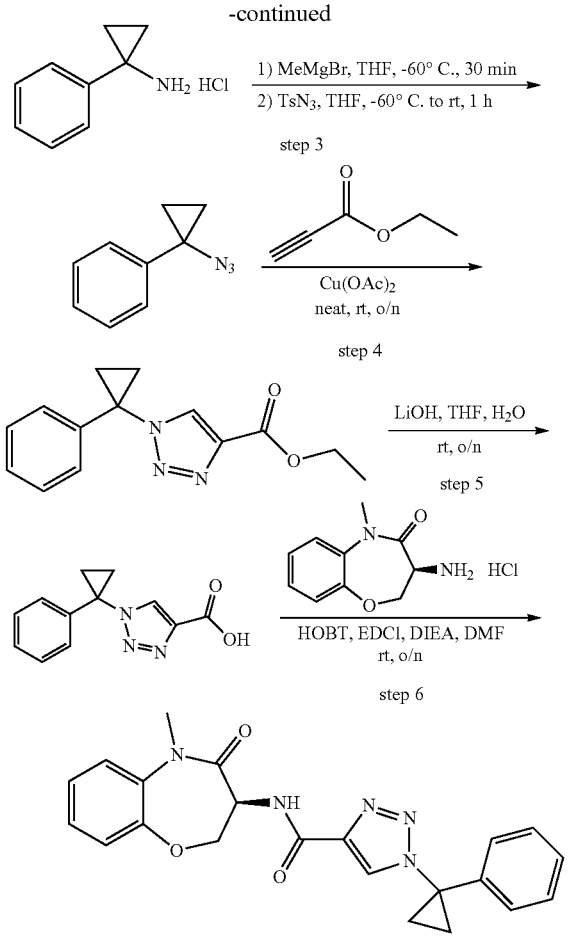

Step 1: Preparation of tert-butyl 1-phenylcyclopropylcarbamate

To a stirring mixture of 1-phenylcyclopropanecarboxylic acid (10.0 g, 61.7 mmol) and diphenyl phosphorazidate (17.0 g, 61.7 mmol) in toluene (100 mL) was added triethylamine (18.6 g, 185 mmol). The reaction mixture was stirred for 5 hours at 100° C., cooled to room temperature and then 2-methylpropan-2-ol (33.7 mg, 0.216 mmol) was added. The reaction mixture was stirred overnight at room temperature and concentrated under high vacuum. The residue was diluted with water (100 mL) and extracted with ethyl acetate (3×100 mL). The combined organic layers were washed with brine, dried over anhydrous sodium sulfate, filtered and concentrated under vacuum. The residue was purified by column chromatography (ethyl acetate/petroleum ether, 1/5) to afford the title compound (4.00 g, 28%) as a yellow solid. LC-MS (Method C): m/z=234.2 [M+H]+, 1.345 min.

Step 2: Preparation of 1-phenylcyclopropanamine hydrochloride

Tert-butyl 1-phenylcyclopropylcarbamate (4.0 g, 17.2 mmol) was added to a solution of hydrogen chloride in dioxane (4 N, 50 mL, 200 mmol). The reaction mixture was stirred for 3 hours at room temperature and concentrated under high vacuum to afford the title compound (2.00 g, 88%) as a white solid. LC-MS (Method C): m/z=134.2 [M+H]+, 0.775 min.

Step 3: Preparation of (1-azidocyclopropyl)benzene

To a stirring solution of 1-phenylcyclopropanamine hydrochloride (320 mg, 1.89 mmol) in ether (10 mL) was added a solution of methylmagnesium bromide in ether (3 M, 1.89 mL, 5.67 mmol) at −60° C. under an argon atmosphere. After stirring for 30 minutes at −60° C., 4-methylbenzenesulfonyl azide (745 mg, 3.78 mmol) was added. The reaction mixture was stirred for 1 hour at −60° C., quenched with water (20 mL) and extracted with ethyl acetate (3×20 mL). The combined organic layers were washed with brine, dried over anhydrous sodium sulfate, and filtered. The filtrate was concentrated under vacuum to afford the title compound (500 mg crude) as a yellow solid.

Step 4: Preparation of ethyl 1-(1-phenylcyclopropyl)-1H-1,2,3-triazole-4-carboxylate Cupric acetate (468 mg, 3.14 mmol) was added to a solution of (1-azidocyclopropyl)benzene in ethyl propiolate (5 mL). The reaction mixture was stirred overnight at room temperature and concentrated under high vacuum. The residue was purified by column chromatography (ethyl acetate/petroleum ether, 1/3) to afford the title compound (100 mg, 12%) as a yellow oil. LC-MS (Method C): m/z=258.1 [M+H]+, 1.250 min.

Step 5: Preparation of 1-(1-phenylcyclopropyl)-1H-1,2,3-triazole-4-carboxylic acid Lithium hydroxide (18.7 mg, 0.78 mmol) was added to a solution of ethyl 1-(1-phenylcyclopropyl)-1H-1,2,3-triazole-4-carboxylate (100 mg, 0.39 mmol) in tetrahydrofuran (3 mL) and water (1 mL). The resulting solution was stirred overnight at room temperature, concentrated under vacuum and diluted with water (5 mL). The pH of the solution was adjusted to 5 with aqueous hydrochloric acid (1 N, 5 mL). The resulting solution was extracted with ethyl acetate (3×5 mL). The combined organic layers were washed with brine, dried over anhydrous sodium sulfate, and filtered. The filtrate was concentrated under vacuum to afford the title compound (30 mg crude) as a white solid. LC-MS (Method D): m/z=230.2 [M+H]+, 0.532 min.

Step 6: Preparation of (S)—N-(5-methyl-4-oxo-2,3,4,5-tetrahydrobenzo[b][1,4]oxazepin-3-yl)-1-(1-phenylcyclopropyl)-1H-1,2,3-triazole-4-carboxamide The crude product obtained using Amide Coupling Procedure C was purified by Prep-HPLC with the following conditions: Column: XBridge Shield RP18 OBD Column, 5 μm, 19×150 mm; Mobile Phase A: water (0.1% formic acid), Mobile Phase B: ACN; Flow rate: 20 mL/min; Gradient: 35% B to 65% B over 7 min; 220 nm; Rt: 6 min to afford the title compound. 1H NMR (300 MHz, DMSO-$d_6$) δ 8.88 (s, 1H), 8.58 (d, J=8.1 Hz, 1H), 7.53-7.49 (m, 1H), 7.39-7.20 (m, 5H), 7.07-7.04 (m, 2H), 4.89-4.81 (m, 1H), 4.65-4.55 (m, 1H), 4.43-4.30 (m, 1H), 3.32 (s, 3H), 1.79-1.78 (m, 2H), 1.73-1.64 (m, 2H). LC-MS (Method D): m/z=404.1 [M+H]+, 1.992 min.

Example 88: (S)—N-(5-methyl-4-oxo-2,3,4,5-tetra-hydrobenzo[b][1,4]oxazepin-3-yl)-2-(1-phenylcyclo-propyl)-1H-imidazole-5-carboxamide

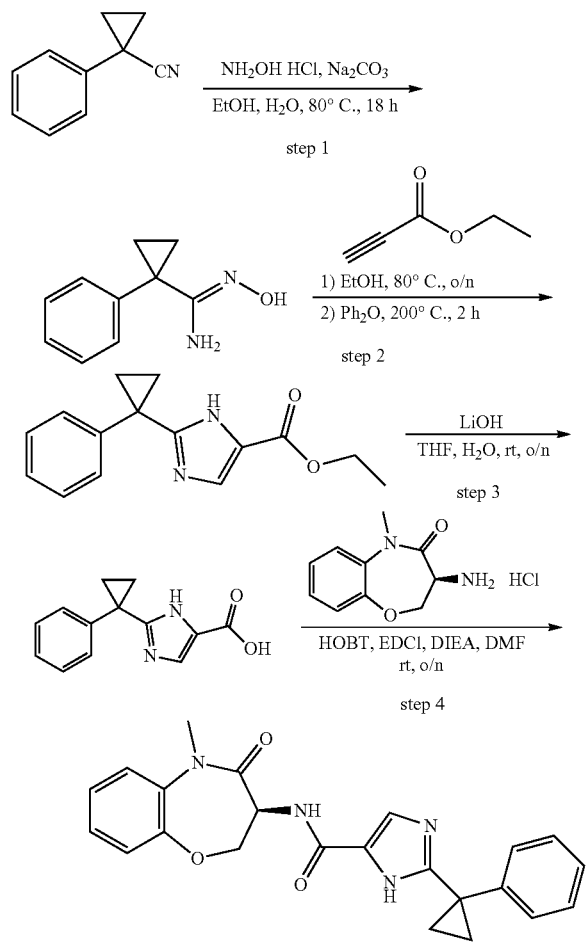

Step 1: Preparation of (Z)—N'-hydroxy-1-phenyl-cyclopropanecarboximidamide

Hydroxylamine hydrochloride (1.4 g, 20.3 mmol) was added to a mixture of 1-phenylcyclopropanecarbonitrile (1.5 g, 10.5 mmol) and sodium carbonate (2.2 g, 20.7 mmol) in ethanol (20 mL) and water (10 mL). The resulting mixture was stirred at 80° C. for 18 hours. After cooling to room temperature, the reaction mixture was diluted with water (50 mL) and extracted with dichloromethane (3×80 mL). The combined organic layers were washed with brine, dried over anhydrous sodium sulfate, filtered and concentrated under vacuum. The residue was purified by column chromatography (ethyl acetate/petroleum ether, 1/20) to afford the title compound (1.2 g, 68%) as a white solid. LC-MS (Method E): m/z=176.8 [M+H]$^+$, 0.371 min.

Step 2: Preparation of ethyl 2-(1-phenylcyclopropyl)-1H-imidazole-5-carboxylate A solution of (Z)—N'-hydroxy-1-phenylcyclopropanecarboximidamide (1.2 g, 6.8 mmol) and ethyl propiolate (1.0 g, 10.2 mmol) in ethanol (50 mL) was stirred at 80° C. overnight and concentrated under vacuum. The residue was dissolved in oxydibenzene (20 mL) and the mixture was stirred at 200° C. for 2 hours. The resulting mixture was concentrated and purified by column chromatography (ethyl acetate/petroleum ether, 1/5) to afford the title compound (0.7 g, 40%) as a yellow solid. LC-MS (Method C): m/z=257.0 [M+H]$^+$, 1.200 min.

Step 3: Preparation of 2-(1-phenylcyclopropyl)-1H-imidazole-5-carboxylic acid Lithium hydroxide (288 mg, 7.2 mmol) was added to a solution of 2-(1-phenylcyclopropyl)-1H-imidazole-5-carboxylate (300 mg, 1.2 mmol) in tetrahydrofuran (9 mL) and water (3 mL). The reaction mixture was stirred overnight at room temperature, diluted with water (20 mL), adjusted pH to 5 with aqueous hydrochloric acid (1 N, 10 mL) and extracted with ethyl acetate (3×20 mL). The combined organic layers were washed with brine, dried over anhydrous sodium sulfate, and filtered. The filtrate was concentrated under vacuum to afford the title compound (130 mg crude) as a yellow solid. LC-MS (Method C): m/z=229.1 [M+H]$^+$, 0.906 min.

Step 4: Preparation of (S)—N-(5-methyl-4-oxo-2,3,4,5-tetrahydrobenzo[b][1,4]oxazepin-3-yl)-2-(1-phenylcyclopropyl)-1H-imidazole-5-carboxamide The crude product obtained using Amide Coupling Procedure C was purified by Prep-HPLC with the following conditions: Column: X Bridge Prep C18 OBD Column, 5 μm, 19×150 mm; Mobile Phase A: water (10 mmol/L NH$_4$HCO$_3$), Mobile Phase B: ACN; Flow rate: 20 mL/min; Gradient: 35% B to 60% B over 7 min; UV 254 & 220 nm to afford the title compound. $^1$H NMR (300 MHz, DMSO-d$_6$) δ 12.28 (s, 1H), 7.86 (d, J=8.1 Hz, 1H), 7.52-7.49 (m, 2H), 7.37-7.19 (m, 8H), 4.89-4.79 (m, 1H), 4.54-4.38 (m, 2H), 3.33 (s, 3H), 1.48-1.40 (m, 2H), 1.28-1.20 (m, 2H). LC-MS (Method O): m/z=403.1 [M+H]$^+$, 1.389 min.

Example 89A: 5-benzyl-N-((1aR,2R,8bS)-5,7-difluoro-3-oxo-1,1a,2,3,4,8b-hexahydrobenzo[b]cyclopropa[d]azepin-2-yl)-1,3,4-oxadiazole-2-carboxamide

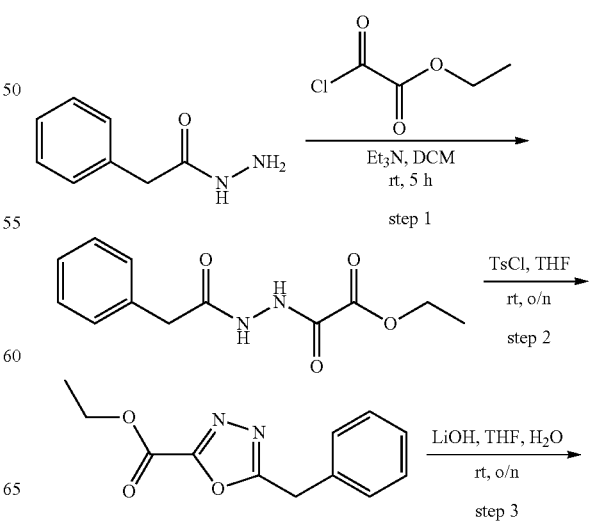

391

-continued

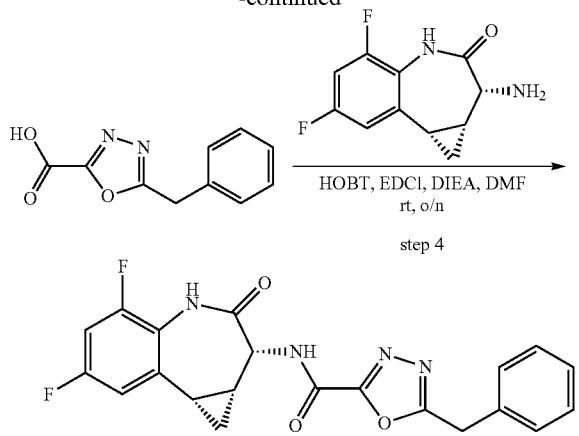

Step 1: Preparation of ethyl 2-oxo-2-(2-(2-phenylacetyl)hydrazinyl)acetate

Ethyl 2-chloro-2-oxoacetate (603 mg, 4.4 mmol) was added to a stirring solution of 2-phenylacetohydrazide (660 mg, 4.4 mmol) and triethylamine (1.33 g, 13.2 mmol) in dichloromethane (20 mL). The reaction mixture was stirred at room temperature for 5 hours, quenched by the addition of water (20 mL) and extracted with dichloromethane (3×25 mL). The combined organic layers were washed with brine, dried over anhydrous sodium sulfate, filtered and concentrated under vacuum. The residue was purified by column chromatography (ethyl acetate/petroleum ether, 1/3) to afford the title compound (550 mg, 50%) as a yellow oil. LC-MS (Method S): m/z=251.0 [M+H]$^+$, 0.679 min.

Step 2: Preparation of ethyl 5-benzyl-1,3,4-oxadiazole-2-carboxylate

Tosyl chloride (840 mg, 4.4 mmol) was added to a stirring solution of ethyl 2-oxo-2-(2-(2-phenylacetyl)hydrazinyl)acetate (666 mg, 6.6 mmol) in tetrahydrofuran (25 mL). The reaction mixture was stirred overnight at room temperature, quenched by the addition of water (20 mL) and extracted with dichloromethane (3×25 mL). The combined organic layers were washed with brine, dried over anhydrous sodium sulfate, filtered and concentrated under vacuum. The residue was purified by column chromatography (ethyl acetate/petroleum ether, 1/3) to afford the title compound (500 mg, 98%) as a yellow oil. LC-MS (Method C): m/z=233.0 [M+H]$^+$, 1.200 min.

Step 3: Preparation of 5-benzyl-1,3,4-oxadiazole-2-carboxylic acid

Lithium hydroxide (103 mg, 4.3 mmol) was added to a stirring solution of ethyl 5-benzyl-1,3,4-oxadiazole-2-carboxylate (500 mg, 2.15 mmol) in tetrahydrofuran (5 mL) and water (2 mL). The reaction mixture was stirred overnight at room temperature, concentrated under vacuum and diluted with water (20 mL). The pH value of the mixture was adjusted to pH=6 with aqueous hydrochloric acid (1 N, 10 mL). The resulting solution was extracted with ethyl acetate (3×50 mL). The combined organic layers were washed with brine, dried over anhydrous sodium sulfate, filtered and concentrated under vacuum to afford the title compound

392

(250 mg crude) as a yellow semi-solid. LC-MS (Method I): m/z=205.0 [M+H]$^+$, 0.058 min.

Step 4: Preparation of 5-benzyl-N-((1aR,2R,8bS)-5,7-difluoro-3-oxo-1,1a,2,3,4,8b-hexahydrobenzo[b]cyclopropa[d]azepin-2-yl)-1,3,4-oxadiazole-2-carboxamide The crude product obtained using Amide Coupling Procedure C was purified by Prep-HPLC with the following conditions: Column, XBridge C18 OBD Prep Column, 5 μm, 19 mm×250 mm; mobile phase, water (10 mmol/L NH$_4$HCO$_3$) and ACN (30.0% ACN up to 60.0% over 7 min); Detector, UV 254 nm to afford the title compound. $^1$H NMR (400 MHz, CD$_3$OD) δ 7.38-7.29 (m, 5H), 7.12-7.08 (m, 1H), 6.98-6.93 (m, 1H), 4.82 (d, J=0.8 Hz, 1H), 4.36 (s, 2H), 2.31-2.25 (m, 1H), 2.12-2.07 (m, 1H), 1.67-1.63 (m, 1H), 1.23-1.17 (m, 1H). LC-MS (Method V): m/z=411.05 [M+H]$^+$, 2.915 min.

Example 89B: 5-benzyl-N-((1aS,2S,8bR)-5,7-difluoro-3-oxo-1,1a,2,3,4,8b-hexahydrobenzo[b]cyclopropa[d]azepin-2-yl)-1,3,4-oxadiazole-2-carboxamide

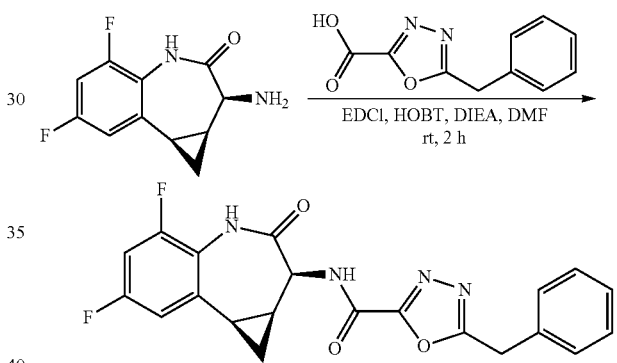

The crude product obtained using Amide Coupling Procedure C was purified by Prep-HPLC with the following conditions: Column, XBridge C18 OBD Prep Column, 5 μm, 19 mm×250 mm; mobile phase, water (10 mmol/L NH$_4$HCO$_3$) and ACN (30.0% ACN to 60.0% over 7 min); Detector, UV 254 nm to afford the title compound. $^1$H NMR (400 MHz, CD$_3$OD) δ 7.39-7.28 (m, 5H), 7.11-7.08 (m, 1H), 6.98-6.93 (m, 1H), 4.81 (d, J=0.8 Hz, 1H), 4.36 (s, 2H), 2.31-2.25 (m, 1H), 2.12-2.07 (m, 1H), 1.67-1.63 (m, 1H), 1.23-1.17 (m, 1H). LC-MS (Method Q): m/z=411.30 [M+H]$^+$, 0.965 min.

Example 90A: 1-benzyl-N-((1aR,2R,8bS)-5,7-difluoro-3-oxo-1,1a,2,3,4,8b-hexahydrobenzo[b]cyclopropa[d]azepin-2-yl)-1H-1,2,3-triazole-4-carboxamide

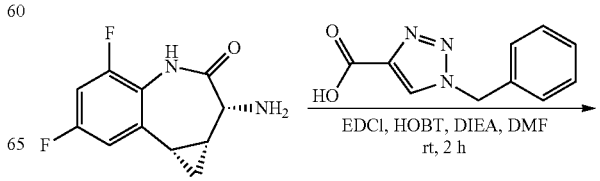

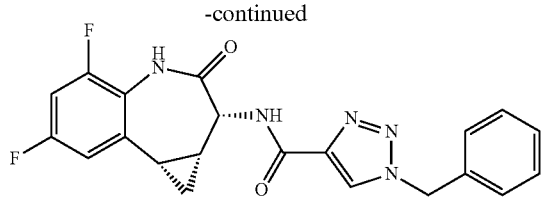
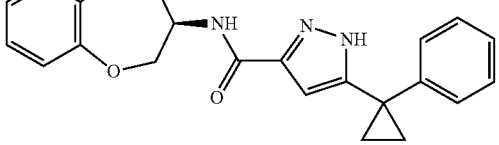

The crude product obtained using Amide Coupling Procedure C was purified by Prep-HPLC with the following conditions: Column, XBridge C18 OBD Prep Column, 5 μm, 19 mm×250 mm; mobile phase, water (10 mmol/L NH$_4$HCO$_3$) and ACN (30.0% ACN up to 60.0% over 7 min); Detector, UV 254 nm to afford the title compound. $^1$H NMR (400 MHz, DMSO-d$_6$) δ 9.90 (br. s, 1H), 8.77 (s, 1H), 8.51 (d, J=7.0 Hz, 1H), 7.43-7.33 (m, 5H), 7.32-7.26 (m, 1H), 7.24-7.19 (m, 1H), 5.67 (s, 2H), 4.63 (d, J=6.9 Hz, 1H), 2.32-2.26 (m, 1H), 2.06-2.00 (m, 1H), 1.44-1.40 (m, 1H), 1.14-1.08 (m, 1H). LC-MS (Method D): m/z=410.10 [M+H]$^+$, 1.876 min.

Example 90B: 1-benzyl-N-((1aS,2S,8bR)-5,7-difluoro-3-oxo-1,1a,2,3,4,8b-hexahydrobenzo[b]cyclopropa[d]azepin-2-yl)-1H-1,2,3-triazole-4-carboxamide

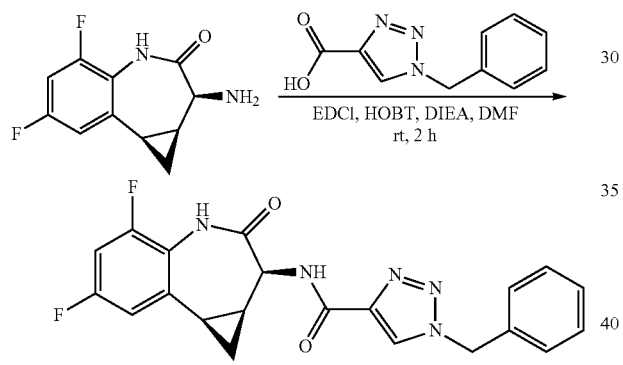

The crude product obtained using Amide Coupling Procedure C was purified by Prep-HPLC with the following conditions: Column, XBridge C18 OBD Prep Column, 5 μm, 19 mm×250 mm; mobile phase, water (10 mmol/L NH$_4$HCO$_3$) and ACN (30.0% ACN to 60.0% over 7 min); Detector, UV 254 nm to afford the title compound. $^1$H NMR (400 MHz, DMSO-d$_6$) δ 9.90 (s, 1H), 8.77 (s, 1H), 8.51 (d, J=7.0 Hz, 1H), 7.46-7.33 (m, 5H), 7.30-7.26 (m, 1H), 7.24-7.19 (m, 1H), 5.67 (s, 2H), 4.63 (d, J=6.9 Hz, 1H), 2.32-2.26 (m, 1H), 2.05-2.00 (m, 1H), 1.45-1.40 (m, 1H), 1.14-1.08 (m, 1H). LC-MS (Method J): m/z=410.15 [M+H]$^+$, 1.269 min.

Example 91: (S)—N-(4-oxo-2,3,4,5-tetrahydropyrido[3,2-b][1,4]oxazepin-3-yl)-5-(1-phenylcyclopropyl)-1H-pyrazole-3-carboxamide

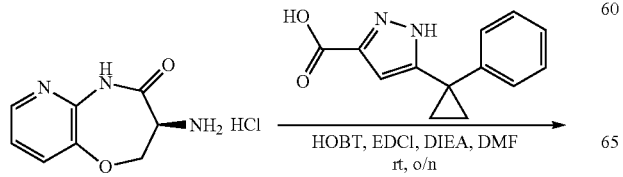

The crude product obtained using Amide Coupling Procedure C was purified by Prep-HPLC with the following conditions: Column: X Bridge Prep Phenyl OBD Column, 5 μm, 19×150 mm; Mobile Phase A:water (0.1% formic acid), Mobile Phase B: ACN; Flow rate: 20 mL/min; Gradient: 25% B to 60% B over 7 min; UV 254 &220 nm to afford the title compound. $^1$H NMR (400 MHz, DMSO-d$_6$) δ 13.18 (s, 1H), 10.53 (s, 1H), 8.24-8.14 (m, 2H), 7.56 (dd, J=8.0, 1.6 Hz, 1H), 7.34-7.15 (m, 6H), 6.38 (s, 1H), 4.84-4.77 (m, 1H), 4.52-4.41 (m, 2H), 1.35-1.30 (m, 4H). LC-MS (Method D): m/z=390.1 [M+H]$^+$, 1.537 min.

Example 92: 1-benzyl-N-((2R,3S)-2,5-dimethyl-4-oxo-2,3,4,5-tetrahydropyrido[3,2-b][1,4]oxazepin-3-yl)-4-fluoro-1H-pyrazole-3-carboxamide

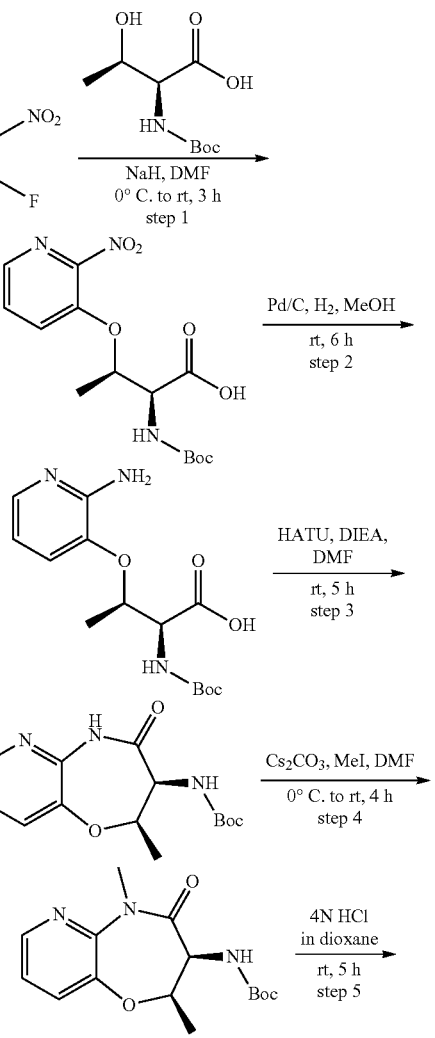

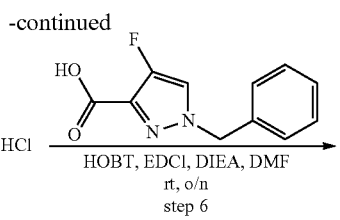
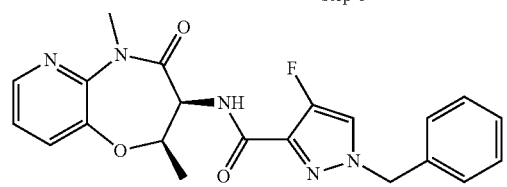

Step 1: Preparation of (2S,3R)-2-(tert-butoxycarbonylamino)-3-(2-nitropyridin-3-yloxy)-butanoic acid Sodium hydride (60%, 9.2 g, 230 mmol) was added to a stirring solution of (2S,3R)-2-(tert-butoxycarbonylamino)-3-hydroxybutanoic acid (25 g, 115 mmol) in N,N-dimethylformamide (500 mL) and the reaction mixture was stirred at 0° C. for 1 hour. After addition of 3-fluoro-2-nitropyridine (16.4 g, 115 mmol), the reaction mixture was stirred at room temperature for another 2 hours and then quenched by the addition of hydrochloride acid (3 N, 20 mL). The pH value of the reaction solution was adjusted to 3-4 with hydrogen chloride (3 N, 20 mL). The resulting solution was extracted with ethyl acetate (3×150 mL). The organic layers were combined, dried over anhydrous sodium sulfate and concentrated under reduced pressure. The residue was purified by reverse phase column chromatography (acetonitrile/water, 1/2) to afford the title compound (3.8 g, 10%) as a light yellow oil. LC-MS (Method C): m/z=286.1 [M+H−56]$^+$, 1.167 min.

Step 2: Preparation of (2S,3R)-3-(2-aminopyridin-3-yloxy)-2-(tert-butoxycarbonylamino)-butanoic acid (2S,3R)-2-(tert-butoxycarbonylamino)-3-(2-nitropyridin-3-yloxy)butanoic acid (3.77 g, 11 mmol) in methanol (30 mL) was hydrogenated in the presence of palladium carbon (10%, 1.0 g) under a hydrogen atmosphere (2-3 atm). The reaction mixture was stirred for 6 hours at room temperature. The solids were removed by filtration and the filtrate was concentrated under vacuum to afford the title compound (3.12 g, 91%) as a colorless oil. LC-MS (Method C): m/z=312.1 [M+H]$^+$, 0.887 min.

Step 3: Preparation of tert-butyl (2R,3S)-2-methyl-4-oxo-2,3,4,5-tetrahydropyrido[3,2-b][1,4]oxazepin-3-ylcarbamate N,N-diisopropylethylamine (1.43 g, 11 mmol) was added to a stirring solution of (2S,3R)-3-(2-aminopyridin-3-yloxy)-2-(tert-butoxycarbonylamino)butanoic acid (3.0 g, 10 mmol) and N,N,N',N'-tetramethyl-O-(7-azabenzotriazol-1-yl)uronium hexafluorophosphate (4.18 g, 11 mmol) in N,N-dimethylformamide (50 mL). The reaction mixture was stirred for 5 hours at room temperature, quenched by the addition of water (20 mL) and extracted with ethyl acetate (3×100 mL). The combined organic layers were washed with brine, dried over anhydrous sodium sulfate and concentrated under vacuum. The residue was purified by column chromatography (methanol/dichloromethane, 1/20) to afford the title compound (2.2 g, 78%) as a white solid. LC-MS (Method C): m/z=294.1 [M+H]$^+$, 1.136 min.

Step 4: Preparation of tert-butyl (2R,3S)-2,5-dimethyl-4-oxo-2,3,4,5-tetrahydropyrido[3,2-b][1,4]oxazepin-3-ylcarbamate Iodomethane (388 mg, 2.73 mmol) was added dropwise to a stirring solution of tert-butyl (2R,3S)-2-methyl-4-oxo-2,3,4,5-tetrahydropyrido[3,2-b][1,4]oxazepin-3-ylcarbamate (800 mg, 2.73 mmol) and cesium carbonate (890 mg, 2.73 mmol) in N,N-dimethylformamide (15 mL). The reaction mixture was stirred for 1 hour at 0° C. and 3 hours at room temperature, diluted with water (20 mL) and extracted with ethyl acetate (3×100 mL). The combined organic layers were washed with brine, dried over anhydrous sodium sulfate, filtered and concentrated under vacuum. The residue was purified by column chromatography (methanol/dichloromethane, 1/10) to afford the title compound (670 mg, 80%) as a white solid. LC-MS (Method C): m/z=308.2 [M+H]$^+$, 1.250 min.

Step 5: Preparation of (2R,3S)-3-amino-2,5-dimethyl-2,3-dihydropyrido[3,2-b][1,4]oxazepin-4(5H)-one hydrochloride Tert-butyl (2R,3S)-2,5-dimethyl-4-oxo-2,3,4,5-tetrahydropyrido[3,2-b][1,4]oxazepin-3-ylcarbamate (670 mg, 2.18 mmol) was added to a solution of hydrogen chloride in dioxane (4 M, 10 mL, 40 mmol). The reaction mixture was stirred for 5 hours at room temperature and concentrated under reduced pressure to afford the title compound (460 mg crude) as a white solid. LC-MS (Method E): m/z=207.90 [M+H]$^+$, 0.432 min.

Step 6: Preparation of 1-benzyl-N-((2R,3S)-2,5-dimethyl-4-oxo-2,3,4,5-tetrahydropyrido[3,2-b][1,4]oxazepin-3-yl)-4-fluoro-1H-pyrazole-3-carboxamide The crude product obtained using Amide Coupling Procedure C was purified by Prep-HPLC with the following conditions: Column: X Bridge C18 OBD Prep Column, 5 μm, 19 mm×250 mm; Mobile Phase A: water (10 mmol/L NH$_4$HCO$_3$), Mobile Phase B: ACN; Flow rate: 20 mL/min; Gradient: 40% B to 60% B in 7 min; UV 254 & 220 nm to afford the title compound. $^1$H NMR (400 MHz, DMSO-d$_6$) δ 8.36 (dd, J=4.4, 1.6 Hz, 1H), 8.15 (d, J=4.4 Hz, 1H), 7.76 (dd, J=8.0, 1.6 Hz, 1H), 7.61 (d, J=6.4 Hz, 1H), 7.42-7.31 (m, 4H), 7.31-7.27 (m, 2H), 5.37 (s, 2H), 5.00-4.93 (m, 1H), 4.92-4.88 (m, 1H), 3.40 (s, 3H), 1.32 (d, J=6.0 Hz, 3H). LC-MS (Method F): m/z=409.9 [M+H]$^+$, 1.336 min.

Example 93: 1-benzyl-N-((2S,3S)-2,5-dimethyl-4-oxo-2,3,4,5-tetrahydropyrido[3,2-b][1,4]oxazepin-3-yl)-4-fluoro-1H-pyrazole-3-carboxamide

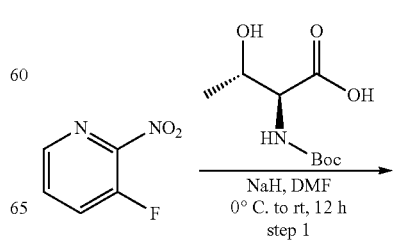

-continued

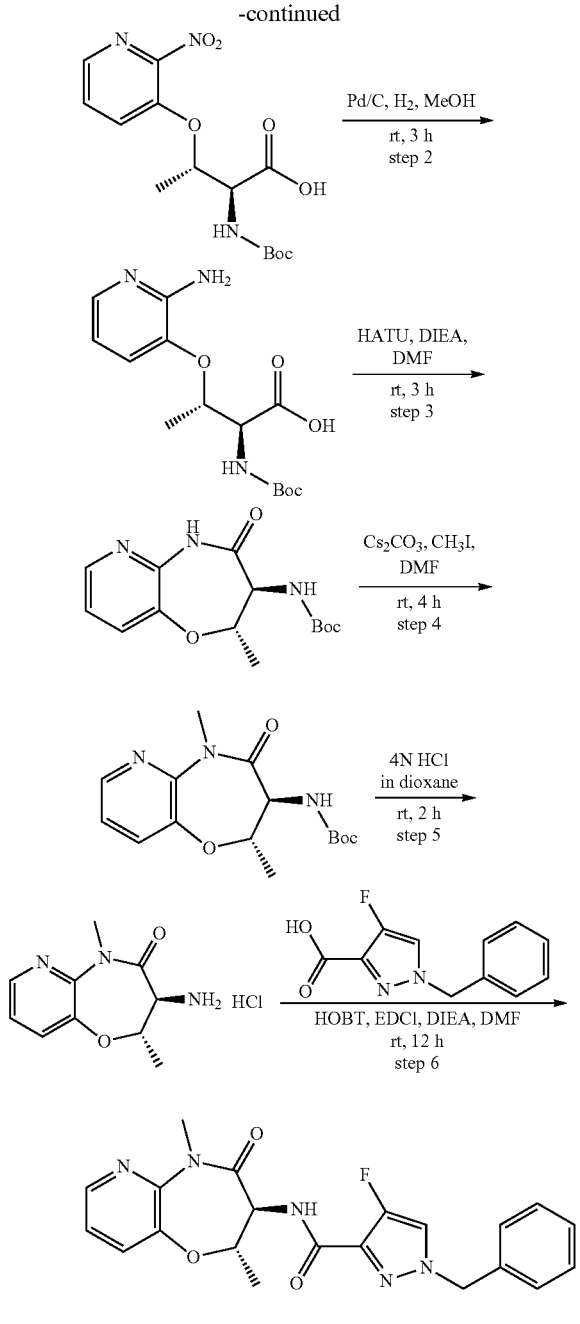

The title compound was prepared from (2S,3S)-2-(tert-butoxycarbonylamino)-3-hydroxybutanoic acid using the procedure described in Example 92.

The crude product obtained was purified by Prep-HPLC with the following conditions: Column: X Bridge Prep C18 OBD Column 19×150 mm, 5 μm; Mobile Phase A: water (10 mmol/L NH$_4$HCO$_3$), Mobile Phase B: ACN; Flow rate: 20 mL/min; Gradient: 25% B to 55% B over 7 min; UV 254 & 220 nm to afford the title compound. $^1$H NMR (400 MHz, DMSO-d$_6$) δ 8.46 (d, J=8.4 Hz, 1H), 8.38 (dd, J=4.8, 1.2 Hz, 1H), 8.14 (d, J=4.4 Hz, 1H), 7.63 (dd, J=8.0, 1.6 Hz, 1H), 7.42-7.27 (m, 6H), 5.36 (s, 2H), 5.10-5.01 (m, 1H), 4.45-4.40 (m, 1H), 3.34 (s, 3H), 1.26 (d, J=6.0 Hz, 3H). LC-MS (Method D): m/z=410.1 [M+H]$^+$, 1.923 min.

Example 94: 5-benzyl-N-((2R,3S)-2,5-dimethyl-4-oxo-2,3,4,5-tetrahydropyrido[3,2-b][1,4]oxazepin-3-yl)-4H-1,2,4-triazole-3-carboxamide

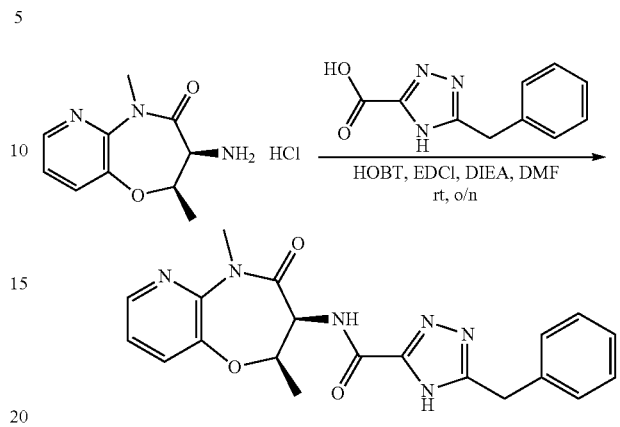

N,N-diisopropylethylamine (95 mg, 0.73 mmol) was added to a mixture of 5-benzyl-4H-1,2,4-triazole-3-carboxylic acid (50 mg, 0.24 mmol), (2R,3S)-3-amino-2,5-dimethyl-2,3-dihydropyrido[3,2-b][1,4]oxazepin-4(5H)-one hydrochloride (50 mg, 0.24 mmol), N-(3-dimethylaminopropyl))-N'-ethylcarbodiimide hydrochloride (60 mg, 0.32 mmol) and 1-hydroxybenzotriazole (43 mg, 0.32 mmol) in N,N-dimethylformamide (2 mL). The reaction mixture was stirred overnight at room temperature, diluted with water (20 mL) and extracted with ethyl acetate (3×50 mL). The organic layers were combined, washed with brine, dried over anhydrous sodium sulfate, filtered and concentrated under vacuum. The crude product obtained using Amide Coupling Procedure C was purified by Prep-HPLC with the following conditions: Column: X Bridge Shield RP18 OBD Column, 5 μm, 19×150 mm; Mobile Phase A: water (0.05% TFA), Mobile Phase B: ACN; Flow rate: 20 mL/min; Gradient: 5% B to 5% B over 4 min; UV 254 & 220 nm to afford the title compound. $^1$H NMR (400 MHz, DMSO-d$_6$) δ 14.46 (s, 1H), 8.36 (dd, J=4.8, 1.6 Hz, 1H), 7.98 (d, J=6.0 Hz, 1H), 7.76 (dd, J=8.0, 1.6 Hz, 1H), 7.38-7.23 (m, 6H), 5.01-4.94 (m, 1H), 4.93-4.89 (m, 1H), 4.14 (s, 2H), 3.40 (s, 3H), 1.31 (d, J=6.0 Hz, 3H). LC-MS (Method D): m/z=393.1 [M+H]$^+$, 1.725 min.

Example 95: 5-benzyl-N-((2S,3S)-2,5-dimethyl-4-oxo-2,3,4,5-tetrahydropyrido[3,2-b][1,4]oxazepin-3-yl)-4H-1,2,4-triazole-3-carboxamide

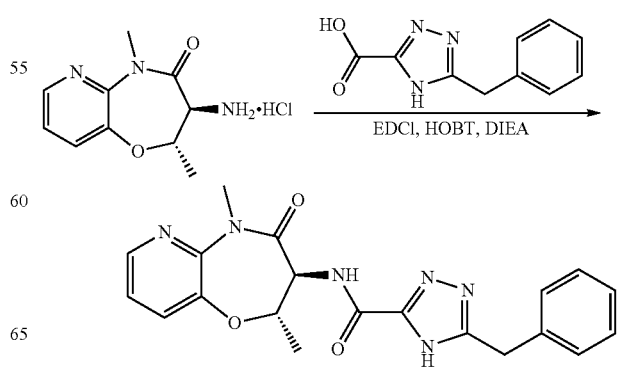

Example 96: 5-benzyl-N-((2R,3S)-2-methyl-4-oxo-2,3,4,5-tetrahydropyrido[3,2-b][1,4]oxazepin-3-yl)-4H-1,2,4-triazole-3-carboxamide

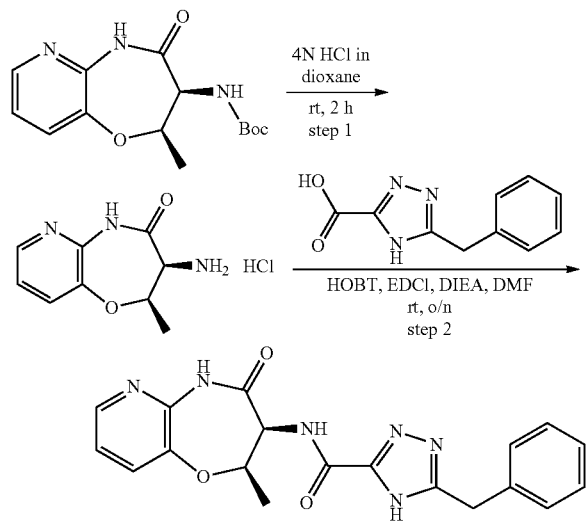

Step 1: Preparation of (2R,3S)-3-amino-2-methyl-2,3-dihydropyrido[3,2-b][1,4]oxazepin-4(5H)-one hydrochloride Tert-butyl (2R,3S)-2-methyl-4-oxo-2,3,4,5-tetrahydropyrido[3,2-b][1,4]oxazepin-3-ylcarbamate (100 mg, 0.34 mmol) was added to a solution of hydrogen chloride in dioxane (4 M, 5 mL). The reaction mixture was stirred for 2 hours at room temperature and concentrated under reduced pressure to afford the title compound (100 mg crude) as a white solid. LC-MS (Method E): m/z=194.0 [M+H]$^+$, 0.432 min.

Step 2: Preparation of 5-benzyl-N-((2R,3S)-2-methyl-4-oxo-2,3,4,5-tetrahydropyrido[3,2-b][1,4]oxazepin-3-yl)-4H-1,2,4-triazole-3-carboxamide The crude product obtained using Amide Coupling Procedure C was purified by Prep-HPLC with the following conditions: Column: X Bridge C18 OBD Prep Column, 10 µm, 19 mm×250 mm; Mobile Phase A: water (0.1% formic acid), Mobile Phase B: ACN; Flow rate: 20 mL/min; Gradient: 20% B to 35% B over 7 min UV 254 & 220 nm to afford the title compound. $^1$H NMR (300 MHz, DMSO-d$_6$) δ 14.41 (s, 1H), 10.84 (s, 1H), 8.19-8.08 (m, 2H), 7.62 (dd, J=8.1, 1.2 Hz, 1H), 7.37-7.20 (m, 6H), 4.98-4.86 (m, 2H), 4.15 (s, 2H), 1.30 (d, J=6.0 Hz, 3H). LC-MS (Method D): m/z=379.1 [M+H]$^+$, 1.546 min.

Example 97: 5-benzyl-N-((2S,3S)-2-methyl-4-oxo-2,3,4,5-tetrahydropyrido[3,2-b][1,4]oxazepin-3-yl)-4H-1,2,4-triazole-3-carboxamide

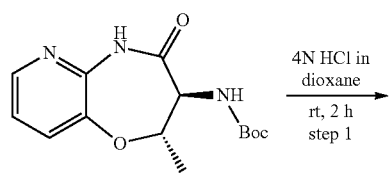

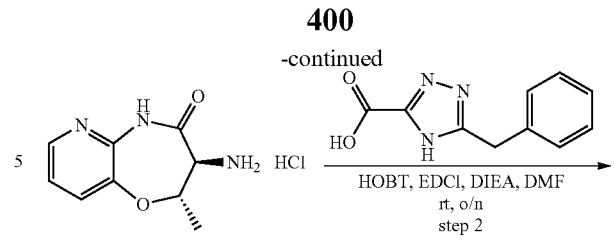

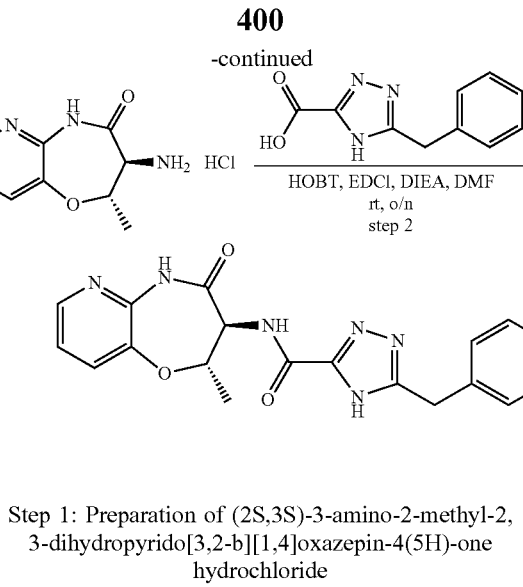

Step 1: Preparation of (2S,3S)-3-amino-2-methyl-2,3-dihydropyrido[3,2-b][1,4]oxazepin-4(5H)-one hydrochloride Tert-butyl (2S,3S)-2-methyl-4-oxo-2,3,4,5-tetrahydropyrido[3,2-b][1,4]oxazepin-3-yl carbamate (50 mg, 0.17 mmol) was added to a solution of hydrogen chloride in dioxane (4 M, 5 mL, 20 mmol). The reaction mixture was stirred for 2 hours at room temperature and concentrated under vacuum to afford the title compound (35 mg crude) as a white solid. LC-MS (Method E): m/z=194.0 [M+H]$^+$, 0.432 min.

Step 2: Preparation of 5-benzyl-N-((2S,3S)-2-methyl-4-oxo-2,3,4,5-tetrahydropyrido[3,2-b][1,4]oxazepin-3-yl)-4H-1,2,4-triazole-3-carboxamide The crude product obtained using Amide Coupling Procedure C was purified by Prep-HPLC with the following conditions: Column: X Select CSH prep C18 OBD Prep Column, 5 µm, 19 mm×150 mm; Mobile Phase A: water (0.1% formic acid), Mobile Phase B: ACN; Flow rate: 20 mL/min; Gradient: 15% B to 60% B over 7 min; UV 254 & 220 nm to afford the title compound. $^1$H NMR (400 MHz, DMSO-d$_6$) δ 14.36 (s, 1H), 10.56 (s, 1H), 8.68 (d, J=8.8 Hz, 1H), 8.23-8.20 (m, 1H), 7.56 (d, J=8.8 Hz, 1H), 7.39-7.17 (m, 6H), 5.11-4.90 (m, 1H), 4.44 (m, 1H), 4.16 (s, 2H), 1.32 (d, J=6.0 Hz, 3H). LC-MS (Method F): m/z=378.95 [M+H]$^+$, 0.932 min.

Example 98A and 98B: (R)-5-benzyl-N-(8'-oxo-6',7',8',9'-tetrahydrospiro[cyclopropane-1,5'-pyrido[2,3-b]azepin]-7'-yl)-4H-1,2,4-triazole-3-carboxamide (98A) and (S)-5-benzyl-N-(8'-oxo-6',7',8',9'-tetrahydrospiro[cyclopropane-1,5'-pyrido[2,3-b]azepin]-7'-yl)-4H-1,2,4-triazole-3-carboxamide (98B)

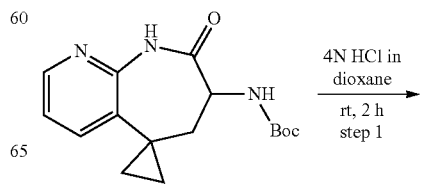

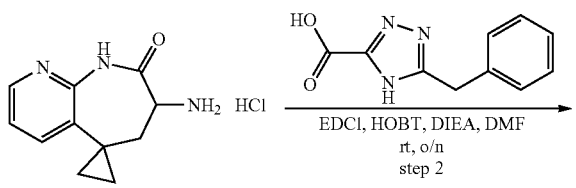

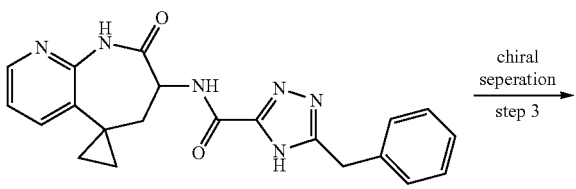

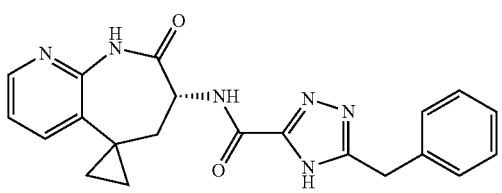

+

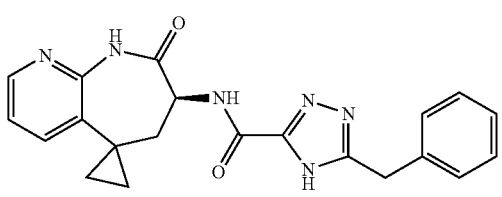

Step 1: Preparation of 7'-amino-6',7'-dihydrospiro[cyclopropane-1,5'-pyrido[2,3-b]azepin]-8'(9'H)-one hydrochloride A solution of hydrogen chloride in 1,4-dioxane (4 N, 10 mL, 40 mmol) was added to a solution of tert-butyl (8'-oxo-6',7',8',9'-tetrahydrospiro[cyclopropane-1,5'-pyrido[2,3-b]azepin]-7'-yl)carbamate (100 mg, 0.34 mmol) in 1,4-dioxane (4 mL). The reaction mixture was stirred for 2 hours at room temperature and concentrated under high vacuum to afford the title compound (80 mg crude) as a white solid. LC-MS (Method C): m/z=204.1 [M+H]$^+$, 0.677 min.

Step 2: Preparation of 5-benzyl-N-(8'-oxo-6',7',8',9'-tetrahydrospiro[cyclopropane-1,5'-pyrido[2,3-b]azepin]-7'-yl)-4H-1,2,4-triazole-3-carboxamide The crude product obtained using Amide Coupling Procedure C was purified by Prep-HPLC with the following conditions: Column: XBridge Prep C18 OBD Column, 5 µm, 19×150 mm; Mobile Phase A: waters (0.05% TFA), Mobile Phase B: ACN; Flow rate: 20 mL/min; Gradient: 35% B to 65% B over 7 min; 254/220 nm to afford the title compound (50 mg, 56%) as a white solid. LC-MS (Method V): m/z=389.2 [M+H]$^+$, 0.982 min.

Step 2: Preparation of (R)-5-benzyl-N-(8'-oxo-6',7',8',9'-tetrahydrospiro[cyclopropane-1,5'-pyrido[2,3-b]azepin]-7'-yl)-4H-1,2,4-triazole-3-carboxamide (First Eluting Isomer) and (S)-5-benzyl-N-(8'-oxo-6',7',8',9'-tetrahydrospiro[cyclopropane-1,5'-pyrido[2,3-b]azepin]-7'-yl)-4H-1,2,4-triazole-3-carboxamide (Second Eluting Isomer)

The racemate of 5-benzyl-N-(8'-oxo-6',7',8',9'-tetrahydrospiro[cyclopropane-1,5'-pyrido[2,3-b]azepin]-7'-yl)-4H-1,2,4-triazole-3-carboxamide (50 mg, 0.128 mmol) was separated by Prep-Chiral-HPLC with the following conditions: Column: Chiralpak ID-2, 2×25 cm, 5 µm; Mobile Phase A: hexane/DCM 4.5:1, Mobile Phase B: EtOH; Flow rate: 17 mL/min; Gradient: 50% B to 50% B over 22 min; UV 254 & 220 nm; RT 1: 11.72 min; RT 2: 18.02 min to afford the title compounds:

Example 98A (first eluting isomer): $^1$H NMR (300 MHz, DMSO-d$_6$) δ 14.28 (s, 1H), 10.37 (s, 1H), 8.27 (dd, J=4.8, 1.8 Hz, 1H), 7.69 (dd, J=7.6, 1.8 Hz, 1H), 7.34-7.08 (m, 6H), 4.42-4.33 (m, 1H), 3.30 (s, 3H), 2.82-2.68 (m, 1H), 1.72 (s, 1H), 1.23-1.05 (m, 1H), 0.88-0.78 (m, 1H), 0.70-0.65 (m, 1H), 0.40-0.25 (m, 1H). LC-MS (Method D): m/z=389.2 [M+H]$^+$, 1.499 min.

Example 98B (second eluting isomer): $^1$H NMR (300 MHz, DMSO-d$_6$) δ 10.38 (d, J=2.8 Hz, 1H), 8.37-8.22 (m, 2H), 7.71-7.67 (m, 1H), 7.44-7.08 (m, 6H), 4.43-4.34 (m, 1H), 4.06 (s, 2H), 2.78-2.71 (m, 1H), 1.73 (t, J=12.3 Hz, 1H), 1.23-1.05 (m, 2H), 0.86-0.79 (m, 1H), 0.71-0.64 (m, 1H), 0.27 (s, 1H). LC-MS (Method D): m/z=389.2 [M+H]$^+$, 1.503 min.

Example 99: (S)—N-(5-methyl-4-oxo-2,3,4,5-tetrahydropyrido[3,2-b][1,4]oxazepin-3-yl)-5-(1-phenylcyclopropyl)-1H-imidazole-2-carboxamide

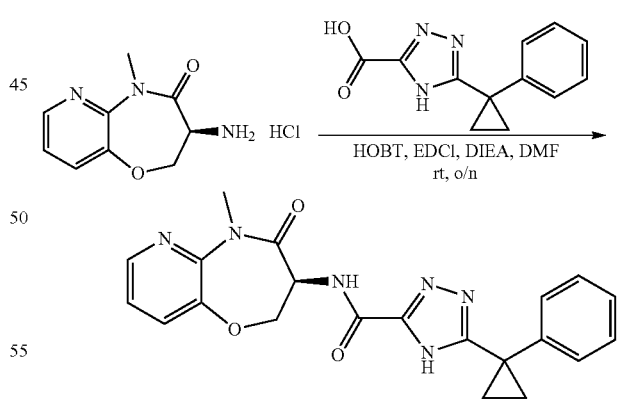

The crude product obtained using Amide Coupling Procedure C was purified by Prep-HPLC with the following conditions: column: X bridge Prep C18, 19×150 mm, 5 µm; Mobile phase: Phase A: water (10 mmol/L NH$_4$HCO$_3$); Phase B: ACN; Flow rate: 20 mL/min; Gradient: 25% B to 55% B over 7 min; Detector, UV 220 & 254 nm; Rt: 6.32 min to afford the title compound. $^1$H NMR (300 MHz, DMSO-d$_6$) δ 12.80 (s, 1H), 8.50-8.32 (m, 2H), 7.72-7.70 (m, 1H), 7.39-7.15 (m, 6H), 6.78-6.65 (m, 1H), 4.92-4.63 (m, 2H), 4.52-4.48 (m, 1H), 3.36 (s, 3H), 1.35-1.30 (m, 2H), 1.28-1.11 (m, 2H). LC-MS (Method O): m/z=404.0 [M+H]+, 1.412 min.

Example 100A and 100B: 4-(2-fluorophenoxy)-N-((1aS,2S,8bR)-4-methyl-3-oxo-1,1a,2,3,4,8b-hexahydrocyclopropa[d]pyrido[2,3-b]azepin-2-yl)picolinamide (100A) and 4-(2-fluorophenoxy)-N-((1aR,2R,8bS)-4-methyl-3-oxo-1,1a,2,3,4,8b-hexahydrocyclopropa[d]pyrido[2,3-b]azepin-2-yl)picolinamide (100B)

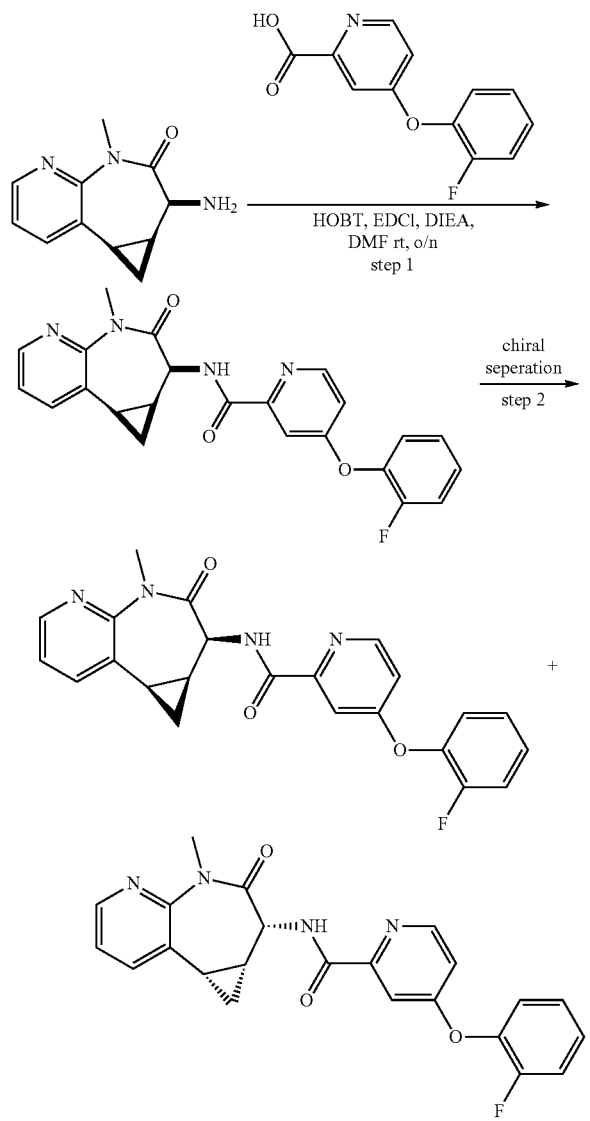

Step 1: Preparation of 4-(2-fluorophenoxy)-N-(cis-4-methyl-3-oxo-1,1a,2,3,4,8b-hexahydro cyclopropa[d]pyrido[2,3-b]azepin-2-yl)picolinamide The crude product obtained using Amide Coupling Procedure C was purified by prep-TLC (ethyl acetate/petroleum ether, 1/3) to afford the title racemic compound. LC-MS (Method J): m/z=419.1 [M+H]+, 1.330 min.

Step 2: Preparation of 4-(2-fluorophenoxy)-N-((1aS,2S,8bR)-4-methyl-3-oxo-1,1a,2,3,4,8b-hexahydrocyclopropa[d]pyrido[2,3-b]azepin-2-yl)picolinamide (First Eluting Isomer) and 4-(2-fluorophenoxy)-N-((1aR,2R,8bS)-4-methyl-3-oxo-1,1a,2,3,4,8b-hexahydrocyclopropa[d]pyrido[2,3-b]azepin-2-yl)picolinamide (Second Eluting Isomer)

The racemate of 4-(2-fluorophenoxy)-N-(cis-4-methyl-3-oxo-1,1a,2,3,4,8b-hexahydro cyclopropa[d]pyrido[2,3-b]azepin-2-yl)picolinamide (25 mg, 0.096 mmol) was separated by Prep-Chiral-HPLC with the following conditions: Column: Chiralpak IA, 2×25 cm, 5 µm; Mobile Phase A: hexane, Mobile Phase B: EtOH; Flow rate: 16 mL/min; Gradient: 50% B to 50% B over 19 min; 220/254 nm; RT1: 13.609 min; RT2: 15.738 min to afford the title compounds:

Example 100A (first eluting isomer): $^1$H NMR (300 MHz, Methanol-$d_4$) δ 8.59 (d, J=5.6 Hz, 1H), 8.39 (dd, J=4.7, 1.8 Hz, 1H), 7.95 (dd, J=7.7, 1.8 Hz, 1H), 7.55 (d, J=2.5 Hz, 1H), 7.42-7.27 (m, 5H), 7.15 (dd, J=5.6, 2.6 Hz, 1H), 4.66 (s, 1H), 3.42 (s, 3H), 2.32-2.26 (m, 1H), 2.17-2.06 (m, 1H), 1.36-1.32 (m, 1H), 1.23-1.14 (m, 1H). LC-MS (Method J): m/z=419.2 [M+H]+, 1.467 min.

Example 100B (second eluting isomer): $^1$H NMR (300 MHz, Methanol-$d_4$) δ 8.58 (d, J=5.6 Hz, 1H), 8.38 (dd, J=4.7, 1.8 Hz, 1H), 7.95 (dd, J=7.7, 1.8 Hz, 1H), 7.55 (d, J=2.6 Hz, 1H), 7.41-7.28 (m, 5H), 7.14 (dd, J=5.6, 2.6 Hz, 1H), 4.65 (s, 1H), 3.42 (s, 3H), 2.35-2.25 (m, 1H), 2.15-2.03 (m, 1H), 1.37-1.25 (m, 1H), 1.24-1.16 (m, 1H). LC-MS (Method T): m/z=419.3 [M+H]+, 2.774 min.

Example 101A and 101B: (R)-5-benzyl-N-(1,4-dimethyl-5-oxo-1,4,5,6,7,8-hexahydropyrazolo[4,3-b]azepin-6-yl)-4H-1,2,4-triazole-3-carboxamide (101A) and (S)-5-benzyl-N-(1,4-dimethyl-5-oxo-1,4,5,6,7,8-hexahydropyrazolo[4,3-b]azepin-6-yl)-4H-1,2,4-triazole-3-carboxamide (101B)

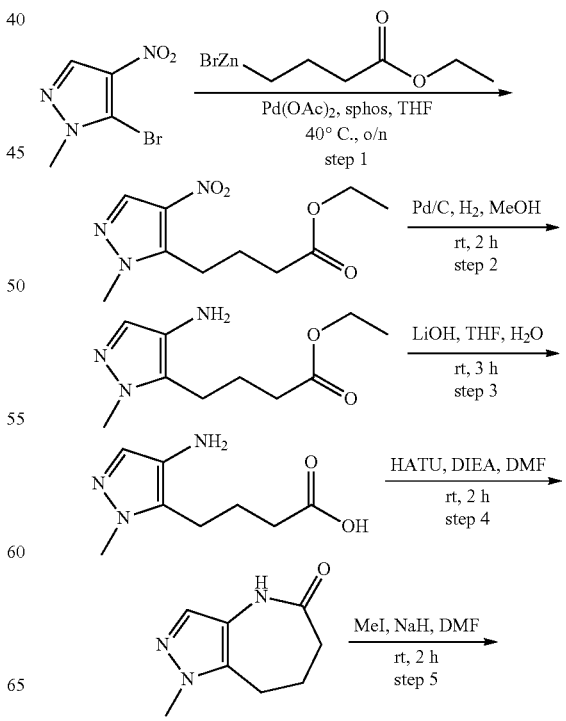

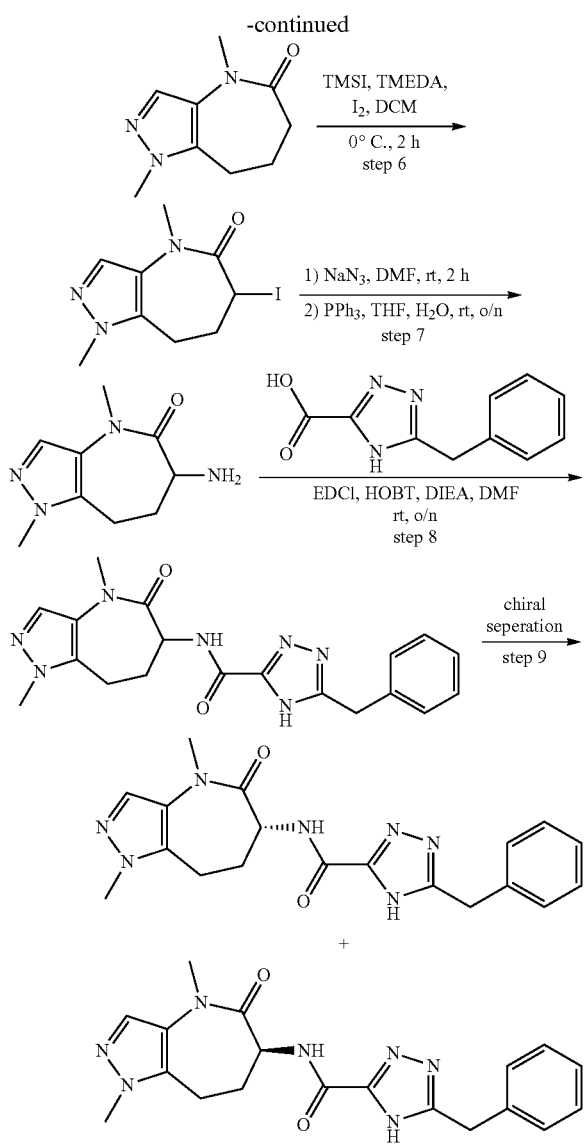

Step 1: Preparation of ethyl 4-(1-methyl-4-nitro-1H-pyrazol-5-yl)butanoate

To a stirring solution of 5-bromo-1-methyl-4-nitro-1H-pyrazole (2.0 g, 9.76 mmol), (4-ethoxy-4-oxobutyl)zinc(II) bromide (0.5 M in tetrahydrofuran) (29.2 mL, 14.6 mmol) and dicyclohexyl(2',6'-dimethoxybiphenyl-2-yl)phosphine (402.3 mg, 0.98 mmol) in tetrahydrofuran (100 mL) was added a solution of palladium diacetate (109.8 mg, 0.49 mmol) in tetrahydrofuran dropwise with stirring under a nitrogen atmosphere. The resulting mixture was heated overnight at 40° C. The reaction mixture was concentrated under high vacuum and the residue was purified by column chromatography (methanol/dichloromethane, 1/99) to afford the title compound (445 mg, 18.9%) as a yellow oil. LC-MS (Method C): m/z=242.1 [M+H]$^+$, 1.156 min.

Step 2: Preparation of ethyl 4-(4-amino-1-methyl-1H-pyrazol-5-yl)butanoate

Ethyl 4-(1-methyl-4-nitro-1H-pyrazol-5-yl)butanoate (405 mg, 1.68 mmol) was hydrogenated in the presence of palladium on carbon (10%, 41 mg) under a hydrogen atmosphere (2-3 atm) in methanol (20 mL). The reaction mixture was stirred for 2 hours at room temperature. Then the solids were removed by filtration and the solvents were evaporated under vacuum to afford the title compound (320 mg crude) as a yellow solid. LC-MS (Method C): m/z=212.2 [M+H]$^+$, 0.768 min.

Step 3: Preparation of 4-(4-amino-1-methyl-1H-pyrazol-5-yl)butanoic acid

A solution of ethyl 4-(4-amino-1-methyl-1H-pyrazol-5-yl)butanoate (320 mg, 1.51 mmol) and lithium hydroxide (108.9 mg, 4.53 mmol) in tetrahydrofuran/water=3/1 (4 mL) was stirred for 3 hours at room temperature. The pH value of the solution was adjusted to 6-7 with hydrochloride acid (1 N). The resulting solution was concentrated under vacuum to afford the title compound (220 mg crude) as a yellow solid. LC-MS (Method C): m/z=184.1 [M+H]$^+$, 0.318 min.

Step 4: Preparation of 1-methyl-7,8-dihydropyrazolo[4,3-b]azepin-5(1H,4H,6H)-one N,N-diisopropylethylamine (465.2 mg, 3.6 mmol) was added to a stirring solution of 4-(4-amino-1-methyl-1H-pyrazol-5-yl)butanoic acid (220 mg, 1.2 mmol) and N,N,N',N'-tetramethyl-O-(7-azabenzotriazol-1-yl)uronium hexafluorophosphate (548.2 mg, 1.44 mmol) in N,N-dimethylformamide (5 mL). The reaction mixture was stirred for 2 hours at room temperature, diluted with water (10 mL) and extracted with ethyl acetate (3×20 mL). The combined organic layers were washed with brine, dried over anhydrous sodium sulfate, filtered and concentrated under vacuum. The residue was purified by column chromatography (ethyl acetate/petroleum ether, 1/4) to afford the title compound (160 mg, 80.8%) as a yellow solid. LC-MS (Method C): m/z=166.2 [M+H]$^+$, 0.751 min.

Step 5: Preparation of 1,4-dimethyl-7,8-dihydropyrazolo[4,3-b]azepin-5(1H,4H,6H)-one Iodomethane (150.5 mg, 1.06 mmol) was added dropwise to a stirred solution of 1-methyl-7,8-dihydropyrazolo[4,3-b]azepin-5(1H,4H,6H)-one (160 mg, 0.96 mmol) and sodium hydride (60%) (42.4 mg, 1.06 mmol) in N,N-dimethylformamide (5 mL) with stirring. The reaction mixture was stirred for 2 hours at room temperature, quenched by water (10 mL) and extracted with ethyl acetate (3×20 mL). The combined organic phases were dried over anhydrous sodium sulfate, filtered and concentrated under vacuum. The residue was purified by column chromatography (petroleum ether/ethyl acetate, 3/1) to afford the title compound (140 mg, 81.5%) as a yellow solid. LC-MS (Method C): m/z=180.2 [M+H]$^+$, 0.816 min.

Step 6: Preparation of 6-iodo-1,4-dimethyl-7,8-dihydropyrazolo[4,3-b]azepin-5(1H,4H,6H)-one $N^1,N^1,N^2,N^2$-tetramethylethane-1,2-diamine (271.4 mg, 2.34 mmol) was added to a stirring solution of 1,4-dimethyl-7,8-dihydropyrazolo[4,3-b]azepin-5(1H,4H,6H)-one (140 mg, 0.78 mmol) in dichloromethane (5 mL) at 0° C. followed by the addition of iodotrimethylsilane (468 mg, 2.34 mmol). The reaction mixture was stirred for 1 hour at 0° C. After adding iodine (137.2 mg, 0.54 mmol), the reaction mixture was stirred for another 1 hour at 0° C. and quenched with aqueous sodium thiosulfate (5%, 15 mL). The reaction mixture was stirred for another 15 minutes and extracted with ethyl acetate (3×20 mL). The combined organic layers were washed with brine, dried over anhydrous sodium sulfate, filtered and concentrated under vacuum to afford the title compound (214 mg crude) as a yellow solid, which was used directly in the next step without further purification. LC-MS (Method C): m/z=306.0 [M+H]$^+$, 0.953 min.

Step 7: Preparation of 6-amino-1,4-dimethyl-7,8-dihydropyrazolo[4,3-b]azepin-5(1H,4H,6H)-one To a solution of 6-iodo-1,4-dimethyl-7,8-dihydropyrazolo [4,3-b]azepin-5(1H,4H,6H)-one (214 mg, 0.70 mmol) in N,N-dimethylformamide (4 mL) was added sodium azide (136.9 mg, 2.1 mmol). The reaction mixture was stirred for 2 hours at room temperature and concentrated under reduced pressure. The residue was dissolved in tetrahydrofuran (6 mL) and water (2 mL) and triphenylphosphine (551.8 mg, 2.1 mmol) was added in one portion. The reaction mixture was stirred at 50° C. overnight, diluted with water (10 mL) and extracted with ethyl acetate (3×20 mL). The combined organic layers were washed with brine, dried over anhydrous sodium sulfate, filtered and concentrated under vacuum. The residue was purified by column chromatography (methanol/dichloromethane, 1/10) to afford the title compound (100 mg, 73.6%) as a yellow solid. LC-MS (Method C): m/z=195.1 [M+H]$^+$, 0.386 min.

Step 8: Preparation of 5-benzyl-N-(1,4-dimethyl-5-oxo-1,4,5,6,7,8-hexahydropyrazolo[4,3-b]azepin-6-yl)-4H-1,2,4-triazole-3-carboxamide The crude product obtained using Amide Coupling Procedure C was purified by Prep-HPLC with the following conditions: column: X bridge Prep C18, 19×150 mm, 5 µm; Mobile phase: Phase A: water (10 mmol/L NH$_4$HCO$_3$); Phase B: ACN (20% to 80% over 12 min); Detector, UV 220 & 254 nm to afford the title compound. LC-MS (Method C): m/z=380.2 [M+H]$^+$, 1.290 min.

Step 9: Preparation of (R)-5-benzyl-N-(1,4-dimethyl-5-oxo-1,4,5,6,7,8-hexahydropyrazolo[4,3-b] azepin-6-yl)-4H-1,2,4-triazole-3-carboxamide (First Eluting Isomer) and (S)-5-benzyl-N-(1,4-dimethyl-5-oxo-1,4,5,6,7,8-hexahydropyrazolo[4,3-b]azepin-6-yl)-4H-1,2,4-triazole-3-carboxamide (Second Eluting Isomer)

The racemate of 5-benzyl-N-(1,4-dimethyl-5-oxo-1,4,5,6, 7,8-hexahydropyrazolo[4,3-b]azepin-6-yl)-4H-1,2,4-triazole-3-carboxamide (50 mg, 0.13 mmol) were separated by Prep-Chiral-HPLC with the following conditions: Column: Chiralpak IA, 2×25 cm, 5 µm; Mobile Phase A: Hex, Mobile Phase B: EtOH; Flow rate: 15 mL/min; Gradient: 60% B to 60% B over 21 min; 220/254 nm; RT1: 12.12 min; RT2: 18.44 min.

Example 101A (first eluting isomer): $^1$H NMR (400 MHz, Methanol-d$_4$) δ 7.51 (s, 1H), 7.34-7.22 (m, 5H), 4.60 (dd, J=2.0, 10.0 Hz, 1H), 4.17 (s, 2H), 3.80 (s, 3H), 3.36 (s, 3H), 3.20-3.11 (m, 1H), 2.99-2.91 (m, 1H), 2.48-2.41 (m, 1H), 2.25-2.14 (m, 1H). LC-MS (Method V): m/z=380.1 [M+H]$^+$, 2.240 min.

Example 101B (second eluting isomer): $^1$H NMR (400 MHz, Methanol-d$_4$) δ 7.51 (s, 1H), 7.35-7.22 (m, 5H), 4.60 (dd, J=2.4, 10.4 Hz, 1H), 4.17 (s, 2H), 3.80 (s, 3H), 3.36 (s, 3H), 3.20-3.11 (m, 1H), 2.99-2.91 (m, 1H), 2.49-2.41 (m, 1H), 2.25-2.14 (m, 1H). LC-MS (Method D): m/z=380.2 [M+H]$^+$, 1.471 min.

Example 102A & 102B: 5-((R)-2,3-dihydro-1H-inden-1-yl)-N—((S)-4-oxo-2,3,4,5-tetrahydropyrido [3,2-b][1,4]oxazepin-3-yl)-4H-1,2,4-triazole-3-carboxamide and 5-((S)-2,3-dihydro-1H-inden-1-yl)-N—((S)-4-oxo-2,3,4,5-tetrahydropyrido[3,2-b][1,4] oxazepin-3-yl)-4H-1,2,4-triazole-3-carboxamide

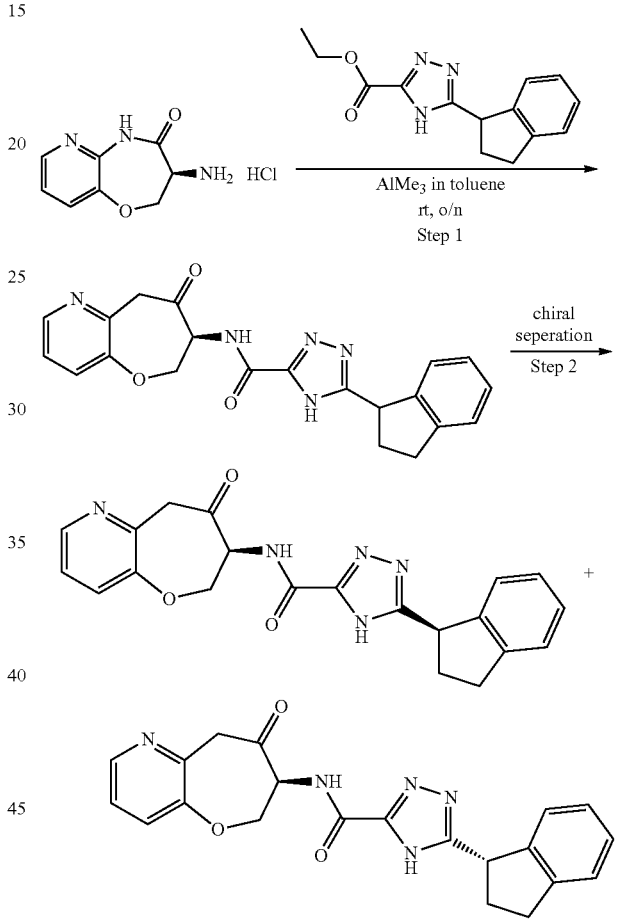

Step 1: Preparation of 5-(2,3-dihydro-1H-inden-1-yl)-N—((S)-4-oxo-2,3,4,5-tetrahydropyrido[3,2-b] [1,4]oxazepin-3-yl)-4H-1,2,4-triazole-3-carboxamide The crude product obtained using the procedure described in Example 54 was purified by Prep-HPLC with the following conditions: Column: XBridge C18 OBD Prep Column, 5 µm, 19 mm×250 mm; Mobile Phase A: water (10 mmol/L NH$_4$HCO$_3$), Mobile Phase B: ACN; Flow rate: 20 mL/min; Gradient: 20% B to 36% B over 7 min; 254 nm; Rt: 7 min to afford the title compound. LC-MS (Method D): m/z=391.1 [M+H]$^+$, 1.593 min.

409

Step 2: Preparation of 5-((R)-2,3-dihydro-1H-inden-1-yl)-N—((S)-4-oxo-2,3,4,5-tetrahydropyrido[3,2-b][1,4]oxazepin-3-yl)-4H-1,2,4-triazole-3-carboxamide and 5-((S)-2,3-dihydro-1H-inden-1-yl)-N—((S)-4-oxo-2,3,4,5-tetrahydropyrido[3,2-b][1,4]oxazepin-3-yl)-4H-1,2,4-triazole-3-carboxamide The racemate of 5-(2,3-dihydro-1H-inden-1-yl)-N—((S)-4-oxo-2,3,4,5-tetrahydropyrido[3,2-b][1,4]oxazepin-3-yl)-4H-1,2,4-triazole-3-carboxamide (10 mg) was separated by Prep-Chiral-HPLC with the following conditions: Column: CHIRALPAK IA, 2.12×15 cm, 5 μm; Mobile Phase A: Hex:DCM 4.5:1, Mobile Phase B: EtOH; Flow rate: 20 mL/min; Gradient: 50% B to 50% B over 17.5 min; 220/254 nm; RT1: 10.95 min; RT2: 15.02 min to afford the title compounds.

Example 102A (First eluting isomer): $^1$H NMR (400 MHz, Methanol-$d_4$) δ 8.14-8.13 (m, 1H), 7.57-7.55 (m, 1H), 7.33-7.31 (m, 1H), 7.31-7.10 (m, 3H), 7.09-7.07 (m, 1H), 5.04-4.91 (m, 1H), 4.69-4.61 (m, 2H), 4.47-4.42 (m, 1H), 3.18-3.15 (m, 1H), 3.07-3.03 (m, 1H), 2.65-2.63 (m, 1H), 2.44-2.39 (m, 1H). LC-MS (Method T): m/z=391.3 [M+H]$^+$, 1.133 min.

Example 102B (Second eluting isomer): $^1$H NMR (400 MHz, Methanol-$d_4$) δ 8.14-8.13 (m, 1H), 7.57-7.55 (m, 1H), 7.33-7.31 (m, 1H), 7.31-7.10 (m, 3H), 7.09-7.07 (m, 1H), 5.04-4.91 (m, 1H), 4.69-4.61 (m, 2H), 4.47-4.42 (m, 1H), 3.18-3.15 (m, 1H), 3.07-3.03 (m, 1H), 2.65-2.63 (m, 1H), 2.44-2.39 (m, 1H). LC-MS (Method T): m/z=391.3 [M+H]$^+$, 1.135 min.

Example 103A and 103B: (R)-5-benzyl-N-(7,9-difluoro-2-oxo-1,2,3,4-tetrahydrospiro[benzo[b]azepine-5,1'-cyclopropan]-3-yl)-4H-1,2,4-triazole-3-carboxamide and (S)-5-benzyl-N-(7,9-difluoro-2-oxo-1,2,3,4-tetrahydrospiro[benzo[b]azepine-5,1'-cyclopropan]-3-yl)-4H-1,2,4-triazole-3-carboxamide

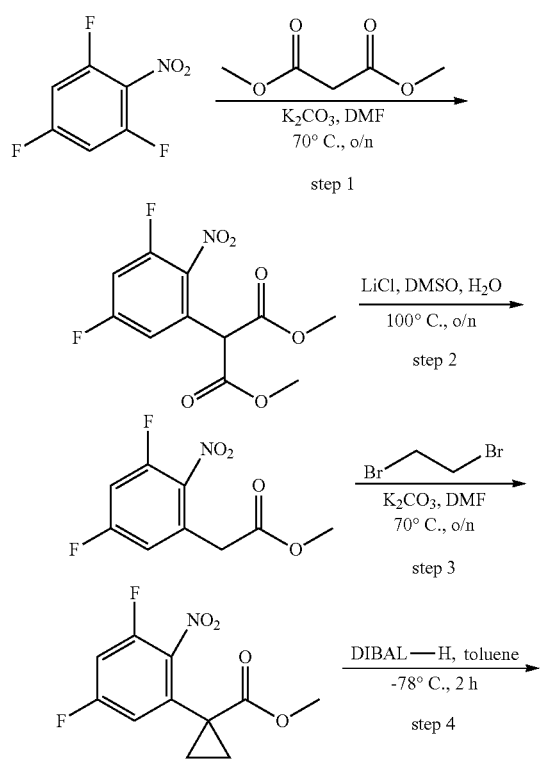

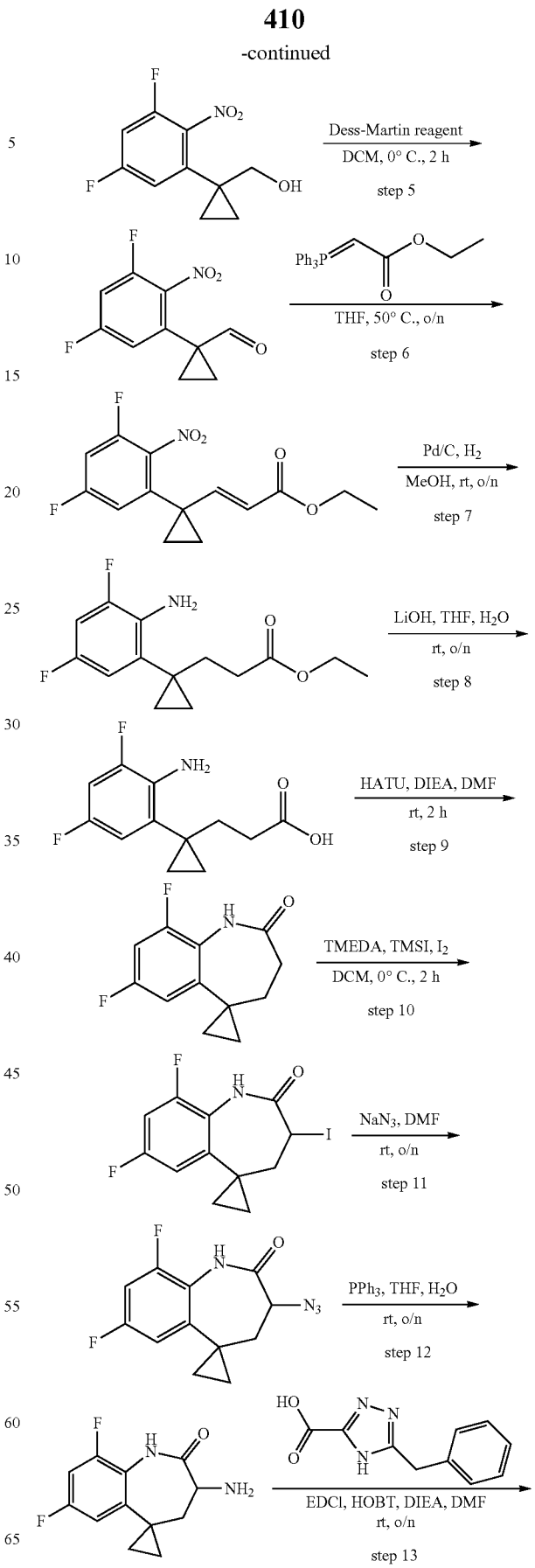

-continued

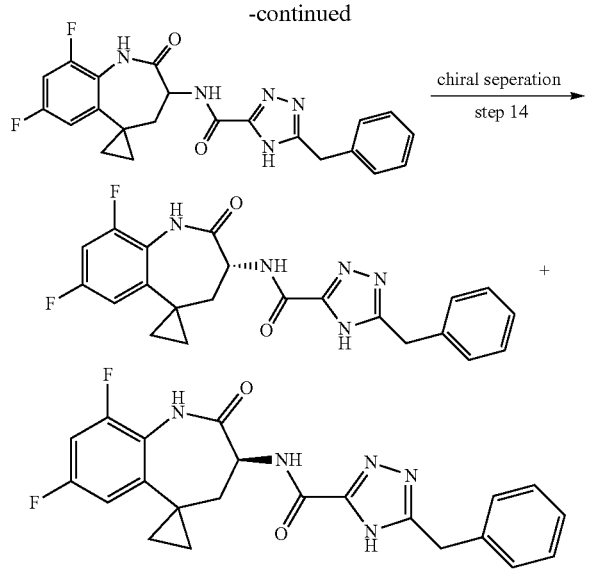

Step 1: Preparation of dimethyl 2-(3,5-difluoro-2-nitrophenyl)malonate

Dimethyl malonate (15 g, 114 mmol) was added dropwise to a stirring mixture of 1,3,5-trifluoro-2-nitrobenzene (10 g, 56 mmol) and potassium carbonate (23 g, 168 mmol) in N,N-dimethylformamide (150 mL). The reaction mixture was stirred overnight at 70° C. and quenched by the addition of water (50 mL). The resulting solution was extracted with ethyl acetate (3×100 mL). The combined organic layers were washed with brine, dried over anhydrous sodium sulfate, filtered and concentrated under vacuum. The residue was purified by column chromatography (ethyl acetate/petroleum ether, 1/8) to afford the title compound (15 g, 92%) as yellow oil. LC-MS (Method C): m/z=290.0 [M+H]$^+$, 1.235 min.

Step 2: Preparation of methyl 2-(3,5-difluoro-2-nitrophenyl)acetate

A solution of lithium chloride (6.3 g, 150 mmol) in water (20 mL) was added to a solution of dimethyl 2-(3,5-difluoro-2-nitrophenyl)malonate (15 g, 52 mmol) in dimethyl sulfoxide (50 mL). The reaction mixture was stirred overnight at 100° C. and quenched by the addition of water (250 mL). The resulting solution was extracted with ethyl acetate (3×150 mL). The combined organic layers were washed with brine, dried over anhydrous sodium sulfate, filtered and concentrated under vacuum to afford the title compound (11 g crude) as a yellow oil, which was used directly in the next step without further purification.

Step 3: Preparation of methyl 1-(3,5-difluoro-2-nitrophenyl)cyclopropanecarboxylate 1,2-Dibromoethane (13 g, 70 mmol) was added dropwise to a stirring solution of methyl 2-(3,5-difluoro-2-nitrophenyl)acetate (11 g, 48 mmol) and potassium carbonate (20 g, 145 mmol) in N,N-dimethylformamide (50 mL). The reaction mixture was stirred overnight at 70° C. and quenched by the addition of water (250 mL). The resulting solution was extracted with ethyl acetate (3×250 mL). The combined organic layers were washed with brine, dried over anhydrous sodium sulfate, filtered and concentrated under vacuum. The residue was purified by column chromatography (ethyl acetate/petroleum ether, 1/8) to afford the title compound (1.1 g, 9%) as a yellow oil. LC-MS (Method C): m/z=258.1 [M+H]$^+$, 1.291 min.

Step 4: Preparation of (1-(3,5-difluoro-2-nitrophenyl)cyclopropyl)methanol

A solution of diisobutylaluminium hydride in toluene (1 M, 9.4 mL, 9.4 mmol) was added dropwise to a stirring solution of methyl 1-(3,5-difluoro-2-nitrophenyl)cyclopropanecarboxylate (1.1 g, 4.3 mmol) in toluene (30 mL) at −78° C. under nitrogen atmosphere. The reaction mixture was stirred at −78° C. for 2 hours, quenched by the addition of water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/6) to afford the title compound (0.92 g, 94%) as a yellow oil. LC-MS (Method C): m/z=230.1 [M+H]$^+$, 1.192 min.

Step 5: Preparation of 1-(3,5-difluoro-2-nitrophenyl)cyclopropanecarbaldehyde

Dess-Martin periodinane (3.4 g, 8 mmol) was added to a stirring solution of (1-(3,5-difluoro-2-nitrophenyl)cyclopropyl)methanol (0.92 g, 4 mmol) in dichloromethane (30 mL). The reaction mixture was stirred at 0° C. for 2 hours, quenched by the addition of water (50 mL) and extracted with dichloromethane (3×50 mL). The combined organic layers were washed with brine, dried over sodium sulfate, filtered and concentrated under vacuum. The residue was purified by column chromatography (ethyl acetate/petroleum ether, 1/6) to afford the title compound (0.85 mg, 92%) as yellow oil.

Step 6: Preparation of (E)-ethyl 3-(1-(3,5-difluoro-2-nitrophenyl)cyclopropyl)acrylate Ethyl (triphenylphosphoranylidene) acetate (1.5 g, 4.3 mmol) was added to a stirring solution of 1-(3,5-difluoro-2-nitrophenyl)cyclopropanecarbaldehyde (800 mg, 3.5 mmol) in tetrahydrofuran (50 mL). The reaction mixture was stirred overnight at 50° C., quenched by the addition of water (100 mL) and extracted with dichloromethane (3×100 mL). The combined organic layers were washed with brine, dried over anhydrous sodium sulfate, filtered and concentrated under vacuum. The residue was purified by column chromatography (ethyl acetate/petroleum ether, 1/8) to afford the title compound (0.64 g, 61%) as a yellow oil. LC-MS (Method C): m/z=298.0 [M+H]$^+$, 1.382 min.

Step 7: Preparation of ethyl 3-(1-(2-amino-3,5-difluorophenyl)cyclopropyl)propanoate (E)-ethyl 3-(1-(3,5-difluoro-2-nitrophenyl)cyclopropyl)acrylate (640 mg, 2.2 mmol) in methanol (30 mL) was hydrogenated in presence of palladium on carbon (10%, 65 mg) under a hydrogen atmosphere (2-3 atm). After stirring overnight at room temperature under a hydrogen atmosphere, the reaction mixture was filtered through Celite. The filtrate was concentrated under vacuum to afford the title compound (400 mg crude) as a yellow oil. LC-MS (Method C): m/z=270.1 [M+H]$^+$, 1.361 min.

Step 8: Preparation of 3-(1-(2-amino-3,5-difluorophenyl)cyclopropyl)propanoic acid Lithium hydroxide (180 mg, 7.5 mmol) was added to a solution of ethyl 3-(1-(2-amino-3,5-difluorophenyl)cyclopropyl)propanoate (400 mg, 1.5 mmol) in tetrahydrofuran (30 mL) and water (10 mL). The reaction mixture was stirred at room temperature reduce overnight. After removal of tetrahydrofuran under reduced pressure, the resulting solution was adjusted to pH=7 with aqueous hydrochloric acid (1 N, 10 mL). The resulting solution was extracted with ethyl acetate (3×50 mL). The combined organic layers were washed with brine, dried over anhydrous sodium sulfate, and filtered. The filtrate was concentrated under vacuum to afford the title compound (320 mg crude) as a yellow oil. LC-MS (Method C): m/z=242.1 [M+H]$^+$, 1.143 min.

Step 9: Preparation of 7,9-difluoro-3,4-dihydrospiro[benzo[b]azepine-5,1'-cyclopropan]-2(1H)-one N,N-diisopropylethylamine (515 mg, 4.0 mmol) was added to a mixture of 3-(1-(2-amino-3,5-difluorophenyl)cyclopropyl)propanoic acid (320 mg, 1.3 mmol) and N,N,N',N'-tetramethyl-O-(7-azabenzotriazol-1-yl)uronium hexafluorophosphate (608 mg, 1.6 mmol) in N,N-dimethylformamide (10 mL). The reaction mixture was stirred at room temperature for 2 hours and quenched by the addition of water (50 mL). The resulting solution was extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/6) to afford the title compound (270 mg, 91%) as a yellow oil. LC-MS (Method C): m/z=224.1 [M+H]$^+$, 1.303 min.

Step 10: Preparation of 7,9-difluoro-3-iodo-3,4-dihydrospiro[benzo[b]azepine-5,1'-cyclopropan]-2(1H)-one N,N,N',N'-tetramethylethylenediamine (418 mg, 3.6 mmol) was added into a solution of 7,9-difluoro-3,4-dihydrospiro[benzo[b]azepine-5,1'-cyclopropan]-2(1H)-one (270 mg, 1.2 mmol) in dichloromethane (40 mL) at 0° C. followed by addition of iodotrimethylsilane (720 mg, 3.6 mmol) dropwise over 20 min. The mixture was stirred for 1 hour at 0° C. and then iodine (457 mg, 1.8 mmol) was added into the mixture. After stirring for an additional 1 hour at 0° C., the reaction mixture was quenched by the addition of aqueous sodium thio sulfate (5%, 20 mL) and extracted with ethyl acetate (3×50 mL). The combined organic layers were washed with brine, dried over anhydrous sodium sulfate, and filtered. The filtrate was concentrated under vacuum to afford the title compound (410 mg crude) as yellow oil. LC-MS (Method C): m/z=350.1 [M+H]$^+$, 1.262 min.

Step 11: Preparation of 3-azido-7,9-difluoro-3,4-dihydrospiro[benzo[b]azepine-5,1'-cyclopropan]-2(1H)-one Sodium azide (117 mg, 1.8 mmol) was added to a solution of 7,9-difluoro-3-iodo-3,4-dihydrospiro[benzo[b]azepine-5,1'-cyclopropan]-2(1H)-one (410 mg, 1.2 mmol) in N,N-dimethylformamide (20 mL). The resulting mixture was stirred overnight at room temperature and quenched by the addition of water (40 mL). The resulting solution was extracted with ethyl acetate (3×50 mL). The combined organic layers were washed with brine, dried over sodium sulfate, and filtered. The filtrate was concentrated under vacuum to afford the title compound (260 mg crude) as a yellow oil. LC-MS (Method E): m/z=265.1 [M+H]$^+$, 0.875 min.

Step 12: Preparation of 3-amino-7,9-difluoro-3,4-dihydrospiro[benzo[b]azepine-5,1'-cyclopropan]-2(1H)-one Triphenylphosphine (393 mg, 1.5 mmol) was added to a solution of 3-azido-7,9-difluoro-3,4-dihydrospiro[benzo[b]azepine-5,1'-cyclopropan]-2(1H)-one (260 mg, 1.0 mmol) in tetrahydrofuran (10 mL) and water (1 mL). The resulting mixture was stirred overnight at room temperature, diluted with water (20 mL) and extracted with dichloromethane (3×50 mL). The combined organic layers were washed with brine, dried over anhydrous sodium sulfate, filtered and concentrated under vacuum. The residue was purified by column chromatography (ethyl acetate/petroleum ether, 5/1) to afford the title compound (210 mg, 90%) as a yellow oil. LC-MS (Method C): m/z=239.1 [M+H]$^+$, 0.814 min.

Step 13: Preparation of 5-benzyl-N-(7,9-difluoro-2-oxo-1,2,3,4-tetrahydrospiro[benzo[b]azepine-5,1'-cyclopropan]-3-yl)-4H-1,2,4-triazole-3-carboxamide The crude product obtained using Amide Coupling Procedure C was purified by Prep-HPLC with the following conditions: Column: XBridge Prep C18 OBD Column 19×150 mm, 5 µm; Mobile Phase A: water (10 mmol/L NH$_4$HCO$_3$), Mobile Phase B: ACN; Flow rate: 30 mL/min; Gradient: 25% B to 55% B over 7 min; UV 254 & 220 nm to afford the title compound (30 mg, 26%) as a white solid. LC-MS (Method O): m/z=423.9 [M+H]$^+$, 1.204 min.

Step 14: Preparation of (R)-5-benzyl-N-(7,9-difluoro-2-oxo-1,2,3,4-tetrahydrospiro[benzo[b]azepine-5,1'-cyclopropan]-3-yl)-4H-1,2,4-triazole-3-carboxamide (Example 103A) and (S)-5-benzyl-N-(7,9-difluoro-2-oxo-1,2,3,4-tetrahydrospiro[benzo[b]azepine-5,1'-cyclopropan]-3-yl)-4H-1,2,4-triazole-3-carboxamide (Example 103B)

The racemate of 5-benzyl-N-(7,9-difluoro-2-oxo-1,2,3,4-tetrahydrospiro[benzo[b]azepine-5,1'-cyclopropan]-3-yl)-4H-1,2,4-triazole-3-carboxamide was separated by Prep-Chiral-HPLC with the following conditions: Column: Chiralpak IA, 2×25 cm, 5 µm; Mobile Phase A: hexanes, Mobile Phase B: EtOH; Flow rate: 16 mL/min; Gradient: 55% B to 55% B over 27 min; UV 220 & 254 nm; Rt1: 13.94 min; Rt2: 21.44 min to afford the two title compounds.

Example 103A (first eluting isomer): $^1$H NMR (400 MHz, Methanol-d$_4$) δ 7.33-7.26 (m, 5H), 7.10-6.99 (m, 2H), 4.72-4.62 (m, 1H), 4.17 (s, 2H), 3.08-2.99 (m, 1H), 1.63-1.57 (m, 1H), 1.25-1.18 (m, 1H), 1.07-1.01 (m, 1H), 0.85-0.77 (m, 1H), 0.59-0.52 (m, 1H). LC-MS (Method O): m/z=423.9 [M+H]$^+$, 1.204 min.

Example 103B (second eluting isomer): $^1$H NMR (400 MHz, Methanol-d$_4$) δ 7.36-7.23 (m, 5H), 7.07-6.98 (m, 2H), 4.73-4.64 (m, 1H), 4.23 (s, 2H), 3.07-2.96 (m, 1H), 1.68-1.53 (m, 1H), 1.25-1.18 (m, 1H), 1.06-0.99 (m, 1H), 0.84-0.77 (m, 1H), 0.59-0.52 (m, 1H). LC-MS (Method V): m/z=424.2 [M+H]$^+$, 2.031 min.

Example 104A and 104B: (R)-5-benzyl-N-(2-methyl-5-oxo-2,4,5,6,7,8-hexahydropyrazolo[4,3-b]azepin-6-yl)-4H-1,2,4-triazole-3-carboxamide and (S)-5-benzyl-N-(2-methyl-5-oxo-2,4,5,6,7,8-hexahydropyrazolo[4,3-b]azepin-6-yl)-4H-1,2,4-triazole-3-carboxamide

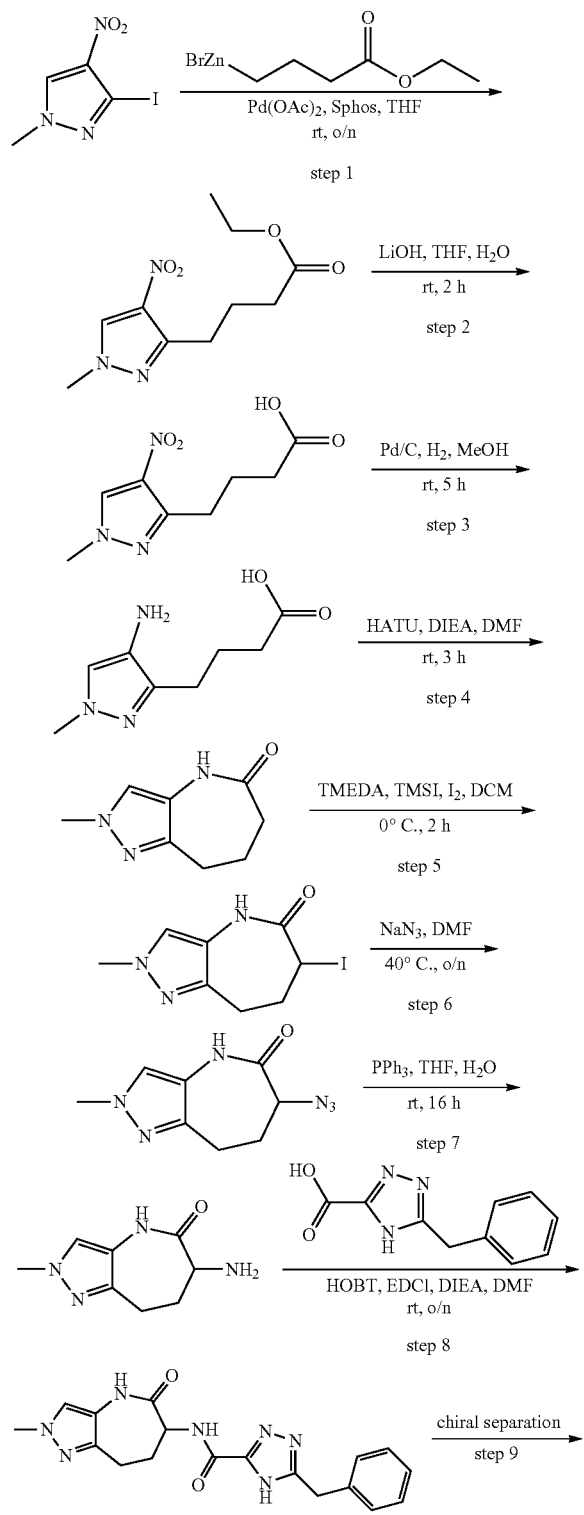

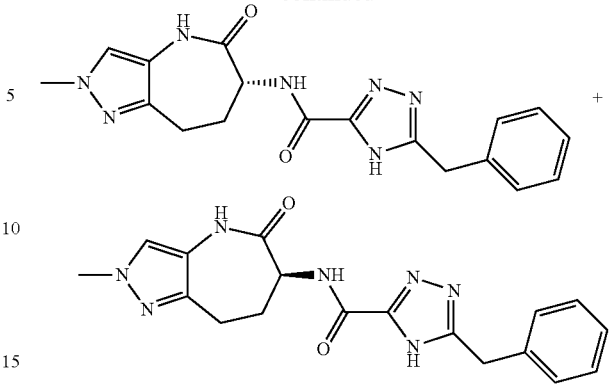

Step 1: Preparation of ethyl 4-(1-methyl-4-nitro-1H-pyrazol-3-yl)butanoate

A solution of (4-ethoxy-4-oxobutyl)zinc(II) bromide in tetrahydrofuran (0.5 M, 41.5 mL, 20.7 mmol) was added to a stirring mixture of 3-iodo-1-methyl-4-nitro-1H-pyrazole (4.32 g, 17.1 mmol) and dicyclohexyl(2',6'-dimethoxybiphenyl-2-yl)phosphine (864 mg, 2.1 mmol) in tetrahydrofuran (50 mL) under nitrogen atmosphere, followed by the addition of a mixture of palladium diacetate (432 mg, 1.9 mmol) in tetrahydrofuran dropwise. The resulting mixture was stirred overnight at room temperature and concentrated under high vacuum. The residue was purified by column chromatography (methanol/dichloromethane, 1/99) to afford the title compound (1.7 g, 41.3%) as a yellow oil. LC-MS (Method E): m/z=242.1 [M+H]$^+$, 0.852 min.

Step 2: Preparation of 4-(1-methyl-4-nitro-1H-pyrazol-3-yl)butanoic acid

Lithium hydroxide (339 mg, 14.1 mmol) was added to a mixture of ethyl 4-(1-methyl-4-nitro-1H-pyrazol-3-yl)butanoate (1.7 g, 7.05 mmol) in tetrahydrofuran (30 mL) and water (10 mL). The reaction mixture was stirred for 2 hours at room temperature. After removal of tetrahydrofuran under reduced pressure, the pH value of the solution was adjusted to 6-7 with aqueous hydrochloride acid (1 N, 20 mL). The resulting solution was extracted with ethyl acetate (3×50 mL). The combined organic layers were washed with brine, dried over anhydrous sodium sulfate, and filtered. The filtrate was concentrated under high vacuum to afford the title compound (1.2 g crude) as a yellow solid. LC-MS (Method E): m/z=213.9 [M+H]$^+$, 0.617 min.

Step 3: Preparation of 4-(4-amino-1-methyl-1H-pyrazol-3-yl)butanoic acid

A solution of 4-(1-methyl-4-nitro-1H-pyrazol-3-yl)butanoic acid (1.2 g, 5.61 mmol) in methanol (20 mL) was hydrogenated in the presence of palladium on carbon (10%, 120 mg) under a hydrogen atmosphere (2-3 atm). After stirring for 5 hours at room temperature under a hydrogen atmosphere, the reaction mixture was filtered through Celite. The filtrate was concentrated under vacuum to afford the title compound (1 g crude) as a yellow solid. LC-MS (Method C): m/z=184.1 [M+H]$^+$, 0.304 min.

Step 4: Preparation of 2-methyl-7,8-dihydropyrazolo[4,3-b]azepin-5(2H,4H,6H)-one N,N-diisopropylethylamine (2.2 g, 17.05 mmol) was added to a stirred mixture of 4-(4-amino-1-methyl-1H- pyrazol-3-yl)butanoic acid (1.0 g, 5.46 mmol) and N,N,N',N'-tetramethyl-O-(7-azabenzotriazol-1-yl)uronium hexafluorophosphate (2.5 g, 6.58 mmol) in N,N-dimethylformamide (20 mL). The reaction mixture was stirred for 3 hours at room temperature and diluted with water (50 mL). The resulting solution was extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (560 mg, 62.1%) as a yellow solid. LC-MS (Method C): m/z=166.2 [M+H]$^+$, 0.331 min.

Step 5: Preparation of 6-iodo-2-methyl-7,8-dihydropyrazolo[4,3-b]azepin-5(2H,4H,6H)-one $N^1,N^1,N^2,N^2$-tetramethylethane-1,2-diamine (1.01 g, 8.73 mmol) was added to a stirring mixture of 2-methyl-7,8-dihydropyrazolo[4,3-b]azepin-5(2H,4H,6H)-one (0.48 g, 2.91 mmol) in dichloromethane (30 mL) at 0° C. followed by adding iodotrimethylsilane (1.16 g, 5.82 mmol) dropwise over 20 min. The reaction mixture was stirred for 1 hour at 0° C. Iodine (1.11 g, 4.37 mmol) was added to the mixture. The reaction mixture was stirred for an additional 1 hour at 0° C. and quenched by the addition of aqueous sodium thiosulfate (5%, 20 mL). The resulting solution was stirred for 15 minutes and extracted with ethyl acetate (3×50 mL). The combined organic layers were washed with brine, dried over anhydrous sodium sulfate, and filtered. The filtrate was concentrated under vacuum to afford the title compound (550 mg crude) as a yellow solid. LC-MS (Method I): m/z=291.9 [M+H]$^+$, 0.522 min.

Step 6: Preparation of 6-azido-2-methyl-7,8-dihydropyrazolo[4,3-b]azepin-5(2H,4H,6H)-one Sodium azide (246 mg, 3.78 mmol) was added to a solution of 6-iodo-2-methyl-7,8-dihydropyrazolo[4,3-b]azepin-5(2H,4H, 6H)-one (550 mg, 1.89 mmol) in N,N-dimethylformamide (4 mL). The reaction mixture was stirred overnight at 40° C., diluted with water (50 mL) and extracted with ethyl acetate (3×50 mL). The combined organic layers were washed with brine, dried over anhydrous sodium sulfate, filtered and concentrated under reduced pressure to afford the title compound (480 mg crude) as a brown solid, which was used directly in the next step without further purification. LC-MS (Method I): m/z=207.0 [M+H]$^+$, 0.481 min.

Step 7: Preparation of 6-amino-2-methyl-7,8-dihydropyrazolo[4,3-b]azepin-5(2H,4H,6H)-one Triphenylphosphine (1.5 g, 7.28 mmol) was added to a solution of 6-azido-2-methyl-7,8-dihydropyrazolo[4,3-b]azepin-5(2H,4H,6H)-one (0.48 g, 2.18 mmol) in tetrahydrofuran (10 mL) and water (1 mL). The resulting mixture was stirred for 16 hours at room temperature, diluted with water (50 mL) and extracted with dichloromethane (3×50 mL). The combined organic layers were washed with brine, dried over anhydrous sodium sulfate, filtered and concentrated under vacuum. The residue was purified by column chromatography (methanol/dichloromethane, 3/97) to afford the title compound (300 mg, 70.9%) as a yellow oil. LC-MS (Method R): m/z=181.3 [M+H]$^+$, 0.655 min.

Step 8: Preparation of 5-benzyl-N-(2-methyl-5-oxo-2,4,5,6,7,8-hexahydropyrazolo[4,3-b]azepin-6-yl)-4H-1,2,4-triazole-3-carboxamide The crude product obtained using Amide Coupling Procedure C was purified by Prep-HPLC with the following conditions: Column: XSelect CSH Prep C18 OBD Column, 5 μm, 19×150 mm; Mobile Phase A: water (0.05% TFA), Mobile Phase B: ACN; Flow rate: 20 mL/min; Gradient: 5% B to 47% B over 7 min; UV 254 & 220 nm; Rt: 6.22 min to afford the title compound (50 mg, 26.8%) as a white solid. LC-MS (Method Y): m/z=366.0 [M+H]$^+$, 0.779 min.

Step 9: Preparation of (R)-5-benzyl-N-(2-methyl-5-oxo-2,4,5,6,7,8-hexahydropyrazolo[4,3-b]azepin-6-yl)-4H-1,2,4-triazole-3-carboxamide (Example 104A) and (S)-5-benzyl-N-(2-methyl-5-oxo-2,4,5,6,7,8-hexahydropyrazolo[4,3-b]azepin-6-yl)-4H-1,2,4-triazole-3-carboxamide (Example 104B)

The racemate of 5-benzyl-N-(2-methyl-5-oxo-2,4,5,6,7,8-hexahydropyrazolo[4,3-b]azepin-6-yl)-4H-1,2,4-triazole-3-carboxamide (50 mg, 0.13 mmol) was separated by Prep-Chiral-HPLC with the following conditions: Column: CHIRAL ART Cellulose-SB, 2×25 cm, 5 μm; Mobile Phase A: hexane, Mobile Phase B: i-PrOH; Flow rate: 20 mL/min; Gradient: 50% B to 50% B over 21 min; UV 254 & 220 nm; Rt1: 9.68 min; Rt2: 14.84 min to afford the title compounds:

Example 104A (first eluting isomer): $^1$H NMR (400 MHz, DMSO-d$_6$) δ 14.37 (br. s, 1H), 9.86 (s, 1H), 8.39 (br. s, 1H), 7.40 (s, 1H), 7.34-7.22 (m, 5H), 4.40-4.35 (m, 1H), 4.11 (s, 2H), 3.74 (s, 3H), 2.90-2.81 (m, 2H), 2.26-2.20 (m, 1H), 2.11-1.97 (m, 1H). LC-MS (Method X): m/z=366.2 [M+H]$^+$, 2.165 min.

Example 104B (second eluting isomer): $^1$H NMR (400 MHz, DMSO-d$_6$) δ 14.37 (br. s, 1H), 9.86 (s, 1H), 8.39 (br. s, 1H), 7.40 (s, 1H), 7.34-7.22 (m, 5H), 4.40-4.35 (m, 1H), 4.11 (s, 2H), 3.74 (s, 3H), 2.89-2.84 (m, 2H), 2.25-2.21 (m, 1H), 2.11-1.97 (m, 1H). LC-MS (Method T): m/z=366.3 [M+H]$^+$, 0.858 min.

Example 105A and 105B: (S)-5-benzyl-N-(2,4-dimethyl-5-oxo-2,4,5,6,7,8-hexahydropyrazolo[4,3-b]azepin-6-yl)-4H-1,2,4-triazole-3-carboxamide and (R)-5-benzyl-N-(2,4-dimethyl-5-oxo-2,4,5,6,7,8-hexahydropyrazolo[4,3-b]azepin-6-yl)-4H-1,2,4-triazole-3-carboxamide

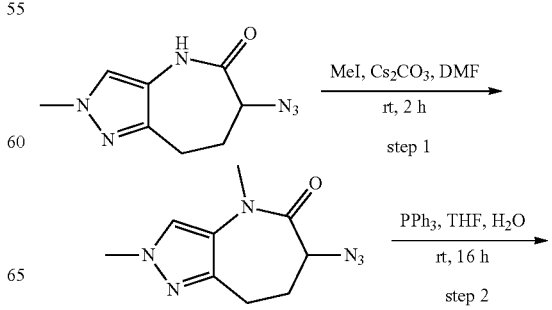

Step 1: Preparation of 6-azido-2,4-dimethyl-7,8-dihydropyrazolo[4,3-b]azepin-5(2H,4H,6H)-one

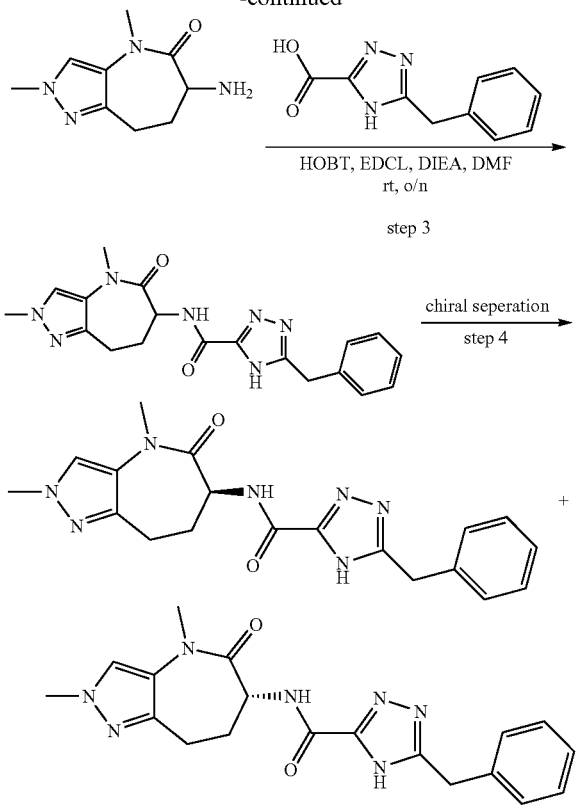

Iodomethane (664 mg, 4.68 mmol) was added dropwise to a stirred mixture of 6-azido-2-methyl-7,8-dihydropyrazolo[4,3-b]azepin-5(2H,4H,6H)-one (480 mg, 2.33 mmol) and cesium carbonate (1.5 g, 4.66 mmol) in N,N-dimethylformamide (10 mL). The reaction mixture was stirred for 2 hours at room temperature and quenched by the addition of water (50 mL). The resulting solution was extracted with ethyl acetate (3×50 mL). The combined organic phases were washed with brine, dried over anhydrous sodium sulfate, and filtered. The filtrate was concentrated under vacuum to afford the title compound (480 mg crude) as a brown solid. LC-MS (Method I): m/z=221.0 [M+H]$^+$, 0.565 min.

Step 2: Preparation of 6-amino-2,4-dimethyl-7,8-dihydropyrazolo[4,3-b]azepin-5(2H,4H,6H)-one Triphenylphosphine (2.44 g, 9.31 mmol) was added to a solution of 6-azido-2,4-dimethyl-7,8-dihydropyrazolo[4,3-b]azepin-5(2H,4H,6H)-one (480 mg, 2.18 mmol) in tetrahydrofuran (10 mL) and water (1 mL). The resulting mixture was stirred for 16 hours at room temperature, diluted with water (50 mL) and extracted with dichloromethane (3×50 mL). The combined organic layers were washed with brine, dried over anhydrous sodium sulfate, filtered and concentrated to dryness under vacuum. The residue was purified by column chromatography (methanol/dichloromethane, 3/97) to afford the title compound (300 mg, 71%) as a yellow oil. LC-MS (Method I): m/z=195.0 [M+H]$^+$, 0.168 min.

Step 3: Preparation of 5-benzyl-N-(2,4-dimethyl-5-oxo-2,4,5,6,7,8-hexahydropyrazolo[4,3-b]azepin-6-yl)-4H-1,2,4-triazole-3-carboxamide The crude product obtained using Amide Coupling Procedure C was purified by Prep-HPLC with the following conditions: Column: XBridge C18 OBD Prep Column, 100 Å, 5 μm, 19 mm×250 mm; Mobile Phase A: water (0.1% formic acid), Mobile Phase B: ACN; Flow rate: 20 mL/min; Gradient: 15% B to 30% B over 10 min; UV 254 & 220 nm; Rt: 7 min to afford the title compound (50 mg, 26.8%) as a white solid. LC-MS (Method Q): m/z=380.4 [M+H]$^+$, 0.786 min.

Step 4: Preparation of (S)-5-benzyl-N-(2,4-dimethyl-5-oxo-2,4,5,6,7,8-hexahydropyrazolo[4,3-b]azepin-6-yl)-4H-1,2,4-triazole-3-carboxamide (Example 105A) and (R)-5-benzyl-N-(2,4-dimethyl-5-oxo-2,4,5,6,7,8-hexahydropyrazolo[4,3-b]azepin-6-yl)-4H-1,2,4-triazole-3-carboxamide (Example 105B)

The racemate of 5-benzyl-N-(2,4-dimethyl-5-oxo-2,4,5,6,7,8-hexahydropyrazolo[4,3-b]azepin-6-yl)-4H-1,2,4-triazole-3-carboxamide (50 mg, 0.13 mmol) was separated by Prep-Chiral-HPLC with the following conditions: Column: CHIRALPAK IC, 2×25 cm, 5 μm; Mobile Phase A: hexane:DCM=4.5:1, Mobile Phase B: EtOH; Flow rate: 16 mL/min; Gradient: 50% B to 50% B over 21 min; UV 220 & 254 nm; Rt1: 8.88 min; Rt2: 16.76 min to afford the title compounds:

Example 105A (first eluting isomer): $^1$H NMR (400 MHz, DMSO-d$_6$) δ 14.35 (br. s, 1H), 8.32 (br. s, 1H), 7.83 (s, 1H), 7.34-7.22 (m, 5H), 4.53-4.45 (m, 1H), 4.11 (s, 2H), 3.79 (s, 3H), 3.19 (s, 3H), 2.85-2.66 (m, 2H), 2.35-2.31 (m, 1H), 2.30-2.26 (m, 1H). LC-MS (Method T): m/z=380.2 [M+H]$^+$, 0.958 min.

Example 105B (second eluting isomer): $^1$H NMR (400 MHz, DMSO-d$_6$) δ 14.29 (br. s, 1H), 8.30 (br. s, 1H), 7.83 (s, 1H), 7.34-7.22 (m, 5H), 4.52-4.46 (m, 1H), 4.11 (s, 2H), 3.79 (s, 3H), 3.19 (s, 3H), 2.85-2.68 (m, 2H), 2.35-2.31 (m, 1H), 2.30-2.27 (m, 1H). LC-MS (Method T): m/z=380.2 [M+H]$^+$, 0.953 min.

Example 106: (S)—N-(5-methyl-4-oxo-2,3,4,5-tetrahydropyrido[3,2-b][1,4]oxazepin-3-yl)-5-(1-phenylcyclopropyl)-4H-1,2,4-triazole-3-carboxamide

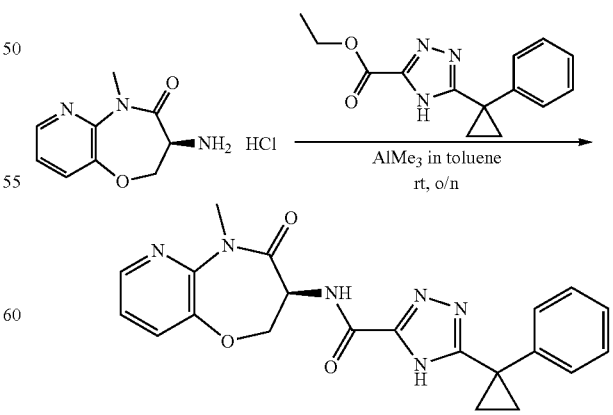

The crude product obtained using the procedure described in Example 54 was purified by Prep-HPLC with the following conditions: Column: XSelect CSH Prep C18 OBD Column, 5 μm, 19×150 mm; Mobile Phase A: water (0.1% formic acid); Mobile Phase B: ACN; Flow rate: 20 mL/min; Gradient: 30% B to 60% B over 7 min; Detector, UV 254 & 220 nm; Rt: 5.47 min to afford the title compound. $^1$H NMR (400 MHz, DMSO-$d_6$) δ 14.11 (s, 1H), 8.49 (d, J=7.9 Hz, 1H), 8.37 (dd, J=4.8, 1.5 Hz, 1H), 7.71 (dd, J=8.0, 1.5 Hz, 1H), 7.40-7.22 (m, 6H), 4.92-4.66 (m, 2H), 4.56-4.55 (m, 1H), 3.36 (s, 3H), 1.52-1.27 (m, 4H). LC-MS (Method O): m/z=405.0 [M+H]$^+$, 1.126 min.

Example 107A and 107B: (R)-5-benzyl-N-(9-methyl-8-oxo-6,7,8,9-tetrahydro-5H-pyrido[2,3-b]azepin-7-yl)-4H-1,2,4-triazole-3-carboxamide and (S)-5-benzyl-N-(9-methyl-8-oxo-6,7,8,9-tetrahydro-5H-pyrido[2,3-b]azepin-7-yl)-4H-1,2,4-triazole-3-carboxamide

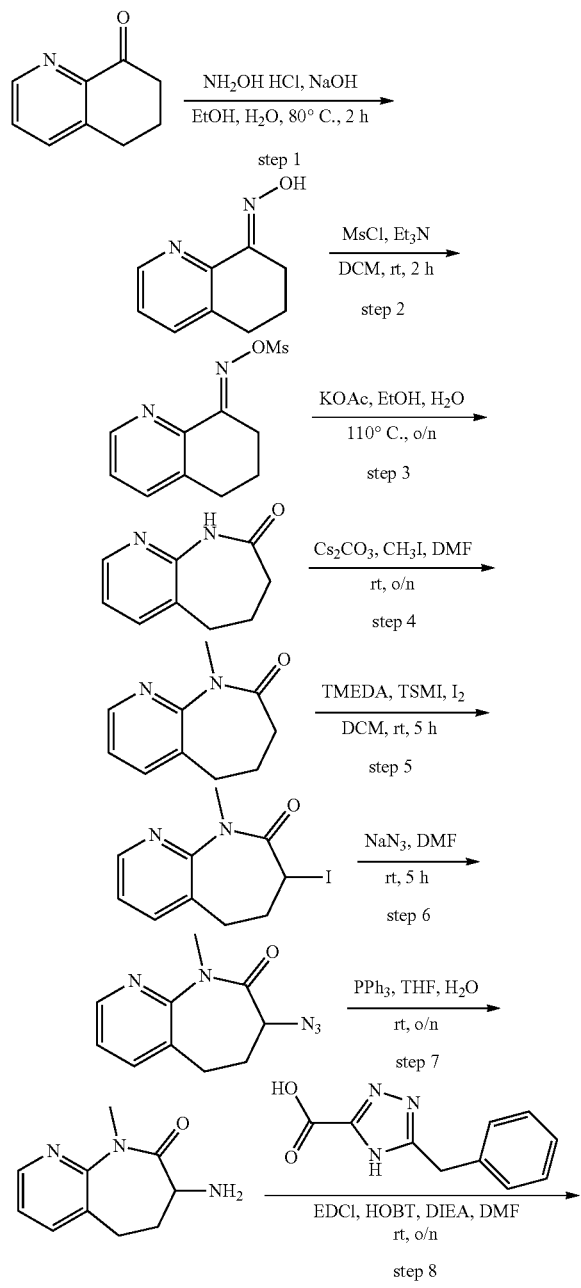

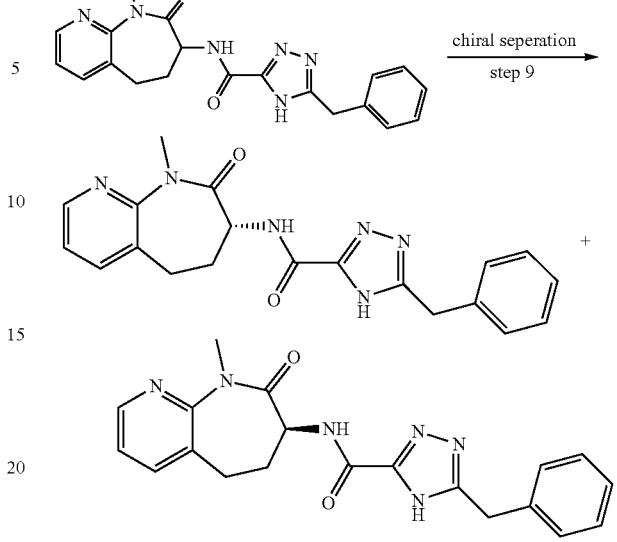

Step 1: Preparation of (E)-6,7-dihydroquinolin-8(5H)-one oxime

Hydroxylamine hydrochloride (1.4 g, 20.3 mmol) was added to a solution of 6,7-dihydroquinolin-8(5H)-one (1.5 g, 10.2 mmol) and sodium hydroxide (1.2 g, 30.0 mmol) in ethanol (20 mL) and water (10 mL). The resulting mixture was stirred at 80° C. for 2 hours. The reaction mixture was diluted with water (50 mL) and extracted with dichloromethane (3×80 mL). The combined organic layers were washed with brine, dried over anhydrous sodium sulfate, filtered and concentrated under vacuum. The residue was purified by column chromatography (ethyl acetate/petroleum ether, 1/20) to afford the title compound (1.4 g, 86.4%) as a white solid. LC-MS (Method E): m/z=163.1 [M+H]$^+$, 0.362 min.

Step 2: Preparation of (E)-6,7-dihydroquinolin-8(5H)-one O-methylsulfonyl oxime Triethylamine (3.5 g, 30.6 mmol) and methanesulfonyl chloride (0.74 g, 6.4 mmol) were added to a solution of (E)-6,7-dihydroquinolin-8(5H)-one oxime (1.4 g, 8.64 mmol) in dichloromethane (20 mL). The reaction mixture was stirred at room temperature for 2 hours, diluted with water (30 mL) and extracted with ethyl acetate (3×50 mL). The combined organic layers were washed with brine, dried with anhydrous sodium sulfate and concentrated under vacuum. The residue was purified by column chromatography (ethyl acetate/petroleum ether, 1/5) to afford the title compound (1.7 g, 82%) as a yellow solid. LC-MS (Method C): m/z=241.0 [M+H]$^+$, 0.810 min.

Step 3: Preparation of 6,7-dihydro-5H-pyrido[2,3-b]azepin-8(9H)-one

Potassium acetate (5 g, 51 mmol) was added to a solution of (E)-6,7-dihydroquinolin-8(5H)-one O-methylsulfonyl oxime (1.7 g, 7 mmol) in ethanol (40 mL) and water (20 mL). The reaction mixture was stirred overnight at 110° C. and concentrated under reduced pressure. The residue was diluted with water (30 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/5) to afford the title compound (1.0 g, 87%) as a yellow solid. LC-MS (Method C): m/z=162.8 [M+H]+, 0.612 min.

Step 4: Preparation of 9-methyl-6,7-dihydro-5H-pyrido[2,3-b]azepin-8(9H)-one

Iodomethane (1.0 g, 0.70 mmol) was added dropwise to a stirring mixture of 6,7-dihydro-5H-pyrido[2,3-b]azepin-8(9H)-one (1.0 g, 0.60 mmol) and cesium carbonate (3.0 g, 0.92 mmol) in N,N-dimethylformamide (20 mL). The reaction mixture was stirred at room temperature overnight, quenched by the addition of water (50 mL) and extracted with ethyl acetate (3×60 mL). The combined organic layers were washed with brine, dried over anhydrous sodium sulfate, filtered and concentrated under vacuum. The residue was purified by column chromatography (ethyl acetate/petroleum ether, 1/30) to afford the title compound (0.97 g, 89.8%) as a yellow solid. LC-MS (Method C): m/z=177.1 [M+H]+, 1.192 min.

Step 5: Preparation of 7-iodo-9-methyl-6,7-dihydro-5H-pyrido[2,3-b]azepin-8(9H)-one $N^1,N^1,N^2,N^2$-tetramethylethane-1,2-diamine (1.9 g, 16.4 mmol) was added to a stirring mixture of 9-methyl-6,7-dihydro-5H-pyrido[2,3-b]azepin-8(9H)-one (0.97 g, 5.5 mmol) in dichloromethane (100 mL) at 0° C. followed by the addition of iodotrimethylsilane (3.3 g, 16.5 mmol) over 20 minutes. The reaction mixture was stirred for 1 hour at 0° C. After adding iodine (4.2 g, 16.5 mmol), the reaction mixture was stirred for an additional 4 hours at room temperature before quenching by the addition of aqueous sodium thiosulfate (5%, 30 mL). The resulting solution was stirred for 15 minutes and extracted with ethyl acetate (3×100 mL). The combined organic phases were washed with brine, dried over anhydrous sodium sulfate, filtered and concentrated under vacuum. The residue was purified by column chromatography (ethyl acetate/petroleum ether, 1/30) to afford the title compound (1.5 g, 89.8%) as a white solid. LC-MS (Method C): m/z=303.0 [M+H]+, 1.350 min.

Step 6: Preparation of 7-azido-9-methyl-6,7-dihydro-5H-pyrido[2,3-b]azepin-8(9H)-one Sodium azide (650 mg, 10.0 mmol) was added to a solution of 7-iodo-9-methyl-6,7-dihydro-5H-pyrido[2,3-b]azepin-8(9H)-one (1.5 g, 4.9 mmol) in N,N-dimethylformamide (10 mL). The reaction mixture was stirred for 5 hours at room temperature, diluted with water (30 mL) and extracted with ethyl acetate (3×30 mL). The combined organic layers were washed with brine, dried over anhydrous sodium sulfate, filtered and concentrated under vacuum. The residue was purified by column chromatography (methanol/dichloromethane, 1/10) to afford the title compound (900 mg, 84%) as a white solid. LC-MS (Method C): m/z=218.2 [M+H]+, 0.586 min.

Step 7: Preparation of 7-amino-6,7-dihydro-5H-pyrido[2,3-b]azepin-8(9H)-one

Triphenylphosphine (1.6 g, 6.1 mmol) was added to a solution of 7-azido-9-methyl-6,7-dihydro-5H-pyrido[2,3-b]azepin-8(9H)-one (0.9 g, 4.1 mmol) in tetrahydrofuran (10 mL) and water (10 mL). The reaction mixture was stirred at room temperature overnight, diluted with water (30 mL) and extracted with ethyl acetate (3×50 mL). The combined organic layers were washed with brine, dried over anhydrous sodium sulfate, filtered and concentrated under vacuum. The residue was purified by column chromatography (methanol/dichloromethane, 1/10) to afford the title compound (0.65 g, 82%) as a white solid. LC-MS (Method C): m/z=192.1 [M+H]+, 0.386 min.

Step 8: Preparation of 5-benzyl-N-(9-methyl-8-oxo-6,7,8,9-tetrahydro-5H-pyrido[2,3-b]azepin-7-yl)-4H-1,2,4-triazole-3-carboxamide N,N-diisopropylethylamine (201.2 mg, 1.56 mmol) was added to a mixture of 5-benzyl-4H-1,2,4-triazole-3-carboxylic acid (104.6 mg, 0.52 mmol), 7-amino-9-methyl-6,7-dihydro-5H-pyrido[2,3-b]azepin-8(9H)-one (100 mg, 0.52 mmol), N-(3-dimethylaminopropyl))-N'-ethylcarbodiimide hydrochloride (119.6 mg, 0.62 mmol) and 1-hydroxybenzotriazole (84.2 mg, 0.62 mmol) in N,N-dimethylformamide (4 mL). The reaction mixture was stirred overnight at room temperature, diluted with water (30 mL) and extracted with ethyl acetate (3×50 mL). The combined organic layers were washed with brine, dried over anhydrous sodium sulfate, filtered and concentrated under vacuum. The residue was purified by Prep-HPLC with the following conditions: Column: XBridge Shield RP18 OBD Column, 5 μm, 19×150 mm; Mobile Phase A: water (10 mmol/L $NH_4HCO_3$), Mobile Phase B: ACN; Flow rate: 20 mL/min; Gradient: 10% B to 35% B over 11 min; UV 254 & 220 nm; Rt: 10 min to afford the title compound (50 mg, 25%) as a white solid. LC-MS (Method D): m/z=377.2 [M+H]+, 1.551 min.

Step 9: Preparation of (R)-5-benzyl-N-(9-methyl-8-oxo-6,7,8,9-tetrahydro-5H-pyrido[2,3-b]azepin-7-yl)-4H-1,2,4-triazole-3-carboxamide (Example 107A) and (S)-5-benzyl-N-(9-methyl-8-oxo-6,7,8,9-tetrahydro-5H-pyrido[2,3-b]azepin-7-yl)-4H-1,2,4-triazole-3-carboxamide (Example 107B)

The racemate of 5-benzyl-N-(9-methyl-8-oxo-6,7,8,9-tetrahydro-5H-pyrido[2,3-b]azepin-7-yl)-4H-1,2,4-triazole-3-carboxamide (50 mg, 0.14 mmol) was separated by Prep-Chiral-HPLC with the following conditions: Column: Chiralpak ID-2, 2×25 cm, 5 μm; Mobile Phase A: hexane, Mobile Phase B: MeOH:EtOH=1:1; Flow rate: 17 mL/min; Gradient: 60% B to 60% B over 23 min; UV 220 & 254 nm; Rt1: 8.53 min; Rt2: 18.27 min to afford the title compounds:

Example 107A (first eluting isomer): $^1$H NMR (300 MHz, DMSO-$d_6$) δ 14.35 (br. s, 1H), 8.52-8.42 (m, 2H), 7.82-7.79 (m, 1H), 7.34-7.21 (m, 6H), 4.35-4.26 (m, 1H), 4.10 (s, 2H), 3.34 (s, 3H), 2.75-2.62 (m, 2H), 2.41-2.16 (m, 2H). LC-MS (Method D): m/z=377.2 [M+H]+, 1.551 min.

Example 107B (second eluting isomer): $^1$H NMR (300 MHz, DMSO-$d_6$) δ 14.35 (br. s, 1H), 8.45-8.41 (m, 2H), 7.83-7.79 (m, 1H), 7.35-7.15 (m, 6H), 4.35-4.23 (m, 1H), 4.10 (s, 2H), 3.34 (s, 3H), 2.75-2.61 (m, 2H), 2.50-2.20 (m, 2H). LC-MS (Method D): m/z=377.2 [M+H]+, 1.546 min.

Example 108: (S)-2-benzyl-N-(5-methyl-4-oxo-2,3,4,5-tetrahydropyrido[3,2-b][1,4]oxazepin-3-yl)-1H-imidazole-5-carboxamide

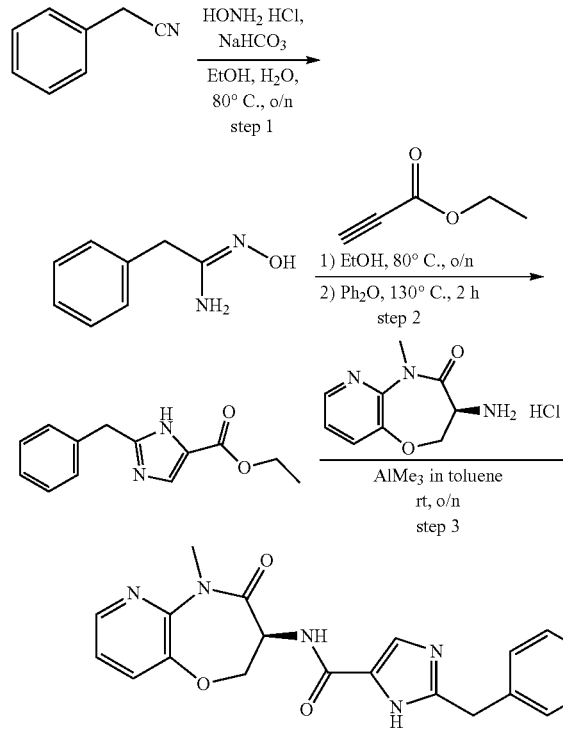

Step 1: Preparation of (Z)—N'-hydroxy-2-phenylacetimidamide

Sodium bicarbonate (1.44 g, 17.1 mmol) was added to a mixture of 2-phenylacetonitrile (1.0 g, 8.54 mmol) and hydroxylamine hydrochloride (1.19 g, 17.1 mmol) in ethanol (15 mL) and water (5.0 mL). The reaction mixture was stirred at 80° C. overnight, diluted with water (50 mL) and extracted with ethyl acetate (3×50 mL). The combined organic layers were washed with brine, dried over anhydrous sodium sulfate and concentrated under vacuum. The residue was purified by column chromatography (methanol/dichloromethane, 5/95) to afford the title compound (1.15 g, 90%) as a white solid. MS (Method I): m/z=151.1 [M+H]$^+$, 0.194 min.

Step 2: Preparation of ethyl 2-benzyl-1H-imidazole-5-carboxylate

A reaction mixture of (Z)—N'-hydroxy-2-phenylacetimidamide (1.0 g, 6.67 mmol) and ethyl propiolate (1.96 g, 20 mmol) in ethanol (20 mL) was stirred at 80° C. overnight. Diphenylether (50 mL) was added to the mixture and stirred at 130° C. for 2 hours. The reaction mixture was quenched by the addition of water (50 mL) and extracted with ethyl acetate (3×50 mL). The combined organic layers were washed with brine, dried over anhydrous sodium sulfate, filtered and concentrated under vacuum. The residue was purified by column chromatography (methanol/dichloromethane, 1/99) to afford the title compound (650 mg, 43%) as a gray solid. LC-MS (Method L): m/z=231.1 [M+H]$^+$, 1.197 min.

Step 3: Preparation of (S)-2-benzyl-N-(5-methyl-4-oxo-2,3,4,5-tetrahydropyrido[3,2-b][1,4]oxazepin-3-yl)-1H-imidazole-5-carboxamide The crude product obtained using the procedure described in Example 54 was purified by Prep-HPLC with the following conditions: Column: XBridge Shield RP18 OBD Column, 5 µm, 19×150 mm; Mobile Phase A: water (10 mmol/L NH$_4$HCO$_3$), Mobile Phase B: ACN; Flow rate: 20 mL/min; Gradient: 20% B to 45% B over 7 min; UV 254 & 220 nm; Rt: 6 min to afford the title compound. $^1$H NMR (400 MHz, DMSO-d$_6$) δ 12.41 (s, 1H), 8.36 (dd, J=4.8, 1.6 Hz, 1H), 8.01 (d, J=8.0 Hz, 1H), 7.71 (dd, J=8.0, 1.6 Hz, 1H), 7.57 (d, J=2.1 Hz, 1H), 7.38-7.17 (m, 6H), 4.90-4.76 (m, 1H), 4.64 (dd, J=11.5, 9.8 Hz, 1H), 4.54-4.45 (m, 1H), 4.02 (s, 2H), 3.36 (s, 3H). LC-MS (Method O): m/z=378.0 [M+H]$^+$, 1.047 min.

Example 109A and 109B: (S)-1-benzyl-N-(2,4-dimethyl-5-oxo-2,4,5,6,7,8-hexahydropyrazolo[4,3-b]azepin-6-yl)-4-fluoro-1H-pyrazole-3-carboxamide and (R)-1-benzyl-N-(2,4-dimethyl-5-oxo-2,4,5,6,7,8-hexahydropyrazolo[4,3-b]azepin-6-yl)-4-fluoro-1H-pyrazole-3-carboxamide

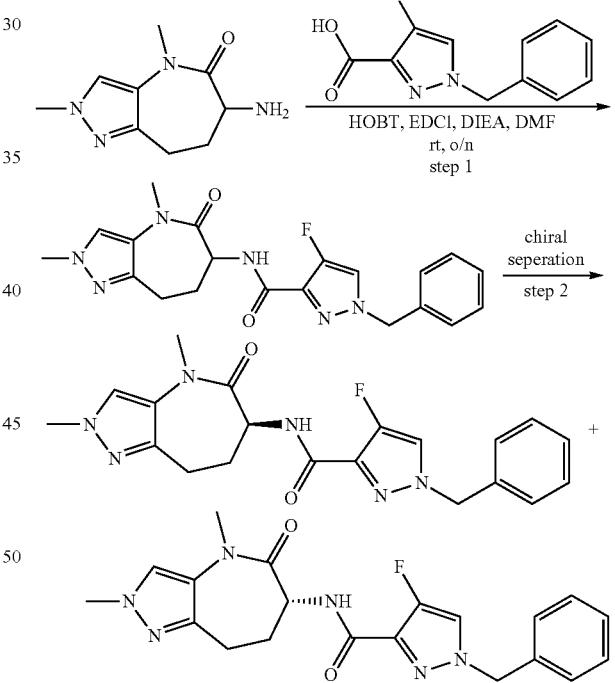

Step 1: Preparation of 1-benzyl-N-(2,4-dimethyl-5-oxo-2,4,5,6,7,8-hexahydropyrazolo[4,3-b]azepin-6-yl)-4-fluoro-1H-pyrazole-3-carboxamide The crude product obtained using Amide Coupling Procedure C was purified by Prep-HPLC with the following conditions: Column: XBridge Shield RP18 OBD Column, 5 µm, 19×150 mm; Mobile Phase A: water (10 mmol/L NH$_4$HCO$_3$), Mobile Phase B: ACN; Flow rate: 20 mL/min; Gradient: 20% B to 50% B over 7 min; UV 254 & 220 nm;

Rt: 6 min to afford the title compound (80 mg, 55.6%) as a white solid. LC-MS (Method Q): m/z=397.4 [M+H]⁺, 1.115 min.

Step 2: Preparation of (S)-1-benzyl-N-(2,4-dimethyl-5-oxo-2,4,5,6,7,8-hexahydropyrazolo[4,3-b]azepin-6-yl)-4-fluoro-1H-pyrazole-3-carboxamide (Example 109A) and (R)-1-benzyl-N-(2,4-dimethyl-5-oxo-2,4,5,6,7,8-hexahydropyrazolo[4,3-b]azepin-6-yl)-4-fluoro-1H-pyrazole-3-carboxamide (Example 109B)

The racemate of 1-benzyl-N-(2,4-dimethyl-5-oxo-2,4,5,6,7,8-hexahydropyrazolo[4,3-b]azepin-6-yl)-4-fluoro-1H-pyrazole-3-carboxamide (80 mg, 0.20 mmol) was separated by Prep-Chiral-HPLC with the following conditions: Column: Lux 5u Cellulose-3, AXIA Packed, 2.12×25 cm, 5 μm; Mobile Phase A: hexane, Mobile Phase B: EtOH; Flow rate: 20 mL/min; Gradient: 40% B to 40% B over 15 min; UV 254 & 220 nm; Rt1: 9.89 min; Rt2: 12.58 min to afford the title compounds:

Example 109A (first eluting isomer): ¹H NMR (400 MHz, DMSO-d₆) δ 8.13 (d, J=4.4 Hz, 1H), 7.92 (d, J=7.2 Hz, 1H), 7.83 (s, 1H), 7.40-7.31 (m, 3H), 7.31-7.28 (m, 2H), 5.33 (s, 2H), 4.50-4.44 (m, 1H), 3.78 (s, 3H), 3.18 (s, 3H), 2.84-2.77 (m, 1H), 2.75-2.67 (m, 1H), 2.33-2.24 (m, 1H), 2.16-2.04 (m, 1H). LC-MS (Method T): m/z=397.2 [M+H]⁺, 1.155 min.

Example 109B (second eluting isomer): ¹H NMR (400 MHz, DMSO-d₆) δ 8.13 (d, J=4.4 Hz, 1H), 7.93 (d, J=7.2 Hz, 1H), 7.83 (s, 1H), 7.40-7.31 (m, 3H), 7.31-7.26 (m, 2H), 5.33 (s, 2H), 4.51-4.42 (m, 1H), 3.78 (s, 3H), 3.18 (s, 3H), 2.87-2.63 (m, 2H), 2.35-2.21 (m, 1H), 2.18-2.03 (m, 1H). LC-MS (Method T): m/z=397.2 [M+H]⁺, 1.154 min.

Example 110A and 110B: 5-benzyl-N-((1aR,2R,8bS)-3-oxo-1,1a,2,3,4,8b-hexahydrocyclopropa[d]pyrido[2,3-b]azepin-2-yl)-4H-1,2,4-triazole-3-carboxamide and 5-benzyl-N-((1aS,2S,8bR)-3-oxo-1,1a,2,3,4,8b-hexahydrocyclopropa[d]pyrido[2,3-b]azepin-2-yl)-4H-1,2,4-triazole-3-carboxamide

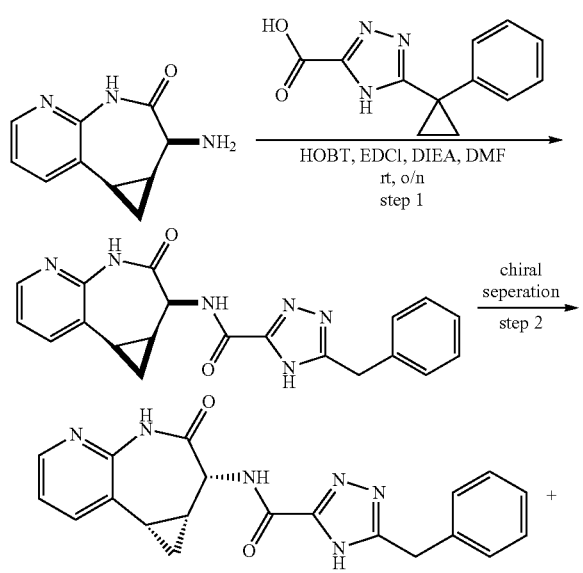

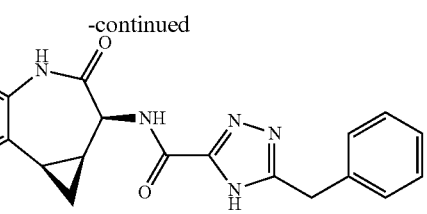

Step 1: Preparation of 5-benzyl-N-(cis-3-oxo-1,1a,2,3,4,8b-hexahydrocyclopropa[d]pyrido[2,3-b]azepin-2-yl)-4H-1,2,4-triazole-3-carboxamide The crude product obtained using Amide Coupling Procedure C was purified by Prep-TLC (ethyl acetate/petroleum ether, 1/3) to afford the title compound (20 mg, 26.7%) as a yellow solid. LC-MS (Method I): m/z=375.2 [M+H]⁺, 1.007 min.

Step 2: Preparation of 5-benzyl-N-((1aR,2R,8bS)-3-oxo-1,1a,2,3,4,8b-hexahydrocyclopropa[d]pyrido[2,3-b]azepin-2-yl)-4H-1,2,4-triazole-3-carboxamide (Example 110A) and 5-ben-zyl-N-((1aS,2S,8bR)-3-oxo-1,1a,2,3,4,8b-hexahydrocyclopropa[d]pyrido[2,3-b]azepin-2-yl)-4H-1,2,4-triazole-3-carboxamide (Example 110B)

The racemate of 5-benzyl-N-(cis-3-oxo-1,1a,2,3,4,8b-hexahydrocyclopropa[d]pyrido[2,3-b]azepin-2-yl)-4H-1,2,4-triazole-3-carboxamide (20 mg, 0.053 mmol) was separated by Prep-Chiral-HPLC with the following conditions: Column: CHIRAL ART Cellulose-SB, 2×25 cm, 5 μm; Mobile Phase A: hexane, Mobile Phase B: EtOH; Flow rate: 20 mL/min; Gradient: 30% B to 30% B over 20 min; UV 254 & 220 nm; Rt1: 12.8 min; Rt2: 16.08 min to afford the title compounds:

Example 110A (first eluting isomer): ¹H NMR (400 MHz, CD₃OD-d₄) δ 8.24 (dd, J=4.8, 1.6 Hz, 1H), 7.91 (dd, J=7.6, 1.6 Hz, 1H), 7.38-7.16 (m, 6H), 4.84 (s, 1H), 4.17 (s, 2H), 2.25-2.21 (m, 1H), 2.15-2.09 (m, 1H), 1.62-1.57 (m, 1H), 1.16-1.12 (m, 1H). LC-MS (Method J): m/z=375.2 [M+H]⁺, 1.007 min.

Example 110B (second eluting isomer): ¹H NMR (300 MHz, CD₃OD-d₄) δ 8.23 (dd, J=4.8, 1.8 Hz, 1H), 7.90 (dd, J=7.5, 1.8 Hz, 1H), 7.39-7.13 (m, 6H), 4.84 (s, 1H), 4.18 (s, 2H), 2.19-2.09 (m, 2H), 1.64-1.55 (m, 1H), 1.17-1.10 (m, 1H). LC-MS (Method F): m/z=374.9 [M+H]⁺, 0.919 min.

Example 111A and 111B: (R)-1-benzyl-4-fluoro-N-(9-methyl-8-oxo-6,7,8,9-tetrahydro-5H-pyrido[2,3-b]azepin-7-yl)-1H-pyrazole-3-carboxamide and (S)-1-benzyl-4-fluoro-N-(9-methyl-8-oxo-6,7,8,9-tetrahydro-5H-pyrido[2,3-b]azepin-7-yl)-1H-pyrazole-3-carboxamide

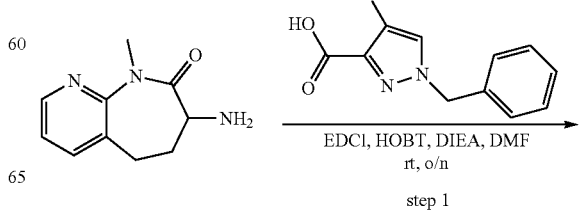

429

-continued

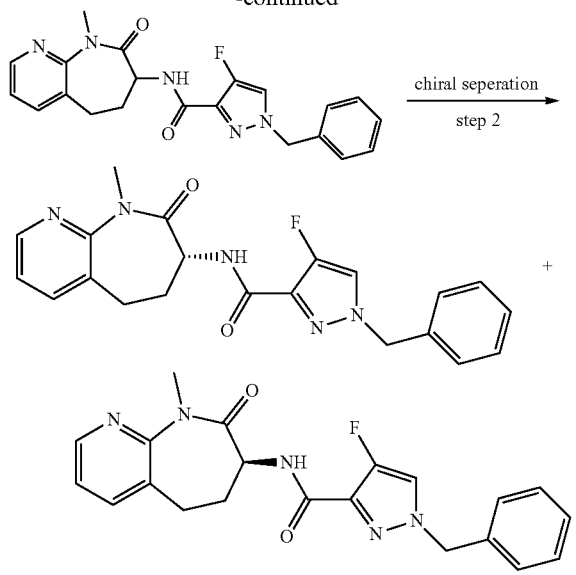

Step 1 Preparation of 1-benzyl-4-fluoro-N-(9-methyl-8-oxo-6,7,8,9-tetrahydro-5H-pyrido[2,3-b]azepin-7-yl)-1H-pyrazole-3-carboxamide N,N-diisopropylethylamine (201.2 mg, 1.56 mmol) was added to a mixture of 1-benzyl-4-fluoro-1H-pyrazole-3-carboxylic acid (104.6 mg, 0.52 mmol), 7-amino-9-methyl-6,7-dihydro-5H-pyrido[2,3-b]azepin-8(9H)-one (100 mg, 0.52 mmol), N-(3-dimethylaminopropyl))-N'-ethylcarbodiimide hydrochloride (119.6 mg, 0.62 mmol) and 1-hydroxybenzotriazole (84.2 mg, 0.62 mmol) in N,N-dimethylformamide (3 mL). The reaction mixture was stirred overnight at room temperature, diluted with water (10 mL) and extracted with ethyl acetate (3×10 mL). The combined organic layers were washed with brine, dried over anhydrous sodium sulfate, filtered and concentrated under vacuum. The crude product obtained using Amide Coupling Procedure C was purified by Prep-HPLC with the following conditions: Column: XSelect CSH Prep C18 OBD Column, 5 μm, 19×150 mm; Mobile Phase A: water (0.1% formic acid), Mobile Phase B: ACN; Flow rate: 20 mL/min; Gradient: 35% B to 55% B over 7 min; UV 254 & 220 nm; Rt: 5.6 min to afford the title compound (32 mg, 25.4%) as a white solid. LC-MS (Method D): m/z=394.2 [M+H]$^+$, 1.571 min.

Step 2: Preparation of (R)-1-benzyl-4-fluoro-N-(9-methyl-8-oxo-6,7,8,9-tetrahydro-5H-pyrido[2,3-b]azepin-7-yl)-1H-pyrazole-3-carboxamide (Example 111A) and (S)-1-benzyl-4-fluoro-N-(9-methyl-8-oxo-6,7,8,9-tetrahydro-5H-pyrido[2,3-b]azepin-7-yl)-1H-pyrazole-3-carboxamide (Example 111B)

The racemate of 1-benzyl-4-fluoro-N-(9-methyl-8-oxo-6,7,8,9-tetrahydro-5H-pyrido[2,3-b]azepin-7-yl)-1H-pyrazole-3-carboxamide (32 mg, 0.081 mmol) was separated by Prep-Chiral-HPLC with the following conditions: Column: CHIRAL ART Cellulose-SB, 2×25 cm, 5 μm; Mobile Phase A: hexane, Mobile Phase B: EtOH; Flow rate: 20 mL/min; Gradient: 30% B to 30% B over 15 min; UV 254 & 220 nm; Rt1: 11.47 min; Rt2: 13.24 min to afford the title compounds:

430

Example 111A (first eluting isomer): $^1$H NMR (300 MHz, DMSO-d$_6$) δ 8.42-8.40 (m, 1H), 8.10-8.02 (m, 2H), 7.80-7.77 (m, 1H), 7.39-7.24 (m, 6H), 5.31 (s, 2H), 4.32-4.23 (m, 1H), 3.33 (s, 3H), 2.78-2.60 (m, 2H), 2.38-2.25 (m, 2H). LC-MS (Method D): m/z=394.2 [M+H]$^+$, 1.571 min.

Example 111B (second eluting isomer): $^1$H NMR (300 MHz, DMSO-d$_6$) δ 8.42-8.40 (m, 1H), 8.10-8.02 (m, 2H), 7.80-7.77 (m, 1H), 7.39-7.24 (m, 6H), 5.31 (s, 2H), 4.32-4.23 (m, 1H), 3.32 (s, 3H), 2.72-2.66 (m, 2H), 2.39-2.26 (m, 2H). LC-MS (Method D): m/z=394.2 [M+H]$^+$, 1.570 min.

Example 112: 5-benzyl-N-((2R,3S)-2,5-dimethyl-4-oxo-2,3,4,5-tetrahydropyrido[3,2-b][1,4]oxazepin-3-yl)isoxazole-3-carboxamide

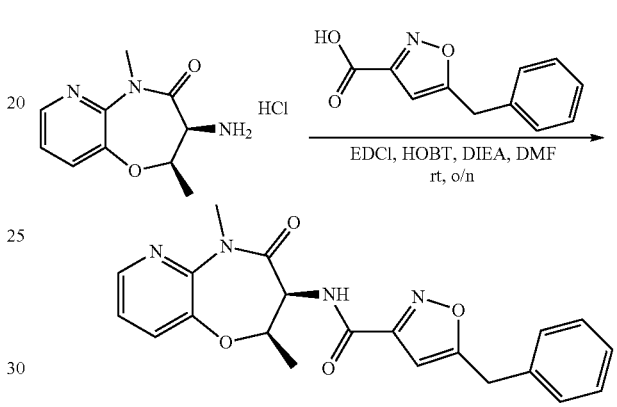

The crude product obtained using Amide Coupling Procedure C was purified by Prep-HPLC with the following conditions: Column: XBridge C18 OBD Prep Column, 5 μm, 19×250 mm; Mobile Phase A: water (10 mmol/L NH$_4$HCO$_3$), Mobile Phase B: ACN; Flow rate: 20 mL/min; Gradient: 30% B to 60% B in 7 min; UV 254 & 220 nm; Rt: 7 min to afford the title compound. $^1$H NMR (400 MHz, DMSO-d$_6$) δ 8.35 (dd, J=4.7, 1.5 Hz, 1H), 8.27 (d, J=7.0 Hz, 1H), 7.73 (dd, J=7.9, 1.5 Hz, 1H), 7.39-7.23 (m, 6H), 6.61 (s, 1H), 4.99-4.87 (m, 2H), 4.22 (s, 2H), 3.39 (s, 3H), 1.36 (d, J=6.2 Hz, 3H). LC-MS (Method X): m/z=393.2 [M+H]$^+$, 3.187 min.

Example 113: (S)—N-(1-methyl-2-oxo-1,2,3,4-tetrahydropyrido[3,4-b][1,4]oxazepin-3-yl)-5-(1-phenylcyclopropyl)-4H-1,2,4-triazole-3-carboxamide

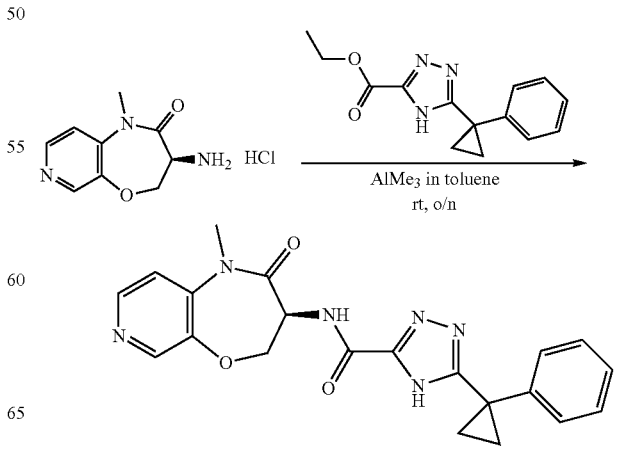

The crude product obtained using the procedure described in Example 54 was purified by Prep-HPLC with the following conditions: Column: XBridge Shield RP18 OBD Column, 5 μm, 19×150 mm; Mobile Phase A: water (0.05% TFA), Mobile Phase B: ACN; Flow rate: 20 mL/min; Gradient: 10% B to 40% B over 7 min; UV 254 & 220 nm; Rt: 6 min to afford the title compound. $^1$H NMR (400 MHz, DMSO-d$_6$) δ 14.11 (s, 1H), 8.91-8.36 (m, 3H), 7.53 (d, J=5.3 Hz, 1H), 7.33 (m, 5H), 4.94-4.82 (m, 1H), 4.82-4.70 (m, 1H), 4.51 (dd, J=9.6, 7.2 Hz, 1H), 3.32 (s, 3H), 1.59-1.20 (m, 4H). LC-MS (Method O): m/z=405.0 [M+H]$^+$, 1.127 min.

Example 114A and 114B: (S)-1-benzyl-N-(1,4-dimethyl-5-oxo-1,4,5,6,7,8-hexahydropyrazolo[4,3-b]azepin-6-yl)-4-fluoro-1H-pyrazole-3-carboxamide and (R)-1-benzyl-N-(1,4-dimethyl-5-oxo-1,4,5,6,7,8-hexahydropyrazolo[4,3-b]azepin-6-yl)-4-fluoro-1H-pyrazole-3-carboxamide

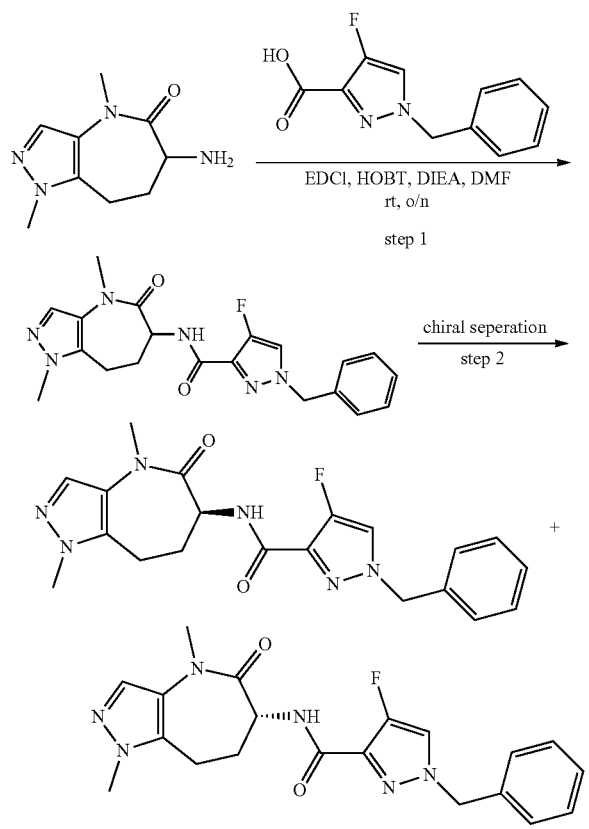

Step 1: Preparation of 1-benzyl-N-(1,4-dimethyl-5-oxo-1,4,5,6,7,8-hexahydropyrazolo[4,3-b]azepin-6-yl)-4-fluoro-1H-pyrazole-3-carboxamide The crude product obtained using Amide Coupling Procedure C was purified by Prep-HPLC with the following conditions: Column: XBridge Prep Phenyl OBD Column 19×150 mm 5 μm; Mobile Phase A: water (10 mmol/L NH$_4$HCO$_3$), Mobile Phase B: ACN; Flow rate: 20 mL/min; Gradient: 25% B to 50% B over 7 min; UV 254 & 220 nm; Rt: 6 min to afford the title compound (50 mg, 48.6%) as a white solid. LC-MS (Method C): m/z=397.2 [M+H]$^+$, 1.512 min.

Step 2: Preparation of (S)-1-benzyl-N-(1,4-dimethyl-5-oxo-1,4,5,6,7,8-hexahydropyrazolo[4,3-b]azepin-6-yl)-4-fluoro-1H-pyrazole-3-carboxamide (Example 114A) and (R)-1-benzyl-N-(1,4-dimethyl-5-oxo-1,4,5,6,7,8-hexahydropyrazolo[4,3-b]azepin-6-yl)-4-fluoro-1H-pyrazole-3-carboxamide (Example 114B)

The racemate of 1-benzyl-N-(1,4-dimethyl-5-oxo-1,4,5,6,7,8-hexahydropyrazolo[4,3-b]azepin-6-yl)-4-fluoro-1H-pyrazole-3-carboxamide (50 mg, 0.13 mmol) was separated by Prep-Chiral-HPLC with the following conditions: Column: CHIRAL ART Cellulose-SB, 2×25 cm, 5 μm; Mobile Phase A: hexane, Mobile Phase B: EtOH; Flow rate: 20 mL/min; Gradient: 50% B to 50% B over 18 min; UV 254 & 220 nm; Rt1: 12.54 min; Rt2: 15.41 min. to afford the title compounds:

Example 114A (first eluting isomer): $^1$H NMR (400 MHz, DMSO-d$_6$) δ 8.14 (d, J=4.0 Hz, 1H), 8.07 (d, J=6.4 Hz, 1H), 7.50 (s, 1H), 7.41-7.27 (m, 5H), 5.34 (s, 2H), 4.43-4.37 (m, 1H), 3.74 (s, 3H), 3.24 (s, 3H), 3.06-2.96 (m, 1H), 2.91-2.84 (m, 1H), 2.30-2.23 (m, 1H), 2.10-1.99 (m, 1H). LC-MS (Method D): m/z=397.1 [M+H]$^+$, 1.500 min.

Example 114B (second eluting isomer): $^1$H NMR (400 MHz, DMSO-d$_6$) δ 8.14 (d, J=4.4 Hz, 1H), 8.07 (d, J=6.8 Hz, 1H), 7.50 (s, 1H), 7.41-7.26 (m, 5H), 5.34 (s, 2H), 4.43-4.37 (m, 1H), 3.74 (s, 3H), 3.24 (s, 3H), 3.06-2.96 (m, 1H), 2.91-2.83 (m, 1H), 2.30-2.22 (m, 1H), 2.10-1.99 (m, 1H). LC-MS (Method D): m/z=397.1 [M+H]$^+$, 1.514 min.

Example 115: (S)-4-fluoro-1-(4-fluorobenzyl)-N-(5-methyl-4-oxo-2,3,4,5-tetrahydropyrido[3,2-b][1,4]oxazepin-3-yl)-1H-pyrazole-3-carboxamide

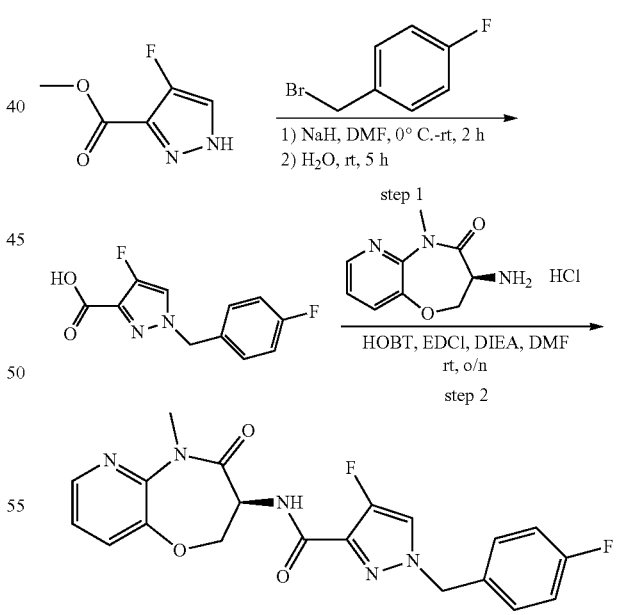

Step 1: Preparation of 4-fluoro-1-(4-fluorobenzyl)-1H-pyrazole-3-carboxylic acid Sodium hydride (60%, 152 mg, 3.8 mmol) was added to a solution of methyl 4-fluoro-1H-pyrazole-3-carboxylate (200 mg, 1.27 mmol) in N,N-dimethylformamide (10 mL) at 0° C. The resulting mixture was stirred at room temperature for 0.5 hour followed by addition of 1-(bromomethyl)-4-fluorobenzene (264 mg, 1.40 mmol). The reaction mixture was stirred at room temperature for another 1.5 hours and quenched by addition of water (20 mL). The resulting solution was then stirred at room temperature for 5 hours. The pH value of the solution was adjusted to 7 with aqueous hydrochloric acid (1 N, 10 mL). The resulting solution was extracted with ethyl acetate (3×50 mL). The combined organic layers were washed with brine, dried over anhydrous sodium sulfate, filtered and concentrated under vacuum. The residue was purified by Prep-HPLC with the following conditions: Column: XBridge C18 OBD Prep Column, 100 Å, 5 μm, 19 mm×250 mm; Mobile Phase A: water (0.1% formic acid), Mobile Phase B: ACN; Flow rate: 20 mL/min; Gradient: 40% B to 60% B over 9 min; UV 254 & 220 nm; Rt: 7 min to afford the title compound (100 mg, 33.2%). LC-MS (Method S): m/z=239.2 [M+H]$^+$, 1.093 min.

Step 2: Preparation of (S)-4-fluoro-1-(4-fluorobenzyl)-N-(5-methyl-4-oxo-2,3,4,5-tetrahydropyrido[3,2-b][1,4]oxazepin-3-yl)-1H-pyrazole-3-carboxamide The crude product obtained using Amide Coupling Procedure C was purified by Prep-HPLC with the following conditions: Column: XBridge Prep C18 OBD Column 19×150 mm 5 μm; Mobile Phase A: water (10 mmol/L NH$_4$HCO$_3$), Mobile Phase B: ACN; Flow rate: 20 mL/min; Gradient: 25% B to 55% B over 7 min; UV 254 & 220 nm; Rt: 6.32 min to afford the title compound. $^1$H NMR (400 MHz, DMSO-d$_6$) δ 8.37-8.35 (m, 1H), 8.27 (d, J=8 Hz, 1H), 8.14 (d, J=4.4 Hz, 1H), 7.71-7.69 (m, 1H), 7.36-7.32 (m, 3H), 7.25-7.20 (m, 2H), 5.33 (s, 2H), 4.87-4.81 (m, 1H), 4.70-4.65 (m, 1H), 4.52-4.48 (m, 1H), 3.35 (s, 3H). LC-MS (Method X): m/z=414.2 [M+H]$^+$, 2.606 min.

Example 116: (S)—N-(5,6-dihydro-4H-benzo[f]imidazo[1,2-a]azepin-4-yl)-5-(2-fluorophenoxy)pyridazine-3-carboxamide

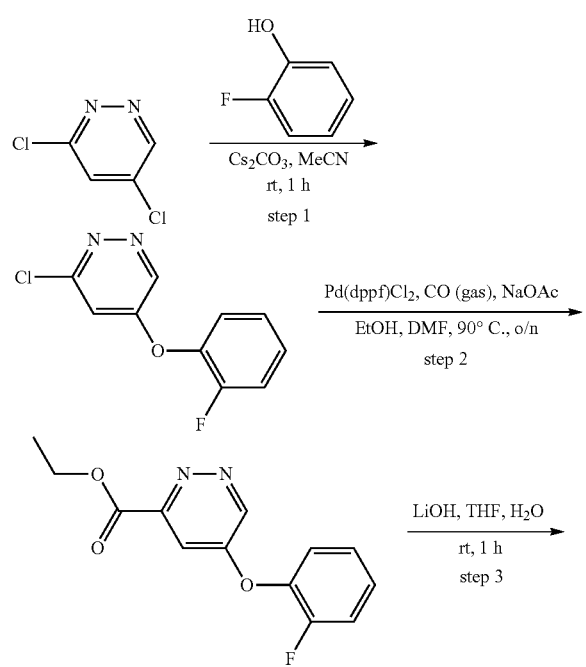

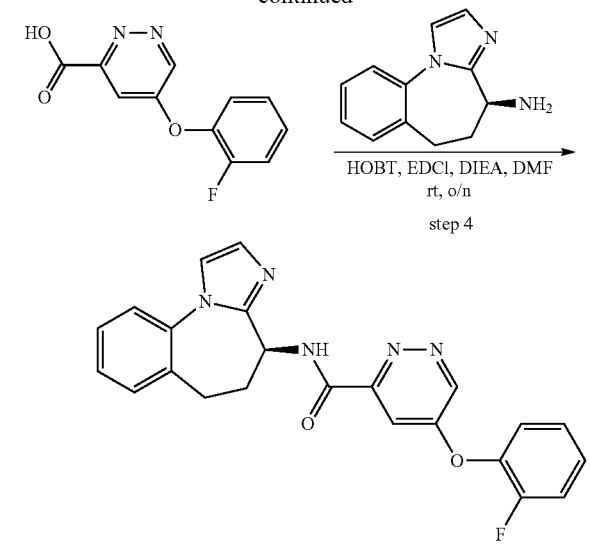

Step 1: Preparation of 3-chloro-5-(2-fluorophenoxy)pyridazine

2-Fluorophenol (2 g, 17.8 mmol) was added dropwise to a stirring mixture of 3,5-dichloropyridazine (3.17 g, 21.4 mmol) and cesium carbonate (8.7 g, 26.9 mmol) in acetonitrile (40 mL). The reaction mixture was stirred at room temperature for 1 hour under a nitrogen atmosphere. The solids were removed by filtration and the filtrate was concentrated under vacuum. The residue was purified by column chromatography (petroleum ether) to afford the title compound (2.8 g, 70%) as a white solid. LC-MS (Method X): m/z=225.1 [M+H]$^+$, 0.919 min.

Step 2: Preparation of ethyl 5-(2-fluorophenoxy)pyridazine-3-carboxylate 1,1'-Bis(diphenylphosphino)ferrocene-palladium(II)dichloride dichloromethane (0.95 g, 1.16 mmol) was added to a mixture of 3-chloro-5-(2-fluorophenoxy)pyridazine (2.6 g, 11.6 mmol) and sodium acetate (1.9 g, 23.2 mmol) in ethanol (125 mL) and N,N-dimethylformamide (25 mL). The reaction mixture was stirred overnight at 90° C. under a carbon monooxide atmosphere (1 MPa). After cooling to room temperature, the reaction mixture was concentrated under vacuum. The residue was purified by column chromatography (ethyl acetate/petroleum ether, 1/10) to afford the title compound (2.4 g, 79%) as a colorless oil. LC-MS (Method X): m/z=263.1 [M+H]$^+$, 0.905 min.

Step 3: Preparation of 5-(2-fluorophenoxy)pyridazine-3-carboxylic acid

Lithium hydroxide (48 mg, 2 mmol) was added to a stirring solution of ethyl 5-(2-fluorophenoxy)pyridazine-3-carboxylate (131 mg, 0.5 mmol) in tetrahydrofuran (8 mL) and water (2 mL). The reaction mixture was stirred for 1 hour at room temperature. After removal of tetrahydrofuran under reduced pressure, the residue was diluted with water (20 mL). The pH of the resulting solution was adjusted to 4 with aqueous hydrochloride acid (2 N, 5 mL). The resulting solution was extracted with ethyl acetate (3×20 mL). The combined organic layers were washed with brine, dried over anhydrous sodium sulfate, and filtered. The filtrate was concentrated under vacuum to afford the title compound (100 mg crude) as a white solid. LC-MS (Method R): m/z=235.2 [M+H]$^+$, 0.507 min.

Step 4: Preparation of (S)—N-(5,6-dihydro-4H-benzo[f]imidazo[1,2-a]azepin-4-yl)-5-(2-fluorophenoxy)pyridazine-3-carboxamide The crude product obtained using Amide Coupling Procedure C was purified by Prep-HPLC with the following conditions: Column: XBridge Prep C18 OBD Column 19×150 mm 5 μm; Mobile Phase A: water (10 mmol/L NH$_4$HCO$_3$), Mobile Phase B: ACN, Flow rate: 30 mL/min; Gradient: 45% B to 50% B over 5 min; UV 254 & 220 nm to afford the title compound. $^1$H NMR (400 MHz, Methanol-d$_4$) δ 9.25 (d, J=2.8 Hz, 1H), 7.51-7.32 (m, 10H), 7.08 (d, J=1.2 Hz, 1H), 5.11-5.06 (m, 1H), 2.88-2.81 (m, 1H), 2.80-2.71 (m, 1H), 2.66-2.57 (m, 1H), 2.51-2.42 (m, 1H). LC-MS (Method D): m/z=416.1 [M+H]$^+$, 1.337 min.

Example 117: N-((2R,3S)-2,5-dimethyl-4-oxo-2,3,4,5-tetrahydropyrido[3,2-b][1,4]oxazepin-3-yl)-4-(2-fluorophenoxy)picolinamide

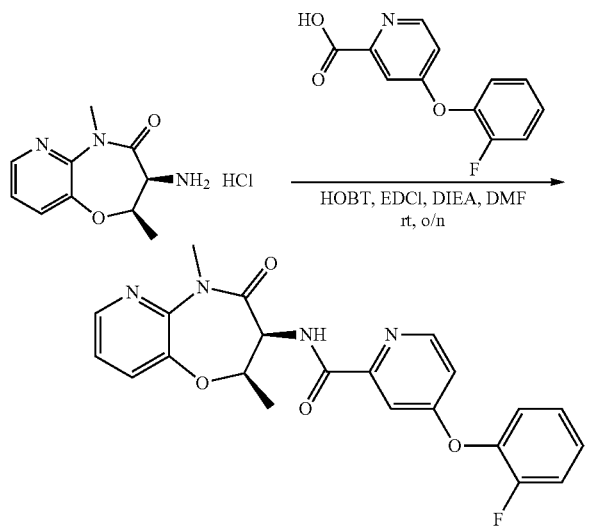

The crude product obtained using Amide Coupling Procedure C was purified by Prep-HPLC with the following conditions: Column: XBridge Shield RP18 OBD Column, 5 μm, 19×150 mm; Mobile Phase A: water (0.1% formic acid), Mobile Phase B: ACN; Flow rate: 20 mL/min; Gradient: 35% B to 85% B over 7 min; UV 254 & 220 nm; Rt: 6.35 min to afford the title compound. $^1$H NMR (400 MHz, DMSO-d$_6$) δ 8.75 (d, J=6.8 Hz, 1H), 8.64 (d, J=5.6 Hz, 1H), 8.36 (dd, J=4.8, 1.6 Hz, 1H), 7.76 (dd, J=8.0, 1.6 Hz, 1H), 7.54-7.39 (m, 3H), 7.38-7.33 (m, 3H), 7.27-7.29 (m, 1H), 5.02-4.95 (m, 1H), 4.94-4.89 (m, 1H), 3.41 (s, 3H), 1.32 (d, J=6.0 Hz, 3H). LC-MS (Method Q): m/z=423.0 [M+H]$^+$, 2.885 min.

Example 118A & 118B: (R)-5-benzyl-N-(1-methyl-5-oxo-1,4,5,6,7,8-hexahydropyrazolo[4,3-b]azepin-6-yl)-4H-1,2,4-triazole-3-carboxamide and (S)-5-benzyl-N-(1-methyl-5-oxo-1,4,5,6,7,8-hexahydropyrazolo[4,3-b]azepin-6-yl)-4H-1,2,4-triazole-3-carboxamide

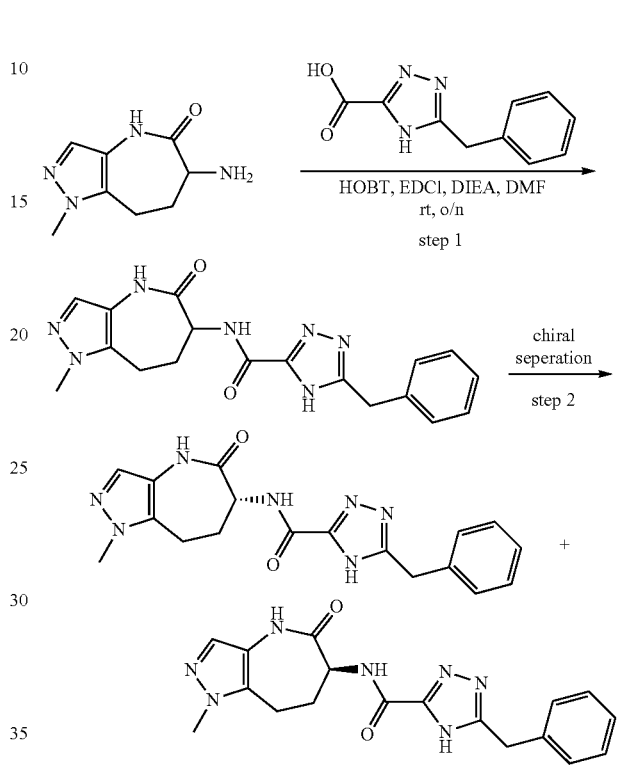

Step 1: Preparation of 5-benzyl-N-(1-methyl-5-oxo-1,4,5,6,7,8-hexahydropyrazolo[4,3-b]azepin-6-yl)-4H-1,2,4-triazole-3-carboxamide The crude product obtained using Amide Coupling Procedure C was purified by Prep-HPLC with the following conditions: Column: XBridge Prep Phenyl OBD Column 19×150 mm 5 μm; Mobile Phase A: water (0.1% formic acid), Mobile Phase B: ACN; Flow rate: 20 mL/min; Gradient: 5% B to 35% B over 10 min; UV 254 & 220 nm; Rt: 9 min to afford the title compound (50 mg, 38.1%) as a white solid. LC-MS (Method C): m/z=366.2 [M+H]$^+$, 1.174 min.

Step 2: (R)-5-benzyl-N-(1-methyl-5-oxo-1,4,5,6,7,8-hexahydropyrazolo[4,3-b]azepin-6-yl)-4H-1,2,4-triazole-3-carboxamide (Example 118A) and (S)-5-benzyl-N-(1-methyl-5-oxo-1,4,5,6,7,8-hexahydropyrazolo[4,3-b]azepin-6-yl)-4H-1,2,4-triazole-3-carboxamide (Example 118B)

The racemate of 5-benzyl-N-(1-methyl-5-oxo-1,4,5,6,7,8-hexahydropyrazolo[4,3-b]azepin-6-yl)-4H-1,2,4-triazole-3-carboxamide (50 mg, 0.14 mmol) was separated by Prep-Chiral-HPLC with the following conditions: Column: CHIRAL ART Cellulose-SB, 2×25 cm, 5 μm; Mobile Phase A: hexane, Mobile Phase B: EtOH; Flow rate: 20 mL/min; Gradient: 50% B to 50% B over 12 min; 254/220 nm; Rt1: 8.84 min; Rt2: 10.81 min to afford the title compounds:

Example 118A (first eluting isomer): $^1$H NMR (400 MHz, DMSO-d$_6$) δ 10.00 (s, 1H), 8.53 (d, J=5.6 Hz, 1H), 7.41-7.29 (m, 5H), 7.17 (s, 1H), 4.41-4.37 (m, 1H), 4.18 (s, 2H), 3.76 (s, 3H), 3.05-3.00 (m, 2H), 2.34-2.30 (m, 1H), 2.10-2.05 (m, 1H). LC-MS (Method D): m/z=366.1 [M+H]$^+$, 1.180 min.

Example 118B (second eluting isomer): $^1$H NMR (400 MHz, DMSO-d$_6$) δ 9.94 (s, 1H), 8.46 (d, J=6.0 Hz, 1H), 7.35-7.10 (m, 5H), 7.10 (s, 1H), 4.35-4.30 (m, 1H), 4.12 (s, 2H), 3.69 (s, 3H), 3.00-2.92 (m, 2H), 2.27-2.23 (m, 1H), 2.04-1.98 (m, 1H). LC-MS (Method D): m/z=366.1 [M+H]$^+$, 1.177 min.

Example 119A & 119B: 5-benzyl-N-((7R,7aR,8aS)-5-methyl-6-oxo-5,6,7,7a,8,8a-hexahydro-cyclopropa[d]pyrazino[2,3-b]azepin-7-yl)-4H-1,2,4-triazole-3-carboxamide and 5-benzyl-N-((7S,7aS,8aR)-5-methyl-6-oxo-5,6,7,7a,8,8a-hexahydrocyclopropa[d]pyrazino[2,3-b]azepin-7-yl)-4H-1,2,4-triazole-3-carboxamide

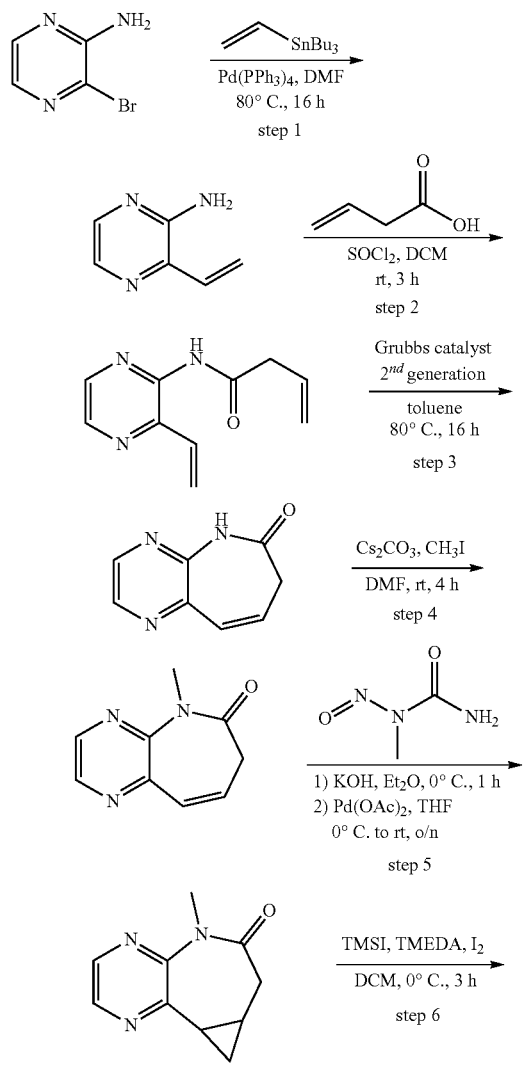

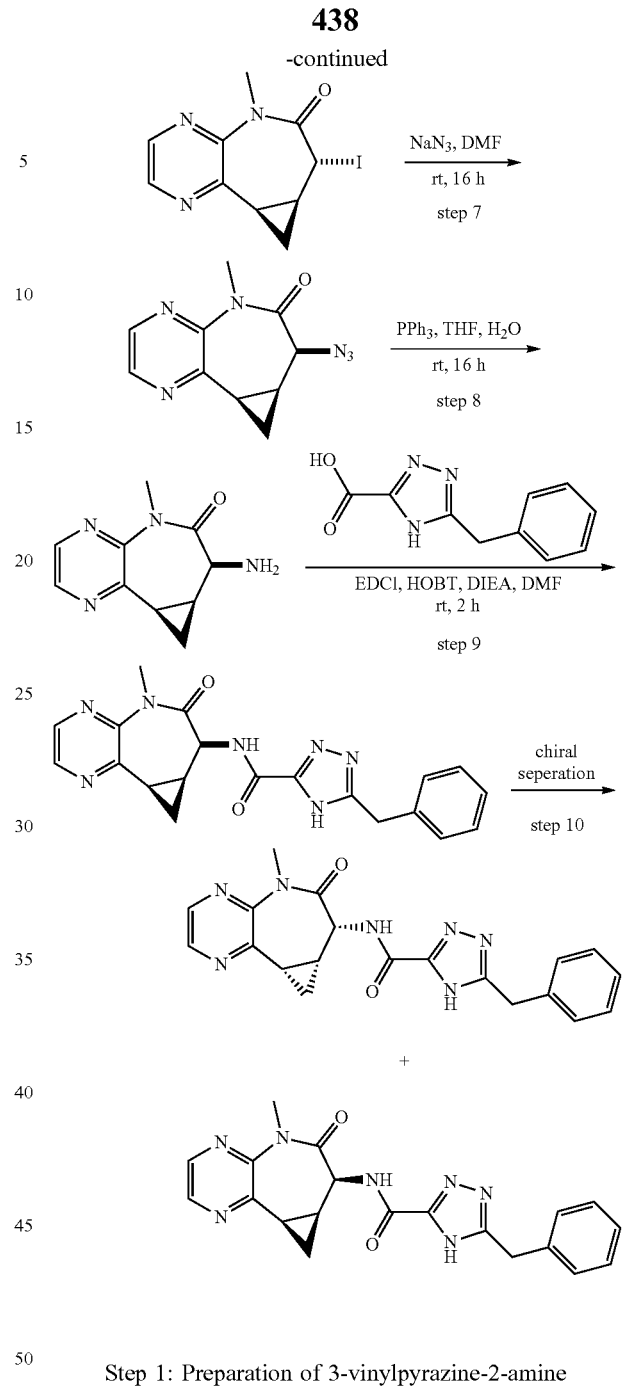

Step 1: Preparation of 3-vinylpyrazine-2-amine

To a solution of 3-bromopyrazin-2-amine (10 g, 57 mmol) in N,N-dimethylformamide (50 mL) was added tributyl(ethenyl)stannane (20 g, 63 mmol) and tetrakis(triphenylphosphine)palladium (2.7 g, 2.3 mmol) under a nitrogen atmosphere. The resulting mixture was stirred for 16 hours at 80° C., quenched by the addition of water (200 mL) and extracted with dichloromethane (3×200 mL). The combined organic layers were washed with brine, dried over sodium sulfate, filtered and concentrated under vacuum. The residue was purified by column chromatography (methanol/dichloromethane, 3/97) to afford the title compound (6.0 g, 86%) as a yellow solid. LC-MS (Method C): m/z=122.1 [M+H]$^+$, 0.658 min.

Step 2: Preparation of N-(3-vinylpyrazine-2-yl)but-3-enamide

Thionyl chloride (9.3 g, 46.5 mmol) was added to a solution of but-3-enoic acid (4.0 g, 46.5 mmol) in dichloromethane (20 mL) dropwise. After stirring for 1 hour at room temperature, the resulting mixture was added to a solution of triethylamine (11.8 g, 116.6 mmol) and 3-vinylpyrazine-2-amine (4.7 g, 38.7 mmol) in dichloromethane (20 mL). The reaction mixture was stirred for 2 hours at room temperature, quenched by the addition of water (50 mL) and extracted with dichloromethane (3×50 mL). The combined organic layers were washed with brine, dried over sodium sulfate, filtered and concentrated under vacuum. The residue was purified by column chromatography (ethyl acetate/petroleum ether, 3/1) to afford the title compound (5.7 g, 78%) as a yellow oil. LC-MS (Method C): m/z=190.1 $[M+H]^+$, 0.881 min.

Step 3: Preparation of (Z)-5H-pyrazino[2,3-b]azepin-6(7H)-one

[1,3-Bis(2,4,6-trimethylphenyl)imidazolidin-2-ylidene]dichloro(phenylmethylidene) ruthenium tricyclohexylphosphine (340 mg, 0.4 mmol) was added to a solution of N-(3-vinylpyrazine-2-yl)but-3-enamide (380 mg, 2 mmol) in toluene (50 mL). The resulting solution was stirred for 16 hours at 80° C. and then concentrated under vacuum. The residue was purified by column chromatography (ethyl acetate/petroleum ether, 5/1) to afford the title compound (210 mg, 65%) as a yellow oil. LC-MS (Method C): m/z=162.1 $[M+H]^+$, 0.762 min.

Step 4: Preparation of (Z)-5-methyl-5H-pyrazino[2,3-b]azepin-6(7H)-one

Iodomethane (180 mg, 1.3 mmol) was added dropwise to a stirring solution of (Z)-5H-pyrazino[2,3-b]azepin-6(7H)-one (210 mg, 1.3 mmol) and cesium carbonate (1.3 g, 3.9 mmol) in N,N-dimethylformamide (30 mL). The reaction mixture was stirred for 4 hours at room temperature, diluted with water (60 mL) and extracted with ethyl acetate (3×30 mL). The combined organic layers were washed with brine, dried over anhydrous sodium sulfate, filtered and concentrated under vacuum. The residue was purified by column chromatography (ethyl acetate/petroleum ether, 4/1) to afford the title compound (200 mg, 88%) as a yellow solid. LC-MS (Method E): m/z=176.1 $[M+H]^+$, 0.776 min.

Step 5: Preparation of 5-methyl-7,7a,8,8a-tetrahydrocyclopropa[d]pyrazino[2,3-b]azepin-6(5H)-one To a solution of potassium hydroxide (4 g, 71.4 mmol) in water (6 mL) was added a solution of 1-methyl-1-nitrosourea (2.1 g, 20 mmol) in ether (30 mL) dropwise at 0° C. under a nitrogen atmosphere. The resulting mixture was stirred for 1 hour at 0° C. and then the organic phase was separated to provide a solution of diazomethane (30 mL). To a solution of (Z)-5-methyl-5H-pyrazino[2,3-b]azepin-6(7H)-one (200 mg, 1.1 mmol) in tetrahydrofuran (10 mL) was added the solution of diazomethane (30 mL) dropwise, followed by adding a mixture of palladium diacetate (25 mg, 0.11 mmol) in tetrahydrofuran (5 mL) dropwise at 0° C. The reaction mixture was stirred overnight at room temperature. The solids were removed by filtration and the filtrate was concentrated under vacuum to afford the title compound (110 mg crude) as a yellow oil. LC-MS (Method E): m/z=190.1 $[M+H]^+$, 0.825 min.

Step 6: Preparation of trans-7-iodo-5-methyl-7,7a,8,8a-tetrahydrocyclopropa[d]pyrazino[2,3-b]azepin-6(5H)-one To a mixture of 5-methyl-7,7a,8,8a-tetrahydrocyclopropa[d]pyrazino[2,3-b]azepin-6(5H)-one (110 mg, 0.6 mmol) in dichloromethane (20 mL) was added N,N,N',N'-tetramethylethylene-diamine (210 mg, 1.8 mmol) followed by the addition of iodotrimethylsilane (360 mg, 1.8 mmol) at 0° C. After stirring for 2 hours at 0° C., iodine (230 mg, 0.9 mmol) was added. The reaction mixture was stirred for 1 hour at 0° C., quenched with aqueous sodium thiosulfate (5%, 40 mL) and extracted with dichloromethane (3×30 mL). The combined organic layers were washed with brine, dried over anhydrous sodium sulfate, and filtered. The filtrate was concentrated under vacuum to afford the title compound (132 mg crude) as a yellow oil. LC-MS (Method E): m/z=316.1 $[M+H]^+$, 0.840 min.

Step 7: Preparation of cis-7-azido-5-methyl-7,7a,8,8a-tetrahydrocyclopropa[d]pyrazino[2,3-b]azepin-6(5H)-one Sodium azide (39 mg, 0.6 mmol) was added to a mixture of trans-7-iodo-5-methyl-7,7a,8,8a-tetrahydrocyclopropa[d]pyrazino[2,3-b]azepin-6(5H)-one (132 mg, 0.4 mmol) in N,N-dimethylformamide (10 mL). The resulting mixture was stirred for 16 hours at room temperature, quenched by the addition of water (30 mL) and extracted with ethyl acetate (3×30 mL). The combined organic layers were washed with brine, dried over sodium sulfate, and filtered. The filtrate was concentrated under vacuum to afford the title compound (60 mg crude) as a yellow oil. LC-MS (Method C): m/z=231.1 $[M+H]^+$, 1.036 min.

Step 8: Preparation of cis-7-amino-5-methyl-7,7a,8,8a-tetrahydrocyclopropa[d]pyrazino[2,3-b]azepin-6(5H)-one Triphenylphosphine (102 mg, 0.39 mmol) was added to a mixture of cis-7-azido-5-methyl-7,7a,8,8a-tetrahydrocyclopropa[d]pyrazino[2,3-b]azepin-6(5H)-one (60 mg, 0.26 mmol) in tetrahydrofuran (10 mL) and water (1 mL). The resulting mixture was stirred for 16 hours at room temperature, diluted with water (30 mL) and extracted with ethyl acetate (3×30 mL). The combined organic layers were washed with brine, dried over anhydrous sodium sulfate, filtered and concentrated to dryness under vacuum. The residue was purified by column chromatography (methanol/dichloromethane, 1/19) to afford the title compound (40 mg, 75%) as a yellow oil. LC-MS (Method E): m/z=205.1 $[M+H]^+$, 0.406 min.

Step 9: Preparation of 5-benzyl-N-cis-5-methyl-6-oxo-5,6,7,7a,8,8a-hexahydrocyclopropa[d]pyrazino[2,3-b]azepin-7-yl)-4H-1,2,4-triazole-3-carboxamide N,N-diisopropylethylamine (93 mg, 0.72 mmol) was added to a mixture of 5-benzyl-4H-1,2,4-triazole-3-carboxylic acid (51 mg, 0.24 mmol), cis-7-amino-5-methyl-7,7a,8,8a-tetrahydrocyclopropa[d]pyrazino[2,3-b]azepin-6(5H)-one (40 mg, 0.20 mmol), N-(3-dimethylamino-propyl))-N'-ethylcarbodiimide hydrochloride (46 mg, 0.24 mmol) and 1-hydroxybenzotriazole (32 mg, 0.24 mmol) in N,N-dimethylformamide (4 mL). The reaction mixture was stirred overnight at room temperature, diluted with water (20 mL) and extracted with ethyl acetate (3×30 mL). The combined organic layers were washed with brine, dried over anhydrous sodium sulfate, filtered and concentrated under vacuum. The residue was purified by Prep-HPLC with the following conditions: Column: XBridge Prep C18 OBD Column 19×150 mm, 5 μm; Mobile Phase A: water (10 mmol/L $NH_4HCO_3$), Mobile Phase B: ACN; Flow rate: 30 mL/min; Gradient: 25% B to 55% B over 7 min; UV 254 & 220 nm to afford the title compound (20 mg, 26%) as a white solid. LC-MS (Method D): m/z=390.2 [M+H]$^+$, 1.386 min.

Step 10: Preparation of 5-benzyl-N-((7R,7aR,8aS)-5-methyl-6-oxo-5,6,7,7a,8,8a-hexahydro-cyclopropa[d]pyrazino[2,3-b]azepin-7-yl)-4H-1,2,4-triazole-3-carboxamide (Example 119A) and 5-benzyl-N-((7S,7aS,8aR)-5-methyl-6-oxo-5,6,7,7a,8,8a-hexahydrocyclopropa[d]-pyrazino[2,3-b]azepin-7-yl)-4H-1,2,4-triazole-3-carboxamide (Example 119B)

The racemate of 5-benzyl-N-cis-5-methyl-6-oxo-5,6,7,7a,8,8a-hexahydrocyclopropa[d]-pyrazino[2,3-b]azepin-7-yl)-4H-1,2,4-triazole-3-carboxamide (20 mg, 0.05 mmol) was separated by Prep-Chiral-HPLC with the following conditions: Column: Chiralpak IA, 2×25 cm, 5 μm; Mobile Phase A: hexane, Mobile Phase B: EtOH; Flow rate: 16 mL/min; Gradient: 55% B to 55% B over 27 min; 220/254 nm; Rt1: 13.94 min; Rt2: 21.44 min to afford the title compounds:

Example 119A (first eluting isomer): $^1$H NMR (400 MHz, Methanol-d$_4$) δ 8.44-8.40 (m, 2H), 7.36-7.21 (m, 5H), 4.81 (s, 1H), 4.18 (s, 2H), 3.42 (s, 3H), 2.66-2.58 (m, 1H), 2.29-2.18 (m, 1H), 1.57-1.48 (m, 1H), 1.36-1.25 (m, 1H). LC-MS (Method D): m/z=390.1 [M+H]$^+$, 1.389 min.

Example 119B (second eluting isomer): $^1$H NMR (400 MHz, Methanol-d$_4$) δ 8.46-8.38 (m, 2H), 7.39-7.21 (m, 5H), 4.81 (s, 1H), 4.18 (s, 2H), 3.42 (s, 3H), 2.66-2.58 (m, 1H), 2.30-2.22 (m, 1H), 1.57-1.50 (m, 1H), 1.35-1.26 (m, 1H). LC-MS (Method D): m/z=390.2 [M+H]$^+$, 1.384 min.

Example 120A and 120B: 5-benzyl-N-((1aS,2S,8bR)-4-methyl-3-oxo-1,1a,2,3,4,8b-hexahydrocyclopropa[d]pyrido[2,3-b]azepin-2-yl)-1,3,4-thiadiazole-2-carboxamide and 5-benzyl-N-((1aR,2R,8bS)-4-methyl-3-oxo-1,1a,2,3,4,8b-hexahydrocyclopropa-[d]pyrido[2,3-b]azepin-2-yl)-1,3,4-thiadiazole-2-carboxamide

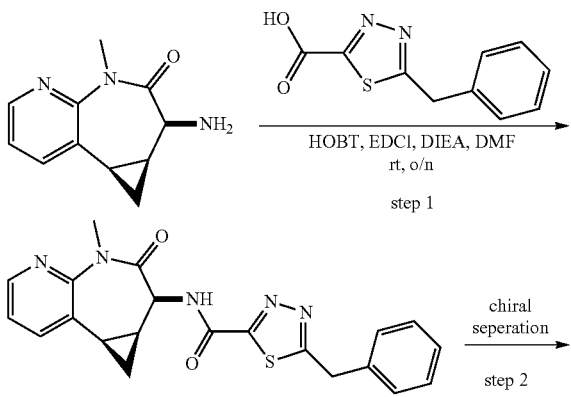

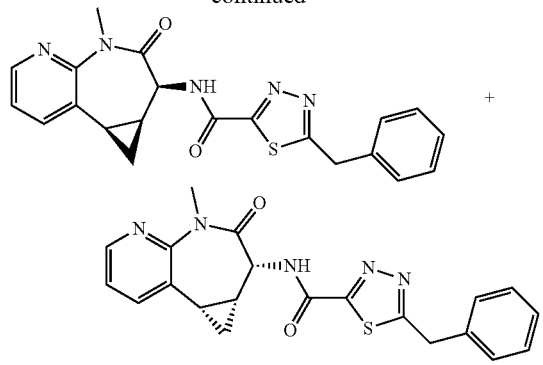

Step 1: Preparation of 5-benzyl-N-(cis-4-methyl-3-oxo-1,1a,2,3,4,8b-hexahydrocyclopropa[d]pyrido[2,3-b]azepin-2-yl)-1,3,4-thiadiazole-2-carboxamide The crude product obtained using Amide Coupling Procedure C was purified by Prep-HPLC with the following conditions: Column: XBridge Prep C18 OBD Column 19×150 mm 5 μm; Mobile Phase A: water (10 mmol/L $NH_4HCO_3$), Mobile Phase B: ACN; Flow rate: 20 mL/min; Gradient: 25% B to 55% B over 7 min; UV 254 & 220 nm; Rt: 6.32 min to afford the title compound (20 mg, 32.9%) as a white solid. LC-MS (Method I): m/z=406.2 [M+H]$^+$, 1.001 min.

Step 2: Preparation of 5-benzyl-N-((1aS,2S,8bR)-4-methyl-3-oxo-1,1a,2,3,4,8b-hexahydrocyclopropa[d]pyrido[2,3-b]azepin-2-yl)-1,3,4-thiadiazole-2-carboxamide (Example 120A) and 5-benzyl-N-((1aR,2R,8bS)-4-methyl-3-oxo-1,1a,2,3,4,8b-hexahydrocyclopropa-[d]pyrido[2,3-b]azepin-2-yl)-1,3,4-thiadiazole-2-carboxamide (Example 120B)

The racemate of 5-benzyl-N-(cis-4-methyl-3-oxo-1,1a,2,3,4,8b-hexahydrocyclopropa-[d]-pyrido[2,3-b]azepin-2-yl)-1,3,4-thiadiazole-2-carboxamide (20 mg, 0.049 mmol) was separated by Prep-chiral-separation with following conditions: Column: Lux Cellulose-4, 0.46×5 cm, 3 μm; Mobile Phase A: hexane; Mobile Phase B: EtOH; Flow rate: 1.0 mL/min; Gradient: 50% B to 50% B over 8 min; UV 254 & 220 nm; Rt1: 4.09 min; Rt2: 6.43 min to afford the title compounds:

Example 120A (first eluting isomer): $^1$H NMR (400 MHz, Methanol-d$_4$) δ 8.38 (dd, J=4.8, 2.0 Hz, 1H), 7.94 (dd, J=7.6, 2.0 Hz, 1H), 7.41-7.26 (m, 6H), 4.64 (s, 1H), 4.53 (s, 2H), 3.41 (s, 3H), 2.33-2.25 (m, 1H), 2.15-2.06 (m, 1H), 1.34-1.28 (m, 1H), 1.21-1.12 (m, 1H). LC-MS (Method D): m/z=406.1 [M+H]$^+$, 1.703 min.

Example 120B (second eluting isomer): $^1$H NMR (400 MHz, Methanol-d$_4$) δ 8.36 (dd, J=4.8, 2.0 Hz, 1H), 7.91 (dd, J=7.6, 2.0 Hz, 1H), 7.38-7.24 (m, 6H), 4.62 (s, 1H), 4.50 (s, 2H), 3.38 (s, 3H), 2.29-2.24 (m, 1H), 2.12-2.06 (m, 1H), 1.32-1.26 (m, 1H), 1.22-1.14 (m, 1H). LC-MS (Method V): m/z=406.1 [M+H]$^+$, 2.915 min.

Example 121A & 121B: (R)-4-(2,4-difluorophenoxy)-N-(9-methyl-8-oxo-6,7,8,9-tetrahydro-5H-pyrido[2,3-b]azepin-7-yl)picolinamide and (S)-4-(2,4-difluorophenoxy)-N-(9-methyl-8-oxo-6,7,8,9-tetrahydro-5H-pyrido[2,3-b]azepin-7-yl)picolinamide

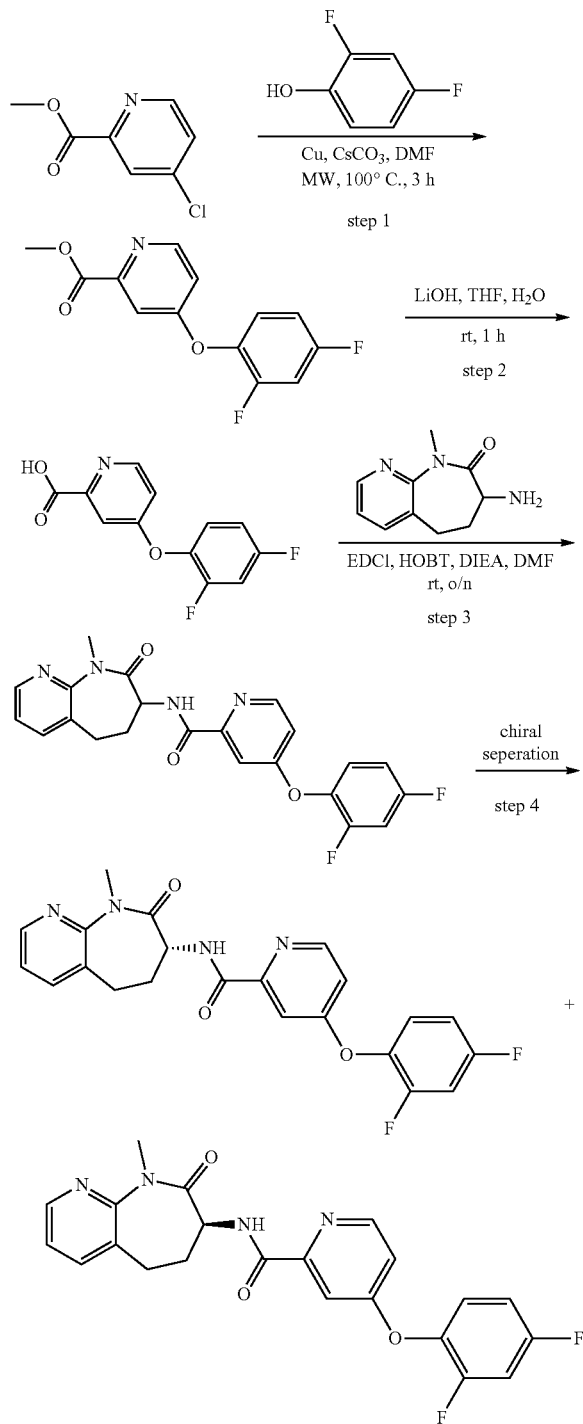

Step 1: Preparation of methyl 4-(2,4-difluorophenoxy)picolinate

To a sealed tube were added methyl 4-chloropicolinate (1 g, 5.85 mmol), 2,4-difluorophenol (1.14 g, 8.77 mmol), cesium carbonate (5.7 g, 17.5 mmol), copper powder (0.38 g, 5.94 mmol) and N,N-dimethylformamide (10 mL). The resulting mixture was heated at 100° C. by microwave irradiation and stirred for 3 hours, diluted with water (20 mL) and extracted with ethyl acetate (3×50 mL). The combined organic layers were washed with brine, dried over anhydrous sodium sulfate, and filtered. The filtrate was concentrated under vacuum to afford the title compound (0.5 g crude) as a white solid. LC-MS (Method I): m/z=265.9 [M+H]$^+$, 0.926 min.

Step 2: Preparation of 4-(2,4-difluorophenoxy)picolinic acid

Lithium hydroxide (260 mg, 10.8 mmol) was added to a stirring mixture of methyl 4-phenoxypicolinate (500 mg, 1.89 mmol) in tetrahydrofuran (10 mL) and water (5 mL). The resulting solution was stirred overnight at room temperature. After removal of tetrahydrofuran under reduced pressure, the pH of the aqueous solution was adjusted to 6 with aqueous hydrochloric acid (1 N, 10 mL). The resulting mixture was extracted with ethyl acetate (3×30 mL). The combined organic layers were washed with brine, dried over anhydrous sodium sulfate, and filtered. The filtrate was concentrated under vacuum to afford the title compound (200 mg crude) as a white solid, which was used directly in the next step without further purification. LC-MS (Method X): m/z=252.2 [M+H]$^+$, 0.639 min.

Step 3: Preparation of 4-(2,4-difluorophenoxy)-N-(9-methyl-8-oxo-6,7,8,9-tetrahydro-5H-pyrido[2,3-b]azepin-7-yl)picolinamide The crude product obtained using Amide Coupling Procedure C was purified by Prep-HPLC with the following conditions: Column: XBridge Shield RP18 OBD Column, 19×150 mm 5 μm; Mobile Phase A: water (10 mmol/L NH$_4$HCO$_3$), Mobile Phase B: ACN; Flow rate: 20 mL/min; Gradient: 40% B to 70% B over 7 min; 254 & 220 nm; Rt: 5.590 min to afford the title compound (80 mg, 40.1%) as a white solid. LC-MS (Method R): m/z=425.3 [M+H]$^+$, 1.442 min.

Step 4: Preparation of (R)-4-(2,4-difluorophenoxy)-N-(9-methyl-8-oxo-6,7,8,9-tetrahydro-5H-pyrido[2,3-b]azepin-7-yl)picolinamide (Example 121A) and (S)-4-(2,4-difluorophenoxy)-N-(9-methyl-8-oxo-6,7,8,9-tetrahydro-5H-pyrido[2,3-b]azepin-7-yl)picolinamide (Example 121B)

The racemate of 4-(2,4-difluorophenoxy)-N-(9-methyl-8-oxo-6,7,8,9-tetrahydro-5H-pyrido[2,3-b]azepin-7-yl)picolinamide (80 mg, 0.19 mmol) was separated by Prep-Chiral-HPLC with the following conditions: Column: Chiralpak ID-2, 2×25 cm, 5 μm; Mobile Phase A: hexane, Mobile Phase B: EtOH; Flow rate: 15 mL/min; Gradient: 55% B to 55% B over 23 min; UV 220 & 254 nm; Rt1: 14.83 min; Rt2: 18.87 min to afford the title compounds:

Example 121A (first eluting isomer): $^1$H NMR (400 MHz, DMSO-d$_6$) δ 8.88 (d, J=8.0 Hz, 1H), 8.60 (d, J=5.6 Hz, 1H), 8.44-8.43 (m, 1H), 7.84-7.81 (m, 1H), 7.65-7.48 (m, 2H), 7.36-7.22 (m, 4H), 4.36-4.29 (m, 1H), 3.36 (s, 3H), 2.81-2.70 (m, 2H), 2.50-2.44 (m, 1H), 2.35-2.21 (m, 1H). LC-MS (Method T): m/z=425.25 [M+H]$^+$, 1.432 min.

Example 121B (second eluting isomer): $^1$H NMR (400 MHz, DMSO-d$_6$) δ 8.88 (d, J=7.6 Hz, 1H), 8.60 (d, J=5.6 Hz, 1H), 8.44-8.43 (m, 1H), 7.84-7.81 (m, 1H), 7.61-7.50

(m, 2H), 7.34-7.24 (m, 4H), 4.34-4.31 (m, 1H), 3.36 (s, 3H), 2.77-2.73 (m, 2H), 2.51-2.50 (m, 1H), 2.31-2.21 (m, 1H). LC-MS (Method X): m/z=425.25 [M+H]+, 1.437 min.

Example 122: 3-benzyl-N-((2R,3S)-2,5-dimethyl-4-oxo-2,3,4,5-tetrahydropyrido[3,2-b][1,4]oxazepin-3-yl)isoxazole-5-carboxamide

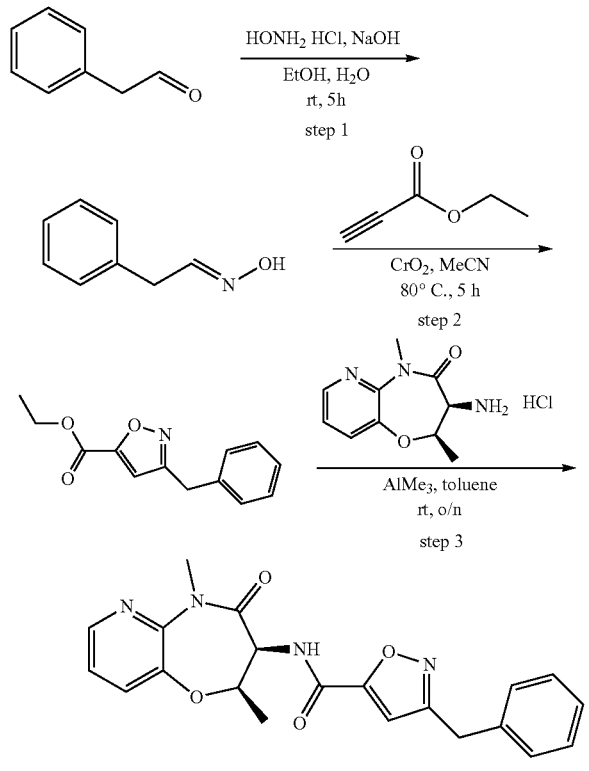

Step 1: Preparation of (E)-2-phenylacetaldehyde oxime

Sodium hydroxide (1.2 g, 30.0 mmol) was added to a mixture of 2-phenylacetaldehyde (1.2 g, 10.0 mmol) and hydroxylamine hydrochloride (1.4 g, 20.3 mmol) in ethanol (40 mL) and water (20 mL). The resulting mixture was stirred at room temperature for 5 hours, diluted with water (50 mL) and extracted with dichloromethane (3×80 mL). The combined organic layers were washed with brine, dried over anhydrous sodium sulfate, filtered and concentrated under vacuum. The residue was purified by column chromatography (methanol/dichloromethane, 1/20) to afford the title compound (400 mg, 29.6%) as a white solid. LC-MS (Method E): m/z=136.0 [M+H]+, 0.371 min.

Step 2: Preparation of ethyl 3-benzylisoxazole-5-carboxylate

Ethyl propiolate (2.7 g, 27.5 mmol) was added to a mixture of (E)-2-phenylacetaldehyde oxime (400 mg, 2.9 mmol) and chromium oxide (2.5 g, 29.7 mmol) in acetonitrile (50 mL). The reaction mixture was stirred at 80° C. for 5 hours. Solids were removed by filtration and the filtrate was evaporated under vacuum. The residue was purified by column chromatography (ethyl acetate/petroleum ether, 1/2) to afford the title compound (200 mg, 40%) as a yellow solid. LC-MS (Method C): m/z=232.0 [M+H]+, 1.200 min.

Step 3: Preparation of 3-benzyl-N-((2R,3S)-2,5-dimethyl-4-oxo-2,3,4,5-tetrahydropyrido[3,2-b][1,4]oxazepin-3-yl)isoxazole-5-carboxamide The crude product obtained using the procedure described in Example 54 was purified by Prep-HPLC with the following conditions: Column: XBridge C18 OBD Prep Column, 100 Å, 19×250 mm 5 μm; Mobile Phase A: water (10 mmol/L NH4HCO3), Mobile Phase B: ACN; Flow rate: 20 mL/min; Gradient: 35% B to 55% B over 7 min; UV 254 & 220 nm; Rt: 7 min to afford the title compound. 1H NMR (400 MHz, DMSO-d6) δ 8.73 (d, J=7.6 Hz, 1H), 8.34-8.33 (m, 1H), 7.71-7.69 (m, 1H), 7.36-7.24 (m, 6H), 7.18 (s, 1H), 5.03-4.99 (m, 1H), 4.84-4.78 (m, 1H), 4.06 (s, 2H), 3.40 (s, 3H), 1.37 (d, J=6.4 Hz, 3H). LC-MS (Method D): m/z=393.1 [M+H]+, 1.787 min.

Example 123: (S)-5-benzyl-N-(4-oxo-2,3,4,5-tetrahydropyrido[3,2-b][1,4]oxazepin-3-yl)thiazole-2-carboxamide

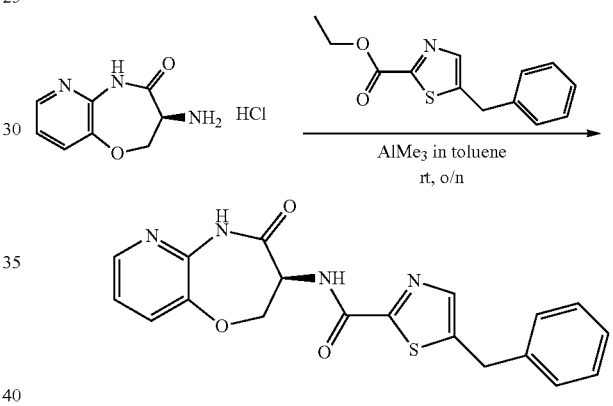

The crude product obtained using the procedure described in Example 54 was purified by Prep-HPLC with the following conditions: Column: XBridge C18 OBD Prep Column, 100 Å, 5 μm, 19 mm×250 mm; Mobile Phase A: water (10 mmol/L NH4HCO3), Mobile Phase B: ACN; Flow rate: 20 mL/min; Gradient: 20% B to 40% B over 7 min; UV 254 & 220 nm; Rt: 7 min to afford the title compound. 1H NMR (300 MHz, DMSO-d6) δ 10.56 (s, 1H), 8.92 (d, J=7.9 Hz, 1H), 8.15 (dd, J=4.7, 1.5 Hz, 1H), 7.88 (s, 1H), 7.56 (dd, J=8.0, 1.5 Hz, 1H), 7.41-7.12 (m, 6H), 4.88-4.74 (m, 1H), 4.62-4.41 (m, 2H), 4.28 (s, 2H). LC-MS (Method O): m/z=381.0 [M+H]+, 1.290 min.

Example 124: 5-benzyl-N-((2R,3S)-2,5-dimethyl-4-oxo-2,3,4,5-tetrahydropyrido[3,2-b][1,4]oxazepin-3-yl)thiazole-2-carboxamide

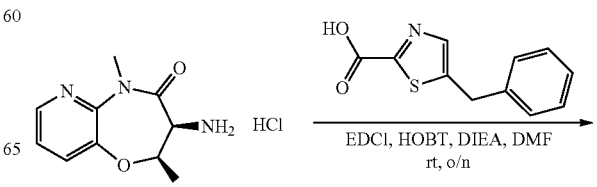

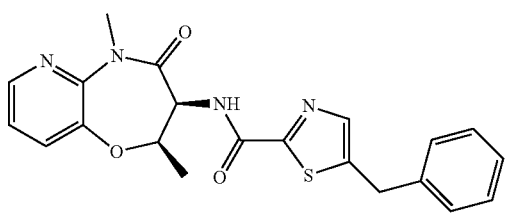

The crude product obtained using Amide Coupling Procedure C was purified by Prep-HPLC with the following conditions: Column: XBridge C18 OBD Prep Column, 19×150 mm, 5 μm; Mobile Phase A: water (10 mmol/L $NH_4HCO_3$), Mobile Phase B: ACN; Flow rate: 20 mL/min; Gradient: 40% B to 60% B over 7 min; UV 254 & 220 nm to afford the title compound (18.8 mg, 9%) as a white semi-solid. $^1$H NMR (400 MHz, Methanol-$d_4$) δ 8.36-8.30 (m, 1H), 7.76-7.65 (m, 2H), 7.37-7.22 (m, 6H), 5.04-4.96 (m, 2H), 4.26 (s, 2H), 3.50 (s, 3H), 1.42 (d, J=6.0 Hz, 3H). LC-MS (Method D): m/z=409.2 [M+H]$^+$, 1.638 min.

Example 125A & 125B: (R)-5-benzyl-N-(9'-methyl-8'-oxo-6',7',8',9'-tetrahydrospiro[cyclopropane-1,5'-pyrido[2,3-b]azepin]-7'-yl)-4H-1,2,4-triazole-3-carboxamide (125A) and (S)-5-benzyl-N-(9'-methyl-8'-oxo-6',7',8',9'-tetrahydrospiro[cyclopropane-1,5'-pyrido[2,3-b]azepin]-7'-yl)-4H-1,2,4-triazole-3-carboxamide (125B)

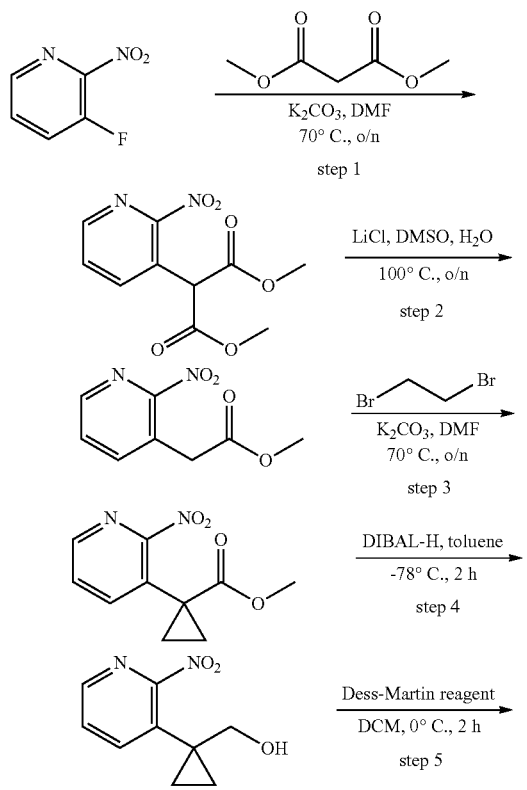

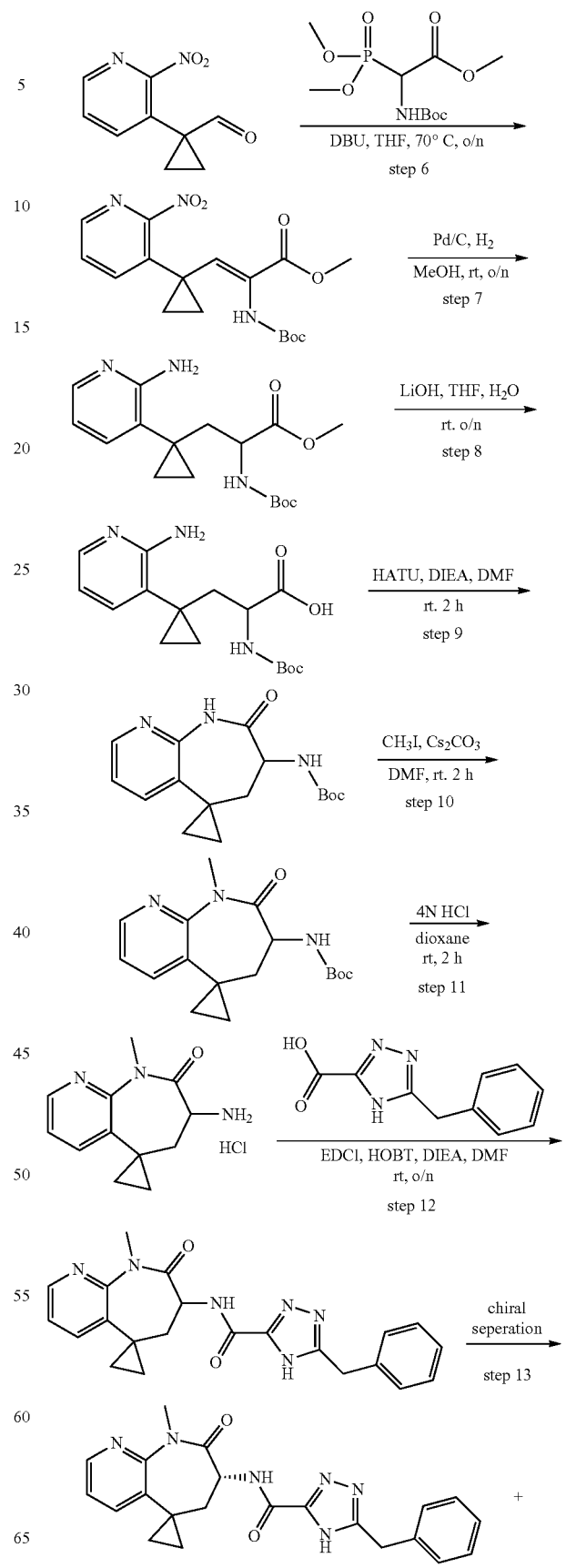

-continued

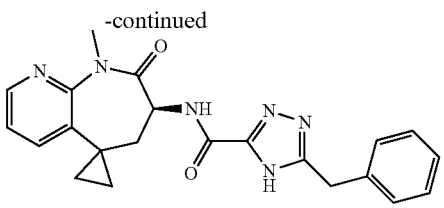

Step 1: Preparation of dimethyl 2-(2-nitropyridin-3-yl)malonate

Dimethyl malonate (14 g, 105.6 mmol) was added dropwise to a stirring mixture of 3-fluoro-2-nitropyridine (10 g, 70.4 mmol) and potassium carbonate (19.5 g, 140.8 mmol) in N,N-dimethylformamide (25 mL) at room temperature. The reaction mixture was stirred overnight at 70° C., quenched by the addition of water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (18 g, 89.8%) as a brown oil. LC-MS (Method R): m/z=255.1 [M+H]$^+$, 0.762 min.

Step 2: Preparation of methyl 2-(2-nitropyridin-3-yl)acetate

A solution of lithium chloride (8 g, 189 mmol) in water (10 mL) was added to a mixture of dimethyl 2-(2-nitropyridin-3-yl)malonate (16 g, 63 mmol) in dimethyl sulfoxide (50 mL). The reaction mixture was stirred at 100° C. overnight, quenched by the addition of water (50 mL) and extracted with ethyl acetate (3×50 mL). The combined organic layers were washed with brine, dried over anhydrous sodium sulfate, filtered and concentrated under vacuum to afford the title compound (12 g crude) as a brown oil. LC-MS (Method R): m/z=197.1 [M+H]$^+$, 0.673 min.

Step 3: Preparation of methyl 1-(2-nitropyridin-3-yl)cyclopropanecarboxylate 1,2-Dibromoethane (17 g, 91.8 mmol) was added dropwise to a stirring mixture of 3-fluoro-2-nitropyridine (12 g, 61.2 mmol) and potassium carbonate (25.3 g, 183.6 mmol) in N,N-dimethylformamide (25 mL) at room temperature. The reaction mixture was stirred overnight at 70° C., quenched by the addition of water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/3) to afford the title compound (5 g, 36.8%) as a red oil. LC-MS (Method R): m/z=223.1 [M+H]$^+$, 0.802 min.

Step 4: Preparation of (1-(2-nitropyridin-3-yl)cyclopropyl)methanol

A solution of diisobutylaluminium hydride in toluene (1 M, 45 mL, 45 mmol) was added dropwise to a stirring solution of methyl 1-(2-nitropyridin-3-yl)cyclopropanecarboxylate (5 g, 22.5 mmol) in toluene (50 mL) at −78° C. The reaction mixture was stirred at −78° C. for 2 hours, quenched by the addition of water (2 mL) and concentrated under vacuum. The residue was purified by column chromatography (ethyl acetate/petroleum ether, 1/3) to afford the title compound (3 g, 68.6%) as a yellow solid. LC-MS (Method C): m/z=195.1 [M+H]$^+$, 0.975 min.

Step 5: Preparation of 1-(2-nitropyridin-3-yl)cyclopropanecarbaldehyde

Dess-Martin periodinane (13 g, 30.9 mmol) was added to a stirring solution of (1-(2-nitropyridin-3-yl)cyclopropyl)methanol (3 g, 15.5 mmol) in dichloromethane (100 mL). The reaction mixture was stirred at 0° C. for 2 hours, quenched by the addition of water (50 mL) and extracted with dichloromethane (3×50 mL). The combined organic layers were washed with brine, dried over sodium sulfate, filtered and concentrated under vacuum. The residue was purified by column chromatography (ethyl acetate/petroleum ether, 1/3) to afford the title compound (2.5 g, 84.2%) as a yellow oil. LC-MS (Method C): m/z=193.0 [M+H]$^+$, 1.002 min.

Step 6: Preparation of (Z)-methyl 2-(tert-butoxycarbonylamino)-3-(1-(2-nitropyridin-3-yl)cyclopropyl)acrylate 1,8-Diazabicyclo[5.4.0]undec-7-ene (4 g, 26 mmol) was added to a stirring solution of methyl 2-{[(tert-butoxy)carbonyl]amino}-2-(dimethoxyphosphoryl)acetate (7.7 g, 26 mmol) in tetrahydrofuran (50 mL). The reaction mixture was stirred at 70° C. for 1 hour followed by the addition of a solution of 1-(2-nitropyridin-3-yl)cyclopropanecarbaldehyde (2.5 g, 13 mmol) in tetrahydrofuran (50 mL). Then the reaction mixture was stirred overnight at 70° C., quenched by the addition of water (50 mL) and extracted with dichloromethane (3×100 mL). The combined organic layers were washed with brine, dried over anhydrous sodium sulfate, filtered and concentrated under vacuum. The residue was purified by column chromatography (ethyl acetate/petroleum ether, 1/4) to afford the title compound (3 g, 63.5%) as a yellow solid. LC-MS (Method E): m/z=364.0 [M+H]$^+$, 0.860 min.

Step 7: Preparation of methyl 3-(1-(2-aminopyridin-3-yl)cyclopropyl)-2-(tert-butoxycarbonyl-amino)propanoate (Z)-methyl 2-(tert-butoxycarbonylamino)-3-(1-(2-nitropyridin-3-yl)cyclopropyl)acrylate (3 g, 8.26 mmol) in methanol (50 mL) was hydrogenated in the presence of palladium on carbon (10%, 0.3 g) under a hydrogen atmosphere (2-3 atm). The reaction mixture was stirred overnight at room temperature under a hydrogen atmosphere. The solids were removed by filtration and the filtrate was concentrated under high vacuum to afford the title compound (2.5 g crude) as a white solid. LC-MS (Method C): m/z=336.1 [M+H]$^+$, 0.926 min.

Step 8: Preparation of 3-(1-(2-aminopyridin-3-yl)cyclopropyl)-2-(tert-butoxycarbonylamino) propanoic acid Lithium hydroxide (358 mg, 14.9 mmol) was added to a solution of methyl 3-(1-(2-aminopyridin-3-yl)cyclopropyl)-2-(tert-butoxycarbonylamino)propanoate (2.5 g, 7.46 mmol) in tetrahydrofuran (15 mL) and water (5 mL). The reaction mixture was stirred at room temperature overnight and concentrated under vacuum. The residue was diluted with water (20 mL) and adjusted to pH=7 with aqueous hydrochloride acid (1 N, 10 mL) and extracted with ethyl acetate (3×10 mL). The combined organic layers were washed with brine, dried over anhydrous sodium sulfate and concentrated under vacuum to afford the title compound (1 g crude) as a white solid. LC-MS (Method R): m/z=322.1 [M+H]$^+$, 0.580 min.

Step 9: Preparation of tert-butyl (8'-oxo-6',7',8',9'-tetrahydrospiro[cyclopropane-1,5'-pyrido[2,3-b]azepin]-7'-yl)carbamate N,N-diisopropylethylamine (1.2 g, 9.34 mmol) was added to a mixture of 3-(1-(2-aminopyridin-3-yl)cyclopropyl)-2-(tert-butoxycarbonylamino)propanoic acid (1 g, 3.11 mmol), 2-(7-aza-1H-benzotriazole-1-yl)-1,1,3,3-tetramethyluronium hexafluorophosphate (1.59 g, 3.73 mmol) in N,N-dimethylformamide (20 mL). The reaction mixture was stirred for 2 hours at room temperature, quenched by the addition of water (20 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/3) to afford the title compound (500 mg, 53%) as a yellow solid. LC-MS (Method R): m/z=304.0 [M+H]$^+$, 0.842 min.

Step 10: Preparation of tert-butyl (9'-methyl-8'-oxo-6',7',8',9'-tetrahydrospiro[cyclopropane-1,5'-pyrido[2,3-b]azepin]-7'-yl)carbamate Iodomethane (52 mg, 0.36 mmol) was added dropwise to a stirring solution of tert-butyl(8'-oxo-6',7',8',9'-tetrahydrospiro[cyclopropane-1,5'-pyrido[2,3-b]azepin]-7'-yl)carbamate (110 mg, 0.36 mmol) and cesium carbonate (119 mg, 0.36 mmol) in N,N-dimethylformamide (5 mL) at 0° C. The reaction mixture was stirred 2 hours at room temperature, quenched by the addition of water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (110 mg, 95.6%) as a white solid. LC-MS (Method C): m/z=218.1 [M+H−100]$^+$, 1.613 min.

Step 11: Preparation of 7'-amino-9'-methyl-6',7'-dihydrospiro[cyclopropane-1,5'-pyrido[2,3-b]azepin]-8'(9'H)-one hydrochloride A solution of hydrogen chloride in 1,4-dioxane (4 M, 10 mL, 40 mmol) was added to a solution of tert-butyl (9'-methyl-8'-oxo-6',7',8',9'-tetrahydrospiro[cyclopropane-1,5'-pyrido[2,3-b]azepin]-7'-yl)carbamate (110 mg, 0.34 mmol) in 1,4-dioxane (4 mL). The reaction mixture was stirred for 2 hours at room temperature and concentrated under high vacuum to afford the title compound (80 mg crude) as a white solid. LC-MS (Method C): m/z=218.1 [M+H]$^+$, 0.777 min.

Step 12: Preparation of 5-benzyl-N-(9'-methyl-8'-oxo-6',7',8',9'-tetrahydrospiro-[cyclopropane-1,5'-pyrido[2,3-b]azepin]-7'-yl)-4H-1,2,4-triazole-3-carboxamide N,N-diisopropylethylamine (107 mg, 0.828 mmol) was added to a mixture of 5-benzyl-4H-1,2,4-triazole-3-carboxylic acid (62 mg, 0.304 mmol), 7'-amino-9'-methyl-6',7'-dihydrospiro[cyclopropane-1,5'-pyrido[2,3-b]azepin]-8' (9'H)-one hydrochloride (60 mg, 0.276 mmol), N-(3-dimethylaminopropyl))-N'-ethylcarbodiimide hydrochloride (69 mg, 0.359 mmol) and 1-hydroxybenzotriazole (49 mg, 0.359 mmol) in N,N-dimethylformamide (4 mL). The reaction mixture was stirred overnight at room temperature, diluted with water (20 mL) and extracted with ethyl acetate (3×50 mL). The combined organic layers were washed with brine, dried over anhydrous sodium sulfate, filtered and concentrated under vacuum. The residue was purified by Prep-HPLC with the following conditions: Column: X Bridge Prep C18 OBD Column 19×150 mm, 5 µm; Mobile Phase A: water (10 mmol/L NH$_4$HCO$_3$), Mobile Phase B: ACN; Flow rate: 30 mL/min; Gradient: 25% B to 55% B over 7 min; UV 254 & 220 nm to afford the title compound. LC-MS (Method D): m/z=403.1 [M+H]$^+$, 1.460 min.

Step 13: Preparation of (R)-5-benzyl-N-(9'-methyl-8'-oxo-6',7',8',9'-tetrahydrospiro-[cyclopropane-1,5'-pyrido[2,3-b]azepin]-7'-yl)-4H-1,2,4-triazole-3-carboxamide (First Eluting Isomer) and (S)-5-benzyl-N-(9'-methyl-8'-oxo-6',7',8',9'-tetrahydrospiro [cyclopropane-1,5'-pyrido[2,3-b]azepin]-7'-yl)-4H-1,2,4-triazole-3-carboxamide (Second Eluting Isomer)

The racemate of 5-benzyl-N-(9'-methyl-8'-oxo-6',7',8',9'-tetrahydrospiro-[cyclopropane-1,5'-pyrido[2,3-b]azepin]-7'-yl)-4H-1,2,4-triazole-3-carboxamide (60 mg, 0.149 mmol) was separated by Prep-Chiral-HPLC with the following conditions: Column: Chiralpak ID-2, 2×25 cm, 5 µm; Mobile Phase A: hexane/DCM (4.5/1), Mobile Phase B: EtOH; Flow rate: 17 mL/min; Gradient: 50% B to 50% B over 22 min; UV 254 & 220 nm; RT 1: 11.72 min; RT 2: 18.02 min to afford the title compounds:

Example 125A (first eluting isomer): $^1$H NMR (300 MHz, DMSO-d$_6$) δ 14.27 (s, 1H), 8.41 (dd, J=4.8, 1.8 Hz, 2H), 7.75 (dd, J=7.6, 1.8 Hz, 1H), 7.34-7.18 (m, 6H), 4.42-4.33 (m, 1H), 4.09 (s, 2H), 3.31 (s, 3H), 2.73-2.63 (m, 1H), 1.73-1.62 (m, 1H), 1.09-1.05 (m, 1H), 0.70 (d, J=5.4 Hz, 2H), 0.36 (d, J=10.0 Hz, 1H). LC-MS (Method D): m/z=403.1 [M+H]$^+$, 1.661 min.

Example 125B (second eluting isomer): $^1$H NMR (300 MHz, DMSO-d$_6$) δ 14.27 (s, 1H), 8.41 (dd, J=4.8, 1.8 Hz, 2H), 7.75 (dd, J=7.6, 1.8 Hz, 1H), 7.35-7.18 (m, 6H), 4.40-4.33 (m, 1H), 4.09 (s, 2H), 3.30 (s, 3H), 2.69 (t, J=10.6 Hz, 1H), 1.68 (t, J=12.3 Hz, 1H), 1.07 (d, J=10.0 Hz, 1H), 0.70 (d, J=5.5 Hz, 2H), 0.36 (d, J=9.9 Hz, 1H). LC-MS (Method D): m/z=403.1 [M+H]$^+$, 1.673 min.

Example 126: (S)-5-benzyl-4-fluoro-N-(5-methyl-4-oxo-2,3,4,5-tetrahydropyrido[3,2-b][1,4]oxazepin-3-yl)thiazole-2-carboxamide

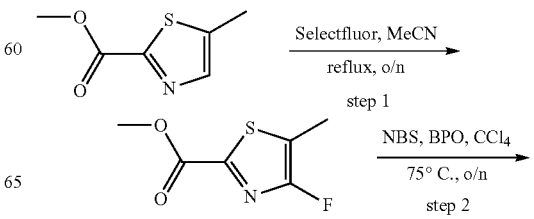

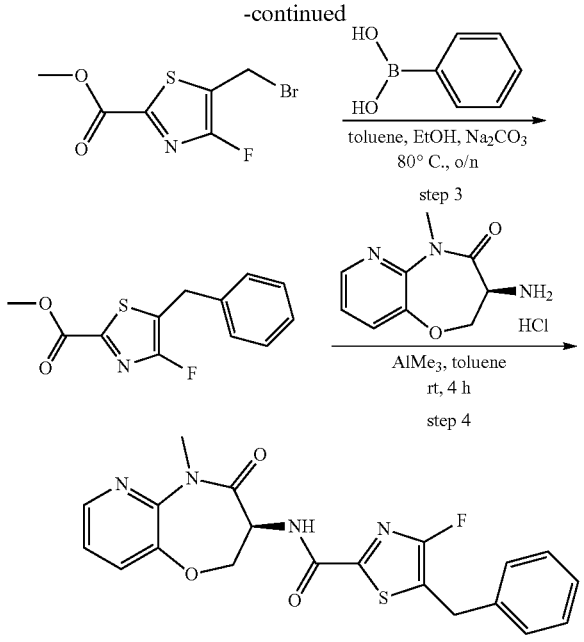

Step 1: Preparation of methyl 4-fluoro-5-methylthiazole-2-carboxylate

1-Chloromethyl-4-fluoro-1,4-diazoniabicyclo[2.2.2]octane bis(tetrafluoroborate) (7.0 g, 19.8 mmol) was added to a mixture of methyl 4-fluoro-5-methylthiazole-2-carboxylate (1.6 g, 10.2 mmol) in acetonitrile (50 mL) under a nitrogen atmosphere. The reaction mixture was heated to reflux and stirred overnight, diluted with water (50 mL) and extracted with ethyl acetate (3×40 mL). The combined organic layers were dried over anhydrous sodium sulfate, filtered and concentrated under vacuum. The residue was purified by column chromatography (ethyl acetate/petroleum ether, 1/3) to afford the title compound (600 mg, 33.7%) as a white solid. LC-MS (Method C): m/z=176.1 [M+H]$^+$, 1.240 min.

Step 2: Preparation of methyl 5-(bromomethyl)-4-fluorothiazole-2-carboxylate Benzoyl peroxide (10 mg, 0.04 mmol) was added to a mixture of N-bromosuccinimide (650 mg, 3.6 mmol) and methyl 4-fluoro-5-methylthiazole-2-carboxylate (600 mg, 3.4 mmol) in carbon tetrachloride (20 mL). The reaction mixture was stirred overnight at 75° C. Solids were removed by filtration. The filtrate was diluted with water (20 mL) and extracted with ethyl acetate (3×20 mL). The combined organic layers were washed with saturated sodium bicarbonate (20 mL) and brine, dried over anhydrous sodium sulfate, filtered and concentrated under vacuum. The residue was purified by column chromatography (ethyl acetate/petroleum ether, 1/2) to afford the title compound (600 mg, 68.9%) as a yellow solid. LC-MS (Method F): m/z=254 [M+H]$^+$, 1.490 min.

Step 3: Preparation of methyl 5-benzyl-4-fluorothiazole-2-carboxylate

Tetrakis(triphenylphosphine)palladium (147 mg, 0.13 mmol) was added to a mixture of methyl 5-(bromomethyl)-4-fluorothiazole-2-carboxylate (582 mg, 2.3 mmol), phenylboronic acid (402 mg, 3.3 mmol) and sodium carbonate (1 g, 9.4 mmol) in toluene (20 mL) and ethanol (10 mL) under a nitrogen atmosphere. The reaction mixture was stirred at 80° C. overnight, quenched by the addition of water (20 mL) and extracted with ethyl acetate (3×40 mL). The combined organic layers were washed with brine, dried over anhydrous sodium sulfate, filtered and concentrated under vacuum. The residue was purified by column chromatography (ethyl acetate/petroleum ether, 1/2) to afford the title compound (400 mg, 66.6%) as a yellow solid. LC-MS (Method C): m/z=252.2 [M+H]$^+$, 1.971 min.

Step 4: (S)-5-benzyl-4-fluoro-N-(5-methyl-4-oxo-2,3,4,5-tetrahydropyrido[3,2-b][1,4]oxazepin-3-yl)thiazole-2-carboxamide The crude product obtained using the procedure described in Example 54 was purified by Prep-HPLC with the following conditions: Column: XBridge Prep C18 OBD Column, 19×150 mm, 5 μm; Mobile phase A: water (10 mmol/L NH$_4$HCO$_3$), Mobile phase B: ACN; 40% ACN up to 70% B over 7 min; UV 254 & 220 nm to afford the title compound. $^1$H NMR (400 MHz, DMSO-d$_6$) δ 9.14 (d, J=7.6 Hz, 1H), 8.36 (dd, J=4.8, 1.6 Hz, 1H), 7.70 (dd, J=8.0, 1.6 Hz, 1H), 7.39-7.21 (m, 6H), 4.88-4.71 (m, 2H), 4.51 (t, J=5.6 Hz, 1H), 4.17 (s, 2H), 3.34 (s, 3H). LC-MS (Method V): m/z=413.00 [M+H]$^+$, 2.480 min.

Example 127: 1-(4-Cyanobenzyl)-N-((2R,3S)-2,5-dimethyl-4-oxo-2,3,4,5-tetrahydropyrido[3,2-b][1,4]oxazepin-3-yl)-4-fluoro-1H-pyrazole-3-carboxamide

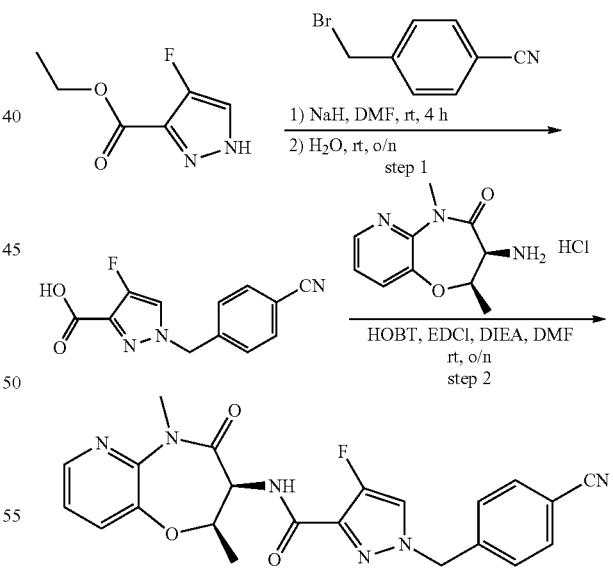

Step 1: Preparation of 1-(4-cyanobenzyl)-4-fluoro-1H-pyrazole-3-carboxylic acid Sodium hydride (60%, 144 mg, 6 mmol) was added to a stirring mixture of ethyl 4-fluoro-1H-pyrazole-3-carboxylate (474 mg, 3 mmol) in N,N-dimethylformamide (20 mL). The resulting mixture was stirred for 2 hours at room temperature, followed by the addition of 4-(bromomethyl)

benzonitrile (585 mg, 3 mmol). The resulting mixture was stirred for 2 hours at room temperature. After the addition of water (20 mL), the reaction mixture was stirred overnight at room temperature, the pH was adjusted to 6 with aqueous hydrochloric acid (1 N, 10 mL) and extracted with ethyl acetate (3×50 mL). The combined organic layers were washed with brine, dried over anhydrous sodium sulfate, filtered and concentrated under vacuum. The residue was purified by Prep-HPLC with the following conditions: Column: XBridge C18 OBD Prep Column, 100 Å, 5 μm, 19 mm×250 mm; Mobile Phase A: Water (0.1% formic acid), Mobile Phase B: ACN; Flow rate: 20 mL/min; Gradient: 30% B to 50% B over 7 min; UV 254 & 220 nm; Rt: 7 min to afford the title compound (250 mg, 34%) as a white solid. LC-MS (Method C): m/z=246.1 [M+H]+, 0.969 min.

Step 2: Preparation of 1-(4-cyanobenzyl)-N-((2R, 3S)-2,5-dimethyl-4-oxo-2,3,4,5 tetrahydropyrido[3, 2-b][1,4]oxazepin-3-yl)-4-fluoro-1H-pyrazole-3-carboxamide The crude product obtained using Amide Coupling Procedure C was purified by Prep-HPLC with the following conditions: Column: XBridge C18 OBD Prep Column, 100 Å, 5 μm, 19 mm×250 mm; Mobile Phase A: Water (0.1% formic acid), Mobile Phase B: ACN; Flow rate: 20 mL/min; Gradient: 25% B to 48% B over 12 min; UV 254 & 220 nm; Rt: 7 min to afford the title compound. $^1$H NMR (400 MHz, DMSO-$d_6$) δ 8.35 (dd, J=4.8, 1.6 Hz, 1H), 8.20 (d, J=4.4 Hz, 1H), 7.88-7.85 (m, 2H), 7.75 (dd, J=8.0, 1.6 Hz, 1H), 7.61 (d, J=6.4 Hz, 1H), 7.44-7.41 (m, 2H), 7.36 (dd, J=8.0, 4.8 Hz, 1H), 5.50 (s, 2H), 4.99-4.88 (m, 2H), 3.39 (s, 3H), 1.31 (d, J=6.4 Hz, 3H). LC-MS (Method X): m/z=435.2 [M+H]+, 1.355 min.

Example 128: 1-(3-Cyanobenzyl)-N-((2R,3S)-2,5-dimethyl-4-oxo-2,3,4,5-tetrahydropyrido[3,2-b][1,4]oxazepin-3-yl)-4-fluoro-1H-pyrazole-3-carboxamide Step 1: Preparation of 1-(3-cyanobenzyl)-4-fluoro-1H-pyrazole-3-carboxylic acid Sodium hydride (60%, 144 mg, 6 mmol) was added to a stirring mixture of ethyl 4-fluoro-1H-pyrazole-3-carboxylate (474 mg, 3 mmol) in N,N-dimethylformamide (20 mL) at 0° C. The resulting mixture was stirred for 2 hours at room temperature, followed by addition of 4-(bromomethyl)benzonitrile (585 mg, 3 mmol). The reaction mixture was stirred for another 2 hours at room temperature. After addition of water (20 mL), the resulting mixture was stirred overnight at room temperature. The pH value of the solution was adjusted to 6 with aqueous hydrochloric acid (1 N, 10 mL). The resulting mixture was extracted with ethyl acetate (3×50 mL). The combined organic layers were washed with brine, dried over anhydrous sodium sulfate, filtered and concentrated under vacuum. The residue was purified by Prep-HPLC with the following conditions: Column: XBridge Prep C18 OBD Column 19×150 mm, 5 μm; Mobile Phase A: water (0.1% formic acid), Mobile Phase B: ACN; Flow rate: 20 mL/min; Gradient: 20% B to 50% B over 7 min; UV 254 & 220 nm; Rt: 6 min to afford the title compound (230 mg, 31%) as a white solid. LC-MS (Method C): m/z=246.1 [M+H]+, 1.236 min.

Step 2: Preparation of 1-(3-cyanobenzyl)-N-((2R, 3S)-2,5-dimethyl-4-oxo-2,3,4,5-tetrahydropyrido[3, 2-b][1,4]oxazepin-3-yl)-4-fluoro-1H-pyrazole-3-carboxamide The crude product obtained using Amide Coupling Procedure C was purified by Prep-HPLC with the following conditions: Column: XBridge C18 OBD Prep Column, 100 Å, 5 μm, 19 mm×250 mm; Mobile Phase A: water (0.1% formic acid), Mobile Phase B: ACN; Flow rate: 20 mL/min; Gradient: 25% B to 48% B over 12 min; UV 254 & 220 nm; Rt: 7 min to afford the title compound. $^1$H NMR (400 MHz, DMSO-$d_6$) δ 8.36 (dd, J=4.8, 1.6 Hz, 1H), 8.19 (d, J=4.4 Hz, 1H), 7.86-7.79 (m, 2H), 7.75 (dd, J=8.0, 1.6 Hz, 1H), 7.62-7.60 (m, 3H), 7.36 (dd, J=8.0, 4.4 Hz, 1H), 5.45 (s, 2H), 4.99-4.88 (m, 2H), 3.40 (s, 3H), 1.32 (d, J=6.0 Hz, 3H). LC-MS (Method D): m/z=435.1 [M+H]+, 1.659 min.

Example 129A and 129B: (S)-5-Benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide and (R)-5-Benzyl-N-(2,4-dimethyl-5-oxo-5,6,7, 8-tetrahydro-4H-pyrazolo[1,5-a][1,3]diazepin-6-yl)-4H-1,2,4-triazole-3-carboxamide

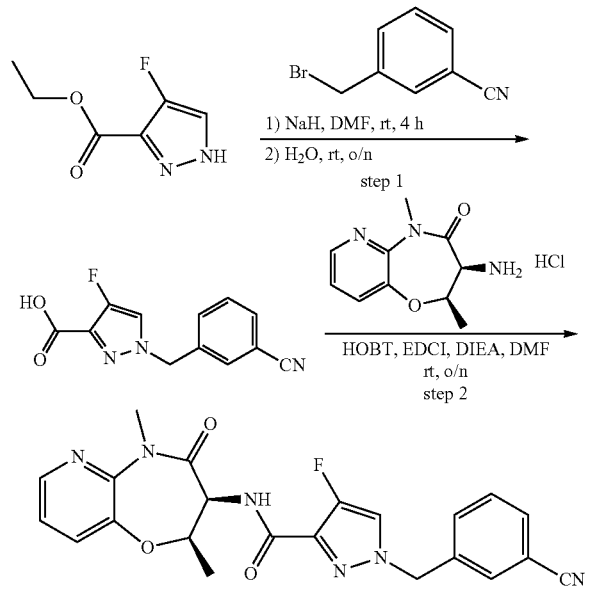

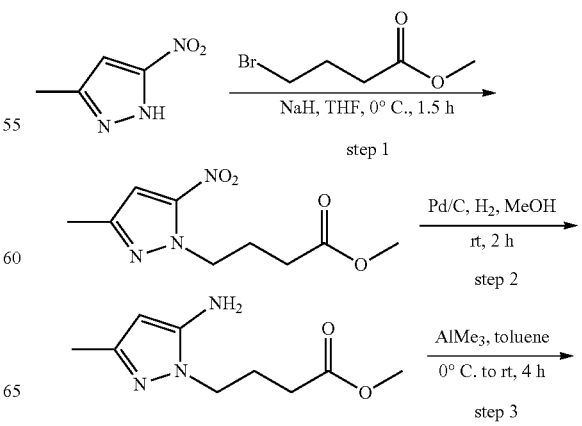

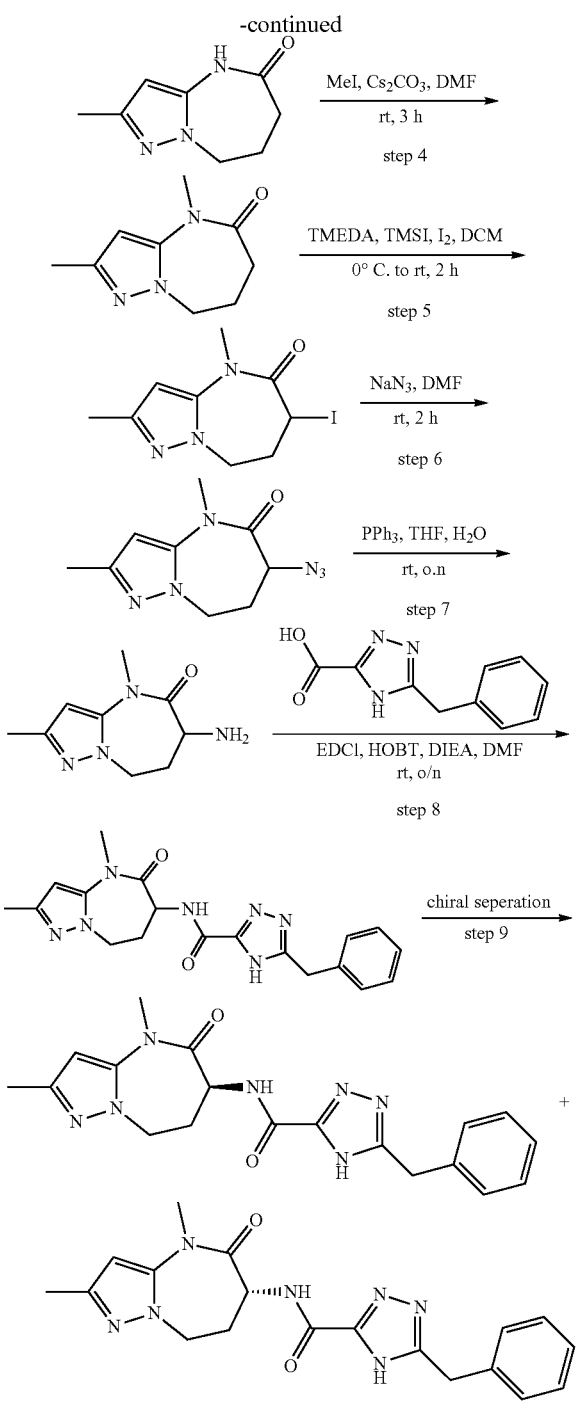

Step 1: Preparation of methyl 4-(3-methyl-5-nitro-1H-pyrazol-1-yl)butanoate

Sodium hydride (60%, 2.5 g, 63 mmol) was added to a mixture of 3-methyl-5-nitro-1H-pyrazole (8 g, 63 mmol) in tetrahydrofuran (80 mL) at 0° C. The resulting mixture was stirred for 0.5 hour at 0° C. followed by the addition of methyl 4-bromobutanoate (11.2 g, 63 mmol). The reaction mixture was stirred for 1 hour at 0° C., quenched by the addition of water (40 mL) and extracted with ethyl acetate (3×60 mL). The combined organic layers were washed with brine, dried over sodium sulfate, filtered and concentrated under vacuum. The residue was purified by column chromatography (ethyl acetate/petroleum ether, 1/10) to afford the title compound (2.2 g, 15%) as a colorless oil. LC-MS (Method C): m/z=228.1 [M+H]$^+$, 1.180 min.

Step 2: Preparation of methyl 4-(5-amino-3-methyl-1H-pyrazol-1-yl)butanoate

A mixture of methyl 4-(3-methyl-5-nitro-1H-pyrazol-1-yl)butanoate (2.2 g, 9.7 mmol) in methanol (50 mL) was hydrogenated in the presence of palladium on carbon (10%, 0.2 g) under a hydrogen atmosphere (2-3 atm). After stirring for 2 hours at room temperature under hydrogen atmosphere, the reaction mixture was filtered through Celite. The filtrate was concentrated under vacuum to afford the title compound (1.8 g, 94%) as a yellow solid. LC-MS (Method C): m/z=198.1 [M+H]$^+$, 0.733 min.

Step 3: Preparation of 2-methyl-7,8-dihydro-4H-pyrazolo[1,5-a][1,3]diazepin-5(6H)-one The crude product obtained using the procedure described in Example 54 was purified by column chromatography (methanol/dichloromethane, 1/10) to afford the title compound (1.0 g, 66%) as a yellow solid. LC-MS (Method C): m/z=166.1 [M+H]$^+$, 0.755 min.

Step 4: Preparation of 2,4-dimethyl-7,8-dihydro-4H-pyrazolo[1,5-a][1,3]diazepin-5(6H)-one Iodomethane (0.74 g, 5.4 mmol) was added dropwise to a stirring mixture of 2-methyl-7,8-dihydro-4H-pyrazolo[1,5-a][1,3]diazepin-5(6H)-one (0.90 g, 5.4 mmol) and cesium carbonate (5.28 g, 16.2 mmol) in N,N-dimethylformamide (15 mL). The reaction mixture was stirred for 3 hours at room temperature, diluted with water (20 mL) and extracted with ethyl acetate (3×50 mL). The combined organic layers were washed with brine, dried over anhydrous sodium sulfate, filtered and concentrated under vacuum. The residue was purified by column chromatography (methanol/dichloromethane, 1/20) to afford the title compound (0.72 g, 74%) as a yellow solid. LC-MS (Method C): m/z=180.1 [M+H]$^+$, 0.865 min.

Step 5: Preparation of 6-iodo-2,4-dimethyl-7,8-dihydro-4H-pyrazolo[1,5-a][1,3]diazepin-5(6H)-one $N^1,N^1,N^2,N^2$-tetramethylethane-1,2-diamine (1.2 g, 12.0 mmol) was added to a stirring mixture of 2,4-dimethyl-7,8-dihydro-4H-pyrazolo[1,5-a][1,3]diazepin-5(6H)-one (720 mg, 4.0 mmol) in dichloromethane (10 mL) at 0° C. followed by addition of iodotrimethylsilane (2.4 g, 12.0 mmol) dropwise over 20 min. The reaction mixture was stirred for 1 hour at 0° C. After addition of iodine (2.0 g, 8.0 mmol), the reaction mixture was stirred for another 1 hour at 0° C. Then the mixture was quenched by the addition of aqueous sodium thiosulfate (5%, 20 mL), stirred for another 15 minutes and extracted with ethyl acetate (3×50 mL). The combined organic layers were washed with brine, dried over anhydrous sodium sulfate, filtered and concentrated under vacuum. The residue was purified by column chromatography (dichloromethane) to afford the title compound (500 mg, 41%) as a yellow solid. LC-MS (Method C): m/z=306.0 [M+H]$^+$, 1.033 min.

Step 6: Preparation of 6-azido-2,4-dimethyl-7,8-dihydro-4H-pyrazolo[1,5-a][1,3]diazepin-5(6H)-one Sodium azide (137 mg, 2.10 mmol) was added to a mixture of 6-iodo-2,4-dimethyl-7,8-dihydro-4H-pyrazolo[1, 5-a][1,3]diazepin-5(6H)-one (500 mg, 1.64 mmol) in N,N-dimethylformamide (10 mL). The resulting mixture was stirred for 2 hours at room temperature, quenched by the addition of water (40 mL) and extracted with ethyl acetate (3×50 mL). The combined organic layers were washed with brine, dried over sodium sulfate, filtered and concentrated under vacuum to afford the title compound (280 mg crude) as a yellow oil. LC-MS (Method S): m/z=221.3 [M+H]$^+$, 0.763 min.

Step 7: Preparation of 6-amino-2,4-dimethyl-7,8-dihydro-4H-pyrazolo[1,5-a][1,3]diazepin-5(6H)-one Triphenylphosphine (734 mg, 2.80 mmol) was added to a stirring mixture of 6-azido-2,4-dimethyl-7,8-dihydro-4H-pyrazolo[1,5-a][1,3]diazepin-5(6H)-one in tetrahydrofuran (10 mL) and water (2 mL). The reaction mixture was stirred overnight at room temperature, diluted with water (20 mL) and extracted with ethyl acetate (3×50 mL). The combined organic layers were washed with brine, dried over anhydrous sodium sulfate, filtered and concentrated under vacuum. The residue was purified by column chromatography (methanol/dichloromethane, 1/10) to afford the title compound (200 mg, 62%) as a yellow oil. LC-MS (Method I): m/z=195.0 [M+H]$^+$, 0.263 min.

Step 8: Preparation of 5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide N,N-diisopropylethylamine (140 mg, 1.13 mmol) was added to a mixture of 5-benzyl-4H-1,2,4-triazole-3-carboxylic acid (73 mg, 0.36 mmol), 6-amino-2,4-dimethyl-7,8-dihydro-4H-pyrazolo[1,5-a][1,3]diazepin-5(6H)-one (70 mg, 0.36 mmol), N-(3-dimethylaminopropyl)-N'-ethylcarbodiimide hydrochloride (77 mg, 0.39 mmol) and 1-hydroxybenzotriazole (65 mg, 0.39 mmol) in N,N-dimethylformamide (2 mL). The reaction mixture was stirred overnight at room temperature, diluted with water (10 mL) and extracted with ethyl acetate (3×20 mL). The combined organic layers were washed with brine, dried over anhydrous sodium sulfate, filtered and concentrated under vacuum. The residue was purified by Prep-HPLC with the following conditions: Column: XBridge Prep C18 OBD Column, 5 μm, 19×150 mm; Mobile Phase A: water (0.1% formic acid), Mobile Phase B: ACN; Flow rate: 20 mL/min; Gradient: 15% B to 45% B over 7 min; UV 254 & 220 nm; Rt: 6 min to afford the title compound (50 mg, 36%) as a white solid. LC-MS (Method Y): m/z=380.2 [M+H]$^+$, 0.750 min.

Step 9: Preparation of (S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide (129A) and (R)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide (129B)

The racemate of 5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide was separated by Prep-Chiral-HPLC with the following conditions: Column: Chiralpak IC, 2×25 cm, 5 μm; Mobile Phase A: hexane, Mobile Phase B: EtOH; Flow rate: 20 mL/min; Gradient: 50% B to 50% B over 22 min; UV 254 & 220 nm; Rt 1: 10.04 min; Rt 2: 18.12 min to afford the title compounds:

Example 129A (first eluting isomer): $^1$H NMR (300 MHz, DMSO-d$_6$) δ 14.31 (s, 1H), 8.55 (s, 1H), 7.40-7.18 (m, 5H), 6.13 (s, 1H), 4.41-4.20 (m, 2H), 4.20-4.02 (m, 3H), 3.23 (s, 3H), 2.65-2.26 (m, 2H), 2.18 (s, 3H). LC-MS (Method D): m/z=380.2 [M+H]$^+$, 1.298 min.

Example 129B (second eluting isomer): $^1$H NMR (300 MHz, DMSO-d$_6$) δ 14.30 (s, 1H), 8.46 (s, 1H), 7.38-7.20 (m, 5H), 6.13 (s, 1H), 4.41-4.20 (m, 2H), 4.20-4.02 (m, 3H), 3.23 (s, 3H), 2.61-2.37 (m, 2H), 2.17 (s, 3H). LC-MS (Method D): m/z=380.2 [M+H]$^+$, 1.300 min.

Example 130: (S)-1-(3-Cyano-5-fluorobenzyl)-4-fluoro-N-(5-methyl-4-oxo-2,3,4,5-tetrahydropyrido[3,2-b][1,4]oxazepin-3-yl)-1H-pyrazole-3-carboxamide

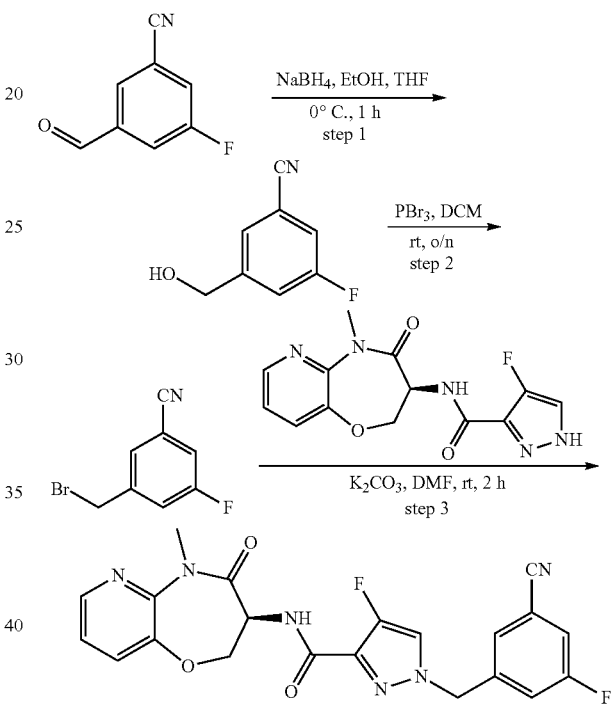

Step 1: Preparation of 3-fluoro-5-(hydroxymethyl)benzonitrile

Sodium borohydride (1.0 g, 6.71 mmol) was added to a stirring mixture of 3-fluoro-5-formylbenzonitrile (306 mg, 8.05 mmol) in ethanol (10 mL) and tetrahydrofuran (10 mL) at 0° C. under nitrogen atmosphere. After stirring at 0° C. for 1 hour, the reaction mixture was concentrated under vacuum, diluted with water (50 mL) and extracted with ethyl acetate (3×50 mL). The combined organic layers were washed with brine, dried over anhydrous sodium sulfate, filtered and concentrated under vacuum to afford the title compound (980 mg crude) as a yellow solid. LC-MS (Method T): m/z=152.3 [M+H]$^+$, 0.671 min.

Step 2: Preparation of 3-(bromomethyl)-5-fluorobenzonitrile

Tribromophosphine (2.9 g, 10.7 mmol) was added to a stirring mixture of 3-fluoro-5-(hydroxymethyl)benzonitrile (0.8 g, 5.30 mmol) in dichloromethane (10 mL). After stirring overnight at room temperature, the reaction mixture was concentrated under vacuum to afford the title compound (0.8 g crude) as a yellow solid, which was used directly in the next step without further purification.

Step 3: Preparation of (S)-1-(3-cyano-5-fluorobenzyl)-4-fluoro-N-(5-methyl-4-oxo-2,3,4,5-tetrahydropyrido[3,2-b][1,4]oxazepin-3-yl)-1H-pyrazole-3-carboxamide Potassium carbonate (55 mg, 0.40 mmol) was added to a stirring mixture of (S)-4-fluoro-N-(5-methyl-4-oxo-2,3,4,5-tetrahydropyrido[3,2-b][1,4]oxazepin-3-yl)-1H-pyrazole-3-carboxamide (40 mg, 0.13 mmol) and 3-(bromomethyl)-5-fluorobenzonitrile (34 mg, 0.16 mmol) in N,N-dimethylformamide (2 mL). After stirring at room temperature for 2 hours, the reaction mixture was diluted with water (20 mL) and extracted with ethyl acetate (3×20 mL). The combined organic layers were washed with brine, dried over anhydrous sodium sulfate, filtered and concentrated under vacuum. The residue was purified by Prep-HPLC with the following conditions: Column: XBridge Prep C18 OBD Column, 5 μm, 19×150 mm; Mobile Phase A: water (10 mmol/L NH$_4$HCO$_3$), Mobile Phase B: ACN; Flow rate: 30 mL/min; Gradient: 35% B to 65% B over 5 min; UV 254 & 220 nm; Rt: 3.75 min to afford the title compound. $^1$H NMR (400 MHz, DMSO-d$_6$) δ 8.37 (dd, J=4.8, 1.6 Hz, 1H), 8.28 (d, J=8.0 Hz, 1H), 8.18 (d, J=4.4 Hz, 1H), 7.90-7.86 (m, 1H), 7.71 (dd, J=7.6, 1.2 Hz, 1H), 7.66 (s, 1H), 7.56-7.52 (m, 1H), 7.36-7.32 (m, 1H), 5.44 (s, 2H), 4.89-4.81 (m, 1H), 4.70-4.64 (m, 1H), 4.54-4.49 (m, 1H), 3.36 (s, 3H). LC-MS (Method X): m/z=439.2 [M+H]$^+$, 1.291 min.

Example 131A and 131B: (S)-5-Benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide and (R)-5-Benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide

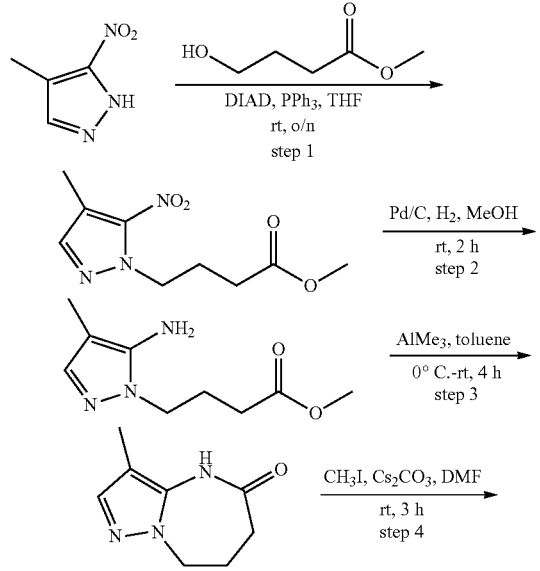

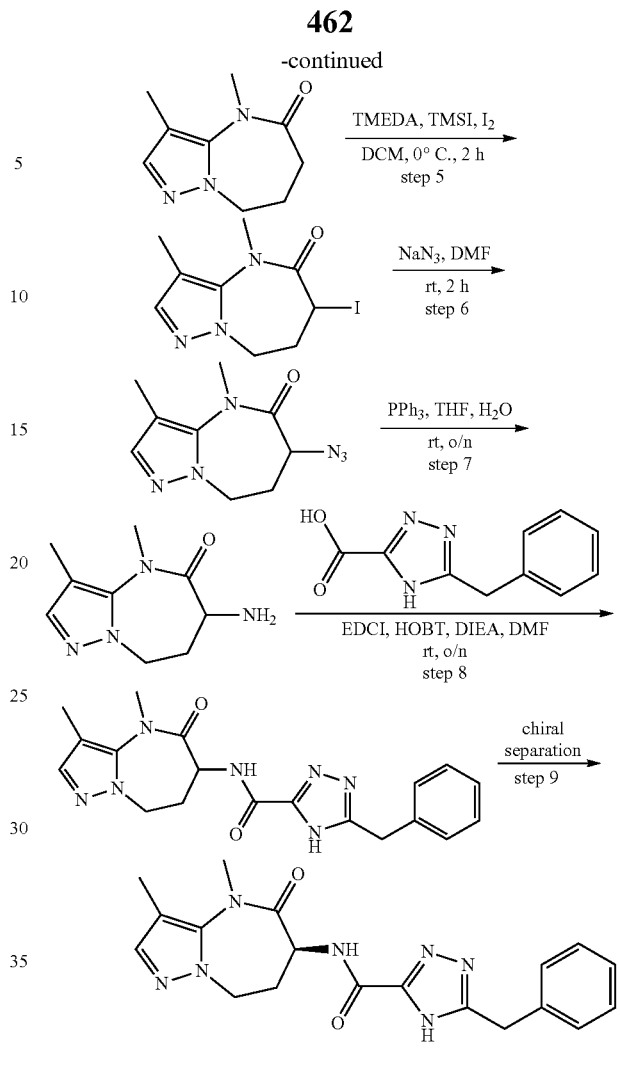

Step 1: Preparation of methyl 4-(4-methyl-5-nitro-1H-pyrazol-1-yl)butanoate

Diisopropyl azodicarboxylate (3.4 g, 16.9 mmol) was slowly added to a stirring mixture of methyl 4-hydroxybutanoate (2 g, 16.9 mmol), 4-methyl-5-nitro-1H-pyrazole (1 g, 7.8 mmol) and triphenylphosphine (4.44 g, 16.9 mmol) in tetrahydrofuran (40 mL) at 0° C. under nitrogen atmosphere. After stirring overnight at room temperature, the reaction mixture was quenched by the addition of water (100 mL) and extracted with ethyl acetate (3×100 mL). The combined organic layers were washed with brine, dried over sodium sulfate, filtered and concentrated under vacuum. The residue was purified by column chromatography (ethyl acetate/ petroleum ether, 1/10) to afford the title compound (1.0 g, 56%) as a colorless oil. LC-MS (Method C): m/z=228.1 [M+H]⁺, 1.130 min.

Step 2: Preparation of methyl
4-(5-amino-4-methyl-1H-pyrazol-1-yl)butanoate

A solution of methyl 4-(4-methyl-5-nitro-1H-pyrazol-1-yl)butanoate (1.0 g, 4.4 mmol) in methanol (30 mL) was hydrogenated in the presence of palladium on carbon (10%, 0.1 g) under a hydrogen atmosphere (2-3 atm). After stirring for 2 hours at room temperature under hydrogen atmosphere, the reaction mixture was filtered through Celite. The filtrate was concentrated under vacuum to afford the title compound (0.85 mg, 97%) as a yellow solid. LC-MS (Method I): m/z=197.9 [M+H]⁺, 1.013 min.

Step 3: Preparation of 3-methyl-7,8-dihydro-4H-pyrazolo[1,5-a][1,3]diazepin-5(6H)-one The crude product obtained using the procedure described in Example 54 was purified by column chromatography (methanol/dichloromethane, 1/10) to afford the title compound (600 mg, 84%) as a yellow solid. LC-MS (Method C): m/z=166.1 [M+H]⁺, 0.782 min.

Step 4: Preparation of 3,4-dimethyl-7,8-dihydro-4H-pyrazolo[1,5-a][1,3]diazepin-5(6H)-one Iodomethane (511 mg, 3.6 mmol) was added to a stirring mixture of 3-methyl-7,8-dihydro-4H-pyrazolo[1,5-a][1,3]diazepin-5(6H)-one (600 mg, 3.6 mmol) and cesium carbonate (3.52 g, 10.8 mmol) in N,N-dimethylformamide (15 mL). The reaction mixture was stirred for 3 hours at room temperature, diluted with water (50 mL) and extracted with ethyl acetate (3×50 mL). The combined organic layers were washed with brine, dried over anhydrous sodium sulfate, filtered and concentrated under vacuum. The residue was purified by column chromatography (methanol/dichloromethane, 1/20) to afford the title compound (480 mg, 78%) as a yellow solid. LC-MS (Method C): m/z=180.1 [M+H]⁺, 0.876 min.

Step 5: Preparation of 6-iodo-3,4-dimethyl-7,8-dihydro-4H-pyrazolo[1,5-a][1,3]diazepin-5(6H)-one N¹,N¹,N²,N²-tetramethylethane-1,2-diamine (0.82 mg, 8.02 mmol) was added to a stirring mixture of 3,4-dimethyl-7,8-dihydro-4H-pyrazolo[1,5-a][1,3]diazepin-5(6H)-one (0.48 mg, 2.67 mmol) in dichloromethane (10 mL) at 0° C. followed by the addition of iodotrimethylsilane (1.6 g, 8.01 mmol). After stirring for 1 hour at 0° C., iodine (1.36 g, 5.35 mmol) was added. The reaction mixture was stirred for another 1 hour at 0° C. and quenched by the addition of aqueous sodium thiosulfate (5%, 20 mL). The resulting mixture was stirred for another 15 minutes and extracted with ethyl acetate (3×50 mL). The combined organic layers were washed with brine, dried over anhydrous sodium sulfate, filtered and concentrated under vacuum. The residue was purified by column chromatography (dichloromethane) to afford the title compound (0.427 g, 52%) as a yellow solid. LC-MS (Method I): m/z=305.9 [M+H]⁺, 0.756 min.

Step 6: Preparation of 6-azido-3,4-dimethyl-7,8-dihydro-4H-pyrazolo[1,5-a][1,3]diazepin-5(6H)-one Sodium azide (137 mg, 2.1 mmol) was added to a stirring mixture of 6-iodo-3,4-dimethyl-7,8-dihydro-4H-pyrazolo[1,5-a][1,3]diazepin-5 (6H)-one (427 mg, 1.39 mmol) in N,N-dimethylformamide (10 mL). The reaction mixture was stirred for 2 hours at room temperature, quenched with water (40 mL) and extracted with ethyl acetate (3×50 mL). The combined organic layers were washed with brine, dried over anhydrous sodium sulfate, filtered and concentrated under vacuum to afford the title compound (400 mg crude) as a yellow oil. LC-MS (Method C): m/z=220.7 [M+H]⁺, 1.383 min.

Step 7: Preparation of 6-amino-3,4-dimethyl-7,8-dihydro-4H-pyrazolo[1,5-a][1,3]diazepin-5(6H)-one Triphenylphosphine (734 mg, 2.80 mmol) was added to a stirring mixture of 6-azido-3,4-dimethyl-7,8-dihydro-4H-pyrazolo[1,5-a][1,3]diazepin-5(6H)-one (400 mg, 1.80 mmol) in tetrahydrofuran (10 mL) and water (2 mL). After stirring overnight at room temperature, the reaction mixture was diluted with water (10 mL) and extracted with ethyl acetate (3×20 mL). The combined organic layers were washed with brine, dried over anhydrous sodium sulfate, filtered and concentrated under vacuum. The residue was purified by column chromatography (methanol/dichloromethane, 1/10) to afford the title compound (232 mg, 86%) as a yellow oil. LC-MS (Method C): m/z=194.7 [M+H]⁺, 0.378 min.

Step 8: Preparation of 5-benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide N,N-diisopropylethylamine (140 mg, 1.13 mmol) was added to a mixture of 5-benzyl-4H-1,2,4-triazole-3-carboxylic acid (73 mg, 0.36 mmol), 6-amino-3,4-dimethyl-7,8-dihydro-4H-pyrazolo[1,5-a][1,3]diazepin-5(6H)-one (70 mg, 0.36 mmol), N-(3-dimethylaminopropyl)-N'-ethylcarbodiimide hydrochloride (77 mg, 0.39 mmol) and 1-hydroxybenzotriazole (65 mg, 0.39 mmol) in N,N-dimethylformamide (2 mL). After stirring overnight at room temperature, the reaction mixture was diluted with water (20 mL) and extracted with ethyl acetate (3×40 mL). The combined organic layers were washed with brine, dried over anhydrous sodium sulfate, filtered and concentrated under vacuum. The residue was purified by Prep-HPLC with the following conditions: Column: XBridge C18 OBD Prep Column 100 Å, 10 µm, 19 mm×250 mm; Mobile Phase A: water (0.05% formic acid), Mobile Phase B: ACN; Flow rate: 20 mL/min; Gradient: 22% B to 43% B over 7 min; UV 254 & 220 nm; Rt: 7 min to afford the title compound (50 mg, 36%) as a white solid. LC-MS (Method T): m/z=380.3 [M+H]⁺, 1.041 min.

Step 9: Preparation of (S)-5-benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide (131A) and (R)-5-benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide (131B)

The racemate of 5-benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide (50 mg, 0.13 mmol) was separated by Prep-Chiral-HPLC with the following conditions: Column: Chiralpak IF, 2×25 cm, 5 µm; Mobile Phase A: hexane, Mobile Phase B: EtOH; Flow rate: 17 mL/min; Gradient: 40% B to 40% B over 24 min; UV 254 & 220 nm; Rt 1: 7.35 min; Rt 2: 8.28 min to afford the title compounds:

Example 131A (first eluting isomer): $^1$H NMR (300 MHz, DMSO-d$_6$) δ 14.31 (s, 1H), 8.34 (d, J=7.7 Hz, 1H), 7.40-7.18 (m, 6H), 4.36-4.09 (m, 5H), 3.22 (s, 3H), 2.61-2.23 (m, 2H), 2.02 (s, 3H). LC-MS (Method D): m/z=380.2 [M+H]$^+$, 1.312 min.

Example 131B (second eluting isomer): $^1$H NMR (300 MHz, DMSO-d$_6$) δ 14.31 (s, 1H), 8.34 (d, J=7.6 Hz, 1H), 7.38-7.20 (m, 6H), 4.30-4.14 (m, 5H), 3.22 (s, 3H), 2.60-2.27 (m, 2H), 2.02 (s, 3H). LC-MS (Method D): m/z=380.2 [M+H]$^+$, 1.312 min.

Example 132: 1-Benzyl-4-chloro-N-((2R,3S)-2,5-dimethyl-4-oxo-2,3,4,5-tetrahydropyrido[3,2-b][1,4]oxazepin-3-yl)-1H-pyrazole-3-carboxamide

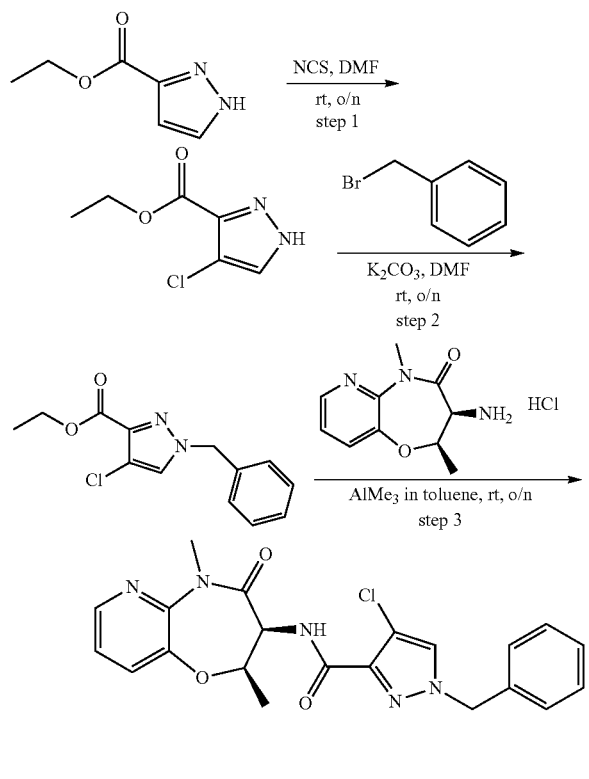

Step 1: Preparation of ethyl 4-chloro-1H-pyrazole-3-carboxylate

1-Chloropyrrolidine-2,5-dione (5.75 g, 42.9 mmol) was added to a stirring mixture of ethyl 1H-pyrazole-3-carboxylate (5.00 g, 35.7 mmol) in N,N-dimethylformamide (40 mL). The reaction mixture was stirred overnight at room temperature and diluted with water (100 mL). The solids were removed by filtration and the filtrate was concentrated under vacuum to afford the title compound (6.0 g crude) as a yellow oil. LC-MS (Method S): m/z=175.2 [M+H]$^+$, 0.695 min.

Step 2: Preparation of ethyl 1-benzyl-4-chloro-1H-pyrazole-3-carboxylate

Potassium carbonate (7.1 g, 51.4 mmol) was added to a stirring mixture of (ethyl 4-chloro-1H-pyrazole-3-carboxylate (3.0 g, 17.1 mmol) and (bromomethyl)benzene (3.6 g, 21.1 mmol) in N,N-dimethylformamide (10 mL). The reaction mixture was stirred at room temperature overnight, diluted with water (30 mL) and extracted with ethyl acetate (3×50 mL). The combined organic layers were washed with brine, dried over anhydrous sodium sulfate, filtered and concentrated to dryness under vacuum. The residue was purified by column chromatography (ethyl acetate/petroleum ether, 1/3) to afford the title compound (2.0 g, 44%) as a colorless oil. LC-MS (Method S): m/z=265.2 [M+H]$^+$, 1.040 min.

Step 3: Preparation of 1-benzyl-4-chloro-N-((2R, 3S)-2,5-dimethyl-4-oxo-2,3,4,5-tetrahydropyrido[3,2-b][1,4]oxazepin-3-yl)-1H-pyrazole-3-carboxamide The crude product obtained using the procedure described in Example 54 was purified by Prep-HPLC with the following conditions: Column: XBridge C18 OBD Prep Column, 100 Å, 5 μm, 19 mm×250 mm; Mobile Phase A: water (10 mmol/L NH$_4$HCO$_3$), Mobile Phase B: ACN; Flow rate: 20 mL/min; Gradient: 40% B to 65% B over 7 min; UV 254 & 220 nm; Rt: 7 min to afford the title compound. $^1$H NMR (400 MHz, DMSO-d$_6$) δ 8.36 (dd, J=4.8, 1.6 Hz, 1H), 8.26 (s, 1H), 7.76-7.71 (m, 2H), 7.42-7.29 (m, 6H), 5.42 (s, 2H), 4.99-4.88 (m, 2H), 3.40 (s, 3H), 1.32 (d, J=6.0 Hz, 3H). LC-MS (Method T): m/z=426.2 [M+H]$^+$, 1.518 min.

Example 133: (S)-4-Fluoro-1-(2-fluorobenzyl)-N-(5-methyl-4-oxo-2,3,4,5-tetrahydropyrido[3,2-b][1,4]oxazepin-3-yl)-1H-pyrazole-3-carboxamide

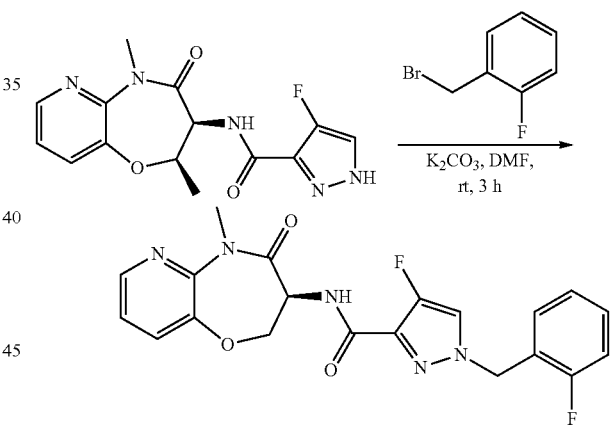

Potassium carbonate (34 mg, 0.25 mmol) was added to a mixture of (S)-4-fluoro-N-(5-methyl-4-oxo-2,3,4,5-tetrahydropyrido[3,2-b][1,4]oxazepin-3-yl)-1H-pyrazole-3-carboxamide (25 mg, 0.08 mmol) and 1-(bromomethyl)-2-fluorobenzene (19 mg, 0.10 mmol) in N,N-dimethylformamide (2 mL). After stirring at room temperature for 3 hours, the reaction mixture was diluted with water (2 mL) and extracted with ethyl acetate (3×20 mL). The combined organic layers were washed with brine, dried over anhydrous sodium sulfate, filtered and concentrated to dryness under vacuum. The residue was purified by Prep-HPLC with the following conditions: Column: XBridge Prep C18 OBD Column, 5 μm, 19×150 mm; Mobile Phase A: water (10 mmol/L NH$_4$HCO$_3$), Mobile Phase B: ACN; Flow rate: 30 mL/min; Gradient: 35% B to 65% B over 5 min; UV 254 & 220 nm; Rt: 3.75 min to afford the title compound. $^1$H NMR (400 MHz, DMSO-d$_6$) δ 8.37 (dd, J=4.8, 1.6 Hz, 1H), 8.24 (d, J=7.6 Hz, 1H), 8.12 (d, J=4.4 Hz, 1H), 7.71 (dd, J=8.0, 1.6 Hz, 1H), 7.46-7.40 (m, 1H), 7.35-7.21 (m, 4H), 5.43 (s, 2H), 4.88-4.80 (m, 1H), 4.70-4.64 (m, 1H), 4.53-4.48 (m, 1H), 3.35 (s, 3H). LC-MS (Method T): m/z=414.2 [M+H]⁺, 1.346 min.

Example 134: 5-Benzyl-N-((2R,3S)-2,5-dimethyl-4-oxo-2,3,4,5-tetrahydropyrido[3,2-b][1,4]oxazepin-3-yl)-1,3,4-oxadiazole-2-carboxamide

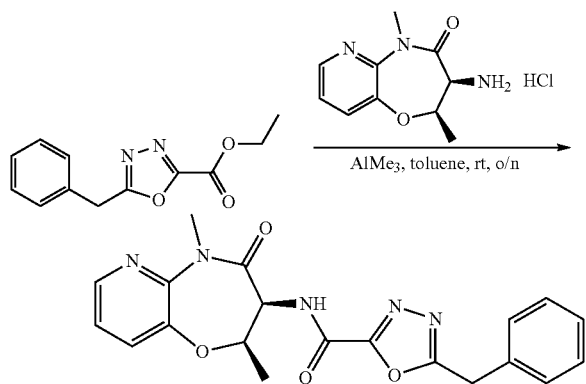

The crude product obtained using the procedure described in Example 54 was purified by Prep-HPLC with the following conditions: Column: XBridge Shield RP18 OBD Column, 5 μm, 19×150 mm; Mobile Phase A: water (10 mmol/L NH₄HCO₃), Mobile Phase B: ACN; Flow rate: 20 mL/min; Gradient: 15% B to 60% B over 15 min; UV 254 & 220 nm; Rt: 14.5 min to afford the title compound (13.3 mg, 17%) as a white solid. ¹H NMR (400 MHz, Methanol-d₄) δ 8.33-8.31 (m, 1H), 7.71-7.67 (m, 1H), 7.37-7.28 (m, 6H), 5.07-4.97 (m, 2H), 4.34 (s, 2H), 3.50 (s, 3H), 1.44 (d, J=6.0 Hz, 3H). LC-MS (Method J): m/z=394.15 [M+H]⁺, 2.483 min.

Example 135: (S)-4-Fluoro-1-(3-fluorobenzyl)-N-(5-methyl-4-oxo-2,3,4,5-tetrahydropyrido[3,2-b][1,4]oxazepin-3-yl)-1H-pyrazole-3-carboxamide

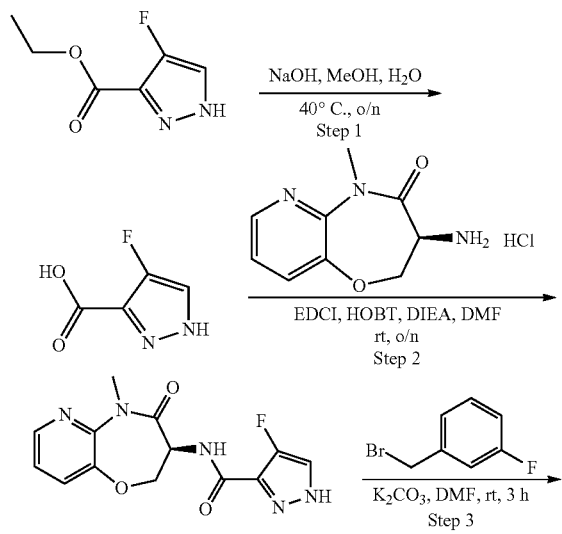

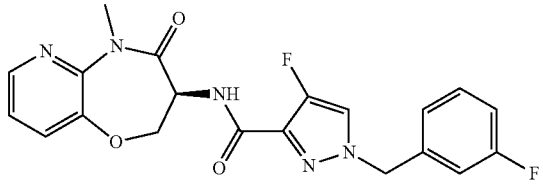

Step 1: Preparation of 4-fluoro-1H-pyrazole-3-carboxylic acid

Sodium hydroxide (253 mg, 6.33 mmol) was added to a mixture of ethyl 4-fluoro-1H-pyrazole-3-carboxylate (500 mg, 3.16 mmol) in methanol (10 mL) and water (4 mL). The resulting solution was heated to 40° C. and stirred overnight. After removal of methanol under reduced pressure, the resulting solution was adjusted to pH=6 with aqueous hydrochloric acid (1 N, 20 mL) and extracted with ethyl acetate (3×50 mL). The combined organic layers were washed with brine, dried over anhydrous sodium sulfate, and filtered. The filtrate was concentrated under vacuum to afford the title compound (400 mg, 97.2%) as a white solid. LC-MS (Method T): m/z=131.4 [M+H]⁺, 0.567 min.

Step 2: Preparation of (S)-4-fluoro-N-(5-methyl-4-oxo-2,3,4,5-tetrahydropyrido[3,2-b][1,4]oxazepin-3-yl)-1H-pyrazole-3-carboxamide N,N-diisopropylethylamine (993 mg, 7.70 mmol) was added to a mixture of (S)-3-amino-5-methyl-2,3-dihydropyrido[3,2-b][1,4]oxazepin-4(5H)-one hydrochloride (354 mg, 1.54 mmol), 4-fluoro-1H-pyrazole-3-carboxylic acid (200 mg, 1.54 mmol), N-(3-dimethylaminopropyl)-N'-ethylcarbodiimide hydrochloride (355 mg, 1.85 mmol) and 1-hydroxybenzotriazole (250 mg, 1.85 mmol) in N,N-dimethylformamide (10 mL). After stirring overnight at room temperature, the reaction mixture was diluted with water (30 mL) and extracted with ethyl acetate (3×50 mL). The combined organic layers were washed with brine, dried over anhydrous sodium sulfate, filtered and concentrated under vacuum. The residue was purified by Prep-TLC (ethyl acetate) to afford the title compound (200 mg, 42.6%) as a white solid. LC-MS (Method T): m/z=306.3 [M+H]⁺, 0.696 min.

Step 3: Preparation of (S)-4-fluoro-1-(3-fluorobenzyl)-N-(5-methyl-4-oxo-2,3,4,5-tetrahydropyrido-[3,2-b][1,4]oxazepin-3-yl)-1H-pyrazole-3-carboxamide Potassium carbonate (68 mg, 0.49 mmol) was added to a mixture of (S)-4-fluoro-N-(5-methyl-4-oxo-2,3,4,5-tetrahydropyrido[3,2-b][1,4]oxazepin-3-yl)-1H-pyrazole-3-carboxamide (50 mg, 0.16 mmol) and 1-(bromomethyl)-3-fluorobenzene (38 mg, 0.20 mmol) in N,N-dimethylformamide (5 mL). After stirring at room temperature for 3 hours, the reaction mixture was diluted with water (5 mL) and extracted with ethyl acetate (3×30 mL). The combined organic layers were washed with brine, dried over anhydrous sodium sulfate, filtered and concentrated under vacuum. The residue was purified by Prep-HPLC with the following conditions: Column: XBridge Shield RP18 OBD Column, 5 μm, 19×150 mm; Mobile Phase A: water (10 mmol/L NH₄HCO₃), Mobile Phase B: ACN; Flow rate: 20 mL/min; Gradient: 35% B to 78% B over 7 min; UV 254 & 220 nm; Rt: 6.5 min to afford the title compound. $^1$H NMR (400 MHz, DMSO-d$_6$) δ 8.36 (d, J=4.0 Hz, 1H), 8.27 (d, J=8.0 Hz, 1H), 8.16 (d, J=4.4 Hz, 1H), 7.70 (d, J=7.6 Hz, 1H), 7.49-7.38 (m, 1H), 7.38-7.28 (m, 1H), 7.22-6.98 (m, 3H), 5.38 (s, 2H), 4.92-4.78 (m, 1H), 4.78-4.61 (m, 1H), 4.61-4.41 (m, 1H), 3.36 (s, 3H). LC-MS (Method T): m/z=414.2 [M+H]$^+$, 1.347 min.

Example 136: 1-Benzyl-N-((2R,3S)-2,5-dimethyl-4-oxo-2,3,4,5-tetrahydropyrido[3,2-b][1,4]oxazepin-3-yl)-1H-1,2,4-triazole-3-carboxamide

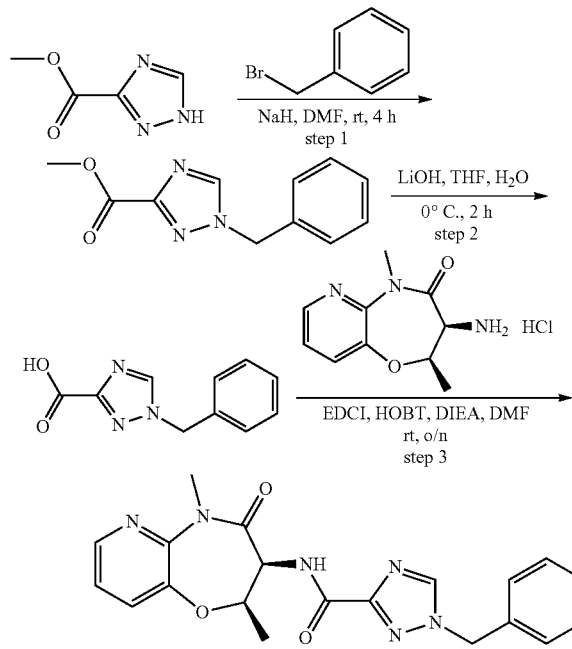

Step 1: Preparation of methyl 1-benzyl-1H-1,2,4-triazole-3-carboxylate

Sodium hydride (60%, 192 mg, 8 mmol) was added to a stirring mixture of methyl 1H-1,2,4-triazole-3-carboxylate (508 mg, 4 mmol) in N,N-dimethylformamide (10 mL). The resulting mixture was stirred at room temperature for 2 hours followed by the addition of (bromomethyl)benzene (680 mg, 4 mmol) under a nitrogen atmosphere. After stirring for another 2 hours, the reaction mixture was quenched by the addition of water (20 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/2) to afford the title compound (400 mg, 46%) as a white solid. LC-MS (Method E): m/z=217.9 [M+H]$^+$, 0.661 min.

Step 2: Preparation of 1-benzyl-1H-1,2,4-triazole-3-carboxylic acid

Lithium hydroxide (48 mg, 2 mmol) was added to a stirring mixture of methyl 1-benzyl-1H-1,2,4-triazole-3-carboxylate (108 mg, 0.5 mmol) in tetrahydrofuran (3 mL) and water (1 mL). After stirring at 0° C. for 2 hours, the pH of the reaction mixture was adjusted to 6 with aqueous hydrochloric acid (1 N, 10 mL) and extracted with ethyl acetate (3×20 mL). The combined organic layers were washed with brine, dried over anhydrous sodium sulfate, and filtered. The filtrate was concentrated under vacuum to afford the title compound (80 mg, 79%) as a white solid. LC-MS (Method E): m/z=203.9 [M+H]$^+$, 0.560 min.

Step 3: Preparation of 1-benzyl-N-((2R,3S)-2,5-dimethyl-4-oxo-2,3,4,5-tetrahydro-pyrido[3,2-b][1,4]oxazepin-3-yl)-1H-1,2,4-triazole-3-carboxamide The crude product obtained using Amide Coupling Procedure C was purified by Prep-HPLC with the following conditions: Column: XBridge C18 OBD Prep Column, 100 Å, 5 μm, 19 mm×250 mm; Mobile Phase A: water (10 mmol/L NH$_4$HCO$_3$), Mobile Phase B: ACN; Flow rate: 20 mL/min; Gradient: 25% B to 75% B over 7 min; UV 254 & 220 nm; Rt: 6.3 min to afford the title compound (31.5 mg, 40%) as a white solid. $^1$H NMR (400 MHz, DMSO-d$_6$) δ 8.86 (s, 1H), 8.36 (dd, J=4.4, 1.2 Hz, 1H), 8.01 (d, J=6.4 Hz, 1H), 7.76 (dd, J=8.0, 1.6 Hz, 1H), 7.41-7.31 (m, 6H), 5.50 (s, 2H), 5.00-4.88 (m, 2H), 3.40 (s, 3H), 1.31 (d, J=6.4 Hz, 3H). LC-MS (Method D): m/z=393.15 [M+H]$^+$, 1.553 min.

Example 137: (S)-4-Fluoro-1-((5-fluoropyridin-3-yl)methyl)-N-(5-methyl-4-oxo-2,3,4,5-tetrahydropyrido[3,2-b][1,4]oxazepin-3-yl)-1H-pyrazole-3-carboxamide

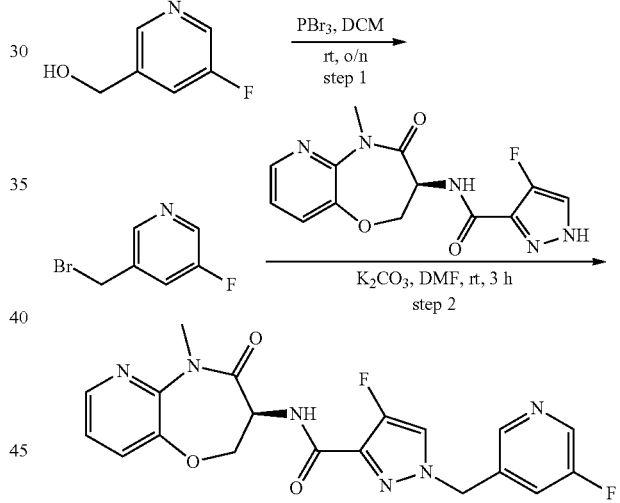

Step 1: Preparation of 3-(bromomethyl)-5-fluoropyridine

Tribromophosphine (853 mg, 3.15 mmol) was added to a solution of (5-fluoropyridin-3-yl)methanol (200 mg, 1.57 mmol) in dichloromethane (2 mL). The reaction mixture was stirred overnight at room temperature. The solvent was evaporated under vacuum to afford the title compound (150 mg crude). LC-MS (Method S): m/z=190.1 [M+H]$^+$, 0.787 min.

Step 2: Preparation of (S)-4-fluoro-1-((5-fluoropyridin-3-yl)methyl)-N-(5-methyl-4-oxo-2,3,4,5-tetrahydropyrido[3,2-b][1,4]oxazepin-3-yl)-1H-pyrazole-3-carboxamide Potassium carbonate (181 mg, 1.31 mmol) was added to a mixture of (S)-4-fluoro-N-(5-methyl-4-oxo-2,3,4,5-tetrahydropyrido[3,2-b][1,4]oxazepin-3-yl)-1H-pyrazole-3-carboxamide (80 mg, 0.26 mmol) and 3-(bromomethyl)-5-fluoropyridine (107 mg, 0.39 mmol) in N,N-dimethylformamide (2 mL). The resulting mixture was stirred at room temperature for 3 hours, diluted with water (2 mL) and extracted with ethyl acetate (3×30 mL). The combined organic layers were washed with brine, dried over anhydrous sodium sulfate, filtered and concentrated to dryness under vacuum. The residue was purified by Prep-HPLC with the following conditions: Column: XBridge C18 OBD Prep Column, 100 Å, 5 μm, 19 mm×250 mm; Mobile Phase A: water (10 mmol/L NH$_4$HCO$_3$); Mobile Phase B: ACN; Flow rate: 20 mL/min; Gradient: 15% B to 35% B over 7 min; UV 254 & 220 nm; Rt: 7 min to afford the title compound. $^1$H NMR (400 MHz, DMSO-d$_6$) δ 8.59 (d, J=2.8 Hz, 1H), 8.46 (s, 1H), 8.37 (dd, J=4.8, 1.6 Hz, 1H), 8.30 (d, J=8.0 Hz, 1H), 8.20 (d, J=4.4 Hz, 1H), 7.72-7.67 (m, 2H), 7.36-7.32 (m, 1H), 5.46 (s, 2H), 4.88-4.81 (m, 1H), 4.70-4.64 (m, 1H), 4.54-4.49 (m, 1H), 3.36 (s, 3H). LC-MS (Method T): m/z=415.2 [M+H]$^+$, 1.057 min.

Example 138: N-((2R,3S)-2,5-dimethyl-4-oxo-2,3,4,5-tetrahydropyrido[3,2-b][1,4]oxazepin-3-yl)-5-(1-phenylcyclopropyl)-1,3,4-oxadiazole-2-carboxamide

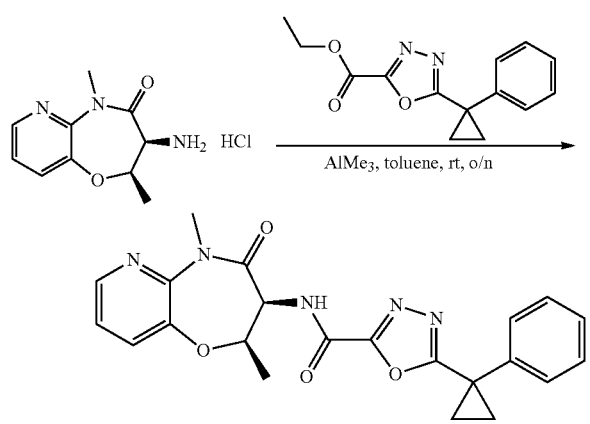

The crude product obtained using the procedure described in Example 54 was purified by Prep-HPLC with the following conditions: Column: XBridge C18 OBD Prep Column, 100 Å, 5 μm, 19 mm×250 mm; Mobile Phase A: water (10 mmol/L NH$_4$HCO$_3$); Mobile Phase B: ACN; Flow rate: 20 mL/min; Gradient: 40% B to 60% B in 7 min; UV 254 & 220 nm; Rt: 7 min to afford the title compound. $^1$H NMR (300 MHz, DMSO-d$_6$) δ 8.58 (s, 1H), 8.36 (dd, J=4.5, 1.5 Hz, 1H), 7.74 (dd, J=8.1, 1.5 Hz, 1H), 7.44-7.29 (m, 6H), 4.96-4.90 (m, 2H), 3.40 (s, 3H), 1.72-1.68 (m, 2H), 1.56-1.52 (m, 2H), 1.39-1.36 (m, 3H). LC-MS (Method D): m/z=420.15 [M+H]$^+$, 1.777 min.

Example 139: N-((2R,3S)-2,5-dimethyl-4-oxo-2,3,4,5-tetrahydropyrido[3,2-b][1,4]oxazepin-3-yl)-5-(2-fluorophenoxy)pyridazine-3-carboxamide

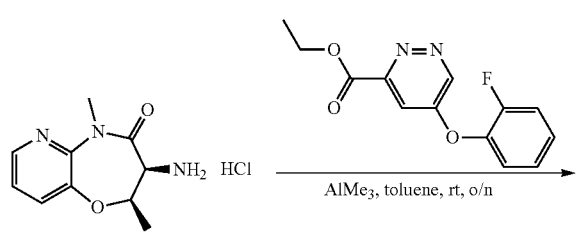

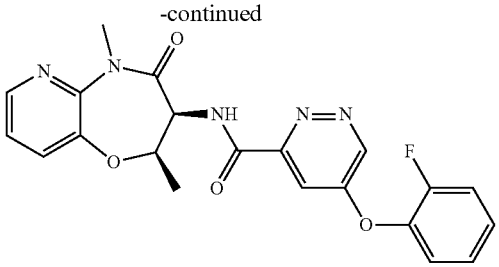

The crude product obtained using the procedure described in Example 54 was purified by Prep-HPLC with the following conditions: Column: XBridge Shield RP18 OBD Column, 5 mm, 19×150 mm; Mobile Phase A: water (10 mmol/L NH$_4$HCO$_3$); Mobile Phase B: ACN; Flow rate: 20 mL/min; Gradient: 25% B to 50% B over 7 min; UV 254 & 220 nm; Rt: 6.5 min to afford the title compound. $^1$H NMR (300 MHz, DMSO-d$_6$) δ 9.48 (d, J=3.0 Hz, 1H), 8.89 (d, J=6.3 Hz, 1H), 8.36 (dd, J=4.8, 1.8 Hz, 1H), 7.77 (dd, J=7.8, 1.5 Hz, 1H), 7.58-7.34 (m, 5H), 7.27 (dd, J=3.0, 0.9 Hz, 1H), 5.05-4.93 (m, 2H), 3.42 (s, 3H), 1.35 (d, J=5.7 Hz, 3H). LC-MS (Method D): m/z=424.1 [M+H]$^+$, 1.747 min.

Example 140: 1-Benzyl-N-((2R,3S)-2,5-dimethyl-4-oxo-2,3,4,5-tetrahydropyrido[3,2-b][1,4]oxazepin-3-yl)-1H-imidazole-4-carboxamide

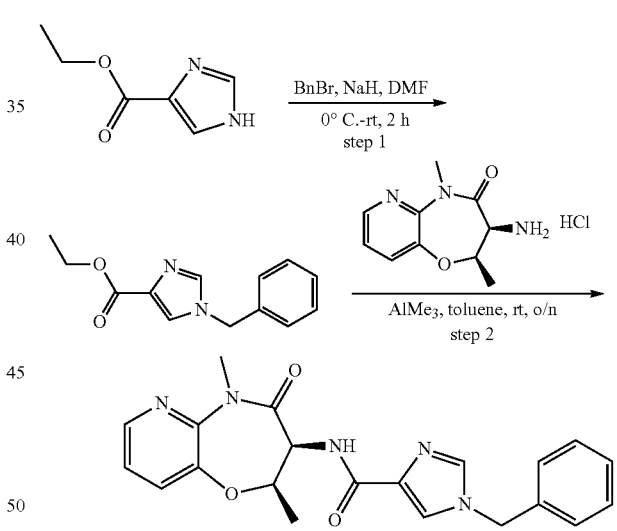

Step 1: Preparation of ethyl 1-benzyl-1H-imidazole-4-carboxylate

Sodium hydride (60%, 0.51 g, 21.3 mmol) was added to a stirring solution of ethyl 1H-imidazole-4-carboxylate (2.0 g, 14.3 mmol) in N,N-dimethylformamide (15 mL). The resulting mixture was stirred for 30 minutes at 0° C. followed by the addition of (bromomethyl)benzene (2.93 g, 17.13 mmol). After stirring at room temperature for 1.5 hours, the reaction mixture was quenched by the addition of water (30 mL) and extracted with ethyl acetate (3×100 mL). The combined organic layers were washed with brine, dried over anhydrous sodium sulfate, filtered and concentrated under vacuum. The residue was purified by column chromatography (ethyl acetate/petroleum ether, 1/1) to afford the title compound (1.0 g, 30%) as a yellow oil. LC-MS (Method C): m/z=231.1 [M+H]$^+$, 0.985 min.

Step 2: Preparation of 1-benzyl-N-((2R,3S)-2,5-dimethyl-4-oxo-2,3,4,5-tetrahydropyrido[3,2-b][1,4]oxazepin-3-yl)-1H-imidazole-4-carboxamide The crude product obtained using the procedure described in Example 54 was purified by Prep-HPLC with the following conditions: Column, XBridge Shield RP18 OBD, 5 μm, 19×150 mm; Mobile Phase A: water (10 mmol/L NH$_4$HCO$_3$); Mobile Phase B: ACN; Flow rate: 20 mL/min; Gradient: 30% B to 55% B over 7 min; Detector: UV 254 & 220 nm to afford the title compound. $^1$H NMR (400 MHz, DMSO-d$_6$) δ 8.33 (dd, J=4.4, 1.2 Hz, 1H), 7.89 (d, J=1.2 Hz, 1H), 7.78-7.71 (m, 3H), 7.37-7.27 (m, 6H), 5.21 (s, 2H), 4.92-4.84 (m, 2H), 3.37 (s, 3H), 1.28 (d, J=6.0 Hz, 3H). LC-MS (Method F): m/z=392.0 [M+H]$^+$, 1.029 min.

Example 141A and 141B: (S)-5-Benzyl-N-(6,7-dihydroimidazo[1,2-d]pyrido[3,2-b][1,4]oxazepin-7-yl)-4H-1,2,4-triazole-3-carboxamide and (R)-5-benzyl-N-(6,7-dihydroimidazo[1,2-d]pyrido[3,2-b][1,4]oxazepin-7-yl)-4H-1,2,4-triazole-3-carboxamide

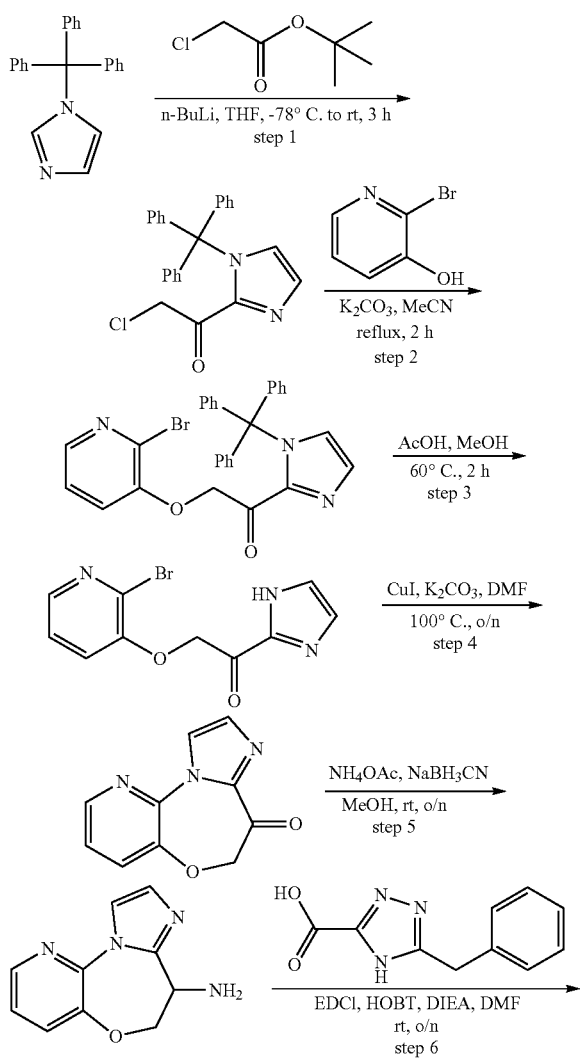

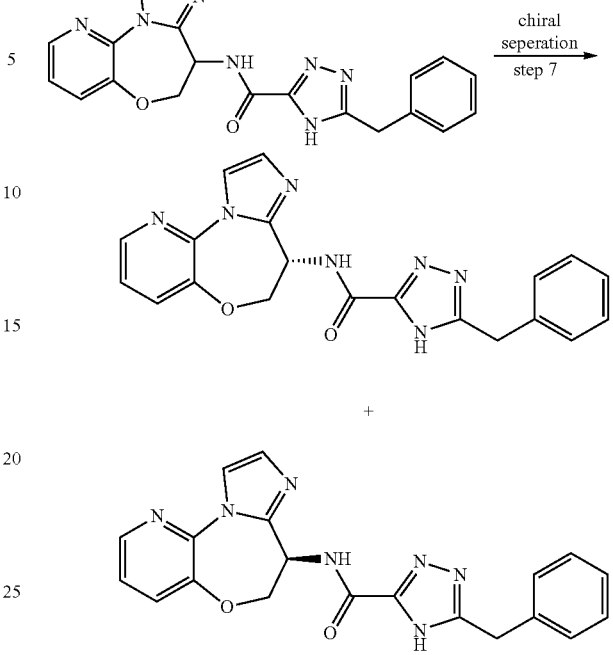

Step 1: Preparation of 2-chloro-1-(1-trityl-1H-imidazol-2-yl)ethanone

A solution of n-butyllithium in hexane (2.5 M, 13.2 mL, 33.0 mmol) was added to a stirred mixture of 1-trityl-1H-imidazole (9.3 g, 30.0 mmol) in tetrahydrofuran (190 mL) dropwise at −78° C. under a nitrogen atmosphere. After the addition was complete, the reaction mixture was warmed to −10° C. slowly and stirred for 1 hour. Then the mixture was cooled to −78° C. again and a solution of tert-butyl 2-chloroacetate (5.4 g, 36.0 mol) in tetrahydrofuran (10 mL) was added in one portion. The resulting mixture was warmed to room temperature with stirring over 2-3 hours, quenched with ice-water (100 mL) and extracted with ethyl acetate (3×100 mL). The combined organic layers were washed with brine, dried over anhydrous sodium sulfate, filtered and concentrated under vacuum. The residue was purified by column chromatography (ethyl acetate/petroleum ether, 1/4) to afford the title compound (900 mg, 7.8%) as a yellow solid.

Step 2: Preparation of 2-(2-bromopyridin-3-yloxy)-1-(1-trityl-1H-imidazol-2-yl)ethanone 2-Chloro-1-(1-trityl-1H-imidazol-2-yl)ethanone (772.0 mg, 2.0 mmol) was added to a stirred mixture of 2-bromopyridin-3-ol (346.0 mg, 2.0 mmol) and potassium carbonate (414.0 mg, 3.0 mmol) in acetonitrile (10 mL) under a nitrogen atmosphere. The resulting mixture was heated to reflux and stirred for 2 hours. After cooling to room temperature, the reaction mixture was diluted with water (20 mL) and extracted with ethyl acetate (3×20 mL). The combined organic layers were washed with brine, dried over anhydrous sodium sulfate, filtered and concentrated under vacuum. The residue was purified by column chromatography (ethyl acetate/petroleum ether, 1/3) to afford the title compound (700 mg, 66.9%) as a yellow solid. LC-MS (Method C): m/z=524.1 [M+H]+, 1.490 min.

Step 3: Preparation of 2-(2-bromopyridin-3-yloxy)-1-(1H-imidazol-2-yl)ethanone

A mixture of 2-(2-bromopyridin-3-yloxy)-1-(1-trityl-1H-imidazol-2-yl)ethanone (700 mg, 1.34 mmol) in methanol/acetic acid (5 mL/1 mL) was heated at reflux and stirred overnight. After cooling to room temperature, the resulting mixture was concentrated under high vacuum. The residue was purified by column chromatography (ethyl acetate/petroleum ether, 1/1) to afford the title compound (300 mg, 79.7%) as a yellow solid. LC-MS (Method R): m/z=282.2 [M+H]+, 0.628 min.

Step 4: Preparation of imidazo[1,2-a]pyrido[3,2-b][1,4]oxazepin-7(6H)-one

Cuprous iodide (19 mg, 0.1 mmol) was added to a mixture of 2-(2-bromopyridin-3-yloxy)-1-(1H-imidazol-2-yl)ethanone (281 mg, 1.0 mmol), L-proline (23.1 mg, 0.2 mmol) and potassium carbonate (345 mg, 2.50 mmol) in toluene (10 mL) under a nitrogen atmosphere. The resulting mixture was stirred overnight at 100° C. After cooling to room temperature, the reaction mixture was diluted with saturated aqueous ammonium chloride (20 mL) and extracted with dichloromethane/methanol (10/1) (3×20 mL). The combined organic layers were dried over anhydrous sodium sulfate, filtered and concentrated under vacuum. The residue was purified by column chromatography (methanol/dichloromethane, 1/40) to afford the title compound (70 mg, 34.8%) as a yellow solid. LC-MS (Method R): m/z=202.3 [M+H]+, 0.540 min.

Step 5: Preparation of 6,7-dihydroimidazo[1,2-d]pyrido[3,2-b][1,4]oxazepin-7-amine Sodium cyanoborohydride (11.0 mg, 0.17 mmol) was added to a stirring mixture of imidazo[1,2-d]pyrido[3,2-b][1,4]oxazepin-7(6H)-one (50.0 mg, 0.29 mmol) and ammonium acetate (383.0 mg, 4.98 mmol) in methanol (5 mL). The resulting mixture was stirred overnight at room temperature. The reaction mixture was concentrated under vacuum. The residue was purified by column chromatography (methanol/dichloromethane, 1/15) to afford the title compound (30 mg, 59.4%) as a yellow solid. LC-MS (Method C): m/z=203.1 [M+H]+, 0.778 min.

Step 7: Preparation of 5-benzyl-N-(6,7-dihydroimidazo[1,2-d]pyrido[3,2-b][1,4]oxazepin-7-yl)-4H-1,2,4-triazole-3-carboxamide The crude product obtained using Amide Coupling Procedure C was purified by Prep-TLC (ethyl acetate/petroleum ether, 3/1) to afford the title compound (16 mg, 27.6%) as a white solid. LC-MS (Method C): m/z=388.1 [M+H]+, 0.921 min.

Step 7: Preparation of (S)-5-benzyl-N-(6,7-dihydroimidazo[1,2-d]pyrido[3,2-b][1,4]oxazepin-7-yl)-4H-1,2,4-triazole-3-carboxamide (141A) and (R)-5-benzyl-N-(6,7-dihydroimidazo[1,2-d]pyrido[3,2-b][1,4]oxazepin-7-yl)-4H-1,2,4-triazole-3-carboxamide (141B)

The racemate of 5-benzyl-N-(6,7-dihydroimidazo[1,2-d]pyrido[3,2-b][1,4]oxazepin-7-yl)-4H-1,2,4-triazole-3-carboxamide (16 mg, 0.041 mmol) was separated by Prep-Chiral-HPLC with the following conditions: Column: Chiralpak IC, 2×25 cm, 5 μm; Mobile Phase A: hexane, Mobile Phase B: EtOH; Flow rate: 16 mL/min; Gradient: 50% B to 50% B over 30 min; UV254 & 220 nm; Rt 1: 16.881; Rt 2: 24.391 to afford the title compounds:

Example 141A (first eluting isomer): 1H NMR (400 MHz, CD3OD-d4) δ 8.43 (s, 1H), 8.31 (dd, J=4.4, 1.2 Hz, 1H), 7.70 (dd, J=8.0, 1.2 Hz, 1H), 7.42 (dd, J=8.0, 4.4 Hz, 1H), 7.33-7.22 (m, 6H), 5.86 (s, 1H), 4.59-4.48 (m, 2H), 4.15 (s, 2H). LC-MS (Method D): m/z=388.1 [M+H]+, 1.139 min.

Example 141B (second eluting isomer): 1H NMR (400 MHz, CD3OD-d4) δ 8.37 (s, 1H), 8.29 (dd, J=4.4, 1.6 Hz, 1H), 7.67 (dd, J=8.0, 1.2 Hz, 1H), 7.38 (dd, J=8.0, 4.4 Hz, 1H), 7.32-7.20 (m, 6H), 5.83 (s, 1H), 4.57-4.47 (m, 2H), 4.10 (s, 2H). LC-MS (Method D): m/z=388.1 [M+H]+, 1.139 min.

Example 142: (S)-5-Benzyl-N-(5-methyl-4-oxo-2,3,4,5-tetrahydropyrido[3,2-b][1,4]oxazepin-3-yl)isoxazole-3-carboxamide

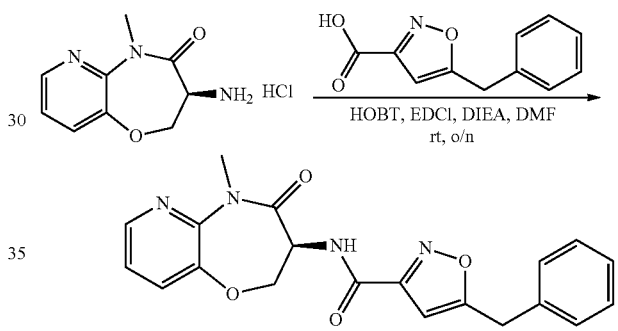

The crude product obtained using Amide Coupling Procedure C was purified by Prep-HPLC with the following conditions: Column: XBridge Shield RP18 OBD Column, 5 μm, 19×150 mm; Mobile Phase A: water (10 mmol/L NH4HCO3), Mobile Phase B: ACN; Flow rate: 20 mL/min; Gradient: 25% B to 50% B over 7 min; UV 254 & 220 nm; Rt: 5.6 min to afford the title compound. 1H NMR (300 MHz, DMSO-d6) δ 8.94 (d, J=7.8 Hz, 1H), 8.33 (dd, J=4.8, 1.5 Hz, 1H), 7.66 (dd, J=7.8, 1.5 Hz, 1H), 7.35-7.21 (m, 6H), 6.52 (s, 1H), 4.86-4.77 (m, 1H), 4.67-4.59 (m, 1H), 4.51-4.44 (m, 1H), 4.19 (s, 2H), 3.31 (s, 3H). LC-MS (Method D): m/z=379.1 [M+H]+, 1.719 min.

Example 143: N-((2R,3S)-2,5-dimethyl-4-oxo-2,3,4,5-tetrahydropyrido[3,2-b][1,4]oxazepin-3-yl)-4-fluoro-1-(4-fluorobenzyl)-1H-pyrazole-3-carboxamide

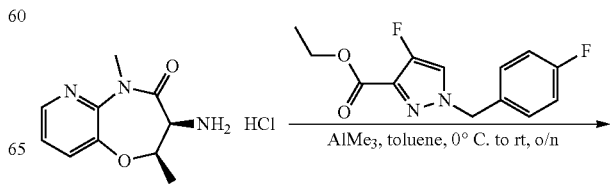

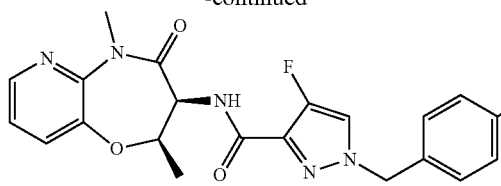

The crude product obtained using the procedure described in Example 54 was purified by Prep-HPLC with the following conditions: Column: XBridge Shield RP18 OBD Column, 5 μm, 19×150 mm; Mobile Phase A: water (10 mmol/L NH₄HCO₃), Mobile Phase B: ACN; Flow rate: 20 mL/min; Gradient: 25% B to 65% B over 7 min; UV 254 & 220 nm; Rt: 5 min to afford the title compound (26.2 mg, 28%) as a white solid. ¹H NMR (300 MHz, DMSO-d₆) δ 8.32 (dd, J=4.8, 1.5 Hz, 1H), 8.10 (d, J=4.5 Hz, 1H), 7.71 (dd, J=7.8, 1.5 Hz, 1H), 7.56 (d, J=6.6 Hz, 1H), 7.35-7.29 (m, 3H), 7.22-7.14 (m, 2H), 5.31 (s, 2H), 4.94-4.83 (m, 2H), 3.36 (s, 3H), 1.27 (d, J=6.3 Hz, 3H). LC-MS (Method D): m/z=428.1 [M+H]⁺, 1.771 min.

Example 144: (S)-1-(3-cyanobenzyl)-4-fluoro-N-(5-methyl-4-oxo-2,3,4,5-tetrahydropyrido[3,2-b][1,4]oxazepin-3-yl)-1H-pyrazole-3-carboxamide

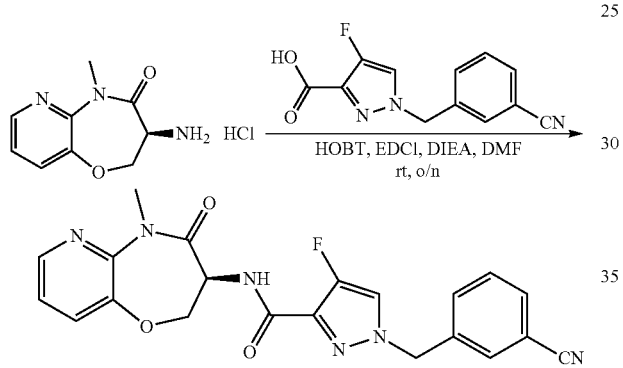

The crude product obtained using Amide Coupling Procedure C was purified by Prep-HPLC with the following conditions: Column: XBridge Shield RP 18 OBD Column, 5 μm, 19×150 mm; Mobile Phase A: water (10 mmol/L NH₄HCO₃), Mobile Phase B: ACN; Flow rate: 20 mL/min; Gradient: 25% B to 50% B over 7 min; UV 254 & 220 nm; Rt: 5.5 min to afford the title compound. ¹H NMR (300 MHz, DMSO-d₆) δ 8.32 (dd, J=4.8, 1.5 Hz, 1H), 8.22 (d, J=7.8 Hz, 1H), 8.14 (d, J=4.2 Hz, 1H), 7.81-7.74 (m, 2H), 7.68-7.64 (m, 1H), 7.61-7.55 (m, 2H), 7.32-7.27 (m, 1H), 5.39 (s, 2H), 4.85-4.76 (m, 1H), 4.67-4.59 (m, 1H), 4.50-4.44 (m, 1H), 3.32 (s, 3H). LC-MS (Method D): m/z=421.1 [M+H]⁺, 1.550 min.

Example 145A and 145B: (S)—N-(9-methyl-8-oxo-6,7,8,9-tetrahydro-5H-pyrido[2,3-b]azepin-7-yl)-5-(1-phenylcyclopropyl)-1,3,4-oxadiazole-2-carboxamide and (R)—N-(9-methyl-8-oxo-6,7,8,9-tetrahydro-5H-pyrido[2,3-b]azepin-7-yl)-5-(1-phenylcyclopropyl)-1,3,4-oxadiazole-2-carboxamide

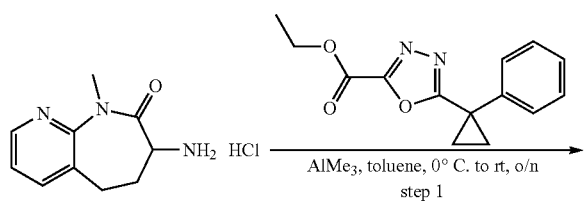

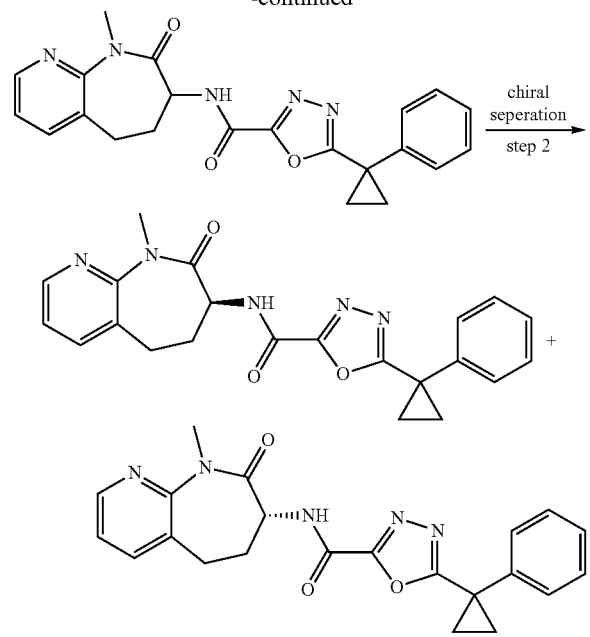

Step 1: Preparation of N-(9-methyl-8-oxo-6,7,8,9-tetrahydro-5H-pyrido[2,3-b]azepin-7-yl)-5-(1-phenylcyclopropyl)-1,3,4-oxadiazole-2-carboxamide The crude product obtained using the procedure described in Example 54 was purified by Prep-HPLC: Column: XBridge Shield RP18 OBD, 19×150 mm, 5 μm; Mobile phase: Phase A: water (10 mmol/L NH₄HCO₃); Phase B: ACN (35.0% ACN to 41.0% over 7 min); Detector, UV220 & 254 nm; Rt: 5.88 min to afford the title compound (45 mg, 25.4%) as a white solid. LC-MS (Method E): m/z=404.00 [M+H]⁺, 0.833 min.

Step 2: Preparation of (S)—N-(9-methyl-8-oxo-6,7,8,9-tetrahydro-5H-pyrido[2,3-b]azepin-7-yl)-5-(1-phenylcyclopropyl)-1,3,4-oxadiazole-2-carboxamide (First Eluting Isomer) and (R)—N-(9-methyl-8-oxo-6,7,8,9-tetrahydro-5H-pyrido[2,3-b]azepin-7-yl)-5-(1-phenylcyclopropyl)-1,3,4-oxadiazole-2-carboxamide (Second Eluting Isomer)

The racemate of N-(9-methyl-8-oxo-6,7,8,9-tetrahydro-5H-pyrido[2,3-b]azepin-7-yl)-5-(1-phenylcyclopropyl)-1,3,4-oxadiazole-2-carboxamide (45 mg, 0.11 mmol) was separated by Prep-Chiral-HPLC with the following conditions: Column: Chiralpak IA, 5 μm, 2.12×15 cm; Mobile Phase A: hexane, Mobile Phase B: IPA; Flow rate: 20 mL/min; Gradient: 50% B to 50% B over 13.5 min; UV 220 & 254 nm; Rt 1: 8.78; Rt 2: 11.03 to afford the title compounds:

Example 145A (first eluting isomer): ¹H NMR (400 MHz, Methanol-d₄) δ 8.41 (dd, J=4.9, 1.8 Hz, 1H), 7.78 (dd, J=7.5, 1.8 Hz, 1H), 7.45-7.42 (m, 2H), 7.38-7.25 (m, 4H), 4.48-4.44 (m, 1H), 3.45 (s, 3H), 2.91-2.76 (m, 2H), 2.60-2.49 (m, 1H), 2.37-2.28 (m, 1H), 1.77-1.74 (m, 2H), 1.55-1.53 (m, 2H). LC-MS (Method X): m/z=404.10 [M+H]⁺, 1.180 min.

Example 145B (second eluting isomer): ¹H NMR (400 MHz, Methanol-d₄) δ 8.41 (dd, J=4.9, 1.8 Hz, 1H), 7.79 (dd, J=7.6, 1.8 Hz, 1H), 7.46-7.42 (m, 2H), 7.38-7.25 (m, 4H), 4.49-4.44 (m, 1H), 3.45 (s, 3H), 2.90-2.77 (m, 2H), 2.60-

2.49 (m, 1H), 2.37-2.28 (m, 1H), 1.77-1.74 (m, 2H), 1.55-1.53 (m, 2H). LC-MS (Method X): m/z=404.00 [M+H]+, 1.179 min.

Example 146: (S)-5-benzyl-N-(5-methyl-4-oxo-2,3,4,5-tetrahydropyrido[3,2-b][1,4]oxazepin-3-yl)-1,3,4-oxadiazole-2-carboxamide

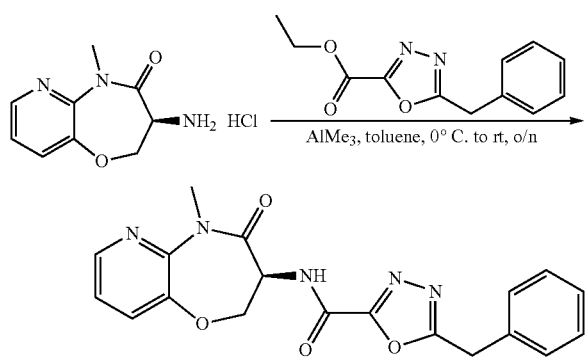

The crude product obtained using the procedure described in Example 54 was purified by Prep-HPLC with the following conditions: Column: XBridge Shield RP18 OBD Column, 5 mm, 19×150 mm; Mobile Phase A: water (10 mmol/L NH$_4$HCO$_3$), Mobile Phase B: ACN; Flow rate: 20 mL/min; Gradient: 35% B to 65% B over 7 min; UV 254 & 220 nm; Rt: 5 min to afford the title compound. $^1$H NMR (300 MHz, DMSO-d$_6$) δ 9.50 (s, 1H), 8.33 (dd, J=4.8, 1.5 Hz, 1H), 7.69-7.65 (m, 1H), 7.38-7.24 (m, 6H), 4.84-4.65 (m, 2H), 4.53-4.47 (m, 1H), 4.34 (s, 2H), 3.31 (s, 3H). LC-MS (Method D): m/z=380.1 [M+H]+, 1.531 min.

Example 147: 5-benzyl-N-((2R,3S)-2,5-dimethyl-8-(methylsulfonyl)-4-oxo-2,3,4,5-tetrahydropyrido[3,2-b][1,4]oxazepin-3-yl)-4H-1,2,4-triazole-3-carboxamide

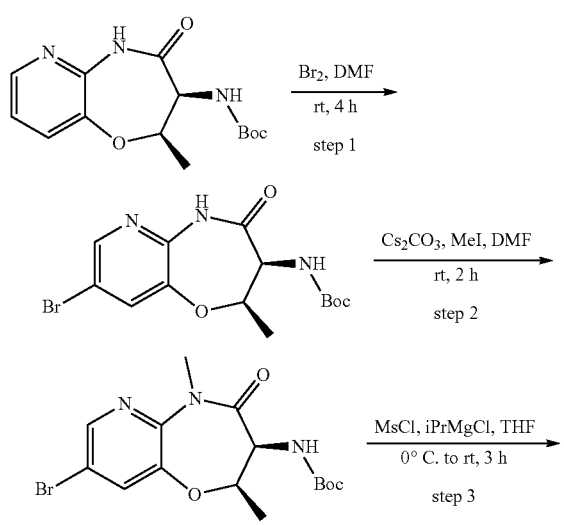

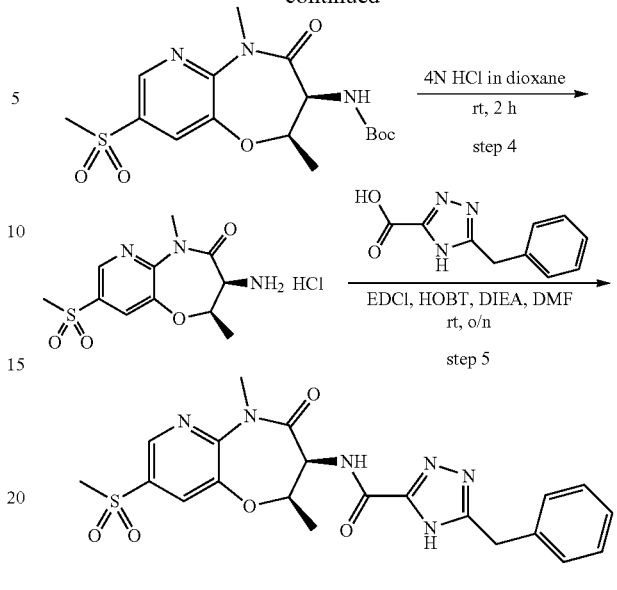

Step 1: Preparation of tert-butyl (2R,3S)-8-bromo-2-methyl-4-oxo-2,3,4,5-tetrahydropyrido[3,2-b][1,4]oxazepin-3-ylcarbamate Bromine (1.63 g, 10.2 mmol) was added to a stirring mixture of tert-butyl (2R,3S)-2-methyl-4-oxo-2,3,4,5-tetrahydropyrido[3,2-b][1,4]oxazepin-3-ylcarbamate (1.0 g, 3.4 mmol) in N,N-dimethylformamide (30 mL). The reaction mixture was stirred at room temperature for 4 hours and quenched by the addition of aqueous sodium thio sulfate (5%, 20 mL). The resulting solution was extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (900 mg, 71%) as a white solid. LC-MS (Method C): m/z=372.0 [M+H]+, 1.283 min.

Step 2: Preparation of tert-butyl (2R,3S)-8-bromo-2,5-dimethyl-4-oxo-2,3,4,5-tetrahydro-pyrido[3,2-b][1,4]oxazepin-3-ylcarbamate Iodomethane (306 mg, 2.2 mmol) was added to a stirring mixture of tert-butyl (2R,3S)-8-bromo-2-methyl-4-oxo-2,3,4,5-tetrahydropyrido[3,2-b][1,4]oxazepin-3-ylcarbamate (800 mg, 2.2 mmol) and cesium carbonate (703 mg, 2.2 mmol) in N,N-dimethylformamide (20 mL). The reaction mixture was stirred for 2 hours at room temperature, diluted with water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/6) to afford the title compound (650 mg, 79%) as a white solid. LC-MS (Method C): m/z=330.0 [M+H−56]+, 1.408 min.

Step 3: Preparation of tert-butyl (2R,3S)-2,5-dimethyl-8-(methylsulfonyl)-4-oxo-2,3,4,5-tetrahydro-pyrido[3,2-b][1,4]oxazepin-3-ylcarbamate A solution of isopropylmagnesium chloride in tetrahydrofuran (2.0 M, 0.52 mL, 1.04 mmol) was added to a stirring mixture of tert-butyl (2R,3S)-8-bromo-2,5-dimethyl-4-oxo-2,3,4,5-tetrahydropyrido[3,2-b][1,4]oxazepin-3-ylcarbamate (200 mg, 0.52 mmol) in tetrahydrofuran (5 mL) at 0° C. The reaction mixture was stirred for 1 hour at 0° C. followed by the addition of methane sulfonyl chloride (60 mg, 0.52 mmol). The reaction mixture was stirred for another 2 hours at room temperature, diluted with water (15 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (55 mg, 28%) as a white solid. LC-MS (Method C): m/z=330.1 [M+H−56]$^+$, 1.208 min.

Step 4: Preparation of (2R,3S)-3-amino-2,5-dimethyl-8-(methylsulfonyl)-2,3-dihydropyrido-[3,2-b][1,4]oxazepin-4(5H)-one hydrochloride To a stirring mixture of tert-butyl (2R,3S)-2,5-dimethyl-8-(methylsulfonyl)-4-oxo-2,3,4,5-tetrahydropyrido[3,2-b][1,4]oxazepin-3-ylcarbamate (55 mg, 0.15 mmol) in 1,4-dioxane (5 mL) was added a solution of hydrogen chloride in 1,4-dioxane (4 M, 2 mL, 8 mmol). The reaction mixture was stirred for 2 hours at room temperature and concentrated under high vacuum to afford the title compound (46 mg crude) as a white solid, which was used directly in the next step without further purification. LC-MS (Method C): m/z=286.1 [M+H]$^+$, 0.783 min.

Step 5: Preparation of 5-benzyl-N-((2R,3S)-2,5-dimethyl-8-(methylsulfonyl)-4-oxo-2,3,4,5-tetrahydropyrido[3,2-b][1,4]oxazepin-3-yl)-4H-1,2,4-triazole-3-carboxamide The crude product obtained using Amide Coupling Procedure C was purified by Prep-HPLC with the following conditions: Column: XBridge C18 OBD Prep Column, 100 Å, 5 μm, 19 mm×250 mm; Mobile Phase A: water (10 mmol/L NH$_4$HCO$_3$), Mobile Phase B: ACN; Flow rate: 20 mL/min; Gradient: 40% B to 60% B over 7 min; UV 254 & 220 nm; Rt: 7 min to afford the title compound. $^1$H NMR (400 MHz, DMSO-d$_6$) δ 14.40 (s, 1H), 8.81 (d, J=2.0 Hz, 1H), 8.22 (d, J=2.0 Hz, 1H), 8.01 (br s, 1H), 7.36-7.21 (m, 5H), 5.15-5.04 (m, 2H), 4.16 (s, 2H), 3.45 (s, 3H), 3.39 (s, 3H), 1.35 (d, J=6.4 Hz, 3H). LC-MS (Method D): m/z=471.1 [M+H]$^+$, 1.519 min.

Example 148A and 148B: (S)-5-benzyl-N-(9-methyl-8-oxo-6,7,8,9-tetrahydro-5H-pyrido[2,3-b]azepin-7-yl)-1,3,4-oxadiazole-2-carboxamide and (R)-5-benzyl-N-(9-methyl-8-oxo-6,7,8,9-tetrahydro-5H-pyrido[2,3-b]azepin-7-yl)-1,3,4-oxadiazole-2-carboxamide

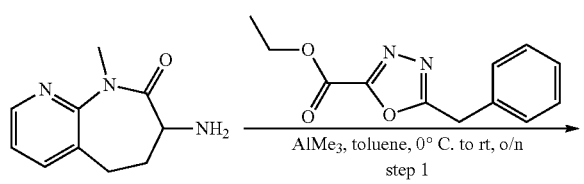

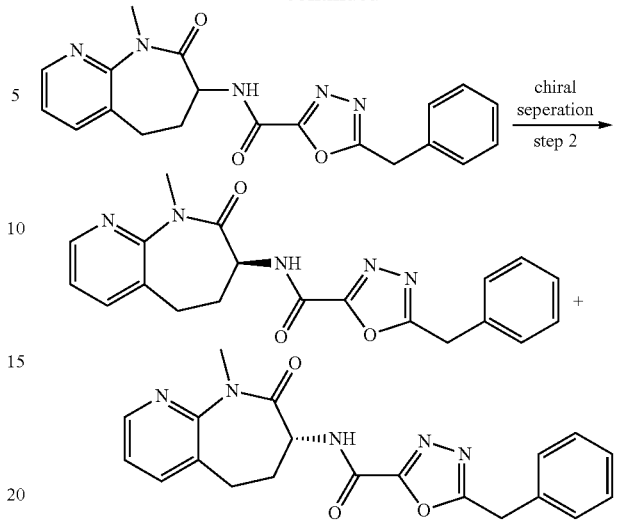

Step 1: Preparation of 5-benzyl-N-(9-methyl-8-oxo-6,7,8,9-tetrahydro-5H-pyrido[2,3-b]azepin-7-yl)-1,3,4-oxadiazole-2-carboxamide The crude product obtained using the procedure described in Example 54 was purified by Prep-HPLC with the following conditions: Column: XSelect CSH Prep C18 OBD Column, 5 mm, 19×150 mm; Mobile Phase A: water (0.1% formic acid); Mobile Phase B: ACN; Flow rate: 20 mL/min; Gradient: 40% B to 52% B over 4 min; UV 254 & 220 nm; Rt: 4 min to afford the title compound (20 mg, 14.2%) as a white solid. LC-MS (Method D): m/z=378.1 [M+H]$^+$, 1.492 min.

Step 2: Preparation of (S)-5-benzyl-N-(9-methyl-8-oxo-6,7,8,9-tetrahydro-5H-pyrido[2,3-b]azepin-7-yl)-1,3,4-oxadiazole-2-carboxamide (First Eluting Isomer) and (R)-5-benzyl-N-(9-methyl-8-oxo-6,7,8,9-tetrahydro-5H-pyrido[2,3-b]azepin-7-yl)-1,3,4-oxadiazole-2-carboxamide (Second Eluting Isomer)

The racemate of 5-benzyl-N-(9-methyl-8-oxo-6,7,8,9-tetrahydro-5H-pyrido[2,3-b]azepin-7-yl)-1,3,4-oxadiazole-2-carboxamide (20 mg) was separated by Prep-Chiral-HPLC with the following conditions: Column: CHIRALPAK IA, 2.12×15 cm, 5 μm; Mobile Phase A: hexane; Mobile Phase B: IPA; Flow rate: 20 mL/min; Gradient: 50% B to 50% B over 12 min; UV 254 & 220 nm; Rt 1: 7.106; Rt 2: 9.363 min to afford the title compounds:

Example 148A (first eluting isomer): $^1$H NMR (300 MHz, CD$_3$OD-d$_4$) δ 8.44 (dd, J=5.1, 1.8 Hz, 1H), 7.81 (dd, J=7.5, 1.5 Hz, 1H), 7.38-7.26 (m, 6H), 4.54-4.46 (m, 1H), 4.34 (s, 2H), 3.48 (s, 3H), 2.90-2.78 (m, 2H), 2.65-2.51 (m, 1H), 2.41-2.97 (m, 1H). LC-MS (Method D): m/z=378.1 [M+H]$^+$, 1.492 min.

Example 148B (second eluting isomer): $^1$H NMR (300 MHz, CD$_3$OD-d$_4$) δ 8.41 (dd, J=4.8, 1.8 Hz, 1H), 7.78 (dd, J=7.2, 1.5 Hz, 1H), 7.39-7.21 (m, 6H), 4.52-4.41 (m, 1H), 4.31 (s, 2H), 3.45 (s, 3H), 2.91-2.75 (m, 2H), 2.64-2.45 (m, 1H), 2.41-2.25 (m, 1H). LC-MS (Method D): m/z=378.1 [M+H]$^+$, 1.496 min.

Example 149: (S)-5-(2-fluorophenoxy)-N-(5-methyl-4-oxo-2,3,4,5-tetrahydropyrido[3,2-b][1,4]oxazepin-3-yl)pyridazine-3-carboxamide

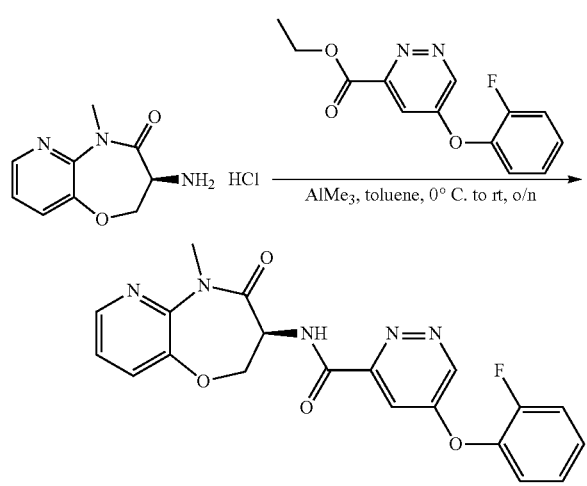

The crude product obtained using the procedure described in Example 54 was purified by Prep-HPLC with the following conditions: Column: XBridge C18 OBD Prep Column, 100 Å, 5 mm, 19 mm×250 mm; Mobile Phase A: water (10 mmol/L NH$_4$HCO$_3$), Mobile Phase B: ACN; Flow rate: 20 mL/min; Gradient: 40% B to 60% B over 7 min; UV 254 & 220 nm; Rt: 6.5 min to afford the title compound. $^1$H NMR (300 MHz, DMSO-d$_6$) δ 9.45-9.42 (m, 2H), 8.34-8.31 (m, 1H), 7.69-7.65 (m, 1H), 7.53-7.38 (m, 3H), 7.37-7.27 (m, 2H), 7.22 (d, J=3.6 Hz, 1H), 4.91-4.74 (m, 2H), 4.56-4.50 (m, 1H), 3.32 (s, 3H). LC-MS (Method V): m/z=410.1 [M+H]$^+$, 2.765 min.

Example 150: 5-benzyl-N-((2R,3S)-8-cyano-2,5-dimethyl-4-oxo-2,3,4,5-tetrahydropyrido[3,2-b][1,4]oxazepin-3-yl)-4H-1,2,4-triazole-3-carboxamide

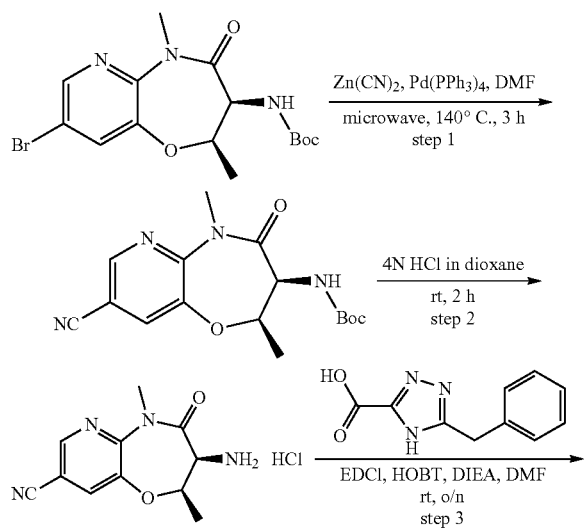

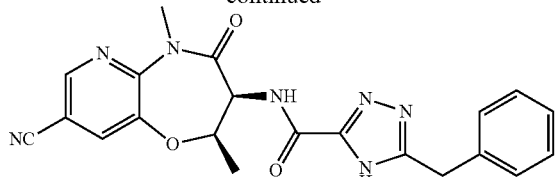

Step 1: Preparation of tert-butyl (2R,3S)-8-cyano-2,5-dimethyl-4-oxo-2,3,4,5-tetrahydropyrido-[3,2-b][1,4]oxazepin-3-ylcarbamate Tetrakis(triphenylphosphanyl)palladium (60 mg, 0.052 mmol) was added to a suspension of zinc cyanide (80 mg, 0.68 mmol) and tert-butyl (2R,3S)-8-bromo-2,5-dimethyl-4-oxo-2,3,4,5-tetrahydropyrido[3,2-b][1,4]oxazepin-3-yl-carbamate (200 mg, 0.52 mmol) in N,N-dimethylformamide (2 mL) under a nitrogen atmosphere. The reaction mixture was heated at 140° C. under microwave and stirred for 3 hours. The reaction mixture was filtered, and the filtrate was concentrated under vacuum. The residue was purified by column chromatography (ethyl acetate/petroleum ether, 1/3) to afford the title compound (110 mg, 64%) as a white solid. LC-MS (Method C): m/z=277.1 [M+H−56]$^+$, 1.300 min.

Step 2: Preparation of (2R,3S)-3-amino-2,5-dimethyl-4-oxo-2,3,4,5-tetrahydropyrido[3,2-b][1,4]oxazepine-8-carbonitrile hydrochloride To a solution of tert-butyl (2R,3S)-8-cyano-2,5-dimethyl-4-oxo-2,3,4,5-tetrahydro-pyrido[3,2-b][1,4]oxazepin-3-yl-carbamate (68 mg, 0.21 mmol) in 1,4-dioxane (5 mL) was added a solution of hydrogen chloride in 1,4-dioxane (4 M, 2 mL, 8 mmol). The resulting mixture was stirred for 2 hours at room temperature and concentrated under high vacuum to afford the title compound (55 mg crude) as a white solid, which was used directly in the next step without further purification. LC-MS (Method C): m/z=233.1 [M+H]$^+$, 0.825 min.

Step 3: Preparation of 5-benzyl-N-((2R,3S)-8-cyano-2,5-dimethyl-4-oxo-2,3,4,5-tetrahydro-pyrido[3,2-b][1,4]oxazepin-3-yl)-4H-1,2,4-triazole-3-carboxamide The crude product obtained using Amide Coupling Procedure C was purified by Prep-HPLC with the following conditions: Column: XSelect CSH Prep C18 OBD Column, 5 µm, 19×150 mm; Mobile Phase A: water (0.1% formic acid), Mobile Phase B: ACN; Flow rate: 20 mL/min; Gradient: 30% B to 65% B over 7 min; UV 254 & 220 nm; Rt: 6 min to afford the title compound. $^1$H NMR (400 MHz, DMSO-d$_6$) δ 14.43 (s, 1H), 8.82 (d, J=1.6 Hz, 1H), 8.31 (d, J=2.0 Hz, 1H), 8.00 (br s, 1H), 7.36-7.23 (m, 5H), 5.08-5.01 (m, 2H), 4.15 (s, 2H), 3.42 (s, 3H), 1.33 (d, J=6.0 Hz, 3H). LC-MS (Method F): m/z=418.0 [M+H]$^+$, 1.187 min.

Example 151: (S)-5-benzyl-4-cyano-N-(5-methyl-4-oxo-2,3,4,5-tetrahydropyrido[3,2-b][1,4]oxazepin-3-yl)thiazole-2-carboxamide

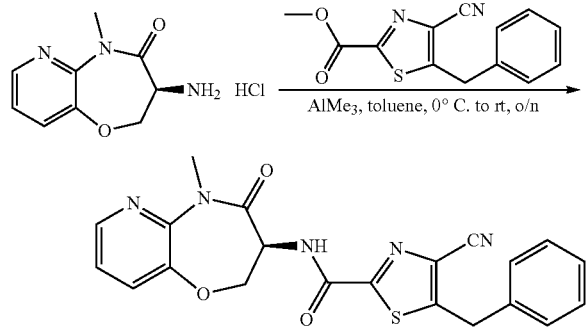

The crude product obtained using the procedure described in Example 54 was purified by Prep-HPLC with the following conditions: Column: XBridge Prep C18 OBD Column 5 µm, 19×150 mm; Mobile Phase A: water (10 mmol/L NH$_4$HCO$_3$), Mobile Phase B: ACN; Flow rate: 20 mL/min; Gradient: 25% B to 55% B over 7 min; 254 nm; Rt: 6.32 min to afford the title compound. $^1$H NMR (400 MHz, CD$_3$OD-d$_4$) δ 8.35 (dd, J=4.8, 1.6 Hz, 1H), 7.67 (dd, J=8.0, 1.6 Hz, 1H), 7.43-7.26 (m, 6H), 4.98 (dd, J=11.5, 7.4 Hz, 1H), 4.70-4.55 (m, 2H), 4.42 (s, 2H), 3.48 (s, 3H). LC-MS (Method Q): m/z=420.3 [M+H]$^+$, 1.503 min.

Example 152A and 152B: (R)-1-(3-cyanobenzyl)-4-fluoro-N-(9-methyl-8-oxo-6,7,8,9-tetrahydro-5H-pyrido[2,3-b]azepin-7-yl)-1H-pyrazole-3-carboxamide and (S)-1-(3-cyanobenzyl)-4-fluoro-N-(9-methyl-8-oxo-6,7,8,9-tetrahydro-5H-pyrido[2,3-b]azepin-7-yl)-1H-pyrazole-3-carboxamide

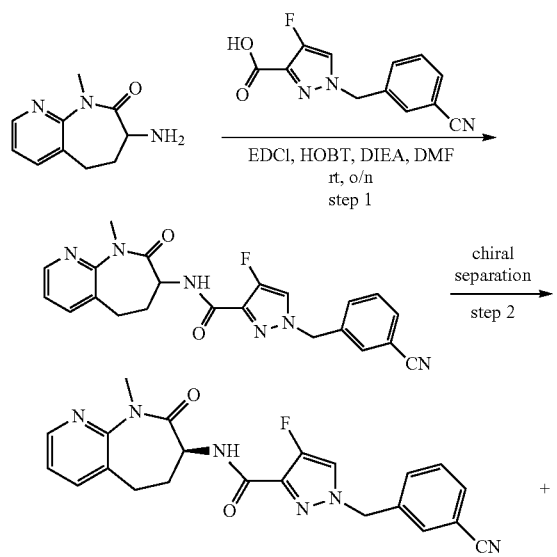

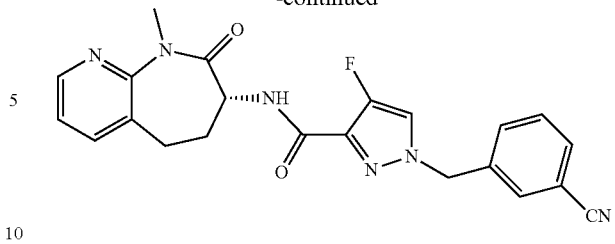

Step 1: Preparation of 1-(3-cyanobenzyl)-4-fluoro-N-(9-methyl-8-oxo-6,7,8,9-tetrahydro-5H-pyrido[2,3-b]azepin-7-yl)-1H-pyrazole-3-carboxamide The crude product obtained using Amide Coupling Procedure C was purified by Prep-HPLC with the following conditions: Column: XBridge C18 OBD Prep Column, 100 Å, 5 µm, 19 mm×250 mm; Mobile Phase A: water (10 mmol/L NH$_4$HCO$_3$), Mobile Phase B: ACN; Flow rate: 20 mL/min; Gradient: 20% B to 50% B over 7 min; UV 254 & 220 nm; Rt: 7 min to afford the title compound (65 mg, 60%) as a white solid. LC-MS (Method D): m/z=419.1 [M+H]$^+$, 1.508 min.

Step 2: Preparation of (R)-1-(3-cyanobenzyl)-4-fluoro-N-(9-methyl-8-oxo-6,7,8,9-tetrahydro-5H-pyrido[2,3-b]azepin-7-yl)-1H-pyrazole-3-carboxamide (First Eluting Isomer) and (S)-1-(3-cyanobenzyl)-4-fluoro-N-(9-methyl-8-oxo-6,7,8,9-tetrahydro-5H-pyrido[2,3-b]azepin-7-yl)-1H-pyrazole-3-carboxamide (Second Eluting Isomer)

The racemate of 1-(3-cyanobenzyl)-4-fluoro-N-(9-methyl-8-oxo-6,7,8,9-tetrahydro-5H-pyrido[2,3-b]azepin-7-yl)-1H-pyrazole-3-carboxamide (65 mg, 0.16 mmol) was separated by Prep-Chiral-HPLC with the following conditions: Column: Chiralpak ID-2, 5 µm, 2×25 cm; Mobile Phase A: hexane, Mobile Phase B: EtOH; Flow rate: 16 mL/min; Gradient: 60% B to 60 B % over 20 min; UV 254 & 220 nm; Rt 1: 12.92 min; Rt 2: 16.60 min to afford the title compounds:

Example 152A (first eluting isomer): $^1$H NMR (400 MHz, DMSO-d$_6$) δ 8.44 (dd, J=4.8, 1.6 Hz, 1H), 8.16 (d, J=4.4 Hz, 1H), 8.08 (d, J=7.6 Hz, 1H), 7.85-7.78 (m, 3H), 7.64-7.58 (m, 2H), 7.30-7.26 (m, 1H), 5.42 (s, 2H), 4.34-4.26 (m, 1H), 3.35 (s, 3H), 2.78-2.65 (m, 2H), 2.43-2.25 (m, 2H). LC-MS (Method F): m/z=419.0 [M+H]$^+$, 1.070 min.

Example 152B (second eluting isomer): $^1$H NMR (400 MHz, DMSO-d$_6$) δ 8.44 (dd, J=4.8, 1.6 Hz, 1H), 8.16 (d, J=4.4 Hz, 1H), 8.08 (d, J=7.6 Hz, 1H), 7.85-7.78 (m, 3H), 7.64-7.58 (m, 2H), 7.30-7.26 (m, 1H), 5.42 (s, 2H), 4.34-4.26 (m, 1H), 3.35 (s, 3H), 2.78-2.64 (m, 2H), 2.43-2.24 (m, 2H). LC-MS (Method F): m/z=419.1 [M+H]$^+$, 1.071 min.

Example 153: (S)-1-(2-cyanobenzyl)-4-fluoro-N-(5-methyl-4-oxo-2,3,4,5-tetrahydropyrido[3,2-b][1,4]oxazepin-3-yl)-1H-pyrazole-3-carboxamide

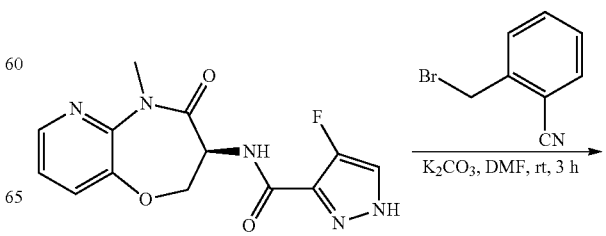

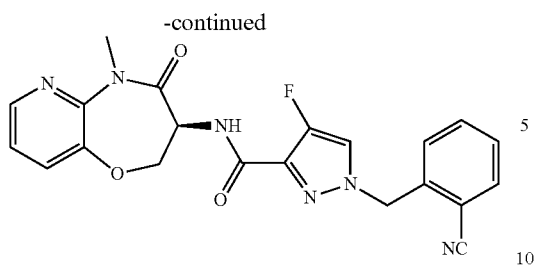
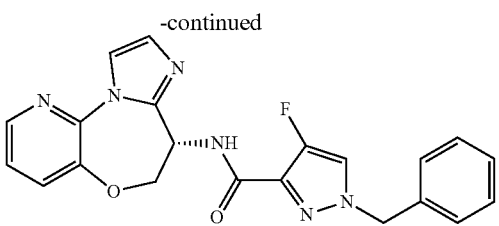

2-(Bromomethyl) benzonitrile (39 mg, 0.20 mmol) was added to a stirring mixture of (S)-4-fluoro-N-(5-methyl-4-oxo-2,3,4,5-tetrahydropyrido[3,2-b][1,4]oxazepin-3-yl)-1H-pyrazole-3-carboxamide (50 mg, 0.16 mmol) and potassium carbonate (68 mg, 0.49 mmol) in N,N-dimethylformamide (4 mL). The resulting mixture was stirred at room temperature for 3 hours, diluted with water (5 mL) and extracted with ethyl acetate (3×20 mL). The combined organic layers were washed with brine, dried over anhydrous sodium sulfate, filtered and concentrated to dry under vacuum. The residue was purified by Prep-HPLC with the following conditions: Column: XBridge Prep C18 OBD Column 5 μm, 19×150 mm; Mobile Phase A: water (10 mmol/L NH$_4$HCO$_3$), Mobile Phase B: ACN; Flow rate: 20 mL/min; Gradient: 25% B to 55% B over 7 min; 254 nm; Rt: 6.32 min to afford the title compound. $^1$H NMR (400 MHz, CD$_3$OD-d$_4$) δ 8.35 (dd, J=4.8, 1.6 Hz, 1H), 7.88 (d, J=4.5 Hz, 1H), 7.83 (dd, J=7.7, 1.3 Hz, 1H), 7.73-7.66 (m, 2H), 7.56 (td, J=7.6, 1.1 Hz, 1H), 7.38 (d, J=7.9 Hz, 1H), 7.32 (dd, J=8.0, 4.8 Hz, 1H), 5.59 (s, 2H), 5.01 (dd, J=11.5, 7.2 Hz, 1H), 4.68 (dd, J=9.8, 7.2 Hz, 1H), 4.50 (dd, J=11.5, 9.9 Hz, 1H), 3.49 (s, 3H). LC-MS (Method Q): m/z=421.3 [M+H]$^+$, 1.201 min.

Example 154A and 154B: (R)-1-benzyl-N-(6,7-dihydroimidazo[1,2-d]pyrido[3,2-b][1,4]oxazepin-7-yl)-4-fluoro-1H-pyrazole-3-carboxamide and (S)-1-benzyl-N-(6,7-dihydroimidazo[1,2-d]pyrido[3,2-b][1,4]oxazepin-7-yl)-4-fluoro-1H-pyrazole-3-carboxamide

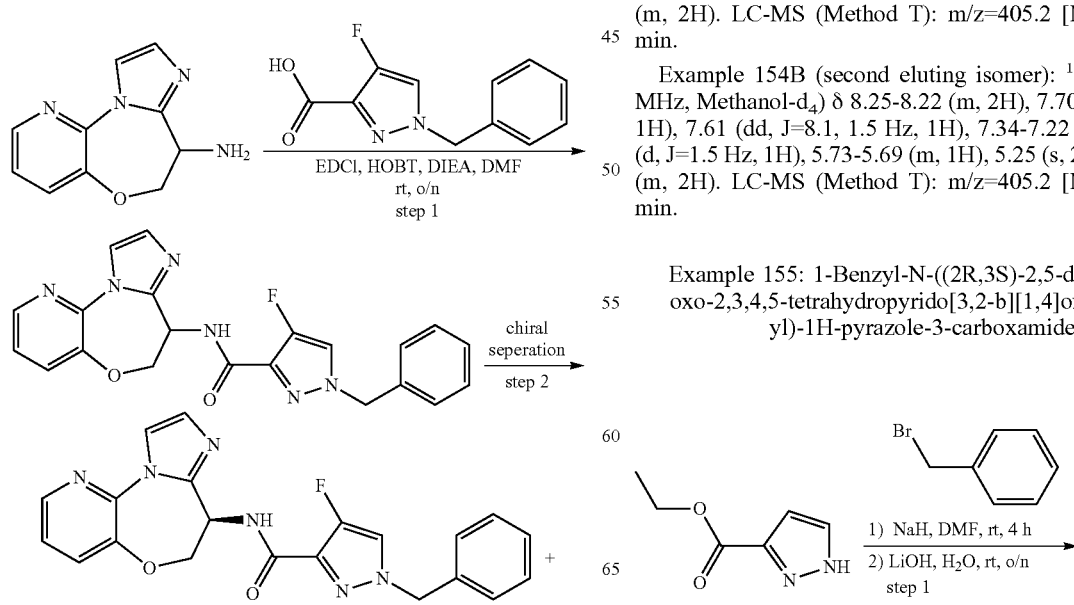

Step 1: Preparation of 1-benzyl-N-(6,7-dihydroimidazo[1,2-d]pyrido[3,2-b][1,4]oxazepin-7-yl)-4-fluoro-1H-pyrazole-3-carboxamide The crude product obtained using Amide Coupling Procedure C was purified by Prep-TLC (ethyl acetate/petroleum ether, 3/1) to afford the title compound (16 mg, 33.0%) as a white solid. LC-MS (Method S): m/z=405.2 [M+H]$^+$, 0.954 min.

Step 2: Preparation of (S)-1-benzyl-N-(6,7-dihydroimidazo[1,2-d]pyrido[3,2-b][1,4]oxazepin-7-yl)-4-fluoro-1H-pyrazole-3-carboxamide (First Eluting Isomer) and (R)-1-benzyl-N-(6,7-dihydroimidazo[1,2-d]pyrido[3,2-b][1,4]oxazepin-7-yl)-4-fluoro-1H-pyrazole-3-carboxamide (Second Eluting Isomer)

The racemate of 1-benzyl-N-(6,7-dihydroimidazo[1,2-d]pyrido[3,2-b][1,4]oxazepin-7-yl)-4-fluoro-1H-pyrazole-3-carboxamide (16 mg, 0.039 mmol) was separated by Prep-Chiral-HPLC with the following conditions: Column: CHIRALPAK IC, 5 μm, 2×25 cm; Mobile Phase A: hexane:DCM=5:1, Mobile Phase B: EtOH; Flow rate: 16 mL/min; Gradient: 50% B to 50% B over 26 min; UV 254 & 220 nm; Rt 1: 3.96 min; Rt 2: 6.18 min to afford the title compounds:

Example 154A (first eluting isomer): $^1$H NMR (300 MHz, Methanol-d$_4$) δ 8.25-8.22 (m, 2H), 7.70 (d, J=4.5 Hz, 1H), 7.61 (dd, J=8.1, 1.5 Hz, 1H), 7.34-7.22 (m, 6H), 7.07 (d, J=1.5 Hz, 1H), 5.73-5.69 (m, 1H), 5.25 (s, 2H), 4.47-4.44 (m, 2H). LC-MS (Method T): m/z=405.2 [M+H]$^+$, 1.063 min.

Example 154B (second eluting isomer): $^1$H NMR (300 MHz, Methanol-d$_4$) δ 8.25-8.22 (m, 2H), 7.70 (d, J=4.5 Hz, 1H), 7.61 (dd, J=8.1, 1.5 Hz, 1H), 7.34-7.22 (m, 6H), 7.07 (d, J=1.5 Hz, 1H), 5.73-5.69 (m, 1H), 5.25 (s, 2H), 4.47-4.44 (m, 2H). LC-MS (Method T): m/z=405.2 [M+H]$^+$, 1.069 min.

Example 155: 1-Benzyl-N-((2R,3S)-2,5-dimethyl-4-oxo-2,3,4,5-tetrahydropyrido[3,2-b][1,4]oxazepin-3-yl)-1H-pyrazole-3-carboxamide -continued

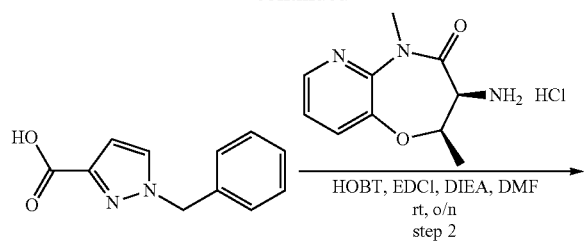

Step 1: Preparation of
1-benzyl-1H-pyrazole-3-carboxylic acid

Sodium hydride (96 mg, 4 mmol) was added to a stirring mixture of ethyl 1H-pyrazole-3-carboxylate (280 mg, 2 mmol) in N,N-dimethylformamide (20 mL). The resulting mixture was stirred at room temperature for 2 hours followed by the addition of (bromomethyl)benzene (340 mg, 2 mmol). After stirring for another 2 hours, the reaction mixture was diluted with water (5 mL). Lithium hydroxide (96 mg, 4 mmol) was added and the resulting mixture was stirred overnight at room temperature, the pH was adjusted to 6 with hydrochloric acid (2 N, 20 mL), and extracted with ethyl acetate (3×20 mL). The combined organic layers were washed with brine, dried over anhydrous sodium sulfate, filtered and concentrated under vacuum. The residue was purified by Prep-HPLC with the following conditions: Column: XBridge Shield RP18 OBD Column, 5 µm, 19×150 mm; Mobile Phase A: water (0.1% formic acid), Mobile Phase B: ACN; Flow rate: 20 mL/min; Gradient: 30% B to 55% B over 7 min; UV 254 & 220 nm; Rt: 4.9 min to afford the title compound (220 mg, 54.4%) as a white solid. LC-MS (Method E): m/z=202.9 [M+H]$^+$, 0.855 min.

Step 2: Preparation of 1-benzyl-N-((2R,3S)-2,5-dimethyl-4-oxo-2,3,4,5-tetrahydro-pyrido[3,2-b][1,4]oxazepin-3-yl)-1H-pyrazole-3-carboxamide The crude product obtained using Amide Coupling Procedure C was purified by Prep-HPLC with the following conditions: Column: XBridge Shield RP18 OBD Column, 5 µm, 19×150 mm; Mobile Phase A: water (0.1% formic acid), Mobile Phase B: ACN; Flow rate: 20 mL/min; Gradient: 25% B to 75% B over 7 min; UV 254 & 220 nm; Rt: 3.3 min to afford the title compound. $^1$H NMR (400 MHz, DMSO-d$_6$) δ 8.36 (dd, J=4.8, 1.6 Hz, 1H), 7.97 (d, J=2.0 Hz, 1H), 7.76 (dd, J=8.0, 1.6 Hz, 1H), 7.70 (d, J=6.4 Hz, 1H), 7.42-7.25 (m, 6H), 6.70 (d, J=2.0 Hz, 1H), 5.46 (s, 2H), 4.99-4.89 (m, 2H), 3.40 (s, 3H), 1.32 (d, J=6.0 Hz, 3H). LC-MS (Method V): m/z=392.1 [M+H]$^+$, 2.961 min.

Example 156A and 156B: 4-fluoro-1-(4-fluorobenzyl)-N-((1aR,2R,8bS)-4-methyl-3-oxo-1,1a,2,3,4,8b-hexahydrocyclopropa[d]pyrido[2,3-b]azepin-2-yl)-1H-pyrazole-3-carboxamide and 4-fluoro-1-(4-fluorobenzyl)-N-((1aS,2S,8bR)-4-methyl-3-oxo-1,1a,2,3,4,8b-hexahydrocyclopropa[d]pyrido[2,3-b]azepin-2-yl)-1H-pyrazole-3-carboxamide

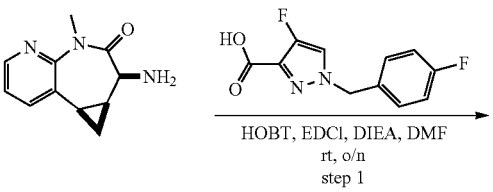

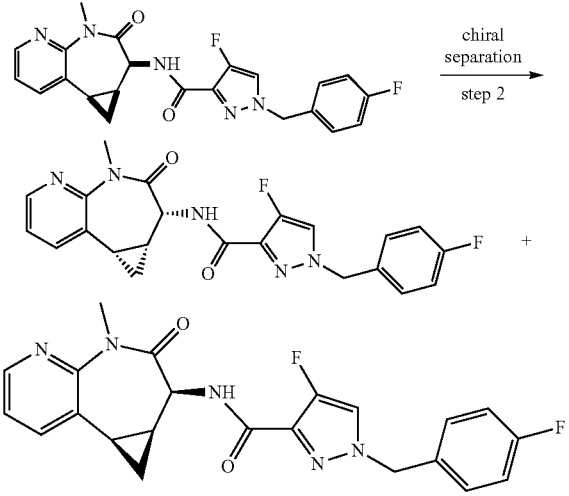

The crude product obtained using Amide Coupling Procedure C was purified by Prep-TLC (methanol/dichloromethane, 1/20) to afford the title compound as a white solid.

The racemate was separated by Prep-Chiral-HPLC with the following conditions: Column: Chiralpak IC, 2×25 cm, 5 µm; Mobile Phase A: Hexane, Mobile Phase B: EtOH; Flow rate: 19 mL/min; Gradient: 35% B to 35% B over 18.5 min; UV 220 & 254 nm; Rt1: 13.00; Rt2: 15.67 to afford the title compounds:

Example 156A (first eluting isomer): $^1$H NMR (400 MHz, CD$_3$OD-d$_4$) δ 8.35 (dd, J=4.8, 2.0 Hz, 1H), 7.92 (dd, J=7.6, 1.6 Hz, 1H), 7.77 (d, J=4.4 Hz, 1H), 7.38-7.35 (m, 2H), 7.27 (dd, J=8.0, 4.8 Hz, 1H), 7.14-7.07 (m, 2H), 5.31 (s, 2H), 4.63 (s, 1H), 3.39 (s, 3H), 2.28-2.22 (m, 1H), 2.10-2.05 (m, 1H), 1.27-1.20 (m, 1H), 1.18-1.12 (m, 1H). LC-MS (Method D): m/z=424.1 [M+H]$^+$, 1.658 min.

Example 156B (second eluting isomer): $^1$H NMR (400 MHz, CD$_3$OD-d$_4$) δ 8.35 (dd, J=4.8, 2.0 Hz, 1H), 7.92 (dd, J=8.0, 2.0 Hz, 1H), 7.76 (d, J=4.4 Hz, 1H), 7.49-7.35 (m, 2H), 7.26 (dd, J=7.6, 4.8 Hz, 1H), 7.12-7.08 (m, 2H), 5.31 (s, 2H), 4.63 (s, 1H), 3.39 (s, 3H), 2.28-2.22 (m, 1H), 2.10-2.04 (m, 1H), 1.26-1.19 (m, 1H), 1.18-1.27 (m, 1H). LC-MS (Method D): m/z=424.1 [M+H]$^+$, 1.664 min.

Example 157A and 157B: 5-benzyl-N-((1aR,2R,8bS)-4-methyl-3-oxo-1,1a,2,3,4,8b-hexahydrocyclopropa[d]pyrido[2,3-b]azepin-2-yl)-1,3,4-oxadiazole-2-carboxamide and 5-benzyl-N-((1aS,2S,8bR)-4-methyl-3-oxo-1,1a,2,3,4,8b-hexahydrocyclopropa[d]pyrido[2,3-b]azepin-2-yl)-1,3,4-oxadiazole-2-carboxamide

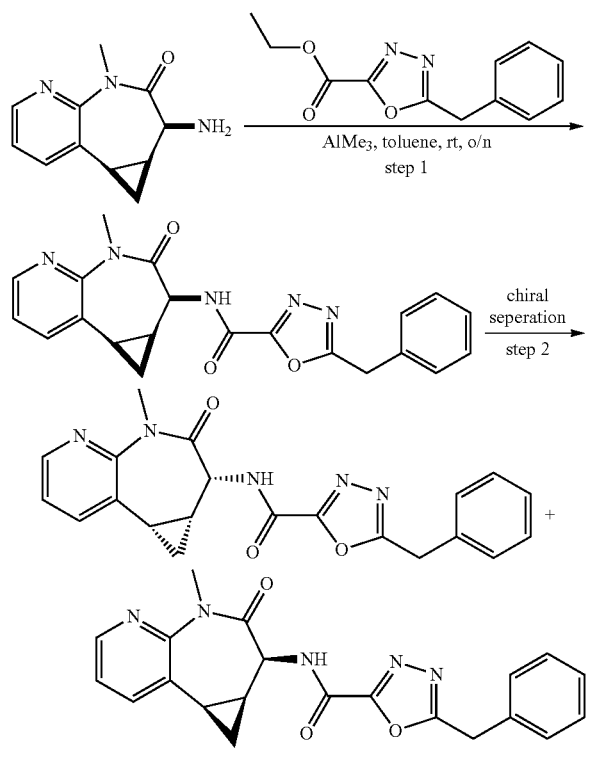

The crude product obtained using the procedure described in Example 54 was purified by column chromatography (ethyl acetate/petroleum ether, 1/1) to afford the title compound as a white solid.

The racemate was separated by Prep-Chiral-HPLC with the following conditions: Column: CHIRALPAK AS-H, 2.0 cm I.D×25 cm, 5 μm; Mobile Phase A: Hexane, Mobile Phase B: EtOH; Flow rate: 16 mL/min; Gradient: 50% B to 50% B over 16 min; UV 220 & 254 nm; Rt1: 8.212; Rt2: 10.554 to afford the title compounds:

Example 157A (first eluting isomer): $^1$H NMR (300 MHz, DMSO-$d_6$) δ 9.48 (d, J=6.6 Hz, 1H), 8.39 (dd, J=4.8, 1.8 Hz, 1H), 7.99 (dd, J=7.5, 1.8 Hz, 1H), 7.37-7.27 (m, 6H), 4.42 (d, J=6.3 Hz, 1H), 4.38 (s, 2H), 3.34 (s, 3H), 2.31-2.26 (m, 1H), 2.07-1.96 (m, 1H), 1.23-1.08 (m, 2H). LC-MS (Method X): m/z=390.1 [M+H]$^+$, 2.745 min.

Example 157B (second eluting isomer): $^1$H NMR (300 MHz, DMSO-$d_6$) δ 9.47 (d, J=6.0 Hz, 1H), 8.39 (dd, J=6.6, 1.8 Hz, 1H), 7.97 (dd, J=7.5, 1.8 Hz, 1H), 7.37-7.21 (m, 6H), 4.43 (d, J=6.3 Hz, 1H), 4.39 (s, 2H), 3.33 (s, 3H), 2.32-2.26 (m, 1H), 2.03-1.99 (m, 1H), 1.23-1.08 (m, 2H). LC-MS (Method D): m/z=390.1 [M+H]$^+$, 1.533 min.

Example 158: (S)-1-benzyl-5-cyano-N-(5-methyl-4-oxo-2,3,4,5-tetrahydropyrido[3,2-b][1,4]oxazepin-3-yl)-1H-pyrazole-3-carboxamide

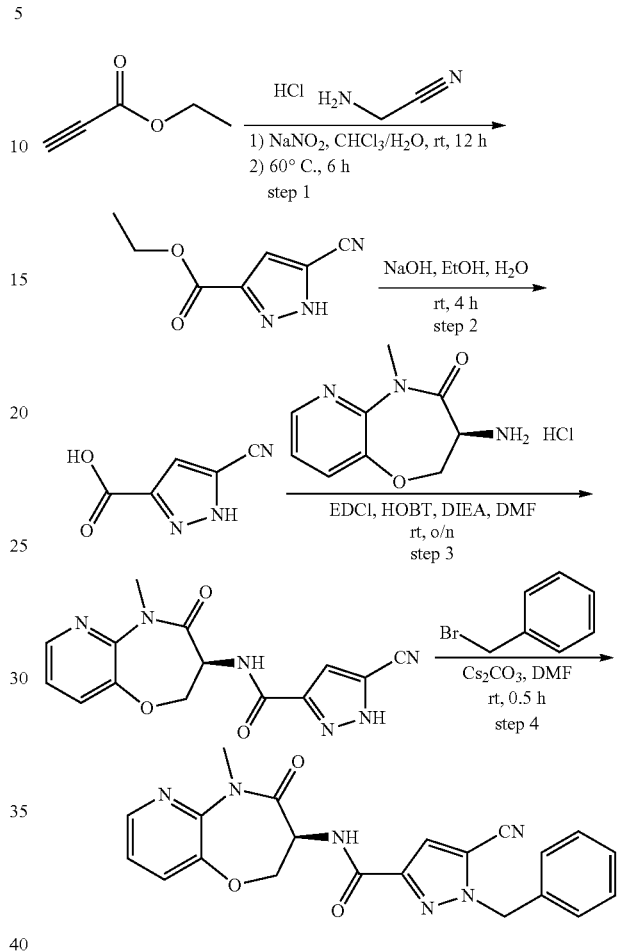

Step 1: Preparation of ethyl 5-cyano-1H-pyrazole-3-carboxylate

Sodium nitrite (10.56 g, 153 mmol) was added to a mixture of ethyl propiolate (5.00 g, 51.1 mmol) and 2-aminoacetonitrile hydrochloride (9.44 g, 102 mmol) in chloroform (150 mL) and water (5 mL). The reaction mixture was stirred for 12 hours at room temperature, then heated to 60° C. and stirred for another 6 hours. After cooling to room temperature, the resulting mixture was filtered. The filtrate was washed with brine, dried over anhydrous sodium sulfate, filtered and concentrated under vacuum. The residue was purified by column chromatography (ethyl acetate/petroleum ether, 1/9) to afford the title compound (2.90 g, 35%) as a yellow solid. LC-MS (Method C): m/z=166.1 [M+H]$^+$, 1.032 min.

Step 2: Preparation of 5-cyano-1H-pyrazole-3-carboxylic acid

A solution of sodium hydroxide in water (2 M, 30 mL, 60 mmol) was added to a mixture of ethyl 5-cyano-1H-pyrazole-3-carboxylate (1.5 g, 9.09 mmol) in ethanol (25 mL). The reaction mixture was stirred for 4 hours at room temperature. After removal of ethanol under reduced pressure, the pH value of the solution was adjusted to 3-4 with aqueous hydrochloric acid (1 M, 100 ml, 100 mmol). The resulting solution was extracted with ethyl acetate (3×50 mL). The combined organic layers were washed with brine, dried over anhydrous sodium sulfate, filtered and concentrated under high vacuum to afford the title compound (400 mg crude) as a yellow solid. $^1$H NMR (400 MHz, DMSO-$d_6$) δ 14.89 (s, 1H), 7.43 (s, 1H), 3.15 (s, 1H).

Step 3: Preparation of (S)-5-cyano-N-(5-methyl-4-oxo-2,3,4,5-tetrahydropyrido[3,2-b][1,4]oxazepin-3-yl)-1H-pyrazole-3-carboxamide The crude product obtained using Amide Coupling Procedure C was purified by column chromatography (ethyl acetate/petroleum ether, 1/1) to afford the title compound (180 mg, 53%) as a yellow solid. LC-MS (Method S): m/z=313.2 [M+H]$^+$, 0.749 min.

Step 4: Preparation of ((S)-1-benzyl-5-cyano-N-(5-methyl-4-oxo-2,3,4,5-tetrahydropyrido[3,2-b][1,4]oxazepin-3-yl)-1H-pyrazole-3-carboxamide Cesium carbonate (80 mg, 0.25 mmol) was added to a mixture of (S)-5-cyano-N-(5-methyl-4-oxo-2,3,4,5-tetrahydropyrido[3,2-b][1,4]oxazepin-3-yl)-1H-pyrazole-3-carboxamide (60 mg, 0.19 mmol) and (bromomethyl)benzene (39 mg, 0.23 mmol) in N,N-dimethylformamide (3 mL). The reaction mixture was stirred for 0.5 hour at room temperature, diluted with water (50 mL) and extracted with ethyl acetate (3×30 mL). The combined organic layers were washed with brine, dried over anhydrous sodium sulfate, filtered and concentrated under vacuum. The residue was purified by Prep-HPLC with the following conditions: Column, XBridge Shield RP18 OBD, 5 μm, 19×150 mm; Mobile Phase A: Water (0.1% formic acid); Mobile Phase B: MeCN; Flow rate: 20 mL/min; Gradient: 20% B to 45% B over 7 min; UV 254 & 220 nm; Rt: 7 min to afford the title compound: $^1$H NMR (400 MHz, DMSO-$d_6$) δ 8.67 (d, J=7.9 Hz, 1H), 8.35 (dd, J=4.7, 1.6 Hz, 1H), 7.69 (dd, J=8.0, 1.6 Hz, 1H), 7.58 (s, 1H), 7.44-7.29 (m, 4H), 7.28-7.22 (m, 2H), 5.65 (s, 2H), 4.90-4.84 (m, 1H), 4.73-4.67 (m, 1H), 4.54-4.50 (m, 1H), 3.35 (s, 3H). LC-MS (Method T): m/z=403.2 [M+H]$^+$, 1.412 min.

Example 159: (S)-5-cyano-1-(4-fluorobenzyl)-N-(5-methyl-4-oxo-2,3,4,5-tetrahydropyrido[3,2-b][1,4]oxazepin-3-yl)-1H-pyrazole-3-carboxamide

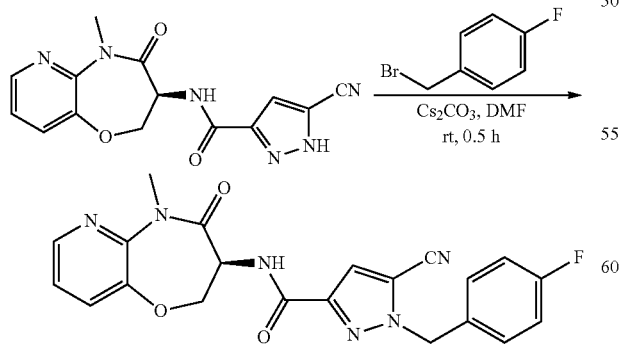

The crude product obtained using the procedure described in Example 158, Step 4 was purified by Prep-HPLC with the following conditions: Column: XBridge Shield RP18 OBD, 5 μm, 19×150 mm; Mobile Phase A: Water (10 mmol/L NH$_4$HCO$_3$); Phase B: ACN; Flow rate: 20 mL/min; Gradient: 35% B to 60% B over 12 min; UV 254 & 220 nm; Rt: 6.5 min to afford the title compound: $^1$H NMR (400 MHz, DMSO-$d_6$) δ 8.67 (d, J=7.9 Hz, 1H), 8.36 (dd, J=4.8, 1.6 Hz, 1H), 7.70 (dd, J=7.9, 1.6 Hz, 1H), 7.59 (s, 1H), 7.36-7.29 (m, 3H), 7.27-7.20 (m, 2H), 5.64 (s, 2H), 4.90-4.84 (m, 1H), 4.72-4.67 (m, 1H), 4.54-4.50 (m, 1H), 3.36 (s, 3H). LC-MS (Method T): m/z=421.1 [M+H]$^+$, 1.433 min.

Example 160A and 160B: (S)-5-benzyl-N-(5'-methyl-4'-oxo-4',5'-dihydro-3'H-spiro[cyclopropane-1,2'-pyrido[3,2-b][1,4]oxazepin]-3'-yl)-1,3,4-oxadiazole-2-carboxamide and (R)-5-benzyl-N-(5'-methyl-4'-oxo-4',5'-dihydro-3'H-spiro[cyclopropane-1,2'-pyrido[3,2-b][1,4]oxazepin]-3'-yl)-1,3,4-oxadiazole-2-carboxamide

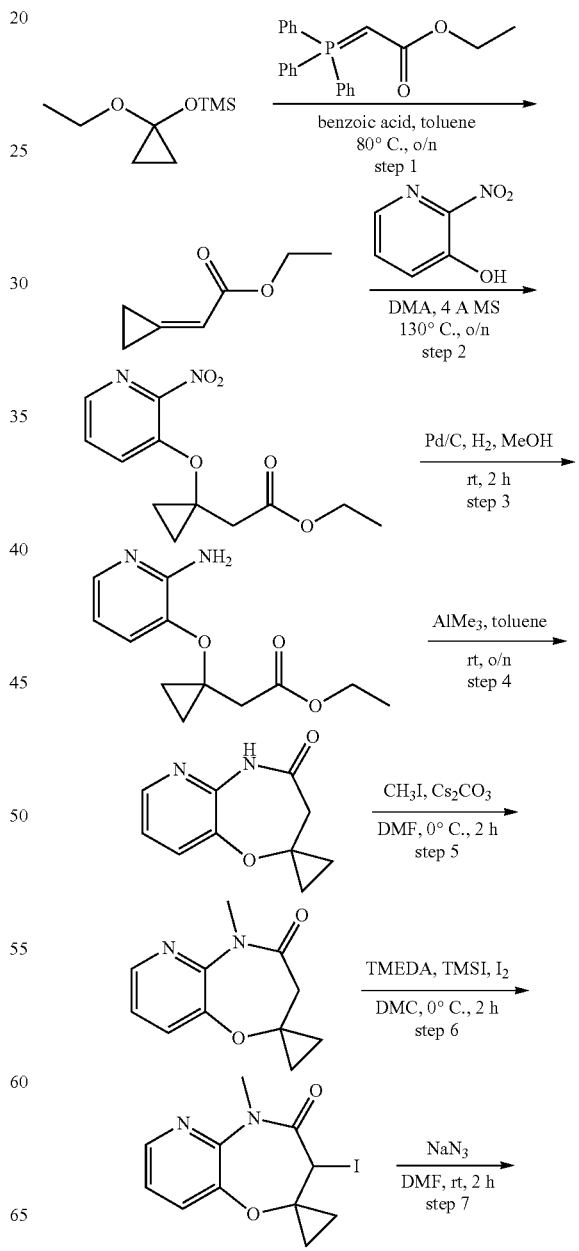

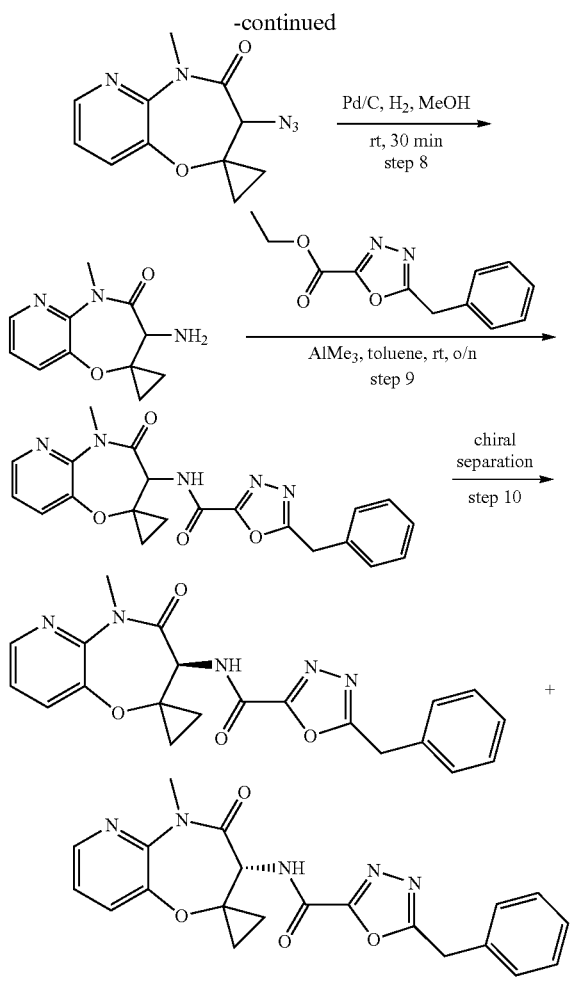

Step 1: Preparation of ethyl 2-cyclopropylideneacetate

Ethyl 2-(triphenylphosphoranylidene)acetate (52 g, 149.42 mmol) was added to a mixture of (1-ethoxycyclopropoxy)trimethylsilane (20 g, 114.94 mmol) and benzoic acid (1.83 g, 14.95 mmol) in toluene (150 mL). The reaction mixture was stirred at 80° C. overnight under nitrogen atmosphere. After cooling to room temperature, the reaction mixture was concentrated under reduced pressure. The residue was purified by column chromatography (dichloromethane/petroleum ether, 1/1) to afford the title compound (2.1 g, 14%) as a colorless oil. LC-MS (Method S): m/z=127.2 [M+H]$^+$, 0.886 min.

Step 2: Preparation of ethyl 2-(1-((2-nitropyridin-3-yl)oxy)cyclopropyl)acetate 2-Nitropyridin-3-ol (3.36 g, 24.00 mmol) was added to a mixture of ethyl 2-cyclopropylideneacetate (1.00 g, 7.93 mmol) and molecular sieves 4 Å (2.80 g) in dimethylacetamide (40 mL). The reaction mixture was stirred at 130° C. overnight under nitrogen atmosphere. After cooling to room temperature, the mixture was diluted with diethyl ether (150 mL) and washed with aqueous sodium hydroxide (0.2 M, 3×200 mL). The combined organic layers were dried over anhydrous sodium sulfate, filtered and concentrated under vacuum. The residue was purified by column chromatography (dichloromethane/petroleum ether, 2/1) to afford the title compound (450 mg, 21%) as a yellow oil. LC-MS (Method S): m/z=267.2 [M+H]$^+$, 0.935 min.

Step 3: Preparation of ethyl 2-(1-((2-aminopyridin-3-yl)oxy)cyclopropyl)acetate A mixture of ethyl 2-(1-((2-nitropyridin-3-yl)oxy)cyclopropyl)acetate (800 mg, 3.00 mmol) in methanol (30 mL) was hydrogenated in the presence of palladium on carbon (10%, 80 mg) under hydrogen atmosphere (2-3 atm). The reaction mixture was stirred for 2 hours at room temperature. The mixture was filtered through Celite and the filtrate was concentrated under high vacuum to afford the title compound (650 mg, 92%) as a yellow oil. LC-MS (Method S): m/z=237.1 [M+H]$^+$, 0.587 min.

Step 4: Preparation of 3'H-spiro[cyclopropane-1,2'-pyrido[3,2-b][1,4]oxazepin]-4'(5'H)-one A solution of trimethylaluminum in toluene (2 M, 5.3 mL, 10.55 mmol) was added dropwise to a stirring mixture of ethyl 2-(1-((2-aminopyridin-3-yl)oxy)cyclopropyl)acetate (500 mg, 2.11 mmol) in toluene (50 mL). The resulting mixture was stirred overnight at room temperature, quenched by the addition of water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/3) to afford the title compound (290 mg, 72%) as a yellow oil. LC-MS (Method S): m/z=191.1 [M+H]$^+$, 0.704 min.

Step 5: Preparation of 5'-methyl-3'H-spiro[cyclopropane-1,2'-pyrido[3,2-b][1,4]oxazepin]-4'(5'H)-one Iodomethane (178 mg, 1.26 mmol) was added dropwise to a stirring mixture of 3'H-spiro[cyclopropane-1,2'-pyrido[3,2-b][1,4]oxazepin]-4'(5'H)-one (200 mg, 1.05 mmol) and cesium carbonate (341 mg, 1.05 mmol) in N,N-dimethylformamide (10 mL). The reaction mixture was stirred for 2 hours at 0° C., diluted with water (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 3/17) to afford the title compound (150 mg, 69%) as a white solid. LC-MS (Method S): m/z=205.1 [M+H]$^+$, 0.767 min.

Step 6: Preparation of 3'-iodo-5'-methyl-3'H-spiro[cyclopropane-1,2'-pyrido[3,2-b][1,4]oxazepin]-4'(5'H)-one N,N,N',N'-tetramethylethylenediamine (0.49 g, 4.25 mmol) was added to a mixture of 5'-methyl-3'H-spiro[cyclopropane-1,2'-pyrido[3,2-b][1,4]oxazepin]-4'(5'H)-one (0.18 g, 0.85 mmol) in dichloromethane (40 mL) at 0° C. followed by addition of iodotrimethylsilane (1.70 g, 8.50 mmol) dropwise over 20 minutes. The mixture was stirred for 1 hour at 0° C. and then a solution of iodine (0.32 g, 1.25 mmol) in dichloromethane (100 mL) was added to the mixture. The reaction mixture was stirred for another 1 hour at 0° C., quenched by the addition of aqueous sodium thiosulfate (5%, 20 mL) and extracted with dichloromethane (3×50 mL). The combined organic layers were washed with brine, dried over anhydrous sodium sulfate, filtered and concentrated under vacuum to afford the title compound (280 mg crude) as a yellow oil. LC-MS (Method C): m/z=330.8 [M+H]$^+$, 0.946 min.

Step 7: Preparation of 3'-azido-5'-methyl-3'H-spiro [cyclopropane-1,2'-pyrido[3,2-b][1,4]oxazepin]-4' (5'H)-one Sodium azide (109 mg, 1.68 mmol) was added to a mixture of 3'-iodo-5'-methyl-3'H-spiro[cyclopropane-1,2'-pyrido[3,2-b][1,4]oxazepin]-4'(5'H)-one (280 mg, 0.84 mmol) in N,N-dimethylformamide (5 mL). The resulting mixture was stirred for 2 hours at room temperature, quenched by the addition of water (40 mL) and extracted with ethyl acetate (3×50 mL). The combined organic layers were washed with brine, dried over sodium sulfate, filtered and concentrated under vacuum. The residue was purified by Prep-TLC (ethyl acetate/petroleum ether, 1/2) to afford the title compound (70 mg, 33%) as a yellow solid. LC-MS (Method C): m/z=246.0 [M+H]$^+$, 0.925 min.

Step 8: Preparation of 3'-amino-5'-methyl-3'H-spiro [cyclopropane-1,2'-pyrido[3,2-b][1,4]oxazepin]-4' (5'H)-one A mixture of 3'-Azido-5'-methyl-3'H-spiro[cyclopropane-1,2'-pyrido[3,2-b][1,4]oxazepin]-4'(5'H)-one (70 mg, 0.28 mmol) in methanol (10 mL) was hydrogenated in the presence of palladium on carbon (10%, 10 mg) under hydrogen atmosphere (2-3 atm). After stirring for 30 minutes at room temperature the reaction mixture was filtered through Celite and the filtrate was concentrated under vacuum to afford the title compound (50 mg, 78%) as a white solid. LC-MS (Method S): m/z=220.2 [M+H]$^+$, 0.690 min.

Step 9: Preparation of 5-benzyl-N-(5'-methyl-4'-oxo-4',5'-dihydro-3'H-spiro[cyclopropane-1,2'-pyrido[3,2-b][1,4]oxazepin]-3'-yl)-1,3,4-oxadiazole-2-carboxamide The crude product obtained using the procedure described in Example 54 was purified by Prep-TLC (ethyl acetate/petroleum ether, 1/1) to afford the title compound (42 mg, 45%) as a white solid. LC-MS (Method S): m/z=406.0 [M+H]$^+$, 1.024 min.

Step 10: Preparation of (S)-5-benzyl-N-(5'-methyl-4'-oxo-4',5'-dihydro-3'H-spiro[cyclopropane-1,2'-pyrido[3,2-b][1,4]oxazepin]-3'-yl)-1,3,4-oxadiazole-2-carboxamide and (R)-5-benzyl-N-(5'-methyl-4'-oxo-4',5'-dihydro-3'H-spiro[cyclopropane-1,2'-pyrido[3,2-b][1,4]oxazepin]-3'-yl)-1,3,4-oxadiazole-2-carboxamide The racemate of 5-benzyl-N-(5'-methyl-4'-oxo-4',5'-dihydro-3'H-spiro[cyclopropane-1,2'-pyrido[3,2-b][1,4]oxazepin]-3'-yl)-1,3,4-oxadiazole-2-carboxamide (42 mg, 0.10 mmol) was separated by Prep-Chiral-HPLC with the following conditions: Column: CHIRALPAK IA, 2.12×15 cm, 5 μm; Mobile Phase A: Hexane, Mobile Phase B: IPA; Flow rate: 20 mL/min; Gradient: 50% B to 50% B over 14 min; UV 254 & 220 nm; Rt 1: 12.359; Rt 2: 20.087 to afford the title compounds:

Example 160A (first eluting isomer): $^1$H NMR (300 MHz, DMSO-d$_6$) δ 9.01 (d, J=8.7 Hz, 1H), 8.39 (dd, J=4.8, 1.5 Hz, 1H), 7.74 (dd, J=8.1, 1.5 Hz, 1H), 7.39-7.27 (m, 6H), 5.20 (d, J=8.4 Hz, 1H), 4.35 (s, 2H), 3.40 (s, 3H), 1.36-1.28 (m, 1H), 1.16-1.02 (m, 1H), 1.00-0.94 (m, 1H), 0.58-0.50 (m, 1H). LC-MS (Method V): m/z=406.1 [M+H]$^+$, 2.745 min.

Example 160B (second eluting isomer): $^1$H NMR (300 MHz, DMSO-d$_6$) δ 9.01 (d, J=8.4 Hz, 1H), 8.39 (dd, J=4.8, 1.5 Hz, 1H), 7.74 (dd, J=8.1, 1.5 Hz, 1H), 7.39-7.27 (m, 6H), 5.20 (d, J=8.4 Hz, 1H), 4.35 (s, 2H), 3.40 (s, 3H), 1.36-1.31 (m, 1H), 1.16-1.03 (m, 1H), 1.00-0.94 (m, 1H), 0.58-0.50 (m, 1H). LC-MS (Method D): m/z=406.1 [M+H]$^+$, 1.652 min.

Example 161: (S)-5-(3-cyanobenzyl)-N-(5-methyl-4-oxo-2,3,4,5-tetrahydropyrido[3,2-b][1,4]oxazepin-3-yl)-4H-1,2,4-triazole-3-carboxamide

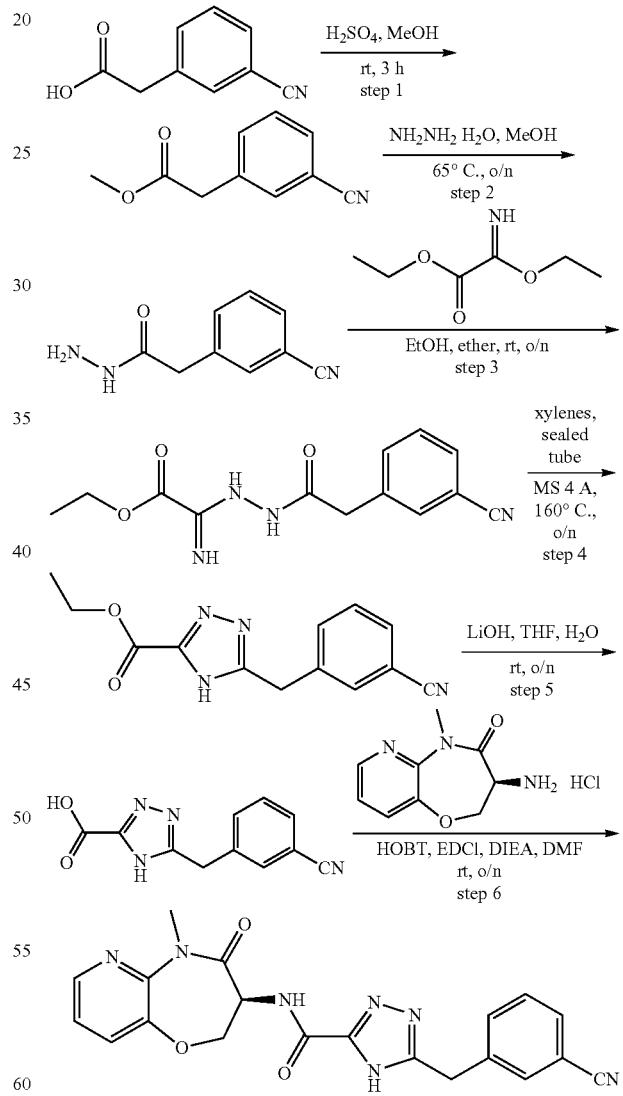

Step 1: Preparation of methyl 2-(3-cyanophenyl)acetate

Sulfuric acid (98%, 2.0 mL) was added to a mixture of 2-(3-cyanophenyl)acetic acid (3.5 g, 22.0 mmol) in methanol (80 mL). The resulting mixture was stirred at room temperature for 3 hours and concentrated under vacuum. The residue was diluted with water (40 mL) and extracted with ethyl acetate (3×60 mL). The combined organic layers were washed with brine, dried over anhydrous sodium sulfate, filtered and concentrated under vacuum to afford the title compound (3.30 g, 87%) as a colorless oil. LC-MS (Method S): m/z=176.2 [M+H]$^+$, 0.504 min.

Step 2: Preparation of 2-(3-cyanophenyl)acetohydrazide

Hydrazine hydrate (80%, 3.3 mL, 85.0 mmol) was added to a mixture of methyl 2-(3-cyanophenyl)acetate in methanol (50 mL). The reaction mixture was stirred at 65° C. overnight and then concentrated under reduced pressure. The residue was diluted with water (40 mL) and extracted with ethyl acetate (3×100 mL). The combined organic layers were dried over anhydrous sodium sulfate, and filtered. The filtrate was concentrated under vacuum to afford the crude title compound (2.4 g, 80%) as a white solid. LC-MS (Method S): m/z=176.2 [M+H]$^+$, 0.506 min.

Step 3: Preparation of ethyl 2-(2-(2-(3-cyanophenyl)acetyl)hydrazinyl)-2-iminoacetate Ethyl 2-ethoxy-2-iminoacetate (1.82 g, 12.6 mmol) was added to a stirring mixture of 2-(3-cyanophenyl)acetohydrazide (2.0 g, 11.5 mmol) in ethanol (20 mL) and diethyl ether (60 mL). The reaction mixture was stirred at room temperature overnight. The white solid was collected by filtration and rinsed with diethyl ether to afford the title compound (2.88 g, 92%) as a white solid. LC-MS (Method C): m/z=275.1 [M+H]$^+$, 0.913 min.

Step 4: Preparation of ethyl 5-(3-cyanobenzyl)-4H-1,2,4-triazole-3-carboxylate Molecular sieves 4 Å (50 mg) was added to a mixture of ethyl 2-(2-(2-(3-cyanophenyl)-acetyl)hydrazinyl)-2-iminoacetate (1.0 g, 3.65 mmol) in xylene (10 mL). The reaction mixture was stirred at 160° C. overnight in a sealed tube and concentrated under high vacuum. The residue was purified by column chromatography (ethyl acetate/petroleum ether, 1/1) to afford the title compound (500 mg, 54%) as a white solid. LC-MS (Method S): m/z=257.2 [M+H]$^+$, 0.767 min.

Step 5: Preparation of 5-(3-cyanobenzyl)-4H-1,2,4-triazole-3-carboxylic acid A solution of lithium hydroxide (94 mg, 4.0 mmol) in water (5 mL) was added to a solution of ethyl 5-(3-cyanobenzyl)-4H-1,2,4-triazole-3-carboxylate (500 mg, 2.0 mmol) in tetrahydrofuran (15 mL). The resulting mixture was stirred at room temperature overnight. After removal of tetrahydrofuran under reduced pressure, the resulting solution was adjusted to pH=7 with aqueous hydrochloric acid (1 N, 10 mL) and extracted with ethyl acetate (3×20 mL). The combined organic layers were washed with brine, dried over anhydrous sodium sulfate, filtered and concentrated under vacuum to afford the title compound (430 mg crude) as a white solid. LC-MS (Method C): m/z=229.1 [M+H]$^+$, 0.816 min.

Step 6: Preparation of (S)-5-(3-cyanobenzyl)-N-(5-methyl-4-oxo-2,3,4,5-tetrahydropyrido[3,2-b][1,4]oxazepin-3-yl)-4H-1,2,4-triazole-3-carboxamide The crude product obtained using Amide Coupling Procedure C was purified by Prep-HPLC with the following conditions: Column: XBridge C18 OBD Prep Column, 100 Å, 5 μm, 19 mm×250 mm; Mobile Phase A: Water (0.1% formic acid), Mobile Phase B: ACN; Flow rate: 20 mL/min; Gradient: 20% B to 45% B over 7 min; UV 254 & 220 nm; Rt: 7 min to afford the title compound: $^1$H NMR (400 MHz, DMSO-d$_6$) δ 14.53 (br s, 1H), 8.68 (s, 1H), 8.37 (dd, J=4.4, 1.2 Hz, 1H), 7.79-7.69 (m, 3H), 7.64-7.61 (m, 1H), 7.58-7.53 (m, 1H), 7.36-7.32 (m, 1H), 4.90-4.82 (m, 1H), 4.75-4.69 (m, 1H), 4.55-4.49 (m, 1H), 4.22 (s, 2H), 3.36 (s, 3H). LC-MS (Method T): m/z=404.2 [M+H]$^+$, 1.095 min.

Example 162: (S)-5-(3-cyano-5-fluorobenzyl)-N-(5-methyl-4-oxo-2,3,4,5-tetrahydropyrido[3,2-b][1,4]oxazepin-3-yl)-4H-1,2,4-triazole-3-carboxamide

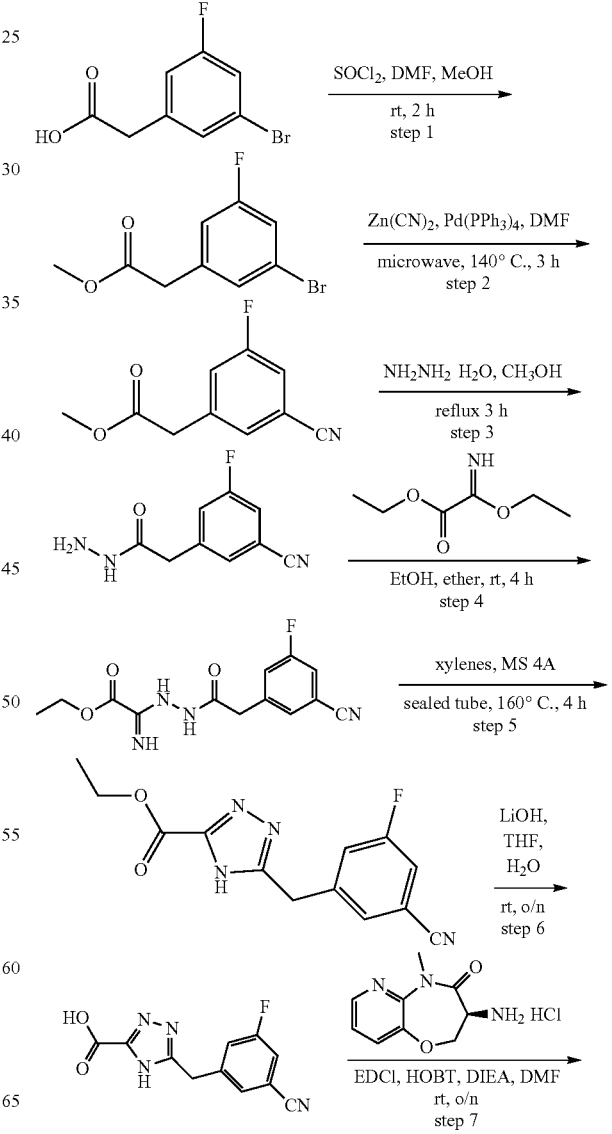

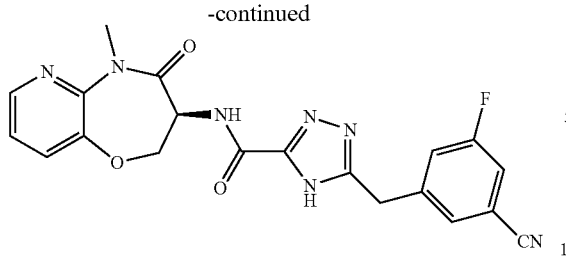

Step 1: Preparation of methyl 2-(3-bromo-5-fluorophenyl)acetate

Thionyl chloride (4.26 g, 35.8 mmol) was added to a stirring mixture of methyl 2-(3-bromo-5-fluorophenyl)acetic acid (2.6 g, 11.93 mmol) in methanol (30 mL) dropwise, followed by the addition of N,N-dimethylformamide (two drops). The reaction mixture was stirred for 2 hours at room temperature and concentrated under high vacuum. The residue was purified by column chromatography (ethyl acetate/petroleum ether, 1/8) to afford the title compound (2.79 g, 92.2%) as a yellow solid. LC-MS (Method S): m/z=247.1 [M+H]$^+$, 1.079 min.

Step 2: Preparation of methyl 2-(3-cyano-5-fluorophenyl)acetate

Tetrakis(triphenylphosphanyl)palladium (1.2 g, 1.05 mmol) was added to a mixture of methyl 2-(3-bromo-5-fluorophenyl)acetate (2.6 g, 10.5 mmol) and dicyanozinc (1.64 g, 14.17 mmol) in N,N-dimethylformamide (30 mL) under nitrogen atmosphere. The reaction mixture was heated at 140° C. by microwave and stirred for 3 hours. After cooling to room temperature, the reaction mixture was concentrated under vacuum. The residue was purified by column chromatography (ethyl acetate/petroleum ether, 1/10) to afford the title compound (1.12 g, 54%) as a yellow solid. LC-MS (Method C): m/z=194 [M+H]$^+$, 0.914 min.

Step 3: Preparation of 2-(3-cyano-5-fluorophenyl)acetohydrazide

Hydrazine hydrate (1.45 g, 29 mmol) was added to a mixture of methyl 2-(3-cyano-5-fluorophenyl)acetate (1.12 g, 5.80 mmol) in methanol (20 mL). The resulting mixture was heated at reflux, stirred for 3 hours and concentrated under high vacuum. The residue was diluted with water (30 mL) and extracted with ethyl acetate (3×20 mL). The combined organic layers were washed with brine, dried over anhydrous sodium sulfate, filtered and concentrated under vacuum. The residue was purified by column chromatography (ethyl acetate/petroleum ether, 3/1) to afford the title compound (0.92 g, 82.2%) as a white solid. LC-MS (Method S): m/z=194 [M+H]$^+$, 0.30 min.

Step 4: Preparation of ethyl 2-(2-(2-(3-cyano-5-fluorophenyl)acetyl)hydrazinyl)-2-iminoacetate Ethyl 2-ethoxy-2-iminoacetate (692 mg, 4.77 mmol) was added to a stirred mixture of 2-(3-cyano-5-fluorophenyl)acetohydrazide (910 mg, 4.77 mmol) in ethanol (5 mL) and diethyl ether (15 mL). The reaction mixture was stirred for 4 hours at room temperature. The solid was collected by filtration and dried under high vacuum to afford the title compound (160 mg, 80.8%) as a white solid. LC-MS (Method C): m/z=293 [M+H]$^+$, 0.727 min.

Step 5: Preparation of ethyl 5-(3-cyano-5-fluorobenzyl)-4H-1,2,4-triazole-3-carboxylate A mixture of ethyl 2-(2-(2-(3-cyano-5-fluorophenyl)acetyl)hydrazinyl)-2-iminoacetate (1 g, 3.42 mmol) and 4 Å molecular sieves in xylenes (20 mL) was stirred for 4 hours at 160° C. After cooling to room temperature, the reaction mixture was concentrated under high vacuum. The residue was purified by column chromatography (ethyl acetate/petroleum ether, 1/1) to afford the title compound (0.75 g, 79.5%) as a white solid. LC-MS (Method C): m/z=275.0 [M+H]$^+$, 0.811 min.

Step 6: Preparation of 5-(3-cyano-5-fluorobenzyl)-4H-1,2,4-triazole-3-carboxylic acid Lithium hydroxide (79.2 mg, 3.3 mmol) was added to a stirring mixture of ethyl 5-(3-cyano-5-fluorobenzyl)-4H-1,2,4-triazole-3-carboxylate (140 mg, 0.78 mmol) in tetrahydrofuran (10 mL) and water (3 mL). The reaction mixture was stirred overnight at room temperature. After removal of tetrahydrofuran under reduced pressure, the resulting solution was adjusted to pH=6 with aqueous hydrochloric acid (1 M, 20 mL, 20 mmol), and extracted with ethyl acetate (3×30 mL). The combined organic layers were washed with brine, dried over anhydrous sodium sulfate, filtered and concentrated under vacuum to afford the title compound (250 mg crude) as a yellow solid. LC-MS (Method C): m/z=247.0 [M+H]$^+$, 0.633 min.

Step 7: Preparation of (S)-5-(3-cyano-5-fluorobenzyl)-N-(5-methyl-4-oxo-2,3,4,5-tetrahydropyrido[3,2-b][1,4]oxazepin-3-yl)-4H-1,2,4-triazole-3-carboxamide The crude product obtained using Amide Coupling Procedure C was purified by Prep-HPLC with the following conditions: Column: X bridge Prep C18, 19×150 mm, 5 μm; Mobile phase: Phase A: water (10 mmol/L NH$_4$HCO$_3$); Phase B: MeCN (20% to 80% over 12 min); Detector, UV 220 & 254 nm to afford the title compound: $^1$H NMR (300 MHz, DMSO-d$_6$) δ 14.37 (s, 1H), 8.56 (s, 1H), 8.37 (dd, J=4.8, 1.5 Hz, 1H), 7.77-7.67 (m, 3H), 7.59-7.55 (m, 1H), 7.33 (dd, J=8.1, 4.8 Hz, 1H), 4.91-4.71 (m, 2H), 4.45-4.48 (m, 1H), 4.26 (s, 2H), 3.36 (s, 3H). LC-MS (Method D): m/z=422.1 [M+H]$^+$, 1.367 min.

Example 163: (S)-5-(3-cyanobenzyl)-N-(5-methyl-4-oxo-2,3,4,5-tetrahydrobenzo[b][1,4]oxazepin-3-yl)-4H-1,2,4-triazole-3-carboxamide

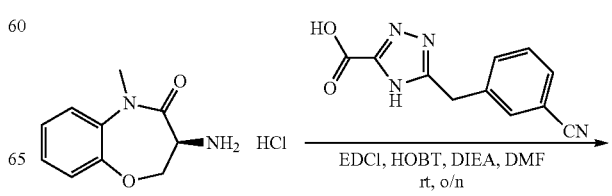

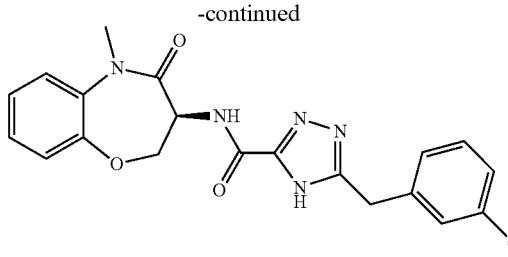

The crude product obtained using Amide Coupling Procedure C was purified by Prep-HPLC with the following conditions: Column: SunFire Prep C18 OBD Column 19×150 mm 5 μm 10 nm; Mobile Phase A: Water (10 mmol/L NH$_4$HCO$_3$), Mobile Phase B: ACN; Flow rate: 20 mL/min; Gradient: 25% B to 75% B in 7 min; UV 254 & 220 nm; Rt: 6.34 min.: $^1$H NMR (400 MHz, DMSO-d$_6$) δ 8.48 (s, 1H), 7.78-7.73 (m, 2H), 7.64-7.61 (m, 1H), 7.57-7.49 (m, 2H), 7.36-7.22 (m, 3H), 4.87-4.79 (m, 1H), 4.62-4.56 (m, 1H), 4.44-4.38 (m, 1H), 4.20 (s, 2H), 3.32 (s, 3H). LCMS (Method D): m/z=403.1 [M+H]$^+$, 1.367 min.

Example 164: (S)-5-(3-cyanobenzyl)-N-(5-methyl-4-oxo-2,3,4,5-tetrahydrobenzo[b][1,4]oxazepin-3-yl)thiazole-2-carboxamide

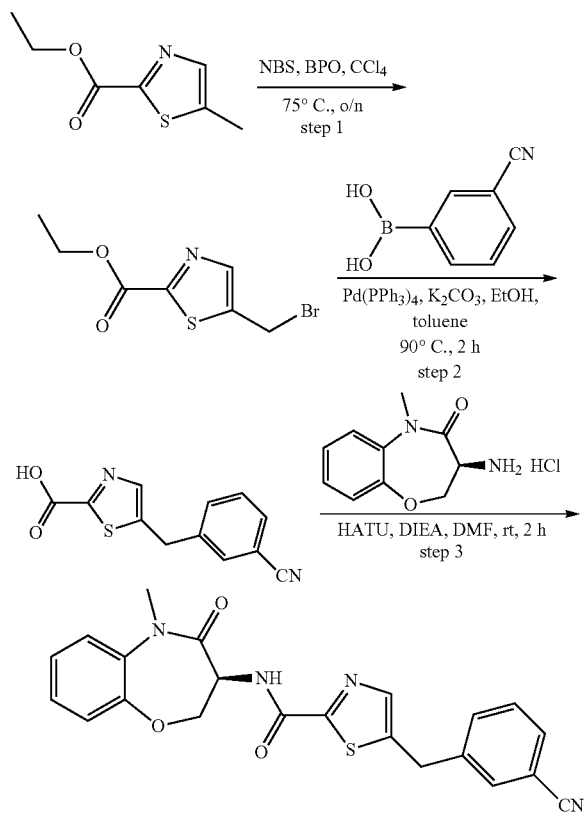

Step 1: Preparation of ethyl 5-(bromomethyl)thiazole-2carboxylate

Benzoyl peroxide (6 mg, 0.02 mmol) was added to a mixture of ethyl 5-methylthiazole-2-carboxylate (420 mg, 2.45 mmol) and N-bromosuccinimide (459 mg, 2.58 mmol) in carbon tetrachloride (6 mL). The resulting mixture was stirred overnight at 75° C. under nitrogen atmosphere, quenched by the addition of water (20 mL) and extracted with ethyl acetate (3×20 mL). The combined organic layers were dried over anhydrous sodium sulfate, filtered and concentrated under vacuum. The residue was purified by column chromatography (ethyl acetate/petroleum ether, 1/2) to afford the title compound (300 mg, 48.8%) as a yellow solid. LC-MS (Method S): m/z=252.3 [M+H]$^+$, 0.928 min.

Step 2: Preparation of 5-(3-cyanobenzyl)thiazole2-carboxylic acid

Tetrakis(triphenylphosphine)palladium (28 mg, 0.02 mmol) was added to a mixture of ethyl 5-(bromomethyl)thiazole-2carboxylate (300 mg, 1.20 mmol), (3-cyanophenyl)boronic acid (194 mg, 1.32 mmol) and potassium carbonate (190 mg, 1.37 mmol) in toluene/ethanol (5 mL/5 mL) under nitrogen atmosphere. The resulting mixture was stirred for 2 hours at 90° C. After cooling to room temperature, the reaction mixture was concentrated under vacuum. The residue was diluted with water (30 mL), the pH value of the resulting solution was adjusted to 3 with aqueous hydrochloric acid (1 M, 50 mL, 50 mmol) and extracted with ethyl acetate (3×30 mL). The combined organic layers were washed with brine, dried over anhydrous sodium sulfate, filtered and concentrated under vacuum. The residue was purified by column chromatography (methanol/dichloromethane, 1/10) to afford the title compound (100 mg, 34.1%) as a yellow oil. LC-MS (Method C): m/z=245.2 [M+H]$^+$, 1.208 min.

Step 3: Preparation of (S)-5-(3-cyanobenzyl)-N-(5-methyl-4-oxo-2,3,4,5-tetrahydrobenzo[b][1,4]oxazepin-3-yl)thiazole-2-carboxamide The crude product obtained using Amide Coupling Procedure B was purified by Prep-HPLC with the following conditions: Column: XBridge Shield RP18 OBD Column, 5 μm, 19×150 mm; Mobile Phase A: Water (10 mmol/L NH$_4$HCO$_3$), Mobile Phase B: ACN; Flow rate: 20 mL/min; Gradient: 25% B to 65% B over 7 min; UV 254 & 220 nm; Rt: 6.5 min to afford the title compound: $^1$H NMR (300 MHz, DMSO-d$_6$) δ 8.82 (d, J=8.0 Hz, 1H), 7.93-7.90 (m, 1H), 7.84-7.80 (m, 1H), 7.78-7.71 (m, 1H), 7.70-7.63 (m, 1H), 7.62-7.44 (m, 2H), 7.40-7.20 (m, 3H), 4.88-4.75 (m, 1H), 4.73-4.60 (m, 1H), 4.48-4.37 (m, 1H), 4.34 (s, 2H), 3.30 (s, 3H). LC-MS (Method V): m/z=419.2 [M+H]$^+$, 3.361 min.

Example 165: (S)-1-benzyl-5-fluoro-N-(5-methyl-4-oxo-2,3,4,5-tetrahydropyrido[3,2-b][1,4]oxazepin-3-yl)-1H-pyrazole-3-carboxamide

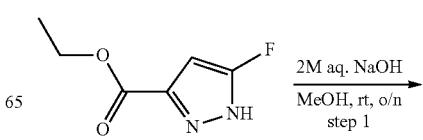

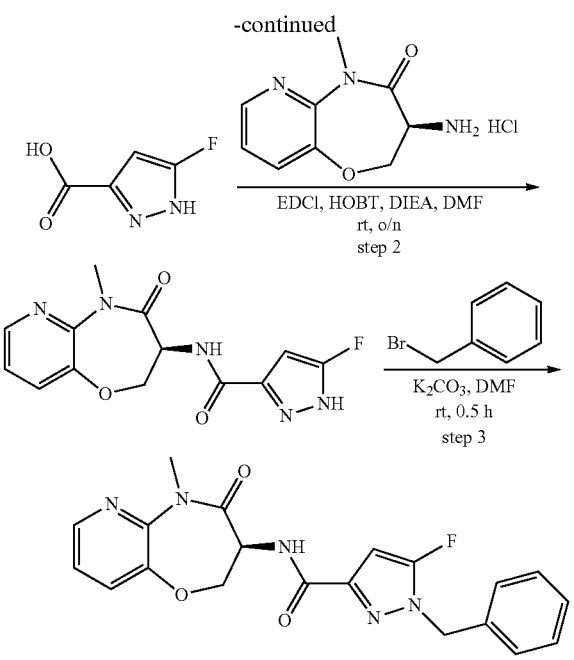

Step 1: Preparation of 5-fluoro-1H-pyrazole-3-carboxylic acid

A solution of sodium hydroxide (2 M, 0.63 mL, 1.26 mmol) was added to a stirring mixture of ethyl 5-fluoro-1H-pyrazole-3-carboxylate (100 mg, 0.63 mmol) in methanol (5 mL). The reaction mixture was stirred at room temperature overnight. After removal of methanol under reduced pressure, the resulting solution was adjusted to pH=5 with aqueous hydrochloric acid (1 N, 2 mL) and extracted with ethyl acetate (3×30 mL). The combined organic layers were washed with brine, dried over anhydrous sodium sulfate, and filtered. The filtrate was concentrated under vacuum to afford the title compound (80 mg, 97%) as a white solid. $^1$H NMR (300 MHz, DMSO-$d_6$) δ 13.67 (s, 1H), δ 13.49 (s, 1H), δ 6.47 (dd, J=6.3, 2.2 Hz, 1H).

Step 2: Preparation of (S)-5-fluoro-N-(5-methyl-4-oxo-2,3,4,5-tetrahydropyrido[3,2-b][1,4]oxazepin-3-yl)-1H-pyrazole-3-carboxamide The crude product obtained using Amide Coupling Procedure C was purified by column chromatography (methanol/dichloromethane, 1/10) to afford the title compound (100 mg, 56.8%) as a white solid. LC-MS (Method E): m/z=306.1 [M+H]$^+$, 0.898 min.

Step 3: Preparation of (S)-1-benzyl-5-fluoro-N-(5-methyl-4-oxo-2,3,4,5-tetrahydropyrido[3,2-b][1,4]oxazepin-3-yl)-1H-pyrazole-3-carboxamide The crude product obtained using the procedure described in Example 158, Step 4 was purified by Prep-HPLC with the following conditions: Column, XBridge Prep C18 OBD Column, 5 μm, 19×150 mm; Mobile phase: Phase A: Water (0.05% TFA), Phase B: MeCN; Flow rate: 20 mL/min; Gradient: 25% B to 55% B in 7 min; Detector, UV 254 & 220 nm to afford the title compound: $^1$H NMR (300 MHz, CD$_3$OD-$d_4$) δ 8.30 (dd, J=4.7, 1.6 Hz, 1H), 7.63 (dd, J=8.0, 1.6 Hz, 1H), 7.40-7.20 (m, 6H), 6.27 (d, J=5.6 Hz, 1H), 5.30 (s, 2H), 4.96 (dd, J=11.6, 7.2 Hz, 1H), 4.62 (dd, J=9.8, 7.2 Hz, 1H), 4.46 (dd, J=11.6, 9.8 Hz, 1H), 3.44 (s, 3H). LC-MS (Method D): m/z=396.1 [M+H]$^+$, 1.659 min.

Example 166: (S)-5-fluoro-1-(4-fluorobenzyl)-N-(5-methyl-4-oxo-2,3,4,5-tetrahydropyrido[3,2-b][1,4]oxazepin-3-yl)-1H-pyrazole-3-carboxamide

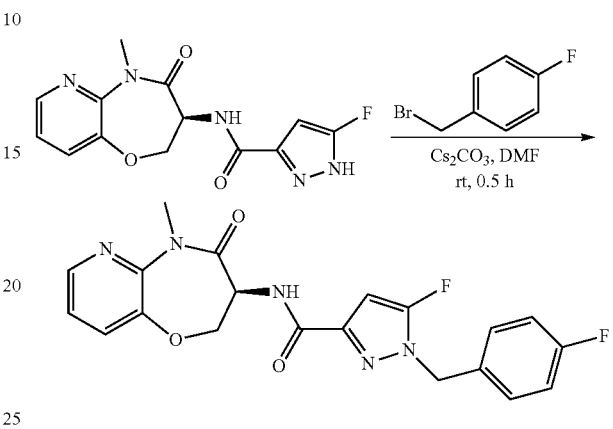

The crude product obtained using the procedure described in Example 158, Step 4 was purified by Prep-HPLC with the following conditions: Column, XBridge Prep C18 OBD Column, 5 μm, 19×150 mm; Mobile Phase A: Water (0.05% TFA), Mobile Phase B: MeCN; Flow rate: 20 mL/min; Gradient: 5% B to 55% B over 7 min; Detector, UV 254 & 220 nm to afford the title compound: $^1$H NMR (300 MHz, CD$_3$OD-$d_4$) δ 8.30 (dd, J=4.8, 1.6 Hz, 1H), 7.63 (dd, J=8.0, 1.6 Hz, 1H), 7.33-7.25 (m, 3H), 7.14-7.01 (m, 2H), 6.27 (d, J=5.6 Hz, 1H), 5.29 (s, 2H), 4.96 (dd, J=11.5, 7.2 Hz, 1H), 4.62 (dd, J=9.8, 7.2 Hz, 1H), 4.46 (dd, J=11.5, 9.8 Hz, 1H), 3.44 (s, 3H). LC-MS (Method D): m/z=414.1 [M+H]$^+$, 1.667 min.

Example 167: (S)-5-cyano-1-(3-cyanobenzyl)-N-(5-methyl-4-oxo-2,3,4,5-tetrahydropyrido[3,2-b][1,4]oxazepin-3-yl)-1H-pyrazole-3-carboxamide

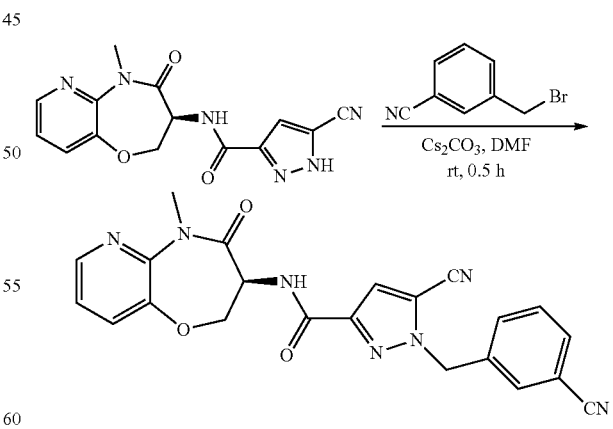

The crude product obtained using the procedure described in Example 158, Step 4 was purified by Prep-HPLC with the following conditions: Column: XBridge Shield RP18 OBD, 5 μm, 19×150 mm; Mobile Phase A: Water (10 mmol/L NH$_4$HCO$_3$); Mobile Phase B: MeCN; Flow rate: 20 mL/min; Gradient: 25% B to 55% B over 7 min; UV 254 &

220 nm; Rt: 6.32 min to afford the title compound: $^1$H NMR (400 MHz, DMSO-d$_6$) δ 8.67 (d, J=7.9 Hz, 1H), 8.36 (dd, J=4.7, 1.6 Hz, 1H), 7.87-7.82 (m, 1H), 7.80-7.75 (m, 1H), 7.69 (dd, J=8.0, 1.6 Hz, 1H), 7.65-7.58 (m, 2H), 7.52-7.58 (m, 1H), 7.35-7.28 (m, 1H), 5.73 (s, 2H), 4.90-4.81 (m, 1H), 4.72-4.63 (m, 1H), 4.54-4.47 (m, 1H), 3.35 (s, 3H). LC-MS (Method T): m/z=428.1 [M+H]$^+$, 1.320 min.

Example 168: (S)-1-((5-cyanopyridin-3-yl)methyl)-4-fluoro-N-(5-methyl-4-oxo-2,3,4,5-tetrahydropyrido[3,2-b][1,4]oxazepin-3-yl)-1H-pyrazole-3-carboxamide

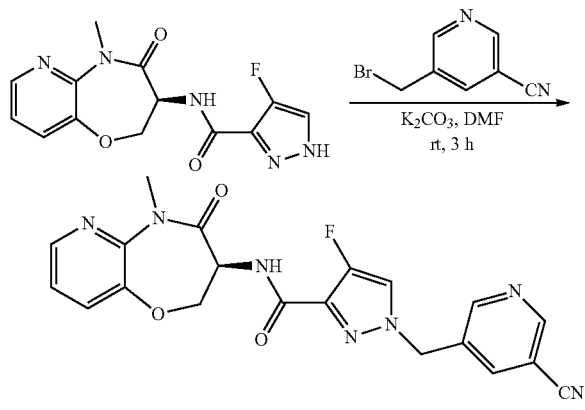

5-(Bromomethyl)nicotinonitrile (35 mg, 0.18 mmol) was added into a stirring mixture of (S)-4-fluoro-N-(5-methyl-4-oxo-2,3,4,5-tetrahydropyrido[3,2-b][1,4]oxazepin-3-yl)-1H-pyrazole-3-carboxamide (45 mg, 0.15 mmol) and potassium carbonate (62 mg, 0.45 mmol) in N,N-dimethylformamide (4 mL). The resulting mixture was stirred at room temperature for 3 hours, diluted with water (20 mL) and extracted with ethyl acetate (3×20 mL). The combined organic layers were washed with brine, dried over anhydrous sodium sulfate, filtered and concentrated under vacuum. The crude product obtained using the procedure described in Example 158, Step 4 was purified by Prep-HPLC with the following conditions: Column: XBridge Shield RP18 OBD Column, 5 μm, 19×150 mm; Mobile Phase A: Water (10 mmol/L NH$_4$HCO$_3$), Mobile Phase B: ACN; Flow rate: 20 mL/min; Gradient: 35% B to 50% B over 7 min; UV 254 & 220 nm; Rt: 6.5 min to afford the title compound: $^1$H NMR (400 MHz, CD$_3$OD-d$_4$) δ 8.91 (d, J=1.9 Hz, 1H), 8.82 (d, J=2.1 Hz, 1H), 8.35 (dd, J=4.8, 1.6 Hz, 1H), 8.19 (t, J=2.0 Hz, 1H), 7.92 (d, J=4.4 Hz, 1H), 7.68 (dd, J=8.0, 1.6 Hz, 1H), 7.32 (dd, J=8.0, 4.8 Hz, 1H), 5.48 (s, 2H), 5.02 (dd, J=11.5, 7.2 Hz, 1H), 4.69 (dd, J=9.9, 7.2 Hz, 1H), 4.51 (dd, J=11.5, 9.9 Hz, 1H), 3.50 (s, 3H). LC-MS (Method D): m/z=422.0 [M+H]$^+$, 1.328 min.

Example 169: (S)-5-benzyl-N-(5-trideuteriomethyl-4-oxo-2,3,4,5-tetrahydropyrido[3,2-b][1,4]oxazepin-3-yl)-4H-1,2,4-triazole-3-carboxamide

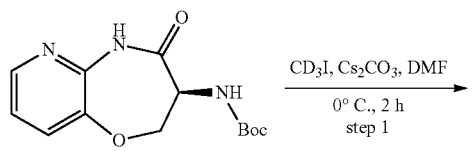

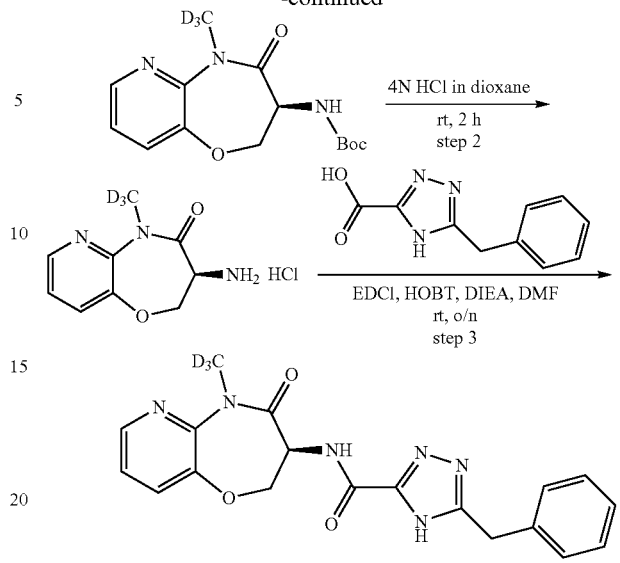

Step 1: Preparation of (S)-tert-butyl (5-trideuteriomethyl-4-oxo-2,3,4,5-tetrahydropyrido[3,2-b][1,4]oxazepin-3-yl)carbamate Trideuterated iodomethane (233.5 mg, 1.61 mmol) was added to a stirring mixture of (S)-tert-butyl 4-oxo-2,3,4,5-tetrahydropyrido[3,2-b][1,4]oxazepin-3-ylcarbamate (450 mg, 1.61 mmol) and cesium carbonate (629.2 mg, 1.93 mmol) in N,N-dimethylformamide (10 mL) at 0° C. The reaction mixture was stirred at 0° C. for 2 hours, diluted with water (20 mL) and extracted with ethyl acetate (3×20 mL). The combined organic layers were washed with brine, dried over anhydrous sodium sulfate and concentrated under vacuum to afford the title compound (360 mg, 75.5%) as a white solid. LC-MS (Method E): m/z=297.2 [M+H]$^+$, 0.903 min.

Step 2: Preparation of (S)-3-amino-5-trideuteriomethyl-2,3-dihydropyrido[3,2-b][1,4]oxazepin-4(5H)-one hydrochloride (S)-tert-butyl (5-trideuteriomethyl-4-oxo-2,3,4,5-tetrahydropyrido[3,2-b][1,4]oxazepin-3-yl)carbamate (200 mg, 0.68 mmol) was added to a solution of hydrochloride in 1,4-dioxane (4 M, 5 mL, 20 mmol). The reaction mixture was stirred at room temperature for 2 hours and concentrated under vacuum to afford the title compound (140 mg crude) as a white solid. LC-MS (Method E): m/z=197.1 [M+H]$^+$, 0.761 min.

Step 3: Preparation of (S)-5-benzyl-N-(5-trideuteriomethyl-4-oxo-2,3,4,5-tetrahydropyrido[3,2-b][1,4]oxazepin-3-yl)-4H-1,2,4-triazole-3-carboxamide The crude product obtained using Amide Coupling Procedure C was purified by Prep-HPLC with the following conditions: Column, XBridge Prep C18 OBD Column, 5 μm, 19×150 mm; Mobile Phase A: Water (10 mmol/L NH$_4$CO$_3$), Mobile Phase B: MeCN; Flow rate: 20 mL/min; Gradient: 25% B to 50% B over 7 min; Detector, UV 254 & 220 nm to afford the title compound: $^1$H NMR (400 MHz, CD$_3$OD-d$_4$) δ 8.33 (dd, J=4.8, 1.6 Hz, 1H), 7.66 (dd, J=8.0, 1.6 Hz, 1H), 7.38-7.22 (m, 6H), 5.02 (dd, J=11.6, 7.2 Hz, 1H), 4.67 (dd, J=9.9, 7.2 Hz, 1H), 4.51 (dd, J=11.5, 9.9 Hz, 1H), 4.16 (s, 2H). LC-MS (Method D): m/z=382.1 [M+H]+, 1.371 min.

Example 170A and 170B: 1-(3-cyanobenzyl)-N-((1aS,2S,8bR)-5,7-difluoro-3-oxo-1,1a,2,3,4,8b-hexahydrobenzo[b]cyclopropa[d]azepin-2-yl)-4-fluoro-1H-pyrazole-3-carboxamide and 1-(3-cyanobenzyl)-N-((1aR,2R,8bS)-5,7-difluoro-3-oxo-1,1a,2,3,4,8b-hexahydrobenzo[b]cyclopropa[d]azepin-2-yl)-4-fluoro-1H-pyrazole-3-carboxamide

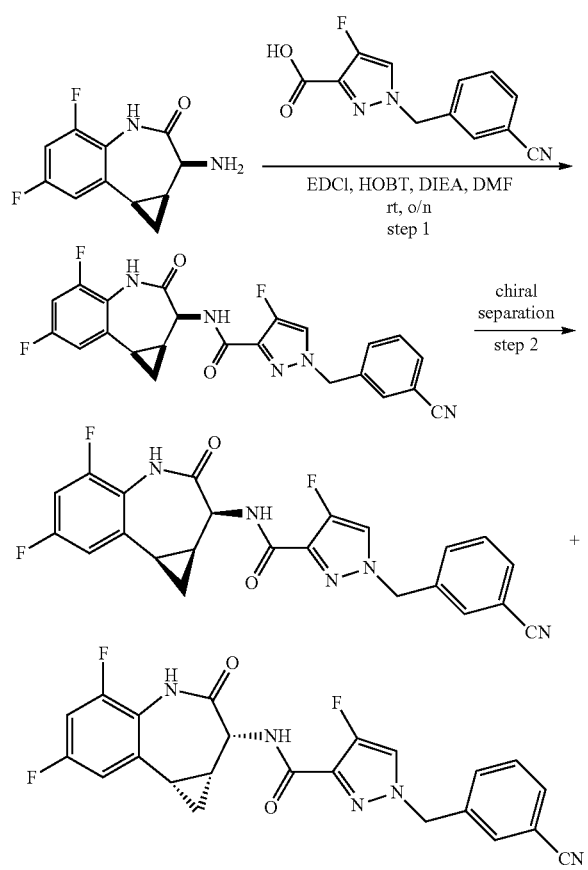

The crude product obtained using Amide Coupling Procedure C was purified by Prep-TLC (ethyl acetate/petroleum ether, 3/1) to afford the title compound as a white solid.

The racemate was separated by Prep-Chiral-HPLC with the following conditions: Column: (R,R)WHELK-01 5/100 Kromasil, 2.11 cm×25 cm (5 μm); Mobile Phase A: Hexane, Mobile Phase B: EtOH; Flow rate: 20 mL/min; Gradient: 60% B to 60% B over 22 min; UV 254 & 220 nm; Rt1: 14.06; Rt2: 18.79 to afford the title compounds:

Example 170A (first eluting isomer): 1H NMR (400 MHz, CD3OD-d4) δ 7.88 (d, J=4.4, Hz, 1H), 7.75-7.72 (m, 2H), 7.66-7.63 (m, 1H), 7.61-7.56 (m, 1H), 7.13-7.09 (m, 1H), 6.99-6.92 (m, 1H), 5.23 (s, 2H), 4.82 (s, 1H), 2.31-2.24 (m, 1H), 2.15-2.09 (m, 1H), 1.66-1.61 (m, 1H), 1.22-1.17 (m, 1H). LC-MS (Method D): m/z=452.1 [M+H]+, 1.627 min.

Example 170B (second eluting isomer): 1H NMR (400 MHz, CD3OD-d4) δ 7.88 (d, J=4.4 Hz, 1H), 7.74-7.72 (m, 2H), 7.67-7.63 (m, 1H), 7.61-7.56 (m, 1H), 7.13-7.09 (m, 1H), 6.99-6.92 (m, 1H), 5.43 (s, 2H), 4.82 (s, 1H), 2.29-2.25 (m, 1H), 2.15-2.11 (m, 1H), 1.66-1.60 (m, 1H), 1.22-1.15 (m, 1H). LC-MS (Method V): m/z=452.1 [M+H]+, 2.781 min.

Example 171: (S)-1-(3-cyanobenzyl)-N-(5-methyl-4-oxo-2,3,4,5-tetrahydropyrido[3,2-b][1,4]oxazepin-3-yl)-1H-1,2,4-triazole-3-carboxamide

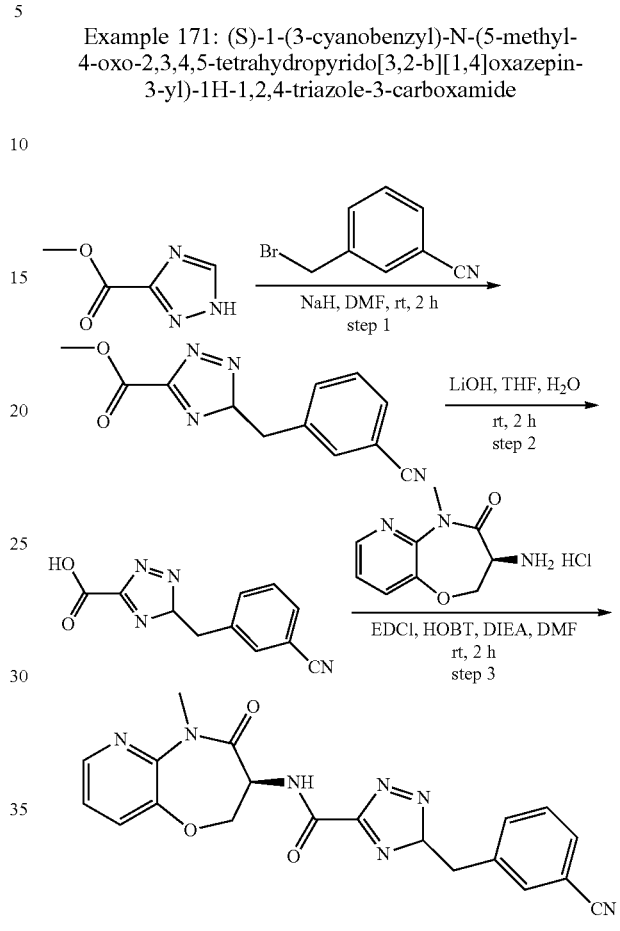

Step 1: Preparation of methyl 1-(3-cyanobenzyl)-1H-1,2,4-triazole-3-carboxylate

Sodium hydride (60%, 0.38 g, 9.5 mmol) was added to a stirring mixture of methyl 1H-1,2,4-triazole-3-carboxylate (1.0 g, 7.87 mmol) in N,N-dimethylformamide (20 mL). The resulting mixture was stirred for 1 hour at room temperature, followed by the addition of 3-(bromomethyl)benzonitrile (1.69 g, 8.67 mmol). The resulting mixture was stirred for another 1 hour at room temperature, diluted with water (30 mL) and extracted with dichloromethane (3×50 mL). The combined organic layers were washed with brine, dried over anhydrous sodium sulfate, filtered and concentrated under vacuum. The residue was purified by column chromatography (ethyl acetate/petroleum ether, 1/4) to afford the title compound (600 mg, 31.5%) as a white solid. LC-MS (Method C): m/z=243.1 [M+H]+, 0.925 min.

Step 2: Preparation of 1-(3-cyanobenzyl)-1H-1,2,4-triazole-3-carboxylic acid

A solution of lithium hydroxide (360 mg, 15.0 mmol) in water (10 ml) was added to a stirring mixture of 1-(3-cyanobenzyl)-1H-1,2,4-triazole-3-carboxylate (600 mg, 2.48 mmol) in tetrahydrofuran (20 ml). The reaction mixture was stirred at room temperature for 2 hours. After removal of tetrahydrofuran under reduced pressure, the resulting solution was adjusted to pH=7 with aqueous hydrochloric acid (1 N, 10 mL), and extracted with ethyl acetate (3×50 mL). The combined organic layers were washed with brine, dried over anhydrous sodium sulfate, filtered and concentrated under vacuum to afford the title compound (250 mg, 17.7%) as a white solid. LC-MS (Method X): m/z=229.1 [M+H]$^+$, 1.227 min.

Step 3: Preparation of (S)-1-(3-cyanobenzyl)-N-(5-methyl-4-oxo-2,3,4,5-tetrahydropyrido[3,2-b][1,4]oxazepin-3-yl)-1H-1,2,4-triazole-3-carboxamide The crude product obtained using Amide Coupling Procedure C was purified by Prep-HPLC with the following conditions: Column: XBridge Prep C18 OBD Column 19×150 mm 5 μm; Mobile Phase A: Water (10 mmol/L NH$_4$HCO$_3$), Mobile Phase B: MeCN; Flow rate: 20 mL/min; Gradient: 20% B to 45% B over 7 min; 254 nm; Rt: 6 min to afford the title compound: $^1$H NMR (400 MHz, CD$_3$OD-d$_4$) δ 8.64 (s, 1H), 8.33 (dd, J=4.8, 1.6 Hz, 1H), 7.77-7.64 (m, 4H), 7.57 (t, J=7.7 Hz, 1H), 7.30 (dd, J=8.0, 4.8 Hz, 1H), 5.55 (s, 2H), 5.03 (dd, J=11.7, 7.3 Hz, 1H), 4.69 (dd, J=9.9, 7.1 Hz, 1H), 4.52 (dd, J=11.2, 9.6 Hz, 1H), 3.47 (s, 3H). LC-MS (Method D): m/z=404.2 [M+H]$^+$, 1.371 min.

Example 172: 1-(3-cyanobenzyl)-N-((2R,3S)-2,5-dimethyl-4-oxo-2,3,4,5-tetrahydropyrido[3,2-b][1,4]oxazepin-3-yl)-1H-1,2,4-triazole-3-carboxamide

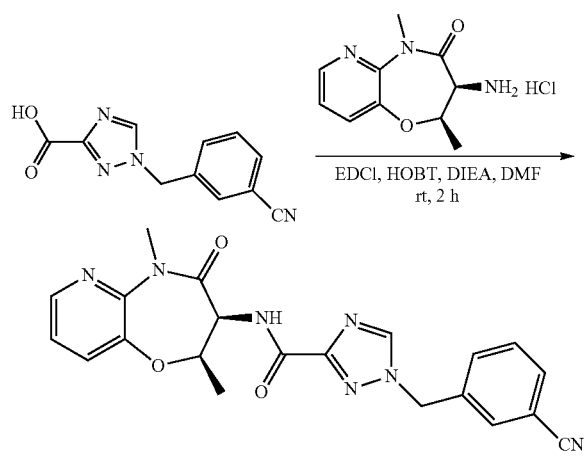

The crude product obtained using Amide Coupling Procedure C was purified by Prep-HPLC with the following conditions: Column: XBridge Prep C18 OBD Column, 5 μm, 19×150 mm; Mobile Phase A: Water (10 mmol/L NH$_4$HCO$_3$), Mobile Phase B: MeCN; Flow rate: 20 mL/min; Gradient: 25% B to 75% B over 7 min; 254 nm; Rt: 6.25 min to afford the title compound: $^1$H NMR (300 MHz, CD$_3$OD-d$_4$) δ 8.66 (s, 1H), 8.33 (dd, J=4.8, 1.6 Hz, 1H), 7.78-7.65 (m, 4H), 7.57 (t, J=7.8 Hz, 1H), 7.32 (dd, J=8.0, 4.8 Hz, 1H), 5.56 (s, 2H), 5.07-5.01 (m, 2H), 3.49 (s, 3H), 1.38 (d, J=5.9 Hz, 3H). LC-MS (Method D): m/z=418.2 [M+H]$^+$, 1.477 min.

Example 173: (S)—N-(5-trideuteriomethyl-4-oxo-2,3,4,5-tetrahydropyrido[3,2-b][1,4]oxazepin-3-yl)-5-(1-phenylcyclopropyl)-1,3,4-oxadiazole-2-carboxamide

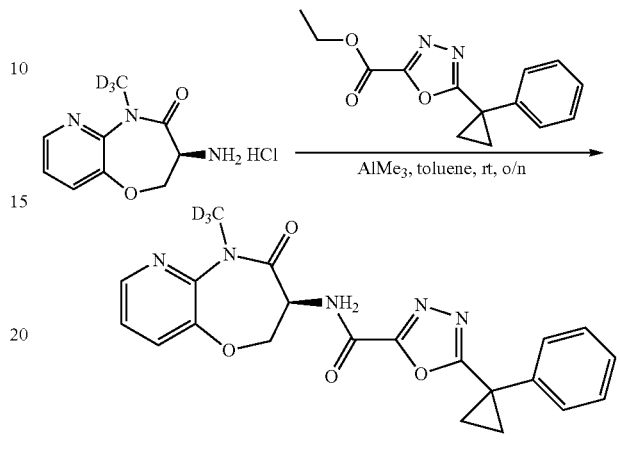

The crude product obtained using the procedure described in Example 54 was purified by Prep-HPLC with the following conditions: Column, XBridge Prep C18 OBD Column, 5 μm, 19×150 mm; Mobile phase: Phase A: Water (10 mmol/L NH$_4$HCO$_3$), Phase B: MeCN; Flow rate: 20 mL/min; Gradient: 25% B to 50% B over 7 min; Detector, UV 254 nm to afford the title compound: $^1$H NMR (300 MHz, DMSO-d$_6$) δ 9.49 (d, J=7.6 Hz, 1H), 8.36 (dd, J=4.7, 1.6 Hz, 1H), 7.70 (dd, J=8.0, 1.6 Hz, 1H), 7.50-7.28 (m, 6H), 4.87-4.62 (m, 2H), 4.50 (dd, J=9.3, 7.1 Hz, 1H), 1.72-1.62 (m, 2H), 1.55-1.44 (m, 2H). LC-MS (Method D): m/z=409.1 [M+H]$^+$, 1.624 min.

Example 174: 5-benzyl-N-((2R,3S)-2-methyl-5-trideuteriomethyl-4-oxo-2,3,4,5-tetrahydropyrido[3,2-b][1,4]oxazepin-3-yl)-1,3,4-oxadiazole-2-carboxamide

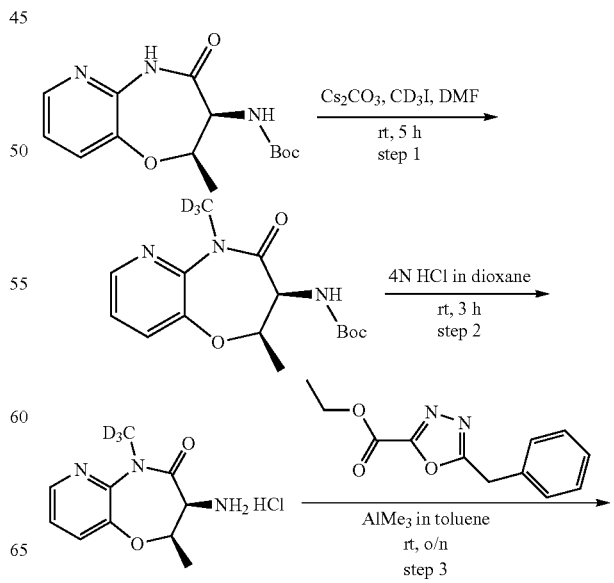

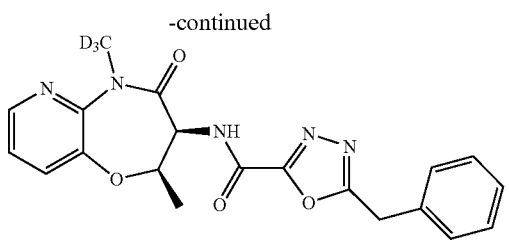

Step 1: Preparation of tert-butyl ((2R,3S)-2-methyl-5-trideuteriomethyl-4-oxo-2,3,4,5-tetrahydropyrido[3,2-b][1,4]oxazepin-3-yl)carbamate Trideuterated iodomethane (124 mg, 0.85 mmol) was added to a stirring mixture of tert-butyl (2R,3S)-2-methyl-4-oxo-2,3,4,5-tetrahydropyrido[3,2-b][1,4]oxazepin-3-yl-carbamate (250 mg, 0.85 mmol) and cesium carbonate (278 mg, 0.85 mmol) in N,N-dimethylformamide (30 mL). The reaction mixture was stirred at room temperature for 5 hours, diluted with water (20 mL) and extracted with ethyl acetate (3×100 mL). The organic layers were combined, dried over anhydrous sodium sulfate, filtered and concentrated under vacuum. The residue was purified by column chromatography (methanol/dichloromethane, 1/20) to afford the title compound (230 mg, 87.1%) as a white solid. LC-MS (Method C): m/z=311.1 [M+H]$^+$, 1.260 min.

Step 2: Preparation of (2R,3S)-3-amino-2-imethyl-5-trideuterated methyl-2,3-dihydropyrido[3,2-b][1,4]oxazepin-4(5H)-one hydrochloride Tert-butyl((2R,3S)-2-methyl-5-trideuteriomethyl-4-oxo-2,3,4,5tetrahydropyrido[3,2-b][1,4]oxazepin-3-yl)carbamate (100 mg, 0.32 mmol) was added to a solution of hydrogen chloride in 1,4-dioxane (4 N, 6.0 mL, 24 mmol). The reaction mixture was stirred at room temperature for 3 hours and concentrated under vacuum to afford the title compound (80 mg, 99%) as a white solid. LC-MS (Method C): m/z=211.1 [M+H]$^+$, 0.757 min.

Step 3: Preparation of 5-benzyl-N-((2R,3S)-2-methyl-5-trideuteriomethyl-4-oxo-2,3,4,5-tetrahydropyrido[3,2-b][1,4]oxazepin-3-yl)-1,3,4-oxadiazole-2-carboxamide The crude product obtained using the procedure described in Example 54 was purified by Prep-HPLC with the following conditions: Column: XBridge Prep OBD C18 Column 19×250 mm, 5 μm; Mobile Phase A: Water (10 mmol/L NH$_4$HCO$_3$), Mobile Phase B: MeCN; Flow rate: 20 mL/min; Gradient: 25% B to 75% B over 7 min; UV 254 & 220 nm; Rt: 6.85 min to afford the title compound: $^1$H NMR (400 MHz, DMSO-d$_6$) δ 8.58 (s, 1H), 8.36 (dd, J=4.8, 1.6 Hz, 1H), 7.74 (dd, J=8.0, 1.6 Hz, 1H), 7.40-7.28 (m, 6H), 4.98-4.90 (m, 2H), 4.38 (s, 2H), 1.37 (d, J=6.4 Hz, 3H). LC-MS (Method D): m/z=397.2 [M+H]$^+$, 1.680 min.

Example 175: (S)-1-benzyl-4-fluoro-N-(5-trideuteriomethyl-4-oxo-2,3,4,5-tetrahydropyrido[3,2-b][1,4]oxazepin-3-yl)-1H-pyrazole-3-carboxamide

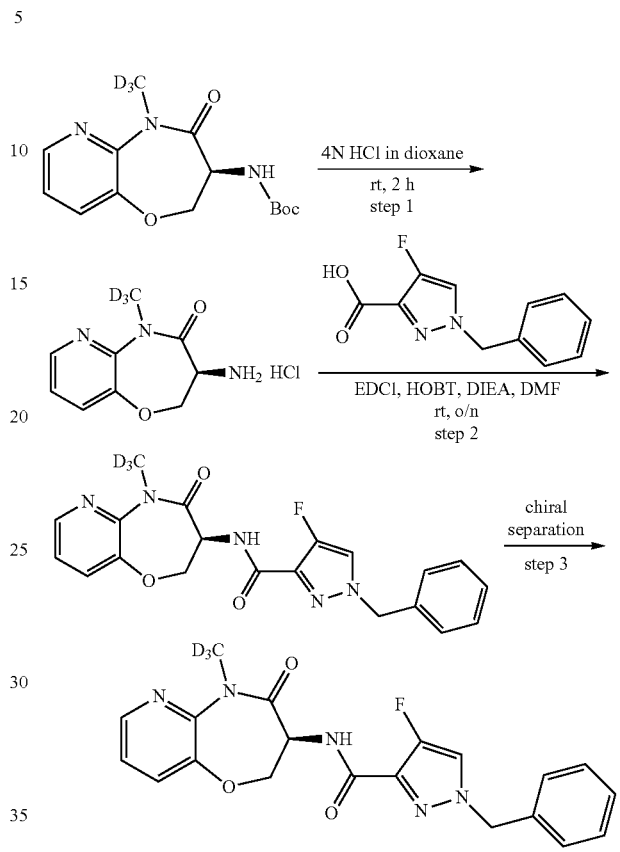

The crude product obtained using Amide Coupling Procedure C was purified by Prep-HPLC with the following conditions: Column, XBridge Prep C18 OBD Column, 5 μm, 19×150 mm; Mobile phase: Phase A: Water (10 mmol/L NH$_4$HCO$_3$), Phase B: MeCN; Flow rate: 20 mL/min; Gradient: 25% B to 65% B over 7 min; Detector, UV 254 nm to afford the title compound: $^1$H NMR (300 MHz, DMSO-d$_6$) δ 8.32 (dd, J=4.7, 1.6 Hz, 1H), 8.21 (d, J=7.8 Hz, 1H), 8.10 (d, J=4.5 Hz, 1H), 7.66 (dd, J=8.0, 1.6 Hz, 1H), 7.42-7.19 (m, 6H), 5.31 (s, 2H), 4.85-4.76 (m, 1H), 4.64 (dd, J=11.5, 9.7 Hz, 1H), 4.47 (dd, J=9.6, 7.4 Hz, 1H). LC-MS (Method J): m/z=399.3 [M+H]$^+$, 1.331 min.

Example 176: 5-benzyl-N-((1aR,2S,8bS)-5,7-difluoro-3-oxo-1,1a,2,3,4,8b-hexahydrobenzo[b]cyclopropa[d]azepin-2-yl)-4H-1,2,4-triazole-3-carboxamide

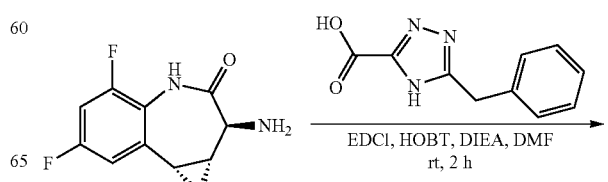

-continued

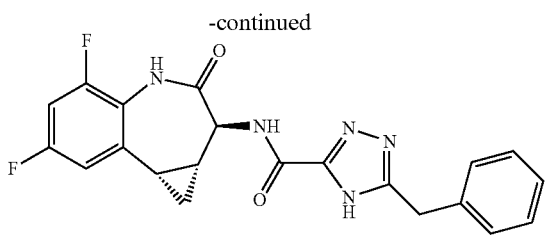

The crude product obtained using Amide Coupling Procedure C was purified by Prep-HPLC with the following conditions: Column: Column: XBridge Prep OBD C18 Column 30×150 mm 5 μm; Mobile Phase A: Water (10 mmol/L NH$_4$HCO$_3$), Mobile Phase B: MeCN; Flow rate: 60 mL/min; Gradient: 25% B to 55% B over 7 min; 254 nm; Rt: 6.32 min to afford the title compound: $^1$H NMR (400 MHz, DMSO-d$_6$) δ 14.34 (br s, 1H), 9.72 (s, 1H), 8.62 (s, 1H), 7.35-7.18 (m, 7H), 4.12 (s, 2H), 3.98 (dd, J=10.5, 7.5 Hz, 1H), 2.26-2.17 (m, 1H), 1.87-1.77 (m, 1H), 1.13-1.04 (m, 1H), 0.60-0.57 (m, 1H). LC-MS (Method Q): m/z=410.5 [M+H]$^+$, 1.773 min.

Example 177A and 177B: 5-benzyl-N-((7S,7aS,8aR)-5-methyl-6-oxo-5,6,7,7a,8,8a-hexahydrocyclopropa[d]pyrazino[2,3-b]azepin-7-yl)-1,3,4-oxadiazole-2-carboxamide and 5-benzyl-N-((7R,7aR,8aS)-5-methyl-6-oxo-5,6,7,7a,8,8a-hexahydrocyclopropa[d]pyrazino[2,3-b]azepin-7-yl)-1,3,4-oxadiazole-2-carboxamide

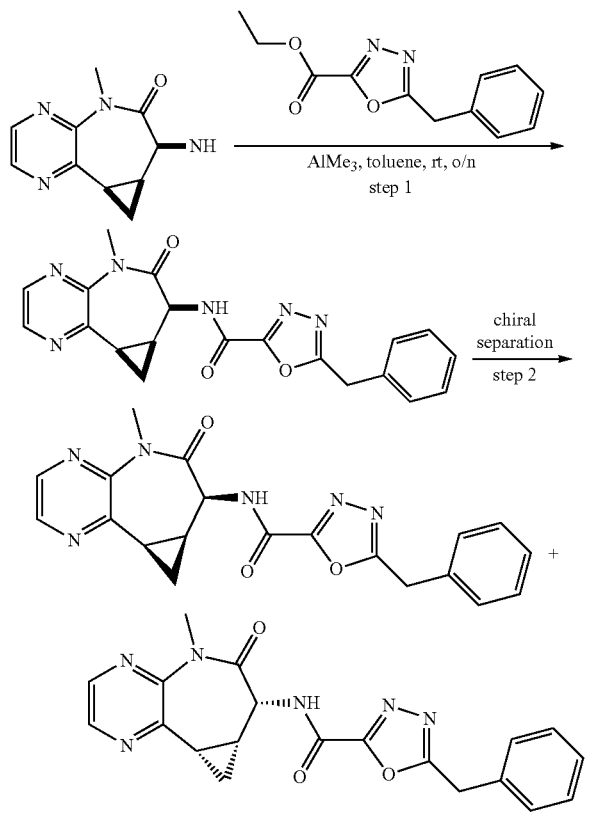

The crude product obtained using the procedure described in Example 54 was purified by Prep-TLC (ethyl acetate/petroleum ether, 3/1) to afford the title compound as a white solid.

The racemate of 5-benzyl-N-(cis-5-methyl-6-oxo-5,6,7,7a,8,8a-hexahydrocyclopropa[d]pyrazino[2,3-b]azepin-7-yl)-1,3,4-oxadiazole-2-carboxamide (40 mg, 0.10 mmol) was separated by Prep-Chiral-HPLC with the following conditions: Column: CHIRAL ART Cellulose-SB S-5 μm, 250×20 mm, 5 μm; Mobile Phase A:Hexane, Mobile Phase B: EtOH; Flow rate: 20 mL/min; Gradient: 50% B to 50% B over 26 min; 220/254 nm; Rt1: 19.32; Rt 2: 23.55 to afford the title compounds:

Example 177A (first eluting isomer): $^1$H NMR (400 MHz, CD$_3$OD-d$_4$) δ 8.42-8.37 (m, 2H), 7.37-7.25 (m, 5H), 4.77 (s, 1H), 4.33 (s, 2H), 3.40 (s, 3H), 2.65-2.57 (m, 1H), 2.25-2.17 (m, 1H), 1.55-1.48 (m, 1H), 1.35-1.30 (m, 1H). LCMS (Method D): m/z=391.1 [M+H]$^+$, 1.231 min.

Example 177B (second eluting isomer): $^1$H NMR (400 MHz, CD$_3$OD-d$_4$) δ 8.42-8.37 (m, 2H), 7.36-7.25 (m, 5H), 4.77 (s, 1H), 4.33 (s, 2H), 3.39 (s, 3H), 2.64-2.56 (m, 1H), 2.24-2.16 (m, 1H), 1.54-1.46 (m, 1H), 1.34-1.28 (m, 1H). LC-MS (Method D): m/z=391.1 [M+H]$^+$, 1.225 min.

Example 178A and 178B: (S)-4-fluoro-1-(2-fluorobenzyl)-N-(5-methyl-6-oxo-6,7,8,9-tetrahydro-5H-pyrazino[2,3-b]azepin-7-yl)-1H-pyrazole-3-carboxamide and (R)-4-fluoro-1-(2-fluorobenzyl)-N-(5-methyl-6-oxo-6,7,8,9-tetrahydro-5H-pyrazino[2,3-b]azepin-7-yl)-1H-pyrazole-3-carboxamide

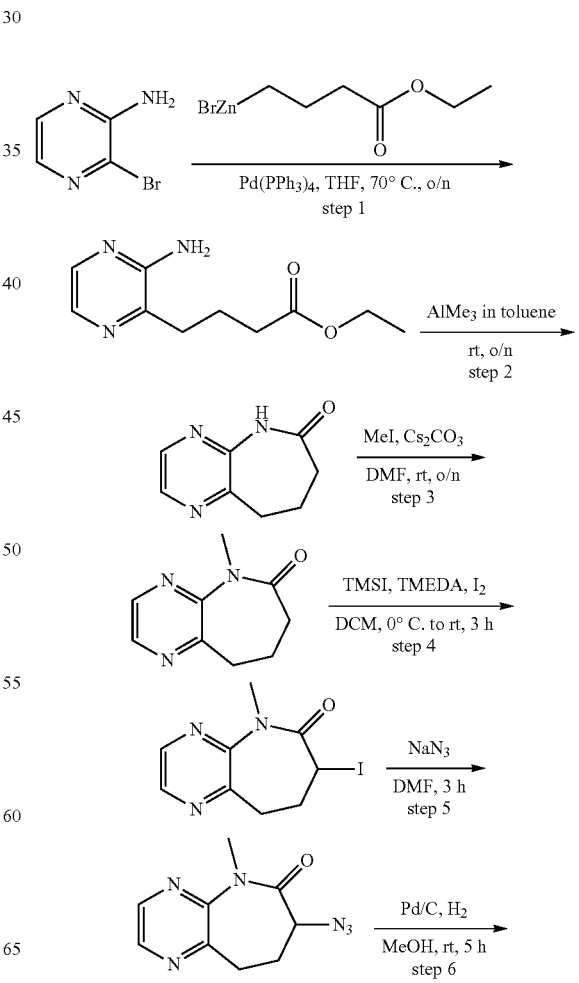

-continued

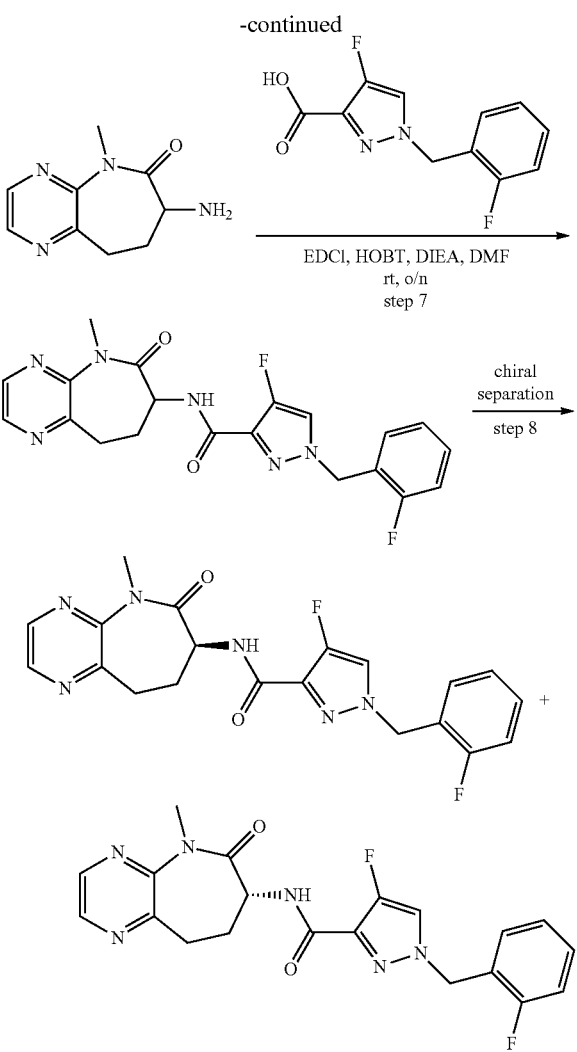

Step 1: Preparation of ethyl 4-(3-aminopyrazin-2-yl)butanoate

A solution of (4-ethoxy-4-oxobutyl)zinc(II) bromide in tetrahydrofuran (0.5 M, 26.0 mL, 13.0 mmol) was added to a mixture of 3-bromopyrazin-2-amine (1.0 g, 5.8 mmol) and tetrakis(triphenylphosphanyl)palladium (0.67 g, 0.58 mmol) in tetrahydrofuran (60 mL) under a nitrogen atmosphere. The resulting mixture was stirred overnight at 70° C. After cooling to room temperature, the reaction mixture was concentrated under reduced pressure. The resulting residue was purified by column chromatography (methanol/dichloromethane, 1/10) to afford the title compound (0.45 g, 37.0%) as a light yellow oil. LC-MS (Method S): m/z=210.2 [M+H]$^+$, 0.592 min.

Step 2: Preparation of 8,9-dihydro-5H-pyrazino[2,3-b]azepin-6(7H)-one

A solution of trimethylaluminum in toluene (2 M, 6.0 mL, 12.0 mmol) was added to a stirring mixture of ethyl 4-(3-aminopyrazin-2-yl)butanoate (450 mg, 2.2 mmol) in toluene (20 mL). After stirring overnight at room temperature, the reaction mixture was quenched by the addition of water (50 mL) and extracted with dichloromethane (3×50 mL). The combined organic layers were washed with brine, dried over anhydrous sodium sulfate, filtered and concentrated under reduced pressure. The resulting residue was purified by column chromatography (methanol/dichloromethane, 1/10) to afford the title compound (0.32 g, 91.0%) as a light yellow solid. LC-MS (Method S): m/z=164.2 [M+H]$^+$, 0.473 min.

Step 3: Preparation of 5-methyl-8,9-dihydro-5H-pyrazino[2,3-b]azepin-6(7H)-one

Iodomethane (313 mg, 2.2 mmol) was added dropwise to a stirring mixture of 8,9-dihydro-5H-pyrazino[2,3-b]azepin-6(7H)-one (320 mg, 2.0 mmol) and cesium carbonate (717 mg, 2.2 mmol) in N,N-dimethylformamide (15 mL). After stirring overnight at room temperature, the reaction mixture was diluted with water (20 mL) and extracted with ethyl acetate (3×50 mL). The combined organic layers were washed with brine, dried over anhydrous sodium sulfate, filtered and concentrated under reduced pressure. The resulting residue was purified by column chromatography (methanol/dichloromethane, 1/10) to afford the title compound (300 mg, 87.0%) as a light yellow solid. LC-MS (Method S): m/z=178.1 [M+H]$^+$, 0.570 min.

Step 4: Preparation of 7-iodo-5-methyl-8,9-dihydro-5H-pyrazino[2,3-b]azepin-6(7H)-one To a mixture of 5-methyl-8,9-dihydro-5H-pyrazino[2,3-b]azepin-6(7H)-one (300 mg, 1.70 mmol) and N,N,N',N'-tetramethylethylenediamine (1.97 g, 17.0 mmol) in dichloromethane (80 mL) at 0° C. was added iodotrimethylsilane (2.38 g, 17.0 mmol) dropwise over 30 minutes. The resulting mixture was stirred for 2 hours at 0° C., followed by the addition of a solution of iodine (0.65 g, 2.6 mmol) in dichloromethane (100 mL) dropwise over 30 minutes. After stirring for 1 hour at room temperature, the reaction mixture was quenched by the addition of aqueous sodium thiosulfate (5%, 20 mL) and extracted with ethyl acetate (3×50 mL). The combined organic layers were washed with brine, dried over anhydrous sodium sulfate, filtered and concentrated under reduced pressure to afford the title compound (450 mg crude, 87.7%) as a yellow oil. LC-MS (Method S): m/z=304.1 [M+H]$^+$, 0.610 min.

Step 5: Preparation of 7-azido-5-methyl-8,9-dihydro-5H-pyrazino[2,3-b]azepin-6(7H)-one Sodium azide (290 mg, 4.47 mmol) was added to a stirring mixture of 7-iodo-5-methyl-8,9-dihydro-5H-pyrazino[2,3-b]azepin-6(7H)-one (450 mg, 1.49 mmol) in N,N-dimethylformamide (50 mL). After stirred at room temperature for 3 hours, the reaction mixture was quenched by the addition of water (40 mL) and extracted with ethyl acetate (3×50 mL). The combined organic layers were washed with brine, dried over sodium sulfate, filtered and concentrated under vacuum to afford the title compound (260 mg crude) as a yellow oil. LC-MS (Method S): m/z=219.1 [M+H]$^+$, 0.600 min.

Step 6: Preparation of 7-amino-5-methyl-8,9-dihydro-5H-pyrazino[2,3-b]azepin-6(7H)-one 7-Azido-5-methyl-8,9-dihydro-5H-pyrazino[2,3-b]azepin-6(7H)-one (260 mg, 1.2 mmol) in methanol (20 mL) was hydrogenated in the presence of palladium on carbon (10%, 26 mg) under a hydrogen atmosphere (2-3 atm). After stirring for 5 hours at room temperature under a hydrogen atmosphere, the reaction mixture was filtered through Celite. The filtrate was concentrated under reduced pressure and dried under high vacuum to afford the title compound (200 mg, 88%) as a colorless oil. LC-MS (Method S): m/z=193.1 [M+H]$^+$, 0.356 min.

Step 7: Preparation of 4-fluoro-1-(2-fluorobenzyl)-N-(5-methyl-6-oxo-6,7,8,9-tetrahydro-5H-pyrazino[2,3-b]azepin-7-yl)-1H-pyrazole-3-carboxamide The crude product obtained using Amide Coupling Procedure C was purified by Prep-HPLC with the following conditions: Column: XBridge Shield C18 OBD Column, 5 μm, 19×150 mm; Mobile Phase A: Water (10 mmol/L NH₄HCO₃), Mobile Phase B: MeCN; Flow rate: 20 mL/min; Gradient: 35% B to 50% B in 8 min; UV 254 & 220 nm; Rt: 6.82 min to afford the title compound (30 mg, 28%) as a white solid. LC-MS (Method O): m/z=413.1 [M+H]⁺, 1.396 min.

Step 8: Preparation of (S)-4-fluoro-1-(2-fluorobenzyl)-N-(5-methyl-6-oxo-6,7,8,9-tetrahydro-5H-pyrazino[2,3-b]azepin-7-yl)-1H-pyrazole-3-carboxamide and (R)-4-fluoro-1-(2-fluorobenzyl)-N-(5-methyl-6-oxo-6,7,8,9-tetrahydro-5H-pyrazino[2,3-b]azepin-7-yl)-1H-pyrazole-3-carboxamide The racemate of 4-fluoro-1-(2-fluorobenzyl)-N-(5-methyl-6-oxo-6,7,8,9-tetrahydro-5H-pyrazino[2,3-b]azepin-7-yl)-1H-pyrazole-3-carboxamide (30.0 mg, 0.07 mmol) was separated by Prep-Chiral-HPLC with the following conditions: Column: CHIRALPAK IF, 2×25 cm, 5 μm; Mobile Phase A: Hexane, Mobile Phase B: EtOH; Flow rate: 16 mL/min; Gradient: 50% B to 50% B in 30 min; UV 254 & 220 nm; Rt1: 17.00 min; Rt2: 24.16 min to afford the title compounds:

Example 178A (first eluting isomer): ¹H NMR (400 MHz, CD₃OD-d₄) δ 8.48 (d, J=2.8 Hz, 1H), 8.39 (d, J=2.8 Hz, 1H), 7.77 (d, J=4.4 Hz, 1H), 7.45-7.38 (m, 1H), 7.34-7.29 (m, 1H), 7.24-7.15 (m, 2H), 5.41 (s, 2H), 4.58-4.52 (m, 1H), 3.50 (s, 3H), 3.18-3.08 (m, 1H), 3.04-2.98 (m, 1H), 2.80-2.69 (m, 1H), 2.41-2.31 (m, 1H). LC-MS (Method T): m/z=413.1 [M+H]⁺, 1.198 min.

Example 178B (second eluting isomer): ¹H NMR (400 MHz, CD₃OD-d₄) δ 8.47 (d, J=2.8 Hz, 1H), 8.38 (d, J=2.8 Hz, 1H), 7.78 (d, J=4.4 Hz, 1H), 7.45-7.38 (m, 1H), 7.34-7.29 (m, 1H), 7.25-7.15 (m, 2H), 5.41 (s, 2H), 4.58-4.52 (m, 1H), 3.50 (s, 3H), 3.19-3.08 (m, 1H), 3.05-2.98 (m, 1H), 2.81-2.69 (m, 1H), 2.41-2.32 (m, 1H). LC-MS (Method X): m/z=413.1 [M+H]⁺, 2.354 min.

Example 179A and 179B: 4-fluoro-1-(2-fluorobenzyl)-N-((7S,7aS,8aR)-5-methyl-6-oxo-5,6,7,7a,8,8a-hexahydrocyclopropa[d]pyrazino[2,3-b]azepin-7-yl)-1H-pyrazole-3-carboxamide and 4-fluoro-1-(2-fluorobenzyl)-N-((7R,7aR,8aS)-5-methyl-6-oxo-5,6,7,7a,8,8a-hexahydrocyclopropa[d]pyrazino[2,3-b]azepin-7-yl)-1H-pyrazole-3-carboxamide

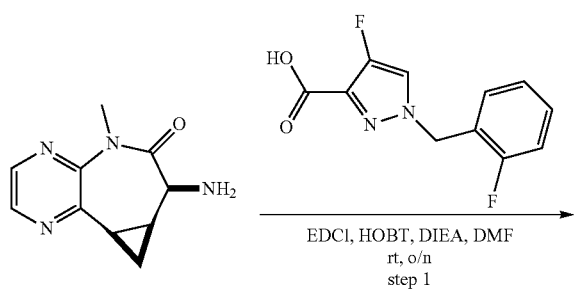

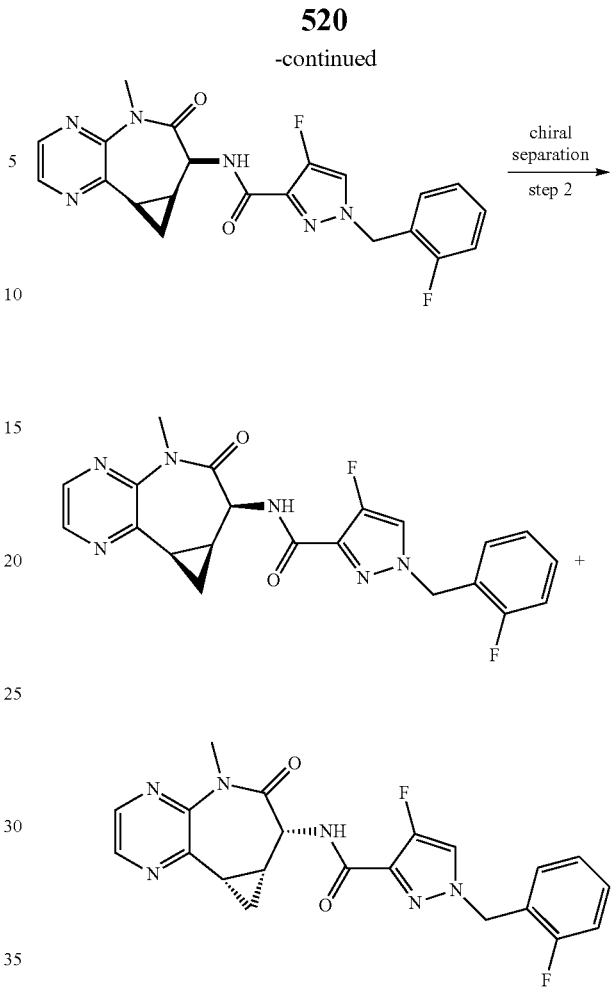

The crude product obtained using Amide Coupling Procedure C was purified by Prep-TLC (ethyl acetate/petroleum ether, 3/1) to afford the title compound as a white solid.

The racemate was separated by Prep-Chiral-HPLC with the following conditions: Column: CHIRALPAK IF, 2×25 cm, 5 μm; Mobile Phase A: Hexane, Mobile Phase B: EtOH; Flow rate: 16 mL/min; Gradient: 50% B to 50% B in 38 min; UV 254 & 220 nm; Rt1: 22.995; Rt2: 30.882 to afford the title compounds:

Example 179A (first eluting isomer): ¹H NMR (400 MHz, CD₃OD-d₄) δ 8.30 (dd, J=2.4, 6.4 Hz, 2H), 7.68 (d, J=4.4 Hz, 1H), 7.34-7.27 (m, 1H), 7.25-7.20 (m, 1H), 7.13-7.04 (m, 2H), 5.23 (s, 2H), 4.66 (s, 1H), 3.31 (s, 3H), 2.54-2.47 (m, 1H), 2.17-2.10 (m, 1H), 1.43-1.37 (m, 1H), 1.22-1.15 (m, 1H). LC-MS (Method D): m/z=425.0 [M+H]⁺, 1.679 min.

Example 179B (second eluting isomer): ¹H NMR (400 MHz, CD₃OD-d₄) δ 8.42 (dd, J=3.2, 6.8 Hz, 2H), 7.80 (d, J=4.4 Hz, 1H), 7.45-7.39 (m, 1H), 7.37-7.32 (m, 1H), 7.25-7.16 (m, 2H), 5.44 (s, 2H), 4.78 (s, 1H), 3.42 (s, 3H), 2.65-2.58 (m, 1H), 2.28-2.22 (m, 1H), 1.54-1.49 (m, 1H), 1.33-1.27 (m, 1H). LC-MS (Method D): m/z=425.0 [M+H]⁺, 1.684 min.

Example 180A and 180B: (S)—N-(5-methyl-6-oxo-6,7,8,9-tetrahydro-5H-pyrazino[2,3-b]azepin-7-yl)-5-(1-phenylcyclopropyl)-1,3,4-oxadiazole-2-carboxamide and (R)—N-(5-methyl-6-oxo-6,7,8,9-tetrahydro-5H-pyrazino[2,3-b]azepin-7-yl)-5-(1-phenylcyclopropyl)-1,3,4-oxadiazole-2-carboxamide

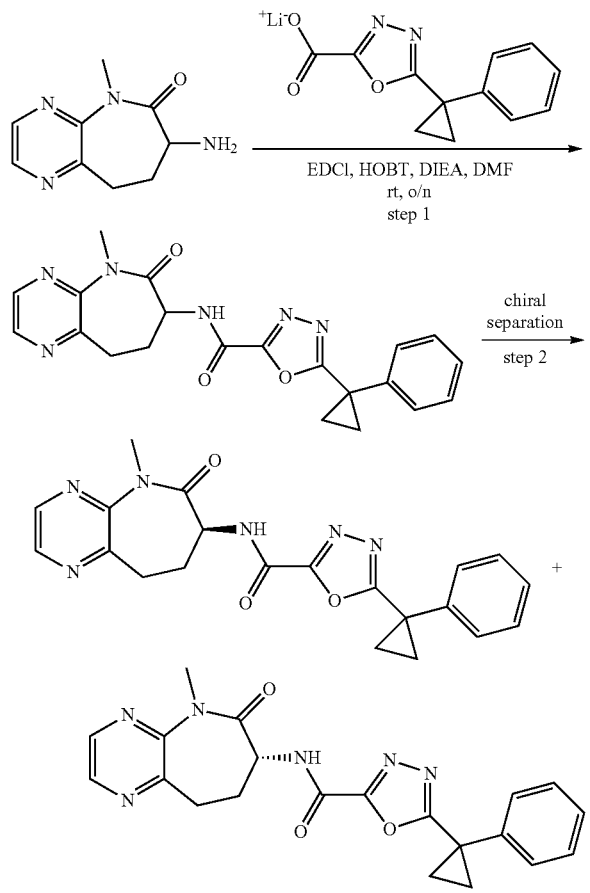

The crude product obtained using Amide Coupling Procedure C was purified by Prep-TLC (ethyl acetate/petroleum ether, 1/1) to afford the title compound.

The racemate of N-(5-methyl-6-oxo-6,7,8,9-tetrahydro-5H-pyrazino[2,3-b]azepin-7-yl)-5-(1-phenylcyclopropyl)-1,3,4-oxadiazole-2-carboxamide (30 mg, 0.08 mmol) was separated by Prep-Chiral-HPLC with the following conditions: Column: CHIRALPAK IE, 2×25 cm, 5 μm; Mobile Phase A: Hexane, Mobile Phase B: MeOH; Flow rate: 20 mL/min; Gradient: 100% B to 100% B over 16 min; UV 254 & 220 nm; Rt 1: 10.459 min; Rt 2: 12.463 min to afford the title compounds:

Example 180A (first eluting isomer): $^1$H NMR (400 MHz, CD$_3$OD-d$_4$) δ 8.49 (d, J=2.4 Hz, 1H), 8.40 (d, J=2.8 Hz, 1H), 7.48-7.46 (m, 2H), 7.41-7.31 (m, 3H), 4.57-4.51 (m, 1H), 3.49 (s, 3H), 3.18-3.09 (m, 1H), 3.05-2.99 (m, 1H), 2.74-2.63 (m, 1H), 2.50-2.41 (m, 1H), 1.80-1.77 (m, 2H), 1.59-1.55 (m, 2H). LC-MS (Method D): m/z=405.0 [M+H]$^+$, 1.260 min.

Example 180B (second eluting isomer): $^1$H NMR (400 MHz, CD$_3$OD-d$_4$) δ 8.49 (d, J=2.4 Hz, 1H), 8.40 (d, J=2.8 Hz, 1H), 7.49-7.46 (m, 2H), 7.42-7.31 (m, 3H), 4.57-4.50 (m, 1H), 3.50 (s, 3H), 3.18-3.09 (m, 1H), 3.06-2.99 (m, 1H), 2.74-2.63 (m, 1H), 2.50-2.40 (m, 1H), 1.81-1.77 (m, 2H), 1.60-1.55 (m, 2H). LC-MS (Method D): m/z=405.0 [M+H]$^+$, 1.261 min.

Example 181A and 181B: 5-(3-cyanobenzyl)-N-((1aR,2R,8bS)-5,7-difluoro-3-oxo-1,1a,2,3,4,8b-hexahydrobenzo[b]cyclopropa[d]azepin-2-yl)-4H-1,2,4-triazole-3-carboxamide and 5-(3-cyanobenzyl)-N-((1aS,2S,8bR)-5,7-difluoro-3-oxo-1,1a,2,3,4,8b-hexahydrobenzo[b]cyclopropa[d]azepin-2-yl)-4H-1,2,4-triazole-3-carboxamide

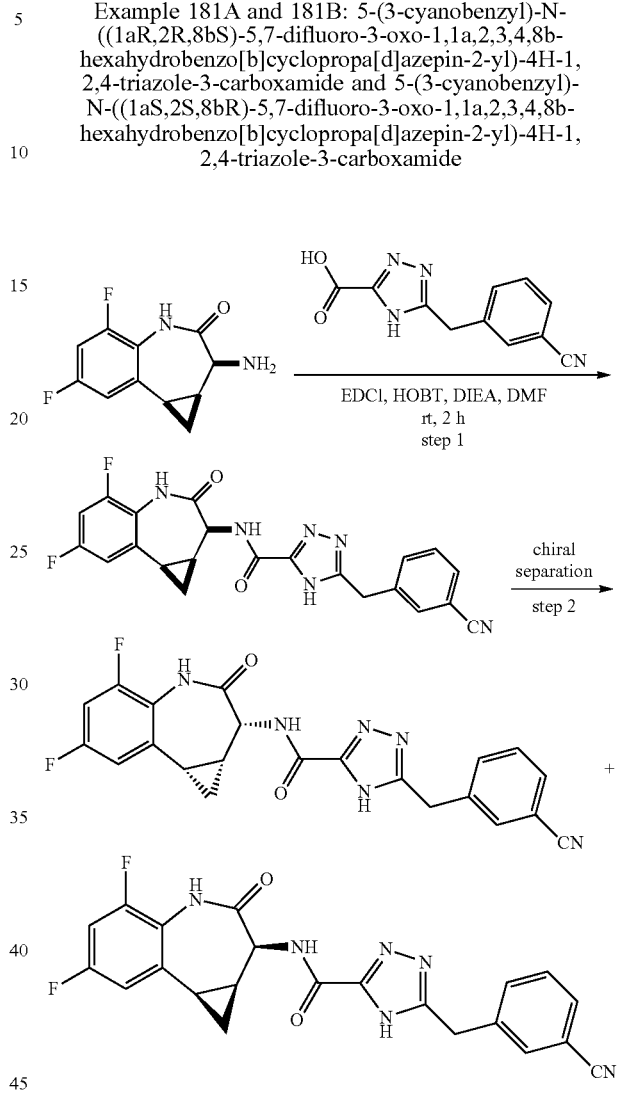

The crude product obtained using Amide Coupling Procedure C was purified by Prep-HPLC with the following conditions: Column: XBridge Shield C18 OBD Column, 5 μm, 19×150 mm; Mobile Phase A:Water (10 mmol/L NH$_4$HCO$_3$), Mobile Phase B: MeCN; Flow rate: 20 mL/min; Gradient: 30% B to 53% B over 8 min; 254 & 220 nm Rt: 7.43 min to afford the title compound as a white solid.

The racemate was separated by Prep-Chiral-HPLC with the following conditions: Column: CHIRALPAK IE, 2×25 cm, 5 μm; Mobile Phase A: Hexane:DCM=5:1, Mobile Phase B: EtOH; Flow rate: 16 mL/min; Gradient: 50% B to 50% B over 23 min; 254 & 220 nm; Rt1: 9.885; Rt2: 16.633 to afford the title compounds:

Example 181A (first eluting isomer): $^1$H NMR (400 MHz, CD$_3$OD-d$_4$) δ 7.71 (s, 1H), 7.65-7.61 (m, 2H), 7.54-7.48 (m, 1H), 7.18-7.05 (m, 1H), 6.99-6.90 (m, 1H), 4.81 (s, 1H), 4.24 (s, 2H), 2.31-2.22 (m, 1H), 2.15-2.07 (m, 1H), 1.74-1.63 (m, 1H), 1.24-1.14 (m, 1H). LC-MS (Method J): m/z=435.4 [M+H]$^+$, 1.200 min.

Example 181B (second eluting isomer): $^1$H NMR (400 MHz, CD$_3$OD-d$_4$) δ 7.70 (s, 1H), 7.66-7.62 (m, 2H), 7.55-

7.49 (m, 1H), 7.19-7.07 (m, 1H), 6.98-6.91 (m, 1H), 4.81 (s, 1H), 4.24 (s, 2H), 2.32-2.23 (m, 1H), 2.16-2.07 (m, 1H), 1.67-1.59 (m, 1H), 1.23-1.14 (m, 1H). LC-MS (Method V): m/z=435.1 [M+H]$^+$, 3.354 min.

Example 182A and 182B: (R)-4-fluoro-N-(5-methyl-6-oxo-6,7,8,9-tetrahydro-5H-pyrazino[2,3-b]azepin-7-yl)-1-((2-methylpyridin-3-yl)methyl)-1H-pyrazole-3-carboxamide and (S)-4-fluoro-N-(5-methyl-6-oxo-6,7,8,9-tetrahydro-5H-pyrazino[2,3-b]azepin-7-yl)-1-((2-methylpyridin-3-yl)methyl)-1H-pyrazole-3-carboxamide

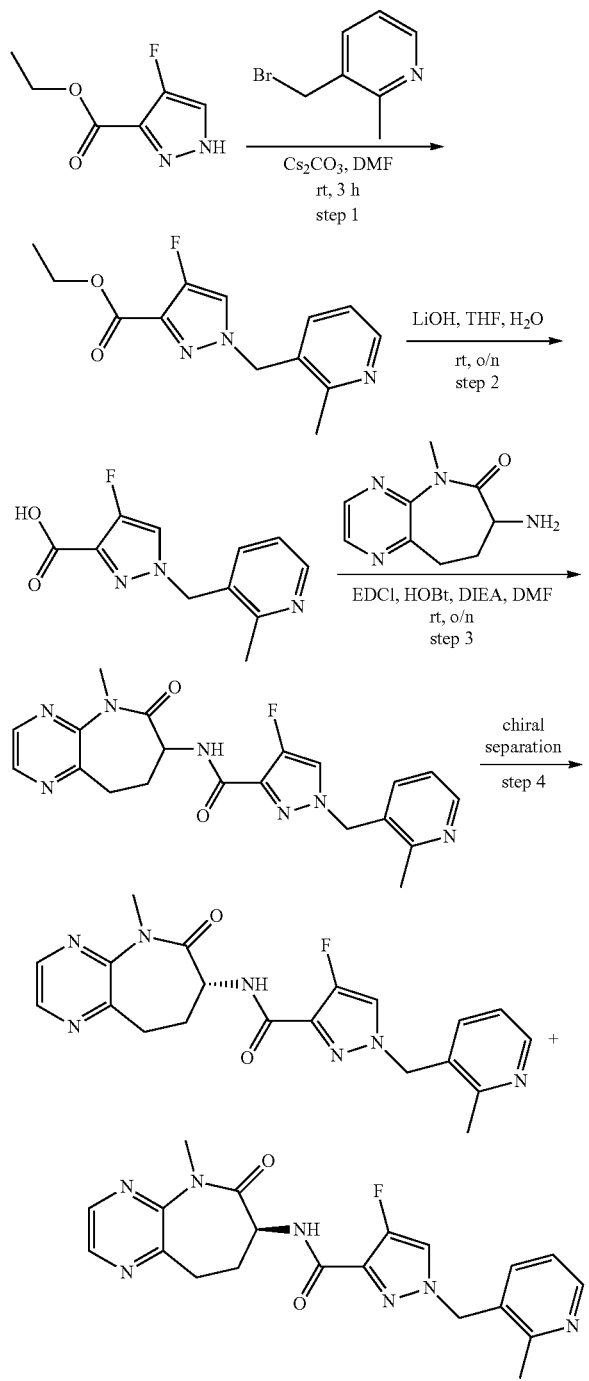

Step 1: Preparation of ethyl 4-fluoro-1-((2-methylpyridin-3-yl)methyl)-1H-pyrazole-3-carboxylate 3-(Bromomethyl)-2-methylpyridine (283 mg, 1.52 mmol) was added to a stirring mixture of ethyl 4-fluoro-1H-pyrazole-3-carboxylate (200 mg, 1.27 mmol) and cesium carbonate (1.24 g, 3.80 mmol) in N,N-dimethylformamide (20 mL). The reaction mixture was stirred at room temperature for 3 hours, quenched by the addition of water (100 mL) and extracted with ethyl acetate (3×100 mL). The combined organic layers were washed with brine, dried over anhydrous sodium sulfate, filtered and concentrated under vacuum. The residue was purified by column chromatography (ethyl acetate/petroleum ether, 1/4) to afford the title compound (300 mg, 90.9%) as a white solid. LC-MS (Method C): m/z=264.1 [M+H]$^+$, 1.291 min.

Step 2: Preparation of 4-fluoro-1-((2-methylpyridin-3-yl)methyl)-1H-pyrazole-3-carboxylic acid Lithium hydroxide (82 mg, 3.42 mmol) was added to a mixture of ethyl 4-fluoro-1-((2-methyl pyridin-3-yl)methyl)-1H-pyrazole-3-carboxylate (300 mg, 1.14 mmol) in tetrahydrofuran (12 mL) and water (4 mL). The reaction mixture was stirred at room temperature overnight. After removal of tetrahydrofuran under reduced pressure, the resulting solution was adjusted to pH=6 with aqueous hydrochloric acid (1 N, 10 mL), and extracted with ethyl acetate (3×60 mL). The combined organic layers were washed with brine, dried over anhydrous sodium sulfate, filtered and concentrated under vacuum to afford the title compound (220 mg crude) as a white solid. LC-MS (Method C): m/z=236.0 [M+H]$^+$, 0.365 min.

Step 3: Preparation of 4-fluoro-N-(5-methyl-6-oxo-6,7,8,9-tetrahydro-5H-pyrazino[2,3-b]azepin-7-yl)-1-((2-methylpyridin-3-yl)methyl)-1H-pyrazole-3-carboxamide The crude product obtained using Amide Coupling Procedure C was purified by Prep-HPLC with the following conditions: Column: XBridge Shield C18 OBD Column, 5 µm, 19×150 mm; Mobile Phase A: Water (10 mmol/L NH$_4$HCO$_3$), Mobile Phase B: MeCN; Flow rate: 20 mL/min; Gradient: 20% B to 33% B over 8 min; UV 254 & 220 nm; Rt: 7.28 min to afford the title compound. LC-MS (Method Y): m/z=410.2 [M+H]$^+$, 0.841 min.

Step 4: Preparation of (R)-4-fluoro-N-(5-methyl-6-oxo-6,7,8,9-tetrahydro-5H-pyrazino[2,3-b]azepin-7-yl)-1-((2-methylpyridin-3-yl)methyl)-1H-pyrazole-3-carboxamide and (S)-4-fluoro-N-(5-methyl-6-oxo-6,7,8,9-tetrahydro-5H-pyrazino[2,3-b]azepin-7-yl)-1-((2-methylpyridin-3-yl)methyl)-1H-pyrazole-3-carboxamide The racemate of 4-fluoro-N-(5-methyl-6-oxo-6,7,8,9-tetrahydro-5H-pyrazino[2,3-b]azepin-7-yl)-1-((2-methylpyridin-3-yl)methyl)-1H-pyrazole-3-carboxamide (40 mg, 0.10 mmol) was separated by Prep-Chiral-HPLC with the following conditions: Column. CHIRAL ART Cellulose-SB, 2×25 cm, 5 µm; Mobile Phase A: Hexane, Mobile Phase B: EtOH; Flow rate: 20 mL/min; Gradient: 50 B % to 50 B % over 13 min; UV 254 & 220 nm; Rt 1: 9.428 min; Rt 2: 11.106 min to afford the title compounds:

Example 182A (first eluting isomer): $^1$H NMR (400 MHz, CD$_3$OD-d$_4$) δ 8.49 (d, J=2.8 Hz, 1H), 8.42-8.39 (m, 2H), 7.80 (d, J=4.4 Hz, 1H), 7.51-7.48 (m, 1H), 7.33-7.29 (m, 1H), 5.45 (s, 2H), 4.58-4.53 (m, 1H), 3.50 (s, 3H), 3.18-3.08 (m, 1H), 3.04-2.98 (m, 1H), 2.81-2.70 (m, 1H), 2.58 (s, 3H), 2.42-2.31 (m, 1H). LC-MS (Method D): m/z=410.0 [M+H]+, 0.715 min.

Example 182B (second eluting isomer): ¹H NMR (400 MHz, CD₃OD-d₄) δ 8.49 (d, J=2.8 Hz, 1H), 8.42-8.39 (m, 2H), 7.80 (d, J=4.4 Hz, 1H), 7.52-7.48 (m, 1H), 7.34-7.29 (m, 1H), 5.45 (s, 2H), 4.58-4.53 (m, 1H), 3.50 (s, 3H), 3.18-3.07 (m, 1H), 3.05-2.98 (m, 1H), 2.81-2.70 (m, 1H), 2.58 (s, 3H), 2.42-2.30 (m, 1H). LC-MS (Method D): m/z=410.0 [M+H]+, 0.720 min.

Example 183A and 183B: 1-benzyl-4-fluoro-N-((1aR,2R,8bS)-4-trideuteriomethyl-7-(methylsulfonyl)-3-oxo-1,1a,2,3,4,8b-hexahydrobenzo[b]cyclopropa[d]azepin-2-yl)-1H-pyrazole-3-carboxamide and 1-benzyl-4-fluoro-N-((1aS,2S,8bR)-4-trideuteriomethyl-7-(methylsulfonyl)-3-oxo-1,1a,2,3,4,8b-hexahydrobenzo[b]cyclopropa[d]azepin-2-yl)-1H-pyrazole-3-carboxamide

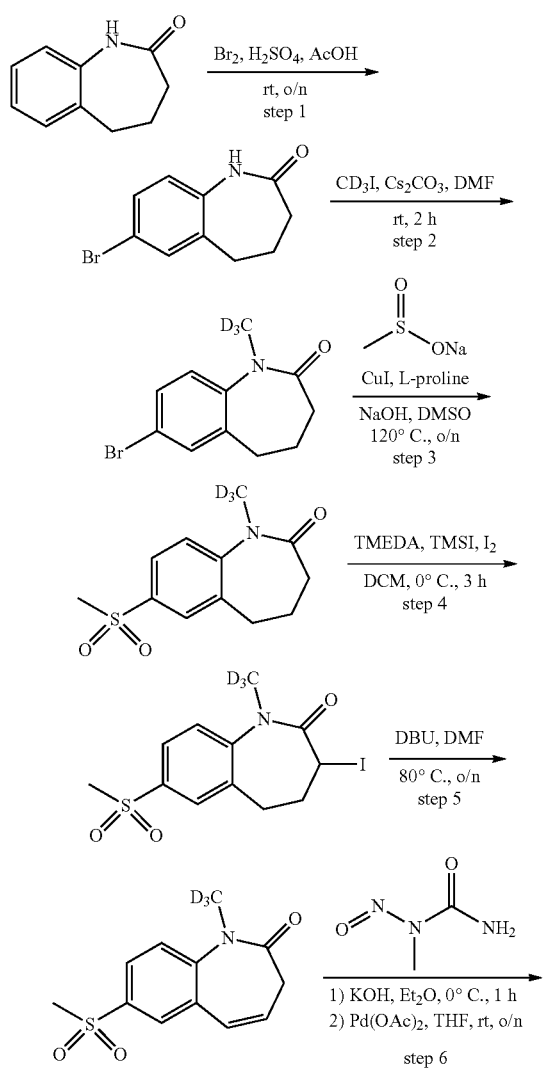

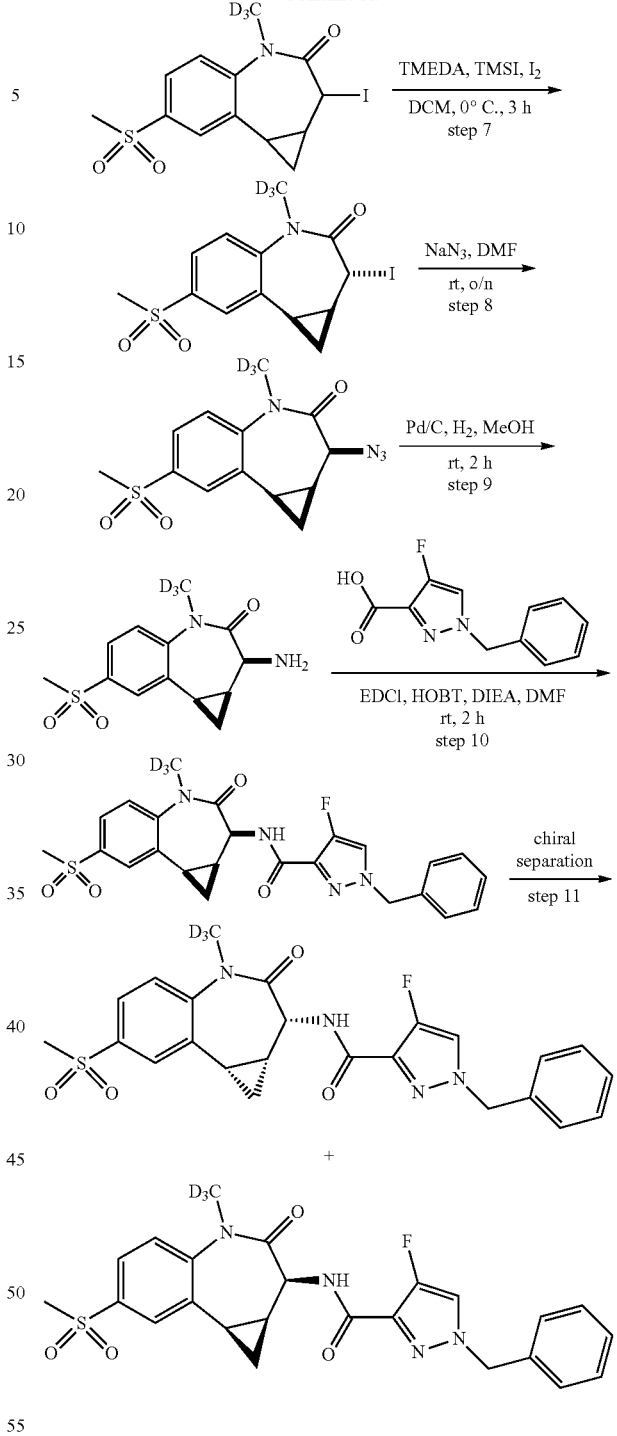

Step 1: Preparation of 7-bromo-4,5-dihydro-1H-benzo[b]azepin-2(3H)-one

A solution of bromine (8 mL, 155 mmol) in acetic acid (100 mL) was added to a solution of 4,5-Dihydro-1H-benzo[b]azepin-2(3H)-one (10 g, 62 mmol) and sulfuric acid (5 mL) in acetic acid (100 mL) dropwise at 0° C. After stirring overnight at room temperature, the reaction mixture was poured into ice water (200 mL), neutralized with ammonium hydroxide (28%, 100 mL) and extracted with ethyl acetate (3×80 mL). The combined organic layers were washed with brine, dried over sodium sulfate, filtered and concentrated under vacuum. The residue was purified by column chromatography (ethyl acetate/petroleum ether, 99/1) to afford the title compound (11.5 g, 77%) as a colorless oil. LC-MS (Method C): m/z=240.0 [M+H]$^+$, 1.152 min.

Step 2: Preparation of 7-bromo-1-trideuteriomethyl-4,5-dihydro-1H-benzo[b]azepin-2(3H)-one Trideuterated iodomethane (5.9 g, 41 mmol) was added dropwise to a stirring mixture of 7-bromo-4,5-dihydro-1H-benzo[b]azepin-2(3H)-one (9 g, 38 mmol) and cesium carbonate (13.4 g, 41 mmol) in N,N-dimethylformamide (30 mL). The reaction mixture was stirred for 2 hours at room temperature, diluted with water (60 mL) and extracted with ethyl acetate (3×50 mL). The combined organic layers were washed with brine, dried over anhydrous sodium sulfate, filtered and concentrated under vacuum. The residue was purified by column chromatography (methanol/dichloromethane, 1/20) to afford the title compound (7.2 g, 75%) as a yellow solid. LC-MS (Method C): m/z=257.1 [M+H]$^+$, 1.234 min.

Step 3: Preparation of 1-trideuteriomethyl-7-(methylsulfonyl)-4,5-dihydro-1H-benzo[b]azepin-2(3H)-one Cuprous iodide (304 mg, 1.6 mmol) was added to a mixture of 7-bromo-1-trideuteriomethyl-4,5-dihydro-1H-benzo[b]azepin-2(3H)-one (4.1 g, 16 mmol), L-proline (368 mg, 3.2 mmol), sodium hydroxide (64 mg, 1.6 mmol) and sodium methanesulphinate (8.16 g, 80 mmol) in dimethyl sulfoxide (20 mL) under nitrogen atmosphere. The reaction mixture was stirred overnight at 120° C. After cooling to room temperature, the reaction mixture was diluted with saturated aqueous ammonium chloride (40 mL) and extracted with ethyl acetate (3×50 mL). The combined organic layers were dried over anhydrous sodium sulfate, filtered and concentrated under vacuum. The residue was purified by column chromatography (methanol/dichloromethane, 1/20) to afford the title compound (2.7 g, 66%) as a yellow solid. LC-MS (Method C): m/z=257.1 [M+H]$^+$, 0.907 min.

Step 4: Preparation of 3-iodo-1-trideuteriomethyl-7-(methylsulfonyl)-4,5-dihydro-1H-benzo[b]azepin-2(3H)-one $N^1,N^1,N^2,N^2$-tetramethylethane-1,2-diamine (3.8 g, 33 mmol) was added to a stirring mixture of 1-trideuteriomethyl-7-(methylsulfonyl)-4,5-dihydro-1H-benzo[b]azepin-2(3H)-one (2.7 g, 11 mmol) in dichloromethane (40 mL) at 0° C., followed by the addition of iodotrimethylsilane (6.6 g, 33 mmol) dropwise over 30 minutes. After stirring for 1 hour at 0° C., a solution of iodine (4.2 g, 16.5 mmol) in dichloromethane (100 mL) was added. The reaction mixture was stirred for 2 hours at 0° C., quenched by the addition of aqueous sodium thiosulfate (5%, 60 mL) and extracted with ethyl acetate (3×50 mL). The combined organic layers were washed with brine, dried over anhydrous sodium sulfate, filtered and concentrated under vacuum. The residue was purified by column chromatography (dichloromethane) to afford the title compound (3.5 g, 88%) as a yellow solid. LC-MS (Method S): m/z=382.9 [M+H]$^+$, 0.826 min.

Step 5: Preparation of 1-trideuterated methyl-7-(methylsulfonyl)-1H-benzo[b]azepin-2(3H)-one 1,8-Diazabicyclo[5.4.0]undec-7-ene (3.8 g, 25.2 mmol) was added to a stirring mixture of 3-iodo-1-trideuterated methyl-7-(methylsulfonyl)-4,5-dihydro-1H-benzo[b]azepin-2(3H)-one (3.2 g, 8.4 mmol) in N,N-dimethylformamide (10 mL) at room temperature. The reaction mixture was stirred overnight at 80° C., quenched by the addition of water (30 mL) and extracted with ethyl acetate (3×50 mL). The combined organic layers were washed with brine, dried over anhydrous sodium sulfate, filtered and concentrated under vacuum. The residue was purified by column chromatography (dichloromethane) to afford the title compound (1.8 g, 85%) as a yellow solid. LC-MS (Method T): m/z=255.2 [M+H]$^+$, 0.698 min.

Step 6: Preparation of 4-trideuteriomethyl-7-(methylsulfonyl)-1,1a,2,8b-tetrahydrobenzo[b]cyclopropa[d]azepin-3(4H)-one 1-Methyl-1-nitrosourea (7.4 g, 70 mmol) was added to a solution of potassium hydroxide (14 g, 350 mmol) in water (21 mL) and ether (100 mL) at 0° C. The resulting mixture was stirred for 1 hour at 0° C. and then the organic phase was separated to provide a solution of diazomethane in ether (100 mL). The solution of diazomethane (100 ml) was added to the mixture of 1-trideuteriomethyl-7-(methylsulfonyl)-1H-benzo[b]azepin-2(3H)-one (1.8 g, 7 mmol) in tetrahydrofuran (30 mL) dropwise, followed by addition of a mixture of palladium diacetate (158 mg, 0.7 mmol) in tetrahydrofuran (10 mL) dropwise at 0° C. The reaction mixture was stirred overnight at room temperature. The solids were removed by filtration and the filtrate was concentrated under vacuum to afford the title compound (1.5 g crude) as a yellow oil. LC-MS (Method E): m/z=268.9 [M+H]$^+$, 0.757 min.

Step 7: Preparation of trans-2-iodo-4-trideuteriomethyl-7-(methylsulfonyl)-1,1a,2,8b-tetrahydrobenzo[b]cyclopropa[d]azepin-3(4H)-one $N^1,N^1,N^2,N^2$-tetramethylethane-1,2-diamine (1.95 g, 16.8 mmol) was added to a stirring mixture of 4-trideuteriomethyl-7-(methylsulfonyl)-1,1a,2,8b-tetrahydrobenzo[b]cyclopropa[d]azepin-3(4H)-one (1.5 g, 5.6 mmol) in dichloromethane (30 mL) at 0° C., followed by the addition of iodotrimethylsilane (3.4 g, 16.8 mmol) dropwise over 30 minutes. After stirring for 1 hour at 0° C., a solution of iodine (2.1 g, 8.4 mmol) in dichloromethane (50 mL) was added. The reaction mixture was stirred for 2 hours at 0° C., quenched by the addition of aqueous sodium thiosulfate (5%, 40 mL) and extracted with ethyl acetate (3×50 mL). The combined organic layers were washed with brine, dried over anhydrous sodium sulfate, filtered and concentrated under vacuum to afford the title compound (1.6 g crude) as a yellow oil. LC-MS (Method S): m/z=394.9 [M+H]$^+$, 0.892 min.

Step 8: Preparation of cis-2-azido-4-trideuteriomethyl-7-(methylsulfonyl)-1,1a,2,8b-tetrahydrobenzo[b]cyclopropa[d]azepin-3(4H)-one Sodium azide (390 mg, 6 mmol) was added to a stirring mixture of trans-2-iodo-4-trideuteriomethyl-7-(methylsulfonyl)-1,1a,2,8b-tetrahydrobenzo[b]cyclopropa[d]azepin-3(4H)-one (1.6 g, 4 mmol) in N,N-dimethylformamide (10 mL). The reaction mixture was stirred overnight at room temperature, quenched with water (40 mL) and extracted with ethyl acetate (3×50 mL). The combined organic layers were washed with brine, dried over anhydrous sodium sulfate, and filtered. The filtrate was concentrated under vacuum to afford the title compound (800 mg crude) as a yellow oil. LC-MS (Method S): m/z=309.9 [M+H]+, 0.855 min.

Step 9: Preparation of cis-2-amino-4-trideuteriomethyl-7-(methylsulfonyl)-1,1a,2,8b-tetrahydrobenzo[b]cyclopropa[d]azepin-3(4H)-one A solution of cis-2-azido-4-trideuteriomethyl-7-(methylsulfonyl)-1,1a,2,8b-tetrahydrobenzo[b]cyclopropa[d]azepin-3(4H)-one (800 mg, 2.59 mmol) in methanol (30 mL) was hydrogenated in the presence of palladium on carbon (10%, 100 mg) under hydrogen atmosphere (2-3 atm). After stirring for 2 hours at room temperature under hydrogen atmosphere, the reaction mixture was filtered through Celite. The filtrate was concentrated under vacuum and the resulting residue was purified by column chromatography (dichloromethane) to afford the title compound (500 mg, 68%) as a yellow solid. LC-MS (Method F): m/z=283.9 [M+H]+, 0.715 min.

Step 10: Preparation of 1-benzyl-4-fluoro-N-(cis-4-trideuteriomethyl-7-(methylsulfonyl)-3-oxo-1,1a,2,3,4,8b-hexahydrobenzo[b]cyclopropa[d]azepin-2-yl)-1H-pyrazole-3-carboxamide The crude product obtained using Amide Coupling Procedure C was purified by Prep-HPLC with the following conditions: Column: Xbridge Prep C18, 5 μm, 19×150 mm; Mobile Phase A: Water (0.1% NH4HCO3), Mobile Phase B: MeCNFlow rate: 20 mL/min; Gradient: 32% B to 55% B over 8 min; 254 & 220 nm; Rt: 7.38 min to afford the title compound. LC-MS (Method E): m/z=486.1 [M+H]+, 1.037 min.

Step 11: Preparation of 1-benzyl-4-fluoro-N-((1aR,2R,8bS)-4-trideuteriomethyl-7-(methylsulfonyl)-3-oxo-1,1a,2,3,4,8b-hexahydrobenzo[b]cyclopropa[d]azepin-2-yl)-1H-pyrazole-3-carboxamide and 1-benzyl-4-fluoro-N-((1aS,2S,8bR)-4-trideuteriomethyl-7-(methylsulfonyl)-3-oxo-1,1a,2,3,4,8b-hexahydrobenzo[b]cyclopropa[d]azepin-2-yl)-1H-pyrazole-3-carboxamide The racemate of 1-benzyl-4-fluoro-N-(cis-4-trideuteriomethyl-7-(methylsulfonyl)-3-oxo-1,1a,2,3,4,8b-hexahydrobenzo[b]cyclopropa[d]azepin-2-yl)-1H-pyrazole-3-carboxamide was separated by Prep-Chiral-HPLC with the following conditions: Column: CHIRALPAK IA, 2.12×15 cm, 5 μm; Mobile Phase A: Hexane, Mobile Phase B: EtOH; Flow rate: 20 mL/min; Gradient: 50% B to 50% B over 22 min; 254 & 220 nm; Rt1: 10.61; Rt2: 16.166 to afford the title compounds:

Example 183A (first eluting isomer): 1H NMR (400 MHz, CD3OD-d4) δ 8.05 (d, J=2.3 Hz, 1H), 7.86 (dd, J=8.5, 2.3 Hz, 1H), 7.75 (d, J=4.5 Hz, 1H), 7.53 (d, J=8.5 Hz, 1H), 7.42-7.31 (m, 5H), 5.33 (s, 2H), 4.66 (s, 1H), 3.17 (s, 3H), 2.47-2.37 (m, 1H), 2.15-2.06 (m, 1H), 1.38-1.30 (m, 1H), 1.26-1.17 (m, 1H). LC-MS (Method V): m/z=486.1 [M+H]+, 3.132 min.

Example 183B (second eluting isomer): 1H NMR (400 MHz, CD3OD-d4) δ 8.05 (d, J=2.3 Hz, 1H), 7.86 (dd, J=8.5, 2.3 Hz, 1H), 7.76 (d, J=4.5 Hz, 1H), 7.53 (d, J=8.5 Hz, 1H), 7.43-7.30 (m, 5H), 5.33 (s, 2H), 4.66 (s, 1H), 3.17 (s, 3H), 2.47-2.37 (m, 1H), 2.15-2.07 (m, 1H), 1.37-1.31 (m, 1H), 1.28-1.17 (m, 1H). LC-MS (Method D): m/z=486.1 [M+H]+, 1.390 min.

Example 184: (S)-4-fluoro-1-((1-methyl-1H-pyrazol-4-yl)methyl)-N-(5-methyl-4-oxo-2,3,4,5-tetrahydropyrido[3,2-b][1,4]oxazepin-3-yl)-1H-pyrazole-3-carboxamide

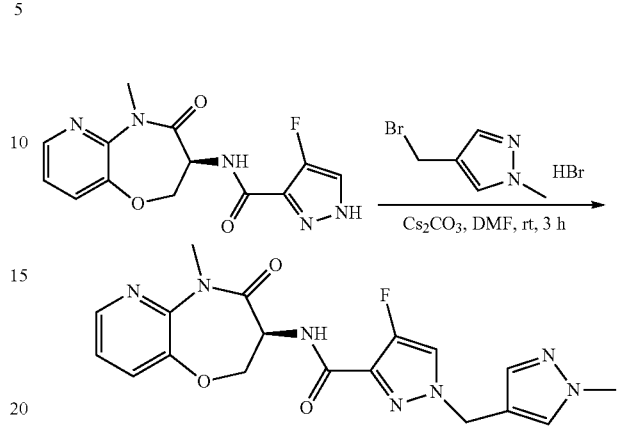

Cesium carbonate (453 mg, 1.39 mmol) was added to a stirring mixture of (S)-4-fluoro-N-(5-methyl-4-oxo-2,3,4,5-tetrahydropyrido[3,2-b][1,4]oxazepin-3-yl)-1H-pyrazole-3-carboxamide (100 mg, 0.33 mmol) and 4-(bromomethyl)-1-methyl-1H-pyrazole hydrochloride (208 mg, 0.82 mmol) in N,N-dimethylformamide (7 mL). After stirring for 3 hours at room temperature, the reaction mixture was quenched by the addition of water (50 mL) and extracted with dichloromethane (3×50 mL). The combined organic layers were dried over anhydrous sodium sulfate, filtered and concentrated under vacuum. The residue was purified by Prep-HPLC with the following conditions: Column; Xbridge Prep C18, 5 μm, 19×150 mm; Mobile Phase A; Water (0.1 mmol/L NH4HCO3), Mobile Phase B; MeCN; Flow rate: 20 mL/min; Gradient: 15% B to 36% B over 10 min; UV 254 & 220 nm to afford the title compound: 1H NMR (300 MHz, DMSO-d6) δ 8.37 (dd, J=4.8, 1.5 Hz, 1H), 8.22 (d, J=7.5 Hz, 1H), 8.01 (d, J=4.2 Hz, 1H), 7.75 (s, 1H), 7.71 (dd, J=8.1, 1.5 Hz, 1H), 7.49 (s, 1H), 7.34 (dd, J=8.1, 4.8 Hz, 1H), 5.19 (s, 2H), 4.91-4.81 (m, 1H), 4.69 (dd, J=11.1, 9.6 Hz, 1H), 4.53 (dd, J=9.6, 7.5 Hz, 1H), 3.82 (s, 3H), 3.37 (s, 3H). LC-MS (Method D): m/z=400.0 [M+H]+, 1.357 min.

Example 188: (S)-5-benzyl-N-(5-methyl-6-oxo-6,7,8,9-tetrahydro-5H-pyrazino[2,3-b]azepin-7-yl)isoxazole-3-carboxamide

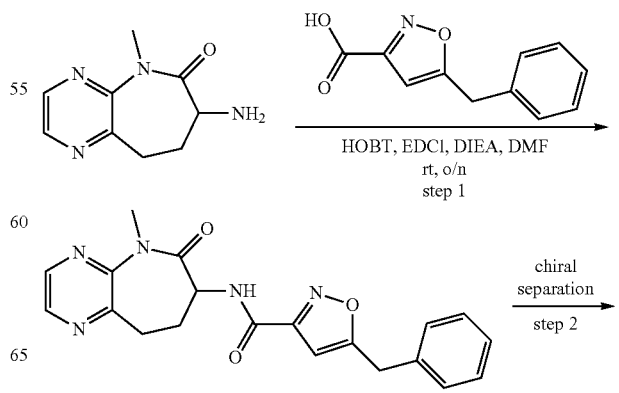

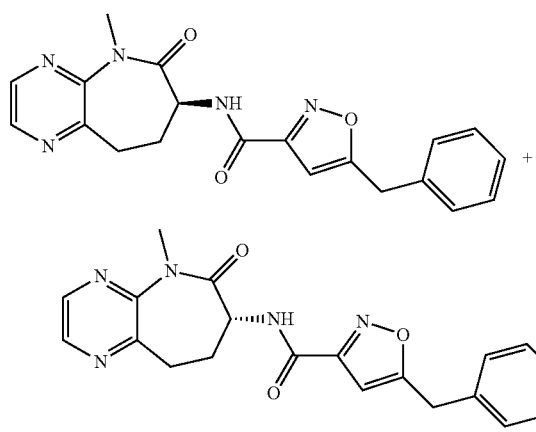

The crude product was purified by Prep-TLC (ethyl acetate/hexane, 3/1) to afford the racemate. LC-MS (Method E): m/z=378.2 [M+H]⁺, 0.998 min. The racemate of 5-benzyl-N-(5-methyl-6-oxo-6,7,8,9-tetrahydro-5H-pyrazino[2,3-b]azepin-7-yl)isoxazole-3-carboxamide was separated by Prep-Chiral-HPLC with the following conditions: Column: CHIRALPAK IA, 2×25 cm, 5 µm; Mobile Phase A: Hexane:DCM=5:1, Mobile Phase B: EtOH; Flow rate: 15 mL/min; Gradient: 50% B to 50% B in 20 min; UV 254 & 220 nm; Rt1: 11.1; Rt2: 15.01 to afford the title compound as the first eluting isomer: ¹H NMR (400 MHz, CD₃OD-d₄) δ 8.48-8.35 (m, 2H), 7.35-7.23 (m, 5H), 6.38 (s, 1H), 4.48 (dd, J=8.0, 12.0 Hz, 1H), 4.16 (s, 2H), 3.47 (s, 3H), 3.15-3.05 (m, 1H), 3.02-2.95 (m, 1H), 2.72-2.61 (m, 1H), 2.43-2.34 (m, 1H). LC-MS (Method D): m/z=378.0 [M+H]⁺, 1.645 min.

Example 190: (S)-5-benzyl-N-(5-methyl-6-oxo-6,7,8,9-tetrahydro-5H-pyrazino[2,3-b]azepin-7-yl)-1,3,4-oxadiazole-2-carboxamide

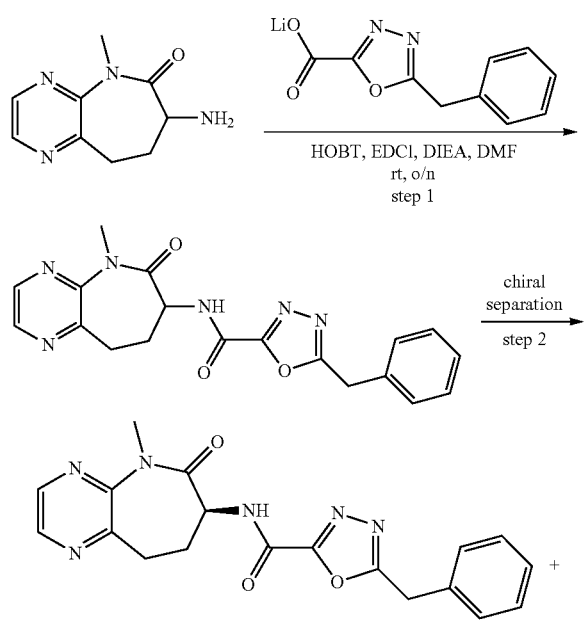

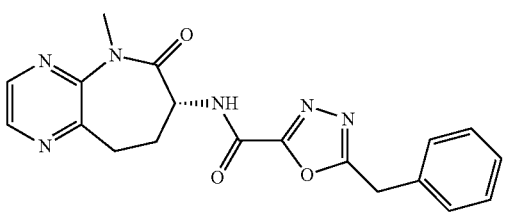

The residue was purified by Prep-TLC (ethyl acetate/hexane, 3/1) to afford the racemate. LC-MS (Method C): m/z=378.1 [M+H]⁺, 1.141 min. The racemate of 5-benzyl-N-(5-methyl-6-oxo-6,7,8,9-tetrahydro-5H-pyrazino[2,3-b]azepin-7-yl)-1,3,4-oxadiazole-2-carboxamide was separated by Prep-Chiral-HPLC with the following conditions: Column: CHIRALPAK IA, 2×25 cm, 5 µm; Mobile Phase A: Hexane:DCM=5: 1, Mobile Phase B: EtOH; Flow rate: 15 mL/min; Gradient: 50% B to 50% B in 20 min; UV 254 & 220 nm; Rt1: 11.1; Rt2: 15.01 to afford the title compound as the first eluting isomer: NMR (400 MHz, CD₃OD-d₄) δ 8.46 (d, J=2.8 Hz, 1H), 8.37 (d, J=2.4 Hz, 1H), 7.37-7.26 (m, 5H), 4.53 (dd, J=12.0, 7.6 Hz, 1H), 4.32 (s, 2H), 3.48 (s, 3H), 3.18-3.06 (m, 1H), 3.03-2.97 (m, 1H), 2.73-2.62 (m, 1H), 2.49-2.39 (m, 1H). LC-MS (Method J): m/z=379.1 [M+H]⁺, 1.072 min.

Example 192: 5-benzyl-N-((2R,3S)-2,5-dimethyl-4-oxo-2,3,4,5-tetrahydropyrido[3,2-b][1,4]oxazepin-3-yl)oxazole-2-carboxamide

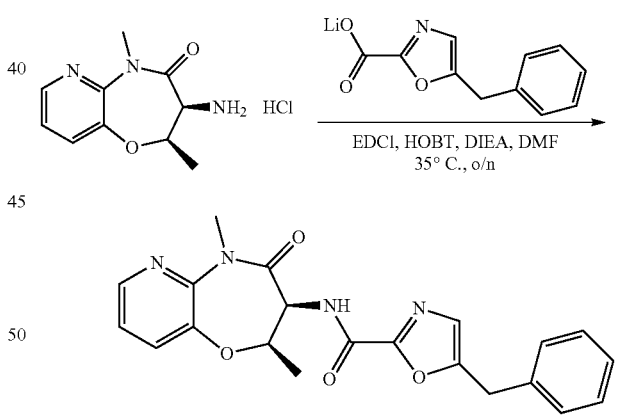

The crude product obtained was purified by Prep-HPLC with the following conditions: Column: Xbridge Prep C18, 5 µm, 19×150 mm; Mobile Phase A: Water (0.1% NH₄HCO₃), Mobile Phase B: MeCN; Flow rate: 20 mL/min; Gradient: 35% B to 66% B over 8 min; UV 254 & 220 nm; Rt: 6.98 min to afford the title compound. ¹H NMR (400 MHz, CD₃OD-d₄) δ 8.34 (dd, J=4.8, 1.6 Hz, 1H), 7.69 (dd, J=8.0, 1.6 Hz, 1H), 7.38-7.22 (m, 6H), 7.04 (s, 1H), 5.07-4.96 (m, 2H), 4.13 (s, 2H), 3.50 (s, 3H), 1.42 (d, J=5.9 Hz, 3H). LC-MS (Method D): m/z=393.1 [M+H]⁺, 1.524 min.

Example 193: 5-benzyl-N-((3S,4R)-1,4-dimethyl-2-oxo-1,2,3,4-tetrahydropyrido[2,3-b][1,4]oxazepin-3-yl)-1,3,4-oxadiazole-2-carboxamide

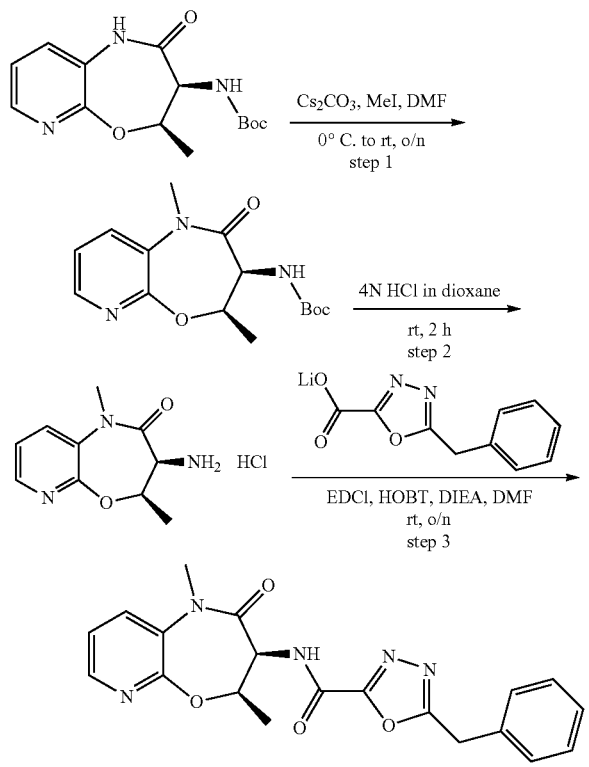

The crude product was purified by Prep-TLC (ethyl acetate/petroleum ether, 3/1) to afford the title compound: $^1$H NMR (400 MHz, CD$_3$OD-d$_4$) δ 8.22-8.19 (m, 1H), 7.94-7.90 (m, 1H), 7.43-7.39 (m, 1H), 7.35-7.26 (m, 5H), 5.14-5.07 (m, 2H), 4.31 (s, 2H), 3.44 (s, 3H), 1.45 (d, J=6.0 Hz, 3H). LC-MS (Method T): m/z=394.1 [M+H]$^+$, 1.202 min.

Example 194: 5-benzyl-N-((7S,7aS,8aR)-5-methyl-6-oxo-5,6,7,7a,8,8a-hexahydrocyclopropa[d]pyrazino[2,3-b]azepin-7-yl)oxazole-2-carboxamide

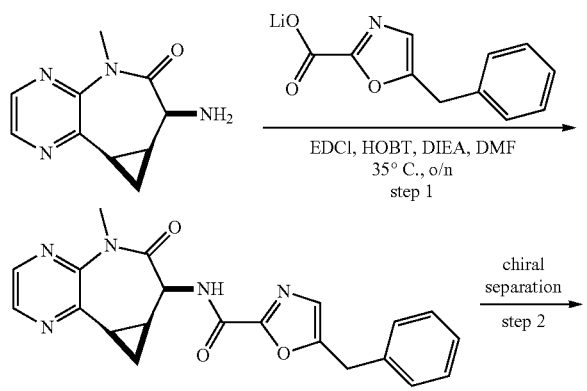

The crude product was purified by Prep-TLC (ethyl acetate/petroleum ether, 3/1) to afford the racemate. LC-MS (Method E): m/z=390.2 [M+H]$^+$, 1.018 min. The racemate of 5-benzyl-N-cis-5-methyl-6-oxo-5,6,7,7a,8,8a-hexahydro-cyclopropa[d]pyrazino[2,3-b]azepin-7-yl)-oxazole-2-carboxamide (50 mg, 0.13 mmol) was separated by Prep-Chiral-HPLC with the following conditions: Column: CHIRAL ART Cellulose-SB, 2×25 cm, 5 μm; Mobile Phase A: MTBE, Mobile Phase B: EtOH; Flow rate: 20 mL/min; Gradient: 30 B to 30 B in 15 min; UV 254 & 220 nm; Rt1: 7.635; Rt2: 9.685 to afford the title compound as the first eluting isomer: $^1$H NMR (400 MHz, CD$_3$OD-d$_4$) δ 8.45-8.40 (m, 2H), 7.39-7.23 (m, 5H), 7.04 (s, 1H), 4.77 (s, 1H), 4.14 (s, 2H), 3.42 (s, 3H), 2.67-2.59 (m, 1H), 2.28-2.20 (m, 1H), 1.57-1.50 (m, 1H), 1.37-1.28 (m, 1H). LC-MS (Method D): m/z=390.1 [M+H]$^+$, 1.361 min.

Example 195: 1-benzyl-N-((7S,7aS,8aR)-5-methyl-6-oxo-5,6,7,7a,8,8a-hexahydrocyclopropa[d]pyrazino[2,3-b]azepin-7-yl)-1H-1,2,3-triazole-4-carboxamide

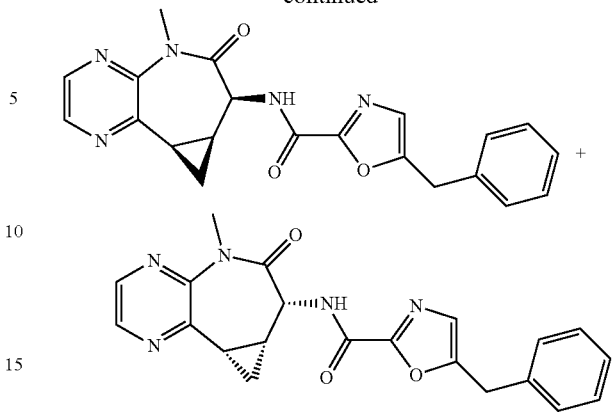

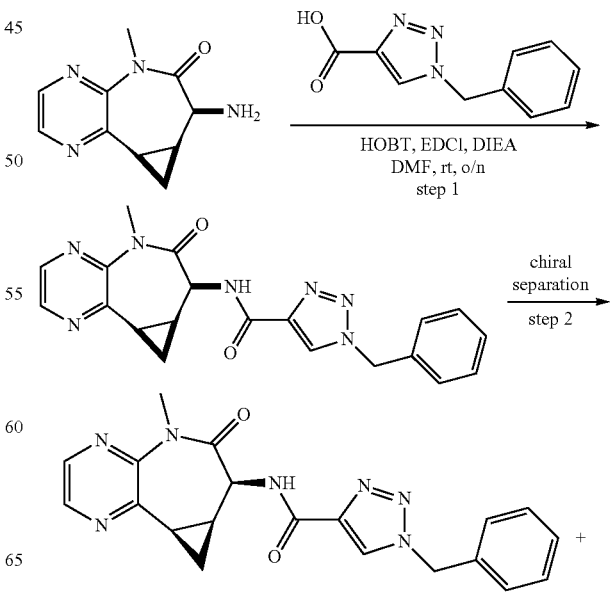

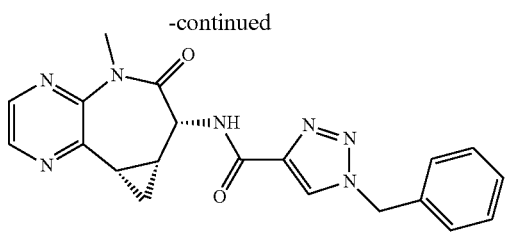

The crude product was purified by Prep-TLC (ethyl acetate/hexane, 3/1) to afford the racemate. LC-MS (Method E): m/z=390.2 [M+H]+, 0.932 min. The racemate of 5-benzyl-N-cis-5-methyl-6-oxo-5,6,7,7a,8,8a-hexahydro-cyclopropa[d]pyrazino[2,3-b]azepin-7-yl)-1H-1,2,3-triazole-2-carboxamide (50 mg, 0.129 mmol) was separated by Prep-Chiral-HPLC with the following conditions: Column: CHIRALPAK IA, 2.12×15 cm, 5 μm; Mobile Phase A: Hexane, Mobile Phase B: IPA; Flow rate: 20 mL/min; Gradient: 50% B to 50% B over 20 min; UV 254 & 220 nm; Rt1: 11.273; Rt2: 15.609 to afford the title compound as the first eluting isomer: 1H NMR (400 MHz, CD3OD-d4) δ 8.42-8.38 (m, 3H), 7.41-7.32 (m, 5H), 5.65 (s, 2H), 4.79 (s, 1H), 3.40 (s, 3H), 2.64-2.57 (m, 1H), 2.26-2.20 (m, 1H), 1.54-1.49 (m, 1H), 1.33-1.26 (m, 1H). LC-MS (Method J): m/z=390.1 [M+H]+, 1.162 min.

Example 197: 5-benzyl-N-((7S,7aS,8aR)-5-methyl-6-oxo-5,6,7,7a,8,8a-hexahydrocyclopropa[d]pyrazino[2,3-b]azepin-7-yl)isoxazole-3-carboxamide

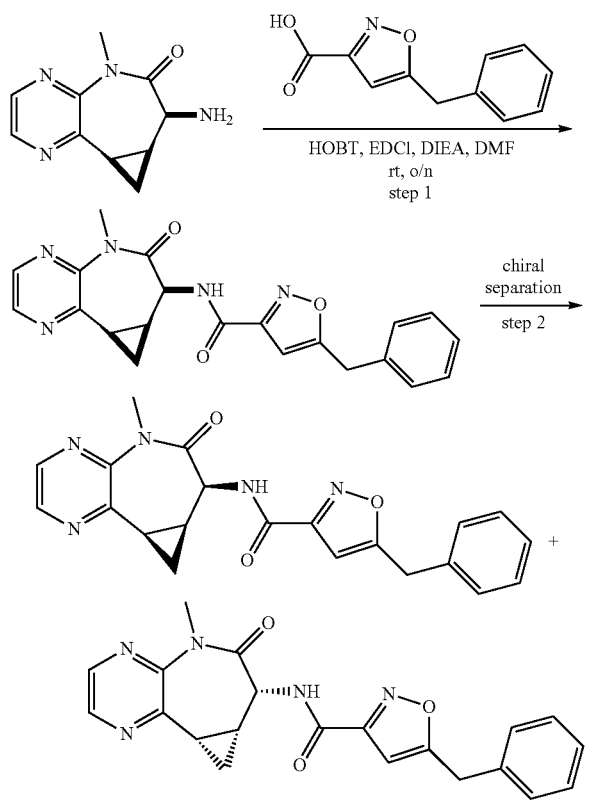

The crude product was purified by Prep-TLC (ethyl acetate/hexane, 3/1) to afford the racemate. LC-MS (Method E): m/z=390.2 [M+H]+, 1.072 min. The racemate of 5-benzyl-N-cis-5-methyl-6-oxo-5,6,7,7a,8,8a-hexahydro-cyclopropa[d]pyrazino[2,3-b]azepin-7-yl)-isoxazole-2-carboxamide was separated by Prep-Chiral-HPLC with the following conditions: Column: CHIRALPAK IA, 2×25 cm, 5 μm; Mobile Phase A: Hexane:DCM=5: 1, Mobile Phase B: EtOH; Flow rate: 15 mL/min; Gradient: 50% B to 50% B in 24 min; UV 254 & 220 nm; Rt1: 15.4; Rt2: 19.4 to afford the title compound as the first eluting isomer: 1H NMR (400 MHz, CD3OD-d4) δ 8.42-8.38 (m, 2H), 7.36-7.24 (m, 5H), 6.44 (s, 1H), 4.76 (s, 1H), 4.18 (s, 2H), 3.57 (s, 3H), 2.64-2.57 (m, 1H), 2.24-2.17 (m, 1H), 1.53-1.48 (m, 1H), 1.32-1.26 (m, 1H). LC-MS (Method D): m/z=390.0 [M+H]+, 1.747 min.

Example 198: 5-benzyl-N-((7S,7aS,8aR)-5-methyl-6-oxo-5,6,7,7a,8,8a-hexahydrocyclopropa[d]pyrazino[2,3-b]azepin-7-yl)-1,3,4-thiadiazole-2-carboxamide

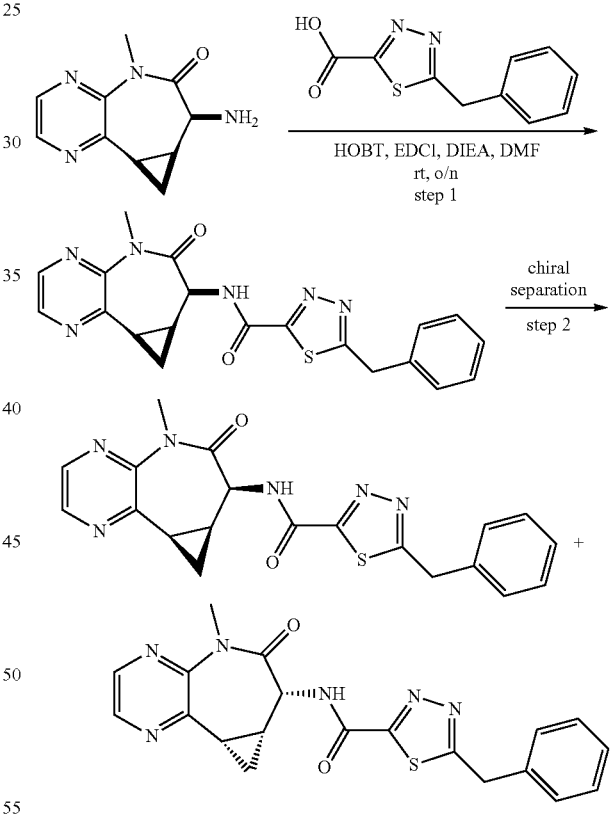

The crude product was purified by Prep-TLC (ethyl acetate/hexane, 3/1) to afford the racemate. LC-MS (Method E): m/z=407.1 [M+H]+, 1.017 min.

The racemate of 5-benzyl-N-(cis-5-methyl-6-oxo-5,6,7,7a,8,8a-hexahydrocyclopropa[d]pyrazino[2,3-b]azepin-7-yl)-1,3,4-thiadiazole-2-carboxamide was separated by Prep-Chiral-HPLC with the following conditions: Column. Chiralpak ID-2, 2×25 cm, 5 μm; Mobile Phase A: MTBE, Mobile Phase B: EtOH; Flow rate: 20 mL/min; Gradient: 30% B to 30% B over 26 min; UV 254 & 220 nm; Rt1:

19.418; Rt2: 22.874 to afford the title compound as the first eluting isomer: NMR (400 MHz, CD$_3$OD-d$_4$) δ 8.41-8.37 (m, 2H), 7.38-7.26 (m, 5H), 4.77 (s, 1H), 4.51 (s, 2H), 3.48 (s, 3H), 2.65-2.58 (m, 1H), 2.28-2.22 (m, 1H), 1.56-1.50 (m, 1H), 1.34-1.27 (m, 1H). LC-MS (Method D): m/z=407.1 [M+H]$^+$, 1.680 min.

Example 200: (S)-5-benzyl-N-(2,4-dimethyl-5-oxo-5,6,7,8-tetrahydro-4H-thiazolo[4,5-b]azepin-6-yl)-1,3,4-oxadiazole-2-carboxamide

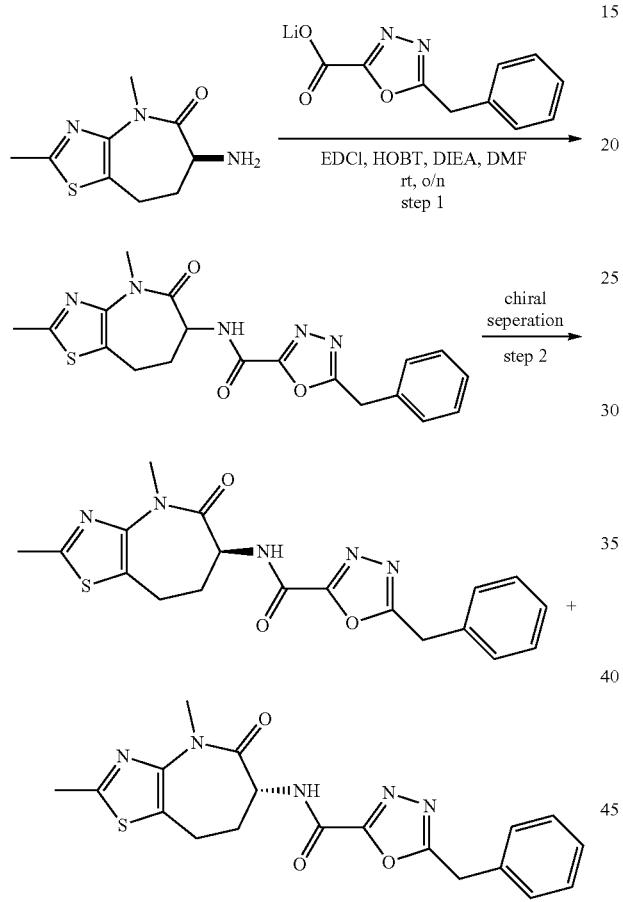

The crude product was purified by Prep-TLC (ethyl acetate/petroleum ether, 3/1) to afford the racemate. LC-MS (Method D): m/z=398.10 [M+H]$^+$, 1.284 min. The racemate of 5-benzyl-N-(2,4-dimethyl-5-oxo-5,6,7,8-tetrahydro-4H-thiazolo[4,5-b]azepin-6-yl)-1,3,4-oxadiazole-2-carboxamide was separated by Prep-Chiral-HPLC with the following conditions: Column: CHIRALPAK IA, 2.12×15 cm, 5 μm; Mobile Phase A: Hexane, Mobile Phase B: EtOH; Flow rate: 20 mL/min; Gradient: 50% B to 50% B over 13 min; UV 220 & 254 nm; Rt1: 7.88; Rt2: 10.109 to afford the title compound as the first eluting isomer: $^1$H NMR (400 MHz, CD$_3$OD-d$_4$) δ 7.41-7.24 (m, 5H), 4.65 (dd, J=11.5, 6.7 Hz, 1H), 4.33 (s, 2H), 3.36 (s, 3H), 3.06-2.84 (m, 2H), 2.72-2.54 (m, 4H), 2.46-2.33 (m, 1H). LC-MS (Method D): m/z=398.10 [M+H]$^+$, 1.283 min.

Example 201: (S)-1-benzyl-N-(5-methyl-4-oxo-2,3,4,5-tetrahydropyrido[3,2-b][1,4]oxazepin-3-yl)-1H-1,2,3-triazole-4-carboxamide

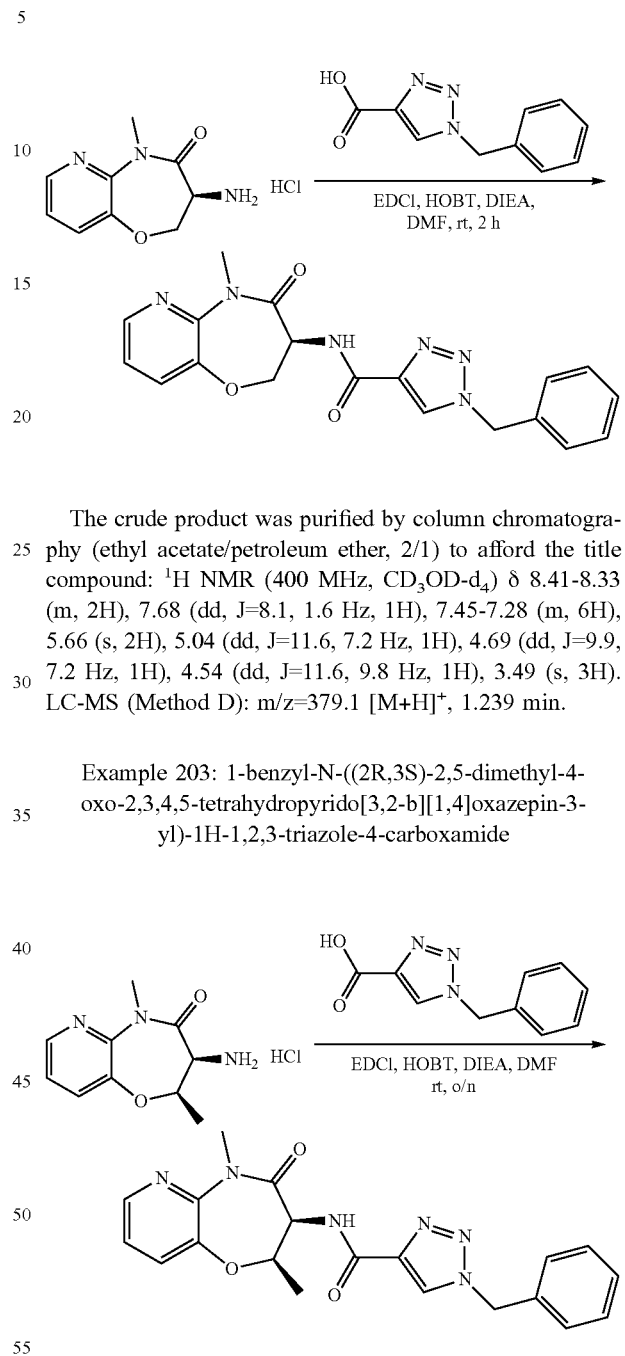

The crude product was purified by column chromatography (ethyl acetate/petroleum ether, 2/1) to afford the title compound: $^1$H NMR (400 MHz, CD$_3$OD-d$_4$) δ 8.41-8.33 (m, 2H), 7.68 (dd, J=8.1, 1.6 Hz, 1H), 7.45-7.28 (m, 6H), 5.66 (s, 2H), 5.04 (dd, J=11.6, 7.2 Hz, 1H), 4.69 (dd, J=9.9, 7.2 Hz, 1H), 4.54 (dd, J=11.6, 9.8 Hz, 1H), 3.49 (s, 3H). LC-MS (Method D): m/z=379.1 [M+H]$^+$, 1.239 min.

Example 203: 1-benzyl-N-((2R,3S)-2,5-dimethyl-4-oxo-2,3,4,5-tetrahydropyrido[3,2-b][1,4]oxazepin-3-yl)-1H-1,2,3-triazole-4-carboxamide The crude product was purified by Prep-HPLC with the following conditions: Column: Xbridge Prep C18, 5 μm, 19×150 mm; Mobile Phase A: Water (0.1% NH$_4$HCO$_3$), Mobile Phase B: MeCN; Flow rate: 20 mL/min; Gradient: 25% B to 66% B over 8 min; UV 254 & 220 nm; Rt: 6.68 min to afford the title compound. $^1$H NMR (300 MHz, CD$_3$OD-d$_4$) δ 8.27 (s, 1H), 8.23-8.20 (m, 1H), 7.56 (dd, J=8.0, 1.6 Hz, 1H), 7.29-7.17 (m, 6H), 5.54 (s, 2H), 4.97-4.85 (m, 2H), 3.38 (s, 3H), 1.31 (d, J=6.2 Hz, 3H). LC-MS (Method Q): m/z=393.2 [M+H]$^+$, 1.354 min.

Example 204: 2-benzyl-N-((2R,3S)-2,5-dimethyl-4-oxo-2,3,4,5-tetrahydropyrido[3,2-b][1,4]oxazepin-3-yl)-2H-1,2,3-triazole-4-carboxamide

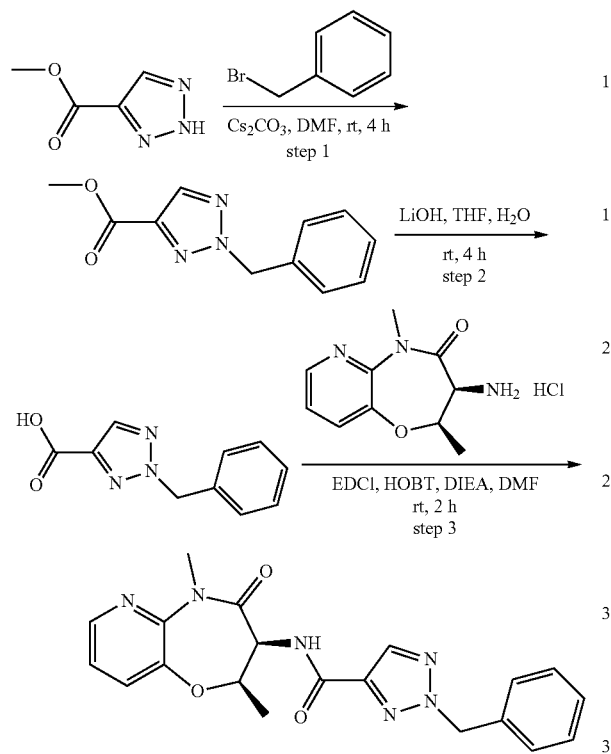

The crude product was purified by Prep-HPLC with the following conditions: Column: Xbridge Prep C18, 5 μm, 19×150 mm; Mobile Phase A: Water (0.1% NH₄HCO₃), Mobile Phase B: MeCN; Flow rate: 20 mL/min; Gradient: 35% B to 72% B over 8 min; UV 254 & 220 nm; Rt: 5.95 min to afford the title compound. $^1$H NMR (300 MHz, CD₃OD-d₄) δ 8.32 (dd, J=4.7, 1.5 Hz, 1H), 8.06 (s, 1H), 7.68 (dd, J=8.0, 1.6 Hz, 1H), 7.40-7.27 (m, 6H), 5.70 (s, 2H), 5.09-4.97 (m, 2H), 3.49 (s, 3H), 1.41 (d, J=6.1 Hz, 3H). LC-MS (Method D): m/z=393.10 [M+H]⁺, 1.479 min.

Example 205: 1-benzyl-N-((3S,4R)-1-trideuteriomethyl-4-methyl-2-oxo-1,2,3,4-tetrahydropyrido[2,3-b][1,4]oxazepin-3-yl)-4-fluoro-1H-pyrazole-3-carboxamide

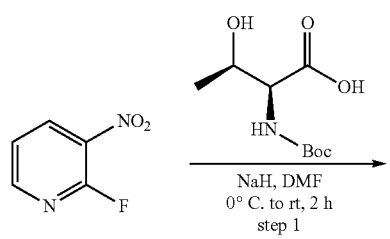

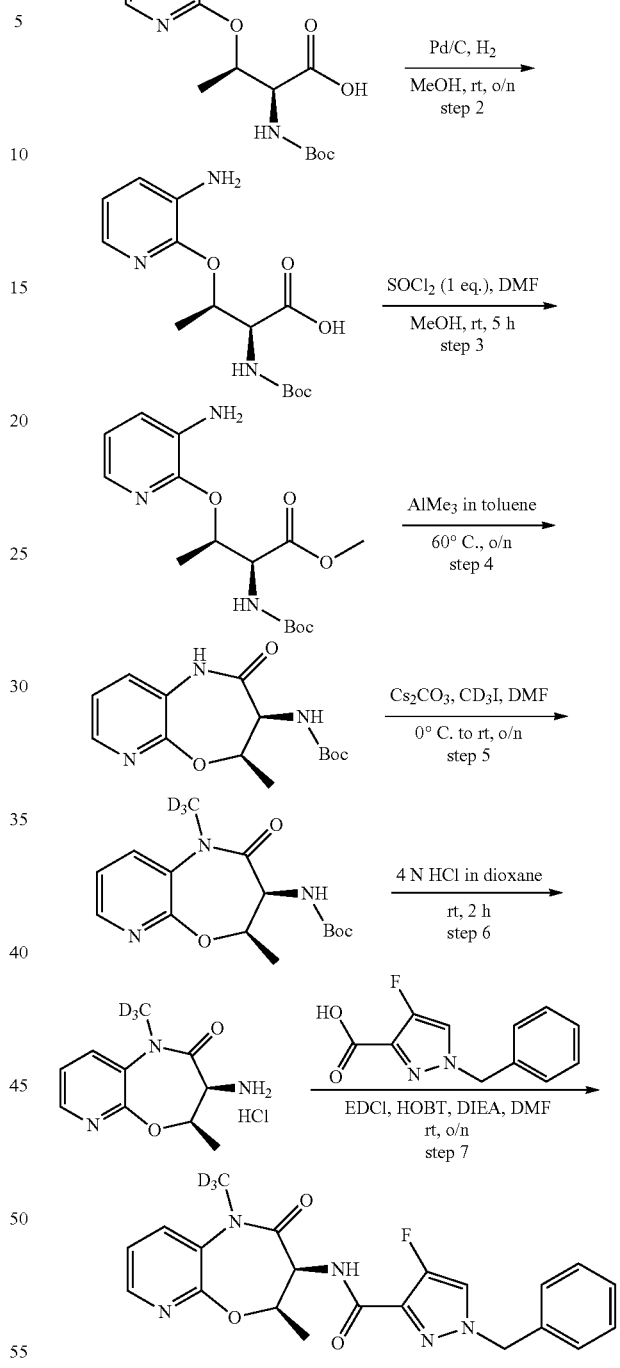

The crude product was purified by Prep-HPLC with the following conditions: Column: Kinetex 5 μm EVO C18 OBD Column, 21.2×150 mm, 5 μm; Mobile Phase A: Water (0.1% formic acid), Mobile Phase B: MeCN; Flow rate: 25 mL/min; Gradient: 30% B to 60% B over 8 min; UV 254 & 220 nm; Rt: 7.52 min to afford the title compound. $^1$H NMR (400 MHz, CD₃OD-d₄) δ 8.23 (dd, J=4.8, 1.6 Hz, 1H), 7.94 (dd, J=8.0, 2.0 Hz, 1H), 7.77 (d, J=4.4 Hz, 1H), 7.46-7.32 (m, 6H), 5.35 (s, 2H), 5.18-5.07 (m, 2H), 1.45 (d, J=6.0 Hz, 3H). LC-MS (Method O): m/z=413.2 [M+H]⁺, 1.472 min.

Example 206: 1-benzyl-N-((1aS,2S,8bR)-7-cyano-4-trideuteriomethyl-3-oxo-1,1a,2,3,4,8b-hexahydrobenzo[b]cyclopropa[d]azepin-2-yl)-4-fluoro-1H-pyrazole-3-carboxamide

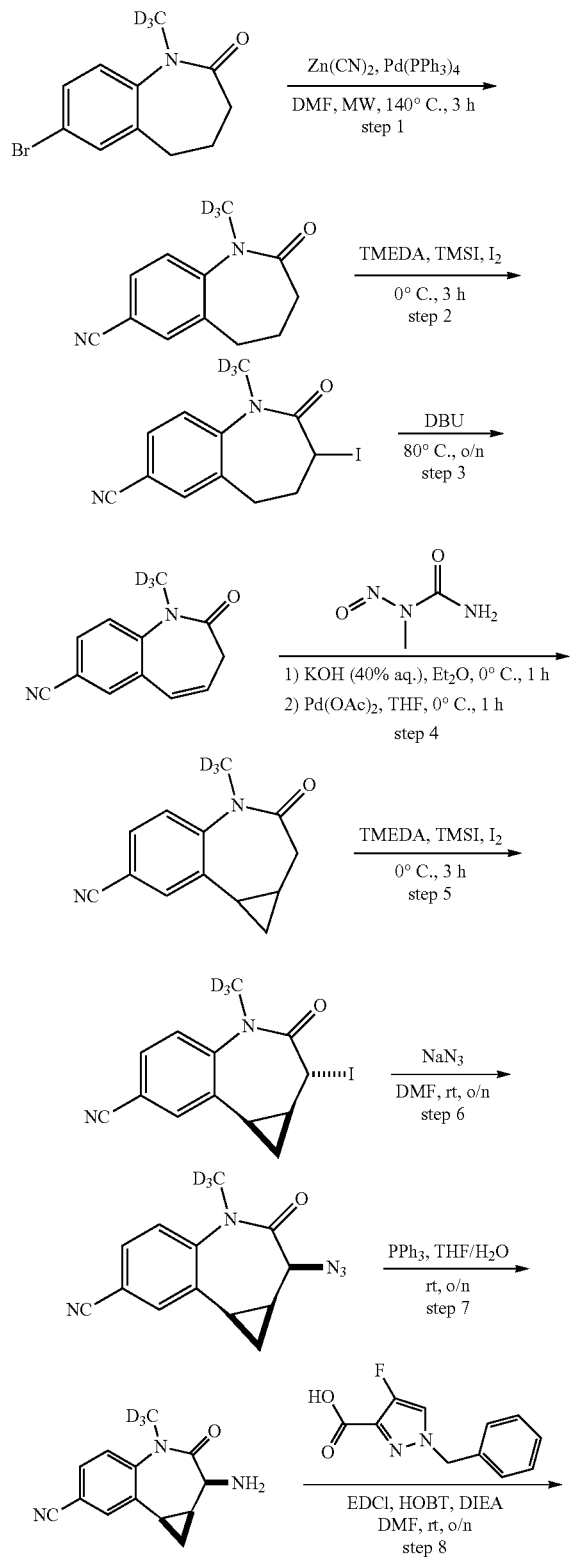

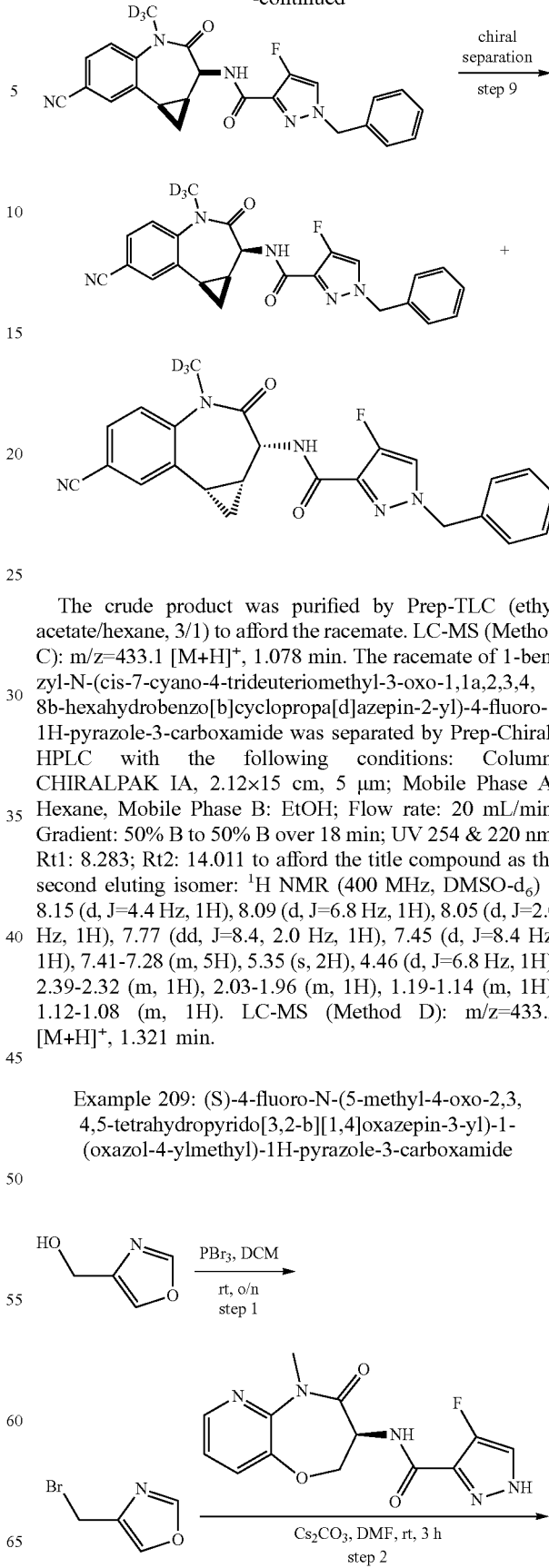

The crude product was purified by Prep-TLC (ethyl acetate/hexane, 3/1) to afford the racemate. LC-MS (Method C): m/z=433.1 [M+H]+, 1.078 min. The racemate of 1-benzyl-N-(cis-7-cyano-4-trideuteriomethyl-3-oxo-1,1a,2,3,4,8b-hexahydrobenzo[b]cyclopropa[d]azepin-2-yl)-4-fluoro-1H-pyrazole-3-carboxamide was separated by Prep-Chiral-HPLC with the following conditions: Column: CHIRALPAK IA, 2.12×15 cm, 5 μm; Mobile Phase A: Hexane, Mobile Phase B: EtOH; Flow rate: 20 mL/min; Gradient: 50% B to 50% B over 18 min; UV 254 & 220 nm; Rt1: 8.283; Rt2: 14.011 to afford the title compound as the second eluting isomer: $^1$H NMR (400 MHz, DMSO-$d_6$) δ 8.15 (d, J=4.4 Hz, 1H), 8.09 (d, J=6.8 Hz, 1H), 8.05 (d, J=2.0 Hz, 1H), 7.77 (dd, J=8.4, 2.0 Hz, 1H), 7.45 (d, J=8.4 Hz, 1H), 7.41-7.28 (m, 5H), 5.35 (s, 2H), 4.46 (d, J=6.8 Hz, 1H), 2.39-2.32 (m, 1H), 2.03-1.96 (m, 1H), 1.19-1.14 (m, 1H), 1.12-1.08 (m, 1H). LC-MS (Method D): m/z=433.2 [M+H]+, 1.321 min.

Example 209: (S)-4-fluoro-N-(5-methyl-4-oxo-2,3,4,5-tetrahydropyrido[3,2-b][1,4]oxazepin-3-yl)-1-(oxazol-4-ylmethyl)-1H-pyrazole-3-carboxamide

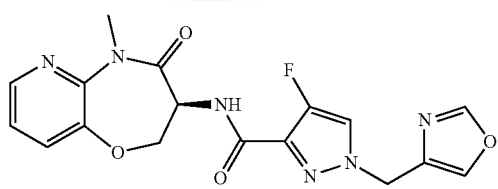

The crude product was purified by Prep-HPLC with the following conditions: Column: Xbridge Prep C18; 19×150 mm; 5 μm; Mobile Phase A: Water (0.1% NH₄HCO₃), Mobile Phase B: MeCN; Flow rate: 20 mL/min; Gradient: 21% B to 25% B over 10 min; UV 254 & 220 nm to afford the title compound: ¹H NMR (300 MHz, DMSO-d₆) δ 8.40 (d, J=0.6 Hz, 1H), 8.36 (dd, J=4.8, 1.5 Hz, 1H), 8.23 (d, J=7.8 Hz, 1H), 8.19 (d, J=0.9 Hz, 1H), 8.04 (d, J=4.5 Hz, 1H), 7.70 (dd, J=7.8, 1.5 Hz, 1H), 7.33 (dd, J=8.1, 4.8 Hz, 1H), 5.28 (s, 2H), 4.89-4.78 (m, 1H), 4.67 (dd, J=11.4, 9.9 Hz, 1H), 4.50 (dd, J=9.6, 7.5 Hz, 1H), 3.35 (s, 3H). LC-MS (Method T): m/z=387.2 [M+H]⁺, 0.973 min.

Example 213: (S)—N-(5-methyl-4-oxo-2,3,4,5-tetrahydropyrido[3,2-b][1,4]oxazepin-3-yl)-5-(pyridin-2-ylmethyl)thiazole-2-carboxamide

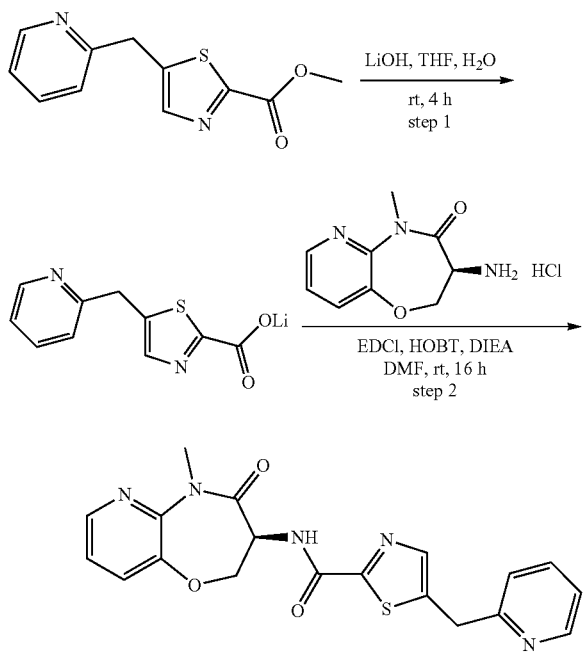

The title compound was prepared according to the methods described herein using the appropriate starting material. The crude product was purified by Prep-TLC (ethyl acetate/petroleum ether, 3/1) to afford the title compound: ¹H NMR (400 MHz, CD₃OD-d₄) δ 8.51-8.48 (m, 1H), 8.33 (dd, J=4.8, 1.6 Hz, 1H), 7.84-7.77 (m, 2H), 7.66 (dd, J=8.0, 1.6 Hz, 1H), 7.44-7.38 (m, 1H), 7.34-7.27 (m, 2H), 4.97 (dd, J=11.5, 7.2 Hz, 1H), 4.67 (dd, J=9.9, 7.2 Hz, 1H), 4.52 (dd, J=11.5, 9.9 Hz, 1H), 4.40 (s, 2H), 3.47 (s, 3H). LC-MS (Method D): m/z=396.0 [M+H]⁺, 1.786 min.

Example 214: (S)-4-fluoro-1-((5-fluoropyridin-2-yl)methyl)-N-(5-methyl-4-oxo-2,3,4,5-tetrahydrobenzo[b][1,4]oxazepin-3-yl)-1H-pyrazole-3-carboxamide

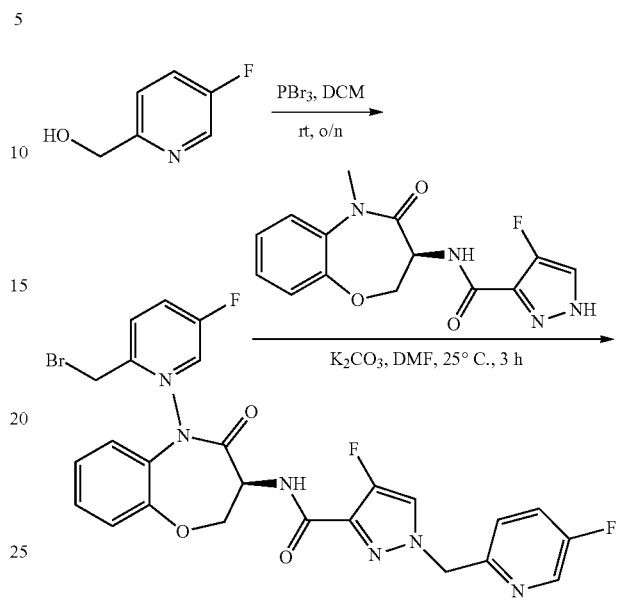

The crude product was purified by Prep-HPLC with the following conditions: Column: Gemini-NX/5u, C18 150× 21.2 mm; Mobile Phase A: Water (10 mmol/L NH₄HCO₃), Mobile Phase B: MeCN; Flow rate: 20 mL/min; Gradient: 45% B to 50% B over 8 min; UV 254 & 220 nm; Rt: 7.33 to afford the title compound: ¹H NMR (300 MHz, CD₃OD-d₄) δ 8.45 (d, J=3.0 Hz, 1H), 7.84 (d, J=4.5 Hz, 1H), 7.65-7.58 (m, 1H), 7.44-7.20 (m, 5H), 5.43 (s, 2H), 4.97 (dd, J=11.4, 7.5 Hz, 1H), 4.56 (dd, J=9.9, 7.5 Hz, 1H), 4.37 (dd, J=11.4, 9.9 Hz, 1H), 3.41 (s, 3H). LC-MS (Method D): m/z=414.1 [M+H]⁺, 1.579 min.

Example 215: (S)-5-benzyl-N-(5-methyl-4-oxo-2,3,4,5-tetrahydropyrido[3,2-b][1,4]oxazepin-3-yl)-1,2,4-oxadiazole-3-carboxamide

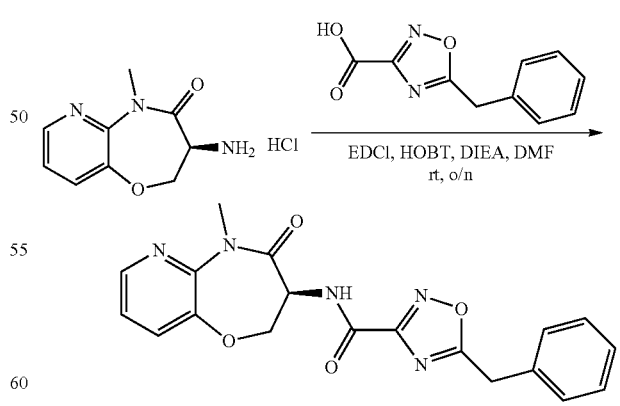

The residue was purified by Prep-HPLC with the following conditions: Column: Xbridge Prep C18, 5 μm, 19×150 mm; Mobile Phase A: Water (0.1% NH₄HCO₃), Mobile Phase B: MeCN; Flow rate: 20 mL/min; Gradient: 30% B to 60% B over 8 min; UV 254 & 220 nm; Rt: 6.65 min to afford the title compound: ¹H NMR (300 MHz, CD₃OD-d₄) δ 8.36-8.31 (m, 1H), 7.69-7.63 (m, 1H), 7.40-7.26 (m, 6H), 5.07-4.97 (m, 1H), 4.71-4.62 (m, 1H), 4.60-4.49 (s, 1H), 4.38 (s, 2H), 3.47 (s, 3H). LC-MS (Method D): m/z=380.1 [M+H]⁺, 1.322 min.

Example 216: (S)-1-((5-chloropyridin-2-yl)methyl)-4-fluoro-N-(5-methyl-4-oxo-2,3,4,5-tetrahydrobenzo[b][1,4]oxazepin-3-yl)-1H-pyrazole-3-carboxamide

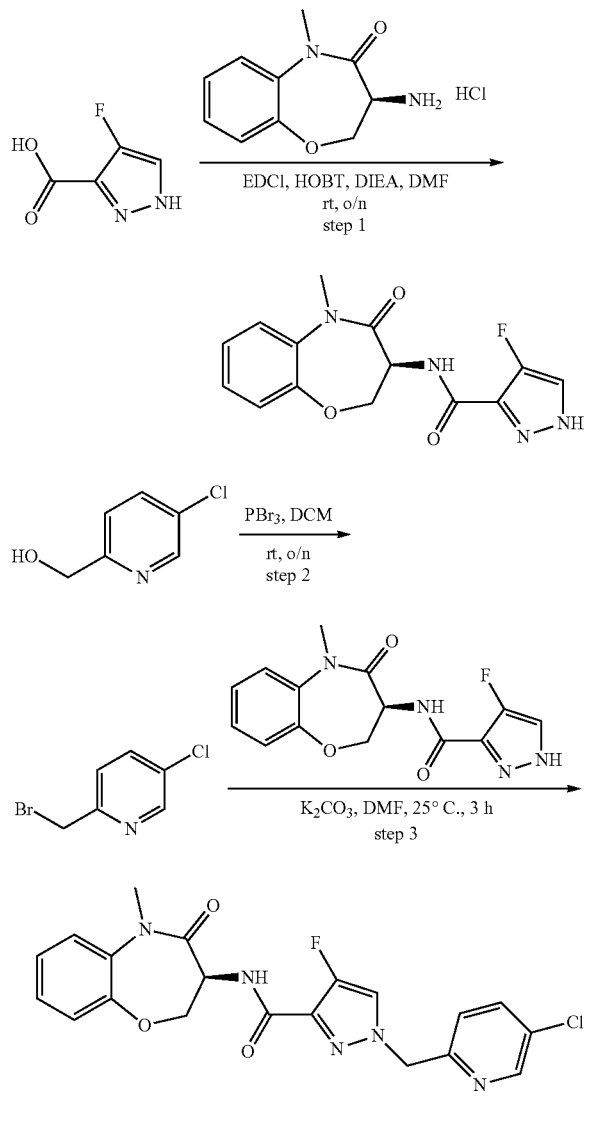

The residue was purified by Prep-HPLC with the following conditions: Column: Gemini-NX/5u, C18 150×21.2 mm; Mobile Phase A: Water (10 mmol/L NH₄HCO₃), Mobile Phase B: MeCN; Flow rate: 20 mL/min; Gradient: 40% B to 55% B over 8 min; UV 254 & 220 nm; Rt: 6.73 min to afford the title compound: ¹H NMR (300 MHz, CD₃OD-d₄) δ 8.51 (d, J=2.4 Hz, 1H), 7.82 (dd, J=8.4, 3.6 Hz, 2H), 7.42-7.35 (m, 1H), 7.32-7.17 (m, 4H), 5.40 (s, 2H), 4.94 (dd, J=11.4, 7.5 Hz, 1H), 4.54 (dd, J=9.9, 7.5 Hz, 1H), 4.34 (dd, J=11.7, 10.2 Hz, 1H), 3.37 (s, 3H). LC-MS (Method D): m/z=430.1 [M+H]⁺, 1.673 min.

Example 217: 5-benzyl-N-((2R,3S)-2,5-dimethyl-4-oxo-2,3,4,5-tetrahydropyrido[3,2-b][1,4]oxazepin-3-yl)-1,3,4-thiadiazole-2-carboxamide

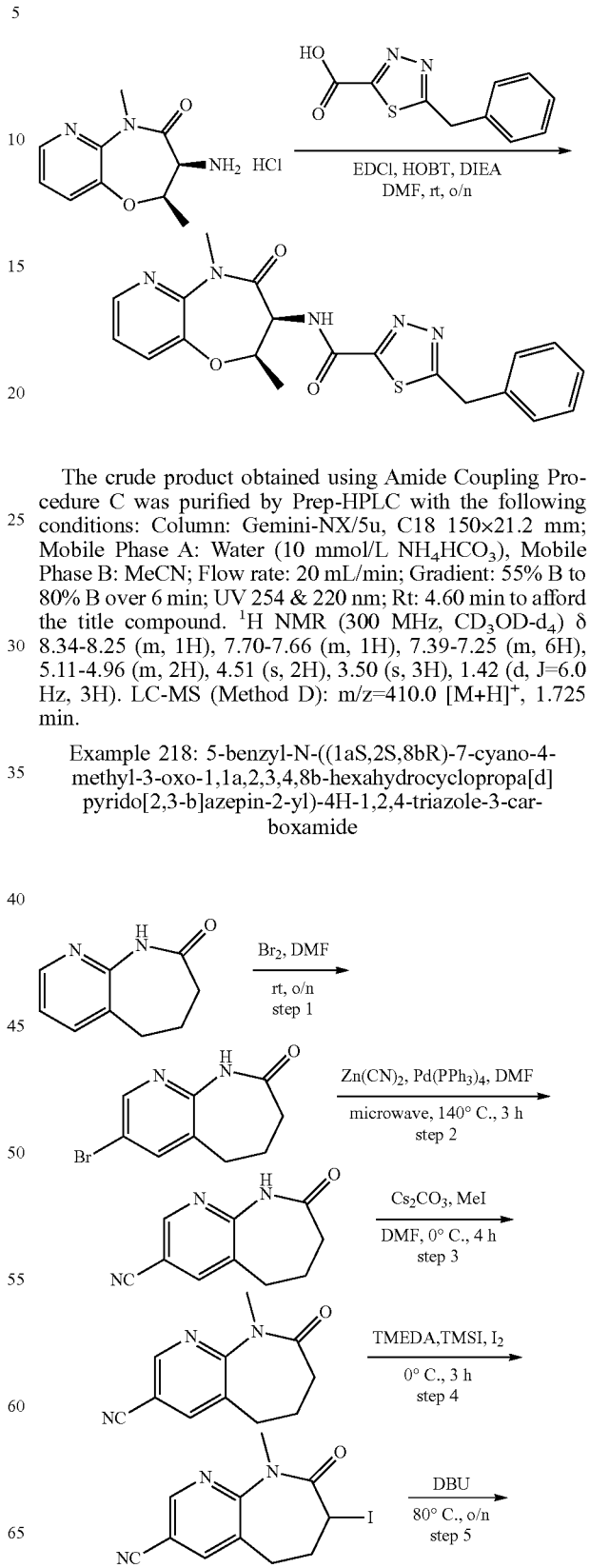

The crude product obtained using Amide Coupling Procedure C was purified by Prep-HPLC with the following conditions: Column: Gemini-NX/5u, C18 150×21.2 mm; Mobile Phase A: Water (10 mmol/L NH₄HCO₃), Mobile Phase B: MeCN; Flow rate: 20 mL/min; Gradient: 55% B to 80% B over 6 min; UV 254 & 220 nm; Rt: 4.60 min to afford the title compound. ¹H NMR (300 MHz, CD₃OD-d₄) δ 8.34-8.25 (m, 1H), 7.70-7.66 (m, 1H), 7.39-7.25 (m, 6H), 5.11-4.96 (m, 2H), 4.51 (s, 2H), 3.50 (s, 3H), 1.42 (d, J=6.0 Hz, 3H). LC-MS (Method D): m/z=410.0 [M+H]⁺, 1.725 min.

Example 218: 5-benzyl-N-((1aS,2S,8bR)-7-cyano-4-methyl-3-oxo-1,1a,2,3,4,8b-hexahydrocyclopropa[d]pyrido[2,3-b]azepin-2-yl)-4H-1,2,4-triazole-3-carboxamide 547
-continued

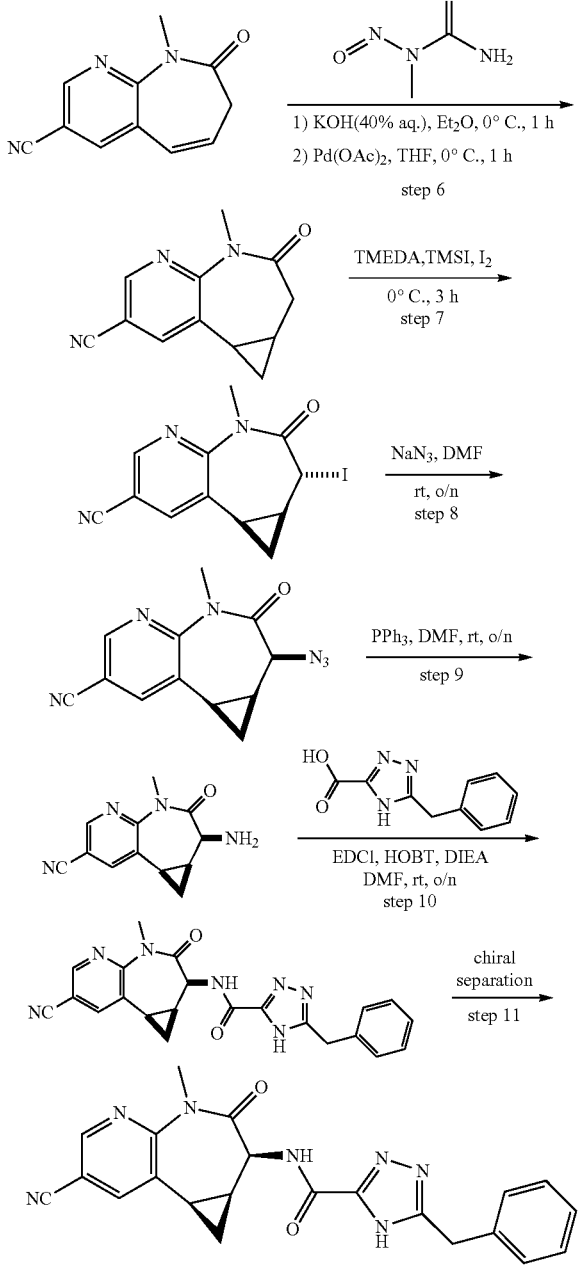

The crude product was purified by Prep-TLC (ethyl acetate/hexane, 3/1) to afford the racemate. LC-MS (Method D): m/z=414.1 [M+H]+, 1.222 min. The racemate of 5-benzyl-N-(cis-7-cyano-4-methyl-3-oxo-1,1a,2,3,4,8b-hexahydrocyclopropa[d]pyrido[2,3-b]azepin-2-yl)-4H-1,2,4-triazole-3-carboxamide was separated was separated by Prep-Chiral-HPLC with the following conditions: Column: CHIRAL ART Cellulose-SB, 2×25 cm, 5 µm; Mobile Phase A: MTBE, Mobile Phase B: EtOH; Flow rate: 20 mL/min; Gradient: 20% B to 20% B over 16 min; UV 254 & 220 nm; Rt1: 7.89; Rt2: 8.598 to afford the title compound as the second eluting isomer: 1H NMR (400 MHz, CD3OD-d4) δ 8.71 (d, J=2.4 Hz, 1H), 8.32 (d, J=2.0 Hz, 1H), 7.37-7.25 (m, 5H), 4.73 (s, 1H), 4.20 (s, 2H), 3.44 (s, 3H), 2.40-2.33 (m, 1H), 2.21-2.14 (m, 1H), 1.46-1.41 (m, 1H), 1.34-1.26 (m, 1H). LC-MS (Method D): m/z=414.1 [M+H]+, 1.221 min.

548

Example 219: (S)-5-(3-cyanobenzyl)-N-(9-methyl-8-oxo-6,7,8,9-tetrahydro-5H-pyrido[2,3-b]azepin-7-yl)thiazole-2-carboxamide

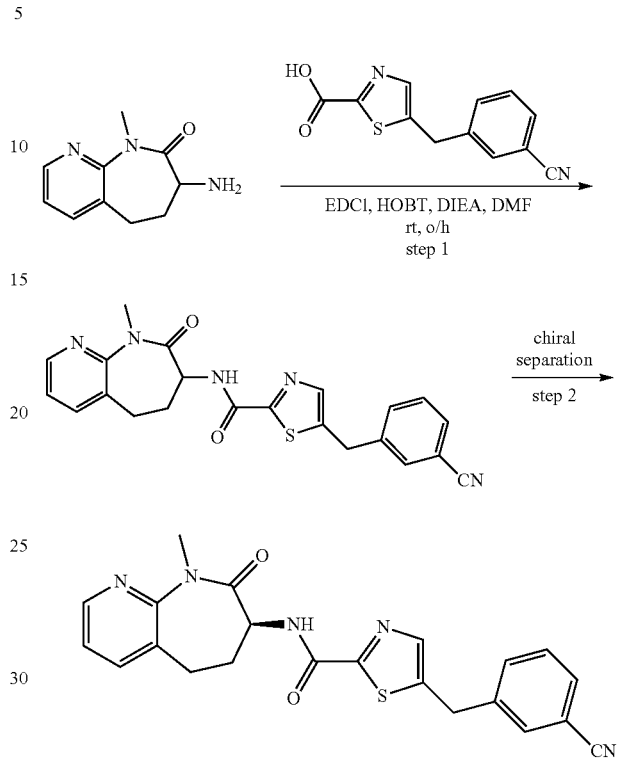

The crude product obtained using Amide Coupling Procedure C was purified by Prep-TLC (ethyl acetate/petroleum ether, 3/1) to afford the racemate. LC-MS (Method S): m/z=418.1 [M+H]+, 1.025 min. The racemate of 5-(3-cyanobenzyl)-N-(9-methyl-8-oxo-6,7,8,9-tetrahydro-5H-pyrido[2,3-b]azepin-7-yl)thiazole-2-carboxamide was separated by Prep-Chiral-HPLC with the following conditions: Column. (R,R)Whelk-O1, 21.1×250 mm, 5 µm; Mobile Phase A: Hexane: Dichloromethane=4.5:1, Mobile Phase B: EtOH; Flow rate: 20 mL/min; Gradient: 70% B to 70% B over 23 min; UV 254 & 220 nm; Rt1: 12.88; Rt2: 18.81 to afford the title compound as the first eluting isomer: 1H NMR (400 MHz, CD3OD-d4) δ 8.44 (dd, J=4.8, 1.6 Hz, 1H), 7.81 (dd, J=7.6, 1.6 Hz, 1H), 7.77 (s, 1H), 7.69 (s, 1H), 7.66-7.61 (m, 2H), 7.55-7.51 (m, 1H), 7.31-7.27 (m, 1H), 4.52-4.46 (m, 1H), 4.35 (s, 2H), 3.48 (s, 3H), 2.94-2.79 (m, 2H) 2.69-2.58 (m, 1H), 2.34-2.24 (m, 1H). LC-MS (Method D): m/z=418.0 [M+H]+, 1.716 min.

Example 220: (S)-4-fluoro-1-((6-methoxypyridin-2-yl)methyl)-N-(5-methyl-4-oxo-2,3,4,5-tetrahydrobenzo[b][1,4]oxazepin-3-yl)-1H-pyrazole-3-carboxamide

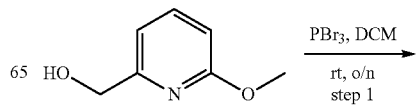

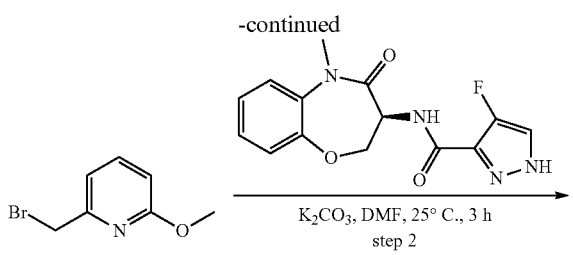

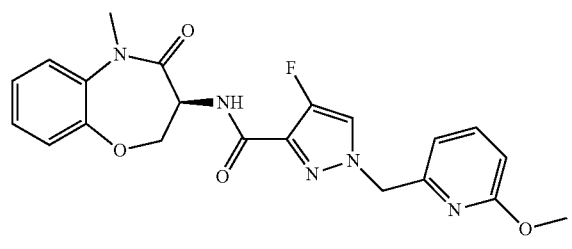

The crude product was purified by Prep-HPLC with the following conditions: Column: Gemini-NX/5u, C18 150× 21.2 mm; Mobile Phase A: Water (10 mmol/L $NH_4HCO_3$), Mobile Phase B: MeCN; Flow rate: 20 mL/min; Gradient: 40% B to 50% B over 8 min; UV 254 & 220 nm; Rt: 8.07 min to afford the title compound. $^1$H NMR (300 MHz, $CD_3OD$-$d_4$) δ 7.85 (d, J=4.5 Hz, 1H), 7.63 (dd, J=8.1, 7.2 Hz, 1H), 7.43-7.40 (m, 1H), 7.39-7.20 (m, 3H), 6.78 (d, J=7.2 Hz, 1H), 6.71 (d, J=8.4 Hz, 1H), 5.32 (s, 2H), 4.98 (dd, J=11.4, 7.5 Hz, 1H), 4.58 (dd, J=9.9, 7.5 Hz, 1H), 4.37 (dd, J=11.4, 9.9 Hz, 1H), 3.86 (s, 3H), 3.40 (s, 3H). LC-MS (Method D): m/z=426.2 [M+H]$^+$, 1.755 min.

Example 221: 5-(difluoro(phenyl)methyl)-N-((2R, 3S)-2,5-dimethyl-4-oxo-2,3,4,5-tetrahydropyrido[3,2-b][1,4]oxazepin-3-yl)-1,3,4-oxadiazole-2-carboxamide

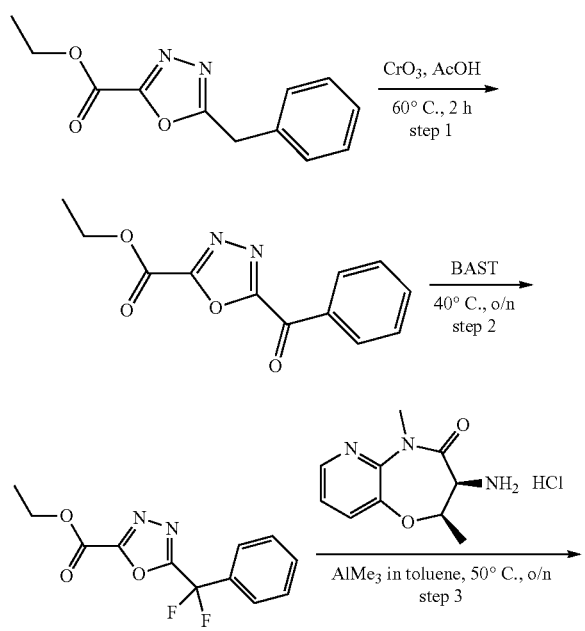

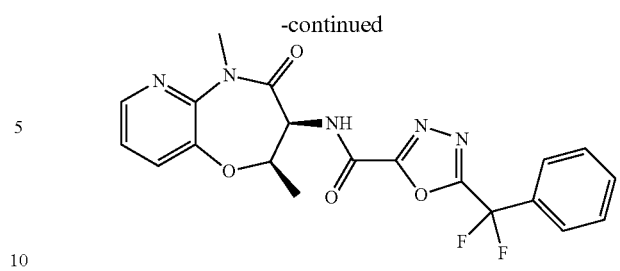

The crude product was purified by Prep-HPLC with the following conditions: Column: Gemini-NX/5u, C18 150× 21.2 mm; Mobile Phase A: Water (10 mmol/L $NH_4HCO_3$), Mobile Phase B: MeCN; Flow rate: 20 mL/min; Gradient: 47% B to 60% B over 10 min; UV 254 & 220 nm; Rt: 8.82 min to afford the title compound. $^1$H NMR (300 MHz, $CD_3OD$-$d_4$) δ 8.33 (dd, J=4.8, 1.8 Hz, 1H), 7.69-7.66 (m, 3H), 7.62-7.53 (m, 3H), 7.32 (dd, J=8.1, 4.8 Hz, 1H), 5.08-4.93 (m, 2H), 3.50 (s, 3H), 1.44 (d, J=6.3 Hz, 3H). LC-MS (Method O): m/z=430.1 [M+H]$^+$, 1.679 min.

Example 222: 5-benzyl-N-((2R,3S)-2,5-dimethyl-4-oxo-2,3,4,5-tetrahydropyrido[3,2-b][1,4]oxazepin-3-yl)-1,2,4-oxadiazole-3-carboxamide

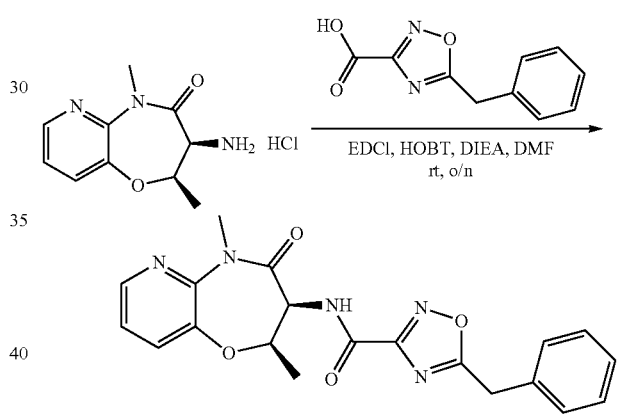

The crude product was purified by Prep-HPLC with the following conditions: Column: Xbridge Prep C18, 5 μm, 19×150 mm; Mobile Phase A: Water (0.1% $NH_4HCO_3$), Mobile Phase B: MeCN; Flow rate: 20 mL/min; Gradient: 40% B to 70% B over 8 min; UV 254 & 220 nm; Rt: 5.87 min to afford the title compound. $^1$H NMR (300 MHz, $CD_3OD$-$d_4$) δ 8.35-8.31 (m, 1H), 7.71-7.66 (m, 1H), 7.41-7.27 (m, 6H), 5.10-4.97 (m, 2H) 4.39 (s, 2H), 3.49 (s, 3H), 1.40 (d, J=6.2 Hz, 3H). LC-MS (Method D): m/z=394.1 [M+H]$^+$, 2.709 min.

Example 223: 5-(4-fluorobenzyl)-N-((7S,7aS,8aR)-5-methyl-6-oxo-5,6,7,7a,8,8a-hexahydrocyclopropa[d]pyrazino[2,3-b]azepin-7-yl)-1,3,4-oxadiazole-2-carboxamide

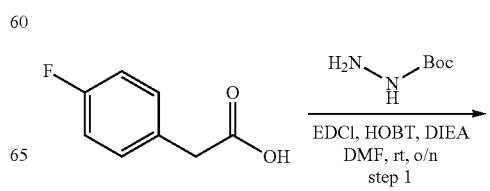

-continued

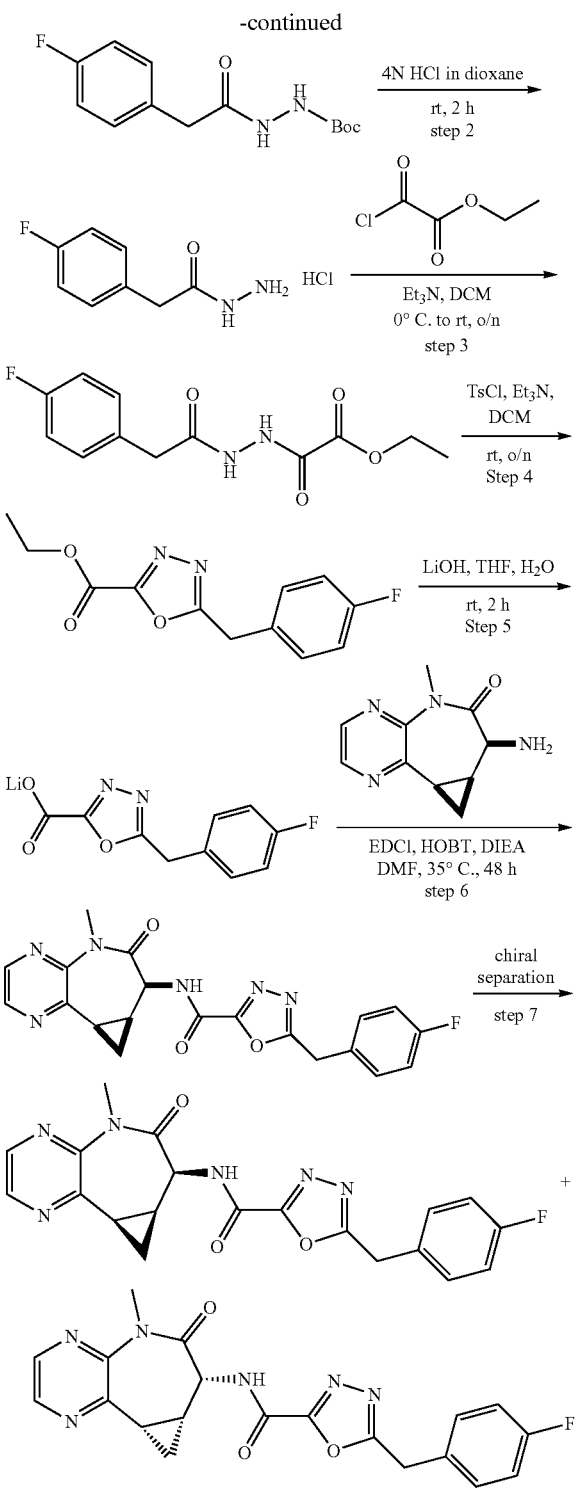

The crude product was purified by Prep-TLC (ethyl acetate/petroleum ether, 3/1) to afford the racemate. LC-MS (Method D): m/z=409.05 [M+H]$^+$, 1.255 min. The racemate of 5-(4-fluorobenzyl)-N-cis-5-methyl-6-oxo-5,6,7,7a,8,8a-hexahydrocyclopropa[d]pyrazino[2,3-b]azepin-7-yl)-1,3,4-oxadiazole-2-carboxamide was separated by Prep-Chiral-HPLC with the following conditions: Column: CHIRALPAK IE, 2×25 cm, 5 μm; Mobile Phase A: MTBE, Mobile Phase B: EtOH; Flow rate: 20 mL/min; Gradient: 30% B to 30% B in 16 min; UV 254 & 220 nm; Rt1: 10.514; Rt2: 13.482 to afford the title compound as the first eluting isomer: $^1$H NMR (400 MHz, CDCl$_3$-d) δ 8.49-8.32 (m, 3H), 7.39-7.28 (m, 2H), 7.14-6.94 (m, 2H), 4.85 (d, J=7.0 Hz, 1H), 4.25 (s, 2H), 3.45 (s, 3H), 2.71-2.62 (m, 1H), 2.30-2.21 (m, 1H), 1.57-1.50 (m, 1H), 1.30-1.22 (m, 1H). LC-MS (Method V): m/z=409.05 [M+H]$^+$, 2.450 min.

Example 224: (S)-4-fluoro-N-(5-methyl-4-oxo-2,3,4,5-tetrahydrobenzo[b][1,4]oxazepin-3-yl)-1-(pyrimidin-2-ylmethyl)-1H-pyrazole-3-carboxamide

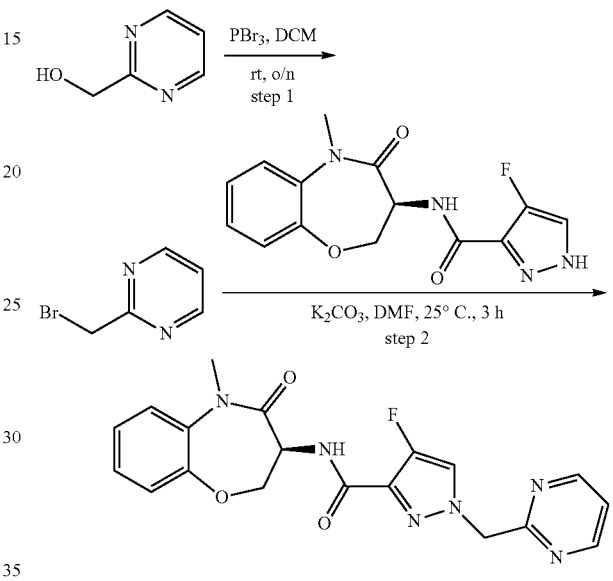

The crude product was purified by the Prep-HPLC with the following conditions: Column: Xbridge Prep C18, 5 μm, 19×150 mm; Mobile Phase A: Water (0.1% NH$_4$HCO$_3$), Mobile Phase B: MeCN; Flow rate: 20 mL/min; Gradient: 16% B to 43% B over 8 min; UV 254 & 220 nm; Rt: 7.47 min to afford the title compound. $^1$H NMR (300 MHz, CD$_3$OD-d$_4$) δ 8.81-8.77 (m, 2H), 7.91-7.87 (m, 1H), 7.48-7.41 (m, 2H), 7.38-7.21 (m, 3H), 5.58 (s, 2H), 5.03-4.95 (m, 1H), 4.62-4.56 (m, 1H), 4.43-4.34 (m, 1H), 3.42 (s, 3H). LC-MS (Method D): m/z=397.0 [M+H]$^+$, 2.334 min.

Example 225: (S)-5-benzyl-N-(1-methyl-2-oxo-2,3,4,5-tetrahydro-1H-benzo[b]azepin-3-yl)-1,3,4-oxadiazole-2-carboxamide

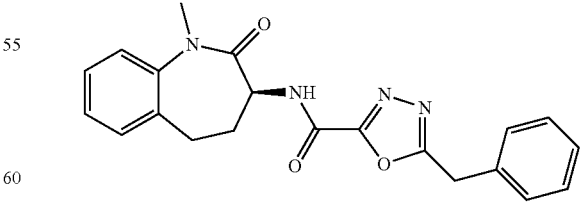

$^1$H NMR (300 MHz, CD$_3$OD-d$_4$) δ 7.47-7.18 (m, 9H), 4.47 (dd, J=11.7, 7.9 Hz, 1H), 4.31 (s, 2H), 3.40 (s, 3H), 2.93-2.82 (m, 1H), 2.73 (dd, J=13.6, 6.8 Hz, 1H), 2.52-2.43 (m, 1H), 2.33-2.21 (m, 1H). LC-MS (Method D): m/z=377.0 [M+H]$^+$, 1.732 min.

The other compounds of Table 1 were, or can be, prepared according to the Examples above and/or general procedures described herein using the appropriate starting materials.

Biological Assays

Compounds were tested for binding and cellular kinase activity according to the following protocols. proGST-hRIPK1 (8-327) enzyme was generated by Proteros GmbH by Baculovirus expression system.

The cellular necroptosis assay (Cell $IC_{50}$ in Tables 5-7) evaluates the ability of compounds to reverse the necrosis induced by human TNFα. Ten concentrations of the test compounds were assessed in duplicate in two different test occasions. FADD-deficient Jurkat cells were purchased from ATCC (ATCC-CRL-2572) and cultured in suspension in RPMI medium supplemented with 10% heat inactivated of FBS and 1% Pen-Strep. The day of the experiment cells were diluted to a density of $0.12 \times 10^5$ cells/mL (5,000 cells/well) with culture medium and added (40 µL) into the 384-well plate containing 0.2 µL/well of test compounds and reference compounds (CRCs) (200×). Cell plates were then incubated at 37° C.-5% $CO_2$. After 30 min, necroptotic cell death was induced with human TNFα (10 ng/mL) and cell viability was evaluated 48 h later by measuring cellular ATP levels using CellTiter-Glo® kit (Promega). Luminescence was read by using Victor V (Perkin Elmer) multilabel plate reader. Data were expressed as % of max viability calculated comparing the values to TNFα untreated control cells which represents 100% of cell viability. CRCs were analysed by Dotmatics and $IC_{50}$ values were calculated by non-linear regression using 4 parameter-logistic equation.

Fluorescent Polarization Binding (FP Binding) assay (Berger S. B. et al. (2015) *Cell Death Discovery*, 1: 15009; Maki J. L. et al. (2012) *Anal Biochem.*, 427(2): 164-174) was performed in polystyrene low volume 384-well black plate, at Room Temperature (RT) in a final volume of 10.1 µl/well using 10 nM of GST-hRIPK1 (8-327) enzyme and 5 nM of fluorescent-labeled ligand (14-(2-{[3-({2-{[4-(cyanomethyl)phenyl]amino}-6-[(5-cyclopropyl-1H-pyrazol-3-yl)amino]-4-pyrimidinyl}amino)propyl]amino}-2-oxoethyl)-16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-2-sulfonate.

Test Compounds were serially diluted in DMSO at 100 fold final concentrations in the assay (1% DMSO final). In each well of a 384-well Plate were dispensed 0.1 µL of compound solution (or DMSO for controls) followed by 5 µL of GST-hRIPK1 (8-327) at twice the final concentrations in assay buffer (50 mM HEPES pH 7.5, 10 mM NaCl, 50 mM $MgCl_2$, 0.02% CHAPS, 0.5 mM DTT and 0.01% Pluronic F127). For negative control the enzyme addition was replaced by assay buffer only.

After addition of 5 µL of fluorescent-labeled ligand at twice the final concentrations in assay buffer, the plate was incubated at RT for 30 min. At the end, the binding was measured as FP value with the Envision (PerkinElmer) plate reader using filter for an excitation λ=531 nm FP and an emission λ=595 nm FP (S & P-pol).

GST-hRIPK1 (8-327) enzyme was generated by Proteros GmbH by Baculovirus expression system.

Test compounds were diluted in DMSO and 0.1 µL of solution was dispensed to each well of a 384-well white solid microplate. The assay buffer was 50 mM HEPES pH 7.5, 50 mM NaCl, 30 mM $MgCl_2$. The buffer was supplemented with 0.02% CHAPS, 0.01% of Pluronic F127, 0.1 mg/mL BSA and 1 mM DTT. $MnCl_2$, 5 mM, was included in the assay buffer on the day of the experiment. The enzymatic reaction comprised 1.5 µg/mL GST-hRIPK1 (8-327) and 50 µM ATP for receptor interacting protein kinase 1 and 15 µM ATP. 5 µL of enzyme and 5 µL of ATP were added to the plate at twice the final assay concentration and incubated at room temperature for 3 hours. Following this reaction, 10 µL of ADP-Glo reagent (Promega) was added to each well and incubated for 40 min at room temperature. This stops the kinase reaction and depletes any remaining ATP. 20 µL of ADP-Glo detection reagent was then added to each well and incubated at room temperature for at least 15 minutes. The detection reagent converts ADP to ATP and introduces luciferase and luciferin to detect ATP. The luminescence is then measured with the Envision (PerkinElmer) plate reader. Test compound inhibition was expressed as percent inhibition of internal assay controls. For concentration response curves, normalized data is fit and $IC_{50}$ determined using XL-fit (IDBS) for Excel. The $IC_{50}$ were averaged to determine a mean value, for a minimum of two independent experiments.

Test compound inhibition was expressed as percent inhibition of internal assay controls. For concentration response curves, normalized data is fit and $IC_{50}$ determined using XL-fit (IDBS) for Excel. The $IC_{50}$ were averaged to determine a mean value, for a minimum of two independent experiments.

Receptor-interacting protein kinase 1 cellular activity and binding of exemplary compounds was determined according to the above general procedure. Results are summarized in Table 5. In the table below, activity is provided as follows: +++=0.0001 µM<$IC_{50}$<1 µM; ++=1 µM<$IC_{50}$<10 µM; +=10 µM<$IC_{50}$; ++*=3 µM<$IC_{50}$.

TABLE 5

| Compound | FP $IC_{50}$ (µM) | ADP $IC_{50}$ (µM) | Cell $IC_{50}$ (µM) |
|---|---|---|---|
| 1A | +++ | | +++ |
| 1B | +++ | | |
| 2 | +++ | +++ | +++ |
| 2A | +++ | | +++ |
| 2B | +++ | | +++ |
| 3 | +++ | | +++ |
| 4 | +++ | | +++ |
| 5 | +++ | | +++ |
| 6 | +++ | | +++ |
| 7 | +++ | | +++ |
| 7A | +++ | | +++ |
| 7B | + | | ++ |
| 8 | +++ | | +++ |
| 9 | +++ | | +++ |
| 10 | +++ | | +++ |
| 11 | +++ | | +++ |
| 11A | +++ | | +++ |
| 11B | ++ | | +++ |
| 12 | +++ | | +++ |
| 12A | +++ | | +++ |
| 12B | +++ | | +++ |
| 13 | +++ | | |
| 14 | +++ | | |
| 15 | | + | |
| 16 | | + | |
| 17 | | + | |
| 18 | | + | |
| 19 | | ++ | |
| 20 | | ++ | |
| 21 | | + | |
| 22 | | + | |
| 23 | | + | |
| 24 | | + | |
| 25 | | + | |
| 26 | | + | |

TABLE 5-continued

| Compound | FP IC$_{50}$ (μM) | ADP IC$_{50}$ (μM) | Cell IC$_{50}$ (μM) |
|---|---|---|---|
| 27 | | + | |
| 30 | +++ | | +++ |
| 32 | +++ | | +++ |
| 33 | + | | |
| 35 | +++ | | +++ |
| 38A | +++ | | +++ |
| 38B | ++* | | |
| 41 | +++ | | +++ |
| 42 | +++ | | +++ |
| 43 | ++ | | |
| 44 | +++ | | +++ |
| 45 | +++ | | +++ |
| 46A | +++ | | |
| 46B | ++* | | |
| 49 | ++ | | |
| 50A | +++ | | |
| 50B | ++ | | |
| 51 | +++ | | +++ |
| 52 | +++ | | +++ |
| 54A | +++ | | +++ |
| 54B | +++ | | +++ |
| 55 | +++ | | +++ |
| 56 | +++ | | +++ |
| 57 | +++ | | +++ |
| 58 | +++ | | +++ |
| 59 | +++ | | +++ |
| 60 | | | |
| 60A | +++ | | +++ |
| 60B | ++* | | |
| 61 | +++ | | +++ |
| 62 | +++ | | +++ |
| 63 | +++ | | +++ |
| 64 | +++ | | +++ |
| 65 | | + | |
| 66 | +++ | | +++ |
| 67A | +++ | | |
| 67B | ++* | | |
| 68A | +++ | | +++ |
| 68B | ++* | | |
| 69A | +++ | | +++ |
| 69B | ++* | | |
| 70A | +++ | | +++ |
| 70B | ++* | | |
| 71A | +++ | | +++ |
| 71B | ++* | | |
| 72 | +++ | | +++ |
| 73 | +++ | | +++ |
| 74 | +++ | | +++ |
| 75A | +++ | | +++ |
| 75B | ++* | | |
| 76 | +++ | | +++ |
| 77 | +++ | | +++ |
| 78 | +++ | | +++ |
| 79 | +++ | | +++ |
| 80A | +++ | | +++ |
| 80B | ++* | | |
| 81A | +++ | | +++ |
| 81B | ++* | | |
| 82A | +++ | | +++ |
| 82B | ++* | | |
| 83A | +++ | | +++ |
| 83B | ++ | | |
| 84 | +++ | | +++ |
| 85 | +++ | | +++ |
| 86 | +++ | | +++ |
| 87 | +++ | | |
| 88 | ++* | | ++ |
| 89A | ++ | | |
| 89B | +++ | | +++ |
| 90A | ++ | | |
| 90B | +++ | | +++ |
| 91 | +++ | | |
| 92 | +++ | | +++ |
| 93 | +++ | | |
| 94 | +++ | | +++ |
| 95 | ++* | | |
| 96 | +++ | | +++ |
| 98A | ++* | | |
| 98B | +++ | | |
| 99 | ++ | | +++ |
| 100A | +++ | | +++ |
| 100B | +++ | | |
| 101A | ++* | | |
| 101B | +++ | | +++ |
| 102A | ++ | | |
| 102B | +++ | | |
| 103A | ++* | | |
| 103B | +++ | | +++ |
| 104A | ++* | | |
| 104B | +++ | | |
| 105A | +++ | | +++ |
| 105B | ++* | | |
| 106 | +++ | | |
| 107A | ++* | | |
| 107B | +++ | | +++ |
| 108 | +++ | | |
| 109A | +++ | | +++ |
| 109B | ++* | | |
| 110A | ++* | | |
| 110B | +++ | | +++ |
| 111A | ++ | | |
| 111B | +++ | | +++ |
| 112 | +++ | | +++ |
| 113 | +++ | | |
| 114A | +++ | | +++ |
| 114B | ++* | | |
| 115 | +++ | | +++ |
| 116 | +++ | | +++ |
| 117 | +++ | | +++ |
| 118A | ++* | | |
| 118B | ++ | | |
| 119A | ++* | | |
| 119B | +++ | | +++ |
| 120A | +++ | | +++ |
| 120B | ++* | | |
| 121A | ++* | | |
| 121B | +++ | | |
| 122 | +++ | | +++ |
| 123 | +++ | | +++ |
| 124 | +++ | | +++ |
| 125A | ++* | | |
| 125B | +++ | | +++ |
| 126 | +++ | | +++ |
| 127 | +++ | | |
| 128 | +++ | | +++ |
| 129A | +++ | | |
| 129B | ++* | | |
| 130 | +++ | | +++ |
| 131A | +++ | | |
| 131B | ++* | | |
| 132 | +++ | | +++ |
| 133 | +++ | | +++ |
| 134 | +++ | | +++ |
| 135 | +++ | | +++ |
| 136 | +++ | | +++ |
| 137 | +++ | | +++ |
| 138 | +++ | | +++ |
| 139 | +++ | | +++ |
| 140 | +++ | | +++ |
| 141A | ++* | | |
| 141B | +++ | | |
| 142 | +++ | | +++ |
| 143 | +++ | | +++ |
| 144 | +++ | | +++ |
| 145A | +++ | | +++ |
| 145B | ++* | | |
| 146 | +++ | | +++ |
| 147 | +++ | | +++ |
| 148A | +++ | | +++ |
| 148B | ++ | | |
| 149 | +++ | | +++ |
| 150 | +++ | | +++ |

TABLE 5-continued

| Compound | FP IC$_{50}$ (μM) | ADP IC$_{50}$ (μM) | Cell IC$_{50}$ (μM) |
|---|---|---|---|
| 151 | +++ | | +++ |
| 152A | ++* | | |
| 152B | +++ | | +++ |
| 153 | +++ | | +++ |
| 154A | ++* | | |
| 154B | +++ | | +++ |
| 155 | +++ | | |
| 156A | ++* | | |
| 156B | +++ | | +++ |
| 157A | ++* | | |
| 157B | +++ | | +++ |
| 158 | +++ | | +++ |
| 159 | +++ | | |
| 160A | +++ | | +++ |
| 160B | ++* | | |
| 161 | +++ | | +++ |
| 162 | +++ | | +++ |
| 163 | +++ | | +++ |
| 164 | +++ | | +++ |
| 165 | +++ | | +++ |
| 166 | +++ | | +++ |
| 167 | +++ | | +++ |
| 168 | +++ | | +++ |
| 169 | +++ | | +++ |
| 170A | +++ | | +++ |
| 170B | ++* | | |
| 171 | +++ | | +++ |
| 172 | +++ | | +++ |
| 173 | +++ | | +++ |
| 174 | +++ | | +++ |
| 175 | +++ | | +++ |
| 176 | +++ | | |
| 177A | +++ | | +++ |
| 177B | ++* | | |
| 178A | +++ | | +++ |
| 178B | ++* | | |
| 179A | +++ | | +++ |
| 179B | ++* | | |
| 180A | +++ | | +++ |
| 180B | ++* | | |
| 181A | ++* | | |
| 181B | +++ | | +++ |
| 182A | ++* | | |
| 182B | +++ | | +++ |
| 183A | ++* | | |
| 183B | +++ | | +++ |
| 184 | +++ | | |
| 188 | +++ | | +++ |
| 190 | +++ | | |
| 192 | +++ | | +++ |
| 193 | +++ | | +++ |
| 194 | +++ | | |
| 195 | +++ | | +++ |
| 197 | +++ | | +++ |
| 198 | +++ | | +++ |
| 200 | +++ | | +++ |
| 201 | +++ | | +++ |
| 203 | +++ | | +++ |
| 204 | +++ | | |
| 205 | +++ | | +++ |
| 206 | +++ | | +++ |
| 207 | ++* | | |
| 208 | +++ | | |
| 209 | +++ | | +++ |
| 213 | +++ | | |
| 214 | +++ | | +++ |
| 215 | +++ | | +++ |
| 216 | +++ | | +++ |
| 217 | +++ | | +++ |
| 218 | +++ | | +++ |
| 219 | +++ | | +++ |
| 220 | +++ | | +++ |
| 221 | +++ | | +++ |
| 222 | +++ | | +++ |
| 223 | +++ | | +++ |
| 224 | +++ | | +++ |
| 225 | +++ | | +++ |
| 226 | +++ | | |
| 227 | +++ | | |

TABLE 6

| Compound | Cell IC$_{50}$ (μM) | Human hepatocyte CL$_{hep}$ Avg (mL/min/kg) | ER MDR1 | Rat unbound CL (mL/min/kg) | Dog unbound CL (mL/min/kg) | Cyno unbound CL (mL/min/kg) |
|---|---|---|---|---|---|---|
| 119B | 0.002 | 0 | 18 | 20 | | 26 |
| 161 | 0.002 | 0 | | | | |
| 163 | 0.001 | 0 | | | | |
| 42 | 0.0006 | 0.8 | 19 | 22 | 64 | 42 |
| 83A | 0.002 | 1.0 | 29 | 116 | | 82 |
| 170A | 0.003 | 3.1 | | | | |
| 177A | 0.002 | 4.2 | 1.4 | 55 | | 58 |
| 146 | 0.0007 | 4.2 | 1.0 | 61 | | 39 |
| 94 | 0.006 | 4.9 | 14 | 44 | | 40 |
| 171 | 0.0007 | 5.1 | 19 | 32 | | |
| 172 | 0.001 | 5.3 | | 65 | | |
| 183B | 0.0008 | 5.3 | 36 | | | |
| 66 | 0.012 | 6.3 | 1.6 | 113 | 36 | 116 |
| 195 | 0.016 | 7.1 | | | | |
| 198 | 0.020 | 8.5 | | | | |
| 134 | 0.003 | 9.0 | 1.1 | 100 | | 140 |
| 75A | 0.003 | 9.1 | 24 | 91 | | 93 |
| 205 | 0.021 | 11 | | | | |
| 148A | 0.0007 | 12 | | | | |
| 197 | 0.003 | 13 | | | | |
| 46A | 0.002 | 16 | 16 | 188 | | |
| 142 | 0.0007 | 16 | | | | |
| 77 | 0.001 | 19 | 0.6 | 595 | | |
| 8 | 0.004 | 19 | 0.8 | 3700 | | |
| 9 | 0.008 | 19 | | | | |

TABLE 6-continued

| Compound | Cell IC$_{50}$ (µM) | Human hepatocyte CL$_{hep}$ Avg (mL/min/kg) | ER MDR1 | Rat unbound CL (mL/min/kg) | Dog unbound CL (mL/min/kg) | Cyno unbound CL (mL/min/kg) |
|---|---|---|---|---|---|---|
| 92 | 0.0007 | | 1.4 | 420 | | |
| 193 | 0.21 | | | | | |

TABLE 7

Comparative Compounds

| | Structure | Cell IC$_{50}$ (µM) | Human hepatocyte CL$_{hep}$ Avg (mL min/kg) | ER MDR1 | Rat unbound CL (mL/ min/kg) | Dog unbound CL (mL/ min/kg) | Cyno unbound CL (ml min/kg) |
|---|---|---|---|---|---|---|---|
| A | 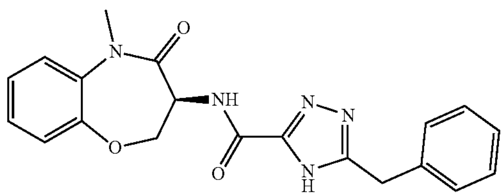 | 0.0005 | 6.8 | 6.4 | 77 | 240 | 117 |
| B | 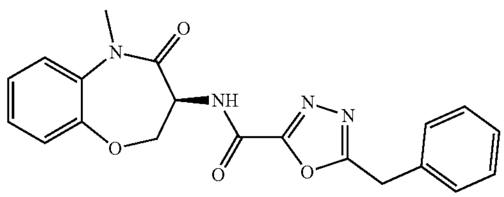 | 0.0003 | 14 | 1.0 | | | |
| C | 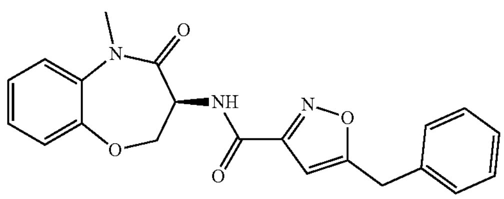 | 0.001 | 19 | 0.9 | | | |

The comparative compounds in Table 7 were prepared as described in Examples 12, 146, and 77, respectively, of WO 2014/125444.

The in vivo efficacy of compounds can be determined in mice using a TNF-driven systemic inflammatory response syndrome model as described by Duprez et. al. (2011, Immunity 35(6), 908-918) and Berger et. al. (2015, Cell Death Disc. 1, 15009). In this model system TNF/zVAD (tumor necrosis factor/Z-Val-Ala-DL-Asp-fluoromethylketone, a caspase inhibitor) treatment results in temperature loss and the production of several inflammatory cytokines. The ability of a test compound to inhibit these inflammatory effects can be measured in this model by dosing mice with test compound 15 minutes before administration of TNF/ zVAD and measuring the inflammatory response. The dose required to inhibit the inflammatory response is a measure of the compounds efficacy at that dose. Using this model, Compound 42 was orally pre-dosed at 5 mg/kg 15 minutes before intraveneous administration of TNF/zVAD and temperature loss in the mice was measured by an implanted temperature chip. Treatment of mice with 5 mg/kg of Compound 42 resulted in 96% inhibition of temperature loss when compared to TNF/zVAD vehicle treated animals. In comparison, WO 2014/125444 discloses in Table 2 that Example 12, corresponding to Example A of Table 7 above, required a dose of 30 mg/kg to achieve 93% inhibition. The decrease in dosing has a number of important potential advantages, including requiring less frequent administration to a patient, increased patient compliance, and improved safety profile such as lower toxicities while achieving similar efficacy.

Based on the known crystal structure of comparative Example C and receptor-interacting protein kinase 1 (Harris et al. J. Med. Chem., 2016, 59 (5), pg. 2163-2178), the phenyl carbon atom adjacent to the azepinone moiety (i.e., $X^9$ of the formulas disclosed herein) interacts with a lipophilic pocket of receptor-interacting protein kinase 1.

Certain compounds were found to have significantly improved metabolic stability when $X^9$ of the formulas disclosed herein is a N atom as compared to a carbon atom. For instance, Compound 42, in comparison to comparative Example A, when tested according to the assay described below, was found to have an average human hepatocyte clearance of 0.8 mL/min/kg versus 6.8 mL/min/kg for comparative Example A. As described in the metabolic stability section below, a CL$_{hep}$ of 6.8 mL/min/kg corresponds to a clearance of approximately 32% of liver blood flow, whereas for Compound 42, a $CL_{hep}$ value of 0.8 mL/min/kg corresponds to a clearance of less than 4% of liver blood flow, demonstrating the significant improvement in stability for compounds when $X^9$ is a N atom. From the data presented above, it will be apparent to those skilled in the art that compounds with lower human $CL_{hep}$ values should allow for lower human clinical doses, less frequent administration to a patient, increased patient compliance, and improved safety profile such as lower toxicities.

MDCKII-MDR1 Permeability

The blood brain barrier (BBB) separates circulating blood from the extracellular fluid of the central nervous system (CNS). The passive membrane permeability (Papp) and the P-gp (P-glycoprotein) substrate efflux potential were determined using the MDCKII-MDR1 cell line as an in vitro model of the effective permeability of a compound through the BBB. A bidirectional assay (Apical to Basolateral (A→B) and Basolateral to Apical (B→A)), in the absence and in the presence of GF120918 (a P-gp inhibitor) was conducted using pre-plated MDCKII-MDR1 cells (Corning HTS Transwell-96) obtained from SOLVO Biotechnology. The assay was run at 3 µM for 90 min (minutes) in triplicate using a HBSS+12.5 mM HEPES pH 7.4 transport buffer. Following incubation of samples from donor and receiver, wells were removed and measured by LC-MS/MS. Samples were extracted by protein precipitation with acetonitrile containing an appropriate internal standard (IS) having a known mass and molecular weight. The precipitate was centrifuged for 10 min at 3000 rpm (revolutions per minute). The supernatants were then collected, diluted if necessary, and injected on to the LC-MS/MS system. Specific parent/daughter ion pairs for the test article and IS were used to selectively measure the test articles. Papp (apparent permeability expressed in nm/sec [nanometer/second]) values were calculated according to the following equation:

$$Papp(\text{nm/sec}) = \left(\frac{dQ}{dt}\right) \times \left(\frac{1}{C0}\right) \times \left(\frac{1}{A}\right)$$

Where dQ/dt is the permeability rate, $C_0$ is the initial concentration in the donor solution (expressed as IS ratio), A and B are the surface areas of the filter (the surface area of the cell monolayer).

Monolayer efflux ratios (ER) were derived using the following equation:

$$EffluxRatio = \left(\frac{B-APapp(\text{nm/sec})}{A-BPapp(\text{nm/sec})}\right).$$

Compounds with a MDCKII-MDR1 efflux ratio of less than or equal to 2.5 are likely to demonstrate ability to cross the blood-brain-barrier.

Metabolic Stability (Hepatocytes)

The metabolic stability of compounds was evaluated in human cryopreserved hepatocytes (BioreclamationIVT, NY, USA) in duplicate. Test articles (or controls) were added to a 24-well incubation plate (Becton Dickinson Labware, USA) containing $0.5 \times 10^6$ hepatocytes/mL in suspension. The plate was held at 37° C. and agitated with constant orbital shaking (orbital speed at 350 rpm). At each time point (0, 5, 10, 15, 20, 30, 45, 60, 90, 120, 150 and 180 min) a Tecan Evo robot aspirated 50 µL of the incubation mixture and 100 µL of acetonitrile containing internal standard to quench the reaction. The quenched mixtures were dispensed into a 96-well plate along with 120 µL of aqueous solution to equilibrate the solvent content at 37%. Samples were centrifuged (3000 rpm for 10 minutes) and the plate sealed prior to injection onto an LC-MS/MS system.

The appropriate parent/daughter ions were monitored for the test article and IS with the LC-MS/MS system. The intrinsic clearance ($Cl_{int}$; expressed µL/min/million cells) was determined from the first order elimination constant (k, $min^{-1}$) of test article decay and the volume of the incubation. These values were scaled to intrinsic organ clearance ($CL_{int}$) using human specific scaling factors ($139 \times 10^6$ hepatocytes/g liver and 25.7 g liver/kg body weight). The intrinsic organ CL was then converted to the hepatic clearance ($CL_{hep}$) using the well-stirred model as shown below, where $Q_h$ is human hepatic blood flow.

$$CL_{hep} = \frac{Q_h * CL_{int}}{(Q_h + CL_{int})}$$

Hepatic clearance is expressed as mL/min/kg. The hepatic clearance relates to the flow of blood through the liver that is completely cleared of the compound. A human $CL_{hep}$ of 20.9 mL/min/kg corresponds to approximately complete compound clearance by the liver or 100% of liver blood flow. Accordingly, a human $CL_{hep}$ of 6 mL/min/kg corresponds to a clearance of approximately 29% of liver blood flow. A human $CL_{hep}$ value of 2 mL/min/kg corresponds to a clearance of approximately 10% of liver blood flow. A human $CL_{hep}$ value of 1 mL/min/kg or less corresponds to a clearance of approximately 5% of liver blood flow or less. A human $CL_{hep}$ value of 0 mL/min/kg corresponds to undetectable compound clearance by the liver.

In certain embodiments provided are compounds having a $CL_{hep}$ of less than 5, 4, 3, 2, or 1 mL/min/kg when tested according to the above human hepatic stability assay. In certain embodiments such compounds do not readily cross the blood brain barrier. In certain embodiments such compounds have a MDCKII-MDR1 efflux ratio of greater than 2.5.

In certain embodiments provided are compounds having a $CL_{hep}$ of less than 10, 9, 8, 7, 6, 5, 4, 3, 2, or 1 mL/min/kg when tested according to the above human hepatic stability assay. In certain embodiments such compounds are able to cross the blood brain barrier. In certain embodiments such compounds have a MDCKII-MDR1 efflux ratio of 2.5 or less.

Protein Binding

The protein binding in plasma was determined using a Rapid Equilibrium Dialysis Device (Thermo Scientific RED Device) or 96-well dialyzer apparatus (HTDialysis LLC). Plasma was spiked with test/control compounds to give a final concentration of 0.5 µM (plasma). If required, plasma samples were pre-incubated (2 hours at 37° C.) with diisopropyl fluorophosphate (DFP) at the final concentration of 100 µM to prevent compound degradation due to amide hydrolysis. Appropriate volumes of spiked samples along with blank phosphate buffer were added to either device and incubated at 37° C. for a total of 5 hours with agitation at 500 rpm. Following incubation, an equal aliquot of dialysed matrix (plasma or buffer) is added to an equal volume of the opposite blank matrix such that the volume of buffer to plasma are equal. Mixed matrix samples were extracted by protein precipitation using acetonitrile containing the appropriate IS. Samples were then centrifuged for 10 min at 2800 rpm. Supernatants were collected and diluted and then injected on to an HPLC-MS/MS or UPLC-MS/MS system. Samples were analyzed by monitoring the appropriate parent/daughter ion transitions for the test and control compounds. The peak area ratios were used to measure test item concentrations. The fraction unbound (Afu) was determined as the ratio of the peak area ratio in buffer divided by the peak area ratio in plasma.

In Vivo Pharmacokinetic (PK) Studies

The PK properties of test articles were determined in male Sprague-Dawley Crl:CD(SD) rats, male Beagle dogs and male cynomolgus monkeys. Studies were conducted to the highest standards of animal welfare in accordance with national legislation and under approval of the internal animal care and use committees.

Compounds were administered by IV bolus to animals following an overnight fast. Compounds for IV administration were formulated as solutions using either 1% DMSO (dimethyl sulfoxide):20% PEG400 (polyethylene glycol 400):79% saline, or 5-50% NMP in D5W (5% dextrose in water). The formulations were administered at dose volumes ranging from 0.5-2 mL/kg. The IV dose ranged from 0.5-1 mg/kg.

Following dose administration, 8-9 serial blood samples were collected over 24 hours. Samples were mixed with anticoagulant and placed on wet ice prior to processing. Plasma was harvested following centrifugation, extracted using protein precipitation with acetonitrile containing IS. The processed supernatant was analyzed using UPLC or LC-MS/MS using specific parent/daughter ion pairs for the test article and IS. Plasma concentrations were determined using a calibration curve prepared using known concentrations of analyte. Pharmacokinetic parameters utilizing measured concentrations were calculated using Phoenix WinNonlin. The unbound plasma clearance was calculated as the ratio of the total body clearance divided by the fraction unbound in plasma.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound of Formula I:

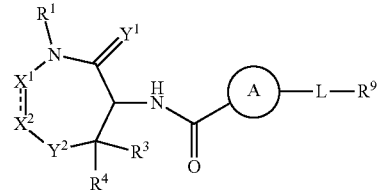

or a pharmaceutically acceptable salt, tautomer, stereoisomer or mixture of stereoisomers thereof, wherein:

$R^1$ is H or optionally substituted $C_1$-$C_6$ alkyl;

$X^1$ and $X^2$ together form an optionally substituted pyridyl:

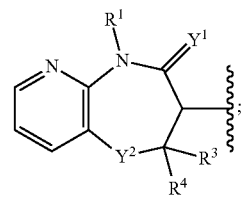

$Y^1$ is O;

$Y^2$ is —$C(R^6)_2$—;

$R^3$ and $R^4$ are independently H, halo, or optionally substituted $C_1$-$C_6$ alkyl, or $R^3$ and $R^4$ together with the carbon atom to which they are attached, form an optionally substituted cycloalkyl or optionally substituted heterocyclyl ring;

each $R^6$ is independently H, halo, or optionally substituted $C_1$-$C_6$ alkyl, or two $R^6$ together with the carbon atom to which they are attached, form a $C_2$-$C_6$ alken-1-yl, optionally substituted cycloalkyl or optionally substituted heterocyclyl ring;

or $R^3$ and $R^6$ together with the carbon atoms to which they are attached, form an optionally substituted cycloalkyl or optionally substituted heterocyclyl ring;

A is an optionally substituted cycloalkyl, optionally substituted heterocyclyl ring or optionally substituted heteroaryl ring;

L is absent, —O—, —S—, —S(O)—, —S(O)$_2$—, —NR'— or —C(R$^8$)$_2$—;

$R^7$ is H or optionally substituted $C_1$-$C_6$ alkyl;

each $R^8$ is independently H, halo, or optionally substituted $C_1$-$C_6$ alkyl, or two $R^8$ together with the carbon atom to which they are attached, form an optionally substituted cycloalkyl or optionally substituted heterocyclyl ring; and $R^9$ is optionally substituted cycloalkyl, optionally substituted heterocyclyl, optionally substituted aryl or optionally substituted heteroaryl;

wherein each optionally substituted pyridyl, optionally substituted $C_1$-$C_6$ alkyl, optionally substituted cycloalkyl, optionally substituted heterocyclyl, optionally substituted aryl, and optionally substituted heteroaryl ring is independently optionally substituted by one or more substituents, provided that the designated atom's normal valence is not exceeded, selected from alkyl, alkenyl, alkynyl, alkoxy, alkylthio, acyl, amido, amino, amidino, aryl, aralkyl, azido, carbamoyl, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, —SH, thioxo, N-oxide, —Si(R$^{100}$)$_3$ wherein each R$^{100}$ is independently hydrogen, alkyl, alkenyl, alkynyl, heteroalkyl, cycloalkyl, aryl, heteroaryl, heterocyclyl, —OC(O)R, and —C(O)OR, wherein R is hydrogen, alkyl, alkenyl, alkynyl, cycloalkyl, heterocyclyl, aryl, heteroalkyl, or heteroaryl; and
further wherein:
each cycloalkyl is independently a saturated or partially unsaturated cyclic alkyl group of from 3 to 20 ring carbon atoms having a single ring or multiple rings, wherein the cycloalkyl may be fused, bridged, or spiro;
each heterocyclyl is independently a saturated or unsaturated cyclic alkyl group of from 2 to 20 ring carbon atoms with one to five ring heteroatoms independently selected from nitrogen, oxygen and sulfur, and may comprise one or more oxo (C=O) or N-oxide (N—O—) moieties and/or a single ring or multiple rings wherein the multiple rings may be fused, bridged, or spiro; and
each heteroaryl is independently an aromatic group having 1 to 20 ring carbon atoms, a single ring, multiple rings, or multiple fused rings, with one to five ring heteroatoms independently selected from nitrogen, oxygen, and sulfur.

2. The compound of claim 1, wherein R$^1$ is methyl.

3. The compound of claim 1, wherein R$^3$ is hydrogen.

4. The compound of claim 1, wherein both R$^3$ and R$^4$ are fluoro, or either R$^3$ or R$^4$ are fluoro and the other is hydrogen, or R$^3$ and R$^4$ form a cyclopropyl or R$^3$ joins with R$^6$ to form a cyclopropyl.

5. The compound of claim 1, wherein R$^3$ joins with R$^6$ to form a cyclopropyl.

6. The compound of claim 1, wherein both R$^3$ and R$^4$ are hydrogen.

7. The compound of claim 1, wherein R$^3$ and R$^4$ together with the carbon atom to which they are attached, form a cyclopropyl.

8. The compound of claim 1, wherein L is absent, —O— or —C(R$^8$)$_2$—.

9. The compound of claim 8, wherein L is —C(R$^8$)$_2$— and two R$^8$ together with the carbon atom to which they are attached, form an optionally substituted cycloalkyl or optionally substituted heterocyclyl ring.

10. The compound of claim 1, wherein R$^9$ is pyridyl, phenyl or 2,3-dihydro-1H-indenyl, each of which is optionally substituted.

11. The compound of claim 10, wherein R$^9$ is optionally substituted phenyl.

12. The compound of claim 10, wherein R$^9$ is pyridyl, phenyl or 2,3-dihydro-1H-indenyl, each independently optionally substituted with one or two substituents selected from cyano, halo, optionally substituted C$_1$-C$_6$ alkyl and C$_1$-C$_6$ alkoxy.

13. The compound of claim 12, wherein R$^9$ is phenyl independently optionally substituted with one or two halo, cyano or C$_1$-C$_6$ alkyl optionally substituted with halo.

14. The compound of claim 13, wherein R$^9$ is phenyl independently optionally substituted with one or two halo or C$_1$-C$_6$ alkyl optionally substituted with halo.

15. The compound of claim 13, wherein R$^9$ is phenyl substituted with cyano.

16. The compound of claim 1, wherein the pyridyl of

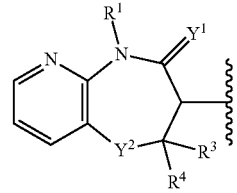

is independently optionally substituted with cyano, halo, alkyl, heteroaryl, aryl, heterocyclyl, cycloalkyl, alkoxy, or —S(O)$_2$—C$_1$-C$_6$ alkyl.

17. The compound of claim 16, wherein the pyridyl is independently optionally substituted with cyano, halo, or —S(O)$_2$—C$_1$-C$_6$ alkyl.

18. The compound of claim 1, wherein the pyridyl of

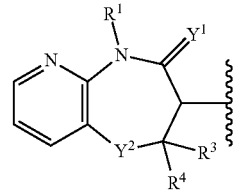

is unsubstituted.

19. The compound of claim 1, wherein the pyridyl of

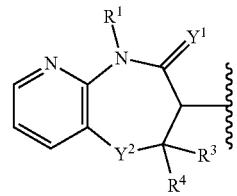

is independently optionally substituted with halo, alkyl, heteroaryl, aryl, heterocyclyl, cycloalkyl, or alkoxy.

20. The compound of claim 1, wherein ring A is phenyl, phenylbenzo[d]thiazolyl, isoxazolyl, oxazolyl, pyrazolyl, triazolyl, 5,6-dihydro-4H-pyrrolo[1,2-b]pyrazolyl, pyrrolyl, thiazolyl, imidazolyl, oxadiazolyl, thiadiazolyl, cyclobutyl, cyclopropyl, or azetidinyl.

21. The compound of claim 1, wherein ring A is oxadiazolyl.

22. The compound of claim 1, wherein L is —C(R$^8$)$_2$— and two R$^8$ together with the carbon atom to which they are attached form a cycloalkyl ring.

23. A pharmaceutical composition comprising a compound of claim 1, or a pharmaceutically acceptable salt, tautomer, stereoisomer or mixture of stereoisomers thereof, and a pharmaceutically acceptable excipient.

24. A compound having the structure:
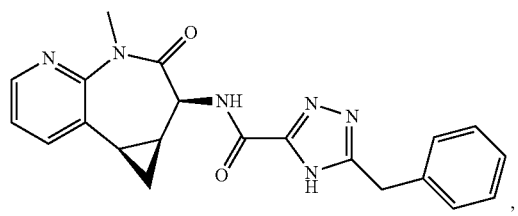
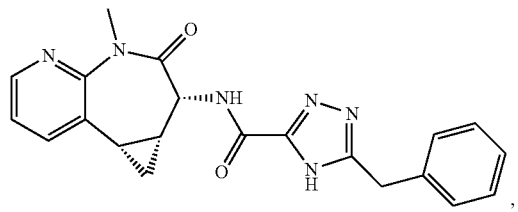
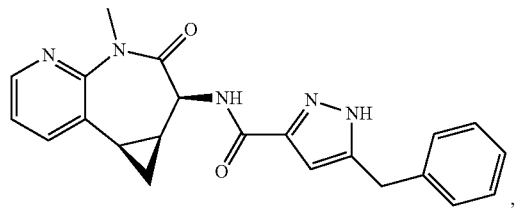
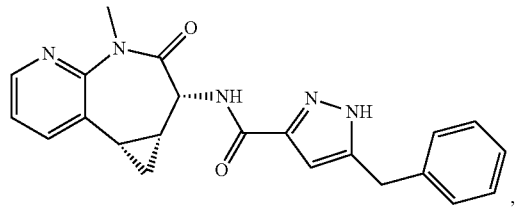
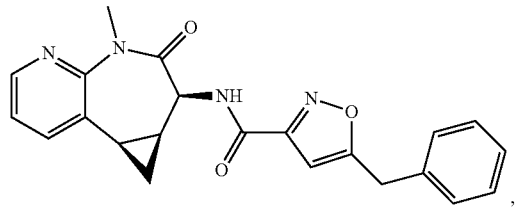
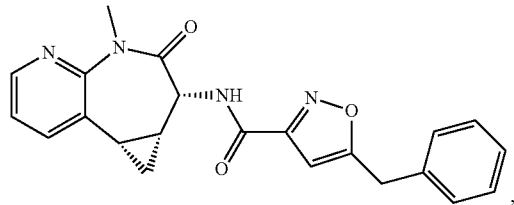
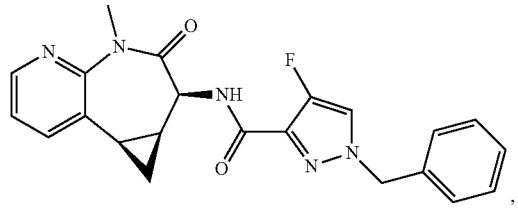
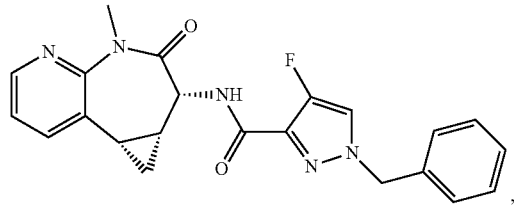
-continued
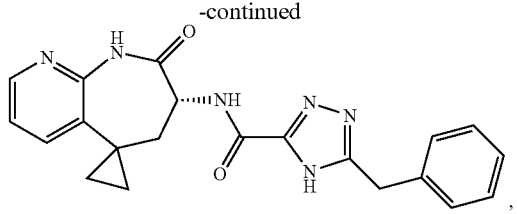
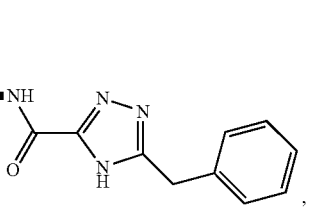
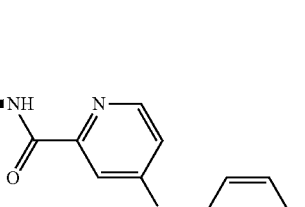
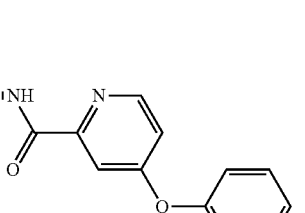
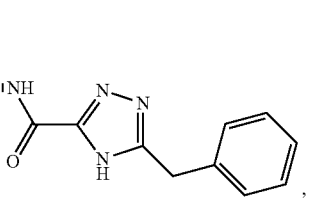
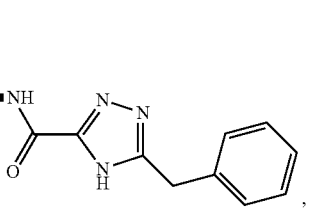
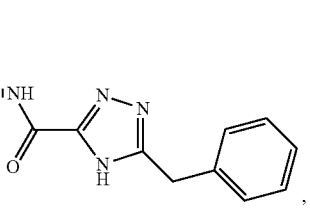

569
-continued
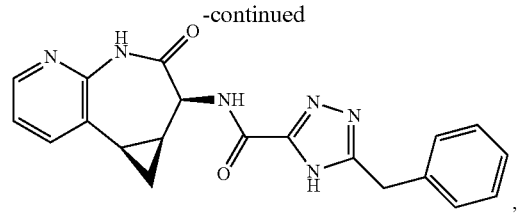,
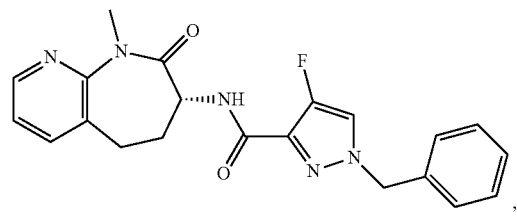,
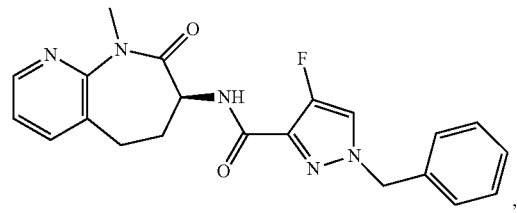,
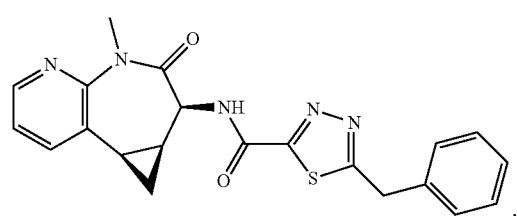,
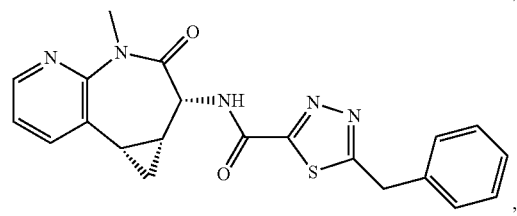,
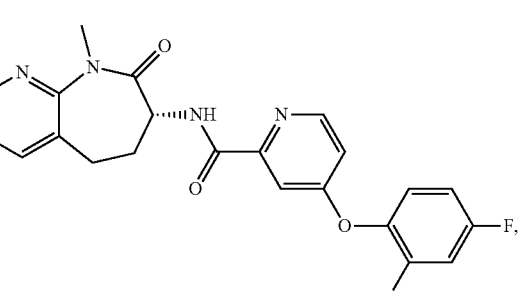,
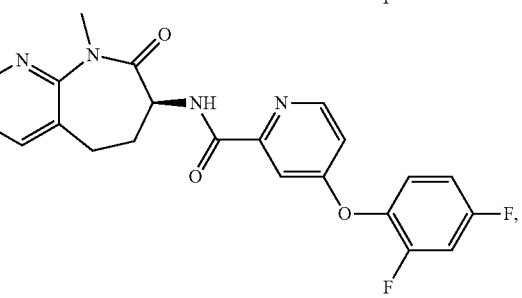,
570
-continued
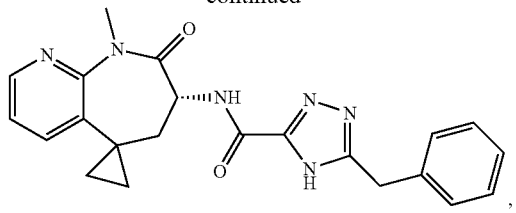,
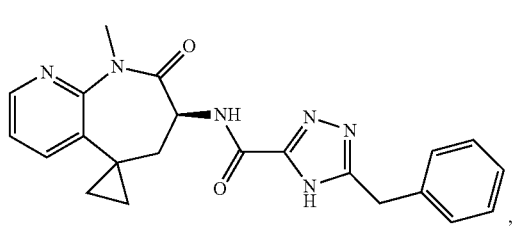,
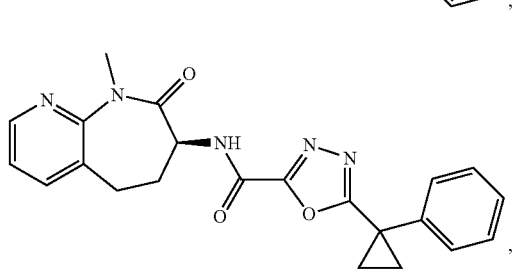,
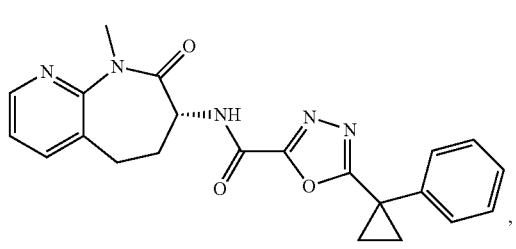,
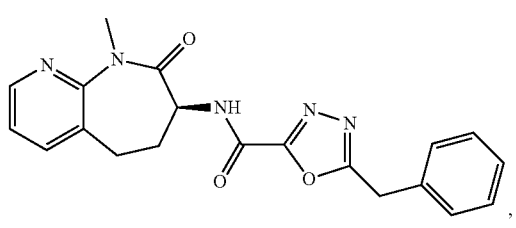,
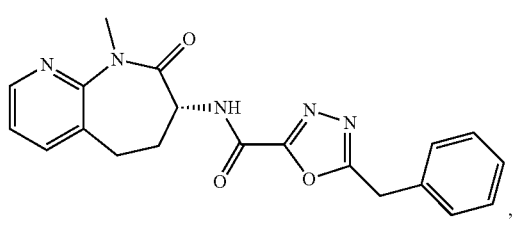,
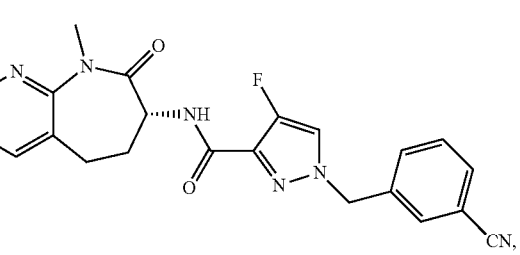, 571
-continued

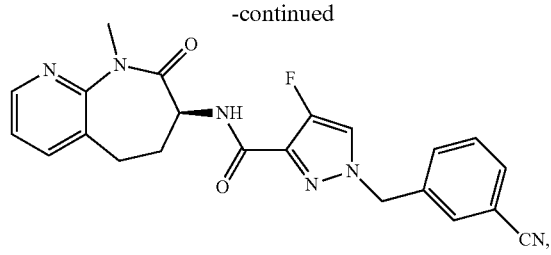

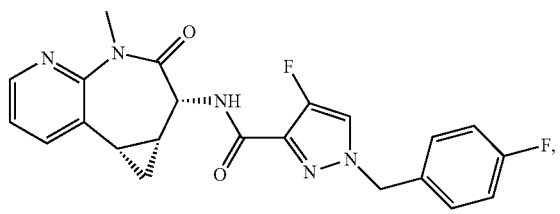

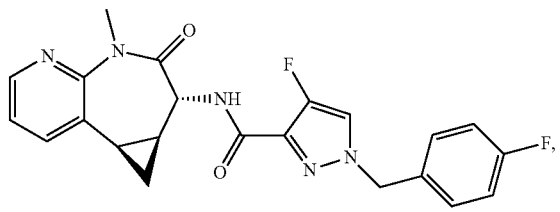

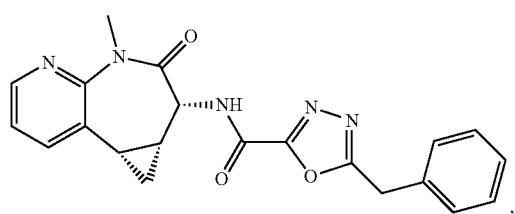

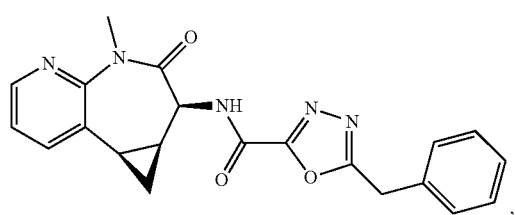

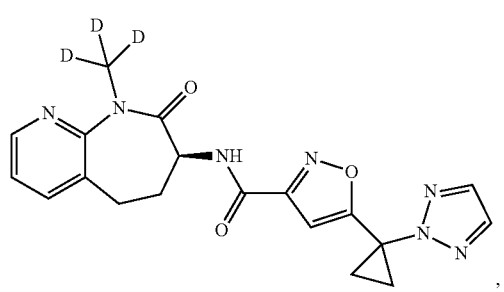

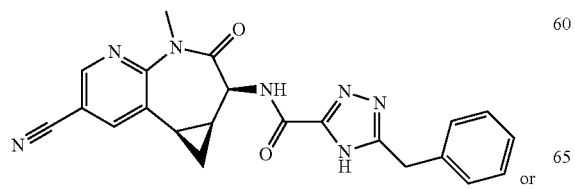

572
-continued

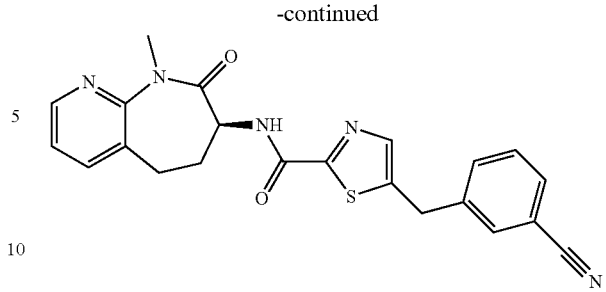

or a pharmaceutically acceptable salt, tautomer, stereoisomer or mixture of stereoisomers thereof.

25. A pharmaceutical composition comprising a compound of claim 24, or a pharmaceutically acceptable salt, tautomer, stereoisomer or mixture of stereoisomers thereof, and a pharmaceutically acceptable excipient.

26. A compound having the structure:

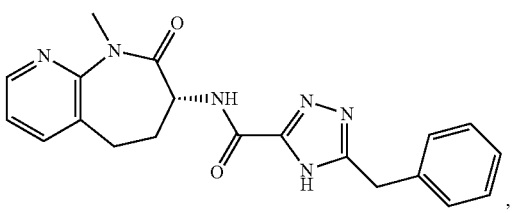

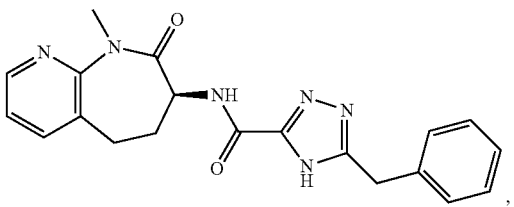

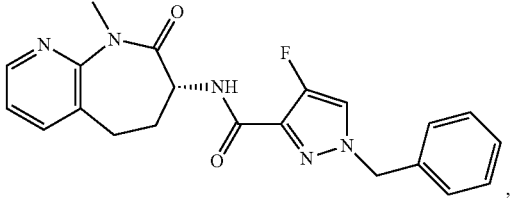

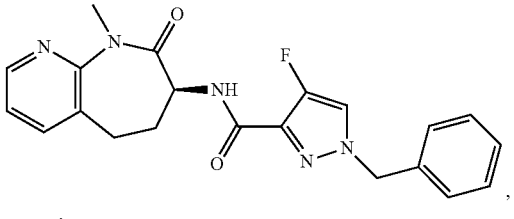

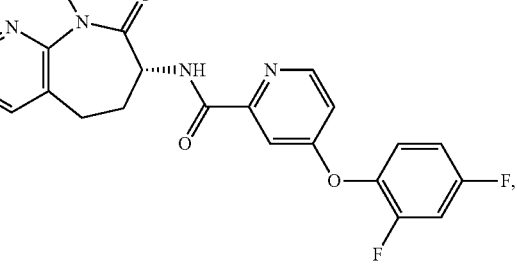

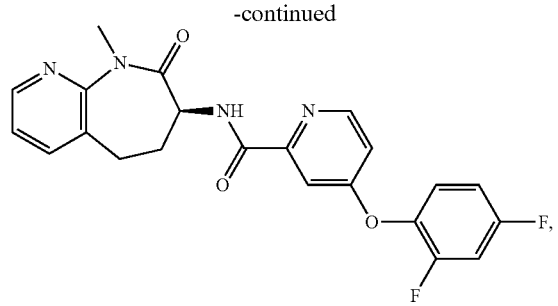
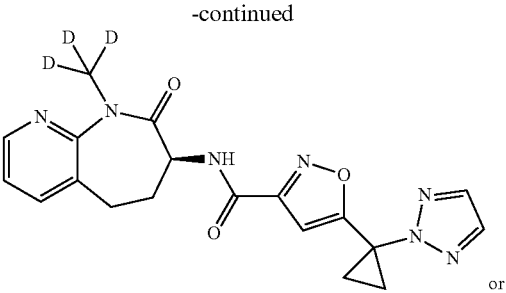
or a pharmaceutically acceptable salt, tautomer, stereoisomer or mixture of stereoisomers thereof.
27. A pharmaceutical composition comprising a compound of claim 26, or a pharmaceutically acceptable salt, tautomer, stereoisomer or mixture of stereoisomers thereof, and a pharmaceutically acceptable excipient.
28. A compound having the structure:
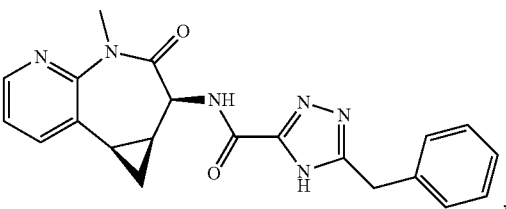
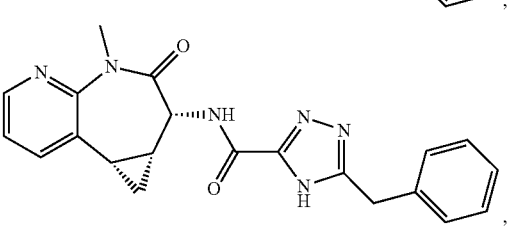
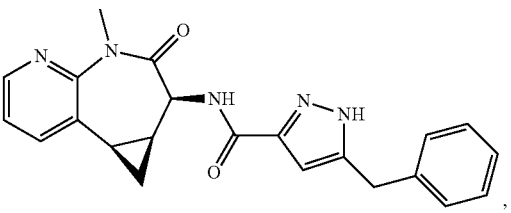
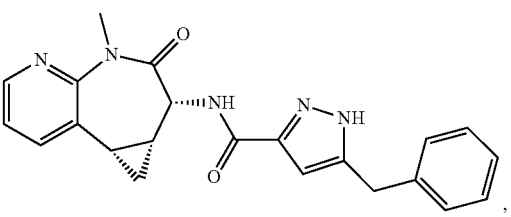

575
-continued
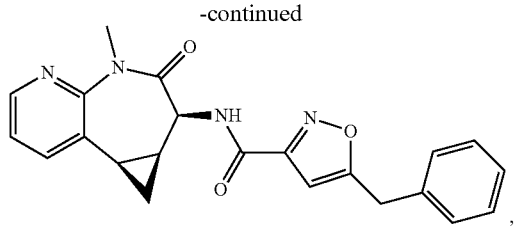
,
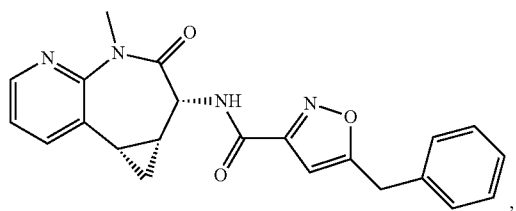
,
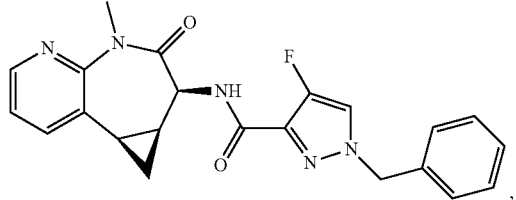
,
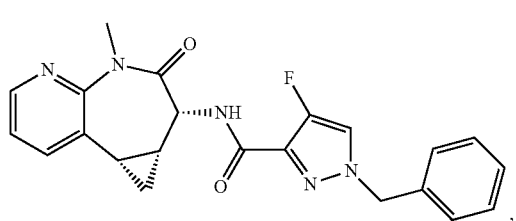
,
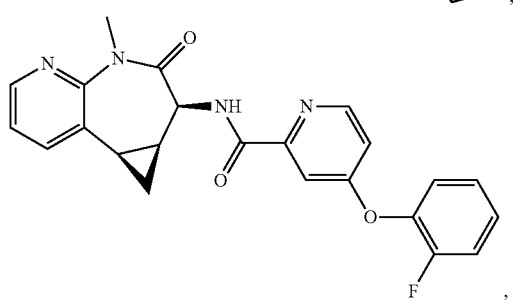
,
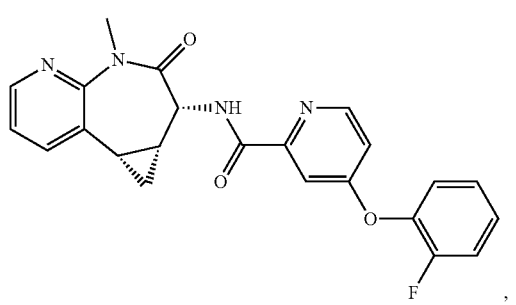
,
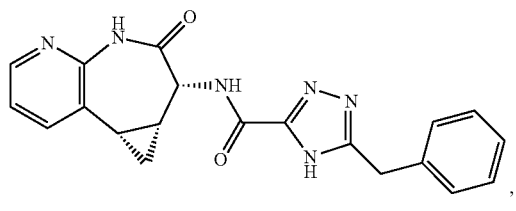
,
576
-continued
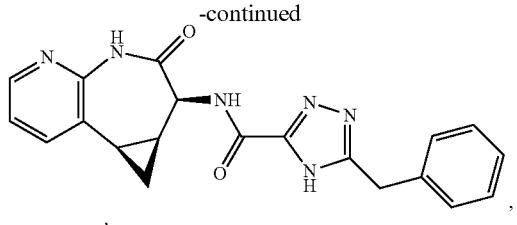
,
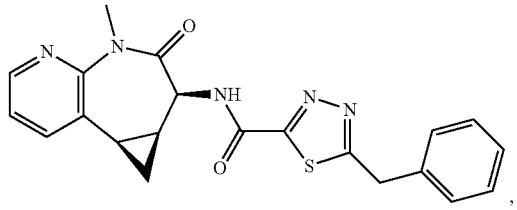
,
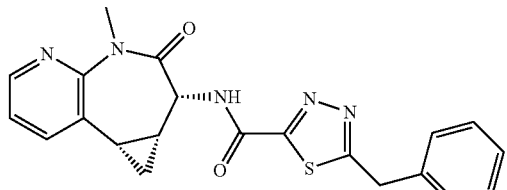
,
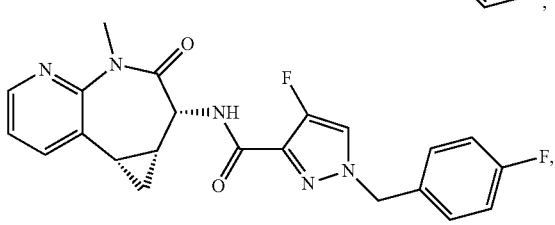
,
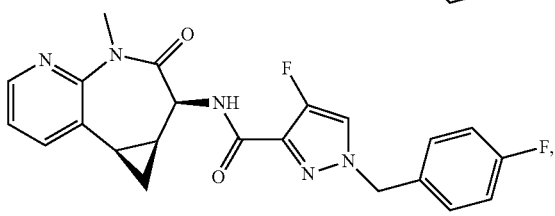
,
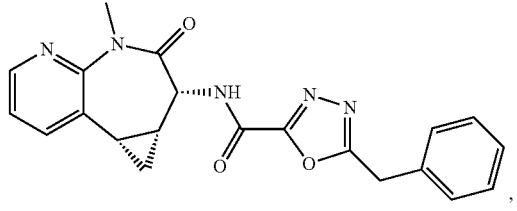
,
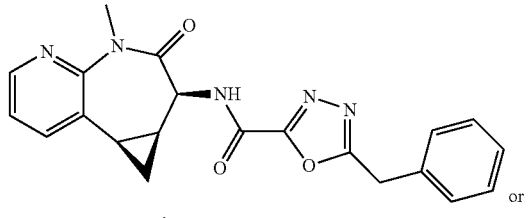
or
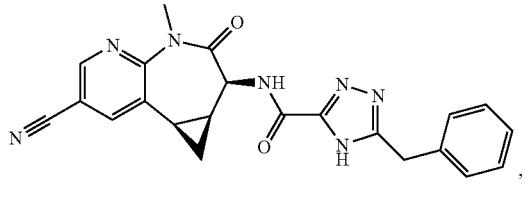
,
or a pharmaceutically acceptable salt, tautomer, stereoisomer or mixture of stereoisomers thereof.

29. A pharmaceutical composition comprising a compound of claim 28, or a pharmaceutically acceptable salt, tautomer, stereoisomer or mixture of stereoisomers thereof, and a pharmaceutically acceptable excipient.

30. A compound having the structure:

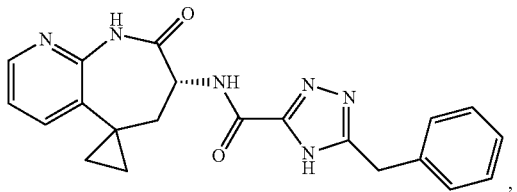

,

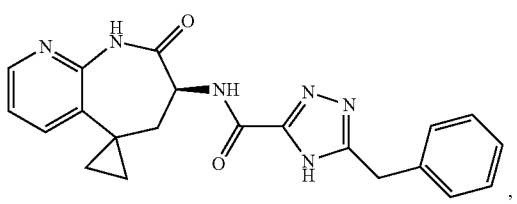

,

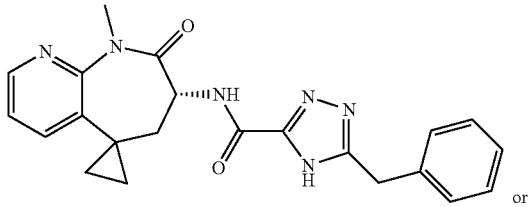

or

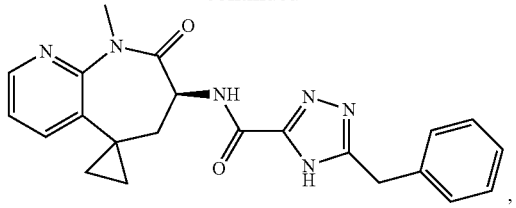

, or a pharmaceutically acceptable salt, tautomer, stereoisomer or mixture of stereoisomers thereof.

31. A pharmaceutical composition comprising a compound of claim 30, or a pharmaceutically acceptable salt, tautomer, stereoisomer or mixture of stereoisomers thereof, and a pharmaceutically acceptable excipient.

32. A compound of claim 26 having the structure:

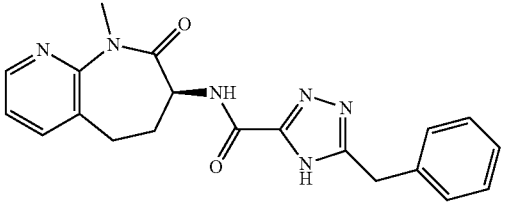 [SMILES: CN1C(=O)[C@@H](NC(=O)c2nnc(Cc3ccccc3)[nH]2)CCc2cccnc21]

or a pharmaceutically acceptable salt, tautomer, stereoisomer or mixture of stereoisomers thereof.

33. A pharmaceutical composition comprising a compound of claim 32, or a pharmaceutically acceptable salt, tautomer, stereoisomer or mixture of stereoisomers thereof, and a pharmaceutically acceptable excipient.

* * * * *